US011248037B2

(12) United States Patent
Dixit et al.

(10) Patent No.: US 11,248,037 B2
(45) Date of Patent: *Feb. 15, 2022

(54) MULTIVALENT HETEROMULTIMER SCAFFOLD DESIGN AND CONSTRUCTS

(71) Applicant: Zymeworks Inc., Vancouver (CA)

(72) Inventors: Surjit Bhimarao Dixit, Richmond (CA); Igor Edmondo Paolo D'Angelo, Port Moody (CA); Mario Sanches, Vancouver (CA); Gordon Yiu Kon Ng, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/417,969

(22) Filed: May 21, 2019

(65) Prior Publication Data

US 2019/0375823 A1 Dec. 12, 2019

Related U.S. Application Data

(63) Continuation of application No. 15/001,078, filed on Jan. 19, 2016, now Pat. No. 10,358,479, which is a continuation of application No. 13/941,450, filed on Jul. 13, 2013, now Pat. No. 9,388,231.

(60) Provisional application No. 61/845,945, filed on Jul. 12, 2013, provisional application No. 61/758,701, filed on Jan. 30, 2013, provisional application No. 61/697,245, filed on Sep. 5, 2012, provisional application No. 61/671,640, filed on Jul. 13, 2012.

(51) Int. Cl.

| | |
|---|---|
| ***C07K 14/765*** | (2006.01) |
| ***C07K 16/28*** | (2006.01) |
| ***C07K 14/76*** | (2006.01) |
| ***C07K 16/00*** | (2006.01) |
| ***C07K 14/485*** | (2006.01) |
| ***C07K 14/605*** | (2006.01) |
| ***C07K 16/40*** | (2006.01) |

(52) U.S. Cl.

CPC .......... *C07K 14/765* (2013.01); *C07K 14/485* (2013.01); *C07K 14/605* (2013.01); *C07K 14/76* (2013.01); *C07K 16/00* (2013.01); *C07K 16/2803* (2013.01); *C07K 16/283* (2013.01); *C07K 16/2809* (2013.01); *C07K 16/2896* (2013.01); *C07K 16/40* (2013.01); *C07K 2317/35* (2013.01); *C07K 2317/622* (2013.01); *C07K 2317/76* (2013.01); *C07K 2319/00* (2013.01); *C07K 2319/31* (2013.01)

(58) Field of Classification Search

None

See application file for complete search history.

(56) References Cited

U.S. PATENT DOCUMENTS

| | | | |
|---|---|---|---|
| 4,179,337 | A | 12/1979 | Davis et al. |
| 4,857,467 | A | 8/1989 | Sreekrishna et al. |
| 4,946,778 | A | 8/1990 | Ladner et al. |
| 4,980,286 | A | 12/1990 | Morgan et al. |
| 5,073,627 | A | 12/1991 | Curtis et al. |
| 5,108,910 | A | 4/1992 | Curtis et al. |
| 5,258,498 | A | 11/1993 | Huston et al. |
| 5,482,858 | A | 1/1996 | Huston et al. |
| 5,576,195 | A | 11/1996 | Robinson et al. |
| 5,641,670 | A | 6/1997 | Treco et al. |
| 5,731,168 | A | 3/1998 | Carter et al. |
| 5,780,594 | A | 7/1998 | Carter et al. |
| 5,837,846 | A | 11/1998 | Huston et al. |
| 5,846,818 | A | 12/1998 | Robinson et al. |
| 5,856,456 | A | 1/1999 | Whitlow et al. |
| 5,869,620 | A | 2/1999 | Whitlow et al. |
| 5,932,448 | A | 8/1999 | Tso et al. |
| 5,990,275 | A | 11/1999 | Whitlow et al. |
| 6,001,606 | A | 12/1999 | Ruben et al. |
| 6,077,692 | A | 6/2000 | Ruben et al. |

(Continued)

FOREIGN PATENT DOCUMENTS

| | | |
|---|---|---|
| DE | DD275463 | 1/1990 |
| EP | 0201239 A1 | 11/1986 |

(Continued)

OTHER PUBLICATIONS

U.S. Appl. No. 13/941,450, Notice of Allowance dated Jun. 23, 2015.

(Continued)

*Primary Examiner* — Sudhakar Katakam

*Assistant Examiner* — Zachary J Miknis

(74) *Attorney, Agent, or Firm* — Kilpatrick Townsend & Stockton LLP

(57) ABSTRACT

Provided herein are multifunctional heteromultimer proteins. In specific embodiments is a heteromultimer comprising: at least two polypeptide constructs, each polypeptide construct comprising at least one cargo polypeptide attached to a transporter polypeptide, said transporter polypeptides derived from a monomeric native protein such that said monomeric constructs associate to form the heteromultimer and said transporter polypeptides associate to form a quasi-native structure of the monomeric native protein or analog thereof. These therapeutically novel molecules encompass heteromultimers comprising constructs that function as scaffolds for the conjugation or fusion of therapeutic molecular entities (cargo polypeptides) resulting in the creation of bispecific or multivalent molecular species. Provided herein is a method for creation of bispecific or multivalent molecular species.

36 Claims, 52 Drawing Sheets

Specification includes a Sequence Listing.

(56) References Cited

U.S. PATENT DOCUMENTS

| | | | |
|---|---|---|---|
| 6,096,289 | A | 8/2000 | Goldenberg et al. |
| 6,350,430 | B1 | 2/2002 | Dooley et al. |
| 6,492,123 | B1 | 12/2002 | Holliger et al. |
| 6,686,179 | B2 | 2/2004 | Fleer et al. |
| 6,905,688 | B2 | 6/2005 | Rosen et al. |
| 6,926,898 | B2 | 8/2005 | Rosen et al. |
| 6,946,134 | B1 | 9/2005 | Rosen et al. |
| 6,972,322 | B2 | 12/2005 | Fleer et al. |
| 6,987,006 | B2 | 1/2006 | Fleer et al. |
| 6,989,365 | B2 | 1/2006 | Fleer et al. |
| 6,994,857 | B2 | 2/2006 | Rosen et al. |
| 7,041,478 | B2 | 5/2006 | Fleer et al. |
| 7,056,701 | B2 | 6/2006 | Fleer et al. |
| 7,094,577 | B2 | 8/2006 | Fleer et al. |
| 7,138,497 | B2 | 11/2006 | Houston et al. |
| 7,141,547 | B2 | 11/2006 | Rosen et al. |
| 7,189,690 | B2 | 3/2007 | Rosen et al. |
| 7,271,149 | B2 | 9/2007 | Glaesner et al. |
| 7,385,032 | B2 | 6/2008 | Holler et al. |
| 7,410,779 | B2 | 8/2008 | Fleer et al. |
| 7,482,013 | B2 | 1/2009 | Turner et al. |
| 7,507,413 | B2 | 3/2009 | Rosen et al. |
| 7,507,414 | B2 | 3/2009 | Rosen et al. |
| 7,521,424 | B2 | 4/2009 | Rosen et al. |
| 7,592,010 | B2 | 9/2009 | Rosen et al. |
| 7,708,996 | B2 | 5/2010 | Yu et al. |
| 7,785,599 | B2 | 8/2010 | Turner et al. |
| 7,799,759 | B2 | 9/2010 | Rosen et al. |
| 7,951,917 | B1 | 5/2011 | Arathoon et al. |
| 7,977,457 | B2 | 7/2011 | Reiter et al. |
| 8,501,185 | B2 | 8/2013 | Heitner et al. |
| 8,704,462 | B2 | 4/2014 | Shteynberg et al. |
| 9,388,231 | B2 * | 7/2016 | Dixit .................... C07K 14/485 |
| 9,499,605 | B2 * | 11/2016 | Dixit ....................... A61P 35/00 |
| 10,155,803 | B2 * | 12/2018 | Dixit ....................... A61P 37/00 |
| 10,358,479 | B2 * | 7/2019 | Dixit .................... C07K 14/605 |
| 10,711,051 | B2 * | 7/2020 | Dixit ....................... A61P 37/00 |
| 2004/0071696 | A1 | 4/2004 | Adams et al. |
| 2004/0171123 | A1 | 9/2004 | Rosen et al. |
| 2005/0186664 | A1 | 8/2005 | Rosen et al. |
| 2007/0041987 | A1 | 2/2007 | Carter et al. |
| 2007/0196363 | A1 | 8/2007 | Arathoon et al. |
| 2008/0261877 | A1 | 10/2008 | Ballance et al. |
| 2008/0267962 | A1 | 10/2008 | Ballance et al. |
| 2008/0269125 | A1 | 10/2008 | Ballance et al. |
| 2008/0269126 | A1 | 10/2008 | Ballance et al. |
| 2008/0269127 | A1 | 10/2008 | Ballance et al. |
| 2009/0060721 | A1 | 3/2009 | Davis et al. |
| 2009/0105140 | A1 | 4/2009 | Rosen et al. |
| 2009/0226466 | A1 | 9/2009 | Fong et al. |
| 2010/0093627 | A1 | 4/2010 | Rosen et al. |
| 2010/0166749 | A1 | 7/2010 | Presta |
| 2010/0189686 | A1 | 7/2010 | Rosen et al. |
| 2010/0196265 | A1 | 8/2010 | Adams et al. |
| 2010/0261650 | A1 | 10/2010 | Ballance et al. |
| 2011/0009312 | A1 | 1/2011 | Rosen et al. |
| 2011/0059076 | A1 | 3/2011 | Mcdonagh et al. |
| 2011/0274691 | A1 | 11/2011 | Arvedson et al. |
| 2011/0287009 | A1 | 11/2011 | Scheer et al. |
| 2012/0149876 | A1 | 6/2012 | Von Kreudenstein et al. |
| 2012/0244577 | A1 | 9/2012 | Dixit et al. |
| 2012/0270801 | A1 | 10/2012 | Frejd et al. |
| 2013/0078249 | A1 | 3/2013 | Ast et al. |
| 2014/0066378 | A1 | 3/2014 | Dixit et al. |
| 2014/0154253 | A1 | 6/2014 | Ng et al. |
| 2014/0200331 | A1 | 7/2014 | Corper et al. |
| 2016/0207979 | A1 | 7/2016 | Dixit et al. |
| 2017/0174745 | A1 | 6/2017 | Dixit et al. |
| 2019/0012744 | A1 | 1/2019 | Katta et al. |
| 2021/0009659 | A1 * | 1/2021 | Dixit ....................... A61P 37/00 |

FOREIGN PATENT DOCUMENTS

| | | | |
|---|---|---|---|
| EP | 0251744 | A2 | 1/1988 |
| EP | 0258067 | A2 | 3/1988 |
| EP | 0322094 | A1 | 6/1989 |
| EP | 0394827 | A1 | 10/1990 |
| EP | 1088888 | A1 | 4/2001 |
| JP | 62096086 | A | 5/1987 |
| JP | 2001-523971 | A | 11/2001 |
| JP | 2011-525476 | | 9/2011 |
| WO | 8605807 | A1 | 10/1986 |
| WO | 8704462 | A1 | 7/1987 |
| WO | 8910036 | A1 | 10/1989 |
| WO | 8910404 | A1 | 11/1989 |
| WO | 9001063 | A1 | 2/1990 |
| WO | 9106657 | A1 | 5/1991 |
| WO | 9311162 | A1 | 6/1993 |
| WO | 9412650 | A2 | 6/1994 |
| WO | 9523857 | A1 | 9/1995 |
| WO | 9629411 | A1 | 9/1996 |
| WO | 9634891 | A1 | 11/1996 |
| WO | 9704658 | A1 | 2/1997 |
| WO | 9724445 | A1 | 7/1997 |
| WO | 98/50431 | A2 | 11/1998 |
| WO | 0045835 | A1 | 8/2000 |
| WO | 0107608 | A1 | 2/2001 |
| WO | 0111046 | A1 | 2/2001 |
| WO | 0121658 | A1 | 3/2001 |
| WO | 2001049866 | | 7/2001 |
| WO | 03012069 | A2 | 2/2003 |
| WO | 03031464 | A2 | 4/2003 |
| WO | 03060071 | A2 | 7/2003 |
| WO | 2004029207 | A2 | 4/2004 |
| WO | 2004082640 | | 9/2004 |
| WO | 2006106905 | A1 | 10/2006 |
| WO | 2007144173 | | 12/2007 |
| WO | 2008131242 | A1 | 10/2008 |
| WO | 2009012784 | | 1/2009 |
| WO | 2009089004 | A1 | 7/2009 |
| WO | 2010027903 | | 3/2010 |
| WO | 2010092135 | A2 | 10/2010 |
| WO | 2010118169 | A2 | 10/2010 |
| WO | 2011028952 | A1 | 3/2011 |
| WO | 2011047180 | A1 | 4/2011 |
| WO | 2011051489 | A2 | 5/2011 |
| WO | 2011069090 | A1 | 6/2011 |
| WO | 2009/109635 | A2 | 9/2011 |
| WO | 2011120134 | A1 | 10/2011 |
| WO | 2011120135 | A1 | 10/2011 |
| WO | 2011143545 | A1 | 11/2011 |
| WO | 2011147982 | A2 | 12/2011 |
| WO | 2012006635 | A1 | 1/2012 |
| WO | 2012058768 | A1 | 5/2012 |
| WO | 2012116453 | A1 | 9/2012 |
| WO | 2013063702 | A1 | 5/2013 |
| WO | 2013166594 | A1 | 11/2013 |
| WO | 2013166604 | A1 | 11/2013 |
| WO | 2014004586 | A1 | 1/2014 |
| WO | 2014012082 | A2 | 1/2014 |
| WO | 2014012085 | A2 | 1/2014 |
| WO | 2014018572 | A2 | 1/2014 |
| WO | 2014082179 | A1 | 6/2014 |
| WO | 2014182970 | A1 | 11/2014 |
| WO | 2015006749 | A2 | 1/2015 |

OTHER PUBLICATIONS

U.S. Appl. No. 15/001,078, Restriction Requirement dated Jun. 21, 2016.

U.S. Appl. No. 15/001,078, Final Office Action dated Jun. 13, 2017.

U.S. Appl. No. 15/001,078, Advisory Action dated Oct. 17, 2017.

U.S. Appl. No. 15/001,078, Non-Final Office Action dated Aug. 13, 2018.

U.S. Appl. No. 15/001,078, Notice of Allowance dated Feb. 25, 2019.

U.S. Appl. No. 15/355,007, Non-Final Office Action dated Mar. 21, 2018.

U.S. Appl. No. 15/355,007, Notice of Allowance dated Aug. 3, 2018.

Polverino de Laureto, P. et al, "Probing the molten globule state of alpha-lactalbumin by limited proteolysis", Biochemistry 34/39, pp. 12596-12604, 1995.

(56) References Cited

OTHER PUBLICATIONS

Taguchi, T. et al, "Pharmaceutical aspects of the recombinant human serum albumindimer: structural characteristics, biological properties, and medical applications", J. Pharm. Sci, 10/9, pp. 3033-3046, Published online May 9, 2012 (May 9, 2012) D0I:10.1002/jps. 23181.
Wolff, S.P. et al, "Fragmentation of proteins by free radicals and its effect on their susceptibility to enzymic hydrolysis", Biochem. J. 234/2, pp. 399-403,1986.
U.S. Appl. No. 13/411,353 , "Non-Final Office action", dated Nov. 22, 2013.
U.S. Appl. No. 13/411,353 , "Final Office action", dated Mar. 7, 2014.
U.S. Appl. No. 13/411,353 , "Non-Final Office Action", dated Jun. 10, 2014, 11 pages.
U.S. Appl. No. 13/411,353 , "Final Office Action", dated Jan. 30, 2015, 12 pages.
U.S. Appl. No. 13/411,353 , "Final Office Action", dated Dec. 21, 2015, 13 pages.
U.S. Appl. No. 13/411,353 , "Notice of Allowance", dated Jun. 29, 2016, 10 pages.
U.S. Appl. No. 15/355,107 Non-Final Office Action dated Mar. 21, 2018.
U.S. Appl. No. 15/355,107 Notice of Allowance dated Aug. 3, 2018.
U.S. Appl. No. 13/411,353, Restriction Requirement dated Sep. 5, 2013.
U.S. Appl. No. 13/941,450, Restriction Requirement dated Jan. 14, 2014.
U.S. Appl. No. 13/941,450, Non-Final Office Action dated Mar. 6, 2014.
U.S. Appl. No. 13/941,450, Final Office Action dated Sep. 24, 2014.
U.S. Appl. No. 16/180,056, filed Sep. 5, 2018.
Ahmed et al., "Cancer Resource: a comprehensive database of cancer-relevant proteins and compound interactions supported by experimental knowledge", Nucleic Acids Res., 39(Database issue ), Jan. 2011, pp. D960-D967.
Altschul et al., "Basic local alignment search tool", J Mol Biol., vol. 215, No. 3, 1990, pp. 403-410.
Altschul et al., "Gapped BLAST and PSI-BLAST: a new generation of protein database search programs", Nucleic Acids Res., vol. 25(17), Sep. 1, 1997, pp. 3389-3402.
Anzenbacherova et al., "Determination of enzyme (angiotensin convertase) inhibitors based on enzymatic reaction followed by HPLCJ", Pharma. Biomed. Anal., vol. 24(5-6), Mar. 2001, pp. 1151-1156.
Atwell et al., "Stable heterodimers from remodeling the domain interface of a homodimer using a phage display library", Journal of Molecular Biology, vol. 270, No. 1, Jul. 4, 1997, pp. 26-35.
Bahadhur et al., "The interface of protein-protein complexes: analysis of contacts and prediction of interactions", Cell. Mol. Life Sci., vol. 65(7-8), Apr. 2008, pp. 1059-1072.
Baker et al., "Insulin-Like Growth Factor I Increases Follicle-Stimulating Hormone (FSH) Content and Gonadotropin-Releasing Hormone-Stimulated FSH Release from Coho Salmon Pituitary Cells In Vitro", Biol. Reprod., vol. 63(3), Sep. 2000, pp. 865-871.
Batterham et al., "Gut hormone PYY3-36 physiologically inhibits food intake", Nature, vol. 418, 2002, pp. 650-654.
Batzer et al., "Enhanced evolutionary PCR using oligonucleotides with inosine at the 3'-terminus", Nucleic Acids Res., vol. 19(18), Sep. 25, 1991, p. 5081.
Bebbington et al., "High-Level Expression of a Recombinant antibody from Myeloma Cells Using a Glutamine Synthetase Gene as an Amplifiable Selectable Marker", Biotechnology, vol. 10, 1992, p. 169.
Biblia et al., "In Pursuit of the Optimal Fed-Batch Process for Monoclonal Antibody Production", Biotechnol. Prog., vol. 11, 1995, pp. 1-13.
Bigbee et al., "Bioassayable growth hormone release in rats in response to a single bout of treadmill exercise", Appl. Physio., vol. 89(6), Dec. 2000, pp. 2174-2178.
Bohua et al., "Bispecific antibody to ErbB2 Overcomes Trastuzumab Resistance through Comprehensive Blockade of ErbB2 Heterodimerization", Cancer Research, vol. 73, No. 21, Sep. 17, 2013, pp. 6471-6483.
Bos, O. J. M., et al., Location and Characterization of the Warfarin binding site of Human Serum Albumin. Biochem Pharmacol, 1998; 37(20): 3905-3909.
Bouchon et al., "Cutting Edge: Inflammatory Responses Can Be Triggered by TREM-1, a Novel Receptor Expressed on Neutrophils and Monocytes", J. Immuno., vol. 164(10), May 15, 2000, pp. 4991-4995.
Bristow, "International Standards for Growth Hormone", Horm. Res., vol. 51 Suppl. 1, 1999, pp. 7-12.
Buchwald et al., "Long-term, continuous intravenous heparin administration by an implantable infusion pump in ambulatory patients with recurrent venous thrombosis", Surgery, vol. 88(4), Oct. 1980, pp. 507-516.
Cao et al., "Further LDL Cholesterol Lowering Through Targeting PCSK9 for Coronary Artery Disease", Endocrine, Metabolic & Immune Disorders—6Drug Targets, vol. 8 Issue 4, Dec. 2008, pp. 238-243.
Carter et al., "Purification, cloning, expression and biological characterization of an interleukin-1 receptor antagonist protein ", Nature, vol. 344, Apr. 12, 1990, pp. 633-638.
Carter et al., "Structure of serum albumin", Adv Protein Chem., vol. 45, 1994, pp. 153-203.
Chames et al., "Therapeutic antibodies: successes, limitations and hopes for the future", British Journal of Pharmacology, vol. 157, No. 2, 2009, pp. 220-223.
Chaudhary et al., "The major histocompatibility complex-related Fe receptor for IgG (FeRn) binds albumin and prolongs its lifespan", J. Exp. Med., vol. 197(3), Feb. 3, 2003, pp. 315-322.
Cochlovius et al., "Treatment of human B cell lymphoma xenografts with a CD3 × CD19 diabody and T cells", Journal of Immunology, vol. 165, No. 2, 2000, pp. 888-895.
Creighton , "Proteins: Structures and Molecular Principles", Nature, vol. 310, 1984, pp. 105-111.
Creighton , "Proteins: Structures and Molecular Properties", Second ed. W. H. Freeman, New York, 1993.
Davis et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, vol. 23, No. 4, Feb. 4, 2010, pp. 195-202.
Dennis et al., "Albumin Binding as a General Strategy for Improving the Pharmacokinetics of Proteins", J. Biol. Chem., vol. 277, 2002, p. 35035-35043.
Dockal et al., "Conformational Transitions of the Three Recombinant Domains of Human Serum Albumin Depending on pH", The Journal of Biological Chemistry, vol. 275, No. 5, Feb. 4, 2000, pp. 3042-3050.
Dockal et al., "Five recombinant fragments of human serum albumin-tools for the characterization of the warfarin binding site", Protein Science, vol. 9, No. 8, 2000, pp. 1455-1465.
Dockal et al., "The three recombinant domains of human serum albumin. Structural characterization and ligand binding properties.", J. Biol. Chem., vol. 274, No. 41, Oct. 8, 1999, p. 29303-29310.
During et al., "Controlled release of dopamine from a polymeric brain implant: in vivo characterization", Ann. Neural., vol. 25(4), Apr. 1989, pp. 351-356.
Eichels et al., "Angiotensin converting enzyme inhibitors block mitogenic signalling pathways in rat cardiac fibroblasts", Naunyn-Schmiedeberg's Arch Pharmacal, vol. 359, 1999, pp. 394-399.
Epsevik et al., "A highly sensitive cell line, WEHI 164 clone 13, for measuring cytotoxic factor/tumor necrosis factor from human monocytes", Journal of Immunological Methods, vol. 95, 1986, pp. 99-105.
Forrer et al., "Enzyme-Linked Immunosorbent Assay for Measurement of JNK, ERK, and p38 Kinase Activities", Biol. Chem., vol. 379(8-9), 1998, pp. 1101-1110.
Gao et al., "Sensitivity of an Epstein-Barr virus-positive tumor line, Daudi, to alpha interferon correlates with expression of a GC-rich viral transcript ", Mol. Cell. Biol., vol. 19(11), 1999, pp. 7305-7313.

(56) References Cited

OTHER PUBLICATIONS

Gaylinn et al., "Molecular Cloning and Expression of a Human Anterior Pituitary Receptor for Growth Hormone-Releasing Hormone.", Molecular Endocrinology, vol. 7, 1993, pp. 77-84.
Gegg et al., "Probing minimal independent folding units in dihydrofolate reductase by molecular dissection", Protein Science, vol. 6, 1997, pp. 1885-1892.
Gillis et al., "T Cell Growth Factor: Parameters of Production and a Quantitative Microassay for Activity", J. Immunol., vol. 120, 1978, pp. 2027-2032.
Gleeson et al., "Transformation of the Methylotrophic Yeast Hansenula Polymorpha.", J. Gen. Microbiol., vol. 132, 1986, pp. 3459-3465.
Goodson , "Medical Applications of Controlled Release", Chapter 6: Dental Application, vol. 2, 1984, pp. pp. 115-138.
Gray et al., "Characterization, primary structure, and evolution of lamprey plasma albumin", Protein Sci., vol. 1(2), Feb. 1992, pp. 289-302.
Gunasekaran et al., "Enhancing antibody Fc heterodimer formation through electrostatic steering effects: applications to bispecific molecules and monovalent IgG", J. Biol. Chem., vol. 285, No. 25, Jun. 18, 2010, p. 19637-19646.
Hall et al., "The crystal and molecular structures of diferric porcine and rabbit serum transferrins at resolutions of 2.15 and 2.60 A, respectively ", Acta Crystallogr D Biol Crystallogr., vol. 58(Pt 1), Jan. 2002, pp. 70-80.
Hardy et al., "Valency of Antibody Binding to Enveloped Virus Particles as Determined by Surface Plasmon Resonance", J Viral., vol. 77, No. 2, 2003, pp. 1649-1652.
Heaney-Kieras et al., "Limited Pepsin Digestion of Human Plasma Albumin", J. Biol. Chem., vol. 252, 1997, pp. 4326-4329.
Henikoff et al., "Amino acid substitution matrices from protein blocks", Proc. Natl. Acad. Sci. USA, vol. 89(22), Nov. 15, 1992, pp. 10915-10919.
Hoffman et al., "Isolation and characterization of mutants constitutive for expression of the fbp 1 gene of Schizosaccharomyces pombe", Genetics, vol. 124(4), Apr. 1990, pp. 807-816.
Howard et al., "Intracerebral dmg delivery in rats with lesion-induced memory deficits", J. Neurosurg., vol. 71(1), Jul. 1989, pp. 105-112.
Hunkapiller et al., "A microchemical facility for the analysis and synthesis of genes and proteins", Nature, vol. 10(5973), Jul. 12, 1984, pp. 105-111.
Igawa et al., "VH/VL interface engineering to promote selective expression and inhibit conformational isomerization of thrombopoietin receptor against single-chain diabody", Protein Engineering, Design & Selection, vol. 23, No. 8, Aug. 2010, pp. 667-677.
Ikeda et al., "A novel bioassay based on human growth hormone (hGH) receptor mediated cell proliferation: measurement of 20K-hGH and its modified forms", Growth Hormone & IGF Research, vol. 10, 2000, pp. 248-255.
Ishikawa et al., "A Novel Specific Bioassay for Serum Human Growth Hormone", J. Clin. Endocrinol Metab., vol. 85(11), Nov. 2000, pp. 4274-4279.
Johnson , "Posttranslational Covalent Modifications of Proteins", Elsevier Inc., Academic Press, New York, 1983, pp. 1-12.
Joliot et al., "Antennapedia homeobox peptide regulates neural morphogenesis", Proc. Natl. Acad. Sci. USA, vol. 88(5), Mar. 1, 1991, pp. 1864-1868.
Kang et al., "Engineering multivalent antibodies to target heregulin-induced HER3 signaling in breast cancer cells", MAbs, vol. 6, 2013, pp. 340-353.
Karlin et al., "Applications and statistics for multiple high-scoring segments in molecular sequences", Proc. Natl. Acad. Sci. USA, vol. 90(12), Jun. 15, 1993, pp. 5873-5887.
Kipriyanov et al., "Recent advances in the generation of bispecific antibodies for tumor immunotherapy", Curr. Opin. Drug Discov. Devel., vol. 7(2), Mar. 2004, pp. 233-242.
Kitamura et al., "Establishment and Characterization of a Unique Human Cell Line That Proliferates Dependently on CM-CSF, IL-3, or Erythropoietin ", Journal of Cellular Physiology, vol. 140, Issue 2, Aug. 1989, pp. 323-334.
Klein et al., "Progress in overcoming the chain association issue in bispecific heterodimeric IgG antibodies", MABS,vol. 4, No. 6,, Nov./Dec. 2012, pp. 653-663.
Koller et al., "Inactivating the beta 2-microglobulin locus in mouse embryonic stem cells by homologous recombination", Proc. Natl. Acad. Sci. USA, vol. 86(22), Nov. 1989, pp. 8932-8935.
Kragh-Hansen et al., "Effect of genetic variation on the thermal stability of human serum albumin", Biochim Biophys Acta., vol. 1747(1), Feb. 14, 2005, pp. 81-88.
Kratz , "Albumin as a drug carrier: design of prodrugs, drug conjugates and nanoparticles", Journal of Controlled Release., vol. 132, May 17, 2008, pp. 171-183.
Ku et al., "Control of homeostasis of CD8+ memory T cells by opposing cytokines", Science, vol. 288, 2000, pp. 675-678.
Kwon et al., "TR1, a new member of the tumor necrosis factor receptor superfamily, induces fibroblast proliferation and inhibits osteoclastogenesis and bone resorption.", FASEB J., vol. 12, 1998, pp. 845-854.
Langer , "New methods of drug delivery", Science, New Series, vol. 249, No. 4976, Sep. 28, 1990, pp. 1527-1533.
Levy et al., "Inhibition of calcification of bioprosthetic heart valves by local controlled-release diphosphonate.", Science, New Series, vol. 228, No. 4696, Apr. 12, 1985, pp. 190-192.
Lewis et al., "Generation of bispecific IgG antibodies by structura-based design of an orthogonal Fab interface", Nature Biotechnology. vol. 32, Jan. 26, 2014, pp. 1-12.
Lu et al., "Fab-scFv fusion protein: an efficient approach to production of bispecific antibody fragments", Journal of Immunological Methods, vol. 267, No. 2, 2002, pp. 213-226.
Ma et al., "Enzyme dynamics point to stepwise conformational selection in catalysis", Current Opinion in Chemical Biology, vol. 14, 2010, pp. 652-659.
Maundrell et al., "Nmt1 of fission yeast. A highly transcribed gene completely repressed by thiamine", J. Biol. Chem., vol. 265(19), Jul. 5, 1990, p. 10857-10864.
Mayo et al., "Molecular Cloning and Expression of a Pituitary-Specific Receptor for Growth Hormone-Releasing Hormone", Mol. Endocrinol., vol. 6(10), Oct. 1992, pp. 1734-1744.
McDonagh et al., "Antitumor activity of a novel bispecific antibody that targets the ErbB2/ErbB3 oncogenic unit and inhibits heregulin-induced activation of ErbB3", Mol. Cancer Ther., vol. 11, No. 3, pp. 582-593, Jan. 2012.
Merchant et al., "An efficient route to human bispecific IgG", Nature Biotechnology, vol. 16, No. 7, Jul. 16, 1998, pp. 677-681.
Minchiotti et al., "Mutations and polymorphisms of the gene of the major human blood protein, serum albumin", Hum. Mutat., vol. 29(8), Aug. 2008, pp. 1007-1016.
Miraglia et al., "Homogeneous Cell- and Bead-Based Assays for High Throughput Screening Using Fluorometric Microvolume Assay Technology", J. of Biomol. Screen. vol. 4, 1999, pp. 193-204.
Miyawaki et al., "Inhibition of gastric inhibitory polypeptide signaling prevents obesity", Nat. Medicine., vol. 8(7), 2002, pp. 738-742.
Moore et al., "A novel bispecific antibody format enables simultaneous bivalent and monovalent co-engagement of distinct target antigens", mAbs, vol. 3, No. 6, 2011, pp. 546-557.
Moore et al., "BLyS: Member of the Tumor Necrosis Factor Family and B Lymphocyte Stimulator", Science, New Series, vol. 285, No. 5425, Jul. 9, 1999, pp. 260-263.
Muller et al., "Bispecific Antibodies for Cancer Immunotherapy", Biodrugs, vol. 24, 2010, pp. 89-98.
Mural et al., "Altered Regulation of Cell Cycle Machinery involved in lnterleukin-1- induced G 1 and G2 Phase Growth Arrest of A375S2 Human Melanoma Cells.", J. Biol. Chem., vol. 276, 2001, pp. 6797-6806.
Nardelli et al., "Dendritic cells and MPIF-1: chemotactic activity and inhibition of endogenous chemokine production by IFN-y and CD40 ligation", J. Leukoc. Biol., vol. 65, 1999, pp. 822-828.

(56) References Cited

OTHER PUBLICATIONS

Needleman et al., "A general method applicable to the search for similarities in the amino acid sequence of two proteins", Journal of Molecular Biology, vol. 48, No. 3, Mar. 28, 1970, pp. 443-453.
Neumann et al., "Native albumin for targeted drug delivery", Expert Opinion On Drug Delivery., vol. 7, No. 8,, Aug. 8, 2010, pp. 915-925.
Ohtsuka et al., "An alternative approach to deoxyoligonucleotides as hybridization probes by insertion of deoxyinosine at ambiguous codon positions", J. Biol. Chem., vol. 260(5), Mar. 10, 1985, pp. 2605-2608.
Osborn et al., "Pharmacokinetic and Pharmacodynamics Studies of a Human Serum Albumin-Interferon-A Fusion Protein in Cynomolgus Monkeys", J. Pharamcology and Experiemental Therapeutics, vol. 330, 2002, pp. 540-548.
PCT/CA2012/050131 , "International Preliminary Report on Patentability", dated Sep. 3, 2013.
PCT/CA2012/050131 , "International Search Report and Written Opinion", dated May 23, 2012, 9 pages.
PCT/US2013/050408 , "International Search Report and Written Opinion", dated Feb. 6, 2014, 14 pages.
Pearson et al., "Improved tools for biological sequence comparison", Proceedings of the National Academy of Sciences, vol. 85, No. 8, Apr. 1988, pp. 2444-2448.
Phizicky et al., "Protein-protein interactions: Methods for Detection and Analysis", Microbial. Rev., vol. 59(1), 1995, pp. 94-123.
Pontoglio et al., "Defective Insulin Secretion in Hepatocyte Nuclear Factor 1 a-deficient Mice", J. Clin. Invest., vol. 101(10), May 15, 1988, pp. 2215-2222.
Poznansky et al., "Enzyme-Albumin Polymers New Approaches to the Use of Enzymes in Medicine", Appl. Biochem. Biotechnol., vol. 10, 1984, pp. 41-56.
Rattan et al., "Protein synthesis, posttranslational modifications, and aging", Ann. NY Acad. Sci., vol. 663, Nov. 21, 1992, pp. 48-62.
Reed et al., "Fragments of Bovine Serum Albumin Produced by Limited Proteolysis: Complementary Behavior of Two Large Fragments," Biochemistry, 1976, vol. 15, No. 24, pp. 5394-5398.
"Zymeworks Announces the Formation of its Therapeutics Advisory Team, and Appointment of VP, Preclinical R&D to Advance its Strategic Therapeutics Initiative," Building Better Biologies, Company, Jan. 5, 2012, Zymeworks Inc., 4 pages.
Ridgway et al., "Knobs-into-holes' engineering of antibody CH3 domains for heavy chain heterodimerization", Protein Engineering, vol. 9, No. 7, Jul. 1996, pp. 617-621.
Robinson et al., "Targeting ErbB2 and ErbB3 with a bispecific single-chain Fv enhances 1-5 targeting selectivity and induces a therapeutic effect in vitro", Br. J. Cancer, vol. 99, Oct. 7, 2008, pp. 1415-1425.
Roopenian et al., "FeRn: the neonatal Fe receptor comes of age", Nat. Rev. Immunol., vol. 7(9), Sep. 2007, pp. 715-725.
Rosenberg et al., "Biological activity of recombinant human interleukin-2 produced in *Escherichia coli*", Science, New Series, vol. 223, No. 4643, Mar. 30, 1984, pp. 1412-1415.
Rossolini et al., "Use of deoxyinosine-containing primers vs degenerate primers for polymerase chain reaction based on ambiguous sequence information", Mol. Cell. Probes, vol. 8(2), Apr. 1994, pp. 91-98.
Rubinstein et al., "Convenient assay for Interferons", J. Viral., vol. 37(2), 1981, pp. 755-758.
Sarav et al., "Renal FeRn reclaims albumin but facilitates elimination of IgG", J. Am. Soc. Nephrol., vol. 20(9), Sep. 2009, pp. 1941-1952.
Saudek et al., "A preliminary trial of the programmable implantable medication system for insulin delivery", N. Engl. J. Med., vol. 21 (9), Aug. 31, 1989, pp. 574-579.
Schecroun et al., "Biological Properties of Salmon Calcitonin IV", J. Bone Miner. Res., vol. 14(8), Aug. 1999, pp. 1425-1431.
Seifter et al., "Analysis for protein modifications and nonprotein cofactors", Methods. Enzymol., vol. 182, 1990, pp. 626-646.
Shekhawat et al., "Split-protein systems: beyond binary proteinprotein interactions", Current Opinion in Chemical Biology., vol. 15, Nov. 7, 2011, pp. 789-797.
Shields et al., "High resolution mapping of the binding site on human IgG1 for Fc gamma RI, Fc gamma RII, Fc gamma RIII, and FcRn and design of IgG1 variants with improved binding to the Fc gamma R", Journal of Biological Chemistry, vol. 276, No. 9, Mar. 2, 2001, pp. 6591-6604.
Smith et al., "Comparison of biosequences", Advances in Applied Mathematics, vol. 2, Issue 4, Dec. 1981, pp. 482-489.
Stains et al., "A general approach for receptor and antibodytargeted detection of native proteins utilizing splitluciferase reassembly", ACS Chemical Biology., vol. 5, No. 10, Jul. 23, 2010, pp. 943-952.
Stanglmaier et al., "Bi20 (FBTA05), A Novel Trifunctional Bispecific Antibody (anti-CD20 3 anti-CD3), Mediates Efficient Killing Of B-cell Lymphoma Cells Even With Very Low CD20 Expression Levels", International Journal of Cancer, vol. 123, 2008, pp. 1181-1189.
Sung et al., "High-Yield Expression of Fully Bioactive N-Terminal Parathyroid Hormone Analog in *Escherichia coli.*", IUBMB Life, vol. 49(2), Feb. 2000, pp. 131-135.
Sutherland et al., "Inactivation of glycogen synthase kinase-3fl by phosphorylation: new kinase connections in insulin and growth-factor signalling", Biochem. J., vol. 296 (Pt 1), Nov. 15, 1993, pp. 15-19.
Syed et al., "Potent Antithrombin Activity and Delayed Clearance From the Circulation Characterize Recombinant Hirudin Genetically Fused to Albumin", Blood, vol. 89, 1997, pp. 3243-3252.
Tafelmeyer et al., "Transforming a (P/a),-barrel enzyme into a split-protein sensor through directed evolution", Chemistry & Biology,vol. 11, May 2004, pp. 681-689.
Testa et al., "Assays for hematopoietic growth factors", Balkwill FR ( ed) Cytokines, A Practical Approach, IRL Press Oxford, 1991, pp. 229-244.
Tijssen et al., "Laboratory Techniques in Biochemistry and Molecular Biology—Hybridization with Nucleic Probes", Chapter 2: Overview of principles of hybridization and the strategy of nucleic acid assays, 1993, pp. 19-78.
Traunecker et al., "Soluble CD4 molecules neutralize human immunodeficiency virus type 1", Nature, vol. 331(6151), Jan. 7, 1988, pp. 84-86.
Troise et al., "Differential binding of human immunoagents and Herceptin to the ErbB2 receptor", FEBS Journal, vol. 275, No. 20, 2008, pp. 4967-4979.
Urso et al., "Differences in Signaling Properties of the Cytoplasmic Domains of the Insulin Receptor and Insulin-like Growth Factor Receptor in 3T3-L1 Adopcytes", J. Biol. Chem., vol. 274, 1999, p. 30864-30873.
Varnerin et al., "Production of Leptin in *Escherichia coli*: A Comparison of Methods", Protein Expr. Purif., vol. 14(3), Dec. 1998, pp. 335-342.
Verhaselt et al., "Bacterial Lipopolysaccharide Stimulates the Production of Cytokines and the Expression of Costimulatory Molecules by Human Peripheral Blood Dendritic Cells", J. Immunol., vol. 158, 1997, pp. 2919-2925.
Waldmann et al., "Albumin catabolism", Albumin Structure, Function and Uses, Permagon Press, 1977, pp. 255-273.
Walz et al., "ILA Murine lnterleukin-4-Ig Fusion Protein Regulates the Expression of Th1- and Th2-Specific Cytokines in the Pancreas of NOD Mice", Harm. Metab. Res., vol. 34(10), Oct. 2002, pp. 561-569.
Weiner et al., "Human neutrophil interactions of a bispecific monoclonal antibody targeting tumor and human Fer RIII", Cancer Immunol. Immunother., vol. 42, 1996, pp. 141-150.
Weinstein et al., "Truncation of the c-myb gene by a retroviral integration in an interleukin 3-dependent myeloid leukemia cell line", Proc. Natl. Acad. Sci. USA, vol. 83, 1986, pp. 5010-5014.
Wishart et al., "DrugBank: a knowledgebase for drugs, drug actions and drug targets", Nucleic Acids Res., vol. 36, Jan. 2008, pp. W496-W502.

(56) References Cited

OTHER PUBLICATIONS

Wu et al., "Humanization of a murine monoclonal antibody by simultaneous optimization of framework and CDR residues", Journal of Molecular Biology, vol. 294, No. 1, Nov. 19, 1999, pp. 151-162.
Wu et al., "Receptor-mediated in vitro gene transformation by a soluble DNA carrier system", J. Biol. Chem., vol. 262(10), Apr. 5, 1987, pp. 4429-4432.
Wurster et al., "Interleukin 21 Is aT Helper (Th) Cell2 Cytokine that Specifically Inhibits the Differentiation of Naive Th Cells into Interferon Y-producing Th1 Cells", J. Exp. Med., vol. 196(7), Oct. 7, 2002, pp. 969-977.
Yeh et al., "Design of yeast-secreted albumin derivatives for human therapy: biological and antiviral properties of a serum albumin-CD4 genetic conjugate", Proc. Natl. Acad. Sci., USA, vol. 89(5), Mar. 1, 1992, pp. 1904-1908.
Zhou et al., "Osteoclast Inhibitory Lectin, a Family of New Osteoclast Inhibitors", J. Biol. Chem., vol. 277(50), Dec. 13, 2002, p. 48808-48815.
Zhu et al., "Remodeling domain interfaces to enhance heterodimer formation", Protein Science, vol. 6, No. 4, Apr. 1997, pp. 781-788.
Zhu et al., "Update of TTD: Therapeutic Target Database", Nucleic Acids Res., vol. 38(Database issue), Nov. 2009, pp. D787-D791.
Zijlstra et al., "Germ-line transmission of a disrupted ~2-microglobulin gene produced by homologous recombination in embryonic stem cells", Nature, vol. 342(6248), Nov. 23, 1989, pp. 435-438.
Hamilton, J. A., et al., Locations of the three primary binding sites for long-chain fatty acids on bovine serum albumin. PNAS, Mar. 1991; 88:2051-2054.
Shekhawat, S.S., and Ghosh, I., Split-protein systems: beyond binary protein-protein interactions. Curr Opin Chem Biol, Nov. 7, 2011; 15(6)789-797.
Sugio, S., et al., Crystal structure of human serum albumin at 2.5 Å resolution. Protein Engineering, 1999; 12 (6):439-446.
U.S. Appl. No. 16/180,056, Office Action dated Nov. 4, 2019.
U.S. Appl. No. 16/180,056, Notice of Allowance dated Mar. 10, 2020.
U.S. Appl. No. 13/941,450 Corrected Notice of Allowability dated Jul. 10, 2015.
U.S. Appl. No. 13/941,450 Corrected Notice of Allowance dated Oct. 9, 2015.
U.S. Appl. No. 15/001,078, Non-Final Office Action dated Nov. 28, 2016.
Seibutsu Kougaku, Biotechnology, 2011, vol. 89, No. 7, pp. 398-400.

* cited by examiner

ABH2

Wildtype Albumin

Annexin based Transporter Polypeptide 1: residues 41-186 (gray)

Annexin based Transporter Polypeptide 2: residues 194-344 (black)

AlbuCORE_1

AlbuCORE_2

AlbuCORE_3

AlbuCORE_4

AlbuCORE_6

AlbuCORE_7

AlbuCORE_9

AlbuCORE_13

ABH2

ABH1

POST-BLUE SEPHAROSE

| Measured (Da) | Theoretical (Da) | Delta (Da) |
|---|---|---|
| 66,620 | 66,470 | +150 |

| Measured (Da) | Theoretical (Da) | Delta (Da) |
|---|---|---|
| 66,100 | 65,880 | +220 |
| 65,985 | 65,880 | +105 |

Anti-CD19 x CD3

SEQUENCE LISTING

<160> NUMBER OF SEQ ID NOS: 189

<210> SEQ ID NO 1
<211> LENGTH: 614
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Asp Ala His
20 25 30

Lys Ser Glu Val Ala His Arg Phe Lys Asp Leu Gly Glu Glu Asn Phe
35 40 45

Lys Ala Leu Val Leu Ile Ala Phe Ala Gln Tyr Leu Gln Gln Cys Pro
50 55 60

Phe Glu Asp His Val Lys Leu Val Asn Glu Val Thr Glu Phe Ala Lys
65 70 75 80

Thr Cys Val Ala Asp Glu Ser Ala Glu Asn Cys Asp Lys Ser Leu His
85 90 95

Thr Leu Phe Gly Asp Lys Leu Cys Thr Val Ala Thr Leu Arg Glu Thr
100 105 110

Tyr Gly Glu Met Ala Asp Cys Cys Ala Lys Gln Glu Pro Glu Arg Asn
115 120 125

Glu Cys Phe Leu Gln His Lys Asp Asp Asn Pro Asn Leu Pro Arg Leu
130 135 140

Val Arg Pro Glu Val Asp Val Met Cys Thr Ala Phe His Asp Asn Glu
145 150 155 160

Glu Thr Phe Leu Lys Lys Tyr Leu Tyr Glu Ile Ala Arg Arg His Pro
165 170 175

Tyr Phe Tyr Ala Pro Glu Leu Leu Phe Phe Ala Lys Arg Tyr Lys Ala
180 185 190

Ala Phe Thr Glu Cys Cys Gln Ala Ala Asp Lys Ala Ala Cys Leu Leu
195 200 205

Pro Lys Leu Asp Glu Leu Arg Asp Glu Gly Lys Ala Ser Ser Ala Lys
210 215 220

Gln Arg Leu Lys Cys Ala Ser Leu Gln Lys Phe Gly Glu Arg Ala Phe
225 230 235 240

-continued

```
Lys Ala Trp Ala Val Ala Arg Leu Ser Gln Arg Phe Pro Lys Ala Glu
                245                 250                 255

Phe Ala Glu Val Ser Lys Leu Val Thr Asp Leu Thr Lys Val His Thr
            260                 265                 270

Glu Cys Cys His Gly Asp Leu Leu Glu Cys Ala Asp Asp Arg Ala Asp
        275                 280                 285

Leu Ala Lys Tyr Ile Cys Glu Asn Gln Asp Ser Ile Ser Ser Lys Leu
    290                 295                 300

Lys Glu Cys Cys Glu Lys Pro Leu Leu Glu Lys Ser His Cys Ile Ala
305                 310                 315                 320

Glu Val Glu Asn Asp Glu Met Pro Ala Asp Leu Pro Ser Leu Ala Ala
                325                 330                 335

Asp Phe Val Glu Ser Lys Asp Val Cys Lys Asn Tyr Ala Glu Ala Lys
            340                 345                 350

Asp Val Phe Leu Gly Met Phe Leu Tyr Glu Tyr Ala Arg Arg His Pro
        355                 360                 365

Asp Tyr Ser Val Val Leu Leu Leu Arg Leu Ala Lys Thr Tyr Glu Thr
    370                 375                 380

Thr Leu Glu Lys Cys Cys Ala Ala Ala Asp Pro His Glu Cys Tyr Ala
385                 390                 395                 400

Lys Val Phe Asp Glu Phe Lys Pro Leu Val Glu Glu Pro Gln Asn Leu
                405                 410                 415

Ile Lys Gln Asn Cys Glu Leu Phe Glu Gln Leu Gly Glu Tyr Lys Phe
            420                 425                 430

Gln Asn Ala Leu Leu Val Arg Tyr Thr Lys Lys Val Pro Gln Val Ser
        435                 440                 445

Thr Pro Thr Leu Val Glu Val Ser Arg Asn Leu Gly Lys Val Gly Ser
    450                 455                 460

Lys Cys Cys Lys His Pro Glu Ala Lys Arg Met Pro Cys Ala Glu Asp
465                 470                 475                 480

Tyr Leu Ser Val Val Leu Asn Gln Leu Cys Val Leu His Glu Lys Thr
                485                 490                 495

Pro Val Ser Asp Arg Val Thr Lys Cys Cys Thr Glu Ser Leu Val Asn
            500                 505                 510

Arg Arg Pro Cys Phe Ser Ala Leu Glu Val Asp Glu Thr Tyr Val Pro
        515                 520                 525

Lys Glu Phe Asn Ala Glu Thr Phe Thr Phe His Ala Asp Ile Cys Thr
    530                 535                 540

Leu Ser Glu Lys Glu Arg Gln Ile Lys Lys Gln Thr Ala Leu Val Glu
545                 550                 555                 560

Leu Val Lys His Lys Pro Lys Ala Thr Lys Glu Gln Leu Lys Ala Val
                565                 570                 575

Met Asp Asp Phe Ala Ala Phe Val Glu Lys Cys Cys Lys Ala Asp Asp
            580                 585                 590

Lys Glu Thr Cys Phe Ala Glu Glu Gly Lys Lys Leu Val Ala Ala Ser
        595                 600                 605

Gln Ala Ala Leu Gly Leu
    610
```

<210> SEQ ID NO 2
<211> LENGTH: 293
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 2

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Cys Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

Cys Leu Leu Pro Lys Leu Asp Glu Leu Arg Asp Glu Gly Lys Ala Ser
180 185 190

Ser Ala Lys Gln Arg Leu Lys Cys Ala Ser Leu Gln Lys Phe Gly Glu
195 200 205

Arg Ala Phe Lys Ala Trp Ala Val Ala Arg Leu Ser Gln Arg Phe Pro
210 215 220

Lys Ala Glu Phe Ala Glu Val Ser Lys Leu Val Thr Asp Leu Thr Lys
225 230 235 240

Val His Thr Glu Cys Cys His Gly Asp Leu Leu Glu Cys Ala Asp Asp
245 250 255

Arg Ala Asp Leu Ala Lys Tyr Ile Cys Glu Asn Gln Asp Ser Ile Ser
260 265 270

Ser Lys Leu Lys Glu Cys Cys Glu Lys Pro Leu Leu Glu Lys Ser His
275 280 285

Cys Ile Ala Glu Val
290

<210> SEQ ID NO 3
<211> LENGTH: 282
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

Ser Leu Ala Ala Asp Phe Val Glu Ser Lys Asp Val Cys Lys Asn Tyr
1 5 10 15

Ala Glu Ala Lys Asp Val Phe Leu Gly Met Phe Leu Tyr Glu Tyr Ala
20 25 30

-continued

```
Arg Arg His Pro Asp Tyr Ser Val Val Leu Leu Leu Arg Leu Ala Lys
        35                  40                  45

Thr Tyr Glu Thr Thr Leu Glu Lys Cys Cys Ala Ala Ala Asp Pro His
    50                  55                  60

Glu Cys Tyr Ala Lys Val Phe Asp Glu Phe Lys Pro Leu Val Glu Glu
65                  70                  75                  80

Pro Gln Asn Leu Ile Lys Gln Asn Cys Glu Leu Phe Glu Gln Leu Gly
                85                  90                  95

Glu Tyr Lys Phe Gln Asn Ala Leu Leu Val Arg Tyr Thr Lys Lys Val
            100                 105                 110

Pro Gln Val Ser Thr Pro Thr Leu Val Glu Val Ser Arg Asn Leu Gly
        115                 120                 125

Lys Val Gly Ser Lys Cys Cys Lys His Pro Glu Ala Lys Arg Met Pro
    130                 135                 140

Cys Ala Glu Asp Tyr Leu Ser Val Val Leu Asn Gln Leu Cys Val Leu
145                 150                 155                 160

His Glu Lys Thr Pro Val Ser Asp Arg Val Thr Lys Cys Cys Thr Glu
                165                 170                 175

Ser Leu Val Asn Arg Arg Pro Cys Phe Ser Ala Leu Glu Val Asp Glu
            180                 185                 190

Thr Tyr Val Pro Lys Glu Phe Asn Ala Glu Thr Phe Thr Phe His Ala
        195                 200                 205

Asp Ile Cys Thr Leu Ser Glu Lys Glu Arg Gln Ile Lys Lys Gln Thr
    210                 215                 220

Ala Leu Val Glu Leu Val Lys His Lys Pro Lys Ala Thr Lys Glu Gln
225                 230                 235                 240

Leu Lys Ala Val Met Asp Asp Phe Ala Ala Phe Val Glu Lys Cys Cys
                245                 250                 255

Lys Ala Asp Asp Lys Glu Thr Cys Phe Ala Glu Glu Gly Lys Lys Leu
            260                 265                 270

Val Ala Ala Ser Gln Ala Ala Leu Gly Leu
        275                 280
```

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly
            20                  25
```

<210> SEQ ID NO 5
<211> LENGTH: 1845
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
gaattcgcca ctatggctgt gatggcccct aggaccctgg tgctgctgct gtccggagct     60

ctggctctga ctcagacctg ggctggagat gcacacaaga gtgaggttgc tcatcggttt    120
```

aaagatttgg gagaagaaaa tttcaaagcc ttggtgttga ttgcctttgc tcagtatctt 180
cagcagtgtc catttgaaga tcatgtaaaa ttagtgaatg aagtaactga atttgcaaaa 240
acatgtgttg ctgatgagtc agctgaaaat tgtgacaaat cacttcatac cctttttgga 300
gacaaattat gcacagttgc aactcttcgt gaaacctatg gtgaaatggc tgactgctgt 360
gcaaaacaag aacctgagag aaatgaatgc ttcttgcaac acaaagatga caacccaaac 420
ctcccccgat tggtgagacc agaggttgat gtgatgtgca ctgcttttca tgacaatgaa 480
gagacatttt tgaaaaaata cttatatgaa attgccagaa gacatcctta cttttatgcc 540
ccggaactcc ttttctttgc taaaaggtat aaagctgctt ttacagaatg ttgccaagct 600
gctgataaag ctgcctgcct gttgccaaag ctcgatgaac ttcgggatga agggaaggct 660
tcgtctgcca aacagagact caagtgtgcc agtctccaaa aatttggaga aagagctttc 720
aaagcatggg cagtagctcg cctgagccag agatttccca aagctgagtt tgcagaagtt 780
tccaagttag tgacagatct taccaaagtc cacacggaat gctgccatgg agatctgctt 840
gaatgtgctg atgacagggc ggaccttgcc aagtatatct gtgaaaatca agattcgatc 900
tccagtaaac tgaaggaatg ctgtgaaaaa cctctgttgg aaaaatccca ctgcattgcc 960
gaagtggaaa atgatgagat gcctgctgac ttgccttcat tagctgctga ttttgttgaa 1020
agtaaggatg tttgcaaaaa ctatgctgag gcaaaggatg tcttcctggg catgtttttg 1080
tatgaatatg caagaaggca tcctgattac tctgtcgtgc tgctgctgag acttgccaag 1140
acatatgaaa ccactctaga gaagtgctgt gccgctgcag atcctcatga atgctatgcc 1200
aaagtgttcg atgaatttaa acctcttgtg gaagagcctc agaatttaat caaacaaaat 1260
tgtgagcttt ttgagcagct tggagagtac aaattccaga atgcgctatt agttcgttac 1320
accaagaaag taccccaagt gtcaactcca actcttgtag aggtctcaag aaacctagga 1380
aaagtgggca gcaaatgttg taaacatcct gaagcaaaaa gaatgccctg tgcagaagac 1440
tatctatccg tggtcctgaa ccagttatgt gtgttgcatg agaaaacgcc agtaagtgac 1500
agagtcacca aatgctgcac agaatccttg gtgaacaggc gaccatgctt ttcagctctg 1560
gaagtcgatg aaacatacgt tcccaaagag tttaatgctg aaacattcac cttccatgca 1620
gatatatgca cactttctga gaaggagaga caaatcaaga aacaaactgc acttgttgag 1680
ctcgtgaaac acaagcccaa ggcaacaaaa gagcaactga aagctgttat ggatgatttc 1740
gcagcttttg tagagaagtg ctgcaaggct gacgataagg agacctgctt tgccgaggag 1800
ggtaaaaaac ttgttgctgc aagtcaagct gccttaggct tatga 1845

<210> SEQ ID NO 6
<211> LENGTH: 882
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
gatgcacaca agagtgaggt tgctcatcgg tttaaagatt tgggagaaga aaatttcaaa 60
gccttggtgt tgattgcctt tgctcagtat cttcagcagt gtccatttga agatcatgta 120
aaattagtga atgaagtaac tgaatttgca aaaacatgtg ttgctgatga gtcagctgaa 180
aattgtgaca aatcacttca taccctttt ggagacaaat tatgcacagt tgcaactctt 240
cgtgaaacct atggtgaaat ggctgactgc tgtgcaaaac aagaacctga gagaaatgaa 300

-continued

```
tgcttcttgc aacacaaaga tgacaaccca aacctccccc gattggtgag accagaggtt    360

gatgtgatgt gcactgcttt tcatgacaat gaagagacat ttttgaaaaa atacttatat    420

gaaattgcca gaagacatcc ttacttttat gccccggaac tcctttttctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgt ga                       882
```

<210> SEQ ID NO 7
<211> LENGTH: 849
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
tcattagctg ctgattttgt tgaaagtaag gatgtttgca aaaactatgc tgaggcaaag     60

gatgtcttcc tgggcatgtt tttgtatgaa tatgcaagaa ggcatcctga ttactctgtc    120

gtgctgctgc tgagacttgc caagacatat gaaaccactc tagagaagtg ctgtgccgct    180

gcagatcctc atgaatgcta tgccaaagtg ttcgatgaat ttaaacctct tgtggaagag    240

cctcagaatt taatcaaaca aaattgtgag ctttttgagc agcttggaga gtacaaattc    300

cagaatgcgc tattagttcg ttacaccaag aaagtacccc aagtgtcaac tccaactctt    360

gtagaggtct caagaaacct aggaaaagtg ggcagcaaat gttgtaaaca tcctgaagca    420

aaaagaatgc cctgtgcaga agactatcta tccgtggtcc tgaaccagtt atgtgtgttg    480

catgagaaaa cgccagtaag tgacagagtc accaaatgct gcacagaatc cttggtgaac    540

aggcgaccat gcttttcagc tctggaagtc gatgaaacat acgttcccaa agagtttaat    600

gctgaaacat tcaccttcca tgcagatata tgcacacttt ctgagaagga gagacaaatc    660

aagaaacaaa ctgcacttgt tgagctcgtg aaacacaagc ccaaggcaac aaaagagcaa    720

ctgaaagctg ttatggatga tttcgcagct tttgtagaga agtgctgcaa ggctgacgat    780

aaggagacct gctttgccga ggagggtaaa aaacttgttg ctgcaagtca agctgcctta    840

ggcttatga                                                            849
```

<210> SEQ ID NO 8
<211> LENGTH: 337
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30
```

-continued

```
Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Ala
```

<210> SEQ ID NO 9
<211> LENGTH: 1014
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
gatgcacaca agagtgaggt tgctcatcgg tttaaagatt tgggagaaga aaatttcaaa      60

gccttggtgt tgattgcctt tgctcagtat cttcagcagt gtccatttga agatcatgta     120

aaattagtga atgaagtaac tgaatttgca aaaacatgtg ttgctgatga gtcagctgaa     180

aattgtgaca aatcacttca tacccttttt ggagacaaat tatgcacagt tgcaactctt     240

cgtgaaacct atggtgaaat ggctgactgc tgtgcaaaac aagaacctga gagaaatgaa     300
```

```
tgcttcttgc aacacaaaga tgacaaccca aacctccccc gattggtgag accagaggtt    360

gatgtgatgt gcactgcttt tcatgacaat gaagagacat ttttgaaaaa atacttatat    420

gaaattgcca gaagacatcc ttacttttat gccccggaac tcctttcctt tgctaaaagg    480

tataaagctg cttttacaga atgttgccaa gctgctgata aagctgcctg cctgttgcca    540

aagctcgatg aacttcggga tgaagggaag gcttcgtctg ccaaacagag actcaagtgt    600

gccagtctcc aaaaatttgg agaaagagct ttcaaagcat gggcagtagc tcgcctgagc    660

cagagatttc ccaaagctga gtttgcagaa gtttccaagt tagtgacaga tcttaccaaa    720

gtccacacgg aatgctgcca tggagatctg cttgaatgtg ctgatgacag ggcggacctt    780

gccaagtata tctgtgaaaa tcaagattcg atctccagta aactgaagga atgctgtgaa    840

aaacctctgt tggaaaaatc ccactgcatt gccgaagtgg aaaatgatga gatgcctgct    900

gacttgcctt cattagctgc tgattttgtt gaaagtaagg atgtttgcaa aaactatgct    960

gaggcaaagg atgtcttcct gggcatgttt ttgtatgaat atgcaagagc atga         1014


<210> SEQ ID NO 10
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Val Val Leu Leu Leu Arg Leu Ala Lys Thr Tyr Glu Thr Thr Leu
1               5                   10                  15

Glu Lys Cys Cys Ala Ala Ala Asp Pro His Glu Cys Tyr Ala Lys Val
            20                  25                  30

Phe Asp Glu Phe Lys Pro Leu Val Glu Glu Pro Gln Asn Leu Ile Lys
        35                  40                  45

Gln Asn Cys Glu Leu Phe Glu Gln Leu Gly Glu Tyr Lys Phe Gln Asn
    50                  55                  60

Ala Leu Leu Val Arg Tyr Thr Lys Lys Val Pro Gln Val Ser Thr Pro
65                  70                  75                  80

Thr Leu Val Glu Val Ser Arg Asn Leu Gly Lys Val Gly Ser Lys Cys
                85                  90                  95

Cys Lys His Pro Glu Ala Lys Arg Met Pro Cys Ala Glu Asp Tyr Leu
            100                 105                 110

Ser Val Val Leu Asn Gln Leu Cys Val Leu His Glu Lys Thr Pro Val
        115                 120                 125

Ser Asp Arg Val Thr Lys Cys Cys Thr Glu Ser Leu Val Asn Arg Arg
    130                 135                 140

Pro Cys Phe Ser Ala Leu Glu Val Asp Glu Thr Tyr Val Pro Lys Glu
145                 150                 155                 160

Phe Asn Ala Glu Thr Phe Thr Phe His Ala Asp Ile Cys Thr Leu Ser
                165                 170                 175

Glu Lys Glu Arg Gln Ile Lys Lys Gln Thr Ala Leu Val Glu Leu Val
            180                 185                 190

Lys His Lys Pro Lys Ala Thr Lys Glu Gln Leu Lys Ala Val Met Asp
        195                 200                 205

Asp Phe Ala Ala Phe Val Glu Lys Cys Cys Lys Ala Asp Asp Lys Glu
    210                 215                 220

Thr Cys Phe Ala Glu Glu Gly Lys Lys Leu Val Ala Ala Ser Gln Ala
```

225 230 235 240

Ala Leu Gly Leu

<210> SEQ ID NO 11
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
tctgtcgtgc tgctgctgag acttgccaag acatatgaaa ccactctaga gaagtgctgt 60
gccgctgcag atcctcatga atgctatgcc aaagtgttcg atgaatttaa acctcttgtg 120
gaagagcctc agaatttaat caaacaaaat tgtgagcttt ttgagcagct tggagagtac 180
aaattccaga atgcgctatt agttcgttac accaagaaag taccccaagt gtcaactcca 240
actcttgtag aggtctcaag aaacctagga aaagtgggca gcaaatgttg taaacatcct 300
gaagcaaaaa gaatgccctg tgcagaagac tatctatccg tggtcctgaa ccagttatgt 360
gtgttgcatg agaaaacgcc agtaagtgac agagtcacca aatgctgcac agaatccttg 420
gtgaacaggc gaccatgctt ttcagctctg gaagtcgatg aaacatacgt tcccaaagag 480
tttaatgctg aaacattcac cttccatgca gatatatgca cactttctga gaaggagaga 540
caaatcaaga aacaaactgc acttgttgag ctcgtgaaac acaagcccaa ggcaacaaaa 600
gagcaactga aagctgttat ggatgatttc gcagcttttg tagagaagtg ctgcaaggct 660
gacgataagg agacctgctt tgccgaggag ggtaaaaaac ttgttgctgc aagtcaagct 720
gccttaggct tatga 735

<210> SEQ ID NO 12
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

His Ala Glu Gly Thr Phe Thr Ser Asp Val Ser Ser Tyr Leu Glu Gly
1 5 10 15

Gln Ala Ala Lys Glu Phe Ile Ala Trp Leu Val Lys Gly Arg Gly
20 25 30

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

His Ser Gln Gly Thr Phe Thr Ser Asp Tyr Ser Lys Tyr Leu Asp Ser
1 5 10 15

Arg Arg Ala Gln Asp Phe Val Gln Trp Leu Met Asn Thr
20 25

<210> SEQ ID NO 14
<211> LENGTH: 314
<212> TYPE: PRT

<213> ORGANISM: Homo sapiens

<400> SEQUENCE: 14

```
Gly Ser Ala Val Ser Pro Tyr Pro Thr Phe Asn Pro Ser Ser Asp Val
1               5                   10                  15

Ala Ala Leu His Lys Ala Ile Met Val Lys Gly Val Asp Glu Ala Thr
            20                  25                  30

Ile Ile Asp Ile Leu Thr Lys Arg Asn Asn Ala Gln Arg Gln Gln Ile
        35                  40                  45

Lys Ala Ala Tyr Leu Gln Glu Thr Gly Lys Pro Leu Asp Glu Thr Leu
    50                  55                  60

Lys Lys Ala Leu Thr Gly His Leu Glu Glu Val Val Leu Ala Leu Leu
65                  70                  75                  80

Lys Thr Pro Ala Gln Phe Asp Ala Asp Glu Leu Arg Ala Ala Met Lys
                85                  90                  95

Gly Leu Gly Thr Asp Glu Asp Thr Leu Ile Glu Ile Leu Ala Ser Arg
            100                 105                 110

Thr Asn Lys Glu Ile Arg Asp Ile Asn Arg Val Tyr Arg Glu Glu Leu
        115                 120                 125

Lys Arg Asp Leu Ala Lys Asp Ile Thr Ser Asp Thr Ser Gly Asp Phe
    130                 135                 140

Arg Asn Ala Leu Leu Ser Leu Ala Lys Gly Asp Arg Ser Glu Asp Phe
145                 150                 155                 160

Gly Val Asn Glu Asp Leu Ala Asp Ser Asp Ala Arg Ala Leu Tyr Glu
                165                 170                 175

Ala Gly Glu Arg Arg Lys Gly Thr Asp Val Asn Val Phe Asn Thr Ile
            180                 185                 190

Leu Thr Thr Arg Ser Tyr Pro Gln Leu Arg Arg Val Phe Gln Lys Tyr
        195                 200                 205

Thr Lys Tyr Ser Lys His Asp Met Asn Lys Val Leu Asp Leu Glu Leu
    210                 215                 220

Lys Gly Asp Ile Glu Lys Cys Leu Thr Ala Ile Val Lys Cys Ala Thr
225                 230                 235                 240

Ser Lys Pro Ala Phe Phe Ala Glu Lys Leu His Gln Ala Met Lys Gly
                245                 250                 255

Val Gly Thr Arg His Lys Ala Leu Ile Arg Ile Met Val Ser Arg Ser
            260                 265                 270

Glu Ile Asp Met Asn Asp Ile Lys Ala Phe Tyr Gln Lys Met Tyr Gly
        275                 280                 285

Ile Ser Leu Cys Gln Ala Ile Leu Asp Glu Thr Lys Gly Asp Tyr Glu
    290                 295                 300

Lys Ile Leu Val Ala Leu Cys Gly Gly Asn
305                 310
```

<210> SEQ ID NO 15
<211> LENGTH: 153
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Ser Ala Val Ser Pro Tyr Pro Thr Phe Asn Pro Ser Ser Asp Val Ala
1               5                   10                  15

Ala Leu His Lys Ala Ile Met Val Lys Gly Val Asp Glu Ala Thr Ile
```

```
            20                  25                  30

Ile Asp Ile Leu Thr Lys Arg Asn Asn Ala Gln Arg Gln Gln Ile Lys
        35                  40                  45

Ala Ala Tyr Leu Gln Glu Thr Gly Lys Pro Leu Asp Glu Thr Leu Lys
    50                  55                  60

Lys Ala Leu Thr Gly His Leu Glu Glu Val Val Leu Ala Leu Leu Lys
65                  70                  75                  80

Thr Pro Ala Gln Phe Asp Ala Asp Glu Leu Arg Ala Ala Met Lys Gly
                85                  90                  95

Leu Gly Thr Asp Glu Asp Thr Leu Ile Glu Ile Leu Ala Ser Arg Thr
            100                 105                 110

Asn Lys Glu Ile Arg Asp Ile Asn Arg Val Tyr Arg Glu Glu Leu Lys
        115                 120                 125

Arg Asp Leu Ala Lys Asp Ile Thr Ser Asp Thr Ser Gly Asp Phe Arg
    130                 135                 140

Asn Ala Leu Leu Ser Leu Ala Lys Gly
145                 150
```

<210> SEQ ID NO 16
<211> LENGTH: 154
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

```
Gly Val Asn Glu Asp Leu Ala Asp Ser Asp Ala Arg Ala Leu Tyr Glu
1               5                   10                  15

Ala Gly Glu Arg Arg Lys Gly Thr Asp Val Asn Val Phe Asn Thr Ile
            20                  25                  30

Leu Thr Thr Arg Ser Tyr Pro Gln Leu Arg Arg Val Phe Gln Lys Tyr
        35                  40                  45

Thr Lys Tyr Ser Lys His Asp Met Asn Lys Val Leu Asp Leu Glu Leu
    50                  55                  60

Lys Gly Asp Ile Glu Lys Cys Leu Thr Ala Ile Val Lys Cys Ala Thr
65                  70                  75                  80

Ser Lys Pro Ala Phe Phe Ala Glu Lys Leu His Gln Ala Met Lys Gly
                85                  90                  95

Val Gly Thr Arg His Lys Ala Leu Ile Arg Ile Met Val Ser Arg Ser
            100                 105                 110

Glu Ile Asp Met Asn Asp Ile Lys Ala Phe Tyr Gln Lys Met Tyr Gly
        115                 120                 125

Ile Ser Leu Cys Gln Ala Ile Leu Asp Glu Thr Lys Gly Asp Tyr Glu
    130                 135                 140

Lys Ile Leu Val Ala Leu Cys Gly Gly Asn
145                 150
```

<210> SEQ ID NO 17
<211> LENGTH: 348
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 17

```
Met Arg Leu Ala Val Gly Ala Leu Leu Val Cys Ala Val Leu Gly Leu
```

```
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly
            340                 345
```

<210> SEQ ID NO 18
<211> LENGTH: 342
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

```
Glu Cys Lys Pro Val Lys Trp Cys Ala Leu Ser His His Glu Arg Leu
1               5                   10                  15
```

```
Lys Cys Asp Glu Trp Ser Val Asn Ser Val Gly Lys Ile Glu Cys Val
            20                  25                  30

Ser Ala Glu Thr Thr Glu Asp Cys Ile Ala Lys Ile Met Asn Gly Glu
        35                  40                  45

Ala Asp Ala Met Ser Leu Asp Gly Gly Phe Val Tyr Ile Ala Gly Lys
    50                  55                  60

Cys Gly Leu Val Pro Val Leu Ala Glu Asn Tyr Asn Lys Ser Asp Asn
65                  70                  75                  80

Cys Glu Asp Thr Pro Glu Ala Gly Tyr Phe Ala Val Ala Val Val Lys
                85                  90                  95

Lys Ser Ala Ser Asp Leu Thr Trp Asp Asn Leu Lys Gly Lys Lys Ser
            100                 105                 110

Cys His Thr Ala Val Gly Arg Thr Ala Gly Trp Asn Ile Pro Met Gly
        115                 120                 125

Leu Leu Tyr Asn Lys Ile Asn His Cys Arg Phe Asp Glu Phe Phe Ser
    130                 135                 140

Glu Gly Cys Ala Pro Gly Ser Lys Lys Asp Ser Ser Leu Cys Lys Leu
145                 150                 155                 160

Cys Met Gly Ser Gly Leu Asn Leu Cys Glu Pro Asn Asn Lys Glu Gly
                165                 170                 175

Tyr Tyr Gly Tyr Thr Gly Ala Phe Arg Cys Leu Val Glu Lys Gly Asp
            180                 185                 190

Val Ala Phe Val Lys His Gln Thr Val Pro Gln Asn Thr Gly Gly Lys
        195                 200                 205

Asn Pro Asp Pro Trp Ala Lys Asn Leu Asn Glu Lys Asp Tyr Glu Leu
    210                 215                 220

Leu Cys Leu Asp Gly Thr Arg Lys Pro Val Glu Glu Tyr Ala Asn Cys
225                 230                 235                 240

His Leu Ala Arg Ala Pro Asn His Ala Val Val Thr Arg Lys Asp Lys
                245                 250                 255

Glu Ala Cys Val His Lys Ile Leu Arg Gln Gln Gln His Leu Phe Gly
            260                 265                 270

Ser Asn Val Thr Asp Cys Ser Gly Asn Phe Cys Leu Phe Arg Ser Glu
        275                 280                 285

Thr Lys Asp Leu Leu Phe Arg Asp Asp Thr Val Cys Leu Ala Lys Leu
    290                 295                 300

His Asp Arg Asn Thr Tyr Glu Lys Tyr Leu Gly Glu Glu Tyr Val Lys
305                 310                 315                 320

Ala Val Gly Asn Leu Arg Lys Cys Ser Thr Ser Ser Leu Leu Glu Ala
                325                 330                 335

Cys Thr Phe Arg Arg Pro
            340


<210> SEQ ID NO 19
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30
```

Glu Val Ala His Arg Phe Lys Asp Leu Gly Glu Glu Asn Phe Lys Ala
35 40 45

Leu Val Leu Ile Ala Phe Ala Gln Tyr Leu Gln Gln Cys Pro Phe Glu
50 55 60

Asp His Val Lys Leu Val Asn Glu Val Thr Glu Phe Ala Lys Thr Cys
65 70 75 80

Val Ala Asp Glu Ser Ala Glu Asn Cys Asp Lys Ser Leu His Thr Leu
85 90 95

Phe Gly Asp Lys Leu Cys Thr Val Ala Thr Leu Arg Glu Thr Tyr Gly
100 105 110

Glu Met Ala Asp Cys Cys Ala Lys Gln Glu Pro Glu Arg Asn Glu Cys
115 120 125

Phe Leu Gln His Lys Asp Asp Asn Pro Asn Leu Pro Arg Leu Val Arg
130 135 140

Pro Glu Val Asp Val Met Cys Thr Ala Phe His Asp Asn Glu Glu Thr
145 150 155 160

Phe Leu Lys Lys Tyr Leu Tyr Glu Ile Ala Arg Arg His Pro Tyr Phe
165 170 175

Tyr Ala Pro Glu Leu Leu Phe Phe Ala Lys Arg Tyr Lys Ala Ala Phe
180 185 190

Thr Glu Cys Cys Gln Ala Ala Asp Lys Ala Ala Cys Leu Leu Pro Lys
195 200 205

Leu Asp Glu Leu Arg Asp Glu Gly Lys Ala Ser Ser Ala Lys Gln Arg
210 215 220

Leu Lys Cys Ala Ser Leu Gln Lys Phe Gly Glu Arg Ala Phe Lys Ala
225 230 235 240

Trp Ala Val Cys Arg Leu Ser Gln Arg Phe Pro Lys Ala Glu Phe Ala
245 250 255

Glu Val Ser Lys Leu Val Thr Asp Leu Thr Lys Val His Thr Glu Cys
260 265 270

Cys His Gly Asp Leu Leu Glu Cys Ala Asp Asp Arg Ala Asp Leu Ala
275 280 285

Lys Tyr Ile Cys Glu Asn Gln Asp Ser Ile Ser Ser Lys Leu Lys Glu
290 295 300

Cys Cys Glu Lys Pro Leu Leu Glu Lys Ser His Cys Ile Ala Glu Val
305 310 315 320

Glu Asn Asp Glu Met Pro Ala Asp Leu Pro Ser Leu Ala Ala Asp Phe
325 330 335

Val Glu Ser Lys Asp Val Cys Lys Asn Tyr Ala Glu Ala Lys Asp Val
340 345 350

Phe Leu Gly Met Phe Leu Tyr Glu Tyr Ala Arg Ala
355 360

<210> SEQ ID NO 20
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Ala Thr Met Ala Val Met Ala Pro Arg Thr Leu Val Leu Leu Leu Ser
1 5 10 15

Gly Ala Leu Ala Leu Thr Gln Thr Trp Ala Gly Ser Cys Val Leu Leu

```
            20                  25                  30

Leu Arg Leu Ala Lys Thr Tyr Glu Thr Thr Leu Glu Lys Cys Cys Ala
        35                  40                  45

Ala Ala Asp Pro His Glu Cys Tyr Ala Lys Val Phe Asp Glu Phe Lys
    50                  55                  60

Pro Leu Val Glu Glu Pro Gln Asn Leu Ile Lys Gln Asn Cys Glu Leu
65                  70                  75                  80

Phe Glu Gln Leu Gly Glu Tyr Lys Phe Gln Asn Ala Leu Leu Val Arg
                85                  90                  95

Tyr Thr Lys Lys Val Pro Gln Val Ser Thr Pro Thr Leu Val Glu Val
            100                 105                 110

Ser Arg Asn Leu Gly Lys Val Gly Ser Lys Cys Cys Lys His Pro Glu
        115                 120                 125

Ala Lys Arg Met Pro Cys Ala Glu Asp Tyr Leu Ser Val Val Leu Asn
    130                 135                 140

Gln Leu Cys Val Leu His Glu Lys Thr Pro Val Ser Asp Arg Val Thr
145                 150                 155                 160

Lys Cys Cys Thr Glu Ser Leu Val Asn Arg Arg Pro Cys Phe Ser Ala
                165                 170                 175

Leu Glu Val Asp Glu Thr Tyr Val Pro Lys Glu Phe Asn Ala Glu Thr
            180                 185                 190

Phe Thr Phe His Ala Asp Ile Cys Thr Leu Ser Glu Lys Glu Arg Gln
        195                 200                 205

Ile Lys Lys Gln Thr Ala Leu Val Glu Leu Val Lys His Lys Pro Lys
    210                 215                 220

Ala Thr Lys Glu Gln Leu Lys Ala Val Met Asp Asp Phe Ala Ala Phe
225                 230                 235                 240

Val Glu Lys Cys Cys Lys Ala Asp Asp Lys Glu Thr Cys Phe Ala Glu
                245                 250                 255

Glu Gly Lys Lys Leu Val Ala Ala Ser Gln Ala Ala Leu Gly Leu
            260                 265                 270


<210> SEQ ID NO 21
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110
```

```
Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Cys Tyr Glu Tyr Ala Arg Ala
        355                 360


<210> SEQ ID NO 22
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Val Val Leu Leu
            20                  25                  30

Leu Arg Leu Cys Lys Thr Tyr Glu Thr Thr Leu Glu Lys Cys Cys Ala
        35                  40                  45

Ala Ala Asp Pro His Glu Cys Tyr Ala Lys Val Phe Asp Glu Phe Lys
    50                  55                  60

Pro Leu Val Glu Glu Pro Gln Asn Leu Ile Lys Gln Asn Cys Glu Leu
65                  70                  75                  80

Phe Glu Gln Leu Gly Glu Tyr Lys Phe Gln Asn Ala Leu Leu Val Arg
                85                  90                  95

Tyr Thr Lys Lys Val Pro Gln Val Ser Thr Pro Thr Leu Val Glu Val
            100                 105                 110
```

```
Ser Arg Asn Leu Gly Lys Val Gly Ser Lys Cys Cys Lys His Pro Glu
        115                 120                 125

Ala Lys Arg Met Pro Cys Ala Glu Asp Tyr Leu Ser Val Val Leu Asn
    130                 135                 140

Gln Leu Cys Val Leu His Glu Lys Thr Pro Val Ser Asp Arg Val Thr
145                 150                 155                 160

Lys Cys Cys Thr Glu Ser Leu Val Asn Arg Arg Pro Cys Phe Ser Ala
                165                 170                 175

Leu Glu Val Asp Glu Thr Tyr Val Pro Lys Glu Phe Asn Ala Glu Thr
            180                 185                 190

Phe Thr Phe His Ala Asp Ile Cys Thr Leu Ser Glu Lys Glu Arg Gln
        195                 200                 205

Ile Lys Lys Gln Thr Ala Leu Val Glu Leu Val Lys His Lys Pro Lys
    210                 215                 220

Ala Thr Lys Glu Gln Leu Lys Ala Val Met Asp Asp Phe Ala Ala Phe
225                 230                 235                 240

Val Glu Lys Cys Cys Lys Ala Asp Asp Lys Glu Thr Cys Phe Ala Glu
                245                 250                 255

Glu Gly Lys Lys Leu Val Ala Ala Ser Gln Ala Ala Leu Gly Leu
            260                 265                 270


<210> SEQ ID NO 23
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
```

```
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Cys Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Ala
        355                 360


<210> SEQ ID NO 24
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Val Val Leu Cys
            20                  25                  30

Leu Arg Leu Ala Lys Thr Tyr Glu Thr Thr Leu Glu Lys Cys Cys Ala
        35                  40                  45

Ala Ala Asp Pro His Glu Cys Tyr Ala Lys Val Phe Asp Glu Phe Lys
    50                  55                  60

Pro Leu Val Glu Glu Pro Gln Asn Leu Ile Lys Gln Asn Cys Glu Leu
65                  70                  75                  80

Phe Glu Gln Leu Gly Glu Tyr Lys Phe Gln Asn Ala Leu Leu Val Arg
                85                  90                  95

Tyr Thr Lys Lys Val Pro Gln Val Ser Thr Pro Thr Leu Val Glu Val
            100                 105                 110

Ser Arg Asn Leu Gly Lys Val Gly Ser Lys Cys Cys Lys His Pro Glu
        115                 120                 125

Ala Lys Arg Met Pro Cys Ala Glu Asp Tyr Leu Ser Val Val Leu Asn
    130                 135                 140

Gln Leu Cys Val Leu His Glu Lys Thr Pro Val Ser Asp Arg Val Thr
145                 150                 155                 160

Lys Cys Cys Thr Glu Ser Leu Val Asn Arg Arg Pro Cys Phe Ser Ala
                165                 170                 175

Leu Glu Val Asp Glu Thr Tyr Val Pro Lys Glu Phe Asn Ala Glu Thr
            180                 185                 190
```

-continued

```
Phe Thr Phe His Ala Asp Ile Cys Thr Leu Ser Glu Lys Glu Arg Gln
        195                 200                 205

Ile Lys Lys Gln Thr Ala Leu Val Glu Leu Val Lys His Lys Pro Lys
    210                 215                 220

Ala Thr Lys Glu Gln Leu Lys Ala Val Met Asp Asp Phe Ala Ala Phe
225                 230                 235                 240

Val Glu Lys Cys Cys Lys Ala Asp Asp Lys Glu Thr Cys Phe Ala Glu
                245                 250                 255

Glu Gly Lys Lys Leu Val Ala Ala Ser Gln Ala Ala Leu Gly Leu
            260                 265                 270


<210> SEQ ID NO 25
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Cys Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285
```

```
Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Ala
        355                 360


<210> SEQ ID NO 26
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Cys Val Leu Leu
            20                  25                  30

Leu Arg Leu Ala Lys Thr Tyr Glu Thr Thr Leu Glu Lys Cys Cys Ala
        35                  40                  45

Ala Ala Asp Pro His Glu Cys Tyr Ala Lys Val Phe Asp Glu Phe Lys
    50                  55                  60

Pro Leu Val Glu Glu Pro Gln Asn Leu Ile Lys Gln Asn Cys Glu Leu
65                  70                  75                  80

Phe Glu Gln Leu Gly Glu Tyr Lys Phe Gln Asn Ala Leu Leu Val Arg
                85                  90                  95

Tyr Thr Lys Lys Val Pro Gln Val Ser Thr Pro Thr Leu Val Glu Val
            100                 105                 110

Ser Arg Asn Leu Gly Lys Val Gly Ser Lys Cys Cys Lys His Pro Glu
        115                 120                 125

Ala Lys Arg Met Pro Cys Ala Glu Asp Tyr Leu Ser Val Val Leu Asn
    130                 135                 140

Gln Leu Cys Val Leu His Glu Lys Thr Pro Val Ser Asp Arg Val Thr
145                 150                 155                 160

Lys Cys Cys Thr Glu Ser Leu Val Asn Arg Arg Pro Cys Phe Ser Ala
                165                 170                 175

Leu Glu Val Asp Glu Thr Tyr Val Pro Lys Glu Phe Asn Ala Glu Thr
            180                 185                 190

Phe Thr Phe His Ala Asp Ile Cys Thr Leu Ser Glu Lys Glu Arg Gln
        195                 200                 205

Ile Lys Lys Gln Thr Ala Leu Val Glu Leu Val Lys His Lys Pro Lys
    210                 215                 220

Ala Thr Lys Glu Gln Leu Lys Ala Val Met Asp Asp Phe Ala Ala Phe
225                 230                 235                 240

Val Glu Lys Cys Cys Lys Ala Asp Asp Lys Glu Thr Cys Phe Ala Glu
                245                 250                 255

Glu Gly Lys Lys Leu Val Ala Ala Ser Gln Ala Ala Leu Gly Leu
            260                 265                 270
```

<210> SEQ ID NO 27
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Cys Arg Ala
        355                 360
```

<210> SEQ ID NO 28
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Val Val Leu Cys
            20                  25                  30

Leu Arg Leu Ala Lys Thr Tyr Glu Thr Thr Leu Glu Lys Cys Cys Ala
        35                  40                  45

Ala Ala Asp Pro His Glu Cys Tyr Ala Lys Val Phe Asp Glu Phe Lys
    50                  55                  60

Pro Leu Val Glu Glu Pro Gln Asn Leu Ile Lys Gln Asn Cys Glu Leu
65                  70                  75                  80

Phe Glu Gln Leu Gly Glu Tyr Lys Phe Gln Asn Ala Leu Leu Val Arg
                85                  90                  95

Tyr Thr Lys Lys Val Pro Gln Val Ser Thr Pro Thr Leu Val Glu Val
            100                 105                 110

Ser Arg Asn Leu Gly Lys Val Gly Ser Lys Cys Cys Lys His Pro Glu
        115                 120                 125

Ala Lys Arg Met Pro Cys Ala Glu Asp Tyr Leu Ser Val Val Leu Asn
    130                 135                 140

Gln Leu Cys Val Leu His Glu Lys Thr Pro Val Ser Asp Arg Val Thr
145                 150                 155                 160

Lys Cys Cys Thr Glu Ser Leu Val Asn Arg Arg Pro Cys Phe Ser Ala
                165                 170                 175

Leu Glu Val Asp Glu Thr Tyr Val Pro Lys Glu Phe Asn Ala Glu Thr
            180                 185                 190

Phe Thr Phe His Ala Asp Ile Cys Thr Leu Ser Glu Lys Glu Arg Gln
        195                 200                 205

Ile Lys Lys Gln Thr Ala Leu Val Glu Leu Val Lys His Lys Pro Lys
    210                 215                 220

Ala Thr Lys Glu Gln Leu Lys Ala Val Met Asp Asp Phe Ala Ala Phe
225                 230                 235                 240

Val Glu Lys Cys Cys Lys Ala Asp Asp Lys Glu Thr Cys Phe Ala Glu
                245                 250                 255

Glu Gly Lys Lys Leu Val Ala Ala Ser Gln Ala Ala Leu Gly Leu
            260                 265                 270
```

<210> SEQ ID NO 29
<211> LENGTH: 364
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30
```

-continued

```
Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Cys Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Ala
        355                 360
```

<210> SEQ ID NO 30
<211> LENGTH: 271
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Val Val Leu Leu
            20                  25                  30
```

Leu Arg Leu Ala Lys Thr Tyr Glu Thr Thr Leu Glu Lys Cys Cys Ala
35 40 45

Ala Ala Asp Pro His Glu Cys Tyr Ala Lys Val Phe Asp Glu Phe Lys
50 55 60

Pro Leu Val Glu Glu Pro Gln Asn Leu Ile Lys Gln Asn Cys Glu Leu
65 70 75 80

Phe Glu Gln Leu Gly Glu Tyr Lys Phe Gln Asn Ala Leu Leu Val Arg
85 90 95

Tyr Thr Lys Lys Val Pro Gln Val Ser Thr Pro Thr Leu Val Glu Val
100 105 110

Ser Arg Asn Leu Gly Lys Val Gly Ser Lys Cys Cys Lys His Pro Glu
115 120 125

Ala Lys Arg Met Pro Cys Ala Glu Asp Tyr Leu Ser Cys Val Leu Asn
130 135 140

Gln Leu Cys Val Leu His Glu Lys Thr Pro Val Ser Asp Arg Val Thr
145 150 155 160

Lys Cys Cys Thr Glu Ser Leu Val Asn Arg Arg Pro Cys Phe Ser Ala
165 170 175

Leu Glu Val Asp Glu Thr Tyr Val Pro Lys Glu Phe Asn Ala Glu Thr
180 185 190

Phe Thr Phe His Ala Asp Ile Cys Thr Leu Ser Glu Lys Glu Arg Gln
195 200 205

Ile Lys Lys Gln Thr Ala Leu Val Glu Leu Val Lys His Lys Pro Lys
210 215 220

Ala Thr Lys Glu Gln Leu Lys Ala Val Met Asp Asp Phe Ala Ala Phe
225 230 235 240

Val Glu Lys Cys Cys Lys Ala Asp Asp Lys Glu Thr Cys Phe Ala Glu
245 250 255

Glu Gly Lys Lys Leu Val Ala Ala Ser Gln Ala Ala Leu Gly Leu
260 265 270

<210> SEQ ID NO 31
<211> LENGTH: 320
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

Ala Thr Met Ala Val Met Ala Pro Arg Thr Leu Val Leu Leu Leu Ser
1 5 10 15

Gly Ala Leu Ala Leu Thr Gln Thr Trp Ala Gly Asp Ala His Lys Ser
20 25 30

Glu Val Ala His Arg Phe Lys Asp Leu Gly Glu Glu Asn Phe Lys Ala
35 40 45

Leu Val Leu Ile Ala Phe Ala Gln Tyr Leu Gln Gln Cys Pro Phe Glu
50 55 60

Asp His Val Lys Leu Val Asn Glu Val Thr Glu Phe Ala Lys Thr Cys
65 70 75 80

Val Ala Asp Glu Ser Ala Glu Asn Cys Asp Lys Ser Leu His Thr Leu
85 90 95

Phe Gly Asp Lys Leu Cys Thr Val Ala Thr Leu Arg Glu Thr Tyr Gly
100 105 110

Glu Met Ala Asp Cys Cys Ala Lys Gln Glu Pro Glu Arg Asn Glu Cys 115 120 125

Phe Leu Gln His Lys Asp Asp Asn Pro Asn Leu Pro Arg Leu Val Arg
130 135 140

Pro Glu Val Asp Val Met Cys Thr Ala Phe His Asp Asn Glu Glu Thr
145 150 155 160

Phe Leu Lys Lys Tyr Leu Tyr Glu Ile Ala Arg Arg His Pro Tyr Phe
165 170 175

Tyr Ala Pro Glu Leu Leu Phe Phe Ala Lys Arg Tyr Lys Ala Ala Phe
180 185 190

Thr Glu Cys Cys Gln Ala Ala Asp Lys Ala Ala Cys Leu Leu Pro Lys
195 200 205

Leu Asp Glu Leu Arg Asp Glu Gly Lys Ala Ser Ser Ala Lys Gln Arg
210 215 220

Leu Lys Cys Ala Ser Leu Gln Lys Phe Gly Glu Arg Ala Phe Lys Ala
225 230 235 240

Trp Ala Val Cys Arg Leu Ser Gln Arg Phe Pro Lys Ala Glu Phe Ala
245 250 255

Glu Val Ser Lys Leu Val Thr Asp Leu Thr Lys Val His Thr Glu Cys
260 265 270

Cys His Gly Asp Leu Leu Glu Cys Ala Asp Asp Arg Ala Asp Leu Ala
275 280 285

Lys Tyr Ile Cys Glu Asn Gln Asp Ser Ile Ser Ser Lys Leu Lys Glu
290 295 300

Cys Cys Glu Lys Pro Leu Leu Glu Lys Ser His Cys Ile Ala Glu Val
305 310 315 320

<210> SEQ ID NO 32
<211> LENGTH: 309
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

Ala Thr Met Ala Val Met Ala Pro Arg Thr Leu Val Leu Leu Leu Ser
1 5 10 15

Gly Ala Leu Ala Leu Thr Gln Thr Trp Ala Gly Ser Leu Ala Ala Asp
20 25 30

Phe Val Glu Ser Lys Asp Val Cys Lys Asn Tyr Ala Glu Ala Lys Asp
35 40 45

Val Phe Leu Gly Met Phe Leu Tyr Glu Tyr Cys Arg Arg His Pro Asp
50 55 60

Tyr Ser Val Val Leu Leu Leu Arg Leu Ala Lys Thr Tyr Glu Thr Thr
65 70 75 80

Leu Glu Lys Cys Cys Ala Ala Ala Asp Pro His Glu Cys Tyr Ala Lys
85 90 95

Val Phe Asp Glu Phe Lys Pro Leu Val Glu Glu Pro Gln Asn Leu Ile
100 105 110

Lys Gln Asn Cys Glu Leu Phe Glu Gln Leu Gly Glu Tyr Lys Phe Gln
115 120 125

Asn Ala Leu Leu Val Arg Tyr Thr Lys Lys Val Pro Gln Val Ser Thr
130 135 140

Pro Thr Leu Val Glu Val Ser Arg Asn Leu Gly Lys Val Gly Ser Lys
145 150 155 160

```
Cys Cys Lys His Pro Glu Ala Lys Arg Met Pro Cys Ala Glu Asp Tyr
                165                 170                 175

Leu Ser Val Val Leu Asn Gln Leu Cys Val Leu His Glu Lys Thr Pro
            180                 185                 190

Val Ser Asp Arg Val Thr Lys Cys Cys Thr Glu Ser Leu Val Asn Arg
        195                 200                 205

Arg Pro Cys Phe Ser Ala Leu Glu Val Asp Glu Thr Tyr Val Pro Lys
    210                 215                 220

Glu Phe Asn Ala Glu Thr Phe Thr Phe His Ala Asp Ile Cys Thr Leu
225                 230                 235                 240

Ser Glu Lys Glu Arg Gln Ile Lys Lys Gln Thr Ala Leu Val Glu Leu
                245                 250                 255

Val Lys His Lys Pro Lys Ala Thr Lys Glu Gln Leu Lys Ala Val Met
            260                 265                 270

Asp Asp Phe Ala Ala Phe Val Glu Lys Cys Cys Lys Ala Asp Asp Lys
        275                 280                 285

Glu Thr Cys Phe Ala Glu Glu Gly Lys Lys Leu Val Ala Ala Ser Gln
    290                 295                 300

Ala Ala Leu Gly Leu
305


<210> SEQ ID NO 33
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205
```

```
Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Cys Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320


<210> SEQ ID NO 34
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Leu Ala Ala Asp
            20                  25                  30

Phe Val Glu Ser Lys Asp Val Cys Lys Asn Tyr Ala Glu Ala Lys Asp
        35                  40                  45

Val Phe Leu Gly Met Phe Cys Tyr Glu Tyr Ala Arg Arg His Pro Asp
    50                  55                  60

Tyr Ser Val Val Leu Leu Leu Arg Leu Ala Lys Thr Tyr Glu Thr Thr
65                  70                  75                  80

Leu Glu Lys Cys Cys Ala Ala Ala Asp Pro His Glu Cys Tyr Ala Lys
                85                  90                  95

Val Phe Asp Glu Phe Lys Pro Leu Val Glu Glu Pro Gln Asn Leu Ile
            100                 105                 110

Lys Gln Asn Cys Glu Leu Phe Glu Gln Leu Gly Glu Tyr Lys Phe Gln
        115                 120                 125

Asn Ala Leu Leu Val Arg Tyr Thr Lys Lys Val Pro Gln Val Ser Thr
    130                 135                 140

Pro Thr Leu Val Glu Val Ser Arg Asn Leu Gly Lys Val Gly Ser Lys
145                 150                 155                 160

Cys Cys Lys His Pro Glu Ala Lys Arg Met Pro Cys Ala Glu Asp Tyr
                165                 170                 175

Leu Ser Val Val Leu Asn Gln Leu Cys Val Leu His Glu Lys Thr Pro
            180                 185                 190

Val Ser Asp Arg Val Thr Lys Cys Cys Thr Glu Ser Leu Val Asn Arg
        195                 200                 205

Arg Pro Cys Phe Ser Ala Leu Glu Val Asp Glu Thr Tyr Val Pro Lys
    210                 215                 220

Glu Phe Asn Ala Glu Thr Phe Thr Phe His Ala Asp Ile Cys Thr Leu
225                 230                 235                 240

Ser Glu Lys Glu Arg Gln Ile Lys Lys Gln Thr Ala Leu Val Glu Leu
```

```
                245                 250                 255

Val Lys His Lys Pro Lys Ala Thr Lys Glu Gln Leu Lys Ala Val Met
            260                 265                 270

Asp Asp Phe Ala Ala Phe Val Glu Lys Cys Cys Lys Ala Asp Asp Lys
        275                 280                 285

Glu Thr Cys Phe Ala Glu Glu Gly Lys Lys Leu Val Ala Ala Ser Gln
    290                 295                 300

Ala Ala Leu Gly Leu
305
```

<210> SEQ ID NO 35
<211> LENGTH: 320
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Cys Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285
```

```
Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320


<210> SEQ ID NO 36
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Leu Ala Ala Asp
            20                  25                  30

Phe Val Glu Ser Lys Asp Val Cys Lys Asn Tyr Ala Glu Ala Lys Asp
        35                  40                  45

Val Phe Leu Gly Met Phe Leu Tyr Glu Tyr Ala Arg Arg His Pro Asp
    50                  55                  60

Tyr Ser Val Val Leu Leu Leu Arg Leu Ala Lys Thr Tyr Glu Thr Thr
65                  70                  75                  80

Leu Glu Lys Cys Cys Ala Ala Ala Asp Pro His Glu Cys Tyr Ala Lys
                85                  90                  95

Val Phe Asp Glu Phe Lys Pro Leu Val Glu Glu Pro Gln Asn Leu Ile
            100                 105                 110

Lys Gln Asn Cys Glu Leu Phe Glu Gln Leu Gly Glu Tyr Lys Phe Gln
        115                 120                 125

Asn Ala Leu Leu Val Arg Tyr Thr Lys Lys Val Pro Gln Val Ser Thr
    130                 135                 140

Pro Thr Leu Val Glu Val Ser Arg Asn Leu Gly Lys Val Gly Ser Lys
145                 150                 155                 160

Cys Cys Lys His Pro Glu Ala Lys Arg Met Pro Cys Ala Glu Asp Tyr
                165                 170                 175

Leu Ser Val Val Leu Cys Gln Leu Cys Val Leu His Glu Lys Thr Pro
            180                 185                 190

Val Ser Asp Arg Val Thr Lys Cys Cys Thr Glu Ser Leu Val Asn Arg
        195                 200                 205

Arg Pro Cys Phe Ser Ala Leu Glu Val Asp Glu Thr Tyr Val Pro Lys
    210                 215                 220

Glu Phe Asn Ala Glu Thr Phe Thr Phe His Ala Asp Ile Cys Thr Leu
225                 230                 235                 240

Ser Glu Lys Glu Arg Gln Ile Lys Lys Gln Thr Ala Leu Val Glu Leu
                245                 250                 255

Val Lys His Lys Pro Lys Ala Thr Lys Glu Gln Leu Lys Ala Val Met
            260                 265                 270

Asp Asp Phe Ala Ala Phe Val Glu Lys Cys Cys Lys Ala Asp Asp Lys
        275                 280                 285

Glu Thr Cys Phe Ala Glu Glu Gly Lys Lys Leu Val Ala Ala Ser Gln
    290                 295                 300

Ala Ala Leu Gly Leu
305


<210> SEQ ID NO 37
```

<211> LENGTH: 320
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Ala Thr Met Ala Val Met Ala Pro Arg Thr Leu Val Leu Leu Leu Ser
1 5 10 15

Gly Ala Leu Ala Leu Thr Gln Thr Trp Ala Gly Asp Ala His Lys Ser
20 25 30

Glu Val Ala His Arg Phe Lys Asp Leu Gly Glu Glu Asn Phe Lys Ala
35 40 45

Leu Val Leu Ile Ala Phe Ala Gln Tyr Leu Gln Gln Cys Pro Phe Glu
50 55 60

Asp His Val Lys Leu Val Asn Glu Val Thr Glu Phe Ala Lys Thr Cys
65 70 75 80

Val Ala Asp Glu Ser Ala Glu Asn Cys Asp Lys Ser Leu His Thr Leu
85 90 95

Phe Gly Asp Lys Leu Cys Thr Val Ala Thr Leu Arg Glu Thr Tyr Gly
100 105 110

Glu Met Ala Asp Cys Cys Ala Lys Gln Glu Pro Glu Arg Asn Glu Cys
115 120 125

Phe Leu Gln His Lys Asp Asp Asn Pro Asn Leu Pro Arg Leu Val Arg
130 135 140

Pro Glu Val Asp Val Met Cys Thr Ala Phe His Asp Asn Glu Glu Thr
145 150 155 160

Phe Leu Lys Lys Tyr Leu Tyr Glu Ile Ala Arg Arg His Pro Tyr Phe
165 170 175

Tyr Ala Pro Glu Leu Leu Phe Phe Ala Lys Arg Tyr Lys Ala Ala Phe
180 185 190

Thr Glu Cys Cys Gln Ala Ala Asp Lys Ala Ala Cys Leu Leu Pro Lys
195 200 205

Leu Asp Glu Leu Arg Asp Glu Gly Lys Ala Ser Ser Cys Lys Gln Arg
210 215 220

Leu Lys Cys Ala Ser Leu Gln Lys Phe Gly Glu Arg Ala Phe Lys Ala
225 230 235 240

Trp Ala Val Ala Arg Leu Ser Gln Arg Phe Pro Lys Ala Glu Phe Ala
245 250 255

Glu Val Ser Lys Leu Val Thr Asp Leu Thr Lys Val His Thr Glu Cys
260 265 270

Cys His Gly Asp Leu Leu Glu Cys Ala Asp Asp Arg Ala Asp Leu Ala
275 280 285

Lys Tyr Ile Cys Glu Asn Gln Asp Ser Ile Ser Ser Lys Leu Lys Glu
290 295 300

Cys Cys Glu Lys Pro Leu Leu Glu Lys Ser His Cys Ile Ala Glu Val
305 310 315 320

<210> SEQ ID NO 38
<211> LENGTH: 309
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

-continued

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Ser Leu Ala Ala Asp
            20                  25                  30

Phe Val Glu Ser Lys Asp Val Cys Lys Asn Tyr Ala Glu Ala Lys Asp
        35                  40                  45

Val Phe Leu Gly Met Phe Leu Tyr Glu Tyr Ala Arg Arg His Pro Asp
    50                  55                  60

Tyr Ser Val Val Leu Leu Leu Arg Leu Ala Lys Thr Tyr Glu Thr Thr
65                  70                  75                  80

Leu Glu Lys Cys Cys Ala Ala Ala Asp Pro His Glu Cys Tyr Ala Lys
                85                  90                  95

Val Phe Asp Glu Phe Lys Pro Leu Val Glu Glu Pro Gln Asn Leu Ile
            100                 105                 110

Lys Gln Asn Cys Glu Leu Phe Glu Gln Leu Gly Glu Tyr Lys Phe Gln
        115                 120                 125

Asn Ala Leu Leu Val Arg Tyr Thr Lys Lys Val Pro Gln Val Ser Thr
    130                 135                 140

Pro Thr Leu Val Glu Val Ser Arg Asn Leu Gly Lys Val Gly Ser Lys
145                 150                 155                 160

Cys Cys Lys His Pro Glu Ala Lys Arg Met Pro Cys Ala Glu Asp Tyr
                165                 170                 175

Leu Ser Cys Val Leu Asn Gln Leu Cys Val Leu His Glu Lys Thr Pro
            180                 185                 190

Val Ser Asp Arg Val Thr Lys Cys Cys Thr Glu Ser Leu Val Asn Arg
        195                 200                 205

Arg Pro Cys Phe Ser Ala Leu Glu Val Asp Glu Thr Tyr Val Pro Lys
    210                 215                 220

Glu Phe Asn Ala Glu Thr Phe Thr Phe His Ala Asp Ile Cys Thr Leu
225                 230                 235                 240

Ser Glu Lys Glu Arg Gln Ile Lys Lys Gln Thr Ala Leu Val Glu Leu
                245                 250                 255

Val Lys His Lys Pro Lys Ala Thr Lys Glu Gln Leu Lys Ala Val Met
            260                 265                 270

Asp Asp Phe Ala Ala Phe Val Glu Lys Cys Cys Lys Ala Asp Asp Lys
        275                 280                 285

Glu Thr Cys Phe Ala Glu Glu Gly Lys Lys Leu Val Ala Ala Ser Gln
    290                 295                 300

Ala Ala Leu Gly Leu
305
```

<210> SEQ ID NO 39
<211> LENGTH: 371
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
```

35 40 45

Leu Val Leu Ile Ala Phe Ala Gln Tyr Leu Gln Gln Cys Pro Phe Glu
50 55 60

Asp His Val Lys Leu Val Asn Glu Val Thr Glu Phe Ala Lys Thr Cys
65 70 75 80

Val Ala Asp Glu Ser Ala Glu Asn Cys Asp Lys Ser Leu His Thr Leu
85 90 95

Phe Gly Asp Lys Leu Cys Thr Val Ala Thr Leu Arg Glu Thr Tyr Gly
100 105 110

Glu Met Ala Asp Cys Cys Ala Lys Gln Glu Pro Glu Arg Asn Glu Cys
115 120 125

Phe Leu Gln His Lys Asp Asp Asn Pro Asn Leu Pro Arg Leu Val Arg
130 135 140

Pro Glu Val Asp Val Met Cys Thr Ala Phe His Asp Asn Glu Glu Thr
145 150 155 160

Phe Leu Lys Lys Tyr Leu Tyr Glu Ile Ala Arg Arg His Pro Tyr Phe
165 170 175

Tyr Ala Pro Glu Leu Leu Phe Phe Ala Lys Arg Tyr Lys Ala Ala Phe
180 185 190

Thr Glu Cys Cys Gln Ala Ala Asp Lys Ala Ala Cys Leu Leu Pro Lys
195 200 205

Leu Asp Glu Leu Arg Asp Glu Gly Lys Ala Ser Ser Ala Lys Gln Arg
210 215 220

Leu Lys Cys Ala Ser Leu Gln Lys Phe Gly Glu Arg Ala Phe Lys Ala
225 230 235 240

Trp Ala Val Ala Arg Leu Ser Gln Arg Phe Pro Lys Ala Glu Phe Ala
245 250 255

Glu Val Ser Lys Leu Val Thr Asp Leu Thr Lys Val His Thr Glu Cys
260 265 270

Cys His Gly Asp Leu Leu Glu Cys Ala Asp Asp Arg Ala Asp Leu Ala
275 280 285

Lys Tyr Ile Cys Glu Asn Gln Asp Ser Ile Ser Ser Lys Leu Lys Glu
290 295 300

Cys Cys Glu Lys Pro Leu Leu Glu Lys Ser His Cys Ile Ala Glu Val
305 310 315 320

Glu Asn Asp Glu Met Pro Ala Asp Leu Pro Ser Leu Ala Ala Asp Phe
325 330 335

Val Glu Ser Lys Asp Val Cys Lys Asn Tyr Ala Glu Ala Lys Asp Val
340 345 350

Phe Leu Gly Met Phe Leu Tyr Glu Tyr Ala Arg Arg His Pro Gly Gly
355 360 365

Gly Gly Ser
370

<210> SEQ ID NO 40
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

Ala Thr Met Ala Val Met Ala Pro Arg Thr Leu Val Leu Leu Leu Ser
1 5 10 15

```
Gly Ala Leu Ala Leu Thr Gln Thr Trp Ala Gly Gly Gly Gly Gly Ser
            20                  25                  30

Asp Tyr Ser Val Val Leu Leu Leu Arg Leu Ala Lys Thr Tyr Glu Thr
        35                  40                  45

Thr Leu Glu Lys Cys Cys Ala Ala Ala Asp Pro His Glu Cys Tyr Ala
    50                  55                  60

Lys Val Phe Asp Glu Phe Lys Pro Leu Val Glu Glu Pro Gln Asn Leu
65                  70                  75                  80

Ile Lys Gln Asn Cys Glu Leu Phe Glu Gln Leu Gly Glu Tyr Lys Phe
                85                  90                  95

Gln Asn Ala Leu Leu Val Arg Tyr Thr Lys Lys Val Pro Gln Val Ser
            100                 105                 110

Thr Pro Thr Leu Val Glu Val Ser Arg Asn Leu Gly Lys Val Gly Ser
        115                 120                 125

Lys Cys Cys Lys His Pro Glu Ala Lys Arg Met Pro Cys Ala Glu Asp
    130                 135                 140

Tyr Leu Ser Val Val Leu Asn Gln Leu Cys Val Leu His Glu Lys Thr
145                 150                 155                 160

Pro Val Ser Asp Arg Val Thr Lys Cys Cys Thr Glu Ser Leu Val Asn
                165                 170                 175

Arg Arg Pro Cys Phe Ser Ala Leu Glu Val Asp Glu Thr Tyr Val Pro
            180                 185                 190

Lys Glu Phe Asn Ala Glu Thr Phe Thr Phe His Ala Asp Ile Cys Thr
        195                 200                 205

Leu Ser Glu Lys Glu Arg Gln Ile Lys Lys Gln Thr Ala Leu Val Glu
    210                 215                 220

Leu Val Lys His Lys Pro Lys Ala Thr Lys Glu Gln Leu Lys Ala Val
225                 230                 235                 240

Met Asp Asp Phe Ala Ala Phe Val Glu Lys Cys Cys Lys Ala Asp Asp
                245                 250                 255

Lys Glu Thr Cys Phe Ala Glu Glu Gly Lys Lys Leu Val Ala Ala Ser
            260                 265                 270

Gln Ala Ala Leu Gly Leu
        275


<210> SEQ ID NO 41
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95
```

```
Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Gly Gly Gly Gly Ser
                325                 330


<210> SEQ ID NO 42
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Gly Gly Gly Gly Ser
            20                  25                  30

Asp Leu Pro Ser Leu Ala Ala Asp Phe Val Glu Ser Lys Asp Val Cys
        35                  40                  45

Lys Asn Tyr Ala Glu Ala Lys Asp Val Phe Leu Gly Met Phe Leu Tyr
    50                  55                  60

Glu Tyr Ala Arg Arg His Pro Asp Tyr Ser Val Val Leu Leu Leu Arg
65                  70                  75                  80

Leu Ala Lys Thr Tyr Glu Thr Thr Leu Glu Lys Cys Cys Ala Ala Ala
                85                  90                  95

Asp Pro His Glu Cys Tyr Ala Lys Val Phe Asp Glu Phe Lys Pro Leu
            100                 105                 110

Val Glu Glu Pro Gln Asn Leu Ile Lys Gln Asn Cys Glu Leu Phe Glu
```

```
        115                 120                 125

Gln Leu Gly Glu Tyr Lys Phe Gln Asn Ala Leu Leu Val Arg Tyr Thr
    130                 135                 140

Lys Lys Val Pro Gln Val Ser Thr Pro Thr Leu Val Glu Val Ser Arg
145                 150                 155                 160

Asn Leu Gly Lys Val Gly Ser Lys Cys Cys Lys His Pro Glu Ala Lys
                165                 170                 175

Arg Met Pro Cys Ala Glu Asp Tyr Leu Ser Val Val Leu Asn Gln Leu
            180                 185                 190

Cys Val Leu His Glu Lys Thr Pro Val Ser Asp Arg Val Thr Lys Cys
        195                 200                 205

Cys Thr Glu Ser Leu Val Asn Arg Arg Pro Cys Phe Ser Ala Leu Glu
    210                 215                 220

Val Asp Glu Thr Tyr Val Pro Lys Glu Phe Asn Ala Glu Thr Phe Thr
225                 230                 235                 240

Phe His Ala Asp Ile Cys Thr Leu Ser Glu Lys Glu Arg Gln Ile Lys
                245                 250                 255

Lys Gln Thr Ala Leu Val Glu Leu Val Lys His Lys Pro Lys Ala Thr
            260                 265                 270

Lys Glu Gln Leu Lys Ala Val Met Asp Asp Phe Ala Ala Phe Val Glu
        275                 280                 285

Lys Cys Cys Lys Ala Asp Asp Lys Glu Thr Cys Phe Ala Glu Glu Gly
    290                 295                 300

Lys Lys Leu Val Ala Ala Ser Gln Ala Ala Leu Gly Leu
305                 310                 315


<210> SEQ ID NO 43
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160
```

```
Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Gly Gly Gly Gly Ser
385                 390                 395
```

<210> SEQ ID NO 44
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Gly Gly Gly Gly Ser
            20                  25                  30

Asp Pro His Glu Cys Tyr Ala Lys Val Phe Asp Glu Phe Lys Pro Leu
        35                  40                  45

Val Glu Glu Pro Gln Asn Leu Ile Lys Gln Asn Cys Glu Leu Phe Glu
    50                  55                  60

Gln Leu Gly Glu Tyr Lys Phe Gln Asn Ala Leu Leu Val Arg Tyr Thr
65                  70                  75                  80

Lys Lys Val Pro Gln Val Ser Thr Pro Thr Leu Val Glu Val Ser Arg
                85                  90                  95

Asn Leu Gly Lys Val Gly Ser Lys Cys Cys Lys His Pro Glu Ala Lys
            100                 105                 110

Arg Met Pro Cys Ala Glu Asp Tyr Leu Ser Val Val Leu Asn Gln Leu
        115                 120                 125
```

Cys Val Leu His Glu Lys Thr Pro Val Ser Asp Arg Val Thr Lys Cys
    130                 135                 140

Cys Thr Glu Ser Leu Val Asn Arg Arg Pro Cys Phe Ser Ala Leu Glu
145                 150                 155                 160

Val Asp Glu Thr Tyr Val Pro Lys Glu Phe Asn Ala Glu Thr Phe Thr
                165                 170                 175

Phe His Ala Asp Ile Cys Thr Leu Ser Glu Lys Glu Arg Gln Ile Lys
            180                 185                 190

Lys Gln Thr Ala Leu Val Glu Leu Val Lys His Lys Pro Lys Ala Thr
        195                 200                 205

Lys Glu Gln Leu Lys Ala Val Met Asp Asp Phe Ala Ala Phe Val Glu
    210                 215                 220

Lys Cys Cys Lys Ala Asp Asp Lys Glu Thr Cys Phe Ala Glu Glu Gly
225                 230                 235                 240

Lys Lys Leu Val Ala Ala Ser Gln Ala Ala Leu Gly Leu
                245                 250

<210> SEQ ID NO 45
<211> LENGTH: 473
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala

```
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350

Phe Leu Gly Met Phe Leu Tyr Glu Tyr Ala Arg Arg His Pro Asp Tyr
        355                 360                 365

Ser Val Val Leu Leu Leu Arg Leu Ala Lys Thr Tyr Glu Thr Thr Leu
    370                 375                 380

Glu Lys Cys Cys Ala Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
            420                 425                 430

Ala Leu Leu Val Arg Tyr Thr Lys Lys Val Pro Gln Val Ser Thr Pro
        435                 440                 445

Thr Leu Val Glu Val Ser Arg Asn Leu Gly Lys Val Gly Ser Lys Cys
    450                 455                 460

Cys Lys His Pro Gly Gly Gly Gly Ser
465                 470


<210> SEQ ID NO 46
<211> LENGTH: 176
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Gly Gly Gly Gly Ser
            20                  25                  30

Glu Ala Lys Arg Met Pro Cys Ala Glu Asp Tyr Leu Ser Val Val Leu
        35                  40                  45

Asn Gln Leu Cys Val Leu His Glu Lys Thr Pro Val Ser Asp Arg Val
    50                  55                  60

Thr Lys Cys Cys Thr Glu Ser Leu Val Asn Arg Arg Pro Cys Phe Ser
65                  70                  75                  80

Ala Leu Glu Val Asp Glu Thr Tyr Val Pro Lys Glu Phe Asn Ala Glu
                85                  90                  95

Thr Phe Thr Phe His Ala Asp Ile Cys Thr Leu Ser Glu Lys Glu Arg
            100                 105                 110
```

```
Gln Ile Lys Lys Gln Thr Ala Leu Val Glu Leu Val Lys His Lys Pro
        115                 120                 125

Lys Ala Thr Lys Glu Gln Leu Lys Ala Val Met Asp Asp Phe Ala Ala
    130                 135                 140

Phe Val Glu Lys Cys Cys Lys Ala Asp Asp Lys Glu Thr Cys Phe Ala
145                 150                 155                 160

Glu Glu Gly Lys Lys Leu Val Ala Ala Ser Gln Ala Ala Leu Gly Leu
                165                 170                 175


<210> SEQ ID NO 47
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Gly Gly
            100                 105                 110

Gly Gly Ser
        115


<210> SEQ ID NO 48
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Gly Gly Gly Gly Ser
            20                  25                  30

Gly Glu Met Ala Asp Cys Cys Ala Lys Gln Glu Pro Glu Arg Asn Glu
        35                  40                  45

Cys Phe Leu Gln His Lys Asp Asp Asn Pro Asn Leu Pro Arg Leu Val
    50                  55                  60

Arg Pro Glu Val Asp Val Met Cys Thr Ala Phe His Asp Asn Glu Glu
65                  70                  75                  80

Thr Phe Leu Lys Lys Tyr Leu Tyr Glu Ile Ala Arg Arg His Pro Tyr
                85                  90                  95

Phe Tyr Ala Pro Glu Leu Leu Phe Phe Ala Lys Arg Tyr Lys Ala Ala
            100                 105                 110
```

-continued

```
Phe Thr Glu Cys Cys Gln Ala Ala Asp Lys Ala Ala Cys Leu Leu Pro
        115                 120                 125

Lys Leu Asp Glu Leu Arg Asp Glu Gly Lys Ala Ser Ser Ala Lys Gln
    130                 135                 140

Arg Leu Lys Cys Ala Ser Leu Gln Lys Phe Gly Glu Arg Ala Phe Lys
145                 150                 155                 160

Ala Trp Ala Val Ala Arg Leu Ser Gln Arg Phe Pro Lys Ala Glu Phe
                165                 170                 175

Ala Glu Val Ser Lys Leu Val Thr Asp Leu Thr Lys Val His Thr Glu
            180                 185                 190

Cys Cys His Gly Asp Leu Leu Glu Cys Ala Asp Asp Arg Ala Asp Leu
        195                 200                 205

Ala Lys Tyr Ile Cys Glu Asn Gln Asp Ser Ile Ser Ser Lys Leu Lys
    210                 215                 220

Glu Cys Cys Glu Lys Pro Leu Leu Glu Lys Ser His Cys Ile Ala Glu
225                 230                 235                 240

Val Glu Asn Asp Glu Met Pro Ala Asp Leu Pro Ser Leu Ala Ala Asp
                245                 250                 255

Phe Val Glu Ser Lys Asp Val Cys Lys Asn Tyr Ala Glu Ala Lys Asp
            260                 265                 270

Val Phe Leu Gly Met Phe Leu Tyr Glu Tyr Ala Arg Arg His Pro Asp
        275                 280                 285

Tyr Ser Val Val Leu Leu Leu Arg Leu Ala Lys Thr Tyr Glu Thr Thr
    290                 295                 300

Leu Glu Lys Cys Cys Ala Ala Ala Asp Pro His Glu Cys Tyr Ala Lys
305                 310                 315                 320

Val Phe Asp Glu Phe Lys Pro Leu Val Glu Glu Pro Gln Asn Leu Ile
                325                 330                 335

Lys Gln Asn Cys Glu Leu Phe Glu Gln Leu Gly Glu Tyr Lys Phe Gln
            340                 345                 350

Asn Ala Leu Leu Val Arg Tyr Thr Lys Lys Val Pro Gln Val Ser Thr
        355                 360                 365

Pro Thr Leu Val Glu Val Ser Arg Asn Leu Gly Lys Val Gly Ser Lys
    370                 375                 380

Cys Cys Lys His Pro Glu Ala Lys Arg Met Pro Cys Ala Glu Asp Tyr
385                 390                 395                 400

Leu Ser Val Val Leu Asn Gln Leu Cys Val Leu His Glu Lys Thr Pro
                405                 410                 415

Val Ser Asp Arg Val Thr Lys Cys Cys Thr Glu Ser Leu Val Asn Arg
            420                 425                 430

Arg Pro Cys Phe Ser Ala Leu Glu Val Asp Glu Thr Tyr Val Pro Lys
        435                 440                 445

Glu Phe Asn Ala Glu Thr Phe Thr Phe His Ala Asp Ile Cys Thr Leu
    450                 455                 460

Ser Glu Lys Glu Arg Gln Ile Lys Lys Gln Thr Ala Leu Val Glu Leu
465                 470                 475                 480

Val Lys His Lys Pro Lys Ala Thr Lys Glu Gln Leu Lys Ala Val Met
                485                 490                 495

Asp Asp Phe Ala Ala Phe Val Glu Lys Cys Cys Lys Ala Asp Asp Lys
            500                 505                 510

Glu Thr Cys Phe Ala Glu Glu Gly Lys Lys Leu Val Ala Ala Ser Gln
        515                 520                 525

Ala Ala Leu Gly Leu
```

530

<210> SEQ ID NO 49
<211> LENGTH: 203
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Gly Gly Gly Gly Ser
        195                 200
```

<210> SEQ ID NO 50
<211> LENGTH: 446
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 50

```
Ala Thr Met Ala Val Met Ala Pro Arg Thr Leu Val Leu Leu Leu Ser
1               5                   10                  15

Gly Ala Leu Ala Leu Thr Gln Thr Trp Ala Gly Gly Gly Gly Gly Ser
            20                  25                  30

Ala Asp Lys Ala Ala Cys Leu Leu Pro Lys Leu Asp Glu Leu Arg Asp
        35                  40                  45

Glu Gly Lys Ala Ser Ser Ala Lys Gln Arg Leu Lys Cys Ala Ser Leu
    50                  55                  60

Gln Lys Phe Gly Glu Arg Ala Phe Lys Ala Trp Ala Val Ala Arg Leu
65                  70                  75                  80

Ser Gln Arg Phe Pro Lys Ala Glu Phe Ala Glu Val Ser Lys Leu Val
```

```
                85                  90                  95

Thr Asp Leu Thr Lys Val His Thr Glu Cys Cys His Gly Asp Leu Leu
            100                 105                 110

Glu Cys Ala Asp Asp Arg Ala Asp Leu Ala Lys Tyr Ile Cys Glu Asn
        115                 120                 125

Gln Asp Ser Ile Ser Ser Lys Leu Lys Glu Cys Cys Glu Lys Pro Leu
    130                 135                 140

Leu Glu Lys Ser His Cys Ile Ala Glu Val Glu Asn Asp Glu Met Pro
145                 150                 155                 160

Ala Asp Leu Pro Ser Leu Ala Ala Asp Phe Val Glu Ser Lys Asp Val
                165                 170                 175

Cys Lys Asn Tyr Ala Glu Ala Lys Asp Val Phe Leu Gly Met Phe Leu
            180                 185                 190

Tyr Glu Tyr Ala Arg Arg His Pro Asp Tyr Ser Val Val Leu Leu Leu
        195                 200                 205

Arg Leu Ala Lys Thr Tyr Glu Thr Thr Leu Glu Lys Cys Cys Ala Ala
    210                 215                 220

Ala Asp Pro His Glu Cys Tyr Ala Lys Val Phe Asp Glu Phe Lys Pro
225                 230                 235                 240

Leu Val Glu Glu Pro Gln Asn Leu Ile Lys Gln Asn Cys Glu Leu Phe
                245                 250                 255

Glu Gln Leu Gly Glu Tyr Lys Phe Gln Asn Ala Leu Leu Val Arg Tyr
            260                 265                 270

Thr Lys Lys Val Pro Gln Val Ser Thr Pro Thr Leu Val Glu Val Ser
        275                 280                 285

Arg Asn Leu Gly Lys Val Gly Ser Lys Cys Cys Lys His Pro Glu Ala
    290                 295                 300

Lys Arg Met Pro Cys Ala Glu Asp Tyr Leu Ser Val Val Leu Asn Gln
305                 310                 315                 320

Leu Cys Val Leu His Glu Lys Thr Pro Val Ser Asp Arg Val Thr Lys
                325                 330                 335

Cys Cys Thr Glu Ser Leu Val Asn Arg Arg Pro Cys Phe Ser Ala Leu
            340                 345                 350

Glu Val Asp Glu Thr Tyr Val Pro Lys Glu Phe Asn Ala Glu Thr Phe
        355                 360                 365

Thr Phe His Ala Asp Ile Cys Thr Leu Ser Glu Lys Glu Arg Gln Ile
    370                 375                 380

Lys Lys Gln Thr Ala Leu Val Glu Leu Val Lys His Lys Pro Lys Ala
385                 390                 395                 400

Thr Lys Glu Gln Leu Lys Ala Val Met Asp Asp Phe Ala Ala Phe Val
                405                 410                 415

Glu Lys Cys Cys Lys Ala Asp Asp Lys Glu Thr Cys Phe Ala Glu Glu
            420                 425                 430

Gly Lys Lys Leu Val Ala Ala Ser Gln Ala Ala Leu Gly Leu
        435                 440                 445
```

<210> SEQ ID NO 51
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Thr Met Ala Val Met Ala Pro Arg Thr Leu Val Leu Leu Leu Ser
1 5 10 15

Gly Ala Leu Ala Leu Thr Gln Thr Trp Ala Gly Asp Ala His Lys Ser
20 25 30

Glu Val Ala His Arg Phe Lys Asp Leu Gly Glu Glu Asn Phe Lys Ala
35 40 45

Leu Val Leu Ile Ala Phe Ala Gln Tyr Leu Gln Gln Cys Pro Phe Glu
50 55 60

Asp His Val Lys Leu Val Asn Glu Val Thr Glu Phe Ala Lys Thr Cys
65 70 75 80

Val Ala Asp Glu Ser Ala Glu Asn Cys Asp Lys Ser Leu His Thr Leu
85 90 95

Phe Gly Asp Lys Leu Cys Thr Val Ala Thr Leu Arg Glu Thr Tyr Gly
100 105 110

Glu Met Ala Asp Cys Cys Ala Lys Gln Glu Pro Glu Arg Asn Glu Cys
115 120 125

Phe Leu Gln His Lys Asp Asp Asn Pro Asn Leu Pro Arg Leu Val Arg
130 135 140

Pro Glu Val Asp Val Met Cys Thr Ala Phe His Asp Asn Glu Glu Thr
145 150 155 160

Phe Leu Lys Lys Tyr Leu Tyr Glu Ile Ala Arg Arg His Pro Tyr Phe
165 170 175

Tyr Ala Pro Glu Leu Leu Phe Phe Ala Lys Arg Tyr Lys Ala Ala Phe
180 185 190

Thr Glu Cys Cys Gln Ala Ala Asp Lys Ala Ala Cys Leu Leu Pro Lys
195 200 205

Leu Asp Glu Leu Arg Asp Glu Gly Lys Ala Ser Ser Ala Lys Gln Arg
210 215 220

Leu Lys Cys Ala Ser Leu Gln Lys Phe Gly Glu Arg Ala Phe Lys Ala
225 230 235 240

Trp Ala Val Ala Arg Leu Ser Gln Arg Phe Pro Lys Ala Glu Phe Ala
245 250 255

Glu Val Ser Lys Leu Val Thr Asp Leu Thr Lys Val His Thr Glu Cys
260 265 270

Cys His Gly Asp Leu Leu Glu Cys Ala Asp Asp Arg Ala Asp Leu Ala
275 280 285

Lys Tyr Ile Cys Glu Asn Gln Asp Ser Ile Ser Ser Lys Leu Lys Glu
290 295 300

Cys Cys Glu Lys Gly Gly Gly Gly Ser
305 310

<210> SEQ ID NO 52
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Ala Thr Met Ala Val Met Ala Pro Arg Thr Leu Val Leu Leu Leu Ser
1 5 10 15

Gly Ala Leu Ala Leu Thr Gln Thr Trp Ala Gly Gly Gly Gly Gly Ser
20 25 30

Pro Leu Leu Glu Lys Ser His Cys Ile Ala Glu Val Glu Asn Asp Glu
35 40 45

```
Met Pro Ala Asp Leu Pro Ser Leu Ala Ala Asp Phe Val Glu Ser Lys
    50                  55                  60

Asp Val Cys Lys Asn Tyr Ala Glu Ala Lys Asp Val Phe Leu Gly Met
65                  70                  75                  80

Phe Leu Tyr Glu Tyr Ala Arg Arg His Pro Asp Tyr Ser Val Val Leu
                85                  90                  95

Leu Leu Arg Leu Ala Lys Thr Tyr Glu Thr Thr Leu Glu Lys Cys Cys
            100                 105                 110

Ala Ala Ala Asp Pro His Glu Cys Tyr Ala Lys Val Phe Asp Glu Phe
        115                 120                 125

Lys Pro Leu Val Glu Glu Pro Gln Asn Leu Ile Lys Gln Asn Cys Glu
    130                 135                 140

Leu Phe Glu Gln Leu Gly Glu Tyr Lys Phe Gln Asn Ala Leu Leu Val
145                 150                 155                 160

Arg Tyr Thr Lys Lys Val Pro Gln Val Ser Thr Pro Thr Leu Val Glu
                165                 170                 175

Val Ser Arg Asn Leu Gly Lys Val Gly Ser Lys Cys Cys Lys His Pro
            180                 185                 190

Glu Ala Lys Arg Met Pro Cys Ala Glu Asp Tyr Leu Ser Val Val Leu
        195                 200                 205

Asn Gln Leu Cys Val Leu His Glu Lys Thr Pro Val Ser Asp Arg Val
    210                 215                 220

Thr Lys Cys Cys Thr Glu Ser Leu Val Asn Arg Arg Pro Cys Phe Ser
225                 230                 235                 240

Ala Leu Glu Val Asp Glu Thr Tyr Val Pro Lys Glu Phe Asn Ala Glu
                245                 250                 255

Thr Phe Thr Phe His Ala Asp Ile Cys Thr Leu Ser Glu Lys Glu Arg
            260                 265                 270

Gln Ile Lys Lys Gln Thr Ala Leu Val Glu Leu Val Lys His Lys Pro
        275                 280                 285

Lys Ala Thr Lys Glu Gln Leu Lys Ala Val Met Asp Asp Phe Ala Ala
    290                 295                 300

Phe Val Glu Lys Cys Cys Lys Ala Asp Asp Lys Glu Thr Cys Phe Ala
305                 310                 315                 320

Glu Glu Gly Lys Lys Leu Val Ala Ala Ser Gln Ala Ala Leu Gly Leu
                325                 330                 335


<210> SEQ ID NO 53
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
```

```
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Gly Gly Gly
    130                 135                 140

Gly Ser
145


<210> SEQ ID NO 54
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Thr Met Ala Val Met Ala Pro Arg Thr Leu Val Leu Leu Leu Ser
1               5                   10                  15

Gly Ala Leu Ala Leu Thr Gln Thr Trp Ala Gly Gly Gly Gly Gly Ser
            20                  25                  30

Leu Val Arg Pro Glu Val Asp Val Met Cys Thr Ala Phe His Asp Asn
        35                  40                  45

Glu Glu Thr Phe Leu Lys Lys Tyr Leu Tyr Glu Ile Ala Arg Arg His
    50                  55                  60

Pro Tyr Phe Tyr Ala Pro Glu Leu Leu Phe Phe Ala Lys Arg Tyr Lys
65                  70                  75                  80

Ala Ala Phe Thr Glu Cys Cys Gln Ala Ala Asp Lys Ala Ala Cys Leu
                85                  90                  95

Leu Pro Lys Leu Asp Glu Leu Arg Asp Glu Gly Lys Ala Ser Ser Ala
            100                 105                 110

Lys Gln Arg Leu Lys Cys Ala Ser Leu Gln Lys Phe Gly Glu Arg Ala
        115                 120                 125

Phe Lys Ala Trp Ala Val Ala Arg Leu Ser Gln Arg Phe Pro Lys Ala
    130                 135                 140

Glu Phe Ala Glu Val Ser Lys Leu Val Thr Asp Leu Thr Lys Val His
145                 150                 155                 160

Thr Glu Cys Cys His Gly Asp Leu Leu Glu Cys Ala Asp Asp Arg Ala
                165                 170                 175

Asp Leu Ala Lys Tyr Ile Cys Glu Asn Gln Asp Ser Ile Ser Ser Lys
            180                 185                 190

Leu Lys Glu Cys Cys Glu Lys Pro Leu Leu Glu Lys Ser His Cys Ile
        195                 200                 205

Ala Glu Val Glu Asn Asp Glu Met Pro Ala Asp Leu Pro Ser Leu Ala
    210                 215                 220

Ala Asp Phe Val Glu Ser Lys Asp Val Cys Lys Asn Tyr Ala Glu Ala
225                 230                 235                 240

Lys Asp Val Phe Leu Gly Met Phe Leu Tyr Glu Tyr Ala Arg Arg His
                245                 250                 255

Pro Asp Tyr Ser Val Val Leu Leu Leu Arg Leu Ala Lys Thr Tyr Glu
            260                 265                 270
```

-continued

```
Thr Thr Leu Glu Lys Cys Cys Ala Ala Ala Asp Pro His Glu Cys Tyr
        275                 280                 285

Ala Lys Val Phe Asp Glu Phe Lys Pro Leu Val Glu Glu Pro Gln Asn
    290                 295                 300

Leu Ile Lys Gln Asn Cys Glu Leu Phe Glu Gln Leu Gly Glu Tyr Lys
305                 310                 315                 320

Phe Gln Asn Ala Leu Leu Val Arg Tyr Thr Lys Lys Val Pro Gln Val
                325                 330                 335

Ser Thr Pro Thr Leu Val Glu Val Ser Arg Asn Leu Gly Lys Val Gly
            340                 345                 350

Ser Lys Cys Cys Lys His Pro Glu Ala Lys Arg Met Pro Cys Ala Glu
        355                 360                 365

Asp Tyr Leu Ser Val Val Leu Asn Gln Leu Cys Val Leu His Glu Lys
    370                 375                 380

Thr Pro Val Ser Asp Arg Val Thr Lys Cys Cys Thr Glu Ser Leu Val
385                 390                 395                 400

Asn Arg Arg Pro Cys Phe Ser Ala Leu Glu Val Asp Glu Thr Tyr Val
                405                 410                 415

Pro Lys Glu Phe Asn Ala Glu Thr Phe Thr Phe His Ala Asp Ile Cys
            420                 425                 430

Thr Leu Ser Glu Lys Glu Arg Gln Ile Lys Lys Gln Thr Ala Leu Val
        435                 440                 445

Glu Leu Val Lys His Lys Pro Lys Ala Thr Lys Glu Gln Leu Lys Ala
    450                 455                 460

Val Met Asp Asp Phe Ala Ala Phe Val Glu Lys Cys Cys Lys Ala Asp
465                 470                 475                 480

Asp Lys Glu Thr Cys Phe Ala Glu Glu Gly Lys Lys Leu Val Ala Ala
                485                 490                 495

Ser Gln Ala Ala Leu Gly Leu
            500
```

<210> SEQ ID NO 55
<211> LENGTH: 1095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
gccactatgg ctgtgatggc ccctaggacc ctggtgctgc tgctgtccgg agctctggct     60

ctgactcaga cctgggctgg agatgcacac aagagtgagg ttgctcatcg gtttaaagat    120

ttgggagaag aaaatttcaa agccttggtg ttgattgcct ttgctcagta tcttcagcag    180

tgtccatttg aagatcatgt aaaattagtg aatgaagtaa ctgaatttgc aaaaacatgt    240

gttgctgatg agtcagctga aaattgtgac aaatcacttc ataccctttt tggagacaaa    300

ttatgcacag ttgcaactct tcgtgaaacc tatggtgaaa tggctgactg ctgtgcaaaa    360

caagaacctg agagaaatga atgcttcttg caacacaaag atgacaaccc aaacctcccc    420

cgattggtga gaccagaggt tgatgtgatg tgcactgctt ttcatgacaa tgaagagaca    480

tttttgaaaa aatacttata tgaaattgcc agaagacatc cttactttta tgccccggaa    540

ctccttttct ttgctaaaag gtataaagct gcttttacag aatgttgcca agctgctgat    600

aaagctgcct gcctgttgcc aaagctcgat gaacttcggg atgaagggaa ggcttcgtct    660

gccaaacaga gactcaagtg tgccagtctc caaaaatttg gagaaagagc tttcaaagca    720
```

tgggcagtat gccgcctgag ccagagattt cccaaagctg agtttgcaga agtttccaag 780
ttagtgacag atcttaccaa agtccacacg gaatgctgcc atggagatct gcttgaatgt 840
gctgatgaca gggcggacct tgccaagtat atctgtgaaa atcaagattc gatctccagt 900
aaactgaagg aatgctgtga aaaacctctg ttggaaaaat cccactgcat tgccgaagtg 960
gaaaatgatg agatgcctgc tgacttgcct tcattagctg ctgattttgt tgaaagtaag 1020
gatgtttgca aaaactatgc tgaggcaaag gatgtcttcc tgggcatgtt tttgtatgaa 1080
tatgcaagag catga 1095

<210> SEQ ID NO 56
<211> LENGTH: 817
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56
cgccactatg gctgtgatgg cccctaggac cctggtgctg ctgctgtccg gagctctggc 60
tctgactcag acctgggctg gatcttgcgt gctgctgctg agacttgcca agacatatga 120
aaccactcta gagaagtgct gtgccgctgc agatcctcat gaatgctatg ccaaagtgtt 180
cgatgaattt aaacctcttg tggaagagcc tcagaattta atcaaacaaa attgtgagct 240
ttttgagcag cttggagagt acaaattcca gaatgcgcta ttagttcgtt acaccaagaa 300
agtaccccaa gtgtcaactc caactcttgt agaggtctca agaaacctag gaaaagtggg 360
cagcaaatgt tgtaaacatc ctgaagcaaa aagaatgccc tgtgcagaag actatctatc 420
cgtggtcctg aaccagttat gtgtgttgca tgagaaaacg ccagtaagtg acagagtcac 480
caaatgctgc acagaatcct tggtgaacag gcgaccatgc ttttcagctc tggaagtcga 540
tgaaacatac gttcccaaag agtttaatgc tgaaacattc accttccatg cagatatatg 600
cacactttct gagaaggaga gacaaatcaa gaaacaaact gcacttgttg agctcgtgaa 660
acacaagccc aaggcaacaa aagagcaact gaaagctgtt atggatgatt tcgcagcttt 720
tgtagagaag tgctgcaagg ctgacgataa ggagacctgc tttgccgagg agggtaaaaa 780
acttgttgct gcaagtcaag ctgccttagg cttatga 817

<210> SEQ ID NO 57
<211> LENGTH: 1095
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 57
gccactatgg ctgtgatggc ccctaggacc ctggtgctgc tgctgtccgg agctctggct 60
ctgactcaga cctgggctgg agatgcacac aagagtgagg ttgctcatcg gtttaaagat 120
ttgggagaag aaaatttcaa agccttggtg ttgattgcct ttgctcagta tcttcagcag 180
tgtccatttg aagatcatgt aaaattagtg aatgaagtaa ctgaatttgc aaaaacatgt 240
gttgctgatg agtcagctga aaattgtgac aaatcacttc ataccctttt tggagacaaa 300
ttatgcacag ttgcaactct tcgtgaaacc tatggtgaaa tggctgactg ctgtgcaaaa 360
caagaacctg agagaaatga atgcttcttg caacacaaag atgacaaccc aaacctcccc 420

-continued

```
cgattggtga gaccagaggt tgatgtgatg tgcactgctt ttcatgacaa tgaagagaca    480

tttttgaaaa aatacttata tgaaattgcc agaagacatc cttactttta tgccccggaa    540

ctccttttct ttgctaaaag gtataaagct gcttttacag aatgttgcca agctgctgat    600

aaagctgcct gcctgttgcc aaagctcgat gaacttcggg atgaagggaa ggcttcgtct    660

gccaaacaga gactcaagtg tgccagtctc caaaaatttg gagaaagagc tttcaaagca    720

tgggcagtag ctcgcctgag ccagagattt cccaaagctg agtttgcaga agtttccaag    780

ttagtgacag atcttaccaa agtccacacg gaatgctgcc atggagatct gcttgaatgt    840

gctgatgaca gggcggacct tgccaagtat atctgtgaaa atcaagattc gatctccagt    900

aaactgaagg aatgctgtga aaaacctctg ttggaaaaat cccactgcat tgccgaagtg    960

gaaaatgatg agatgcctgc tgacttgcct tcattagctg ctgattttgt tgaaagtaag   1020

gatgtttgca aaaactatgc tgaggcaaag gatgtcttcc tgggcatgtt ttgctatgaa   1080

tatgcaagag catga                                                    1095
```

<210> SEQ ID NO 58
<211> LENGTH: 816
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
gccactatgg ctgtgatggc ccctaggacc ctggtgctgc tgctgtccgg agctctggct     60

ctgactcaga cctgggctgg atctgtcgtg ctgctgctga gactttgcaa gacatatgaa    120

accactctag agaagtgctg tgccgctgca gatcctcatg aatgctatgc caaagtgttc    180

gatgaattta aacctcttgt ggaagagcct cagaatttaa tcaaacaaaa ttgtgagctt    240

tttgagcagc ttggagagta caaattccag aatgcgctat tagttcgtta caccaagaaa    300

gtaccccaag tgtcaactcc aactcttgta gaggtctcaa gaaacctagg aaaagtgggc    360

agcaaatgtt gtaaacatcc tgaagcaaaa agaatgccct gtgcagaaga ctatctatcc    420

gtggtcctga accagttatg tgtgttgcat gagaaaacgc cagtaagtga cagagtcacc    480

aaatgctgca cagaatcctt ggtgaacagg cgaccatgct tttcagctct ggaagtcgat    540

gaaacatacg ttcccaaaga gtttaatgct gaaacattca ccttccatgc agatatatgc    600

acactttctg agaaggagag acaaatcaag aaacaaactg cacttgttga gctcgtgaaa    660

cacaagccca aggcaacaaa agagcaactg aaagctgtta tggatgattt cgcagctttt    720

gtagagaagt gctgcaaggc tgacgataag gagacctgct ttgccgagga gggtaaaaaa    780

cttgttgctg caagtcaagc tgccttaggc ttatga                              816
```

<210> SEQ ID NO 59
<211> LENGTH: 1095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
gccactatgg ctgtgatggc ccctaggacc ctggtgctgc tgctgtccgg agctctggct     60

ctgactcaga cctgggctgg agatgcacac aagagtgagg ttgctcatcg gtttaaagat    120

ttgggagaag aaaatttcaa agccttggtg ttgattgcct ttgctcagta tcttcagcag    180
```

tgtccatttg aagatcatgt aaaattagtg aatgaagtaa ctgaatttgc aaaaacatgt 240
gttgctgatg agtcagctga aaattgtgac aaatcacttc ataccctttt tggagacaaa 300
ttatgcacag ttgcaactct tcgtgaaacc tatggtgaaa tggctgactg ctgtgcaaaa 360
caagaacctg agagaaatga atgcttcttg caacacaaag atgacaaccc aaacctcccc 420
cgattggtga gaccagaggt tgatgtgatg tgcactgctt ttcatgacaa tgaagagaca 480
tttttgaaaa aatacttata tgaaattgcc agaagacatc cttactttta tgccccggaa 540
ctccttttct ttgctaaaag gtataaagct gcttttacag aatgttgcca agctgctgat 600
aaagctgcct gcctgttgcc aaagctcgat gaacttcggg atgaagggaa ggcttcgtct 660
gccaaacaga gactcaagtg tgccagtctc caaaaatttg gagaaagagc tttcaaagca 720
tgggcagtat gccgcctgag ccagagattt cccaaagctg agtttgcaga agtttccaag 780
ttagtgacag atcttaccaa agtccacacg gaatgctgcc atggagatct gcttgaatgt 840
gctgatgaca gggcggacct tgccaagtat atctgtgaaa atcaagattc gatctccagt 900
aaactgaagg aatgctgtga aaaacctctg ttggaaaaat cccactgcat tgccgaagtg 960
gaaaatgatg agatgcctgc tgacttgcct tcattagctg ctgattttgt tgaaagtaag 1020
gatgtttgca aaaactatgc tgaggcaaag gatgtcttcc tgggcatgtt tttgtatgaa 1080
tatgcaagag catga 1095

<210> SEQ ID NO 60
<211> LENGTH: 816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gccactatgg ctgtgatggc ccctaggacc ctggtgctgc tgctgtccgg agctctggct 60
ctgactcaga cctgggctgg atctgtcgtg ctgtgcctga gacttgccaa gacatatgaa 120
accactctag agaagtgctg tgccgctgca gatcctcatg aatgctatgc caaagtgttc 180
gatgaattta aacctcttgt ggaagagcct cagaatttaa tcaaacaaaa ttgtgagctt 240
tttgagcagc ttggagagta caaattccag aatgcgctat tagttcgtta caccaagaaa 300
gtaccccaag tgtcaactcc aactcttgta gaggtctcaa gaaacctagg aaaagtgggc 360
agcaaatgtt gtaaacatcc tgaagcaaaa agaatgccct gtgcagaaga ctatctatcc 420
gtggtcctga accagttatg tgtgttgcat gagaaaacgc cagtaagtga cagagtcacc 480
aaatgctgca cagaatcctt ggtgaacagg cgaccatgct tttcagctct ggaagtcgat 540
gaaacatacg ttcccaaaga gtttaatgct gaaacattca ccttccatgc agatatatgc 600
acactttctg agaaggagag acaaatcaag aaacaaactg cacttgttga gctcgtgaaa 660
cacaagccca aggcaacaaa agagcaactg aaagctgtta tggatgattt cgcagctttt 720
gtagagaagt gctgcaaggc tgacgataag gagacctgct ttgccgagga gggtaaaaaa 780
cttgttgctg caagtcaagc tgccttaggc ttatga 816

<210> SEQ ID NO 61
<211> LENGTH: 1095
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
gccactatgg ctgtgatggc ccctaggacc ctggtgctgc tgctgtccgg agctctggct     60
ctgactcaga cctgggctgg agatgcacac aagagtgagg ttgctcatcg gtttaaagat    120
ttgggagaag aaaatttcaa agccttggtg ttgattgcct ttgctcagta tcttcagcag    180
tgtccatttg aagatcatgt aaaattagtg aatgaagtaa ctgaatttgc aaaaacatgt    240
gttgctgatg agtcagctga aaattgtgac aaatcacttc ataccctttt tggagacaaa    300
ttatgcacag ttgcaactct tcgtgaaacc tatggtgaaa tggctgactg ctgtgcaaaa    360
caagaacctg agagaaatga atgcttcttg caacacaaag atgacaaccc aaacctcccc    420
cgattggtga gaccagaggt tgatgtgatg tgcactgctt ttcatgacaa tgaagagaca    480
tttttgaaaa aatacttata tgaaattgcc agaagacatc cttactttta tgccccggaa    540
ctccttttct ttgctaaaag gtataaagct gcttttacag aatgttgcca agctgctgat    600
aaagctgcct gcctgttgcc aaagctcgat gaacttcggg atgaagggaa ggcttcgtct    660
gccaaacaga gactcaagtg tgccagtctc caaaaatttg gagaaagagc tttcaaagca    720
tgcgcagtag ctcgcctgag ccagagattt cccaaagctg agtttgcaga agtttccaag    780
ttagtgacag atcttaccaa agtccacacg gaatgctgcc atggagatct gcttgaatgt    840
gctgatgaca gggcggacct tgccaagtat atctgtgaaa atcaagattc gatctccagt    900
aaactgaagg aatgctgtga aaaacctctg ttggaaaaat cccactgcat tgccgaagtg    960
gaaaatgatg agatgcctgc tgacttgcct tcattagctg ctgattttgt tgaaagtaag   1020
gatgtttgca aaaactatgc tgaggcaaag gatgtcttcc tgggcatgtt tttgtatgaa   1080
tatgcaagag catga                                                    1095
```

<210> SEQ ID NO 62
<211> LENGTH: 816
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62

```
gccactatgg ctgtgatggc ccctaggacc ctggtgctgc tgctgtccgg agctctggct     60
ctgactcaga cctgggctgg atcttgcgtg ctgctgctga gacttgccaa gacatatgaa    120
accactctag agaagtgctg tgccgctgca gatcctcatg aatgctatgc caaagtgttc    180
gatgaattta aacctcttgt ggaagagcct cagaatttaa tcaaacaaaa ttgtgagctt    240
tttgagcagc ttggagagta caaattccag aatgcgctat tagttcgtta caccaagaaa    300
gtaccccaag tgtcaactcc aactcttgta gaggtctcaa gaaacctagg aaaagtgggc    360
agcaaatgtt gtaaacatcc tgaagcaaaa agaatgccct gtgcagaaga ctatctatcc    420
gtggtcctga accagttatg tgtgttgcat gagaaaacgc cagtaagtga cagagtcacc    480
aaatgctgca cagaatcctt ggtgaacagg cgaccatgct tttcagctct ggaagtcgat    540
gaaacatacg ttcccaaaga gtttaatgct gaaacattca ccttccatgc agatatatgc    600
acactttctg agaaggagag acaaatcaag aaacaaactg cacttgttga gctcgtgaaa    660
cacaagccca aggcaacaaa agagcaactg aaagctgtta tggatgattt cgcagctttt    720
gtagagaagt gctgcaaggc tgacgataag gagacctgct ttgccgagga gggtaaaaaa    780
```

cttgttgctg caagtcaagc tgccttaggc ttatga 816

<210> SEQ ID NO 63
<211> LENGTH: 1095
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
gccactatgg ctgtgatggc ccctaggacc ctggtgctgc tgctgtccgg agctctggct 60
ctgactcaga cctgggctgg agatgcacac aagagtgagg ttgctcatcg gtttaaagat 120
ttgggagaag aaaatttcaa agccttggtg ttgattgcct ttgctcagta tcttcagcag 180
tgtccatttg aagatcatgt aaaattagtg aatgaagtaa ctgaatttgc aaaaacatgt 240
gttgctgatg agtcagctga aaattgtgac aaatcacttc ataccctttt tggagacaaa 300
ttatgcacag ttgcaactct tcgtgaaacc tatggtgaaa tggctgactg ctgtgcaaaa 360
caagaacctg agagaaatga atgcttcttg caacacaaag atgacaaccc aaacctcccc 420
cgattggtga gaccagaggt tgatgtgatg tgcactgctt ttcatgacaa tgaagagaca 480
tttttgaaaa aatacttata tgaaattgcc agaagacatc cttactttta tgccccggaa 540
ctccttttct ttgctaaaag gtataaagct gcttttacag aatgttgcca agctgctgat 600
aaagctgcct gcctgttgcc aaagctcgat gaacttcggg atgaagggaa ggcttcgtct 660
gccaaacaga gactcaagtg tgccagtctc caaaaatttg gagaaagagc tttcaaagca 720
tgggcagtag ctcgcctgag ccagagattt cccaaagctg agtttgcaga agtttccaag 780
ttagtgacag atcttaccaa agtccacacg gaatgctgcc atggagatct gcttgaatgt 840
gctgatgaca gggcggacct tgccaagtat atctgtgaaa atcaagattc gatctccagt 900
aaactgaagg aatgctgtga aaaacctctg ttggaaaaat cccactgcat tgccgaagtg 960
gaaaatgatg agatgcctgc tgacttgcct tcattagctg ctgattttgt tgaaagtaag 1020
gatgtttgca aaaactatgc tgaggcaaag gatgtcttcc tgggcatgtt tttgtatgaa 1080
tattgcagag catga 1095

<210> SEQ ID NO 64
<211> LENGTH: 816
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 64
gccactatgg ctgtgatggc ccctaggacc ctggtgctgc tgctgtccgg agctctggct 60
ctgactcaga cctgggctgg atctgtcgtg ctgtgcctga gacttgccaa gacatatgaa 120
accactctag agaagtgctg tgccgctgca gatcctcatg aatgctatgc caaagtgttc 180
gatgaattta aacctcttgt ggaagagcct cagaatttaa tcaaacaaaa ttgtgagctt 240
tttgagcagc ttggagagta caaattccag aatgcgctat tagttcgtta caccaagaaa 300
gtaccccaag tgtcaactcc aactcttgta gaggtctcaa gaaacctagg aaaagtgggc 360
agcaaatgtt gtaaacatcc tgaagcaaaa agaatgccct gtgcagaaga ctatctatcc 420
gtggtcctga accagttatg tgtgttgcat gagaaaacgc cagtaagtga cagagtcacc 480
aaatgctgca cagaatcctt ggtgaacagg cgaccatgct tttcagctct ggaagtcgat 540
gaaacatacg ttcccaaaga gtttaatgct gaaacattca ccttccatgc agatatatgc 600
acactttctg agaaggagag acaaatcaag aaacaaactg cacttgttga gctcgtgaaa 660
cacaagccca aggcaacaaa agagcaactg aaagctgtta tggatgattt cgcagctttt 720
gtagagaagt gctgcaaggc tgacgataag gagacctgct ttgccgagga gggtaaaaaa 780
cttgttgctg caagtcaagc tgccttaggc ttatga 816

<210> SEQ ID NO 65
<211> LENGTH: 1095
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 65
gccactatgg ctgtgatggc ccctaggacc ctggtgctgc tgctgtccgg agctctggct 60
ctgactcaga cctgggctgg agatgcacac aagagtgagg ttgctcatcg gtttaaagat 120
ttgggagaag aaaatttcaa agccttggtg ttgattgcct ttgctcagta tcttcagcag 180
tgtccatttg aagatcatgt aaaattagtg aatgaagtaa ctgaatttgc aaaaacatgt 240
gttgctgatg agtcagctga aaattgtgac aaatcacttc ataccctttt tggagacaaa 300
ttatgcacag ttgcaactct tcgtgaaacc tatggtgaaa tggctgactg ctgtgcaaaa 360
caagaacctg agagaaatga atgcttcttg caacacaaag atgacaaccc aaacctcccc 420
cgattggtga gaccagaggt tgatgtgatg tgcactgctt ttcatgacaa tgaagagaca 480
tttttgaaaa aatacttata tgaaattgcc agaagacatc cttactttta tgccccggaa 540
ctccttttct ttgctaaaag gtataaagct gcttttacag aatgttgcca agctgctgat 600
aaagctgcct gcctgttgcc aaagctcgat gaacttcggg atgaagggaa ggcttcgtct 660
gccaaacaga gatgcaagtg tgccagtctc caaaaatttg gagaaagagc tttcaaagca 720
tgggcagtag ctcgcctgag ccagagattt cccaaagctg agtttgcaga agtttccaag 780
ttagtgacag atcttaccaa agtccacacg gaatgctgcc atggagatct gcttgaatgt 840
gctgatgaca gggcggacct tgccaagtat atctgtgaaa atcaagattc gatctccagt 900
aaactgaagg aatgctgtga aaaacctctg ttggaaaaat cccactgcat tgccgaagtg 960
gaaaatgatg agatgcctgc tgacttgcct tcattagctg ctgattttgt tgaaagtaag 1020
gatgtttgca aaaactatgc tgaggcaaag gatgtcttcc tgggcatgtt tttgtatgaa 1080
tatgcaagag catga 1095

<210> SEQ ID NO 66
<211> LENGTH: 816
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 66
gccactatgg ctgtgatggc ccctaggacc ctggtgctgc tgctgtccgg agctctggct 60
ctgactcaga cctgggctgg atctgtcgtg ctgctgctga gacttgccaa gacatatgaa 120
accactctag agaagtgctg tgccgctgca gatcctcatg aatgctatgc caaagtgttc 180
gatgaattta aacctcttgt ggaagagcct cagaatttaa tcaaacaaaa ttgtgagctt 240

```
tttgagcagc ttggagagta caaattccag aatgcgctat tagttcgtta caccaagaaa    300

gtaccccaag tgtcaactcc aactcttgta gaggtctcaa gaaacctagg aaaagtgggc    360

agcaaatgtt gtaaacatcc tgaagcaaaa agaatgccct gtgcagaaga ctatctatcc    420

tgcgtcctga accagttatg tgtgttgcat gagaaaacgc cagtaagtga cagagtcacc    480

aaatgctgca cagaatcctt ggtgaacagg cgaccatgct tttcagctct ggaagtcgat    540

gaaacatacg ttcccaaaga gtttaatgct gaaacattca ccttccatgc agatatatgc    600

acactttctg agaaggagag acaaatcaag aaacaaactg cacttgttga gctcgtgaaa    660

cacaagccca aggcaacaaa agagcaactg aaagctgtta tggatgattt cgcagctttt    720

gtagagaagt gctgcaaggc tgacgataag gagacctgct ttgccgagga gggtaaaaaa    780

cttgttgctg caagtcaagc tgccttaggc ttatga                              816
```

<210> SEQ ID NO 67
<211> LENGTH: 963
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gccactatgg ctgtgatggc ccctaggacc ctggtgctgc tgctgtccgg agctctggct     60

ctgactcaga cctgggctgg agatgcacac aagagtgagg ttgctcatcg gtttaaagat    120

ttgggagaag aaaatttcaa agccttggtg ttgattgcct ttgctcagta tcttcagcag    180

tgtccatttg aagatcatgt aaaattagtg aatgaagtaa ctgaatttgc aaaaacatgt    240

gttgctgatg agtcagctga aaattgtgac aaatcacttc ataccctttt tggagacaaa    300

ttatgcacag ttgcaactct tcgtgaaacc tatggtgaaa tggctgactg ctgtgcaaaa    360

caagaacctg agagaaatga atgcttcttg caacacaaag atgacaaccc aaacctcccc    420

cgattggtga gaccagaggt tgatgtgatg tgcactgctt ttcatgacaa tgaagagaca    480

tttttgaaaa aatacttata tgaaattgcc agaagacatc cttactttta tgccccggaa    540

ctccttttct ttgctaaaag gtataaagct gcttttacag aatgttgcca agctgctgat    600

aaagctgcct gcctgttgcc aaagctcgat gaacttcggg atgaagggaa ggcttcgtct    660

gccaaacaga gactcaagtg tgccagtctc caaaaatttg gagaaagagc tttcaaagca    720

tgggcagtat gccgcctgag ccagagattt cccaaagctg agtttgcaga agtttccaag    780

ttagtgacag atcttaccaa agtccacacg gaatgctgcc atggagatct gcttgaatgt    840

gctgatgaca gggcggacct tgccaagtat atctgtgaaa atcaagattc gatctccagt    900

aaactgaagg aatgctgtga aaaacctctg ttggaaaaat cccactgcat tgccgaagtg    960

tga                                                                  963
```

<210> SEQ ID NO 68
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
gccactatgg ctgtgatggc ccctaggacc ctggtgctgc tgctgtccgg agctctggct     60

ctgactcaga cctgggctgg atcattagct gctgattttg ttgaaagtaa ggatgtttgc    120
```

```
aaaaactatg ctgaggcaaa ggatgtcttc ctgggcatgt tttgtatga atattgcaga    180

aggcatcctg attactctgt cgtgctgctg ctgagacttg ccaagacata tgaaaccact    240

ctagagaagt gctgtgccgc tgcagatcct catgaatgct atgccaaagt gttcgatgaa    300

tttaaacctc ttgtggaaga gcctcagaat ttaatcaaac aaaattgtga gctttttgag    360

cagcttggag agtacaaatt ccagaatgcg ctattagttc gttacaccaa gaaagtaccc    420

caagtgtcaa ctccaactct tgtagaggtc tcaagaaacc taggaaaagt gggcagcaaa    480

tgttgtaaac atcctgaagc aaaaagaatg ccctgtgcag aagactatct atccgtggtc    540

ctgaaccagt tatgtgtgtt gcatgagaaa acgccagtaa gtgacagagt caccaaatgc    600

tgcacagaat ccttggtgaa caggcgacca tgcttttcag ctctggaagt cgatgaaaca    660

tacgttccca aagagtttaa tgctgaaaca ttcaccttcc atgcagatat atgcacactt    720

tctgagaagg agagacaaat caagaaacaa actgcacttg ttgagctcgt gaaacacaag    780

cccaaggcaa caaaagagca actgaaagct gttatggatg atttcgcagc ttttgtagag    840

aagtgctgca aggctgacga taaggagacc tgctttgccg aggagggtaa aaaacttgtt    900

gctgcaagtc aagctgcctt aggcttatga                                      930
```

```
<210> SEQ ID NO 69
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
```

```
gccactatgg ctgtgatggc ccctaggacc ctggtgctgc tgctgtccgg agctctggct     60

ctgactcaga cctgggctgg agatgcacac aagagtgagg ttgctcatcg gtttaaagat    120

ttgggagaag aaaatttcaa agccttggtg ttgattgcct ttgctcagta tcttcagcag    180

tgtccatttg aagatcatgt aaaattagtg aatgaagtaa ctgaatttgc aaaaacatgt    240

gttgctgatg agtcagctga aaattgtgac aaatcacttc ataccctttt tggagacaaa    300

ttatgcacag ttgcaactct tcgtgaaacc tatggtgaaa tggctgactg ctgtgcaaaa    360

caagaacctg agagaaatga atgcttcttg caacacaaag atgacaaccc aaacctcccc    420

cgattggtga gaccagaggt tgatgtgatg tgcactgctt ttcatgacaa tgaagagaca    480

tttttgaaaa aatacttata tgaaattgcc agaagacatc cttactttta tgccccggaa    540

ctccttttct ttgctaaaag gtataaagct gcttttacag aatgttgcca agctgctgat    600

aaagctgcct gcctgttgcc aaagctcgat gaacttcggg atgaagggaa ggcttcgtct    660

gccaaacaga gactcaagtg tgccagtctc caaaaatttg gagaaagagc tttcaaagca    720

tgggcagtat gccgcctgag ccagagattt cccaaagctg agtttgcaga agtttccaag    780

ttagtgacag atcttaccaa agtccacacg gaatgctgcc atggagatct gcttgaatgt    840

gctgatgaca gggcggacct tgccaagtat atctgtgaaa atcaagattc gatctccagt    900

aaactgaagg aatgctgtga aaaacctctg ttggaaaaat cccactgcat tgccgaagtg    960

tga                                                                   963
```

```
<210> SEQ ID NO 70
<211> LENGTH: 930
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 70
gccactatgg ctgtgatggc ccctaggacc ctggtgctgc tgctgtccgg agctctggct 60
ctgactcaga cctgggctgg atcattagct gctgattttg ttgaaagtaa ggatgtttgc 120
aaaaactatg ctgaggcaaa ggatgtcttc ctgggcatgt tttgctatga atatgcaaga 180
aggcatcctg attactctgt cgtgctgctg ctgagacttg ccaagacata tgaaaccact 240
ctagagaagt gctgtgccgc tgcagatcct catgaatgct atgccaaagt gttcgatgaa 300
tttaaacctc ttgtggaaga gcctcagaat ttaatcaaac aaaattgtga gctttttgag 360
cagcttggag agtacaaatt ccagaatgcg ctattagttc gttacaccaa gaaagtaccc 420
caagtgtcaa ctccaactct tgtagaggtc tcaagaaacc taggaaaagt gggcagcaaa 480
tgttgtaaac atcctgaagc aaaaagaatg ccctgtgcag aagactatct atccgtggtc 540
ctgaaccagt tatgtgtgtt gcatgagaaa acgccagtaa gtgacagagt caccaaatgc 600
tgcacagaat ccttggtgaa caggcgacca tgcttttcag ctctggaagt cgatgaaaca 660
tacgttccca aagagtttaa tgctgaaaca ttcaccttcc atgcagatat atgcacactt 720
tctgagaagg agagacaaat caagaaacaa actgcacttg ttgagctcgt gaaacacaag 780
cccaaggcaa caaaagagca actgaaagct gttatggatg atttcgcagc ttttgtagag 840
aagtgctgca aggctgacga taaggagacc tgctttgccg aggagggtaa aaaacttgtt 900
gctgcaagtc aagctgcctt aggcttatga 930

<210> SEQ ID NO 71
<211> LENGTH: 963
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 71
gccactatgg ctgtgatggc ccctaggacc ctggtgctgc tgctgtccgg agctctggct 60
ctgactcaga cctgggctgg agatgcacac aagagtgagg ttgctcatcg gtttaaagat 120
ttgggagaag aaaatttcaa agccttggtg ttgattgcct ttgctcagta tcttcagcag 180
tgtccatttg aagatcatgt aaaattagtg aatgaagtaa ctgaatttgc aaaaacatgt 240
gttgctgatg agtcagctga aaattgtgac aaatcacttc ataccctttt tggagacaaa 300
ttatgcacag ttgcaactct tcgtgaaacc tatggtgaaa tggctgactg ctgtgcaaaa 360
caagaacctg agagaaatga atgcttcttg caacacaaag atgacaaccc aaacctcccc 420
cgattggtga gaccagaggt tgatgtgatg tgcactgctt ttcatgacaa tgaagagaca 480
tttttgaaaa aatacttata tgaaattgcc agaagacatc cttactttta tgccccggaa 540
ctccttttct ttgctaaaag gtataaagct gcttttacag aatgttgcca agctgctgat 600
aaagctgcct gcctgttgcc aaagctcgat gaacttcggg atgaagggaa ggcttcgtct 660
gccaaacaga gatgcaagtg tgccagtctc caaaaatttg gagaaagagc tttcaaagca 720
tgggcagtag ctcgcctgag ccagagattt cccaaagctg agtttgcaga agtttccaag 780
ttagtgacag atcttaccaa agtccacacg gaatgctgcc atggagatct gcttgaatgt 840
gctgatgaca gggcggacct tgccaagtat atctgtgaaa atcaagattc gatctccagt 900
aaactgaagg aatgctgtga aaaacctctg ttggaaaaat cccactgcat tgccgaagtg 960
tga 963

<210> SEQ ID NO 72
<211> LENGTH: 930
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72
gccactatgg ctgtgatggc ccctaggacc ctggtgctgc tgctgtccgg agctctggct 60
ctgactcaga cctgggctgg atcattagct gctgattttg ttgaaagtaa ggatgtttgc 120
aaaaactatg ctgaggcaaa ggatgtcttc ctgggcatgt ttttgtatga atatgcaaga 180
aggcatcctg attactctgt cgtgctgctg ctgagacttg ccaagacata tgaaaccact 240
ctagagaagt gctgtgccgc tgcagatcct catgaatgct atgccaaagt gttcgatgaa 300
tttaaacctc ttgtggaaga gcctcagaat ttaatcaaac aaaattgtga gctttttgag 360
cagcttggag agtacaaatt ccagaatgcg ctattagttc gttacaccaa gaaagtaccc 420
caagtgtcaa ctccaactct tgtagaggtc tcaagaaacc taggaaaagt gggcagcaaa 480
tgttgtaaac atcctgaagc aaaaagaatg ccctgtgcag aagactatct atccgtggtc 540
ctgtgccagt tatgtgtgtt gcatgagaaa acgccagtaa gtgacagagt caccaaatgc 600
tgcacagaat ccttggtgaa caggcgacca tgcttttcag ctctggaagt cgatgaaaca 660
tacgttccca aagagtttaa tgctgaaaca ttcaccttcc atgcagatat atgcacactt 720
tctgagaagg agagacaaat caagaaacaa actgcacttg ttgagctcgt gaaacacaag 780
cccaaggcaa caaaagagca actgaaagct gttatggatg atttcgcagc ttttgtagag 840
aagtgctgca aggctgacga taaggagacc tgctttgccg aggagggtaa aaaacttgtt 900
gctgcaagtc aagctgcctt aggcttatga 930

<210> SEQ ID NO 73
<211> LENGTH: 963
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73
gccactatgg ctgtgatggc ccctaggacc ctggtgctgc tgctgtccgg agctctggct 60
ctgactcaga cctgggctgg agatgcacac aagagtgagg ttgctcatcg gtttaaagat 120
ttgggagaag aaaatttcaa agccttggtg ttgattgcct ttgctcagta tcttcagcag 180
tgtccatttg aagatcatgt aaaattagtg aatgaagtaa ctgaatttgc aaaaacatgt 240
gttgctgatg agtcagctga aaattgtgac aaatcacttc ataccctttt tggagacaaa 300
ttatgcacag ttgcaactct tcgtgaaacc tatggtgaaa tggctgactg ctgtgcaaaa 360
caagaacctg agagaaatga atgcttcttg caacacaaag atgacaaccc aaacctcccc 420
cgattggtga gaccagaggt tgatgtgatg tgcactgctt ttcatgacaa tgaagagaca 480
tttttgaaaa aatacttata tgaaattgcc agaagacatc cttactttta tgccccggaa 540
ctccttttct ttgctaaaag gtataaagct gcttttacag aatgttgcca agctgctgat 600
aaagctgcct gcctgttgcc aaagctcgat gaacttcggg atgaagggaa ggcttcgtct 660
tgcaaacaga gactcaagtg tgccagtctc caaaaatttg gagaaagagc tttcaaagca 720
tgggcagtag ctcgcctgag ccagagattt cccaaagctg agtttgcaga agtttccaag 780
ttagtgacag atcttaccaa agtccacacg gaatgctgcc atggagatct gcttgaatgt 840
gctgatgaca gggcggacct tgccaagtat atctgtgaaa atcaagattc gatctccagt 900
aaactgaagg aatgctgtga aaaacctctg ttggaaaaat cccactgcat tgccgaagtg 960
tga 963

<210> SEQ ID NO 74
<211> LENGTH: 930
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 74
gccactatgg ctgtgatggc ccctaggacc ctggtgctgc tgctgtccgg agctctggct 60
ctgactcaga cctgggctgg atcattagct gctgattttg ttgaaagtaa ggatgtttgc 120
aaaaactatg ctgaggcaaa ggatgtcttc ctgggcatgt ttttgtatga atatgcaaga 180
aggcatcctg attactctgt cgtgctgctg ctgagacttg ccaagacata tgaaaccact 240
ctagagaagt gctgtgccgc tgcagatcct catgaatgct atgccaaagt gttcgatgaa 300
tttaaacctc ttgtggaaga gcctcagaat ttaatcaaac aaaattgtga gctttttgag 360
cagcttggag agtacaaatt ccagaatgcg ctattagttc gttacaccaa gaaagtaccc 420
caagtgtcaa ctccaactct tgtagaggtc tcaagaaacc taggaaaagt gggcagcaaa 480
tgttgtaaac atcctgaagc aaaaagaatg ccctgtgcag aagactatct atcctgcgtc 540
ctgaaccagt tatgtgtgtt gcatgagaaa acgccagtaa gtgacagagt caccaaatgc 600
tgcacagaat ccttggtgaa caggcgacca tgcttttcag ctctggaagt cgatgaaaca 660
tacgttccca aagagtttaa tgctgaaaca ttcaccttcc atgcagatat atgcacactt 720
tctgagaagg agagacaaat caagaaacaa actgcacttg ttgagctcgt gaaacacaag 780
cccaaggcaa caaaagagca actgaaagct gttatggatg atttcgcagc ttttgtagag 840
aagtgctgca aggctgacga taaggagacc tgctttgccg aggagggtaa aaaacttgtt 900
gctgcaagtc aagctgcctt aggcttatga 930

<210> SEQ ID NO 75
<211> LENGTH: 1116
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 75
gccactatgg ctgtgatggc acctagaaca ctggtcctgc tgctgtcagg ggcactggca 60
ctgactcaga cttgggctgg agatgctcat aagagcgagg tcgctcacag gttcaaggat 120
ctgggggagg aaaactttaa agccctggtg ctgatcgcat tcgcccagta cctgcagcag 180
tgcccctttg aggaccacgt gaagctggtc aacgaggtga cagagttcgc caaaacttgc 240
gtcgccgacg agtcagctga aaattgtgat aagagcctgc atactctgtt tggggataaa 300
ctgtgcaccg tggccacact gagggagacc tatggagaaa tggcagactg ctgtgccaag 360
caggagcccg aacgcaacga gtgcttcctg cagcataaag acgataaccc caatctgcct 420
cgactggtgc ggcctgaagt ggacgtcatg tgtaccgctt tccacgataa tgaggaaaca 480
tttctgaaga aatacctgta tgagattgcc cggagacatc cttactttta tgctccagaa 540
ctgctgttct ttgcaaagcg gtacaaagcc gctttcacag agtgctgtca ggcagccgat 600
aaggctgcat gcctgctgcc aaaactggac gagctgcgcg atgaaggcaa ggccagctcc 660
gctaagcagc gactgaaatg tgcctctctg cagaagttcg gggagcgggc ttttaaagct 720
tgggcagtcg ccagactgag tcagaggttc cccaaggcag agtttgccga agtctcaaag 780
ctggtgactg acctgaccaa agtgcacacc gagtgctgtc atggagacct gctggaatgc 840
gccgacgata gagctgatct ggcaaagtac atctgtgaga atcaggacag catttctagt 900
aagctgaaag agtgctgtga aaagcctctg ctggagaaat cccactgcat cgcagaggtg 960
gaaaacgacg aaatgccagc agatctgcca tccctggcag ctgactttgt cgagtctaag 1020
gatgtgtgta aaaattatgc tgaagcaaag gatgtgttcc tgggcatgtt tctgtacgag 1080
tatgcaaggc gacatccagg aggaggaggc tcctga 1116

<210> SEQ ID NO 76
<211> LENGTH: 837
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76
gccactatgg ctgtgatggc acctagaacc ctggtcctgc tgctgagcgg cgcactggca 60
ctgacacaga cttgggctgg gggggggggg gggagcgact actccgtggt cctgctgctg 120
cggctggcaa aaacttatga gaccacactg gaaaagtgct gtgccgctgc agaccctcac 180
gagtgctacg ccaaagtgtt cgatgagttc aagcccctgg tcgaggaacc tcagaacctg 240
atcaaacaga attgtgagct gttcgaacag ctgggggagt acaagtttca gaacgccctg 300
ctggtgcggt atacaaagaa agtgccacag gtctctactc ccaccctggt ggaggtcagt 360
aggaatctgg gcaaagtggg gtcaaaatgc tgtaagcacc ctgaggccaa gcgcatgcca 420
tgcgctgaag actacctgtc tgtggtcctg aaccagctgt gtgtgctgca tgagaaaacc 480
ccagtgagtg atcgagtcac caagtgctgt acagagagcc tggtgaaccg gagaccctgc 540
ttctccgctc tggaggtgga cgaaacatat gtccctaagg agtttaatgc agaaacattc 600
acttttcacg ccgatatctg tactctgtcc gagaaggaaa gacagattaa gaaacagacc 660
gccctggtgg agctggtcaa gcataaaccc aaggctacaa aagaacagct gaaggcagtg 720
atggacgatt tcgccgcttt tgtggagaaa tgctgtaagg ccgacgataa ggaaacttgc 780
ttcgctgagg aaggaaagaa actggtggca gccagccagg ctgcactggg cctgtga 837

<210> SEQ ID NO 77
<211> LENGTH: 999
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77
gccactatgg ccgtgatggc acctagaaca ctggtcctgc tgctgagcgg ggcactggca 60
ctgacacaga cttgggctgg agacgcacac aaatctgagg tcgctcaccg gttcaaggat 120

```
ctgggcgagg aaaactttaa agccctggtg ctgatcgcct tcgctcagta cctgcagcag    180
tgcccttttg aggaccacgt gaagctggtc aacgaggtga cagagttcgc caaaacttgc    240
gtcgcagacg agtcagccga aaattgtgat aagagcctgc atactctgtt tggggataaa    300
ctgtgtaccg tggccacact gcgcgagacc tatggagaaa tggctgactg ctgtgcaaag    360
caggagcccg aacgaaacga gtgcttcctg cagcataaag acgataaccc caatctgcct    420
aggctggtgc gccctgaagt ggacgtcatg tgtaccgctt tccacgataa tgaggaaaca    480
tttctgaaga aatacctgta tgagattgcc cggagacatc catactttta tgcccccgaa    540
ctgctgttct ttgctaagag atacaaagcc gctttcacag agtgctgtca ggcagccgat    600
aaggctgcat gcctgctgcc aaaactggac gagctgagag atgaaggcaa ggcaagctcc    660
gccaagcaga ggctgaaatg tgcaagcctg cagaagttcg gggagagggc ctttaaagca    720
tgggcagtcg ctcgactgtc ccagcgattc cccaaggctg agtttgcaga agtctctaag    780
ctggtgactg atctgaccaa agtgcacacc gagtgctgtc atggcgacct gctggaatgc    840
gccgacgatc gcgccgatct ggctaagtat atctgtgaga accaggacag tatttctagt    900
aagctgaaag agtgctgtga aaagcctctg ctggagaaat cacactgcat cgctgaggtg    960
gaaaatgacg aaatgccagc aggcggggga ggctcctga                           999
```

<210> SEQ ID NO 78
<211> LENGTH: 954
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
gccactatgg ccgtgatggc acctagaacc ctggtcctgc tgctgagcgg ggcactggca     60
ctgacacaga cttgggctgg gggggggggg ggcagcgacc tgccatccct ggcagctgac    120
ttcgtggagt caaaagatgt ctgcaagaac tacgcagaag ccaaggacgt gttcctgggg    180
atgtttctgt acgagtatgc tcggagacac ccagattaca gcgtggtcct gctgctgcgc    240
ctggccaaaa cttatgagac cacactggaa aagtgctgtg cagccgctga cccccatgag    300
tgctatgcca aagtgttcga tgagttcaag cccctggtcg aggaacctca gaacctgatc    360
aaacagaatt gtgagctgtt cgaacagctg ggcgagtaca agtttcagaa cgccctgctg    420
gtgcgatata caaagaaagt gccacaggtc tctactccca ccctggtgga ggtcagtcga    480
aatctgggca aagtggggtc aaaatgctgt aagcaccctg aggctaagcg gatgccatgc    540
gcagaagact acctgtctgt ggtcctgaat cagctgtgtg tgctgcatga gaaaacccct    600
gtgagtgata gagtcaccaa gtgctgtaca gaaagcctgg tgaacaggcg accatgcttc    660
tccgcactgg aggtggacga aacatatgtc cctaaagagt ttaatgccga aacattcact    720
tttcacgctg atatctgtac tctgtccgag aaggaaaggc agattaagaa acagaccgcc    780
ctggtggagc tggtcaagca taaaccaaag gcaacaaaag aacagctgaa ggccgtgatg    840
gacgatttcg cagcctttgt ggagaaatgc tgtaaggctg acgataagga aacttgtttt    900
gcagaggaag gaaagaaact ggtggctgca tctcaggccg ctctgggcct gtga          954
```

<210> SEQ ID NO 79
<211> LENGTH: 1191
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79
gccactatgg ctgtgatggc tccaagaacc ctggtcctgc tgctgtccgg ggcactggct 60
ctgactcaga catgggctgg ggatgctcat aagtctgagg tcgcccaccg attcaaggat 120
ctgggggagg aaaactttaa agctctggtg ctgatcgcat tcgcccagta cctgcagcag 180
tgcccctttg aggaccacgt gaagctggtc aacgaggtga ccgagttcgc caaaacatgc 240
gtcgccgacg agtcagctga aaattgtgat aagagcctgc atacactgtt tggggataaa 300
ctgtgcactg tggccaccct gcgggagact tatggagaaa tggcagactg ctgtgccaag 360
caggagcccg aaagaaacga gtgcttcctg cagcataaag acgataaccc caatctgcct 420
cgactggtgc ggcctgaagt ggacgtcatg tgtactgcct tccacgataa tgaggaaacc 480
tttctgaaga aatacctgta tgagattgcc cggagacatc cttactttta tgctccagaa 540
ctgctgttct ttgcaaagcg ctacaaagcc gctttcaccg agtgctgtca ggcagccgat 600
aaggctgcat gcctgctgcc aaaactggac gagctgcgcg atgaaggcaa ggccagctcc 660
gctaagcagc gactgaaatg tgccagcctg cagaagttcg gggagagggc ttttaaagct 720
tgggcagtgg ccagactgag tcagaggttc cccaaggcag agtttgccga agtctcaaag 780
ctggtgacag acctgactaa agtgcacaca gagtgctgtc atggagacct gctggaatgc 840
gccgacgatc gcgctgatct ggcaaagtac atctgtgaga atcaggacag catttctagt 900
aagctgaaag agtgctgtga aaagcctctg ctggagaaat cccactgcat cgcagaggtg 960
gaaaacgacg aaatgccagc tgatctgccc tccctggccg ctgactttgt cgagtctaag 1020
gatgtgtgta aaaattatgc tgaagcaaag gatgtgttcc tgggcatgtt tctgtacgag 1080
tatgccaggc gccatccaga ctactctgtg gtcctgctgc tgagactggc caagacctat 1140
gagaccacac tggaaaaatg ctgtgcagcc gctggcgggg gaggcagttg a 1191

<210> SEQ ID NO 80
<211> LENGTH: 762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 80
gccactatgg ctgtgatggc acctagaacc ctggtcctgc tgctgtccgg ggcactggca 60
ctgactcaga cttgggctgg gggaggcggg ggcagcgacc ctcacgagtg ctacgcaaaa 120
gtgttcgatg agttcaagcc cctggtcgag gaacctcaga acctgatcaa acagaattgt 180
gagctgttcg aacagctggg ggagtacaag tttcagaacg ctctgctggt gcggtatacc 240
aagaaagtgc cacaggtcag cacccccaca ctggtggagg tctccaggaa tctgggcaaa 300
gtggggtcta aatgctgtaa gcaccctgag gccaagcgca tgccatgcgc tgaagactac 360
ctgagcgtgg tcctgaacca gctgtgtgtg ctgcatgaga aaacaccagt gtccgatcga 420
gtcacaaagt gctgtactga gagtctggtg aaccggagac cctgcttctc agccctggag 480
gtggacgaaa cttatgtccc taaggagttt aatgcagaaa ctttcacctt tcacgccgat 540
atctgtaccc tgtctgagaa ggaaagacag attaagaaac agacagccct ggtggagctg 600
gtcaagcata aacccaaggc tactaaagaa cagctgaagg cagtgatgga cgatttcgcc 660

-continued gcttttgtcg agaaatgctg taaggccgac gataaggaaa cctgcttcgc tgaggaagga 720
aagaaactgg tggcagccag ccaggctgca ctgggcctgt ga 762

<210> SEQ ID NO 81
<211> LENGTH: 1422
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 81
gccactatgg ctgtgatggc acctcgcacc ctggtcctgc tgctgtccgg ggcactggca 60
ctgactcaga cttgggctgg agatgctcat aagtctgagg tcgctcacag attcaaggat 120
ctgggcgagg aaaactttaa agcactggtg ctgatcgcat tcgcccagta cctgcagcag 180
tgcccctttg aggaccacgt gaagctggtc aacgaagtga ctgagttcgc caaaacctgc 240
gtcgccgacg agtcagctga aaattgtgat aagagcctgc ataccctgtt tggcgataaa 300
ctgtgcacag tggccactct gcgggagaca tatggggaaa tggcagactg ctgtgccaag 360
caggagcctg aaagaaacga gtgcttcctg cagcataaag acgataaccc caatctgcct 420
cgactggtgc ggccagaagt ggacgtcatg tgtacagcct tccacgataa tgaggaaact 480
tttctgaaga aatacctgta tgagattgct cggagacatc cttactttta tgctccagaa 540
ctgctgttct ttgcaaagag gtacaaagcc gctttcaccg agtgctgtca ggcagccgat 600
aaggctgcat gcctgctgcc aaaactggac gagctgcgcg atgaaggaaa ggccagctcc 660
gctaagcagc gactgaaatg tgccagcctg cagaagttcg gcgagcgagc ttttaaagct 720
tgggcagtgg ccagactgtc ccagaggttc cccaaggcag agtttgccga agtctctaag 780
ctggtgaccg acctgacaaa agtgcacacc gagtgctgtc atggggacct gctggaatgc 840
gccgacgatc gcgctgatct ggcaaagtac atctgtgaga atcaggacag tatttctagt 900
aagctgaaag agtgctgtga aaagcctctg ctggagaaat cacactgcat cgcagaggtg 960
gaaaacgacg aaatgccagc agatctgcca tccctggcag ctgacttcgt cgagtctaag 1020
gatgtgtgta aaaattacgc tgaagcaaag gatgtgttcc tggggatgtt tctgtacgag 1080
tatgccaggc gccaccccga ctacagtgtg gtcctgctgc tgcggctggc taagacttat 1140
gagaccacac tggaaaaatg ctgtgcagcc gctgatcctc atgagtgcta tgccaaggtc 1200
ttcgacgagt tcaagcccct ggtggaggaa cctcagaacc tgattaagca gaattgtgag 1260
ctgtttgaac agctgggaga gtacaaattc cagaacgccc tgctggtgag gtatacaaag 1320
aaagtgccac aggtgagtac tcccaccctg gtggaagtct cacgcaatct ggggaaggtc 1380
ggaagcaagt gctgtaaaca cccaggcggg ggaggctcct ga 1422

<210> SEQ ID NO 82
<211> LENGTH: 531
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82
gccactatgg ctgtgatggc acctagaaca ctggtcctgc tgctgagcgg ggcactggca 60
ctgacacaga cttgggctgg agggggaggg gggtctgagg ccaaaaggat gccatgcgct 120
gaagactacc tgagtgtggt cctgaaccag ctgtgtgtgc tgcacgagaa aactcccgtg 180

```
tcagatcgcg tcactaagtg ctgtaccgag agcctggtga accggagacc ctgcttctcc    240

gccctggagg tggacgaaac atatgtccct aaagagttta atgcagaaac cttcacattt    300

cacgccgata tctgtacact gagcgagaag gaacgacaga ttaagaaaca gactgccctg    360

gtggagctgg tcaagcataa acccaaggct accaaagaac agctgaaggc agtgatggac    420

gatttcgccg cttttgtcga gaaatgctgt aaggccgacg ataaggaaac atgcttcgct    480

gaggaaggca agaaactggt ggcagcctct caggctgcac tggggctgtg a             531
```

<210> SEQ ID NO 83
<211> LENGTH: 348
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

```
gccactatgg ctgtgatggc tccaagaaca ctggtcctgc tgctgtccgg ggcactggca     60

ctgactcaga cctgggctgg ggatgctcat aaatctgagg tcgctcaccg gttcaaggac    120

ctgggggagg aaaactttaa agcactggtg ctgatcgcct tcgctcagta cctgcagcag    180

tgcccctttg aagatcacgt gaagctggtc aacgaagtga ctgagttcgc caaaacctgc    240

gtcgcagacg agagcgccga aaattgtgat aagtccctgc atacactgtt tggcgacaaa    300

ctgtgtaccg tggctacact gagagagacc ggcgggggag gcagctga                 348
```

<210> SEQ ID NO 84
<211> LENGTH: 1602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
gccactatgg ctgtgatggc acctagaacc ctggtcctgc tgctgagcgg ggcactggca     60

ctgacacaga cttgggctgg gggggggggg ggcagcggcg agatggctga ctgctgtgca    120

aaacaggagc cagaaaggaa cgaatgcttc ctgcagcaca aggacgataa ccccaatctg    180

cctagactgg tgaggcccga ggtggacgtc atgtgtacag ccttccacga taatgaggaa    240

acttttctga agaaatacct gtatgagatc gcccggagac atccttactt ctatgcacca    300

gaactgctgt tctttgccaa acgctacaag gccgctttta ccgagtgctg tcaggcagcc    360

gataaagctg catgcctgct gccaaagctg gacgagctgc gagatgaagg gaaggctagc    420

tccgcaaaac agagactgaa gtgtgctagc ctgcagaaat tcggagagcg agccttcaag    480

gcatgggcag tggctcgact gtcccagcga ttccctaagg ccgagtttgc tgaagtgtct    540

aaactggtca ccgacctgac aaaggtgcac accgagtgct gtcatggcga cctgctggaa    600

tgcgccgacg atcgcgcaga tctggccaag tacatctgtg agaaccagga cagcatttct    660

agtaagctga aagagtgctg tgaaaaacct ctgctggaga agtcccactg catcgccgag    720

gtggaaaacg acgaaatgcc agctgatctg ccctcactgg ccgctgactt tgtggagagc    780

aaagatgtct gtaagaatta cgcagaagcc aaggatgtgt tcctgggcat gtttctgtac    840

gagtatgcca ggcgccaccc tgactactcc gtggtcctgc tgctgaggct ggctaaaacc    900

tatgagacca cactggaaaa gtgctgtgca gccgctgatc cacatgagtg ctatgccaaa    960
```

```
gtgttcgacg agttcaagcc cctggtcgag gaacctcaga acctgatcaa gcagaattgt   1020

gagctgttcg aacagctggg ggagtacaag tttcagaacg ccctgctggt gagatataca   1080

aagaaagtgc cacaggtctc cactcccacc ctggtggagg tctctaggaa tctgggcaaa   1140

gtggggagta aatgctgtaa gcaccctgag gccaagcgca tgccatgcgc tgaagattac   1200

ctgagtgtgg tcctgaatca gctgtgtgtg ctgcatgaga aaacaccagt gtcagaccgg   1260

gtcactaagt gctgtaccga atcactggtg aaccgacgac catgcttcag cgcactggag   1320

gtggatgaaa cttatgtccc taaggagttt aatgctgaaa cattcacttt tcacgcagac   1380

atctgcaccc tgtctgagaa ggaaagacag attaagaaac agacagccct ggtggagctg   1440

gtcaagcata aacccaaggc cactaaagaa cagctgaagg ctgtgatgga cgatttcgca   1500

gcctttgtcg agaaatgctg taaggcagac gataaggaaa cctgcttcgc cgaggaagga   1560

aagaaactgg tggctgcaag tcaggccgct ctgggcctgt ga                      1602
```

<210> SEQ ID NO 85
<211> LENGTH: 612
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
gccactatgg ccgtgatggc acctcgaaca ctggtcctgc tgctgtccgg ggcactggca     60

ctgactcaga cctgggctgg agatgctcat aaatctgagg tcgctcaccg gttcaaggac    120

ctgggcgagg aaaactttaa agcactggtg ctgatcgcat tcgcccagta cctgcagcag    180

tgcccctttg aggatcacgt gaagctggtc aacgaagtga ctgagttcgc aaaaacctgc    240

gtcgctgacg agagcgcaga aaattgtgat aagtccctgc ataccctgtt tggggacaaa    300

ctgtgtaccg tggctacact gcgagagaca tatggagaaa tggccgattg ctgtgctaag    360

caggagcctg aaagaaacga gtgcttcctg cagcataaag acgataaccc caatctgcct    420

aggctggtgc gcccagaagt ggacgtcatg tgtacagcct tccacgataa tgaggaaact    480

tttctgaaga aatacctgta tgagattgct cggagacatc catactttta tgcacccgaa    540

ctgctgttct ttgccaagcg gtacaaagcc gctttcaccg agtgctgtca ggccggcggg    600

ggaggcagct ga                                                        612
```

<210> SEQ ID NO 86
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 86

```
gccactatgg ctgtgatggc tcctagaacc ctggtcctgc tgctgtccgg ggcactggca     60

ctgactcaga cttgggctgg gggggggggg gggtctgccg ataaagccgc ttgcctgctg    120

cccaagctgg acgagctgag agatgaaggg aaggccagct ccgctaaaca gaggctgaag    180

tgtgcaagtc tgcagaaatt cggagagagg gcctttaagg cttgggcagt ggcacgactg    240

tcccagcgat tccctaaggc agagtttgcc gaagtgtcta aactggtcac cgacctgaca    300

aaggtgcaca ccgagtgctg tcatggcgac ctgctggaat gcgccgacga tcgcgctgat    360

ctggcaaagt acatctgtga gaaccaggac agcatttcta gtaagctgaa agagtgctgt    420
```

```
gaaaaacctc tgctggagaa gtcccactgc atcgctgagg tggaaaacga cgaaatgccc    480
gcagatctgc cttcactggc agccgacttc gtggagagca aagatgtctg taagaattac    540
gctgaagcaa aggatgtgtt cctgggcatg tttctgtacg agtatgcccg gagacaccct    600
gactactccg tggtcctgct gctgaggctg gctaaaacat atgagaccac actggaaaag    660
tgctgtgctg cagccgatcc acatgagtgc tatgccaaag tgttcgacga gttcaagcca    720
ctggtcgagg aaccccagaa cctgatcaag cagaattgtg agctgttcga acagctgggg    780
gagtacaagt ttcagaacgc cctgctggtg cggtatacta agaaagtgcc tcaggtctcc    840
actccaaccc tggtggaggt ctctcgcaat ctgggcaaag tggggagtaa atgctgtaag    900
caccccgagg ccaagcgaat gccttgcgct gaagattacc tgagtgtggt cctgaatcag    960
ctgtgtgtgc tgcatgagaa aactccagtg tcagaccggg tcactaagtg ctgtaccgag   1020
tcactggtga acaggcgacc atgcttcagc gcactggagg tggatgaaac ctatgtcccc   1080
aaggagttta atgcagaaac attcactttc cacgccgaca tctgtacact gagcgagaag   1140
gaaagacaga ttaagaaaca gactgccctg gtggagctgg tcaagcataa acccaaggct   1200
accaaagaac agctgaaggc agtgatggac gatttcgctg catttgtcga gaaatgctgt   1260
aaggccgacg ataaggaaac atgctttgct gaggaaggaa agaaactggt ggccgctagc   1320
caggcagccc tgggcctgtg a                                             1341
```

<210> SEQ ID NO 87
<211> LENGTH: 942
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
gccactatgg ccgtgatggc acctagaacc ctggtcctgc tgctgagcgg ggcactggca     60
ctgacacaga cttgggctgg ggatgcacat aaaagcgagg tcgctcaccg gttcaaggat    120
ctgggcgagg aaaactttaa agcactggtg ctgatcgcct tcgctcagta cctgcagcag    180
tgcccctttg aagaccacgt gaagctggtc aacgaggtga cagagttcgc caaaacttgc    240
gtcgcagacg agtcagccga aaattgtgat aagagcctgc atactctgtt tggggataaa    300
ctgtgtaccg tggccacact gcgcgagacc tatggagaaa tggctgactg ctgtgcaaag    360
caggagcctg aacgaaacga gtgcttcctg cagcataaag acgataaccc caatctgcct    420
aggctggtgc gcccagaagt ggacgtcatg tgtaccgctt tccacgataa tgaggaaaca    480
tttctgaaga aatacctgta tgagattgcc cggagacatc catactttta tgcccccgaa    540
ctgctgttct ttgctaagag atacaaagcc gctttcacag agtgctgtca ggcagccgat    600
aaggctgcat gcctgctgcc caaactggac gagctgagag atgaaggcaa ggcaagctcc    660
gccaagcaga ggctgaaatg tgcatctctg cagaagttcg gggagagggc ctttaaagca    720
tgggcagtgg ctcgactgtc ccagcgattc cctaaggctg agtttgcaga agtctctaag    780
ctggtgactg acctgaccaa agtgcacacc gagtgctgtc atggcgacct gctggaatgc    840
gccgacgatc gcgccgatct ggctaagtat atctgtgaga atcaggacag tatttctagt    900
aagctgaaag agtgctgtga aaagggcggg ggaggctcct ga                       942
```

<210> SEQ ID NO 88
<211> LENGTH: 1011

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88
gccactatgg ctgtgatggc tccaagaacc ctggtgctgc tgctgtccgg ggctctggct 60
ctgactcaga cctgggccgg gggggggggg ggaagccccc tgctggagaa gtcccactgc 120
atcgccgagg tggaaaacga cgaaatgccc gctgatctgc cttctctggc cgctgacttc 180
gtggagagta aagatgtctg taagaattac gcagaagcca aggacgtgtt cctggggatg 240
tttctgtacg agtatgcacg gagacaccct gattactccg tggtcctgct gctgcgcctg 300
gccaaaactt atgagaccac actggaaaag tgctgtgcag ccgctgaccc acatgagtgc 360
tatgctaaag tgttcgatga gttcaagcca ctggtcgagg aaccccagaa cctgatcaag 420
cagaattgtg agctgttcga acagctgggc gagtacaagt ttcagaacgc cctgctggtg 480
cgatatacaa agaaagtgcc tcaggtctca actccaaccc tggtggaggt cagccgaaat 540
ctgggcaaag tggggtccaa atgctgtaag caccccgagg ctaagcggat gccttgcgca 600
gaagactacc tgtcagtggt cctgaaccag ctgtgtgtgc tgcatgagaa aacccccgtg 660
agcgatagag tcaccaagtg ctgtacagag tctctggtga acaggcgccc atgcttcagt 720
gccctggagg tggacgaaac atatgtcccc aaagagttta atgccgaaac attcactttt 780
cacgctgata tctgtactct gtccgagaag gaaaggcaga ttaagaaaca gaccgccctg 840
gtggagctgg tcaagcataa acctaaggca acaaaagaac agctgaaggc cgtgatggac 900
gatttcgcag cctttgtcga gaaatgctgt aaggctgacg ataaggaaac ttgctttgca 960
gaggaaggaa agaaactggt ggctgcatct caggccgctc tgggcctgtg a 1011

<210> SEQ ID NO 89
<211> LENGTH: 441
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89
gccactatgg ctgtcatggc tccaagaaca ctggtcctgc tgctgtccgg ggcactggca 60
ctgactcaga cctgggctgg ggatgctcac aagtctgagg tcgcccacag gttcaaggac 120
ctgggcgagg aaaactttaa agctctggtg ctgatcgcct tcgctcagta cctgcagcag 180
tgcccatttg aagatcacgt gaagctggtc aacgaagtga ctgagttcgc caaaacctgc 240
gtcgcagacg agagcgccga aaattgtgat aagtccctgc atacactgtt tggggacaaa 300
ctgtgcaccg tggccacact gcgggagacc tatggagaaa tggctgattg ctgtgcaaag 360
caggagcccg aacggaatga gtgtttcctg cagcataaag acgataaccc caatctgcct 420
agaggcgggg gaggcagctg a 441

<210> SEQ ID NO 90
<211> LENGTH: 1512
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

-continued

```
gccactatgg ctgtgatggc acctagaaca ctggtcctgc tgctgagcgg ggcactggca     60
ctgacacaga cttgggccgg gggagggga gggagcctgg tgaggcccga ggtggacgtc    120
atgtgcacag ccttccacga taacgaggaa acttttctga agaaatacct gtatgagatc    180
gcccggagac atccatactt ctatgccccc gaactgctgt tctttgctaa acgctacaag    240
gccgctttta ccgagtgctg tcaggcagcc gataaagctg catgcctgct gccaaagctg    300
gacgagctgc gcgatgaagg gaaggctagc tccgcaaaac agcgactgaa gtgtgcaagc    360
ctgcagaaat tcggagagcg agcttttaag gcatgggccg tggctagact gtcccagagg    420
ttccccaagg ccgagtttgc tgaagtgtct aaactggtca ccgacctgac aaaggtgcac    480
accgagtgct gtcatggcga cctgctggaa tgcgccgacg atcgcgcaga tctggccaag    540
tacatctgtg agaatcagga cagcatttct agtaagctga aagagtgctg tgaaaaacct    600
ctgctggaga agtcccactg catcgccgag gtggaaaacg acgaaatgcc cgctgatctg    660
ccttcactgg ccgctgactt cgtggagagc aaagatgtct gtaagaatta cgcagaagcc    720
aaggatgtgt tcctgggcat gtttctgtac gagtatgcaa ggcgacaccc agactactcc    780
gtggtcctgc tgctgaggct ggctaaaacc tatgagacca cactggaaaa gtgctgtgca    840
gccgctgatc ctcatgagtg ctatgccaaa gtgttcgacg agttcaagcc tctggtcgag    900
gaaccacaga acctgatcaa gcagaattgt gagctgttcg aacagctggg ggagtacaag    960
tttcagaacg ccctgctggt gcgctataca aagaaagtgc cccaggtctc cactcctacc   1020
ctggtggagg tctctcggaa tctgggcaaa gtggggagta aatgctgtaa gcacccagag   1080
gctaagagaa tgccctgcgc agaagattac ctgagtgtgg tcctgaacca gctgtgtgtg   1140
ctgcatgaga aaacacctgt gtcagaccgg gtcactaagt gctgtaccga atcactggtg   1200
aaccgacggc cttgcttcag cgccctggag gtggatgaaa cttatgtccc aaaggagttt   1260
aatgcagaaa cattcacttt tcacgccgac atctgtaccc tgtctgagaa ggaaagacag   1320
attaagaaac agacagccct ggtggagctg gtcaagcata aaccaaaggc tactaaagaa   1380
cagctgaagg cagtgatgga cgatttcgca gcctttgtcg agaaatgctg taaggccgac   1440
gataaggaaa cctgcttcgc tgaggaagga aagaaactgg tggctgcaag tcaggccgct   1500
ctgggcctgt ga                                                       1512
```

<210> SEQ ID NO 91
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
tcaagcgagc tgacccagga ccccgccgtg agcgtcgcac tggggcagac cgtgcgcatc     60
acatgccagg gagatagcct gcgatcctac tatgcatctt ggtaccagca gaagccagga    120
caggcacctg tgctggtcat ctatgggaaa aacaatagac catcaggcat ccccgacagg    180
ttcagcggaa gctcctctgg caacacagct tctctgacca ttacaggcgc acaggccgag    240
gacgaagcag attactattg caacagtcgg gatagttcag ggaatcacgt ggtctttgga    300
ggaggaacta agctgaccgt gggaggagga tcaggaggag gaagcggagg aggcagcgga    360
ggaggatctg gaggaggaag tggagaggtg cagctggtcg aaagcggagg aggagtggtc    420
cgacctggag ggtcactgcg actgagctgt gcagcttccg gcttcacatt tgacgattac    480
```

gggatgtcat gggtgagaca ggccccaggg aaaggactgg aatgggtctc cggcatcaac 540
tggaatggag gctctactgg atacgccgac agtgtgaagg gcaggttcac catttcccgc 600
gataacgcta aaaattctct gtatctgcag atgaacagtc tgagggccga ggacactgcc 660
gtgtactatt gtgcccgggg cagatccctg ctgtttgatt actggggcca ggggacactg 720
gtgactgtct ctcgcggcag tgaaaatctg tattttcag 759

<210> SEQ ID NO 92
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Val Phe Gly Gly Gly Thr Lys Leu Thr Val Gly Gly Gly Ser Gly
100 105 110

Gly Gly Ser Gly Gly Gly Ser Gly Gly Gly Ser Gly Gly Gly Ser Gly
115 120 125

Glu Val Gln Leu Val Glu Ser Gly Gly Gly Val Val Arg Pro Gly Gly
130 135 140

Ser Leu Arg Leu Ser Cys Ala Ala Ser Gly Phe Thr Phe Asp Asp Tyr
145 150 155 160

Gly Met Ser Trp Val Arg Gln Ala Pro Gly Lys Gly Leu Glu Trp Val
165 170 175

Ser Gly Ile Asn Trp Asn Gly Gly Ser Thr Gly Tyr Ala Asp Ser Val
180 185 190

Lys Gly Arg Phe Thr Ile Ser Arg Asp Asn Ala Lys Asn Ser Leu Tyr
195 200 205

Leu Gln Met Asn Ser Leu Arg Ala Glu Asp Thr Ala Val Tyr Tyr Cys
210 215 220

Ala Arg Gly Arg Ser Leu Leu Phe Asp Tyr Trp Gly Gln Gly Thr Leu
225 230 235 240

Val Thr Val Ser Arg Gly Ser Glu Asn Leu Tyr Phe Gln
245 250

<210> SEQ ID NO 93
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
gacatccaga tgacccagtc tccatcctcc ctgtctgcat ctgtaggaga cagagtcacc     60

atcacttgcc gggcaagtca ggacgttaac accgctgtag cttggtatca gcagaaacca    120

gggaaagccc ctaagctcct gatctattct gcatcctttt tgtacagtgg ggtcccatca    180

aggttcagtg gcagtcgatc tgggacagat ttcactctca ccatcagcag tctgcaacct    240

gaagattttg caacttacta ctgtcaacag cattacacta ccccacccac tttcggccaa    300

gggaccaaag tggagatcaa aggtggttct ggtggtggtt ctggtggtgg ttctggtggt    360

ggttctggtg gtggttctgg tgaagtgcag ctggtggagt ctgggggagg cttggtacag    420

cctggcgggt ccctgagact ctcctgtgca gcctctggat tcaacattaa agatacttat    480

atccactggg tccggcaagc tccagggaag ggcctggagt gggtcgcacg tatttatccc    540

acaaatggtt acacacggta tgcggactct gtgaagggcc gattcaccat ctccgcagac    600

acttccaaga acaccgcgta tctgcaaatg aacagtctga gagctgagga cacggccgtt    660

tattactgtt caagatgggg cggagacggt ttctacgcta tggactactg gggccaaggg    720

accctggtca ccgtctcctc aggcagcgag aacctgtatt ttcag                    765
```

<210> SEQ ID NO 94
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
```

-continued

```
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Ser Glu Asn Leu Tyr Phe Gln
                245                 250                 255


<210> SEQ ID NO 95
<211> LENGTH: 1767
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

agtagcgaac tgacacagga ccccgcagtg agcgtcgcac tgggacagac agtgcgaatc     60

acttgccagg gggactcact gcggagctac tatgcctcct ggtaccagca gaaaccaggc    120

caggctcccg tgctggtcat ctatggcaag aacaataggc ctagtgggat tccagatcgc    180

ttttcaggga gctcctctgg aaacactgca agtctgacca ttacaggcgc tcaggcagag    240

gacgaagccg attactattg caacagcagg gacagttcag ggaatcacgt ggtcttcgga    300

ggaggaacta agctgaccgt gggaggaggc agcggaggag gatctggagg aggaagtgga    360

ggaggatcag gaggaggaag cggagaggtg cagctggtcg aaagcggagg aggagtggtc    420

cggccaggag ggtccctgag actgtcttgt gccgctagtg gattcacttt tgacgattac    480

ggaatgtcat gggtccggca ggcacctggc aagggactgg agtgggtgag cggcatcaac    540

tggaatggag gctccacagg gtacgctgat tctgtgaaag gacgctttac tattagccga    600

gacaacgcca agaacagcct gtatctgcag atgaactctc tgagagctga ggataccgca    660

gtgtactatt gcgccagggg ccgctctctg ctgttcgact actggggaca gggcacactg    720

gtgactgtct cacgcggggg aagcggggat gctcacaagt ccgaggtcgc acatcgattc    780

aaagacctgg gagaggaaaa ttttaaggcc ctggtgctga tcgccttcgc tcagtatctg    840

cagcagtgcc cttttgaaga ccacgtgaaa ctggtcaacg aggtgaccga gttcgccaag    900

acatgcgtgg ccgacgagag tgctgaaaat tgtgataaat cactgcatac cctgtttgga    960

gataagctgt gtaccgtggc cacactgcgg gagacatacg gcgaaatggc agactgctgt   1020

gccaaacagg agcctgaaag aaacgagtgc ttcctgcagc acaaggacga taaccccaat   1080

ctgcctcgac tggtgcggcc agaagtggac gtcatgtgta ctgctttcca cgataatgag   1140

gaaacctttc tgaagaaata cctgtatgag attgcccgga gacatccata cttttatgcc   1200

cccgaactgc tgttctttgc taagcgctat aaagcagcct tcaccgagtg ctgtcaggct   1260

gcagataagg ccgcttgcct gctgccaaaa ctggacgagc tgagagatga aggcaaagca   1320

agctccgcca agcagaggct gaaatgtgca agcctgcaga agttcggcga gagggccttt   1380

aaagcatggg ccgtggctag actgtctcag aggttcccca aggctgagtt tgcagaagtc   1440

agtaagctgg tgactgacct gaccaaagtg cacacagagt gctgtcatgg cgacctgctg   1500

gaatgcgccg acgatcgcgc cgatctggct aagtacatct gtgagaacca ggactccatt   1560

tctagtaagc tgaaagagtg ctgtgaaaag ccactgctgg agaaatctca ttgcatcgct   1620

gaggtggaaa atgacgaaat gcccgcagat ctgcctagcc tggcagccga cttcgtcgag   1680

tccaaggatg tgtgtaaaaa ctatgccgag gctaaagatg tgtttctggg aatgtttctg   1740

tatgagtatg caagagcatg aggatcc                                       1767
```

-continued

<210> SEQ ID NO 96
<211> LENGTH: 586
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Val Phe Gly Gly Gly Thr Lys Leu Thr Val Gly Gly Gly Ser Gly
100 105 110

Gly Gly Ser Gly Gly Gly Ser Gly Gly Gly Ser Gly Gly Gly Ser Gly
115 120 125

Glu Val Gln Leu Val Glu Ser Gly Gly Gly Val Val Arg Pro Gly Gly
130 135 140

Ser Leu Arg Leu Ser Cys Ala Ala Ser Gly Phe Thr Phe Asp Asp Tyr
145 150 155 160

Gly Met Ser Trp Val Arg Gln Ala Pro Gly Lys Gly Leu Glu Trp Val
165 170 175

Ser Gly Ile Asn Trp Asn Gly Gly Ser Thr Gly Tyr Ala Asp Ser Val
180 185 190

Lys Gly Arg Phe Thr Ile Ser Arg Asp Asn Ala Lys Asn Ser Leu Tyr
195 200 205

Leu Gln Met Asn Ser Leu Arg Ala Glu Asp Thr Ala Val Tyr Tyr Cys
210 215 220

Ala Arg Gly Arg Ser Leu Leu Phe Asp Tyr Trp Gly Gln Gly Thr Leu
225 230 235 240

Val Thr Val Ser Arg Gly Gly Ser Gly Asp Ala His Lys Ser Glu Val
245 250 255

Ala His Arg Phe Lys Asp Leu Gly Glu Glu Asn Phe Lys Ala Leu Val
260 265 270

Leu Ile Ala Phe Ala Gln Tyr Leu Gln Gln Cys Pro Phe Glu Asp His
275 280 285

Val Lys Leu Val Asn Glu Val Thr Glu Phe Ala Lys Thr Cys Val Ala
290 295 300

Asp Glu Ser Ala Glu Asn Cys Asp Lys Ser Leu His Thr Leu Phe Gly
305 310 315 320

Asp Lys Leu Cys Thr Val Ala Thr Leu Arg Glu Thr Tyr Gly Glu Met
325 330 335

Ala Asp Cys Cys Ala Lys Gln Glu Pro Glu Arg Asn Glu Cys Phe Leu
340 345 350

Gln His Lys Asp Asp Asn Pro Asn Leu Pro Arg Leu Val Arg Pro Glu
355 360 365

Val Asp Val Met Cys Thr Ala Phe His Asp Asn Glu Glu Thr Phe Leu
370 375 380

Lys Lys Tyr Leu Tyr Glu Ile Ala Arg Arg His Pro Tyr Phe Tyr Ala
385 390 395 400

Pro Glu Leu Leu Phe Phe Ala Lys Arg Tyr Lys Ala Ala Phe Thr Glu
405 410 415

Cys Cys Gln Ala Ala Asp Lys Ala Ala Cys Leu Leu Pro Lys Leu Asp
420 425 430

Glu Leu Arg Asp Glu Gly Lys Ala Ser Ser Ala Lys Gln Arg Leu Lys
435 440 445

Cys Ala Ser Leu Gln Lys Phe Gly Glu Arg Ala Phe Lys Ala Trp Ala
450 455 460

Val Ala Arg Leu Ser Gln Arg Phe Pro Lys Ala Glu Phe Ala Glu Val
465 470 475 480

Ser Lys Leu Val Thr Asp Leu Thr Lys Val His Thr Glu Cys Cys His
485 490 495

Gly Asp Leu Leu Glu Cys Ala Asp Asp Arg Ala Asp Leu Ala Lys Tyr
500 505 510

Ile Cys Glu Asn Gln Asp Ser Ile Ser Ser Lys Leu Lys Glu Cys Cys
515 520 525

Glu Lys Pro Leu Leu Glu Lys Ser His Cys Ile Ala Glu Val Glu Asn
530 535 540

Asp Glu Met Pro Ala Asp Leu Pro Ser Leu Ala Ala Asp Phe Val Glu
545 550 555 560

Ser Lys Asp Val Cys Lys Asn Tyr Ala Glu Ala Lys Asp Val Phe Leu
565 570 575

Gly Met Phe Leu Tyr Glu Tyr Ala Arg Ala
580 585

<210> SEQ ID NO 97
<211> LENGTH: 1797
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 97
gatgctcata aatctgaggt cgctcaccgg ttcaaggatc tgggcgagga aaactttaaa 60
gcactggtgc tgatcgcttt cgcacagtac ctgcagcagt gccccttga ggaccacgtg 120 aagctggtca acgaggtgac agagttcgcc aaaacttgcg tcgccgacga gtctgctgaa 180
aattgtgata agagtctgca tacactgttt ggagataaac tgtgtactgt ggccaccctg 240
agagagactt atggcgaaat ggcagactgc tgtgccaagc aggagcctga aaggaacgag 300
tgcttcctgc agcataaaga cgataacccc aatctgccta ggctggtgcg cccagaagtg 360
gacgtcatgt gtaccgcctt ccacgataat gaggaaacat ttctgaagaa atacctgtat 420
gagattgccc ggagacatcc atacttttat gcacccgaac tgctgttctt tgccaagaga 480
tacaaagccg ctttcaccga gtgctgtcag gcagccgata aggctgcatg cctgctgcca 540
aaactggacg agctgcgaga tgaagggaag gccagctccg ctaagcagcg gctgaaatgt 600
gctagcctgc agaagttcgg agagcgagcc ttcaaggcat gggctgtggc acgactgtcc 660
cagcggttcc ccaaagcaga gtttgccgaa gtctctaagc tggtgacaga cctgactaaa 720
gtgcacaccg agtgctgtca tggcgacctg ctggaatgcg ccgacgatcg agctgatctg 780
gcaaagtaca tctgtgagaa tcaggacagc atttctagta agctgaaaga gtgctgtgaa 840
aagcctctgc tggagaaatc ccactgcatc gccgaggtgg aaaacgacga aatgccagct 900
gatctgccct cactggccgc tgactttgtc gagagcaagg atgtgtgtaa aaattatgcc 960
gaagctaagg atgtgttcct gggcatgttt ctgtacgagt atgcaagggc aggagggtcc 1020
ggaggctctg gaggaagtgg agggtcagga ggctcaagcg aactgactca ggaccccgct 1080
gtgagcgtcg cactgggaca gactgtgagg atcacctgcc agggggacag cctgcgctcc 1140
tactatgcat cctggtacca gcagaagcct ggccaggccc cagtgctggt catctatggc 1200
aaaaacaatc ggccctcagg gattcctgat cggttcagcg ggtcctctag tggaaacaca 1260
gcttctctga ccattacagg cgctcaggca gaggacgaag ccgattacta ttgcaacagc 1320
cgcgactcaa gcgggaatca tgtggtcttc ggaggaggaa ccaagctgac agtgggagga 1380
ggctctggag gaggcagtgg gggaggctca ggaggaggca gcggaggagg ctccggagag 1440
gtccagctgg tggaaagcgg aggaggagtg gtccgcccag gaggatctct gcgactgagt 1500
tgtgcagcct caggattcac ctttgacgat tacggaatga gttgggtccg gcaggcacct 1560
ggaaagggac tggagtgggt gagcggcatc aactggaatg gcgggagcac tgggtacgct 1620
gattccgtga agggaagatt caccatttcc agggacaacg ccaaaaattc tctgtatctg 1680
cagatgaata gtctgagagc cgaggacaca gctgtgtact attgcgccag ggggaggtct 1740
ctgctgttcg actactgggg gcagggcact ctggtcactg tgtcaagatg aggatcc 1797

<210> SEQ ID NO 98
<211> LENGTH: 596
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Cys Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

Ser Leu His Thr Leu Phe Gly Asp Lys Leu Cys Thr Val Ala Thr Leu
65 70 75 80

Arg Glu Thr Tyr Gly Glu Met Ala Asp Cys Cys Ala Lys Gln Glu Pro
85 90 95

Glu Arg Asn Glu Cys Phe Leu Gln His Lys Asp Asp Asn Pro Asn Leu
100 105 110

Pro Arg Leu Val Arg Pro Glu Val Asp Val Met Cys Thr Ala Phe His
115 120 125

Asp Asn Glu Glu Thr Phe Leu Lys Lys Tyr Leu Tyr Glu Ile Ala Arg
130 135 140

Arg His Pro Tyr Phe Tyr Ala Pro Glu Leu Leu Phe Phe Ala Lys Arg
145 150 155 160

Tyr Lys Ala Ala Phe Thr Glu Cys Cys Gln Ala Ala Asp Lys Ala Ala
165 170 175

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Ala Gly Gly Ser Gly Gly Ser Gly Gly Ser Gly Gly Ser Gly Gly Ser
            340                 345                 350

Ser Glu Leu Thr Gln Asp Pro Ala Val Ser Val Ala Leu Gly Gln Thr
        355                 360                 365

Val Arg Ile Thr Cys Gln Gly Asp Ser Leu Arg Ser Tyr Tyr Ala Ser
    370                 375                 380

Trp Tyr Gln Gln Lys Pro Gly Gln Ala Pro Val Leu Val Ile Tyr Gly
385                 390                 395                 400

Lys Asn Asn Arg Pro Ser Gly Ile Pro Asp Arg Phe Ser Gly Ser Ser
                405                 410                 415

Ser Gly Asn Thr Ala Ser Leu Thr Ile Thr Gly Ala Gln Ala Glu Asp
            420                 425                 430

Glu Ala Asp Tyr Tyr Cys Asn Ser Arg Asp Ser Ser Gly Asn His Val
        435                 440                 445

Val Phe Gly Gly Gly Thr Lys Leu Thr Val Gly Gly Gly Ser Gly Gly
    450                 455                 460

Gly Ser Gly Gly Gly Ser Gly Gly Gly Ser Gly Gly Gly Ser Gly Glu
465                 470                 475                 480

Val Gln Leu Val Glu Ser Gly Gly Gly Val Val Arg Pro Gly Gly Ser
                485                 490                 495

Leu Arg Leu Ser Cys Ala Ala Ser Gly Phe Thr Phe Asp Asp Tyr Gly
            500                 505                 510

Met Ser Trp Val Arg Gln Ala Pro Gly Lys Gly Leu Glu Trp Val Ser
        515                 520                 525

Gly Ile Asn Trp Asn Gly Gly Ser Thr Gly Tyr Ala Asp Ser Val Lys
    530                 535                 540

Gly Arg Phe Thr Ile Ser Arg Asp Asn Ala Lys Asn Ser Leu Tyr Leu
545                 550                 555                 560

Gln Met Asn Ser Leu Arg Ala Glu Asp Thr Ala Val Tyr Tyr Cys Ala
                565                 570                 575

Arg Gly Arg Ser Leu Leu Phe Asp Tyr Trp Gly Gln Gly Thr Leu Val
            580                 585                 590

Thr Val Ser Arg
```

595

<210> SEQ ID NO 99
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
tcctccgagc tgacccagga ccctgccgtg tccgtcgctc tgggacagac cgtgcggatc 60
acatgccagg gagatagcct gagatcctac tatgctagct ggtaccagca gaaacccggc 120
caggcacctg tgctggtcat ctatgggaag aacaatcgcc catctggcat ccccgaccga 180
ttcagtggaa gctcctctgg caacacagcc tctctgacta ttaccggcgc tcaggcagag 240
gacgaagctg attactattg caacagcagg gatagttcag ggaatcacgt ggtctttgga 300
ggaggaacta agctgaccgt gggaggagga tctggaggag gaagtggcgg gggatcagga 360
ggaggaagcg gaggaggcag cggagaggtg cagctggtcg aaagcggagg aggagtggtc 420
agaccaggag ggtctctgag gctgagttgt gccgcttcag gcttcacctt tgacgattac 480
ggaatgtctt gggtgcggca ggcacctgga aagggactgg agtgggtgag tggcatcaac 540
tggaatggag gcagcacagg atacgcagac tccgtgaaag gccgattcac tatttcacgg 600
gataacgcca agaatagcct gtatctgcag atgaacagcc tgagagcaga ggacacagcc 660
gtgtactatt gtgccagggg ccgctctctg ctgtttgatt actgggggca gggaacactg 720
gtgactgtca gccgaggagg atctggaggg agtggaggct caggaggaag cggagggtcc 780
gtggtcctgc tgctgcgact ggctaaaact tacgagacca cactggaaaa gtgctgtgca 840
gccgctgacc cccatgagtg ctatgcaaaa gtgttcgatg agttcaagcc tctggtcgag 900
gaaccacaga acctgatcaa acagaattgt gagctgttcg aacagctggg cgagtacaag 960
tttcagaacg ccctgctggt gagatatacc aagaaagtgc cccaggtctc tacacctact 1020
ctggtggagg tcagtaggaa tctgggcaaa gtggggtcaa aatgctgtaa gcacccagag 1080
gctaagcgca tgccctgcgc agaagactac ctgagcgtgg tcctgaacca gctgtgtgtg 1140
ctgcatgaga aaactccagt gtccgatagg gtcactaagt gctgtaccga aagcctggtg 1200
aaccggagac cttgcttctc cgccctggag gtggacgaaa cctatgtccc aaaagagttt 1260
aatgccgaaa ccttcacatt tcacgctgat atctgtaccc tgtccgagaa ggaacgccag 1320
attaagaaac agacagctct ggtggagctg gtcaagcata aacccaaggc aacaaaagaa 1380
cagctgaagg ccgtgatgga cgatttcgca gcctttgtgg agaaatgctg taaggccgac 1440
gataaggaaa cttgctttgc tgaagaaggg aagaaactgg tcgccgcatc acaggctgct 1500
ctgggactgt gaggatcc 1518

<210> SEQ ID NO 100
<211> LENGTH: 503
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Ser Ser Glu Leu Thr Gln Asp Pro Ala Val Ser Val Ala Leu Gly Gln
1 5 10 15

-continued

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Val Phe Gly Gly Gly Thr Lys Leu Thr Val Gly Gly Gly Ser Gly
100 105 110

Gly Gly Ser Gly Gly Gly Ser Gly Gly Gly Ser Gly Gly Gly Ser Gly
115 120 125

Glu Val Gln Leu Val Glu Ser Gly Gly Gly Val Val Arg Pro Gly Gly
130 135 140

Ser Leu Arg Leu Ser Cys Ala Ala Ser Gly Phe Thr Phe Asp Asp Tyr
145 150 155 160

Gly Met Ser Trp Val Arg Gln Ala Pro Gly Lys Gly Leu Glu Trp Val
165 170 175

Ser Gly Ile Asn Trp Asn Gly Gly Ser Thr Gly Tyr Ala Asp Ser Val
180 185 190

Lys Gly Arg Phe Thr Ile Ser Arg Asp Asn Ala Lys Asn Ser Leu Tyr
195 200 205

Leu Gln Met Asn Ser Leu Arg Ala Glu Asp Thr Ala Val Tyr Tyr Cys
210 215 220

Ala Arg Gly Arg Ser Leu Leu Phe Asp Tyr Trp Gly Gln Gly Thr Leu
225 230 235 240

Val Thr Val Ser Arg Gly Gly Ser Gly Gly Ser Gly Gly Ser Gly Gly
245 250 255

Ser Gly Gly Ser Val Val Leu Leu Leu Arg Leu Ala Lys Thr Tyr Glu
260 265 270

Thr Thr Leu Glu Lys Cys Cys Ala Ala Ala Asp Pro His Glu Cys Tyr
275 280 285

Ala Lys Val Phe Asp Glu Phe Lys Pro Leu Val Glu Glu Pro Gln Asn
290 295 300

Leu Ile Lys Gln Asn Cys Glu Leu Phe Glu Gln Leu Gly Glu Tyr Lys
305 310 315 320

Phe Gln Asn Ala Leu Leu Val Arg Tyr Thr Lys Lys Val Pro Gln Val
325 330 335

Ser Thr Pro Thr Leu Val Glu Val Ser Arg Asn Leu Gly Lys Val Gly
340 345 350

Ser Lys Cys Cys Lys His Pro Glu Ala Lys Arg Met Pro Cys Ala Glu
355 360 365

Asp Tyr Leu Ser Val Val Leu Asn Gln Leu Cys Val Leu His Glu Lys
370 375 380

Thr Pro Val Ser Asp Arg Val Thr Lys Cys Cys Thr Glu Ser Leu Val
385 390 395 400

Asn Arg Arg Pro Cys Phe Ser Ala Leu Glu Val Asp Glu Thr Tyr Val
405 410 415

Pro Lys Glu Phe Asn Ala Glu Thr Phe Thr Phe His Ala Asp Ile Cys
420 425 430

Thr Leu Ser Glu Lys Glu Arg Gln Ile Lys Lys Gln Thr Ala Leu Val 435 440 445

Glu Leu Val Lys His Lys Pro Lys Ala Thr Lys Glu Gln Leu Lys Ala
450 455 460

Val Met Asp Asp Phe Ala Ala Phe Val Glu Lys Cys Cys Lys Ala Asp
465 470 475 480

Asp Lys Glu Thr Cys Phe Ala Glu Glu Gly Lys Lys Leu Val Ala Ala
485 490 495

Ser Gln Ala Ala Leu Gly Leu
500

<210> SEQ ID NO 101
<211> LENGTH: 1518
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101
agcgtcgtcc tgctgctgag actggctaaa acatacgaga ccacactgga aaagtgctgt 60
gccgctgcag accctcacga gtgctatgcc aaagtgttcg atgagttcaa gcctctggtc 120
gaggaaccac agaacctgat caaacagaat tgtgagctgt tcgaacagct gggcgagtac 180
aagtttcaga acgccctgct ggtgaggtat actaagaaag tgccccaggt cagtactcct 240
accctggtgg aggtctcacg gaatctgggg aaagtgggaa gcaaatgctg taagcaccca 300
gaggcaaaga gaatgccctg cgccgaagac tacctgagcg tggtcctgaa ccagctgtgt 360
gtgctgcatg agaaaactcc agtgagcgat agggtcacaa agtgctgtac tgaatccctg 420
gtgaaccgga gaccttgctt ctctgccctg gaggtggacg aaacctatgt cccaaaggag 480
tttaatgctg aaacattcac ttttcacgca gatatctgta cactgagcga gaaggaacgc 540
cagattaaga aacagactgc cctggtggag ctggtcaagc ataaacccaa ggccaccaaa 600
gaacagctga aggctgtgat ggacgatttc gccgcttttg tcgagaaatg ctgtaaggca 660
gacgataagg aaacatgctt cgccgaggaa gggaagaaac tggtggcagc aagccaggct 720
gcactgggac tgggagggtc tggaggcagt ggaggatcag gagggagcgg aggcagctcc 780
gagctgaccc aggaccccgc tgtgagcgtc gcactgggac agaccgtgcg catcacatgt 840
cagggcgatt ccctgcgatc ttactatgct tcctggtacc agcagaaacc cggccaggca 900
cctgtgctgg tcatctatgg aaagaacaat agaccaagtg gcattcccga caggttctca 960
ggctctagtt cagggaacac cgcctccctg accattacag gcgcacaggc cgaggacgaa 1020
gctgattact attgcaactc tcgggatagc tccggcaatc atgtggtctt tgggggaggc 1080
actaagctga ccgtgggggg aggcagtggg ggaggctcag gaggaggcag cggaggaggc 1140
tccggaggag gctctggcga ggtgcagctg gtcgaatccg gaggaggagt ggtccgacca 1200
ggaggaagtc tgcgactgtc atgtgccgct agcgggttca cctttgacga ttacggaatg 1260
agttgggtgc gacaggcacc tggaaaggga ctggagtggg tgtctggcat caactggaat 1320
ggcgggtcca ctggctacgc agactctgtg aaagggaggt ttaccattag ccgcgataac 1380
gccaagaaca gcctgtatct gcagatgaac agcctgcgcg ccgaggacac agctgtgtac 1440
tattgcgcca gggggaggtc actgctgttt gattactggg ggcaggggac tctggtcact 1500
gtgtcacggt gaggatcc 1518

<210> SEQ ID NO 102

<211> LENGTH: 503
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Ser Val Val Leu Leu Leu Arg Leu Ala Lys Thr Tyr Glu Thr Thr Leu
1 5 10 15

Glu Lys Cys Cys Ala Ala Ala Asp Pro His Glu Cys Tyr Ala Lys Val
20 25 30

Phe Asp Glu Phe Lys Pro Leu Val Glu Glu Pro Gln Asn Leu Ile Lys
35 40 45

Gln Asn Cys Glu Leu Phe Glu Gln Leu Gly Glu Tyr Lys Phe Gln Asn
50 55 60

Ala Leu Leu Val Arg Tyr Thr Lys Lys Val Pro Gln Val Ser Thr Pro
65 70 75 80

Thr Leu Val Glu Val Ser Arg Asn Leu Gly Lys Val Gly Ser Lys Cys
85 90 95

Cys Lys His Pro Glu Ala Lys Arg Met Pro Cys Ala Glu Asp Tyr Leu
100 105 110

Ser Val Val Leu Asn Gln Leu Cys Val Leu His Glu Lys Thr Pro Val
115 120 125

Ser Asp Arg Val Thr Lys Cys Cys Thr Glu Ser Leu Val Asn Arg Arg
130 135 140

Pro Cys Phe Ser Ala Leu Glu Val Asp Glu Thr Tyr Val Pro Lys Glu
145 150 155 160

Phe Asn Ala Glu Thr Phe Thr Phe His Ala Asp Ile Cys Thr Leu Ser
165 170 175

Glu Lys Glu Arg Gln Ile Lys Lys Gln Thr Ala Leu Val Glu Leu Val
180 185 190

Lys His Lys Pro Lys Ala Thr Lys Glu Gln Leu Lys Ala Val Met Asp
195 200 205

Asp Phe Ala Ala Phe Val Glu Lys Cys Cys Lys Ala Asp Asp Lys Glu
210 215 220

Thr Cys Phe Ala Glu Glu Gly Lys Lys Leu Val Ala Ala Ser Gln Ala
225 230 235 240

Ala Leu Gly Leu Gly Gly Ser Gly Gly Ser Gly Gly Ser Gly Gly Ser
245 250 255

Gly Gly Ser Ser Glu Leu Thr Gln Asp Pro Ala Val Ser Val Ala Leu
260 265 270

Gly Gln Thr Val Arg Ile Thr Cys Gln Gly Asp Ser Leu Arg Ser Tyr
275 280 285

Tyr Ala Ser Trp Tyr Gln Gln Lys Pro Gly Gln Ala Pro Val Leu Val
290 295 300

Ile Tyr Gly Lys Asn Asn Arg Pro Ser Gly Ile Pro Asp Arg Phe Ser
305 310 315 320

Gly Ser Ser Ser Gly Asn Thr Ala Ser Leu Thr Ile Thr Gly Ala Gln
325 330 335

Ala Glu Asp Glu Ala Asp Tyr Tyr Cys Asn Ser Arg Asp Ser Ser Gly
340 345 350

Asn His Val Val Phe Gly Gly Gly Thr Lys Leu Thr Val Gly Gly Gly
355 360 365

Ser Gly Gly Gly Ser Gly Gly Gly Ser Gly Gly Gly Ser Gly Gly Gly

```
    370                 375                 380

Ser Gly Glu Val Gln Leu Val Glu Ser Gly Gly Gly Val Val Arg Pro
385                 390                 395                 400

Gly Gly Ser Leu Arg Leu Ser Cys Ala Ala Ser Gly Phe Thr Phe Asp
                405                 410                 415

Asp Tyr Gly Met Ser Trp Val Arg Gln Ala Pro Gly Lys Gly Leu Glu
            420                 425                 430

Trp Val Ser Gly Ile Asn Trp Asn Gly Gly Ser Thr Gly Tyr Ala Asp
        435                 440                 445

Ser Val Lys Gly Arg Phe Thr Ile Ser Arg Asp Asn Ala Lys Asn Ser
    450                 455                 460

Leu Tyr Leu Gln Met Asn Ser Leu Arg Ala Glu Asp Thr Ala Val Tyr
465                 470                 475                 480

Tyr Cys Ala Arg Gly Arg Ser Leu Leu Phe Asp Tyr Trp Gly Gln Gly
                485                 490                 495

Thr Leu Val Thr Val Ser Arg
            500


<210> SEQ ID NO 103
<211> LENGTH: 1773
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

gacattcaga tgacacagtc cccaagctcc ctgagcgctt ccgtcggcga tcgagtgact     60

atcacctgcc gagcctctca ggacgtcaac actgctgtgg catggtacca gcagaagcct    120

gggaaagcac caaagctgct gatctactct gccagttttc tgtattctgg agtgcccagt    180

agattctcag gaagcaggtc cggcaccgat tttacactga ctatctctag tctgcagcct    240

gaggacttcg ccacatacta ttgccagcag cactatacca cacccctac atttggacag    300

ggcactaaag tggaaattaa gggcgggtca ggcggaggga gcggaggagg gtccggagga    360

gggtctggag gagggagtgg agaggtgcag ctggtcgaat ccggaggagg actggtgcag    420

cctggaggct cactgaggct gagctgtgcc gcttccggct tcaacatcaa ggatacctac    480

attcattggg tcagacaggc tcctgggaaa ggactggagt gggtggcaag gatctatcca    540

accaatgggt acacacggta tgccgatagc gtgaagggaa gattcactat ttctgctgac    600

actagtaaaa acaccgcata cctgcagatg aatagcctga gggcagagga caccgccgtg    660

tactattgct cccgctgggg gggagacggc ttttacgcca tggattattg gggccagggg    720

accctggtga cagtctcaag cggcgggtca ggagatgcac acaaaagcga ggtcgcccat    780

cgcttcaagg acctgggcga ggaaaatttt aaagccctgg tgctgattgc cttcgctcag    840

tacctgcagc agtgcccatt cgaagaccac gtgaagctgg tcaacgaggt gaccgaattt    900

gccaaaacat gcgtcgctga cgagtccgca gaaaattgtg ataagtctct gcatacactg    960

ttcggcgata aactgtgtac tgtggccacc ctgcgcgaga cttatgggga aatggccgac   1020

tgctgtgcta agcaggagcc agaacgaaac gagtgctttc tgcagcacaa ggacgataac   1080

ccaaatctgc caaggctggt gcgcccagaa gtggacgtca tgtgtactgc tttccacgat   1140

aatgaggaaa cctttctgaa gaaatacctg tatgagatcg cccggagaca tccatacttc   1200

tatgcccccg aactgctgtt ctttgctaaa cggtacaagg cagcctttac cgagtgctgt   1260
```

-continued

```
caggctgcag ataaagccgc ttgcctgctg cctaagctgg acgagctgcg agatgaaggc   1320

aaggcatcct ctgccaaaca gcggctgaag tgtgccagcc tgcagaaatt cggggagcgg   1380

gcttttaagg catgggccgt ggctcgactg tctcagcggt tcccaaaggc tgagtttgca   1440

gaagtcagta aactggtgac agacctgact aaggtgcaca cagagtgctg tcatggcgac   1500

ctgctggaat gcgccgacga tagagccgat ctggctaagt acatctgtga gaaccaggac   1560

agcattagtt caaagctgaa agagtgctgt gaaaaacctc tgctggagaa gagccactgc   1620

atcgcagagg tggaaaatga cgaaatgccc gccgatctgc ctagtctggc agccgacttc   1680

gtcgagtcaa aagatgtgtg taagaactac gccgaagcaa aagatgtgtt tctgggaatg   1740

tttctgtatg agtatgcccg agcctgagga tcc                                 1773
```

```
<210> SEQ ID NO 104
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
                245                 250                 255

Glu Val Ala His Arg Phe Lys Asp Leu Gly Glu Glu Asn Phe Lys Ala
            260                 265                 270
```

```
Leu Val Leu Ile Ala Phe Ala Gln Tyr Leu Gln Gln Cys Pro Phe Glu
        275                 280                 285

Asp His Val Lys Leu Val Asn Glu Val Thr Glu Phe Ala Lys Thr Cys
    290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
            340                 345                 350

Phe Leu Gln His Lys Asp Asp Asn Pro Asn Leu Pro Arg Leu Val Arg
        355                 360                 365

Pro Glu Val Asp Val Met Cys Thr Ala Phe His Asp Asn Glu Glu Thr
    370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
        435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
        515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Ala
            580                 585
```

<210> SEQ ID NO 105
<211> LENGTH: 1803
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 105

```
gacgcacata agtccgaggt cgctcacagg ttcaaagatc tgggcgagga aaactttaag      60

gccctggtgc tgatcgcttt cgcacagtac ctgcagcagt gcccattcga agaccacgtg     120

aaactggtca acgaagtgac tgaatttgcc aagacctgcg tcgccgacga gtccgctgaa     180

aattgtgata aatctctgca tactctgttc ggggataagc tgtgtaccgt ggccacactg     240
```

cgcgagacct atggagaaat ggcagactgc tgtgccaaac aggagccaga acgaaacgag 300
tgctttctgc agcataagga cgataaccca aatctgccaa ggctggtgcg cccagaagtg 360
gacgtcatgt gtaccgcctt ccacgataat gaggaaacat ttctgaagaa atacctgtat 420
gagattgccc ggagacatcc atacttctat gcccccgaac tgctgttctt tgctaagcgc 480
tacaaagccg cttttaccga gtgctgtcag gcagccgata aagctgcatg cctgctgcct 540
aagctggacg agctgaggga tgaaggaaag gccagctccg ctaaacagcg cctgaagtgt 600
gcctctctgc agaaattcgg cgagcgggct tttaaggcat gggctgtcgc acgactgagc 660
cagcggttcc caaaggcaga gtttgccgaa gtctccaaac tggtgactga cctgaccaag 720
gtgcacaccg agtgctgtca tggcgacctg ctggaatgcg ccgacgatag agctgatctg 780
gcaaagtaca tctgtgagaa ccaggacagc atttctagta agctgaaaga gtgctgtgaa 840
aaacccctgc tggagaagag ccactgcatc gcagaggtgg aaaacgacga aatgcctgcc 900
gatctgccaa gtctggccgc tgacttcgtc gagtcaaaag atgtgtgtaa gaattatgcc 960
gaagctaagg atgtgttcct gggcatgttt ctgtacgagt atgcacgagc aggagggagc 1020
ggaggctccg gaggatctgg cgggagtgga ggcgacatcc agatgactca gtccccttca 1080
agcctgagtg cttcagtcgg cgatcgcgtg actattacct gccgagcctc tcaggacgtc 1140
aatacagctg tggcatggta ccagcagaag cccggcaaag ctcctaagct gctgatctac 1200
agcgcatcct ttctgtattc aggggtgccc agcagattct ctggcagtag atcagggaca 1260
gattttacac tgactatttc ctctctgcag cctgaggact tcgccactta ctattgccag 1320
cagcactata ccacaccccc tacatttgga cagggcacta aagtggaaat caagggaggc 1380
agcggaggag gatctggagg aggaagtgga ggaggatcag gaggaggaag cggagaggtc 1440
cagctggtgg aaagcggagg aggactggtg cagcctggag ggtccctgag actgtcttgt 1500
gcagccagtg gcttcaacat caaagatacc tacattcatt gggtcagaca ggctcctggg 1560
aagggactgg agtgggtggc aaggatctat ccaacaaatg gatacactcg gtatgccgat 1620
agcgtgaaag gccggttcac catttcagca gacaccagca agaacacagc ctacctgcag 1680
atgaacagcc tgcgagctga ggacacagca gtgtactatt gcagtcggtg gggcggcgat 1740
ggcttttacg ctatggacta ttgggggcag ggacactgg tgactgtgag ttcttgagga 1800
tcc 1803

<210> SEQ ID NO 106
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu

-continued

```
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Ala Gly Gly Ser Gly Gly Ser Gly Gly Ser Gly Gly Ser Gly Gly Asp
            340                 345                 350

Ile Gln Met Thr Gln Ser Pro Ser Ser Leu Ser Ala Ser Val Gly Asp
        355                 360                 365

Arg Val Thr Ile Thr Cys Arg Ala Ser Gln Asp Val Asn Thr Ala Val
    370                 375                 380

Ala Trp Tyr Gln Gln Lys Pro Gly Lys Ala Pro Lys Leu Leu Ile Tyr
385                 390                 395                 400

Ser Ala Ser Phe Leu Tyr Ser Gly Val Pro Ser Arg Phe Ser Gly Ser
                405                 410                 415

Arg Ser Gly Thr Asp Phe Thr Leu Thr Ile Ser Ser Leu Gln Pro Glu
            420                 425                 430

Asp Phe Ala Thr Tyr Tyr Cys Gln Gln His Tyr Thr Thr Pro Pro Thr
        435                 440                 445

Phe Gly Gln Gly Thr Lys Val Glu Ile Lys Gly Gly Ser Gly Gly Gly
    450                 455                 460

Ser Gly Gly Gly Ser Gly Gly Gly Ser Gly Gly Gly Ser Gly Glu Val
465                 470                 475                 480

Gln Leu Val Glu Ser Gly Gly Gly Leu Val Gln Pro Gly Gly Ser Leu
                485                 490                 495
```

```
Arg Leu Ser Cys Ala Ala Ser Gly Phe Asn Ile Lys Asp Thr Tyr Ile
            500                 505                 510

His Trp Val Arg Gln Ala Pro Gly Lys Gly Leu Glu Trp Val Ala Arg
        515                 520                 525

Ile Tyr Pro Thr Asn Gly Tyr Thr Arg Tyr Ala Asp Ser Val Lys Gly
    530                 535                 540

Arg Phe Thr Ile Ser Ala Asp Thr Ser Lys Asn Thr Ala Tyr Leu Gln
545                 550                 555                 560

Met Asn Ser Leu Arg Ala Glu Asp Thr Ala Val Tyr Tyr Cys Ser Arg
                565                 570                 575

Trp Gly Gly Asp Gly Phe Tyr Ala Met Asp Tyr Trp Gly Gln Gly Thr
            580                 585                 590

Leu Val Thr Val Ser Ser
        595


<210> SEQ ID NO 107
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

gacattcaga tgacacagag cccaagctcc ctgtccgcat ctgtgggcga ccgagtcaca     60

atcacttgcc gggcctccca ggatgtgaac actgctgtcg catggtacca gcagaaacca    120

gggaaggctc ccaaactgct gatctacagt gcatcattcc tgtatagtgg cgtgccatca    180

aggtttagcg gctcccgatc tggaaccgac ttcaccctga caatctctag tctgcagccc    240

gaggattttg ccacatacta ttgccagcag cactatacca cacccctac tttcgggcag    300

ggaaccaagg tggagatcaa gggagggagc ggaggagggt ccggaggagg gtctggaggc    360

gggagtggag gagggtcagg agaggtgcag ctggtcgaaa gcggaggagg actggtgcag    420

cctggaggca gcctgcgact gtcctgtgcc gcttctggct ttaacatcaa ggacacctac    480

attcattggg tgcggcaggc acctggcaaa ggactggagt gggtggctag aatctatcca    540

actaatggat acaccagata tgctgacagc gtgaagggca ggtttactat cagtgctgat    600

acatcaaaga acactgcata cctgcagatg aatagcctgc gcgccgagga taccgctgtg    660

tactattgta gccgatgggg gggagacggc ttctacgcca tggattattg gggacagggc    720

accctggtga cagtctcaag cggagggagt ggaggctcag gaggaagcgg agggtccgga    780

ggctctgtgg tcctgctgct gagactggct aagacctacg agactaccct ggaaaaatgc    840

tgtgcagccg ctgaccccca cgagtgctat gcaaaggtgt tcgatgagtt caagcctctg    900

gtcgaggaac cacagaacct gatcaagcag aattgtgagc tgttcgaaca gctgggcgag    960

tacaagtttc agaacgccct gctggtgagg tatacaaaga aagtgcccca ggtcagcact   1020

cctaccctgg tggaggtctc caggaatctg ggaaggtcg gatctaagtg ctgtaaacac   1080

ccagaggcaa aacgcatgcc ctgcgccgaa gactacctgt ccgtggtcct gaatcagctg   1140

tgtgtgctgc atgagaagac ccctgtgtct gatcgagtca ccaaatgctg tacagaaagt   1200

ctggtgaacc ggagaccctg cttttctgcc ctggaggtgg acgaaacata tgtccctaag   1260

gagttcaatg ccgaaacatt cacttttcac gctgatatct gtacactgtc cgagaaggaa   1320

cgccagatta agaaacagac tgctctggtg gagctggtca agcataaacc aaaggcaacc   1380
```

aaggaacagc tgaaagccgt gatggacgat ttcgcagcct ttgtcgagaa gtgctgtaaa 1440
gccgacgata aggaaacttg tttcgccgag gaaggcaaaa aactggtcgc agcatcacag 1500
gcagcactgg gactgtgagg atcc 1524

<210> SEQ ID NO 108
<211> LENGTH: 505
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 108

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Gly Gly Ser Gly Gly
100 105 110

Gly Ser Gly Gly Gly Ser Gly Gly Gly Ser Gly Gly Gly Ser Gly Glu
115 120 125

Val Gln Leu Val Glu Ser Gly Gly Gly Leu Val Gln Pro Gly Gly Ser
130 135 140

Leu Arg Leu Ser Cys Ala Ala Ser Gly Phe Asn Ile Lys Asp Thr Tyr
145 150 155 160

Ile His Trp Val Arg Gln Ala Pro Gly Lys Gly Leu Glu Trp Val Ala
165 170 175

Arg Ile Tyr Pro Thr Asn Gly Tyr Thr Arg Tyr Ala Asp Ser Val Lys
180 185 190

Gly Arg Phe Thr Ile Ser Ala Asp Thr Ser Lys Asn Thr Ala Tyr Leu
195 200 205

Gln Met Asn Ser Leu Arg Ala Glu Asp Thr Ala Val Tyr Tyr Cys Ser
210 215 220

Arg Trp Gly Gly Asp Gly Phe Tyr Ala Met Asp Tyr Trp Gly Gln Gly
225 230 235 240

Thr Leu Val Thr Val Ser Ser Gly Gly Ser Gly Gly Ser Gly Gly Ser
245 250 255

Gly Gly Ser Gly Gly Ser Val Val Leu Leu Leu Arg Leu Ala Lys Thr
260 265 270

Tyr Glu Thr Thr Leu Glu Lys Cys Cys Ala Ala Ala Asp Pro His Glu
275 280 285

Cys Tyr Ala Lys Val Phe Asp Glu Phe Lys Pro Leu Val Glu Glu Pro
290 295 300

Gln Asn Leu Ile Lys Gln Asn Cys Glu Leu Phe Glu Gln Leu Gly Glu
305 310 315 320

Tyr Lys Phe Gln Asn Ala Leu Leu Val Arg Tyr Thr Lys Lys Val Pro
325 330 335

```
Gln Val Ser Thr Pro Thr Leu Val Glu Val Ser Arg Asn Leu Gly Lys
            340                 345                 350

Val Gly Ser Lys Cys Cys Lys His Pro Glu Ala Lys Arg Met Pro Cys
        355                 360                 365

Ala Glu Asp Tyr Leu Ser Val Val Leu Asn Gln Leu Cys Val Leu His
    370                 375                 380

Glu Lys Thr Pro Val Ser Asp Arg Val Thr Lys Cys Cys Thr Glu Ser
385                 390                 395                 400

Leu Val Asn Arg Arg Pro Cys Phe Ser Ala Leu Glu Val Asp Glu Thr
                405                 410                 415

Tyr Val Pro Lys Glu Phe Asn Ala Glu Thr Phe Thr Phe His Ala Asp
            420                 425                 430

Ile Cys Thr Leu Ser Glu Lys Glu Arg Gln Ile Lys Lys Gln Thr Ala
        435                 440                 445

Leu Val Glu Leu Val Lys His Lys Pro Lys Ala Thr Lys Glu Gln Leu
    450                 455                 460

Lys Ala Val Met Asp Asp Phe Ala Ala Phe Val Glu Lys Cys Cys Lys
465                 470                 475                 480

Ala Asp Asp Lys Glu Thr Cys Phe Ala Glu Glu Gly Lys Lys Leu Val
                485                 490                 495

Ala Ala Ser Gln Ala Ala Leu Gly Leu
            500                 505
```

<210> SEQ ID NO 109
<211> LENGTH: 1524
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
tccgtcgtcc tgctgctgag actggctaag acctacgaga ccacactgga aaaatgctgt     60

gccgctgcag acccccacga gtgctatgcc aaggtgttcg atgagttcaa gcctctggtc    120

gaggaaccac agaacctgat caagcagaat tgtgagctgt tcgaacagct gggcgagtac    180

aaatttcaga acgccctgct ggtgaggtat acaaagaaag tgccccaggt ctctacacct    240

actctggtgg aggtcagtag gaatctgggc aaggtcgggt caaaatgctg taagcaccca    300

gaggccaaac gcatgccctg cgctgaagac tacctgtctg tggtcctgaa ccagctgtgt    360

gtgctgcatg agaagacccc tgtgagcgat cgagtcacca aatgctgtac agaaagcctg    420

gtgaatcgga gaccctgctt ttccgctctg gaggtggacg aaacatatgt ccctaaggag    480

ttcaatgcag aaaccttcac atttcacgcc gatatctgta ctctgtccga gaaggaacgc    540

cagattaaga aacagaccgc cctggtggag ctggtcaagc ataaaccaaa ggctactaag    600

gaacagctga aagcagtgat ggacgatttc gccgcttttg tcgagaaatg ctgtaaggca    660

gacgataagg aaacctgctt tgccgaggaa ggcaagaaac tggtggcagc cagccaggct    720

gcactgggac tgggagggtc cggaggctct ggaggaagtg gagggtcagg aggcgacatc    780

cagatgacac agagcccaag ctccctgtca gcaagcgtgg gcgaccgagt cactattacc    840

tgtcgggcct cccaggatgt gaatactgca gtcgcctggt accagcagaa accaggaaag    900

gctcccaaac tgctgatcta ctccgcatct ttcctgtata gcggcgtgcc atccaggttt    960

agtggatcac gcagcggcac agacttcaca ctgactattt ctagtctgca gcccgaggat   1020
```

```
tttgccactt actattgcca gcagcactat actacccccc ctaccttcgg acagggcaca   1080

aaggtggaga tcaagggagg atctggagga ggaagtggag gaggatcagg aggaggaagc   1140

ggaggaggca gcggagaggt gcagctggtc gaatctggag gaggactggt gcagcctgga   1200

gggtctctgc gactgagttg tgccgcttca ggctttaaca tcaaggacac ctacattcat   1260

tgggtgcggc aggcacctgg gaagggactg gagtgggtcg ctagaatcta tccaactaat   1320

gggtacacca gatatgccga cagcgtgaag ggaaggttca ccattagcgc cgatacatcc   1380

aaaaacactg cttacctgca gatgaacagc ctgcgcgctg aggatacagc agtgtactat   1440

tgcagtcgat ggggcggcga tgggttctac gcaatggact actggggaca ggggactctg   1500

gtcaccgtca gcagctgagg atcc                                            1524
```

<210> SEQ ID NO 110
<211> LENGTH: 505
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Ser Val Val Leu Leu Leu Arg Leu Ala Lys Thr Tyr Glu Thr Thr Leu
1               5                   10                  15

Glu Lys Cys Cys Ala Ala Ala Asp Pro His Glu Cys Tyr Ala Lys Val
            20                  25                  30

Phe Asp Glu Phe Lys Pro Leu Val Glu Glu Pro Gln Asn Leu Ile Lys
        35                  40                  45

Gln Asn Cys Glu Leu Phe Glu Gln Leu Gly Glu Tyr Lys Phe Gln Asn
    50                  55                  60

Ala Leu Leu Val Arg Tyr Thr Lys Lys Val Pro Gln Val Ser Thr Pro
65                  70                  75                  80

Thr Leu Val Glu Val Ser Arg Asn Leu Gly Lys Val Gly Ser Lys Cys
                85                  90                  95

Cys Lys His Pro Glu Ala Lys Arg Met Pro Cys Ala Glu Asp Tyr Leu
            100                 105                 110

Ser Val Val Leu Asn Gln Leu Cys Val Leu His Glu Lys Thr Pro Val
        115                 120                 125

Ser Asp Arg Val Thr Lys Cys Cys Thr Glu Ser Leu Val Asn Arg Arg
    130                 135                 140

Pro Cys Phe Ser Ala Leu Glu Val Asp Glu Thr Tyr Val Pro Lys Glu
145                 150                 155                 160

Phe Asn Ala Glu Thr Phe Thr Phe His Ala Asp Ile Cys Thr Leu Ser
                165                 170                 175

Glu Lys Glu Arg Gln Ile Lys Lys Gln Thr Ala Leu Val Glu Leu Val
            180                 185                 190

Lys His Lys Pro Lys Ala Thr Lys Glu Gln Leu Lys Ala Val Met Asp
        195                 200                 205

Asp Phe Ala Ala Phe Val Glu Lys Cys Cys Lys Ala Asp Asp Lys Glu
    210                 215                 220

Thr Cys Phe Ala Glu Glu Gly Lys Lys Leu Val Ala Ala Ser Gln Ala
225                 230                 235                 240

Ala Leu Gly Leu Gly Gly Ser Gly Gly Ser Gly Gly Ser Gly Gly Ser
                245                 250                 255

Gly Gly Asp Ile Gln Met Thr Gln Ser Pro Ser Ser Leu Ser Ala Ser
            260                 265                 270
```

```
Val Gly Asp Arg Val Thr Ile Thr Cys Arg Ala Ser Gln Asp Val Asn
        275                 280                 285

Thr Ala Val Ala Trp Tyr Gln Gln Lys Pro Gly Lys Ala Pro Lys Leu
    290                 295                 300

Leu Ile Tyr Ser Ala Ser Phe Leu Tyr Ser Gly Val Pro Ser Arg Phe
305                 310                 315                 320

Ser Gly Ser Arg Ser Gly Thr Asp Phe Thr Leu Thr Ile Ser Ser Leu
                325                 330                 335

Gln Pro Glu Asp Phe Ala Thr Tyr Tyr Cys Gln Gln His Tyr Thr Thr
            340                 345                 350

Pro Pro Thr Phe Gly Gln Gly Thr Lys Val Glu Ile Lys Gly Gly Ser
        355                 360                 365

Gly Gly Gly Ser Gly Gly Gly Ser Gly Gly Gly Ser Gly Gly Gly Ser
    370                 375                 380

Gly Glu Val Gln Leu Val Glu Ser Gly Gly Gly Leu Val Gln Pro Gly
385                 390                 395                 400

Gly Ser Leu Arg Leu Ser Cys Ala Ala Ser Gly Phe Asn Ile Lys Asp
                405                 410                 415

Thr Tyr Ile His Trp Val Arg Gln Ala Pro Gly Lys Gly Leu Glu Trp
            420                 425                 430

Val Ala Arg Ile Tyr Pro Thr Asn Gly Tyr Thr Arg Tyr Ala Asp Ser
        435                 440                 445

Val Lys Gly Arg Phe Thr Ile Ser Ala Asp Thr Ser Lys Asn Thr Ala
    450                 455                 460

Tyr Leu Gln Met Asn Ser Leu Arg Ala Glu Asp Thr Ala Val Tyr Tyr
465                 470                 475                 480

Cys Ser Arg Trp Gly Gly Asp Gly Phe Tyr Ala Met Asp Tyr Trp Gly
                485                 490                 495

Gln Gly Thr Leu Val Thr Val Ser Ser
            500                 505
```

<210> SEQ ID NO 111
<211> LENGTH: 2544
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

```
tcaagcgaac tgactcagga ccccgctgtg agcgtcgcac tgggacagac tgtgcggatc     60

acctgccagg gggactccct gagatcttac tatgcctcct ggtaccagca gaaaccaggc    120

caggctcccg tgctggtcat ctatggcaag aacaatagac cttccgggat tccagatagg    180

ttttctggaa gctcctctgg caacacagct agcctgacca ttacaggagc ccaggctgag    240

gacgaagcag attactattg caactccagg gacagttcag gcaatcacgt ggtcttcggc    300

gggggaacaa agctgactgt gggaggagga tcaggaggag gaagcggagg aggcagcgga    360

ggaggatctg gaggaggaag tggagaggtg cagctggtcg aaagcggagg aggagtggtc    420

aggcctggag ggtcactgcg actgagctgt gccgcttccg gattcacatt tgacgattac    480

ggaatgtctt gggtccggca ggcaccagga aagggactgg agtgggtgag tggcatcaac    540

tggaatggag gctctacagg gtacgctgat agtgtgaaag gacgctttac tattagtcga    600

gacaacgcca agaacagcct gtatctgcag atgaacagcc tgagagccga ggatactgct    660
```

```
gtgtactatt gtgccagggg ccgctccctg ctgttcgact actgggggca gggaaccctg    720

gtgacagtct ctaggggggg aagtggcgat gctcacaaga gcgaggtcgc acatcgcttc    780

aaagacctgg gggaggaaaa ttttaaggcc ctggtgctga tcgcattcgc ccagtatctg    840

cagcagtgcc cttttgaaga ccacgtgaaa ctggtcaacg aggtgaccga gttcgccaag    900

acatgcgtgg cagacgagtc cgccgaaaat tgtgataaat ctctgcatac tctgtttggg    960

gataagctgt gtactgtggc caccctgcgg gagacctacg gagaaatggc tgactgctgt   1020

gcaaaacagg agccagaaag aaacgagtgc ttcctgcagc acaaggacga taaccccaat   1080

ctgcctcgac tggtgcggcc cgaagtggac gtcatgtgta ctgccttcca cgataatgag   1140

gaaacctttc tgaagaaata cctgtatgag attgcccgga gacatcccta cttttatgcc   1200

cctgaactgc tgttctttgc taagcggtac aaagcagcct tcaccgagtg ctgtcaggct   1260

gcagataagg ccgcttgcct gctgccaaaa ctggacgagc tgcgagatga agggaaagct   1320

agctccgcaa agcagagact gaaatgtgca agcctgcaga agttcggcga gagggccttt   1380

aaagcttggg cagtggccag actgagccag aggttcccca aggccgagtt tgctgaagtc   1440

tccaagctgg tgacagacct gactaaagtg cacaccgagt gctgtcatgg cgacctgctg   1500

gaatgcgccg acgatcgcgc agatctggcc aaatacatct gtgagaacca ggactctatt   1560

tctagtaagc tgaaagagtg ctgtgaaaag cctctgctgg agaaaagcca ctgcatcgct   1620

gaggtggaaa acgacgaaat gcccgcagat ctgcctagtc tggcagccga ctttgtcgag   1680

tcaaaggatg tgtgtaaaaa ttatgctgaa gcaaaggatg tgttcctggg catgtttctg   1740

tacgagtatg cacgagctgg agggagtgga ggctcaggag gaagcggcgg gtccggaggc   1800

tcaagcgaac tgacccagga ccccgccgtg tctgtcgctc tgggacagac agtgaggatc   1860

acttgccagg gcgactctct gcgcagttac tatgcaagtt ggtatcagca gaagcctggc   1920

caggcccctg tcctggtcat ctatggcaag aataatcgcc ctagtgggat tccagatcga   1980

ttttcagggt cctctagtgg aaacacagct tctctgacta ttaccggcgc acaggccgag   2040

gacgaagccg attactattg caacagcaga gactcaagcg gcaatcatgt ggtcttcgga   2100

ggaggaacca agctgacagt gggaggaggc tcaggcggcg gcagcggagg aggctccggg   2160

ggaggctctg gaggaggcag tggagaggtc cagctggtgg aatccggagg aggagtggtc   2220

cgaccaggag gatcactgag actgtcctgt gctgcatccg gattcacctt cgatgattac   2280

ggaatgagct gggtcaggca ggcacctggc aagggcctgg aatgggtgtc cggcatcaac   2340

tggaatggcg ggtcaaccgg gtacgctgat agcgtgaaag gacggttcac aattagcagg   2400

gataatgcta agaacagctt atatctgcaa atgaacagcc tgcgcgcaga ggacacagcc   2460

gtgtactatt gcgcccgggg gcggagcctg ctgtttgatt actgggggca gggcacactg   2520

gtgaccgtct ctcggtgagg atcc                                          2544
```

<210> SEQ ID NO 112
<211> LENGTH: 845
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
```

-continued

```
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Asp Ala His Lys Ser Glu Val
                245                 250                 255

Ala His Arg Phe Lys Asp Leu Gly Glu Glu Asn Phe Lys Ala Leu Val
            260                 265                 270

Leu Ile Ala Phe Ala Gln Tyr Leu Gln Gln Cys Pro Phe Glu Asp His
        275                 280                 285

Val Lys Leu Val Asn Glu Val Thr Glu Phe Ala Lys Thr Cys Val Ala
    290                 295                 300

Asp Glu Ser Ala Glu Asn Cys Asp Lys Ser Leu His Thr Leu Phe Gly
305                 310                 315                 320

Asp Lys Leu Cys Thr Val Ala Thr Leu Arg Glu Thr Tyr Gly Glu Met
                325                 330                 335

Ala Asp Cys Cys Ala Lys Gln Glu Pro Glu Arg Asn Glu Cys Phe Leu
            340                 345                 350

Gln His Lys Asp Asp Asn Pro Asn Leu Pro Arg Leu Val Arg Pro Glu
        355                 360                 365

Val Asp Val Met Cys Thr Ala Phe His Asp Asn Glu Glu Thr Phe Leu
    370                 375                 380

Lys Lys Tyr Leu Tyr Glu Ile Ala Arg Arg His Pro Tyr Phe Tyr Ala
385                 390                 395                 400

Pro Glu Leu Leu Phe Phe Ala Lys Arg Tyr Lys Ala Ala Phe Thr Glu
                405                 410                 415

Cys Cys Gln Ala Ala Asp Lys Ala Ala Cys Leu Leu Pro Lys Leu Asp
            420                 425                 430

Glu Leu Arg Asp Glu Gly Lys Ala Ser Ser Ala Lys Gln Arg Leu Lys
        435                 440                 445
```

Cys Ala Ser Leu Gln Lys Phe Gly Glu Arg Ala Phe Lys Ala Trp Ala
450 455 460

Val Ala Arg Leu Ser Gln Arg Phe Pro Lys Ala Glu Phe Ala Glu Val
465 470 475 480

Ser Lys Leu Val Thr Asp Leu Thr Lys Val His Thr Glu Cys Cys His
485 490 495

Gly Asp Leu Leu Glu Cys Ala Asp Asp Arg Ala Asp Leu Ala Lys Tyr
500 505 510

Ile Cys Glu Asn Gln Asp Ser Ile Ser Ser Lys Leu Lys Glu Cys Cys
515 520 525

Glu Lys Pro Leu Leu Glu Lys Ser His Cys Ile Ala Glu Val Glu Asn
530 535 540

Asp Glu Met Pro Ala Asp Leu Pro Ser Leu Ala Ala Asp Phe Val Glu
545 550 555 560

Ser Lys Asp Val Cys Lys Asn Tyr Ala Glu Ala Lys Asp Val Phe Leu
565 570 575

Gly Met Phe Leu Tyr Glu Tyr Ala Arg Ala Gly Gly Ser Gly Gly Ser
580 585 590

Gly Gly Ser Gly Gly Ser Gly Gly Ser Ser Glu Leu Thr Gln Asp Pro
595 600 605

Ala Val Ser Val Ala Leu Gly Gln Thr Val Arg Ile Thr Cys Gln Gly
610 615 620

Asp Ser Leu Arg Ser Tyr Tyr Ala Ser Trp Tyr Gln Gln Lys Pro Gly
625 630 635 640

Gln Ala Pro Val Leu Val Ile Tyr Gly Lys Asn Asn Arg Pro Ser Gly
645 650 655

Ile Pro Asp Arg Phe Ser Gly Ser Ser Ser Gly Asn Thr Ala Ser Leu
660 665 670

Thr Ile Thr Gly Ala Gln Ala Glu Asp Glu Ala Asp Tyr Tyr Cys Asn
675 680 685

Ser Arg Asp Ser Ser Gly Asn His Val Val Phe Gly Gly Gly Thr Lys
690 695 700

Leu Thr Val Gly Gly Gly Ser Gly Gly Gly Ser Gly Gly Gly Ser Gly
705 710 715 720

Gly Gly Ser Gly Gly Gly Ser Gly Glu Val Gln Leu Val Glu Ser Gly
725 730 735

Gly Gly Val Val Arg Pro Gly Gly Ser Leu Arg Leu Ser Cys Ala Ala
740 745 750

Ser Gly Phe Thr Phe Asp Asp Tyr Gly Met Ser Trp Val Arg Gln Ala
755 760 765

Pro Gly Lys Gly Leu Glu Trp Val Ser Gly Ile Asn Trp Asn Gly Gly
770 775 780

Ser Thr Gly Tyr Ala Asp Ser Val Lys Gly Arg Phe Thr Ile Ser Arg
785 790 795 800

Asp Asn Ala Lys Asn Ser Leu Tyr Leu Gln Met Asn Ser Leu Arg Ala
805 810 815

Glu Asp Thr Ala Val Tyr Tyr Cys Ala Arg Gly Arg Ser Leu Leu Phe
820 825 830

Asp Tyr Trp Gly Gln Gly Thr Leu Val Thr Val Ser Arg
835 840 845

<210> SEQ ID NO 113
<211> LENGTH: 2295

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 113
agtagcgaac tgacccagga ccccgcagtg agcgtcgcac tggggcagac agtgagaatc 60
acttgccagg gagattctct gaggagttac tatgcctcct ggtaccagca gaaacccggc 120
caggctcctg tgctggtcat ctatgggaag aacaataggc caagcggcat ccccgaccgc 180
ttctccggca gctcctctgg gaacacagct agcctgacta ttaccggcgc tcaggcagag 240
gacgaagcag attactattg caactccagg gatagttcag gcaatcacgt ggtctttggc 300
gggggaacaa agctgactgt gggaggagga agcggaggag gcagcggagg gggatctgga 360
ggaggaagtg gaggaggatc aggagaggtg cagctggtcg aaagcggagg aggagtggtc 420
cgccctggag ggagcctgcg actgtcctgt gccgcttctg gcttcacctt tgacgattac 480
ggaatgagct gggtgcggca ggcaccaggg aagggactgg agtgggtgtc cggcatcaac 540
tggaatggag gctccacagg atacgcagac tctgtgaaag gccgattcac tatttctcgg 600
gataacgcca agaatagtct gtatctgcag atgaacagcc tgagagctga ggacactgca 660
gtgtactatt gtgccagggg ccgcagcctg ctgtttgatt actggggcca gggaaccctg 720
gtgacagtct ccaggggagg atcaggaggg agcggaggct ccggaggatc tggagggagt 780
gtggtcctgc tgctgcgact ggctaaaacc tacgagacca cactggaaaa gtgctgtgca 840
gccgctgacc ctcatgagtg ctatgccaaa gtgttcgatg agttcaagcc actggtcgag 900
gaaccccaga acctgatcaa acagaattgt gagctgttcg aacagctggg cgagtacaag 960
tttcagaacg ccctgctggt gcgctatacc aagaaagtgc ctcaggtcag cacaccaact 1020
ctggtggaag tctcccggaa tctggggaaa gtgggatcta aatgctgtaa gcaccccgag 1080
gctaagagaa tgccttgcgc agaagactac ctgtctgtgg tcctgaacca gctgtgtgtg 1140
ctgcatgaga aaaccccagt gagcgatagg gtcaccaagt gctgtacaga aagtctggtg 1200
aaccggagac catgcttctc agccctggag gtggacgaaa catatgtccc caaagagttt 1260
aatgccgaaa ccttcacatt tcacgctgat atctgtactc tgtccgagaa ggaacgccag 1320
attaagaaac agaccgccct ggtggagctg gtcaagcata aacccaaggc aacaaaagaa 1380
cagctgaagg ccgtgatgga cgatttcgca gcctttgtcg agaaatgctg taaggctgac 1440
gataaggaaa cttgcttcgc agaggaagga aagaaactgg tggctgcaag ccaggcagct 1500
ctgggactgg gaggctcagg aggaagcggc gggtccggag gctctggggg aagctccgag 1560
ctgacccagg acccagccgt gtctgtcgct ctgggccaga ctgtgcgcat cacctgtcag 1620
ggggatagtc tgcgatcata ctatgcaagt tggtatcagc agaaacctgg ccaggcccca 1680
gtcctggtca tctatgggaa gaataatcga ccttccggca tccccgaccg gttctccgga 1740
tctagttcag gcaacacagc ctctctgact attaccggcg cccaggctga ggacgaagct 1800
gattactatt gcaacagcag ggatagctcc ggaaaccacg tggtctttgg aggaggaact 1860
aagctgaccg tgggaggagg aagtggcggg ggatcaggcg gcggaagcgg cggcggcagc 1920
ggaggaggat ctggcgaagt gcagctggtc gaatctggcg gaggagtggt ccggccagga 1980
gggagtctga gactgtcatg tgcagccagc ggcttcacat tcgatgatta cggaatgtct 2040
tgggtgcggc aggcacctgg aaagggcctg gaatgggtga gtggcatcaa ctggaacggc 2100
ggcagtaccg gatacgctga ctcagtgaaa ggcagattca caatttctag agacaatgct 2160

```
aagaatagtt tatatctgca aatgaacagc ctgagagcag aggacactgc cgtgtactat   2220

tgcgcccggg ggaggtcact gctgttcgat tactgggggc agggcactct ggtcactgtg   2280

tcaaggtgag gatcc                                                    2295


<210> SEQ ID NO 114
<211> LENGTH: 762
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Gly Ser Gly Gly Ser Gly Gly
                245                 250                 255

Ser Gly Gly Ser Val Val Leu Leu Leu Arg Leu Ala Lys Thr Tyr Glu
            260                 265                 270

Thr Thr Leu Glu Lys Cys Cys Ala Ala Ala Asp Pro His Glu Cys Tyr
        275                 280                 285

Ala Lys Val Phe Asp Glu Phe Lys Pro Leu Val Glu Glu Pro Gln Asn
    290                 295                 300

Leu Ile Lys Gln Asn Cys Glu Leu Phe Glu Gln Leu Gly Glu Tyr Lys
305                 310                 315                 320

Phe Gln Asn Ala Leu Leu Val Arg Tyr Thr Lys Lys Val Pro Gln Val
```

```
                325                 330                 335

Ser Thr Pro Thr Leu Val Glu Val Ser Arg Asn Leu Gly Lys Val Gly
            340                 345                 350

Ser Lys Cys Cys Lys His Pro Glu Ala Lys Arg Met Pro Cys Ala Glu
        355                 360                 365

Asp Tyr Leu Ser Val Val Leu Asn Gln Leu Cys Val Leu His Glu Lys
    370                 375                 380

Thr Pro Val Ser Asp Arg Val Thr Lys Cys Cys Thr Glu Ser Leu Val
385                 390                 395                 400

Asn Arg Arg Pro Cys Phe Ser Ala Leu Glu Val Asp Glu Thr Tyr Val
                405                 410                 415

Pro Lys Glu Phe Asn Ala Glu Thr Phe Thr Phe His Ala Asp Ile Cys
            420                 425                 430

Thr Leu Ser Glu Lys Glu Arg Gln Ile Lys Lys Gln Thr Ala Leu Val
        435                 440                 445

Glu Leu Val Lys His Lys Pro Lys Ala Thr Lys Glu Gln Leu Lys Ala
    450                 455                 460

Val Met Asp Asp Phe Ala Ala Phe Val Glu Lys Cys Cys Lys Ala Asp
465                 470                 475                 480

Asp Lys Glu Thr Cys Phe Ala Glu Glu Gly Lys Lys Leu Val Ala Ala
                485                 490                 495

Ser Gln Ala Ala Leu Gly Leu Gly Gly Ser Gly Gly Ser Gly Gly Ser
            500                 505                 510

Gly Gly Ser Gly Gly Ser Ser Glu Leu Thr Gln Asp Pro Ala Val Ser
        515                 520                 525

Val Ala Leu Gly Gln Thr Val Arg Ile Thr Cys Gln Gly Asp Ser Leu
    530                 535                 540

Arg Ser Tyr Tyr Ala Ser Trp Tyr Gln Gln Lys Pro Gly Gln Ala Pro
545                 550                 555                 560

Val Leu Val Ile Tyr Gly Lys Asn Asn Arg Pro Ser Gly Ile Pro Asp
                565                 570                 575

Arg Phe Ser Gly Ser Ser Ser Gly Asn Thr Ala Ser Leu Thr Ile Thr
            580                 585                 590

Gly Ala Gln Ala Glu Asp Glu Ala Asp Tyr Tyr Cys Asn Ser Arg Asp
        595                 600                 605

Ser Ser Gly Asn His Val Val Phe Gly Gly Gly Thr Lys Leu Thr Val
    610                 615                 620

Gly Gly Gly Ser Gly Gly Gly Ser Gly Gly Gly Ser Gly Gly Gly Ser
625                 630                 635                 640

Gly Gly Gly Ser Gly Glu Val Gln Leu Val Glu Ser Gly Gly Gly Val
                645                 650                 655

Val Arg Pro Gly Gly Ser Leu Arg Leu Ser Cys Ala Ala Ser Gly Phe
            660                 665                 670

Thr Phe Asp Asp Tyr Gly Met Ser Trp Val Arg Gln Ala Pro Gly Lys
        675                 680                 685

Gly Leu Glu Trp Val Ser Gly Ile Asn Trp Asn Gly Gly Ser Thr Gly
    690                 695                 700

Tyr Ala Asp Ser Val Lys Gly Arg Phe Thr Ile Ser Arg Asp Asn Ala
705                 710                 715                 720

Lys Asn Ser Leu Tyr Leu Gln Met Asn Ser Leu Arg Ala Glu Asp Thr
                725                 730                 735

Ala Val Tyr Tyr Cys Ala Arg Gly Arg Ser Leu Leu Phe Asp Tyr Trp
            740                 745                 750
```

```
Gly Gln Gly Thr Leu Val Thr Val Ser Arg
        755                 760


<210> SEQ ID NO 115
<211> LENGTH: 2556
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

gatattcaga tgactcagtc tcctagctcc ctgtcagcta gcgtcggcga tcgggtgaca     60

atcacttgca gagccagcca ggacgtcaac acagccgtgg cttggtacca gcagaagccc    120

ggaaaagcac ctaagctgct gatctactcc gcctcttttc tgtattctgg cgtgcccagt    180

agattcagtg gatcaaggag cggcaccgat tttaccctga caatctctag tctgcagcct    240

gaggactttg ccacatacta ttgccagcag cactatacca cacccctac tttcgggcag    300

ggaaccaagg tggaaatcaa aggcgggtca ggcggaggga gcggaggagg gtccggagga    360

gggtctggag gagggagtgg agaggtgcag ctggtcgaat ctggaggagg actggtgcag    420

ccaggaggct cactgcggct gagctgtgcc gcttccggct tcaacatcaa agatacctac    480

attcattggg tccgacaggc accaggcaag ggactggagt gggtggctag aatctatccc    540

accaatggct acacacgata tgccgatagc gtgaaagggc ggtttacaat ttctgcagac    600

actagtaaga acaccgccta cctgcagatg aacagcctgc gcgctgagga cactgcagtg    660

tactattgta gtcgatgggg gggagacggc ttctacgcca tggattattg gggacagggc    720

accctggtga cagtctcaag cggagggtcc ggcgatgcac acaagtctga ggtcgctcat    780

agattcaaag acctggggga ggaaaatttt aaggccctgg tgctgattgc attcgcccag    840

tacctgcagc agtgcccctt tgaagaccac gtgaaactgg tcaacgaggt gacagagttc    900

gccaagactt gcgtcgccga cgagagtgct gaaaattgtg ataaatcact gcatacactg    960

tttggggata agctgtgtac tgtggccacc ctgcgggaga cttatggaga aatggcagac   1020

tgctgtgcca aacaggagcc tgaaagaaac gagtgcttcc tgcagcacaa ggacgataac   1080

cctaatctgc caaggctggt gcgcccagaa gtggacgtca tgtgtactgc cttccacgat   1140

aatgaggaaa cctttctgaa gaaatacctg tatgagatcg cccggagaca tccctacttt   1200

tatgctcctg aactgctgtt ctttgcaaaa cggtacaagg cagccttcac cgagtgctgt   1260

caggctgcag ataaggccgc ttgcctgctg cccaaactgg acgagctgcg ggatgaaggc   1320

aaggcttcct ctgcaaagca gagactgaaa tgtgcaagcc tgcagaagtt cggggagagg   1380

gcctttaaag cttgggcagt cgcacgactg agccagcgat tccctaaggc cgagtttgct   1440

gaagtctcca agctggtgac agacctgact aaagtgcaca ccgagtgctg tcatggcgac   1500

ctgctggaat gcgccgacga tcgcgcagat ctggccaagt acatctgtga gaaccaggac   1560

agcattagtt caaagctgaa agagtgctgt gaaaagccac tgctggagaa atcccactgc   1620

attgctgagg tggaaaacga cgaaatgcca gcagatctgc ccagcctggc agccgacttc   1680

gtcgagtcca aggatgtgtg taaaaattat gctgaagcaa aggatgtgtt cctgggcatg   1740

tttctgtacg agtatgccag ggctggaggc agtggaggat caggagggag cggaggctcc   1800

ggaggagaca tccagatgac ccagagccca agctccctgt ccgcttctgt cggcgatagg   1860

gtgactatta cctgccgcgc ctcccaggac gtcaatacag cagtggcctg gtaccagcag   1920
```

```
aaacctggga aggctccaaa actgctgatc tacagtgcat cattcctgta ttcaggagtg   1980

ccaagccgct ttagcgggtc ccgatctgga actgatttca cactgactat ctctagtctg   2040

cagcccgagg actttgccac ctattactgc cagcagcact acactacccc acccaccttc   2100

gggcagggaa caaaggtgga aatcaaaggg gggtccggcg gcgggtctgg cggagggagt   2160

ggaggagggt caggcggcgg gagcggcgag gtccagctgg tggaatccgg cggcggcctg   2220

gtgcagcctg gaggctccct gcgactgtct tgtgctgcaa gtggctttaa catcaaggac   2280

acttacattc attgggtcag gcaggctcct ggcaagggcc tggaatgggt ggcacgaatc   2340

tatccaacaa atggatacac taggtacgcc gatagcgtga aaggcaggtt caccatttca   2400

gccgacacca gcaagaacac agcttacctg caaatgaaca gcctgagggc tgaggacaca   2460

gcagtgtact attgcagccg ctggggcggg gacgggttct atgctatgga ctattggggg   2520

cagggcactc tggtcactgt gtcaagctga ggatcc                             2556
```

```
<210> SEQ ID NO 116
<211> LENGTH: 849
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
```

```
                245                 250                 255

Glu Val Ala His Arg Phe Lys Asp Leu Gly Glu Glu Asn Phe Lys Ala
            260                 265                 270

Leu Val Leu Ile Ala Phe Ala Gln Tyr Leu Gln Gln Cys Pro Phe Glu
        275                 280                 285

Asp His Val Lys Leu Val Asn Glu Val Thr Glu Phe Ala Lys Thr Cys
    290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
            340                 345                 350

Phe Leu Gln His Lys Asp Asp Asn Pro Asn Leu Pro Arg Leu Val Arg
        355                 360                 365

Pro Glu Val Asp Val Met Cys Thr Ala Phe His Asp Asn Glu Glu Thr
    370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
        435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
        515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Ala Gly Gly Ser Gly
            580                 585                 590

Gly Ser Gly Gly Ser Gly Gly Ser Gly Gly Asp Ile Gln Met Thr Gln
        595                 600                 605

Ser Pro Ser Ser Leu Ser Ala Ser Val Gly Asp Arg Val Thr Ile Thr
    610                 615                 620

Cys Arg Ala Ser Gln Asp Val Asn Thr Ala Val Ala Trp Tyr Gln Gln
625                 630                 635                 640

Lys Pro Gly Lys Ala Pro Lys Leu Leu Ile Tyr Ser Ala Ser Phe Leu
                645                 650                 655

Tyr Ser Gly Val Pro Ser Arg Phe Ser Gly Ser Arg Ser Gly Thr Asp
            660                 665                 670
```

```
Phe Thr Leu Thr Ile Ser Ser Leu Gln Pro Glu Asp Phe Ala Thr Tyr
        675                 680                 685

Tyr Cys Gln Gln His Tyr Thr Thr Pro Pro Thr Phe Gly Gln Gly Thr
    690                 695                 700

Lys Val Glu Ile Lys Gly Gly Ser Gly Gly Gly Ser Gly Gly Gly Ser
705                 710                 715                 720

Gly Gly Gly Ser Gly Gly Gly Ser Gly Glu Val Gln Leu Val Glu Ser
                725                 730                 735

Gly Gly Gly Leu Val Gln Pro Gly Gly Ser Leu Arg Leu Ser Cys Ala
            740                 745                 750

Ala Ser Gly Phe Asn Ile Lys Asp Thr Tyr Ile His Trp Val Arg Gln
        755                 760                 765

Ala Pro Gly Lys Gly Leu Glu Trp Val Ala Arg Ile Tyr Pro Thr Asn
    770                 775                 780

Gly Tyr Thr Arg Tyr Ala Asp Ser Val Lys Gly Arg Phe Thr Ile Ser
785                 790                 795                 800

Ala Asp Thr Ser Lys Asn Thr Ala Tyr Leu Gln Met Asn Ser Leu Arg
                805                 810                 815

Ala Glu Asp Thr Ala Val Tyr Tyr Cys Ser Arg Trp Gly Gly Asp Gly
            820                 825                 830

Phe Tyr Ala Met Asp Tyr Trp Gly Gln Gly Thr Leu Val Thr Val Ser
        835                 840                 845

Ser
```

<210> SEQ ID NO 117
<211> LENGTH: 2307
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
gacattcaga tgactcagag cccaagctcc ctgagcgcat ccgtgggcga cagagtcacc     60

atcacatgca gggcctccca ggatgtgaac accgctgtcg catggtacca gcagaaacct    120

gggaaggctc caaaactgct gatctactct gcaagtttcc tgtatagtgg agtgccatca    180

aggttttcag gcagccgctc cgggaccgac ttcactctga ccatctctag tctgcagccc    240

gaggatttcg ccacatacta ttgccagcag cactatacca cacccccctac ctttggccag    300

gggacaaaag tggaaattaa gggagggagc ggaggagggt ccggaggagg gtctggaggc    360

gggagtggag gagggtcagg agaggtgcag ctggtcgaat ccggaggagg actggtgcag    420

ccaggaggca gcctgcggct gtcctgtgcc gcttctggct tcaacatcaa agacacctac    480

attcattggg tgcgccaggc tccaggaaag ggactggagt gggtcgcacg aatctatccc    540

actaatgggt acacccggta tgccgattcc gtgaaaggaa gattcacaat tagtgcagat    600

acatcaaaga acactgccta cctgcagatg aacagcctgc gagcagagga tactgccgtg    660

tactattgta gtcggtgggg gggagacggc ttttacgcca tggattattg gggcaggga    720

accctggtga cagtctcaag cggagggtca ggaggcagcg gaggcagcgg agggtctgga    780

ggcagtgtgg tcctgctgct gaggctggct aaaacctacg agactaccct ggaaaagtgc    840

tgtgcagccg ctgaccccca cgagtgctat gccaaagtgt tcgatgagtt caagccactg    900

gtcgaggaac cccagaacct gatcaaacag aattgtgagc tgttcgaaca gctgggcgag    960
```

-continued

```
tacaagtttc agaacgccct gctggtgcgc tataccaaga aagtgcctca ggtctctaca   1020

ccaactctgg tggaggtcag taggaatctg gggaaagtgg gatcaaagtg ctgtaaacac   1080

cccgaggcca agcgcatgcc ttgcgctgaa gactacctgt ctgtggtcct gaaccagctg   1140

tgtgtgctgc atgagaaaac ccccgtgagc gatcgggtca ccaagtgctg tacagaaagc   1200

ctggtgaacc ggagaccctg cttctccgct ctggaggtgg acgaaacata tgtccctaag   1260

gagtttaatg ctgaaacctt cacatttcac gcagatatct gtacactgtc cgagaaggaa   1320

agacagatta agaaacagac tgccctggtg gagctggtca agcataaacc taaggccaca   1380

aaagaacagc tgaaggctgt gatggacgat ttcgcagcct ttgtcgagaa gtgctgtaaa   1440

gccgacgata aggaaacttg cttcgctgag gaaggaaaga aactggtggc tgcaagccag   1500

gcagctctgg gcctgggagg atcaggaggg agcggaggct ccggaggatc tggaggggac   1560

atccagatga cccagtctcc ttcctctctg tctgctagtg tgggcgaccg cgtcactatt   1620

acctgtcgag ccagccagga tgtgaataca gccgtcgctt ggtaccagca gaagcccggc   1680

aaagcaccta agctgctgat ctactcagcc agctttctgt atagcggggt gccttcccga   1740

ttctccggat ctcggagtgg cactgacttt acactgacta tcagttcact gcagccagag   1800

gatttcgcca cctattactg ccagcagcac tacacaactc cacccacttt tggccagggg   1860

accaaagtgg aaatcaaggg aggctctgga ggaggcagtg gaggaggctc aggaggaggc   1920

agcggaggag gctccggcga agtgcagctg gtcgaatctg gcggcggcct ggtccagcca   1980

ggaggatctc tgaggctgag ttgtgcagcc tcaggcttca acatcaagga tacttacatt   2040

cattgggtgc ggcaggcacc tggaaagggc ctggaatggg tcgctagaat ctatccaact   2100

aatggctaca ccagatatgc cgacagcgtg aaagggcgct ttaccattag cgcagataca   2160

tccaaaaata ccgcttacct gcagatgaat agcctgagag ctgaggatac agcagtgtac   2220

tattgctcca gatggggcgg cgatgggttt tacgcaatgg actactgggg acagggaaca   2280

ctggtcaccg tctcttcttg aggatcc                                       2307
```

<210> SEQ ID NO 118
<211> LENGTH: 766
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
```

-continued

```
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Gly Ser Gly Gly Ser
                245                 250                 255

Gly Gly Ser Gly Gly Ser Val Val Leu Leu Leu Arg Leu Ala Lys Thr
            260                 265                 270

Tyr Glu Thr Thr Leu Glu Lys Cys Cys Ala Ala Ala Asp Pro His Glu
        275                 280                 285

Cys Tyr Ala Lys Val Phe Asp Glu Phe Lys Pro Leu Val Glu Glu Pro
    290                 295                 300

Gln Asn Leu Ile Lys Gln Asn Cys Glu Leu Phe Glu Gln Leu Gly Glu
305                 310                 315                 320

Tyr Lys Phe Gln Asn Ala Leu Leu Val Arg Tyr Thr Lys Lys Val Pro
                325                 330                 335

Gln Val Ser Thr Pro Thr Leu Val Glu Val Ser Arg Asn Leu Gly Lys
            340                 345                 350

Val Gly Ser Lys Cys Cys Lys His Pro Glu Ala Lys Arg Met Pro Cys
        355                 360                 365

Ala Glu Asp Tyr Leu Ser Val Val Leu Asn Gln Leu Cys Val Leu His
    370                 375                 380

Glu Lys Thr Pro Val Ser Asp Arg Val Thr Lys Cys Cys Thr Glu Ser
385                 390                 395                 400

Leu Val Asn Arg Arg Pro Cys Phe Ser Ala Leu Glu Val Asp Glu Thr
                405                 410                 415

Tyr Val Pro Lys Glu Phe Asn Ala Glu Thr Phe Thr Phe His Ala Asp
            420                 425                 430

Ile Cys Thr Leu Ser Glu Lys Glu Arg Gln Ile Lys Lys Gln Thr Ala
        435                 440                 445

Leu Val Glu Leu Val Lys His Lys Pro Lys Ala Thr Lys Glu Gln Leu
    450                 455                 460

Lys Ala Val Met Asp Asp Phe Ala Ala Phe Val Glu Lys Cys Cys Lys
465                 470                 475                 480

Ala Asp Asp Lys Glu Thr Cys Phe Ala Glu Glu Gly Lys Lys Leu Val
                485                 490                 495

Ala Ala Ser Gln Ala Ala Leu Gly Leu Gly Gly Ser Gly Gly Ser Gly
            500                 505                 510

Gly Ser Gly Gly Ser Gly Gly Asp Ile Gln Met Thr Gln Ser Pro Ser
        515                 520                 525

Ser Leu Ser Ala Ser Val Gly Asp Arg Val Thr Ile Thr Cys Arg Ala
    530                 535                 540
```

```
Ser Gln Asp Val Asn Thr Ala Val Ala Trp Tyr Gln Gln Lys Pro Gly
545                 550                 555                 560

Lys Ala Pro Lys Leu Leu Ile Tyr Ser Ala Ser Phe Leu Tyr Ser Gly
                565                 570                 575

Val Pro Ser Arg Phe Ser Gly Ser Arg Ser Gly Thr Asp Phe Thr Leu
            580                 585                 590

Thr Ile Ser Ser Leu Gln Pro Glu Asp Phe Ala Thr Tyr Tyr Cys Gln
        595                 600                 605

Gln His Tyr Thr Thr Pro Pro Thr Phe Gly Gln Gly Thr Lys Val Glu
    610                 615                 620

Ile Lys Gly Gly Ser Gly Gly Gly Ser Gly Gly Gly Ser Gly Gly Gly
625                 630                 635                 640

Ser Gly Gly Gly Ser Gly Glu Val Gln Leu Val Glu Ser Gly Gly Gly
                645                 650                 655

Leu Val Gln Pro Gly Gly Ser Leu Arg Leu Ser Cys Ala Ala Ser Gly
            660                 665                 670

Phe Asn Ile Lys Asp Thr Tyr Ile His Trp Val Arg Gln Ala Pro Gly
        675                 680                 685

Lys Gly Leu Glu Trp Val Ala Arg Ile Tyr Pro Thr Asn Gly Tyr Thr
    690                 695                 700

Arg Tyr Ala Asp Ser Val Lys Gly Arg Phe Thr Ile Ser Ala Asp Thr
705                 710                 715                 720

Ser Lys Asn Thr Ala Tyr Leu Gln Met Asn Ser Leu Arg Ala Glu Asp
                725                 730                 735

Thr Ala Val Tyr Tyr Cys Ser Arg Trp Gly Gly Asp Gly Phe Tyr Ala
            740                 745                 750

Met Asp Tyr Trp Gly Gln Gly Thr Leu Val Thr Val Ser Ser
        755                 760                 765
```

<210> SEQ ID NO 119
<211> LENGTH: 2550
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 119

```
agttctgagc tgacccagga ccccgctgtg agcgtcgcac tgggacagac agtgcggatc     60

acttgccagg gcgacagcct gagatcctac tatgctagct ggtaccagca gaagcctggc    120

caggcaccag tgctggtcat ctatggaaaa aacaatagac ccagcggcat tcctgatagg    180

ttctccggga gctcctctgg aaacacagct agcctgacta ttaccggcgc ccaggctgag    240

gacgaagccg attactattg caacagcagg gacagttcag ggaatcacgt ggtctttgga    300

ggaggaacta agctgaccgt gggaggaggc agcggaggag gatctggagg aggaagtgga    360

ggaggatcag gaggaggaag cggagaggtg cagctggtcg aaagcggagg aggagtggtc    420

aggccaggag ggtccctgcg actgtcttgt gccgctagtg ggttcacttt tgacgattac    480

ggaatgagtt gggtcaggca ggcaccagga aagggactgg agtgggtgag cggcatcaac    540

tggaatggag gcagtacagg ctacgctgat tcagtgaagg ggcgcttcac tatttctcga    600

gacaacgcca aaaatagtct gtatctgcag atgaactcac tgcgcgccga ggatacagct    660

gtgtactatt gcgccagggg ccgctccctg ctgtttgact actgggggca gggaacactg    720

gtgactgtct cacggggggg aagcggagat gcacacaaat ctgaggtcgc ccatagattc    780
```

```
aaggacctgg gcgaggaaaa ttttaaagcc ctggtgctga tcgcattcgc ccagtatctg    840
cagcagtgcc ctttcgaaga ccacgtgaag ctggtcaacg aggtgacaga atttgccaaa    900
acttgcgtcg cagacgagag cgccgaaaat tgtgataagt ccctgcatac cctgttcggc    960
gataaactgt gtaccgtggc cacactgagg gagacatacg gggaaatggc tgactgctgt   1020
gcaaagcagg agcccgaacg caacgagtgc tttctgcagc acaaagacga taacccaaat   1080
ctgccccgac tggtgcggcc tgaagtggac gtcatgtgta ctgccttcca cgataatgag   1140
gaaacctttc tgaagaaata cctgtatgag attgcccgga gacatcccta cttctatgct   1200
cctgaactgc tgttctttgc aaagcggtac aaagcagcct ttaccgagtg ctgtcaggct   1260
gcagataaag ccgcttgcct gctgcctaag ctggacgagc tgagggatga aggcaaggct   1320
agctccgcaa aacagcgcct gaagtgtgct agcctgcaga aattcggcga gcgggccttc   1380
aaggcttggg cagtggccag actgtcacag aggttcccaa aggccgagtt tgctgaagtc   1440
agcaaactgg tgactgacct gaccaaggtg cacaccgagt gctgtcatgg cgacctgctg   1500
gaatgcgccg acgatagagc agatctggcc aagtacatct gtgagaacca ggactccatt   1560
tctagtaagc tgaaagagtg ctgtgaaaaa cccctgctgg agaagtctca ttgcatcgcc   1620
gaggtggaaa acgacgaaat gccagctgat ctgccctctc tggcagccga cttcgtcgag   1680
agtaaagatg tgtgtaagaa ttatgctgaa gcaaaggatg tgttcctggg catgtttctg   1740
tacgagtatg cacgagctgg agggtctgga ggcagtggag gatcaggagg gagcggaggc   1800
gacatccaga tgacccagtc cccttcaagc ctgagtgctt cagtcggcga tcgagtgaca   1860
attacttgcc gggcctctca ggacgtcaat acagcagtgg cttggtatca gcagaagcct   1920
gggaaagcac caaagctgct gatctacagc gcctcctttc tgtattccgg agtgccttct   1980
cggttctctg gcagtagatc agggactgat tttaccctga caatttcctc tctgcagcca   2040
gaggacttcg ccacctacta ttgccagcag cactatacca cacccctac ctttggccag    2100
gggacaaaag tggaaatcaa gggggggaagt ggcgggggat caggcggcgg aagcggcggc   2160
ggcagcggcg gcggatctgg agaggtccag ctggtggaaa gcggaggagg actggtgcag   2220
ccaggaggga gtctgagact gtcatgtgct gcaagcggct tcaacatcaa ggatacctac   2280
attcactggg tcaggcaggc cccaggaaaa ggcctggagt gggtggcccg catctatccc   2340
accaatgggt acacacgcta tgccgattcc gtgaagggac gattcacaat ttccgccgac   2400
acttctaaaa acaccgctta cctgcagatg aacagcctgc gagccgagga cactgctgtg   2460
tactattgtt ctagatgggg cggggacggg ttttacgcaa tggactactg gggcagggg    2520
actctggtca ctgtcagcag ctgaggatcc                                    2550
```

<210> SEQ ID NO 120
<211> LENGTH: 847
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
```

```
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Asp Ala His Lys Ser Glu Val
                245                 250                 255

Ala His Arg Phe Lys Asp Leu Gly Glu Glu Asn Phe Lys Ala Leu Val
            260                 265                 270

Leu Ile Ala Phe Ala Gln Tyr Leu Gln Gln Cys Pro Phe Glu Asp His
        275                 280                 285

Val Lys Leu Val Asn Glu Val Thr Glu Phe Ala Lys Thr Cys Val Ala
    290                 295                 300

Asp Glu Ser Ala Glu Asn Cys Asp Lys Ser Leu His Thr Leu Phe Gly
305                 310                 315                 320

Asp Lys Leu Cys Thr Val Ala Thr Leu Arg Glu Thr Tyr Gly Glu Met
                325                 330                 335

Ala Asp Cys Cys Ala Lys Gln Glu Pro Glu Arg Asn Glu Cys Phe Leu
            340                 345                 350

Gln His Lys Asp Asp Asn Pro Asn Leu Pro Arg Leu Val Arg Pro Glu
        355                 360                 365

Val Asp Val Met Cys Thr Ala Phe His Asp Asn Glu Glu Thr Phe Leu
    370                 375                 380

Lys Lys Tyr Leu Tyr Glu Ile Ala Arg Arg His Pro Tyr Phe Tyr Ala
385                 390                 395                 400

Pro Glu Leu Leu Phe Phe Ala Lys Arg Tyr Lys Ala Ala Phe Thr Glu
                405                 410                 415

Cys Cys Gln Ala Ala Asp Lys Ala Ala Cys Leu Leu Pro Lys Leu Asp
            420                 425                 430

Glu Leu Arg Asp Glu Gly Lys Ala Ser Ser Ala Lys Gln Arg Leu Lys
        435                 440                 445

Cys Ala Ser Leu Gln Lys Phe Gly Glu Arg Ala Phe Lys Ala Trp Ala
    450                 455                 460
```

Val Ala Arg Leu Ser Gln Arg Phe Pro Lys Ala Glu Phe Ala Glu Val
465 470 475 480

Ser Lys Leu Val Thr Asp Leu Thr Lys Val His Thr Glu Cys Cys His
485 490 495

Gly Asp Leu Leu Glu Cys Ala Asp Asp Arg Ala Asp Leu Ala Lys Tyr
500 505 510

Ile Cys Glu Asn Gln Asp Ser Ile Ser Ser Lys Leu Lys Glu Cys Cys
515 520 525

Glu Lys Pro Leu Leu Glu Lys Ser His Cys Ile Ala Glu Val Glu Asn
530 535 540

Asp Glu Met Pro Ala Asp Leu Pro Ser Leu Ala Ala Asp Phe Val Glu
545 550 555 560

Ser Lys Asp Val Cys Lys Asn Tyr Ala Glu Ala Lys Asp Val Phe Leu
565 570 575

Gly Met Phe Leu Tyr Glu Tyr Ala Arg Ala Gly Gly Ser Gly Gly Ser
580 585 590

Gly Gly Ser Gly Gly Ser Gly Gly Asp Ile Gln Met Thr Gln Ser Pro
595 600 605

Ser Ser Leu Ser Ala Ser Val Gly Asp Arg Val Thr Ile Thr Cys Arg
610 615 620

Ala Ser Gln Asp Val Asn Thr Ala Val Ala Trp Tyr Gln Gln Lys Pro
625 630 635 640

Gly Lys Ala Pro Lys Leu Leu Ile Tyr Ser Ala Ser Phe Leu Tyr Ser
645 650 655

Gly Val Pro Ser Arg Phe Ser Gly Ser Arg Ser Gly Thr Asp Phe Thr
660 665 670

Leu Thr Ile Ser Ser Leu Gln Pro Glu Asp Phe Ala Thr Tyr Tyr Cys
675 680 685

Gln Gln His Tyr Thr Thr Pro Pro Thr Phe Gly Gln Gly Thr Lys Val
690 695 700

Glu Ile Lys Gly Gly Ser Gly Gly Gly Ser Gly Gly Gly Ser Gly Gly
705 710 715 720

Gly Ser Gly Gly Gly Ser Gly Glu Val Gln Leu Val Glu Ser Gly Gly
725 730 735

Gly Leu Val Gln Pro Gly Gly Ser Leu Arg Leu Ser Cys Ala Ala Ser
740 745 750

Gly Phe Asn Ile Lys Asp Thr Tyr Ile His Trp Val Arg Gln Ala Pro
755 760 765

Gly Lys Gly Leu Glu Trp Val Ala Arg Ile Tyr Pro Thr Asn Gly Tyr
770 775 780

Thr Arg Tyr Ala Asp Ser Val Lys Gly Arg Phe Thr Ile Ser Ala Asp
785 790 795 800

Thr Ser Lys Asn Thr Ala Tyr Leu Gln Met Asn Ser Leu Arg Ala Glu
805 810 815

Asp Thr Ala Val Tyr Tyr Cys Ser Arg Trp Gly Gly Asp Gly Phe Tyr
820 825 830

Ala Met Asp Tyr Trp Gly Gln Gly Thr Leu Val Thr Val Ser Ser
835 840 845

<210> SEQ ID NO 121
<211> LENGTH: 2550
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 121
gacattcaga tgacccagtc cccaagctcc ctgtctgcta gtgtcggcga tcgggtgact 60
atcacctgca gagcctctca ggacgtcaac acagccgtgg cttggtacca gcagaagcct 120
ggcaaagcac caaagctgct gatctactca gccagctttc tgtatagcgg ggtgccttcc 180
agattctccg gctctaggag tgggactgat tttacactga ctatctctag tctgcagcca 240
gaggacttcg ccacctacta ttgccagcag cactatacca cacccccctac atttgggcag 300
ggaactaaag tggaaattaa gggagggtct ggaggaggga gtggaggagg gtcaggcgga 360
gggagcggag gagggtccgg cgaggtgcag ctggtcgaaa gcggaggagg actggtgcag 420
cctggaggct ctctgaggct gagttgtgcc gcttcaggct tcaacatcaa ggatacctac 480
attcattggg tccgacaggc tccaggcaaa gggctggagt gggtggcaag aatctatccc 540
acaaatggct acactagata tgccgatagc gtgaagggga ggttcacaat tagcgctgac 600
acctccaaaa acacagcata cctgcagatg aatagtctgc gggctgagga cactgcagtg 660
tactattgta gcagatgggg gggagacggc ttttacgcca tggattattg gggacagggc 720
actctggtga ccgtctcaag cggagggagc ggggatgcac acaaatccga ggtcgcccat 780
cgcttcaagg acctgggaga ggaaaatttt aaagccctgg tgctgattgc attcgcccag 840
tacctgcagc agtgcccctt cgaagaccac gtgaagctgg tcaacgaggt gaccgaattt 900
gccaaaacat gcgtcgccga cgagtcagct gaaaattgtg ataagagcct gcataccctg 960
ttcggagata aactgtgtac agtggccact ctgagggaga catatggcga aatggcagac 1020
tgctgtgcca agcaggagcc cgaacgcaac gagtgctttc tgcagcacaa agacgataac 1080
ccaaatctgc ccaggctggt gcgccctgaa gtggacgtca tgtgtactgc cttccacgat 1140
aatgaggaaa cctttctgaa gaaatacctg tatgagatcg cccggagaca tccctacttc 1200
tatgcccctg aactgctgtt ctttgctaaa cggtacaagg cagcctttac cgagtgctgt 1260
caggctgcag ataaagccgc ttgcctgctg cctaagctgg acgagctgag ggatgaagga 1320
aaggcttcct ctgcaaaaca gcgcctgaag tgtgcctccc tgcagaaatt cggcgagcgg 1380
gcttttaagg cttgggcagt ggcacgactg tcccagcgat tcccaaaggc cgagtttgct 1440
gaagtctcta aactggtgac cgacctgaca aaggtgcaca ccgagtgctg tcatggcgac 1500
ctgctggaat gcgccgacga tagagcagat ctggccaagt acatctgtga gaaccaggac 1560
tccattagtt caaagctgaa agagtgctgt gaaaaacccc tgctggagaa gtctcactgc 1620
atcgcagagg tggaaaacga cgaaatgcca gcagatctgc cttccctggc agcagacttc 1680
gtcgagtcta aagatgtgtg taagaattat gctgaagcaa aggatgtgtt cctgggcatg 1740
tttctgtacg agtatgcacg agctggaggc tcaggaggaa gcggagggtc cggaggctct 1800
gggggaagct ccgaactgac ccaggacccc gctgtgagcg tcgcactggg acagactgtg 1860
cgcattacct gccagggaga cagtctgcga tcatactatg cttcctggta ccagcagaag 1920
ccaggccagg cacccgtgct ggtcatctat gggaaaaaca atcgaccttc cggcatcccc 1980
gatcggttct ctggatctag ttcaggcaac acagctagcc tgaccatcac aggggcacag 2040
gccgaggacg aagccgatta ctattgcaac agcagagaca gctccggcaa tcatgtggtc 2100
tttggaggag gaactaagct gaccgtggga ggaggatctg gaggaggaag tggcggggga 2160
tcaggaggag gaagcggagg aggcagcgga gaggtccagc tggtggaaag cggaggagga 2220

-continued

```
gtggtcaggc caggagggtc tctgcgactg agttgtgctg catcaggctt cacttttgac   2280

gattacggaa tgagctgggt caggcaggca ccagggaagg gactggagtg ggtgagcggc   2340

atcaactgga atggaggctc tacaggatac gctgatagtg tgaagggccg cttcactatt   2400

agtcgagaca acgccaaaaa ttcactgtat ctgcagatga atagcctgcg cgccgaggac   2460

acagctgtgt actattgcgc cagaggaagg tcactgctgt ttgattattg ggggcagggc   2520

acactggtca ccgtctcccg ctgaggatcc                                    2550
```

```
<210> SEQ ID NO 122
<211> LENGTH: 847
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
                245                 250                 255

Glu Val Ala His Arg Phe Lys Asp Leu Gly Glu Glu Asn Phe Lys Ala
            260                 265                 270

Leu Val Leu Ile Ala Phe Ala Gln Tyr Leu Gln Gln Cys Pro Phe Glu
        275                 280                 285

Asp His Val Lys Leu Val Asn Glu Val Thr Glu Phe Ala Lys Thr Cys
    290                 295                 300
```

-continued

```
Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
            340                 345                 350

Phe Leu Gln His Lys Asp Asp Asn Pro Asn Leu Pro Arg Leu Val Arg
        355                 360                 365

Pro Glu Val Asp Val Met Cys Thr Ala Phe His Asp Asn Glu Glu Thr
    370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
        435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
        515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Ala Gly Gly Ser Gly
            580                 585                 590

Gly Ser Gly Gly Ser Gly Gly Ser Gly Gly Ser Ser Glu Leu Thr Gln
        595                 600                 605

Asp Pro Ala Val Ser Val Ala Leu Gly Gln Thr Val Arg Ile Thr Cys
    610                 615                 620

Gln Gly Asp Ser Leu Arg Ser Tyr Tyr Ala Ser Trp Tyr Gln Gln Lys
625                 630                 635                 640

Pro Gly Gln Ala Pro Val Leu Val Ile Tyr Gly Lys Asn Asn Arg Pro
                645                 650                 655

Ser Gly Ile Pro Asp Arg Phe Ser Gly Ser Ser Ser Gly Asn Thr Ala
            660                 665                 670

Ser Leu Thr Ile Thr Gly Ala Gln Ala Glu Asp Glu Ala Asp Tyr Tyr
        675                 680                 685

Cys Asn Ser Arg Asp Ser Ser Gly Asn His Val Val Phe Gly Gly Gly
    690                 695                 700

Thr Lys Leu Thr Val Gly Gly Gly Ser Gly Gly Gly Ser Gly Gly Gly
705                 710                 715                 720
```

-continued

```
Ser Gly Gly Gly Ser Gly Gly Gly Ser Gly Glu Val Gln Leu Val Glu
                725                 730                 735

Ser Gly Gly Gly Val Val Arg Pro Gly Gly Ser Leu Arg Leu Ser Cys
            740                 745                 750

Ala Ala Ser Gly Phe Thr Phe Asp Asp Tyr Gly Met Ser Trp Val Arg
        755                 760                 765

Gln Ala Pro Gly Lys Gly Leu Glu Trp Val Ser Gly Ile Asn Trp Asn
    770                 775                 780

Gly Gly Ser Thr Gly Tyr Ala Asp Ser Val Lys Gly Arg Phe Thr Ile
785                 790                 795                 800

Ser Arg Asp Asn Ala Lys Asn Ser Leu Tyr Leu Gln Met Asn Ser Leu
                805                 810                 815

Arg Ala Glu Asp Thr Ala Val Tyr Tyr Cys Ala Arg Gly Arg Ser Leu
            820                 825                 830

Leu Phe Asp Tyr Trp Gly Gln Gly Thr Leu Val Thr Val Ser Arg
        835                 840                 845


<210> SEQ ID NO 123
<211> LENGTH: 2301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123

tcttcagaac tgacccagga ccccgcagtg agcgtcgcac tgggccagac cgtgagaatc     60

acatgccagg gggattccct gaggtcttac tatgctagct ggtaccagca gaagccaggc    120

caggcacccg tgctggtcat ctatggcaaa aacaataggc cttcagggat tccagaccgc    180

tttagcggaa gctcctctgg caacacagca agcctgacaa ttactggcgc tcaggcagag    240

gacgaagccg attactattg caacagcagg gatagttcag gcaatcacgt ggtcttcgga    300

ggaggaacta agctgaccgt gggaggagga tctggaggag gaagtggcgg gggatcagga    360

ggaggaagcg gaggaggcag cggagaggtg cagctggtcg aaagcggagg aggagtggtc    420

cgcccaggag ggtctctgcg actgagttgt gccgcttcag gattcacctt tgacgattac    480

ggaatgtcct gggtgaggca ggcaccaggg aagggactgg agtgggtctc tggcatcaac    540

tggaatggag gctctacagg gtacgctgac agtgtgaagg gacggttcac catttcccgg    600

gataacgcca aaaattctct gtatctgcag atgaatagtc tgcgcgctga ggacaccgca    660

gtgtactatt gtgccagggg ccgcagtctg ctgttcgatt actggggcca gggaacactg    720

gtgactgtca gccgaggagg aagtggaggg tcaggaggca gcggaggcag cggagggtct    780

gtggtcctgc tgctgagact ggctaagaca tacgagacca cactggaaaa atgctgtgca    840

gccgctgacc cccatgagtg ctatgccaag gtgttcgatg agttcaagcc actggtcgag    900

gaaccccaga acctgatcaa gcagaattgt gagctgttcg aacagctggg cgagtacaaa    960

tttcagaacg ccctgctggt gcgctatacc aagaaagtgc ctcaggtctc aaccccaaca   1020

ctggtggagg tcagcaggaa tctgggcaag gtcgggtcca aatgctgtaa gcaccccgag   1080

gcaaaacgca tgccttgcgc cgaagactac ctgtccgtgg tcctgaacca gctgtgtgtg   1140

ctgcatgaga agacacctgt gtctgatcgg gtcactaaat gctgtaccga atctctggtg   1200

aaccggagac cttgctttag tgccctggag gtggacgaaa cttatgtccc aaaggagttc   1260

aatgctgaaa ctttcacctt tcacgcagat atctgtaccc tgagcgagaa ggaaagacag   1320
```

attaagaaac agacagccct ggtggagctg gtcaagcata aaccaaaggc caccaaggaa 1380
cagctgaaag ctgtgatgga cgatttcgca gcctttgtcg agaaatgctg taaggctgac 1440
gataaggaaa catgcttcgc agaggaaggg aagaaactgg tggctgcatc ccaggcagct 1500
ctgggactgg gaggcagtgg aggatcagga gggagcggag gctccggagg agacatccag 1560
atgactcagt ccccaagctc cctgtcagca agcgtgggcg accgggtcac aattacttgt 1620
agagcttctc aggatgtgaa taccgccgtc gcttggtacc agcagaaacc cggcaaggcc 1680
cctaaactgc tgatctactc cgcttctttc ctgtatagcg gagtgccatc ccggttcagc 1740
gggtcaagga gcggaactga cttcaccctg acaatttcta gtctgcagcc tgaggatttt 1800
gccacctact attgccagca gcactatact acccccccta ctttcggaca gggcaccaag 1860
gtggaaatca aaggagggtc tggaggaggg agtggaggag ggtcaggcgg agggagcgga 1920
ggagggtccg gcgaagtcca gctggtcgaa tccggaggag gactggtgca gcctggaggc 1980
tctctgaggc tgagttgtgc agcctcaggc tttaacatca aggacaccta cattcattgg 2040
gtgcggcagg caccagggaa aggactggag tgggtggcca gaatctatcc cacaaatgga 2100
tacactcgat atgccgactc tgtgaagggc cggttcacaa ttagcgcaga tacctccaaa 2160
aacacagcct acctgcagat gaacagcctg cgcgccgagg atactgctgt gtactattgc 2220
agccgatggg gcggggacgg cttctacgct atggactatt gggggcaggg gactctggtg 2280
acagtgagca gctgaggatc c 2301

<210> SEQ ID NO 124
<211> LENGTH: 764
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 124

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Val Phe Gly Gly Gly Thr Lys Leu Thr Val Gly Gly Gly Ser Gly
100 105 110

Gly Gly Ser Gly Gly Gly Ser Gly Gly Gly Ser Gly Gly Gly Ser Gly
115 120 125

Glu Val Gln Leu Val Glu Ser Gly Gly Gly Val Val Arg Pro Gly Gly
130 135 140

Ser Leu Arg Leu Ser Cys Ala Ala Ser Gly Phe Thr Phe Asp Asp Tyr
145 150 155 160

Gly Met Ser Trp Val Arg Gln Ala Pro Gly Lys Gly Leu Glu Trp Val
165 170 175

Ser Gly Ile Asn Trp Asn Gly Gly Ser Thr Gly Tyr Ala Asp Ser Val

-continued

```
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Gly Ser Gly Gly Ser Gly Gly
                245                 250                 255

Ser Gly Gly Ser Val Val Leu Leu Leu Arg Leu Ala Lys Thr Tyr Glu
            260                 265                 270

Thr Thr Leu Glu Lys Cys Cys Ala Ala Ala Asp Pro His Glu Cys Tyr
        275                 280                 285

Ala Lys Val Phe Asp Glu Phe Lys Pro Leu Val Glu Glu Pro Gln Asn
    290                 295                 300

Leu Ile Lys Gln Asn Cys Glu Leu Phe Glu Gln Leu Gly Glu Tyr Lys
305                 310                 315                 320

Phe Gln Asn Ala Leu Leu Val Arg Tyr Thr Lys Lys Val Pro Gln Val
                325                 330                 335

Ser Thr Pro Thr Leu Val Glu Val Ser Arg Asn Leu Gly Lys Val Gly
            340                 345                 350

Ser Lys Cys Cys Lys His Pro Glu Ala Lys Arg Met Pro Cys Ala Glu
        355                 360                 365

Asp Tyr Leu Ser Val Val Leu Asn Gln Leu Cys Val Leu His Glu Lys
    370                 375                 380

Thr Pro Val Ser Asp Arg Val Thr Lys Cys Cys Thr Glu Ser Leu Val
385                 390                 395                 400

Asn Arg Arg Pro Cys Phe Ser Ala Leu Glu Val Asp Glu Thr Tyr Val
                405                 410                 415

Pro Lys Glu Phe Asn Ala Glu Thr Phe Thr Phe His Ala Asp Ile Cys
            420                 425                 430

Thr Leu Ser Glu Lys Glu Arg Gln Ile Lys Lys Gln Thr Ala Leu Val
        435                 440                 445

Glu Leu Val Lys His Lys Pro Lys Ala Thr Lys Glu Gln Leu Lys Ala
    450                 455                 460

Val Met Asp Asp Phe Ala Ala Phe Val Glu Lys Cys Cys Lys Ala Asp
465                 470                 475                 480

Asp Lys Glu Thr Cys Phe Ala Glu Glu Gly Lys Lys Leu Val Ala Ala
                485                 490                 495

Ser Gln Ala Ala Leu Gly Leu Gly Gly Ser Gly Gly Ser Gly Gly Ser
            500                 505                 510

Gly Gly Ser Gly Gly Asp Ile Gln Met Thr Gln Ser Pro Ser Ser Leu
        515                 520                 525

Ser Ala Ser Val Gly Asp Arg Val Thr Ile Thr Cys Arg Ala Ser Gln
    530                 535                 540

Asp Val Asn Thr Ala Val Ala Trp Tyr Gln Gln Lys Pro Gly Lys Ala
545                 550                 555                 560

Pro Lys Leu Leu Ile Tyr Ser Ala Ser Phe Leu Tyr Ser Gly Val Pro
                565                 570                 575

Ser Arg Phe Ser Gly Ser Arg Ser Gly Thr Asp Phe Thr Leu Thr Ile
            580                 585                 590

Ser Ser Leu Gln Pro Glu Asp Phe Ala Thr Tyr Tyr Cys Gln Gln His
        595                 600                 605
```

```
Tyr Thr Thr Pro Pro Thr Phe Gly Gln Gly Thr Lys Val Glu Ile Lys
    610                 615                 620

Gly Gly Ser Gly Gly Gly Ser Gly Gly Gly Ser Gly Gly Gly Ser Gly
625                 630                 635                 640

Gly Gly Ser Gly Glu Val Gln Leu Val Glu Ser Gly Gly Gly Leu Val
                645                 650                 655

Gln Pro Gly Gly Ser Leu Arg Leu Ser Cys Ala Ala Ser Gly Phe Asn
            660                 665                 670

Ile Lys Asp Thr Tyr Ile His Trp Val Arg Gln Ala Pro Gly Lys Gly
        675                 680                 685

Leu Glu Trp Val Ala Arg Ile Tyr Pro Thr Asn Gly Tyr Thr Arg Tyr
    690                 695                 700

Ala Asp Ser Val Lys Gly Arg Phe Thr Ile Ser Ala Asp Thr Ser Lys
705                 710                 715                 720

Asn Thr Ala Tyr Leu Gln Met Asn Ser Leu Arg Ala Glu Asp Thr Ala
                725                 730                 735

Val Tyr Tyr Cys Ser Arg Trp Gly Gly Asp Gly Phe Tyr Ala Met Asp
            740                 745                 750

Tyr Trp Gly Gln Gly Thr Leu Val Thr Val Ser Ser
        755                 760
```

<210> SEQ ID NO 125
<211> LENGTH: 2301
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 125

```
gatattcaga tgacccagag cccaagctcc ctgagtgcat cagtgggcga cagagtcaca     60

atcacttgca gggctagcca ggatgtgaac acagctgtcg catggtacca gcagaaacca    120

ggcaaggctc ccaaactgct gatctacagc gcatccttcc tgtattccgg cgtgccctct    180

aggttttctg ggagtcgctc aggaactgac ttcaccctga caatctctag tctgcagcct    240

gaggattttg ccacctacta ttgccagcag cactacacca caccccctac tttcggccag    300

gggaccaagg tggagatcaa gggcgggagt ggaggcgggt caggcggagg gagcggagga    360

gggtccggag gagggtctgg cgaggtgcag ctggtcgaaa gcggaggagg actggtgcag    420

cctggaggca gtctgcggct gtcatgtgcc gctagcggct tcaacatcaa ggacacctac    480

attcattggg tgcgccaggc accaggaaaa ggcctggagt gggtcgcccg aatctatccc    540

accaatgggt acacaagata tgccgactcc gtgaagggac gctttacaat ttccgctgat    600

acttctaaaa acaccgcata cctgcagatg aatagtctga gagcagagga tactgccgtg    660

tactattgta gcagatgggg gggagacggc ttctacgcca tggactactg gggccagggc    720

actctggtga ccgtctcaag cggagggagc ggaggctccg gaggatctgg agggagtgga    780

ggctcagtgg tcctgctgct gaggctggct aagacctacg agactaccct ggaaaaatgc    840

tgtgcagccg ctgaccccca cgagtgctat gccaaggtgt tcgatgagtt caagccactg    900

gtcgaggaac cccagaacct gatcaagcag aattgtgagc tgttcgaaca gctgggcgag    960

tacaaatttc agaacgccct gctggtgcgc tatacaaaga aagtgcctca ggtcagtact   1020

ccaaccctgg tggaagtctc acggaatctg ggaaaggtcg gcagcaagtg ctgtaaacac   1080

cccgaggcaa aaagaatgcc ttgcgccgaa gactacctga gcgtggtcct gaatcagctg   1140
```

-continued

```
tgtgtgctgc atgagaagac acctgtgagc gatagggtca caaaatgctg tactgaatcc   1200

ctggtgaacc ggagaccttg cttttctgct ctggaggtgg acgaaactta tgtcccaaag   1260

gagttcaatg ccgaaacatt cacttttcac gctgatatct gtaccctgag cgagaaggaa   1320

cgccagatta agaaacagac agccctggtg gagctggtca agcataaacc aaaggcaact   1380

aaggaacagc tgaaagccgt gatggacgat ttcgcagcct ttgtcgagaa gtgctgtaaa   1440

gccgacgata aggaaacctg ctttgctgag gaaggcaaga aactggtggc tgcaagccag   1500

gcagctctgg gactgggagg aagcggaggg tccggaggct ctgggggaag tggagggtcc   1560

tctgagctga cccaggaccc cgctgtgtcc gtcgcactgg gacagaccgt gcgaattaca   1620

tgtcagggcg attcactgcg gagctactat gcttcttggt accagcagaa gcctggccag   1680

gcaccagtgc tggtcatcta tggaaaaaac aatcggccca gtggcattcc tgacagattt   1740

tcaggcagtt caagcgggaa caccgcatcc ctgaccatca caggcgccca ggctgaggac   1800

gaagccgatt actattgcaa ctctagggat tcctctggca atcatgtggt cttcggaggc   1860

gggacaaagc tgactgtggg aggagggagt ggcggagggt caggcggcgg gagcggcggc   1920

gggtccggcg gcgggtctgg agaagtgcag ctggtcgaat ccggaggagg agtggtccgc   1980

ccaggaggca gtctgcgact gtcatgtgca gccagcgggt tcacctttga cgattacgga   2040

atgtcctggg tgcggcaggc accaggcaag ggactggagt gggtgtctgg catcaactgg   2100

aatgggggca gcacaggcta cgctgactct gtgaaggggc gattcactat tagccgggat   2160

aacgccaaaa attccctgta tctgcagatg aacagcctga gagccgagga cacagctgtg   2220

tactattgcg ccagggggcg gtcactgctg tttgattatt gggggcaggg aactctggtc   2280

actgtctcta ggtgaggatc c                                              2301
```

```
<210> SEQ ID NO 126
<211> LENGTH: 764
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140
```

```
Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Gly Ser Gly Gly Ser
                245                 250                 255

Gly Gly Ser Gly Gly Ser Val Val Leu Leu Leu Arg Leu Ala Lys Thr
            260                 265                 270

Tyr Glu Thr Thr Leu Glu Lys Cys Cys Ala Ala Ala Asp Pro His Glu
        275                 280                 285

Cys Tyr Ala Lys Val Phe Asp Glu Phe Lys Pro Leu Val Glu Glu Pro
    290                 295                 300

Gln Asn Leu Ile Lys Gln Asn Cys Glu Leu Phe Glu Gln Leu Gly Glu
305                 310                 315                 320

Tyr Lys Phe Gln Asn Ala Leu Leu Val Arg Tyr Thr Lys Lys Val Pro
                325                 330                 335

Gln Val Ser Thr Pro Thr Leu Val Glu Val Ser Arg Asn Leu Gly Lys
            340                 345                 350

Val Gly Ser Lys Cys Cys Lys His Pro Glu Ala Lys Arg Met Pro Cys
        355                 360                 365

Ala Glu Asp Tyr Leu Ser Val Val Leu Asn Gln Leu Cys Val Leu His
    370                 375                 380

Glu Lys Thr Pro Val Ser Asp Arg Val Thr Lys Cys Cys Thr Glu Ser
385                 390                 395                 400

Leu Val Asn Arg Arg Pro Cys Phe Ser Ala Leu Glu Val Asp Glu Thr
                405                 410                 415

Tyr Val Pro Lys Glu Phe Asn Ala Glu Thr Phe Thr Phe His Ala Asp
            420                 425                 430

Ile Cys Thr Leu Ser Glu Lys Glu Arg Gln Ile Lys Lys Gln Thr Ala
        435                 440                 445

Leu Val Glu Leu Val Lys His Lys Pro Lys Ala Thr Lys Glu Gln Leu
    450                 455                 460

Lys Ala Val Met Asp Asp Phe Ala Ala Phe Val Glu Lys Cys Cys Lys
465                 470                 475                 480

Ala Asp Asp Lys Glu Thr Cys Phe Ala Glu Glu Gly Lys Lys Leu Val
                485                 490                 495

Ala Ala Ser Gln Ala Ala Leu Gly Leu Gly Gly Ser Gly Gly Ser Gly
            500                 505                 510

Gly Ser Gly Gly Ser Gly Gly Ser Ser Glu Leu Thr Gln Asp Pro Ala
        515                 520                 525

Val Ser Val Ala Leu Gly Gln Thr Val Arg Ile Thr Cys Gln Gly Asp
    530                 535                 540

Ser Leu Arg Ser Tyr Tyr Ala Ser Trp Tyr Gln Gln Lys Pro Gly Gln
545                 550                 555                 560

Ala Pro Val Leu Val Ile Tyr Gly Lys Asn Asn Arg Pro Ser Gly Ile
```

```
                565                 570                 575

Pro Asp Arg Phe Ser Gly Ser Ser Ser Gly Asn Thr Ala Ser Leu Thr
            580                 585                 590

Ile Thr Gly Ala Gln Ala Glu Asp Glu Ala Asp Tyr Tyr Cys Asn Ser
        595                 600                 605

Arg Asp Ser Ser Gly Asn His Val Val Phe Gly Gly Gly Thr Lys Leu
    610                 615                 620

Thr Val Gly Gly Gly Ser Gly Gly Gly Ser Gly Gly Gly Ser Gly Gly
625                 630                 635                 640

Gly Ser Gly Gly Gly Ser Gly Glu Val Gln Leu Val Glu Ser Gly Gly
                645                 650                 655

Gly Val Val Arg Pro Gly Gly Ser Leu Arg Leu Ser Cys Ala Ala Ser
            660                 665                 670

Gly Phe Thr Phe Asp Asp Tyr Gly Met Ser Trp Val Arg Gln Ala Pro
        675                 680                 685

Gly Lys Gly Leu Glu Trp Val Ser Gly Ile Asn Trp Asn Gly Gly Ser
    690                 695                 700

Thr Gly Tyr Ala Asp Ser Val Lys Gly Arg Phe Thr Ile Ser Arg Asp
705                 710                 715                 720

Asn Ala Lys Asn Ser Leu Tyr Leu Gln Met Asn Ser Leu Arg Ala Glu
                725                 730                 735

Asp Thr Ala Val Tyr Tyr Cys Ala Arg Gly Arg Ser Leu Leu Phe Asp
            740                 745                 750

Tyr Trp Gly Gln Gly Thr Leu Val Thr Val Ser Arg
        755                 760


<210> SEQ ID NO 127
<211> LENGTH: 3294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

gacattcaga tgacacagag cccaagctcc ctgtctgcaa gtgtcggcga tcgagtgaca      60

atcacttgcc gggcttccca ggacgtcaac actgccgtgg cttggtacca gcagaaacct     120

gggaaggccc caaaactgct gatctactca gctagctttc tgtatagcgg agtgccctcc     180

cggttctccg gatctagaag tggcaccgat tttaccctga caatctctag tctgcagcct     240

gaggacttcg ccacatacta ttgccagcag cactatacca cacccctac ctttgggcag      300

ggaacaaagg tggaaatcaa aggagggtct ggaggaggga gtggaggagg gtcaggcgga     360

gggagcggag gagggtccgg cgaggtgcag ctggtcgaaa gcggaggagg actggtgcag     420

cctggaggct ctctgaggct gagttgtgcc gcttcaggct tcaacatcaa agatacctac     480

attcattggg tccgccaggc tccaggcaag ggactggagt gggtggcacg aatctatccc     540

acaaatggat acactcggta tgccgattcc gtgaaaggca gattcactat tagcgctgac     600

acctccaaga acacagcata cctgcagatg aatagtctgc gagcagagga caccgccgtg     660

tactattgct cacggtgggg gggagacggc ttttacgcca tggattattg gggacagggc     720

actctggtga ccgtctcaag cggagggagc ggagatgcac acaagtccga ggtcgctcat     780

cgcttcaaag acctgggcga ggaaaacttt aaggccctgg tgctgattgc attcgcccag     840

tacctgcagc agtgcccatt cgaggaccac gtgaaactgg tcaacgaagt gactgaattt     900
```

```
gccaagacct gcgtggctga cgagtcagca gaaaattgtg ataaaagcct gcatacactg    960
ttcggcgata agctgtgtac agtggccact ctgagggaga cttatgggga aatggccgac   1020
tgctgtgcta aacaggagcc agaacgcaac gagtgctttc tgcagcacaa ggacgataac   1080
ccaaatctgc ccagactggt gaggcccgaa gtggacgtca tgtgtacagc cttccacgat   1140
aatgaggaaa cttttctgaa gaaataccctg tatgagatcg ctcggagaca tccctacttc   1200
tatgcccctg aactgctgtt ctttgctaag aggtacaaag cagcctttac cgagtgctgt   1260
caggctgcag ataaggccgc ttgcctgctg ccaaaactgg acgagctgag agatgaaggc   1320
aaggcatcct ctgccaagca gaggctgaaa tgtgcctccc tgcagaagtt cggggagagg   1380
gcttttaaag cttgggcagt ggcacgactg agccagcgat tcccaaaggc tgagtttgca   1440
gaagtctcca agctggtgac cgacctgaca aaagtgcaca ccgagtgctg tcatggcgac   1500
ctgctggaat gcgccgacga tcgcgccgat ctggctaagt acatctgtga gaaccaggac   1560
agcattagtt caaagctgaa agagtgctgt gaaaagcctc tgctggagaa atcccactgc   1620
attgcagagg tggaaaacga cgaaatgcca gcagatctgc cttccctggc agcagacttc   1680
gtcgagtcta aggatgtgtg taaaaattac gctgaagcaa aggatgtgtt cctgggcatg   1740
tttctgtacg agtatgccag gcgccaccct gactacagcg tggtcctgct gctgcggctg   1800
gctaaaacct atgagactac cctggaaaag tgctgtgctg cagccgatcc acatgagtgc   1860
tatgccaagg tcttcgacga gttcaagcca ctggtggagg aaccccagaa cctgatcaaa   1920
cagaattgtg agctgtttga acagctgggc gagtacaagt tccagaacgc cctgctggtg   1980
agatatacaa agaaagtccc tcaggtgagt actccaaccc tggtggaagt ctcacggaat   2040
ctgggcaaag tggggagcaa gtgctgtaaa caccccgagg caaagagaat gccttgcgcc   2100
gaagattacc tgtctgtggt cctgaatcag ctgtgtgtgc tgcatgagaa aactcctgtc   2160
agcgaccggg tgactaagtg ctgtaccgaa tccctggtga accgacggcc ttgcttctct   2220
gccctggagg tcgatgaaac atatgtgcca aaggagttta atgcagaaac attcactttt   2280
cacgccgaca tctgtactct gagcgagaag gaaagacaga ttaagaaaca gaccgccctg   2340
gtcgagctgg tgaagcataa accaaaggct accaaggaac agctgaaagc agtcatggac   2400
gatttcgctg catttgtgga gaagtgctgt aaagcagacg ataaggaaac atgcttcgcc   2460
gaggaaggga agaaactggt ggcagctagc caggcagcac tgggactggg aggctcagga   2520
ggaagcggag ggtccggagg ctctggagga agctccgagc tgacccagga ccccgcagtg   2580
tctgtcgcac tgggacagac agtgaggatt acttgtcagg gggacagtct gcgctcatac   2640
tatgctagct ggtaccagca gaaaccaggc caggcacccg tgctggtcat ctatggcaag   2700
aacaatcgcc cttccgggat tccagatcga ttctctgggt ctagttcagg aaacaccgca   2760
tctctgacca tcacaggcgc ccaggctgag gacgaagctg attactattg caacagcaga   2820
gacagctccg gcaatcacgt ggtctttgga ggaggaacta agctgaccgt gggaggagga   2880
tctggaggag gaagtggcgg gggatcagga ggaggaagcg gaggaggcag cggagaggtc   2940
cagctggtgg aaagcggagg aggcgtggtc agaccaggag ggtctctgag actgtcctgt   3000
gctgcatcag gattcacctt tgacgattac ggcatgtctt gggtcaggca ggcacctggg   3060
aagggcctgg aatgggtgag tggcatcaac tggaatggag gctctaccgg gtacgccgat   3120
agtgtgaaag gaaggttcac aattagtcgc gacaacgcta agaacagcct gtatctgcag   3180
atgaatagcc tgcgcgctga ggacacagca gtgtactatt gcgccagggg gaggtcactg   3240
ctgtttgatt attgggggca gggaactctg gtcactgtgt cacggtgagg atcc         3294
```

<210> SEQ ID NO 128
<211> LENGTH: 1095
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 128

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Gly Gly Ser Gly Gly
100 105 110

Gly Ser Gly Gly Gly Ser Gly Gly Gly Ser Gly Gly Gly Ser Gly Glu
115 120 125

Val Gln Leu Val Glu Ser Gly Gly Gly Leu Val Gln Pro Gly Gly Ser
130 135 140

Leu Arg Leu Ser Cys Ala Ala Ser Gly Phe Asn Ile Lys Asp Thr Tyr
145 150 155 160

Ile His Trp Val Arg Gln Ala Pro Gly Lys Gly Leu Glu Trp Val Ala
165 170 175

Arg Ile Tyr Pro Thr Asn Gly Tyr Thr Arg Tyr Ala Asp Ser Val Lys
180 185 190

Gly Arg Phe Thr Ile Ser Ala Asp Thr Ser Lys Asn Thr Ala Tyr Leu
195 200 205

Gln Met Asn Ser Leu Arg Ala Glu Asp Thr Ala Val Tyr Tyr Cys Ser
210 215 220

Arg Trp Gly Gly Asp Gly Phe Tyr Ala Met Asp Tyr Trp Gly Gln Gly
225 230 235 240

Thr Leu Val Thr Val Ser Ser Gly Gly Ser Gly Asp Ala His Lys Ser
245 250 255

Glu Val Ala His Arg Phe Lys Asp Leu Gly Glu Glu Asn Phe Lys Ala
260 265 270

Leu Val Leu Ile Ala Phe Ala Gln Tyr Leu Gln Gln Cys Pro Phe Glu
275 280 285

Asp His Val Lys Leu Val Asn Glu Val Thr Glu Phe Ala Lys Thr Cys
290 295 300

Val Ala Asp Glu Ser Ala Glu Asn Cys Asp Lys Ser Leu His Thr Leu
305 310 315 320

Phe Gly Asp Lys Leu Cys Thr Val Ala Thr Leu Arg Glu Thr Tyr Gly
325 330 335

Glu Met Ala Asp Cys Cys Ala Lys Gln Glu Pro Glu Arg Asn Glu Cys
340 345 350

Phe Leu Gln His Lys Asp Asp Asn Pro Asn Leu Pro Arg Leu Val Arg

-continued

```
        355                 360                 365

Pro Glu Val Asp Val Met Cys Thr Ala Phe His Asp Asn Glu Glu Thr
    370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
        435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
        515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Arg His Pro Asp Tyr
            580                 585                 590

Ser Val Val Leu Leu Leu Arg Leu Ala Lys Thr Tyr Glu Thr Thr Leu
        595                 600                 605

Glu Lys Cys Cys Ala Ala Ala Asp Pro His Glu Cys Tyr Ala Lys Val
    610                 615                 620

Phe Asp Glu Phe Lys Pro Leu Val Glu Glu Pro Gln Asn Leu Ile Lys
625                 630                 635                 640

Gln Asn Cys Glu Leu Phe Glu Gln Leu Gly Glu Tyr Lys Phe Gln Asn
                645                 650                 655

Ala Leu Leu Val Arg Tyr Thr Lys Lys Val Pro Gln Val Ser Thr Pro
            660                 665                 670

Thr Leu Val Glu Val Ser Arg Asn Leu Gly Lys Val Gly Ser Lys Cys
        675                 680                 685

Cys Lys His Pro Glu Ala Lys Arg Met Pro Cys Ala Glu Asp Tyr Leu
    690                 695                 700

Ser Val Val Leu Asn Gln Leu Cys Val Leu His Glu Lys Thr Pro Val
705                 710                 715                 720

Ser Asp Arg Val Thr Lys Cys Cys Thr Glu Ser Leu Val Asn Arg Arg
                725                 730                 735

Pro Cys Phe Ser Ala Leu Glu Val Asp Glu Thr Tyr Val Pro Lys Glu
            740                 745                 750

Phe Asn Ala Glu Thr Phe Thr Phe His Ala Asp Ile Cys Thr Leu Ser
        755                 760                 765

Glu Lys Glu Arg Gln Ile Lys Lys Gln Thr Ala Leu Val Glu Leu Val
    770                 775                 780
```

Lys His Lys Pro Lys Ala Thr Lys Glu Gln Leu Lys Ala Val Met Asp
785 790 795 800

Asp Phe Ala Ala Phe Val Glu Lys Cys Cys Lys Ala Asp Asp Lys Glu
805 810 815

Thr Cys Phe Ala Glu Glu Gly Lys Lys Leu Val Ala Ala Ser Gln Ala
820 825 830

Ala Leu Gly Leu Gly Gly Ser Gly Gly Ser Gly Gly Ser Gly Gly Ser
835 840 845

Gly Gly Ser Ser Glu Leu Thr Gln Asp Pro Ala Val Ser Val Ala Leu
850 855 860

Gly Gln Thr Val Arg Ile Thr Cys Gln Gly Asp Ser Leu Arg Ser Tyr
865 870 875 880

Tyr Ala Ser Trp Tyr Gln Gln Lys Pro Gly Gln Ala Pro Val Leu Val
885 890 895

Ile Tyr Gly Lys Asn Asn Arg Pro Ser Gly Ile Pro Asp Arg Phe Ser
900 905 910

Gly Ser Ser Ser Gly Asn Thr Ala Ser Leu Thr Ile Thr Gly Ala Gln
915 920 925

Ala Glu Asp Glu Ala Asp Tyr Tyr Cys Asn Ser Arg Asp Ser Ser Gly
930 935 940

Asn His Val Val Phe Gly Gly Gly Thr Lys Leu Thr Val Gly Gly Gly
945 950 955 960

Ser Gly Gly Gly Ser Gly Gly Gly Ser Gly Gly Gly Ser Gly Gly Gly
965 970 975

Ser Gly Glu Val Gln Leu Val Glu Ser Gly Gly Gly Val Val Arg Pro
980 985 990

Gly Gly Ser Leu Arg Leu Ser Cys Ala Ala Ser Gly Phe Thr Phe Asp
995 1000 1005

Asp Tyr Gly Met Ser Trp Val Arg Gln Ala Pro Gly Lys Gly Leu
1010 1015 1020

Glu Trp Val Ser Gly Ile Asn Trp Asn Gly Gly Ser Thr Gly Tyr
1025 1030 1035

Ala Asp Ser Val Lys Gly Arg Phe Thr Ile Ser Arg Asp Asn Ala
1040 1045 1050

Lys Asn Ser Leu Tyr Leu Gln Met Asn Ser Leu Arg Ala Glu Asp
1055 1060 1065

Thr Ala Val Tyr Tyr Cys Ala Arg Gly Arg Ser Leu Leu Phe Asp
1070 1075 1080

Tyr Trp Gly Gln Gly Thr Leu Val Thr Val Ser Arg
1085 1090 1095

<210> SEQ ID NO 129
<211> LENGTH: 3294
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 129
agtagcgaac tgacccagga ccccgcagtg agcgtcgcac tggggcagac agtgcgaatc 60
acttgccagg gagacagcct gcggtcctac tatgcttcct ggtaccagca gaaacctggc 120
caggcaccag tgctggtcat ctatgggaag aacaatcggc ccagcggcat ccccgataga 180
ttctccggca gctcctctgg gaacaccgcc tctctgacaa ttactggggc ccaggctgag 240
gacgaagctg attactattg caacagcagg gacagttcag gaaatcacgt ggtctttgga 300
ggaggaacta agctgaccgt gggaggaggc agcggaggag gatctggagg aggaagtgga 360
ggaggatcag gaggaggaag cggagaggtg cagctggtcg aaagcggagg aggagtggtc 420
agacctggag ggtccctgag gctgtcttgt gccgctagtg gcttcacctt tgacgattac 480
ggaatgagtt gggtccggca ggcaccagga aagggactgg agtgggtgtc aggcatcaac 540
tggaatggag gcagtaccgg atacgccgat tcagtgaaag gcaggttcac aatttctcgc 600
gacaacgcta agaatagtct gtatctgcag atgaactcac tgagagctga ggatacagca 660
gtgtactatt gcgccagagg caggtctctg ctgtttgact actgggggca gggaacactg 720
gtgactgtct cacgaggagg aagcggcgat gcacacaagt ccgaggtcgc tcatagattc 780
aaagacctgg gggaggaaaa ttttaaggcc ctggtgctga tcgcattcgc ccagtatctg 840
cagcagtgcc cattcgagga ccacgtgaaa ctggtcaacg aggtgaccga atttgccaag 900
acatgcgtgg ccgacgagag cgctgaaaat tgtgataaat ccctgcatac actgttcggg 960
gataagctgt gtaccgtggc cacactgagg gagacttacg gagaaatggc agactgctgt 1020
gccaaacagg agccagaacg caacgagtgc tttctgcagc acaaggacga taacccaaat 1080
ctgccacgac tggtgcgacc agaagtggac gtcatgtgta cagccttcca cgataatgag 1140
gaaacttttc tgaagaaata cctgtatgag atcgcccgga gacatcccta cttctatgct 1200
cctgaactgc tgttctttgc aaaacggtac aaggcagcct ttaccgagtg ctgtcaggct 1260
gcagataagg ccgcttgcct gctgccaaaa ctggacgagc tgagagatga aggcaaggca 1320
agctccgcca agcagaggct gaaatgtgct agcctgcaga agttcgggga gagggccttc 1380
aaggcttggg cagtggcacg actgtcacag agattcccca aggctgagtt tgcagaagtc 1440
agcaagctgg tgactgacct gaccaaagtg cacaccgagt gctgtcatgg cgacctgctg 1500
gaatgcgccg acgatcgcgc cgatctggct aagtacatct gtgagaacca ggacagcatt 1560
tctagtaagc tgaaagagtg ctgtgaaaag cctctgctgg agaaatccca ctgcatcgcc 1620
gaggtggaaa acgacgaaat gccagctgat ctgccctctc tggcagccga cttcgtcgag 1680
agtaaggatg tgtgtaaaaa ttacgctgaa gcaaaggatg tgttcctggg catgtttctg 1740
tacgagtatg caaggcgaca cccagactac tccgtggtcc tgctgctgcg gctggctaaa 1800
acctatgaga ccacactgga aaagtgctgt gctgcagccg atcctcatga gtgctatgcc 1860
aaggtcttcg acgagttcaa gccactggtg gaggaacccc agaacctgat caagcagaat 1920
tgtgagctgt ttgaacagct gggcgagtac aagttccaga acgccctgct ggtgagatat 1980
acaaagaaag tccctcaggt gtcaacccca acactggtgg aggtcagccg gaatctgggg 2040
aaagtgggca gcaaatgctg taagcacccc gaggcaaaga gaatgccttg cgccgaagat 2100
tacctgtctg tggtcctgaa ccagctgtgt gtgctgcatg agaaaactcc tgtcagtgac 2160
agggtgacca agtgctgtac agaatctctg gtgaaccgac ggccttgctt cagtgccctg 2220
gaggtcgatg aaacatatgt gccaaaggag tttaatgccg aaactttcac ctttcacgct 2280
gacatctgta ctctgagcga gaaggaacgc cagattaaga aacagaccgc cctggtcgag 2340
ctggtgaagc ataaaccaaa ggcaacaaag gaacagctga aagccgtcat ggacgatttc 2400
gctgcatttg tggagaaatg ctgtaaggcc gacgataagg aaacttgctt cgctgaggaa 2460
ggaaagaaac tggtggcagc ttcccaggca gcactgggac tgggagggtc tggaggcagt 2520
ggaggatcag gagggagcgg aggcgacatc cagatgaccc agtccccctc aagcctgagt 2580

```
gcctcagtcg gcgatcgcgt gacaattact tgtcgagctt ctcaggacgt caatacagcc   2640

gtggcttggt atcagcagaa gcctggaaag gcaccaaaac tgctgatcta cagcgcctcc   2700

tttctgtatt ccggcgtgcc ctctcgattc tctggaagtc ggtcaggcac cgattttacc   2760

ctgacaattt cctctctgca gcctgaggac ttcgccacat actattgcca gcagcactat   2820

actacccccc ctacttttgg ccaggggacc aaggtggaaa tcaaaggggg aagtggcggg   2880

ggatcaggcg gcggaagcgg cggcggcagc ggcggcggat ctggagaggt ccagctggtg   2940

gaaagcggag gaggactggt gcagcctgga gggagtctgc gactgtcatg tgctgcaagc   3000

ggcttcaaca tcaaagatac ctacattcat tgggtcaggc aggcccctgg aaagggcctg   3060

gaatgggtgg cacgaatcta tcccactaat ggctacacca gatatgccga ttccgtgaaa   3120

gggcgcttca ctatttccgc tgacacatct aagaacactg catacctgca gatgaacagc   3180

ctgcgcgctg aggacaccgc agtgtactat tgctctcgat ggggcggcga cggcttctac   3240

gcaatggact actgggggca ggggacactg gtgactgtga gcagctgagg atcc         3294
```

```
<210> SEQ ID NO 130
<211> LENGTH: 1095
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240
```

```
Val Thr Val Ser Arg Gly Gly Ser Gly Asp Ala His Lys Ser Glu Val
                245                 250                 255

Ala His Arg Phe Lys Asp Leu Gly Glu Glu Asn Phe Lys Ala Leu Val
            260                 265                 270

Leu Ile Ala Phe Ala Gln Tyr Leu Gln Gln Cys Pro Phe Glu Asp His
        275                 280                 285

Val Lys Leu Val Asn Glu Val Thr Glu Phe Ala Lys Thr Cys Val Ala
    290                 295                 300

Asp Glu Ser Ala Glu Asn Cys Asp Lys Ser Leu His Thr Leu Phe Gly
305                 310                 315                 320

Asp Lys Leu Cys Thr Val Ala Thr Leu Arg Glu Thr Tyr Gly Glu Met
                325                 330                 335

Ala Asp Cys Cys Ala Lys Gln Glu Pro Glu Arg Asn Glu Cys Phe Leu
            340                 345                 350

Gln His Lys Asp Asp Asn Pro Asn Leu Pro Arg Leu Val Arg Pro Glu
        355                 360                 365

Val Asp Val Met Cys Thr Ala Phe His Asp Asn Glu Glu Thr Phe Leu
    370                 375                 380

Lys Lys Tyr Leu Tyr Glu Ile Ala Arg Arg His Pro Tyr Phe Tyr Ala
385                 390                 395                 400

Pro Glu Leu Leu Phe Phe Ala Lys Arg Tyr Lys Ala Ala Phe Thr Glu
                405                 410                 415

Cys Cys Gln Ala Ala Asp Lys Ala Ala Cys Leu Leu Pro Lys Leu Asp
            420                 425                 430

Glu Leu Arg Asp Glu Gly Lys Ala Ser Ser Ala Lys Gln Arg Leu Lys
        435                 440                 445

Cys Ala Ser Leu Gln Lys Phe Gly Glu Arg Ala Phe Lys Ala Trp Ala
    450                 455                 460

Val Ala Arg Leu Ser Gln Arg Phe Pro Lys Ala Glu Phe Ala Glu Val
465                 470                 475                 480

Ser Lys Leu Val Thr Asp Leu Thr Lys Val His Thr Glu Cys Cys His
                485                 490                 495

Gly Asp Leu Leu Glu Cys Ala Asp Asp Arg Ala Asp Leu Ala Lys Tyr
            500                 505                 510

Ile Cys Glu Asn Gln Asp Ser Ile Ser Ser Lys Leu Lys Glu Cys Cys
        515                 520                 525

Glu Lys Pro Leu Leu Glu Lys Ser His Cys Ile Ala Glu Val Glu Asn
    530                 535                 540

Asp Glu Met Pro Ala Asp Leu Pro Ser Leu Ala Ala Asp Phe Val Glu
545                 550                 555                 560

Ser Lys Asp Val Cys Lys Asn Tyr Ala Glu Ala Lys Asp Val Phe Leu
                565                 570                 575

Gly Met Phe Leu Tyr Glu Tyr Ala Arg Arg His Pro Asp Tyr Ser Val
            580                 585                 590

Val Leu Leu Leu Arg Leu Ala Lys Thr Tyr Glu Thr Thr Leu Glu Lys
        595                 600                 605

Cys Cys Ala Ala Ala Asp Pro His Glu Cys Tyr Ala Lys Val Phe Asp
    610                 615                 620

Glu Phe Lys Pro Leu Val Glu Glu Pro Gln Asn Leu Ile Lys Gln Asn
625                 630                 635                 640

Cys Glu Leu Phe Glu Gln Leu Gly Glu Tyr Lys Phe Gln Asn Ala Leu
                645                 650                 655
```

```
Leu Val Arg Tyr Thr Lys Lys Val Pro Gln Val Ser Thr Pro Thr Leu
            660                 665                 670

Val Glu Val Ser Arg Asn Leu Gly Lys Val Gly Ser Lys Cys Cys Lys
        675                 680                 685

His Pro Glu Ala Lys Arg Met Pro Cys Ala Glu Asp Tyr Leu Ser Val
    690                 695                 700

Val Leu Asn Gln Leu Cys Val Leu His Glu Lys Thr Pro Val Ser Asp
705                 710                 715                 720

Arg Val Thr Lys Cys Cys Thr Glu Ser Leu Val Asn Arg Arg Pro Cys
                725                 730                 735

Phe Ser Ala Leu Glu Val Asp Glu Thr Tyr Val Pro Lys Glu Phe Asn
            740                 745                 750

Ala Glu Thr Phe Thr Phe His Ala Asp Ile Cys Thr Leu Ser Glu Lys
        755                 760                 765

Glu Arg Gln Ile Lys Lys Gln Thr Ala Leu Val Glu Leu Val Lys His
    770                 775                 780

Lys Pro Lys Ala Thr Lys Glu Gln Leu Lys Ala Val Met Asp Asp Phe
785                 790                 795                 800

Ala Ala Phe Val Glu Lys Cys Cys Lys Ala Asp Asp Lys Glu Thr Cys
                805                 810                 815

Phe Ala Glu Glu Gly Lys Lys Leu Val Ala Ala Ser Gln Ala Ala Leu
            820                 825                 830

Gly Leu Gly Gly Ser Gly Gly Ser Gly Gly Ser Gly Gly Ser Gly Gly
        835                 840                 845

Asp Ile Gln Met Thr Gln Ser Pro Ser Ser Leu Ser Ala Ser Val Gly
    850                 855                 860

Asp Arg Val Thr Ile Thr Cys Arg Ala Ser Gln Asp Val Asn Thr Ala
865                 870                 875                 880

Val Ala Trp Tyr Gln Gln Lys Pro Gly Lys Ala Pro Lys Leu Leu Ile
                885                 890                 895

Tyr Ser Ala Ser Phe Leu Tyr Ser Gly Val Pro Ser Arg Phe Ser Gly
            900                 905                 910

Ser Arg Ser Gly Thr Asp Phe Thr Leu Thr Ile Ser Ser Leu Gln Pro
        915                 920                 925

Glu Asp Phe Ala Thr Tyr Tyr Cys Gln Gln His Tyr Thr Thr Pro Pro
    930                 935                 940

Thr Phe Gly Gln Gly Thr Lys Val Glu Ile Lys Gly Gly Ser Gly Gly
945                 950                 955                 960

Gly Ser Gly Gly Gly Ser Gly Gly Gly Ser Gly Gly Gly Ser Gly Glu
                965                 970                 975

Val Gln Leu Val Glu Ser Gly Gly Gly Leu Val Gln Pro Gly Gly Ser
            980                 985                 990

Leu Arg Leu Ser Cys Ala Ala Ser  Gly Phe Asn Ile Lys  Asp Thr Tyr
        995                 1000                1005

Ile His  Trp Val Arg Gln Ala  Pro Gly Lys Gly Leu  Glu Trp Val
    1010                1015                1020

Ala Arg  Ile Tyr Pro Thr Asn  Gly Tyr Thr Arg Tyr  Ala Asp Ser
    1025                1030                1035

Val Lys  Gly Arg Phe Thr Ile  Ser Ala Asp Thr Ser  Lys Asn Thr
    1040                1045                1050

Ala Tyr  Leu Gln Met Asn Ser  Leu Arg Ala Glu Asp  Thr Ala Val
    1055                1060                1065

Tyr Tyr  Cys Ser Arg Trp Gly  Gly Asp Gly Phe Tyr  Ala Met Asp
```

1070 1075 1080

Tyr Trp Gly Gln Gly Thr Leu Val Thr Val Ser Ser
1085 1090 1095

<210> SEQ ID NO 131
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Asp Ile Gln Leu Thr Gln Ser Pro Ala Ser Leu Ala Val Ser Leu Gly
1 5 10 15

Gln Arg Ala Thr Ile Ser Cys Lys Ala Ser Gln Ser Val Asp Tyr Asp
20 25 30

Gly Asp Ser Tyr Leu Asn Trp Tyr Gln Gln Ile Pro Gly Gln Pro Pro
35 40 45

Lys Leu Leu Ile Tyr Asp Ala Ser Asn Leu Val Ser Gly Ile Pro Pro
50 55 60

Arg Phe Ser Gly Ser Gly Ser Gly Thr Asp Phe Thr Leu Asn Ile His
65 70 75 80

Pro Val Glu Lys Val Asp Ala Ala Thr Tyr His Cys Gln Gln Ser Thr
85 90 95

Glu Asp Pro Trp Thr Phe Gly Gly Gly Thr Lys Leu Glu Ile Lys Gly
100 105 110

Gly Gly Gly Ser Gly Gly Gly Gly Ser Gly Gly Gly Gly Ser Gln Val
115 120 125

Gln Leu Gln Gln Ser Gly Ala Glu Leu Val Arg Pro Gly Ser Ser Val
130 135 140

Lys Ile Ser Cys Lys Ala Ser Gly Tyr Ala Phe Ser Ser Tyr Trp Met
145 150 155 160

Asn Trp Val Lys Gln Arg Pro Gly Gln Gly Leu Glu Trp Ile Gly Gln
165 170 175

Ile Trp Pro Gly Asp Gly Asp Thr Asn Tyr Asn Gly Lys Phe Lys Gly
180 185 190

Lys Ala Thr Leu Thr Ala Asp Glu Ser Ser Ser Thr Ala Tyr Met Gln
195 200 205

Leu Ser Ser Leu Ala Ser Glu Asp Ser Ala Val Tyr Phe Cys Ala Arg
210 215 220

Arg Glu Thr Thr Thr Val Gly Arg Tyr Tyr Tyr Ala Met Asp Tyr Trp
225 230 235 240

Gly Gln Gly Thr Thr Val Thr Val Ser Ser
245 250

<210> SEQ ID NO 132
<211> LENGTH: 243
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 132

Asp Ile Lys Leu Gln Gln Ser Gly Ala Glu Leu Ala Arg Pro Gly Ala
1 5 10 15

Ser Val Lys Met Ser Cys Lys Thr Ser Gly Tyr Thr Phe Thr Arg Tyr

```
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys
```

<210> SEQ ID NO 133
<211> LENGTH: 3351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
gaattcgcga ccatggccgt gatggcacct agaacactgg tcctgctgct gagcggggca     60

ctggcactga cacagacttg ggctggagac attaagctgc agcagagcgg agctgagctg    120

gcacgaccag gagcaagtgt gaaaatgtca tgcaagacaa gcggctatac ttttaccagg    180

tacactatgc actgggtgaa gcagcgacca ggacagggac tggagtggat cgggtacatt    240

aacccttcca gaggatatac caactacaat cagaagttca aagataaggc caccctgacc    300

acagacaaga gctcctctac agcctatatg cagctgagtt cactgacttc cgaggattct    360

gccgtgtact attgcgctag gtactatgac gatcattatt gtctggacta ctgggggcag    420

ggaactaccc tgacagtgag ctccgtcgag ggagggagtg gaggctcagg aggaagcgga    480

gggtccggag gagtggacga tatccagctg actcagtctc ctgcaattat gtcagccagc    540

ccaggcgaga aggtcacaat gacttgccgc gcctctagtt cagtgtccta tatgaattgg    600

taccagcaga aatctggcac cagtcccaag agatggatct atgatacatc caaggtcgcc    660

tctggggtgc cttacaggtt ttccggctct gggagtggaa cttcatatag cctgaccatt    720

agctccatgg aggctgaaga cgccgctacc tactattgcc agcagtggtc tagtaacccc    780
```

```
ctgacattcg gcgccgggac taaactggag ctgaaggggg gatctgacgc acacaaaagt    840
gaagtcgccc atcggttcaa ggatctgggc gaggaaaatt ttaaagccct ggtgctgatc    900
gccttcgctc agtacctgca gcagtgccct tttgaggacc acgtgaagct ggtcaacgag    960
gtgaccgagt tcgctaaaac atgcgtggct gatgagtctg cagaaaattg tgacaagagt   1020
ctgcatacac tgtttgggga taaactgtgt accgtggcca cactgcgcga gacttacgga   1080
gaaatggccg actgctgtgc taagcaggag cctgaacgaa acgagtgctt cctgcagcac   1140
aaagacgata accctaatct gccacgcctg gtgcgaccag aagtggatgt catgtgtact   1200
gctttccacg acaatgagga aacctttctg aagaaatatc tgtacgagat cgcccggaga   1260
catccatatt tttacgcacc cgaactgctg ttctttgcca aaagatacaa ggcagccttc   1320
accgagtgct gtcaggctgc agataaagcc gcttgcctgc tgcctaagct ggatgagctg   1380
cgagacgaag gaaaggcctc aagcgctaaa cagcggctga agtgtgctag cctgcagaaa   1440
ttcggagagc gagccttcaa ggcatgggca gtggctcggc tgtctcagag attcccaaag   1500
gcagagtttg ccgaagtcag caaactggtg actgacctga ccaaggtgca caccgagtgc   1560
tgtcatggcg atctgctgga atgcgccgac gatagagctg acctggcaaa gtacatctgt   1620
gagaaccagg atagcatttc ctctaaactg aaggagtgct gtgaaaaacc tctgctggag   1680
aagtcccact gcatcgccga ggtggaaaac gatgaaatgc ccgctgacct gccttcactg   1740
gcagccgatt tcgtcgagag caaagacgtg tgtaagaatt acgcagaagc caaggatgtg   1800
ttcctgggca tgtttctgta tgagtacgct aggcgacacc cagactacag cgtggtcctg   1860
ctgctgcggc tggccaagac atatgagaca actctggaaa aatgctgtgc tgcagccgac   1920
cctcatgagt gctatgccaa agtcttcgat gagttcaagc ctctggtgga ggaaccacag   1980
aacctgatta agcagaattg tgagctgttt gaacagctgg gcgagtataa attccagaac   2040
gccctgctgg tgagatacac caagaaagtc cccccaggtgt ccacccctac actggtggaa   2100
gtctctcgga atctgggaaa ggtcggcagt aaatgctgta agcacccaga ggctaaaaga   2160
atgccctgcg cagaagatta cctgtccgtg gtcctgaacc agctgtgtgt gctgcatgag   2220
aagacaccag tctctgacag ggtgaccaaa tgctgtacag aatccctggt gaaccgacgg   2280
ccttgctttt ctgccctgga ggtcgatgaa acctatgtgc caaaggagtt caatgctgaa   2340
actttcacct ttcacgcaga catctgtact ctgagcgaga aagaacgcca gattaagaaa   2400
cagaccgccc tggtcgagct ggtgaaacat aagcccaaag ccacaaaaga acagctgaag   2460
gctgtcatgg acgatttcgc tgcatttgtg gagaaatgct gtaaggcaga cgataaggaa   2520
acctgcttcg ccgaggaagg caagaaactg gtggccgcta gccaggcagc actgggactg   2580
ggagggtccg ggatatccaa gctgacccag tcaccagcca gcctggctgt ctcactgggg   2640
cagagggcca caattagttg taaggcttcc cagtctgtgg actacgatgg agactcctat   2700
ctgaactggt accagcagat cccaggacag ccacctaaac tgctgatcta cgacgccagt   2760
aatctggtgt caggcatccc accccgcttt agtggatcag gcagcgggac agacttcact   2820
ctgaacattc acccagtcga gaaggtggat gctgcaacct accattgcca gcagagcact   2880
gaggacccct ggacctttgg aggcgggaca aaactggaaa tcaagggagg cgggggatca   2940
ggcggaggag gcagcggagg aggagggtcc caggtgcagc tgcagcagtc cggagcagag   3000
ctggtcaggc cagggagttc agtgaaaatt agctgtaagg catccgggta tgccttcagc   3060
tcctactgga tgaattgggt caaacagaga cctggccagg gcctggagtg gatcggacag   3120
```

atttggcccg gggatggaga cactaactac aatgggaagt ttaaaggaaa ggctacactg 3180
actgcagatg aatctagttc aaccgcctac atgcagctga gctccctggc atccgaggac 3240
tctgccgtct atttctgcgc tagaagggaa accacaactg tgggcaggta ctattacgcc 3300
atggactatt ggggccaggg gaccacagtg accgtctcta gttgaggatc c 3351

<210> SEQ ID NO 134
<211> LENGTH: 1114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 134

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Asp Ile Lys
20 25 30

Leu Gln Gln Ser Gly Ala Glu Leu Ala Arg Pro Gly Ala Ser Val Lys
35 40 45

Met Ser Cys Lys Thr Ser Gly Tyr Thr Phe Thr Arg Tyr Thr Met His
50 55 60

Trp Val Lys Gln Arg Pro Gly Gln Gly Leu Glu Trp Ile Gly Tyr Ile
65 70 75 80

Asn Pro Ser Arg Gly Tyr Thr Asn Tyr Asn Gln Lys Phe Lys Asp Lys
85 90 95

Ala Thr Leu Thr Thr Asp Lys Ser Ser Ser Thr Ala Tyr Met Gln Leu
100 105 110

Ser Ser Leu Thr Ser Glu Asp Ser Ala Val Tyr Tyr Cys Ala Arg Tyr
115 120 125

Tyr Asp Asp His Tyr Cys Leu Asp Tyr Trp Gly Gln Gly Thr Thr Leu
130 135 140

Thr Val Ser Ser Val Glu Gly Gly Ser Gly Gly Ser Gly Gly Ser Gly
145 150 155 160

Gly Ser Gly Gly Val Asp Asp Ile Gln Leu Thr Gln Ser Pro Ala Ile
165 170 175

Met Ser Ala Ser Pro Gly Glu Lys Val Thr Met Thr Cys Arg Ala Ser
180 185 190

Ser Ser Val Ser Tyr Met Asn Trp Tyr Gln Gln Lys Ser Gly Thr Ser
195 200 205

Pro Lys Arg Trp Ile Tyr Asp Thr Ser Lys Val Ala Ser Gly Val Pro
210 215 220

Tyr Arg Phe Ser Gly Ser Gly Ser Gly Thr Ser Tyr Ser Leu Thr Ile
225 230 235 240

Ser Ser Met Glu Ala Glu Asp Ala Ala Thr Tyr Tyr Cys Gln Gln Trp
245 250 255

Ser Ser Asn Pro Leu Thr Phe Gly Ala Gly Thr Lys Leu Glu Leu Lys
260 265 270

Gly Gly Ser Asp Ala His Lys Ser Glu Val Ala His Arg Phe Lys Asp
275 280 285

Leu Gly Glu Glu Asn Phe Lys Ala Leu Val Leu Ile Ala Phe Ala Gln
290 295 300

Tyr Leu Gln Gln Cys Pro Phe Glu Asp His Val Lys Leu Val Asn Glu
305 310 315 320

-continued

```
Val Thr Glu Phe Ala Lys Thr Cys Val Ala Asp Glu Ser Ala Glu Asn
                325                 330                 335

Cys Asp Lys Ser Leu His Thr Leu Phe Gly Asp Lys Leu Cys Thr Val
            340                 345                 350

Ala Thr Leu Arg Glu Thr Tyr Gly Glu Met Ala Asp Cys Cys Ala Lys
        355                 360                 365

Gln Glu Pro Glu Arg Asn Glu Cys Phe Leu Gln His Lys Asp Asp Asn
    370                 375                 380

Pro Asn Leu Pro Arg Leu Val Arg Pro Glu Val Asp Val Met Cys Thr
385                 390                 395                 400

Ala Phe His Asp Asn Glu Glu Thr Phe Leu Lys Lys Tyr Leu Tyr Glu
                405                 410                 415

Ile Ala Arg Arg His Pro Tyr Phe Tyr Ala Pro Glu Leu Leu Phe Phe
            420                 425                 430

Ala Lys Arg Tyr Lys Ala Ala Phe Thr Glu Cys Cys Gln Ala Ala Asp
        435                 440                 445

Lys Ala Ala Cys Leu Leu Pro Lys Leu Asp Glu Leu Arg Asp Glu Gly
    450                 455                 460

Lys Ala Ser Ser Ala Lys Gln Arg Leu Lys Cys Ala Ser Leu Gln Lys
465                 470                 475                 480

Phe Gly Glu Arg Ala Phe Lys Ala Trp Ala Val Ala Arg Leu Ser Gln
                485                 490                 495

Arg Phe Pro Lys Ala Glu Phe Ala Glu Val Ser Lys Leu Val Thr Asp
            500                 505                 510

Leu Thr Lys Val His Thr Glu Cys Cys His Gly Asp Leu Leu Glu Cys
        515                 520                 525

Ala Asp Asp Arg Ala Asp Leu Ala Lys Tyr Ile Cys Glu Asn Gln Asp
    530                 535                 540

Ser Ile Ser Ser Lys Leu Lys Glu Cys Cys Glu Lys Pro Leu Leu Glu
545                 550                 555                 560

Lys Ser His Cys Ile Ala Glu Val Glu Asn Asp Glu Met Pro Ala Asp
                565                 570                 575

Leu Pro Ser Leu Ala Ala Asp Phe Val Glu Ser Lys Asp Val Cys Lys
            580                 585                 590

Asn Tyr Ala Glu Ala Lys Asp Val Phe Leu Gly Met Phe Leu Tyr Glu
        595                 600                 605

Tyr Ala Arg Arg His Pro Asp Tyr Ser Val Val Leu Leu Leu Arg Leu
    610                 615                 620

Ala Lys Thr Tyr Glu Thr Thr Leu Glu Lys Cys Cys Ala Ala Ala Asp
625                 630                 635                 640

Pro His Glu Cys Tyr Ala Lys Val Phe Asp Glu Phe Lys Pro Leu Val
                645                 650                 655

Glu Glu Pro Gln Asn Leu Ile Lys Gln Asn Cys Glu Leu Phe Glu Gln
            660                 665                 670

Leu Gly Glu Tyr Lys Phe Gln Asn Ala Leu Leu Val Arg Tyr Thr Lys
        675                 680                 685

Lys Val Pro Gln Val Ser Thr Pro Thr Leu Val Glu Val Ser Arg Asn
    690                 695                 700

Leu Gly Lys Val Gly Ser Lys Cys Cys Lys His Pro Glu Ala Lys Arg
705                 710                 715                 720

Met Pro Cys Ala Glu Asp Tyr Leu Ser Val Val Leu Asn Gln Leu Cys
                725                 730                 735

Val Leu His Glu Lys Thr Pro Val Ser Asp Arg Val Thr Lys Cys Cys
```

740 745 750

Thr Glu Ser Leu Val Asn Arg Arg Pro Cys Phe Ser Ala Leu Glu Val
755 760 765

Asp Glu Thr Tyr Val Pro Lys Glu Phe Asn Ala Glu Thr Phe Thr Phe
770 775 780

His Ala Asp Ile Cys Thr Leu Ser Glu Lys Glu Arg Gln Ile Lys Lys
785 790 795 800

Gln Thr Ala Leu Val Glu Leu Val Lys His Lys Pro Lys Ala Thr Lys
805 810 815

Glu Gln Leu Lys Ala Val Met Asp Asp Phe Ala Ala Phe Val Glu Lys
820 825 830

Cys Cys Lys Ala Asp Asp Lys Glu Thr Cys Phe Ala Glu Glu Gly Lys
835 840 845

Lys Leu Val Ala Ala Ser Gln Ala Ala Leu Gly Leu Gly Gly Ser Gly
850 855 860

Asp Ile Gln Leu Thr Gln Ser Pro Ala Ser Leu Ala Val Ser Leu Gly
865 870 875 880

Gln Arg Ala Thr Ile Ser Cys Lys Ala Ser Gln Ser Val Asp Tyr Asp
885 890 895

Gly Asp Ser Tyr Leu Asn Trp Tyr Gln Gln Ile Pro Gly Gln Pro Pro
900 905 910

Lys Leu Leu Ile Tyr Asp Ala Ser Asn Leu Val Ser Gly Ile Pro Pro
915 920 925

Arg Phe Ser Gly Ser Gly Ser Gly Thr Asp Phe Thr Leu Asn Ile His
930 935 940

Pro Val Glu Lys Val Asp Ala Ala Thr Tyr His Cys Gln Gln Ser Thr
945 950 955 960

Glu Asp Pro Trp Thr Phe Gly Gly Gly Thr Lys Leu Glu Ile Lys Gly
965 970 975

Gly Gly Gly Ser Gly Gly Gly Gly Ser Gly Gly Gly Gly Ser Gln Val
980 985 990

Gln Leu Gln Gln Ser Gly Ala Glu Leu Val Arg Pro Gly Ser Ser Val
995 1000 1005

Lys Ile Ser Cys Lys Ala Ser Gly Tyr Ala Phe Ser Ser Tyr Trp
1010 1015 1020

Met Asn Trp Val Lys Gln Arg Pro Gly Gln Gly Leu Glu Trp Ile
1025 1030 1035

Gly Gln Ile Trp Pro Gly Asp Gly Asp Thr Asn Tyr Asn Gly Lys
1040 1045 1050

Phe Lys Gly Lys Ala Thr Leu Thr Ala Asp Glu Ser Ser Ser Thr
1055 1060 1065

Ala Tyr Met Gln Leu Ser Ser Leu Ala Ser Glu Asp Ser Ala Val
1070 1075 1080

Tyr Phe Cys Ala Arg Arg Glu Thr Thr Thr Val Gly Arg Tyr Tyr
1085 1090 1095

Tyr Ala Met Asp Tyr Trp Gly Gln Gly Thr Thr Val Thr Val Ser
1100 1105 1110

Ser

<210> SEQ ID NO 135
<211> LENGTH: 3351
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 135

```
gaattcgcga ccatggccgt gatggcacct agaacactgg tcctgctgct gagcggggca     60
ctggcactga cacagacttg ggctggagac attcagctga cacagtcccc agcttctctg    120
gcagtctcac tgggccagcg ggcaactatc agctgcaagg cctcacagag cgtggactac    180
gatggagaca gctatctgaa ctggtaccag cagatcccag gacagccacc taaactgctg    240
atctacgacg ccagtaatct ggtgtcaggc atcccaccca gattttccgg atctggcagt    300
gggaccgact tcacactgaa cattcaccca gtggagaagg tcgatgccgc tacctaccat    360
tgccagcaga gcactgagga cccctggacc tttggcgggg gaacaaaact ggaaatcaag    420
ggcggaggag gctctggagg aggagggagt ggaggaggag gatcacaggt gcagctgcag    480
cagtccggag cagagctggt caggccaggc agctccgtga aaattagctg taaggcatcc    540
gggtatgcct tctctagtta ctggatgaat tgggtgaagc agcgaccagg acagggactg    600
gagtggatcg gacagatttg gcctggggat ggagacacta actacaatgg gaagtttaaa    660
ggaaaggcta ctctgaccgc agatgaatca agctccaccg cctacatgca gctgtctagt    720
ctggccagtg aggactcagc tgtctatttc tgcgcacgga gagaaaccac aactgtgggc    780
cgatactatt acgccatgga ttactggggc caggggacca cagtgaccgt ctcaagcggc    840
gggagcgatg ctcacaaatc cgaggtcgca catagattca aggacctggg ggaggaaaac    900
tttaaagccc tggtgctgat cgccttcgct cagtatctgc agcagtgccc ctttgaagac    960
cacgtgaagc tggtcaacga agtgactgag ttcgctaaaa cctgcgtggc cgatgagtct   1020
gctgaaaatt gtgacaagag tctgcatacc ctgtttgggg ataaactgtg tactgtggcc   1080
accctgcgcg agacatacgg agaaatggca gactgctgtg ccaagcagga gcctgaacga   1140
aacgagtgct tcctgcagca caaagacgat aaccctaatc tgccacgcct ggtgcgacca   1200
gaagtggatg tcatgtgtac tgctttccac gacaatgagg aaacctttct gaagaaatat   1260
ctgtacgaga ttgccaggcg ccatccatat ttttacgcac ccgaactgct gttctttgcc   1320
aaaaggtaca aggcagcctt caccgagtgc tgtcaggctg cagataaagc cgcttgcctg   1380
ctgcctaagc tggatgagct gcgagacgaa ggaaaggcct cctctgctaa acagcggctg   1440
aagtgtgcta gcctgcagaa attcggcgag agggccttca aggcatgggc agtggctcga   1500
ctgtctcaga gattcccaaa ggcagagttt gccgaagtca gcaaactggt gacagacctg   1560
actaaggtgc acaccgagtg ctgtcatggc gatctgctgg aatgcgccga cgatcgcgct   1620
gacctggcaa agtacatctg tgagaaccag gatagcatta gttcaaaact gaaggagtgc   1680
tgtgaaaaac ctctgctgga gaagtcccac tgcatcgccg aggtggaaaa cgatgaaatg   1740
ccagctgacc tgccttccct ggcagcagat ttcgtcgagt ctaaagacgt gtgtaagaat   1800
tacgcagaag ccaaggatgt gttcctgggc atgtttctgt atgagtacgc tcgacggcac   1860
cccgactact ccgtggtcct gctgctgagg ctggccaaga catatgagac taccctggaa   1920
aaatgctgtg ctgcagccga ccctcatgag tgctatgcca aagtcttcga tgagttcaag   1980
cctctggtgg aggaaccaca gaacctgatt aagcagaatt gtgagctgtt tgaacagctg   2040
ggcgagtata aattccagaa cgccctgctg gtgcgctaca ccaagaaagt cccccaggtg   2100
agtacaccta ctctggtgga agtctcacgg aatctgggaa aggtcggcag taaatgctgt   2160
aagcacccag aggccaaaag aatgccctgc gctgaagatt acctgtccgt ggtcctgaac   2220
```

```
cagctgtgtg tgctgcatga gaagacaccc gtctctgacc gggtgaccaa atgctgtaca   2280

gaaagcctgg tgaacagaag gccttgcttt tccgccctgg aggtcgatga aacctatgtg   2340

ccaaaggagt tcaatgctga aaccttcaca tttcacgcag acatctgtac tctgagcgag   2400

aaagaaagac agattaagaa acagaccgcc ctggtcgagc tggtgaaaca taagcccaaa   2460

gccacaaaag aacagctgaa ggctgtcatg gacgatttcg ctgcatttgt ggagaaatgc   2520

tgtaaggcag acgataagga aacttgcttc gccgaggaag gcaagaaact ggtggcagct   2580

tcccaggcag cactgggact gggaggctcc ggggacatca agctgcagca gtctggagca   2640

gagctggcta ggcctggagc ctctgtgaaa atgagttgta agacatcagg ctatactttt   2700

accaggtaca ctatgcactg ggtcaaacag agacctggcc agggcctgga gtggatcggc   2760

tacattaatc ccagccgcgg gtataccaac tacaatcaga agttcaaaga taaggcaacc   2820

ctgacaactg acaagagctc ctctacagcc tatatgcagc tgagttcact gactagcgag   2880

gattccgccg tgtattactg cgctcggtat tacgacgatc attattgtct ggactactgg   2940

gggcagggaa ccacactgac agtcagctcc gtggagggag gatctggagg gagtggaggc   3000

tcaggaggaa gcggaggggt ggacgatatc cagctgaccc agtctcctgc tattatgtca   3060

gcaagcccag gcgagaaggt cacaatgact tgcagagcct ctagttcagt gtcctatatg   3120

aattggtatc agcagaaatc cggcacctct cccaagagat ggatctatga tacaagcaag   3180

gtcgcctccg ggtgccttta caggttttcc ggctctggga gtggaacatc atatagcctg   3240

actattagct ccatggaggc tgaagacgct gcaacctatt actgccagca gtggtctagt   3300

aatcccctga ccttcggcgc cgggacaaaa ctggagctga agtgaggatc c            3351
```

<210> SEQ ID NO 136
<211> LENGTH: 1114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

```
Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Asp Ile Gln
            20                  25                  30

Leu Thr Gln Ser Pro Ala Ser Leu Ala Val Ser Leu Gly Gln Arg Ala
        35                  40                  45

Thr Ile Ser Cys Lys Ala Ser Gln Ser Val Asp Tyr Asp Gly Asp Ser
    50                  55                  60

Tyr Leu Asn Trp Tyr Gln Gln Ile Pro Gly Gln Pro Pro Lys Leu Leu
65                  70                  75                  80

Ile Tyr Asp Ala Ser Asn Leu Val Ser Gly Ile Pro Pro Arg Phe Ser
                85                  90                  95

Gly Ser Gly Ser Gly Thr Asp Phe Thr Leu Asn Ile His Pro Val Glu
            100                 105                 110

Lys Val Asp Ala Ala Thr Tyr His Cys Gln Gln Ser Thr Glu Asp Pro
        115                 120                 125

Trp Thr Phe Gly Gly Gly Thr Lys Leu Glu Ile Lys Gly Gly Gly Gly
    130                 135                 140

Ser Gly Gly Gly Gly Ser Gly Gly Gly Gly Ser Gln Val Gln Leu Gln
145                 150                 155                 160
```

-continued

```
Gln Ser Gly Ala Glu Leu Val Arg Pro Gly Ser Ser Val Lys Ile Ser
            165                 170                 175

Cys Lys Ala Ser Gly Tyr Ala Phe Ser Ser Tyr Trp Met Asn Trp Val
            180                 185                 190

Lys Gln Arg Pro Gly Gln Gly Leu Glu Trp Ile Gly Gln Ile Trp Pro
        195                 200                 205

Gly Asp Gly Asp Thr Asn Tyr Asn Gly Lys Phe Lys Gly Lys Ala Thr
    210                 215                 220

Leu Thr Ala Asp Glu Ser Ser Ser Thr Ala Tyr Met Gln Leu Ser Ser
225                 230                 235                 240

Leu Ala Ser Glu Asp Ser Ala Val Tyr Phe Cys Ala Arg Arg Glu Thr
                245                 250                 255

Thr Thr Val Gly Arg Tyr Tyr Tyr Ala Met Asp Tyr Trp Gly Gln Gly
            260                 265                 270

Thr Thr Val Thr Val Ser Ser Gly Gly Ser Asp Ala His Lys Ser Glu
        275                 280                 285

Val Ala His Arg Phe Lys Asp Leu Gly Glu Glu Asn Phe Lys Ala Leu
    290                 295                 300

Val Leu Ile Ala Phe Ala Gln Tyr Leu Gln Gln Cys Pro Phe Glu Asp
305                 310                 315                 320

His Val Lys Leu Val Asn Glu Val Thr Glu Phe Ala Lys Thr Cys Val
                325                 330                 335

Ala Asp Glu Ser Ala Glu Asn Cys Asp Lys Ser Leu His Thr Leu Phe
            340                 345                 350

Gly Asp Lys Leu Cys Thr Val Ala Thr Leu Arg Glu Thr Tyr Gly Glu
        355                 360                 365

Met Ala Asp Cys Cys Ala Lys Gln Glu Pro Glu Arg Asn Glu Cys Phe
    370                 375                 380

Leu Gln His Lys Asp Asp Asn Pro Asn Leu Pro Arg Leu Val Arg Pro
385                 390                 395                 400

Glu Val Asp Val Met Cys Thr Ala Phe His Asp Asn Glu Glu Thr Phe
                405                 410                 415

Leu Lys Lys Tyr Leu Tyr Glu Ile Ala Arg Arg His Pro Tyr Phe Tyr
            420                 425                 430

Ala Pro Glu Leu Leu Phe Phe Ala Lys Arg Tyr Lys Ala Ala Phe Thr
        435                 440                 445

Glu Cys Cys Gln Ala Ala Asp Lys Ala Ala Cys Leu Leu Pro Lys Leu
    450                 455                 460

Asp Glu Leu Arg Asp Glu Gly Lys Ala Ser Ser Ala Lys Gln Arg Leu
465                 470                 475                 480

Lys Cys Ala Ser Leu Gln Lys Phe Gly Glu Arg Ala Phe Lys Ala Trp
                485                 490                 495

Ala Val Ala Arg Leu Ser Gln Arg Phe Pro Lys Ala Glu Phe Ala Glu
            500                 505                 510

Val Ser Lys Leu Val Thr Asp Leu Thr Lys Val His Thr Glu Cys Cys
        515                 520                 525

His Gly Asp Leu Leu Glu Cys Ala Asp Asp Arg Ala Asp Leu Ala Lys
    530                 535                 540

Tyr Ile Cys Glu Asn Gln Asp Ser Ile Ser Ser Lys Leu Lys Glu Cys
545                 550                 555                 560

Cys Glu Lys Pro Leu Leu Glu Lys Ser His Cys Ile Ala Glu Val Glu
                565                 570                 575

Asn Asp Glu Met Pro Ala Asp Leu Pro Ser Leu Ala Ala Asp Phe Val
```

```
            580                 585                 590

Glu Ser Lys Asp Val Cys Lys Asn Tyr Ala Glu Ala Lys Asp Val Phe
        595                 600                 605

Leu Gly Met Phe Leu Tyr Glu Tyr Ala Arg Arg His Pro Asp Tyr Ser
    610                 615                 620

Val Val Leu Leu Leu Arg Leu Ala Lys Thr Tyr Glu Thr Thr Leu Glu
625                 630                 635                 640

Lys Cys Cys Ala Ala Ala Asp Pro His Glu Cys Tyr Ala Lys Val Phe
                645                 650                 655

Asp Glu Phe Lys Pro Leu Val Glu Glu Pro Gln Asn Leu Ile Lys Gln
            660                 665                 670

Asn Cys Glu Leu Phe Glu Gln Leu Gly Glu Tyr Lys Phe Gln Asn Ala
        675                 680                 685

Leu Leu Val Arg Tyr Thr Lys Lys Val Pro Gln Val Ser Thr Pro Thr
    690                 695                 700

Leu Val Glu Val Ser Arg Asn Leu Gly Lys Val Gly Ser Lys Cys Cys
705                 710                 715                 720

Lys His Pro Glu Ala Lys Arg Met Pro Cys Ala Glu Asp Tyr Leu Ser
                725                 730                 735

Val Val Leu Asn Gln Leu Cys Val Leu His Glu Lys Thr Pro Val Ser
            740                 745                 750

Asp Arg Val Thr Lys Cys Cys Thr Glu Ser Leu Val Asn Arg Arg Pro
        755                 760                 765

Cys Phe Ser Ala Leu Glu Val Asp Glu Thr Tyr Val Pro Lys Glu Phe
    770                 775                 780

Asn Ala Glu Thr Phe Thr Phe His Ala Asp Ile Cys Thr Leu Ser Glu
785                 790                 795                 800

Lys Glu Arg Gln Ile Lys Lys Gln Thr Ala Leu Val Glu Leu Val Lys
                805                 810                 815

His Lys Pro Lys Ala Thr Lys Glu Gln Leu Lys Ala Val Met Asp Asp
            820                 825                 830

Phe Ala Ala Phe Val Glu Lys Cys Cys Lys Ala Asp Asp Lys Glu Thr
        835                 840                 845

Cys Phe Ala Glu Glu Gly Lys Lys Leu Val Ala Ala Ser Gln Ala Ala
    850                 855                 860

Leu Gly Leu Gly Gly Ser Gly Asp Ile Lys Leu Gln Gln Ser Gly Ala
865                 870                 875                 880

Glu Leu Ala Arg Pro Gly Ala Ser Val Lys Met Ser Cys Lys Thr Ser
                885                 890                 895

Gly Tyr Thr Phe Thr Arg Tyr Thr Met His Trp Val Lys Gln Arg Pro
            900                 905                 910

Gly Gln Gly Leu Glu Trp Ile Gly Tyr Ile Asn Pro Ser Arg Gly Tyr
        915                 920                 925

Thr Asn Tyr Asn Gln Lys Phe Lys Asp Lys Ala Thr Leu Thr Thr Asp
    930                 935                 940

Lys Ser Ser Ser Thr Ala Tyr Met Gln Leu Ser Ser Leu Thr Ser Glu
945                 950                 955                 960

Asp Ser Ala Val Tyr Tyr Cys Ala Arg Tyr Tyr Asp Asp His Tyr Cys
                965                 970                 975

Leu Asp Tyr Trp Gly Gln Gly Thr Thr Leu Thr Val Ser Ser Val Glu
            980                 985                 990

Gly Gly Ser Gly Gly Ser Gly Gly  Ser Gly Gly Ser Gly  Gly Val Asp
        995                 1000                1005
```

```
Asp Ile  Gln Leu Thr Gln Ser  Pro Ala Ile Met Ser  Ala Ser Pro
    1010                1015                1020

Gly Glu  Lys Val Thr Met Thr  Cys Arg Ala Ser Ser  Ser Val Ser
    1025                1030                1035

Tyr Met  Asn Trp Tyr Gln Gln  Lys Ser Gly Thr Ser  Pro Lys Arg
    1040                1045                1050

Trp Ile  Tyr Asp Thr Ser Lys  Val Ala Ser Gly Val  Pro Tyr Arg
    1055                1060                1065

Phe Ser  Gly Ser Gly Ser Gly  Thr Ser Tyr Ser Leu  Thr Ile Ser
    1070                1075                1080

Ser Met  Glu Ala Glu Asp Ala  Ala Thr Tyr Tyr Cys  Gln Gln Trp
    1085                1090                1095

Ser Ser  Asn Pro Leu Thr Phe  Gly Ala Gly Thr Lys  Leu Glu Leu
    1100                1105                1110

Lys


<210> SEQ ID NO 137
<211> LENGTH: 1845
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

gaattcgcga ccatggctgt gatggctcct agaaccctgg tgctgctgct gtccggcgct     60

ctggctctga ctcagacctg ggctggggat atcaaactgc agcagtctgg agctgagctg    120

gcacgaccag gagccagtgt caaaatgtca tgcaagacta gcggctacac cttcaccaga    180

tataccatgc actgggtgaa gcagaggcca ggacagggac tggaatggat cggatatatt    240

aaccccagcc gcggctacac aaactataat cagaagttca aagacaaggc tacactgacc    300

acagataaga gctcctctac tgcatacatg cagctgagtt cactgaccag cgaggattcc    360

gccgtgtact attgcgctag gtactatgac gatcattact gtctggacta ttggggacag    420

ggcactaccc tgactgtgag ctccgtcgaa ggagggtctg gaggcagtgg aggatcagga    480

gggagcggag gagtggacga tatccagctg acccagagcc ccgccattat gagtgcttca    540

cctggcgaga aggtcaccat gacatgccgc gcctctagtt cagtgtccta catgaattgg    600

tatcagcaga aatccggcac atctcctaag cggtggatct acgatacttc caaagtcgcc    660

tctggggtgc catatcggtt cagcgggtcc ggatctggca ccagttactc actgacaatt    720

agctccatgg aggctgaaga cgccgctacc tactattgtc agcagtggtc tagtaaccct    780

ctgactttcg ggccggaac caaactggag ctgaaggggg gaagtgatgc acacaaatca    840

gaagtcgccc ataggttcaa ggacctgggc gaggaaaatt ttaaagccct ggtgctgatc    900

gctttcgcac agtatctgca gcagtgccca tttgaggatc acgtgaagct ggtcaacgag    960

gtgacagagt tcgccaaaac ttgcgtcgca gacgagagcg ccgaaaattg tgataagtcc   1020

ctgcataccc tgtttgggga taaactgtgt actgtggcca ccctgaggga gacatacgga   1080

gaaatggctg actgctgtgc aaagcaggag cccgaacgca acgagtgctt cctgcagcac   1140

aaagacgata accccaatct gcctaggctg gtgcgccctg aagtggacgt catgtgtacc   1200

gctttccacg ataatgagga aacatttctg aagaaatacc tgtatgagat tgcccggaga   1260

catccttact tttatgctcc agaactgctg ttctttgcaa aacggtacaa ggcagccttc   1320
```

acagagtgct gtcaggctgc agataaagcc gcttgcctgc tgccaaagct ggacgagctg 1380
cgcgatgaag gaaaggcctc aagcgctaaa cagcgactga agtgtgcctc cctgcagaaa 1440
ttcggcgagc gggcttttaa ggcatgggct gtggcacgac tgagccagcg gttccccaag 1500
gcagagtttg ccgaagtctc caaactggtg acagacctga ctaaggtgca caccgagtgc 1560
tgtcatgggg acctgctgga atgcgccgac gatagagctg atctggcaaa gtatatctgt 1620
gagaaccagg actctatttc ctctaaactg aaggagtgct gtgaaaaacc tctgctggag 1680
aagagccact gcatcgcaga ggtggaaaac gacgaaatgc cagccgatct gccctctctg 1740
gcagccgact tcgtcgagag taaagatgtg tgtaagaatt acgccgaagc taaggacgtg 1800
ttcctgggca tgtttctgta cgagtatgca agagcctgag gatcc 1845

<210> SEQ ID NO 138
<211> LENGTH: 612
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Asp Ile Lys
20 25 30

Leu Gln Gln Ser Gly Ala Glu Leu Ala Arg Pro Gly Ala Ser Val Lys
35 40 45

Met Ser Cys Lys Thr Ser Gly Tyr Thr Phe Thr Arg Tyr Thr Met His
50 55 60

Trp Val Lys Gln Arg Pro Gly Gln Gly Leu Glu Trp Ile Gly Tyr Ile
65 70 75 80

Asn Pro Ser Arg Gly Tyr Thr Asn Tyr Asn Gln Lys Phe Lys Asp Lys
85 90 95

Ala Thr Leu Thr Thr Asp Lys Ser Ser Ser Thr Ala Tyr Met Gln Leu
100 105 110

Ser Ser Leu Thr Ser Glu Asp Ser Ala Val Tyr Tyr Cys Ala Arg Tyr
115 120 125

Tyr Asp Asp His Tyr Cys Leu Asp Tyr Trp Gly Gln Gly Thr Thr Leu
130 135 140

Thr Val Ser Ser Val Glu Gly Gly Ser Gly Gly Ser Gly Gly Ser Gly
145 150 155 160

Gly Ser Gly Gly Val Asp Asp Ile Gln Leu Thr Gln Ser Pro Ala Ile
165 170 175

Met Ser Ala Ser Pro Gly Glu Lys Val Thr Met Thr Cys Arg Ala Ser
180 185 190

Ser Ser Val Ser Tyr Met Asn Trp Tyr Gln Gln Lys Ser Gly Thr Ser
195 200 205

Pro Lys Arg Trp Ile Tyr Asp Thr Ser Lys Val Ala Ser Gly Val Pro
210 215 220

Tyr Arg Phe Ser Gly Ser Gly Ser Gly Thr Ser Tyr Ser Leu Thr Ile
225 230 235 240

Ser Ser Met Glu Ala Glu Asp Ala Ala Thr Tyr Tyr Cys Gln Gln Trp
245 250 255

Ser Ser Asn Pro Leu Thr Phe Gly Ala Gly Thr Lys Leu Glu Leu Lys
260 265 270

```
Gly Gly Ser Asp Ala His Lys Ser Glu Val Ala His Arg Phe Lys Asp
        275                 280                 285

Leu Gly Glu Glu Asn Phe Lys Ala Leu Val Leu Ile Ala Phe Ala Gln
    290                 295                 300

Tyr Leu Gln Gln Cys Pro Phe Glu Asp His Val Lys Leu Val Asn Glu
305                 310                 315                 320

Val Thr Glu Phe Ala Lys Thr Cys Val Ala Asp Glu Ser Ala Glu Asn
                325                 330                 335

Cys Asp Lys Ser Leu His Thr Leu Phe Gly Asp Lys Leu Cys Thr Val
            340                 345                 350

Ala Thr Leu Arg Glu Thr Tyr Gly Glu Met Ala Asp Cys Cys Ala Lys
        355                 360                 365

Gln Glu Pro Glu Arg Asn Glu Cys Phe Leu Gln His Lys Asp Asp Asn
    370                 375                 380

Pro Asn Leu Pro Arg Leu Val Arg Pro Glu Val Asp Val Met Cys Thr
385                 390                 395                 400

Ala Phe His Asp Asn Glu Glu Thr Phe Leu Lys Lys Tyr Leu Tyr Glu
                405                 410                 415

Ile Ala Arg Arg His Pro Tyr Phe Tyr Ala Pro Glu Leu Leu Phe Phe
            420                 425                 430

Ala Lys Arg Tyr Lys Ala Ala Phe Thr Glu Cys Cys Gln Ala Ala Asp
        435                 440                 445

Lys Ala Ala Cys Leu Leu Pro Lys Leu Asp Glu Leu Arg Asp Glu Gly
    450                 455                 460

Lys Ala Ser Ser Ala Lys Gln Arg Leu Lys Cys Ala Ser Leu Gln Lys
465                 470                 475                 480

Phe Gly Glu Arg Ala Phe Lys Ala Trp Ala Val Ala Arg Leu Ser Gln
                485                 490                 495

Arg Phe Pro Lys Ala Glu Phe Ala Glu Val Ser Lys Leu Val Thr Asp
            500                 505                 510

Leu Thr Lys Val His Thr Glu Cys Cys His Gly Asp Leu Leu Glu Cys
        515                 520                 525

Ala Asp Asp Arg Ala Asp Leu Ala Lys Tyr Ile Cys Glu Asn Gln Asp
    530                 535                 540

Ser Ile Ser Ser Lys Leu Lys Glu Cys Cys Glu Lys Pro Leu Leu Glu
545                 550                 555                 560

Lys Ser His Cys Ile Ala Glu Val Glu Asn Asp Glu Met Pro Ala Asp
                565                 570                 575

Leu Pro Ser Leu Ala Ala Asp Phe Val Glu Ser Lys Asp Val Cys Lys
            580                 585                 590

Asn Tyr Ala Glu Ala Lys Asp Val Phe Leu Gly Met Phe Leu Tyr Glu
        595                 600                 605

Tyr Ala Arg Ala
    610
```

<210> SEQ ID NO 139
<211> LENGTH: 1590
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139

```
gaattcgcga ccatggccgt gatggctccc cgaacactgg tgctgctgct gtccggcgct     60
```

```
ctggctctga ctcagacttg ggctggctcc gtggtgctgc tgctgcggct ggccaagacc    120

tatgagacca cactggaaaa atgctgtgcc gctgcagatc cacacgagtg ctacgctaag    180

gtgttcgacg agttcaagcc tctggtcgag gaaccacaga acctgatcaa gcagaattgt    240

gagctgttcg aacagctggg cgagtataaa tttcagaacg ccctgctggt gagatacaca    300

aagaaagtgc cccaggtctc tacacctact ctggtggaag tcagtcgaaa tctgggaaag    360

gtcggctcaa agtgctgtaa acacccagag gcaaaacgga tgccctgcgc cgaagactat    420

ctgagcgtgg tcctgaacca gctgtgtgtg ctgcatgaga agacacccgt gtccgatagg    480

gtcaccaaat gctgtacaga atctctggtg aaccggagac cctgcttcag tgccctggag    540

gtggacgaaa cttacgtccc taaggagttt aatgccgaaa ccttcacatt tcacgctgat    600

atctgtactc tgtccgagaa agaacgccag attaagaaac agaccgccct ggtggagctg    660

gtcaagcata aacctaaggc aactaaggaa cagctgaaag ccgtgatgga cgatttcgcc    720

gcttttgtcg agaagtgctg taaagctgac gataaggaaa cctgcttcgc agaggaaggc    780

aagaaactgg tggcagcctc tcaggctgca ctgggactgg gagggagcgg ggacatccag    840

ctgacacagt cccctgcatc tctggccgtg agcctgggac agcgagctac tatttcctgt    900

aaggcatccc agtctgtgga ctatgatggg gacagctatc tgaactggta ccagcagatc    960

ccaggacagc cccctaagct gctgatctac gatgccagca atctggtgtc cggcatccca   1020

ccccgattca gtggatcagg cagcgggaca gattttactc tgaacattca cccagtggag   1080

aaggtcgacg ccgctaccta ccattgccag cagtctactg aggacccctg gaccttcgga   1140

ggcgggacaa agctggaaat caaaggaggc gggggatcag gcggaggagg cagcggagga   1200

ggagggtccc aggtgcagct gcagcagagc ggagcagagc tggtgagacc tggcagctcc   1260

gtcaagattt cttgtaaagc tagtggctat gcattttcta gttactggat gaattgggtg   1320

aagcagaggc ctggacaggg actggagtgg atcggacaga tttggccagg ggatggagac   1380

accaactata atgggaaatt caagggaaaa gccactctga ccgctgacga gtcaagctcc   1440

acagcctata tgcagctgtc tagtctggca agtgaggatt cagccgtgta cttttgcgct   1500

aggcgcgaaa ctaccacagt cggcaggtac tattacgcta tggactactg gggccagggg   1560

actaccgtga ccgtctcaag ctgaggatcc                                    1590
```

```
<210> SEQ ID NO 140
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Ser Val Val
            20                  25                  30

Leu Leu Leu Arg Leu Ala Lys Thr Tyr Glu Thr Thr Leu Glu Lys Cys
        35                  40                  45

Cys Ala Ala Ala Asp Pro His Glu Cys Tyr Ala Lys Val Phe Asp Glu
    50                  55                  60

Phe Lys Pro Leu Val Glu Glu Pro Gln Asn Leu Ile Lys Gln Asn Cys
65                  70                  75                  80
```

-continued

```
Glu Leu Phe Glu Gln Leu Gly Glu Tyr Lys Phe Gln Asn Ala Leu Leu
                85                  90                  95

Val Arg Tyr Thr Lys Lys Val Pro Gln Val Ser Thr Pro Thr Leu Val
            100                 105                 110

Glu Val Ser Arg Asn Leu Gly Lys Val Gly Ser Lys Cys Cys Lys His
        115                 120                 125

Pro Glu Ala Lys Arg Met Pro Cys Ala Glu Asp Tyr Leu Ser Val Val
    130                 135                 140

Leu Asn Gln Leu Cys Val Leu His Glu Lys Thr Pro Val Ser Asp Arg
145                 150                 155                 160

Val Thr Lys Cys Cys Thr Glu Ser Leu Val Asn Arg Arg Pro Cys Phe
                165                 170                 175

Ser Ala Leu Glu Val Asp Glu Thr Tyr Val Pro Lys Glu Phe Asn Ala
            180                 185                 190

Glu Thr Phe Thr Phe His Ala Asp Ile Cys Thr Leu Ser Glu Lys Glu
        195                 200                 205

Arg Gln Ile Lys Lys Gln Thr Ala Leu Val Glu Leu Val Lys His Lys
    210                 215                 220

Pro Lys Ala Thr Lys Glu Gln Leu Lys Ala Val Met Asp Asp Phe Ala
225                 230                 235                 240

Ala Phe Val Glu Lys Cys Cys Lys Ala Asp Asp Lys Glu Thr Cys Phe
                245                 250                 255

Ala Glu Glu Gly Lys Lys Leu Val Ala Ala Ser Gln Ala Ala Leu Gly
            260                 265                 270

Leu Gly Gly Ser Gly Asp Ile Gln Leu Thr Gln Ser Pro Ala Ser Leu
        275                 280                 285

Ala Val Ser Leu Gly Gln Arg Ala Thr Ile Ser Cys Lys Ala Ser Gln
    290                 295                 300

Ser Val Asp Tyr Asp Gly Asp Ser Tyr Leu Asn Trp Tyr Gln Gln Ile
305                 310                 315                 320

Pro Gly Gln Pro Pro Lys Leu Leu Ile Tyr Asp Ala Ser Asn Leu Val
                325                 330                 335

Ser Gly Ile Pro Pro Arg Phe Ser Gly Ser Gly Ser Gly Thr Asp Phe
            340                 345                 350

Thr Leu Asn Ile His Pro Val Glu Lys Val Asp Ala Ala Thr Tyr His
        355                 360                 365

Cys Gln Gln Ser Thr Glu Asp Pro Trp Thr Phe Gly Gly Gly Thr Lys
    370                 375                 380

Leu Glu Ile Lys Gly Gly Gly Gly Ser Gly Gly Gly Gly Ser Gly Gly
385                 390                 395                 400

Gly Gly Ser Gln Val Gln Leu Gln Gln Ser Gly Ala Glu Leu Val Arg
                405                 410                 415

Pro Gly Ser Ser Val Lys Ile Ser Cys Lys Ala Ser Gly Tyr Ala Phe
            420                 425                 430

Ser Ser Tyr Trp Met Asn Trp Val Lys Gln Arg Pro Gly Gln Gly Leu
        435                 440                 445

Glu Trp Ile Gly Gln Ile Trp Pro Gly Asp Gly Asp Thr Asn Tyr Asn
    450                 455                 460

Gly Lys Phe Lys Gly Lys Ala Thr Leu Thr Ala Asp Glu Ser Ser Ser
465                 470                 475                 480

Thr Ala Tyr Met Gln Leu Ser Ser Leu Ala Ser Glu Asp Ser Ala Val
                485                 490                 495

Tyr Phe Cys Ala Arg Arg Glu Thr Thr Thr Val Gly Arg Tyr Tyr Tyr
```

```
            500                 505                 510

Ala Met Asp Tyr Trp Gly Gln Gly Thr Thr Val Thr Val Ser Ser
        515                 520                 525
```

<210> SEQ ID NO 141
<211> LENGTH: 1569
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

```
gaattcgcga ccatggctgt gatggctcct agaacactgg tgctgctgct gtccggggct     60

ctggctctga ctcagacctg ggctggaagc gtggtgctgc tgctgcggct ggcaaagaca    120

tatgagacca cactggaaaa atgctgtgcc gctgcagacc ctcacgagtg ctacgccaag    180

gtgttcgatg agttcaagcc cctggtcgag gaacctcaga acctgatcaa gcagaattgt    240

gagctgttcg aacagctggg cgagtacaaa tttcagaacg ccctgctggt gagatatacc    300

aagaaagtgc cacaggtctc aacccccaca ctggtggaag tcagcagaaa tctgggcaag    360

gtcgggtcca agtgctgtaa acaccctgag gcaaaaagga tgccatgcgc cgaagactac    420

ctgtccgtgg tcctgaacca gctgtgtgtg ctgcatgaga agacaccagt gtctgatagg    480

gtcactaaat gctgtaccga aagcctggtg aaccggagac cttgcttcag cgccctggag    540

gtggacgaaa cctacgtccc aaaggagttt aatgctgaaa ctttcacctt tcacgcagat    600

atctgtaccc tgtccgagaa agaacgccag attaagaaac agacagccct ggtggagctg    660

gtcaagcata aaccaaaggc cactaaggaa cagctgaaag ctgtgatgga cgatttcgcc    720

gcttttgtcg agaagtgctg taaagcagac gataaggaaa cctgcttcgc cgaggaaggg    780

aagaaactgg tggcagcatc tcaggctgca ctgggactgg gagggtctgg cgacattaag    840

ctgcagcaga gtggagcaga gctggcacga ccaggagcat cagtgaagat gagctgtaaa    900

acttccggct acacattcac taggtatacc atgcactggg tgaagcagcg accaggacag    960

ggactggagt ggatcggcta tattaatccc agccgagggt acaccaacta taatcagaag   1020

ttcaaggaca aagctacact gactaccgat aagagctcct ctactgcata catgcagctg   1080

agttcactga cctccgagga ctctgccgtg tactattgcg ctaggtacta tgacgatcat   1140

tactgtctgg attattgggg acagggcaca actctgacag tgagctccgt cgaaggaggc   1200

agtggaggat caggagggag cggaggctcc ggaggagtgg acgatatcca gctgactcag   1260

agccccgcta ttatgtcagc aagccctggc gagaaggtga ccatgacatg ccgggcttct   1320

agttcagtca gctacatgaa ctggtatcag cagaagtctg gaacaagtcc caaacgatgg   1380

atctacgaca cttctaaggt ggccagtggc gtcccttatc ggttctccgg gtctggaagt   1440

ggcacatcat acagcctgac tattagctcc atggaggccg aagatgccgc tacctactat   1500

tgccagcagt ggtctagtaa tcccctgacc tttggggctg gaacaaagct ggagctgaaa   1560

tgaggatcc                                                           1569
```

<210> SEQ ID NO 142
<211> LENGTH: 520
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 142

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Ser Val Val
            20                  25                  30

Leu Leu Leu Arg Leu Ala Lys Thr Tyr Glu Thr Thr Leu Glu Lys Cys
        35                  40                  45

Cys Ala Ala Ala Asp Pro His Glu Cys Tyr Ala Lys Val Phe Asp Glu
    50                  55                  60

Phe Lys Pro Leu Val Glu Glu Pro Gln Asn Leu Ile Lys Gln Asn Cys
65                  70                  75                  80

Glu Leu Phe Glu Gln Leu Gly Glu Tyr Lys Phe Gln Asn Ala Leu Leu
                85                  90                  95

Val Arg Tyr Thr Lys Lys Val Pro Gln Val Ser Thr Pro Thr Leu Val
            100                 105                 110

Glu Val Ser Arg Asn Leu Gly Lys Val Gly Ser Lys Cys Cys Lys His
        115                 120                 125

Pro Glu Ala Lys Arg Met Pro Cys Ala Glu Asp Tyr Leu Ser Val Val
    130                 135                 140

Leu Asn Gln Leu Cys Val Leu His Glu Lys Thr Pro Val Ser Asp Arg
145                 150                 155                 160

Val Thr Lys Cys Cys Thr Glu Ser Leu Val Asn Arg Arg Pro Cys Phe
                165                 170                 175

Ser Ala Leu Glu Val Asp Glu Thr Tyr Val Pro Lys Glu Phe Asn Ala
            180                 185                 190

Glu Thr Phe Thr Phe His Ala Asp Ile Cys Thr Leu Ser Glu Lys Glu
        195                 200                 205

Arg Gln Ile Lys Lys Gln Thr Ala Leu Val Glu Leu Val Lys His Lys
    210                 215                 220

Pro Lys Ala Thr Lys Glu Gln Leu Lys Ala Val Met Asp Asp Phe Ala
225                 230                 235                 240

Ala Phe Val Glu Lys Cys Cys Lys Ala Asp Asp Lys Glu Thr Cys Phe
                245                 250                 255

Ala Glu Glu Gly Lys Lys Leu Val Ala Ala Ser Gln Ala Ala Leu Gly
            260                 265                 270

Leu Gly Gly Ser Gly Asp Ile Lys Leu Gln Gln Ser Gly Ala Glu Leu
        275                 280                 285

Ala Arg Pro Gly Ala Ser Val Lys Met Ser Cys Lys Thr Ser Gly Tyr
    290                 295                 300

Thr Phe Thr Arg Tyr Thr Met His Trp Val Lys Gln Arg Pro Gly Gln
305                 310                 315                 320

Gly Leu Glu Trp Ile Gly Tyr Ile Asn Pro Ser Arg Gly Tyr Thr Asn
                325                 330                 335

Tyr Asn Gln Lys Phe Lys Asp Lys Ala Thr Leu Thr Thr Asp Lys Ser
            340                 345                 350

Ser Ser Thr Ala Tyr Met Gln Leu Ser Ser Leu Thr Ser Glu Asp Ser
        355                 360                 365

Ala Val Tyr Tyr Cys Ala Arg Tyr Tyr Asp Asp His Tyr Cys Leu Asp
    370                 375                 380

Tyr Trp Gly Gln Gly Thr Thr Leu Thr Val Ser Ser Val Glu Gly Gly
385                 390                 395                 400

Ser Gly Gly Ser Gly Gly Ser Gly Gly Ser Gly Gly Val Asp Asp Ile
                405                 410                 415

```
Gln Leu Thr Gln Ser Pro Ala Ile Met Ser Ala Ser Pro Gly Glu Lys
            420                 425                 430

Val Thr Met Thr Cys Arg Ala Ser Ser Ser Val Ser Tyr Met Asn Trp
        435                 440                 445

Tyr Gln Gln Lys Ser Gly Thr Ser Pro Lys Arg Trp Ile Tyr Asp Thr
    450                 455                 460

Ser Lys Val Ala Ser Gly Val Pro Tyr Arg Phe Ser Gly Ser Gly Ser
465                 470                 475                 480

Gly Thr Ser Tyr Ser Leu Thr Ile Ser Ser Met Glu Ala Glu Asp Ala
                485                 490                 495

Ala Thr Tyr Tyr Cys Gln Gln Trp Ser Ser Asn Pro Leu Thr Phe Gly
            500                 505                 510

Ala Gly Thr Lys Leu Glu Leu Lys
        515                 520


<210> SEQ ID NO 143
<211> LENGTH: 1866
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

gaattcgcga ccatggccgt gatggcacct cgcaccctgg tcctgctgct gagcggggca     60

ctggcactga cacagacttg ggctggagat attcagctga ctcagagccc tgcttccctg    120

gcagtcagcc tgggacagcg agcaaccatc tcctgcaagg ccagccagtc cgtggactat    180

gatggcgact cctatctgaa ctggtaccag cagatcccag ggcagccccc taaactgctg    240

atctacgatg cctcaaatct ggtgagcggc atcccaccca gattttctgg aagtggctca    300

gggacagact tcactctgaa cattcacccc gtggagaagg tcgatgccgc tacctaccat    360

tgccagcaga gcacagagga cccttggact tttggcgggg gaaccaaact ggaaatcaag    420

ggaggaggag gcagtggcgg aggagggtca ggaggaggag gaagccaggt gcagctgcag    480

cagagcggag cagagctggt caggccagga agctccgtga aaatttcctg taaggcctct    540

ggctatgctt tctctagtta ctggatgaat tgggtgaagc agcgacctgg acagggactg    600

gagtggatcg ggcagatttg gccaggggat ggagacacca actacaatgg aaagtttaaa    660

ggcaaggcaa ctctgaccgc cgatgaatca agctccacag cctatatgca gctgtctagt    720

ctggcatctg aggacagtgc cgtctacttc tgcgctcgga gagaaaccac aactgtggga    780

cgatactatt acgccatgga ttattggggc caggggacca cagtgaccgt ctcaagcggc    840

gggtccgatg ctcacaaatc tgaggtcgca catcgcttca aggacctggg ggaggaaaac    900

tttaaagccc tggtgctgat cgctttcgca cagtacctgc agcagtgccc ctttgaagac    960

cacgtgaagc tggtcaacga ggtgacagag ttcgccaaaa cttgcgtcgc tgatgagagt   1020

gcagaaaatt gtgacaagtc actgcataca ctgtttggag ataaactgtg taccgtggcc   1080

acactgcggg agacttatgg cgaaatggcc gactgctgtg ctaagcagga gccagaaaga   1140

aacgagtgct tcctgcagca caaagacgat aaccctaatc tgccacgact ggtgcggccc   1200

gaagtggatg tcatgtgtac cgccttccac gacaatgagg aaacatttct gaagaaatat   1260

ctgtacgaga ttgctaggcg ccatccatat tttacgccc ccgaactgct gttctttgct   1320

aaaaggtaca aggcagcctt cactgagtgc tgtcaggctg cagataaagc cgcttgcctg   1380
```

```
ctgcccaagc tggatgagct gcgcgacgaa gggaaggcct cctctgctaa acagcgactg   1440

aagtgtgcat ctctgcagaa attcggagag agggctttta aggcctgggc tgtggcaaga   1500

ctgagccaga ggttccctaa ggcagagttt gccgaagtca gcaaactggt gactgacctg   1560

accaaggtgc acacagagtg ctgtcatggc gatctgctgg aatgcgccga cgatcgcgct   1620

gacctggcaa agtatatctg tgagaatcag gattccatta gttcaaaact gaaggagtgc   1680

tgtgaaaaac ctctgctgga gaagtctcac tgcatcgccg aggtggaaaa cgatgaaatg   1740

cccgctgacc tgccttctct ggcagccgat ttcgtcgaga gtaaagacgt gtgtaagaat   1800

tacgccgaag ctaaggacgt gttcctgggc atgtttctgt atgagtacgc aagagcctga   1860

ggatcc                                                              1866
```

<210> SEQ ID NO 144
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

```
Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Asp Ile Gln
            20                  25                  30

Leu Thr Gln Ser Pro Ala Ser Leu Ala Val Ser Leu Gly Gln Arg Ala
        35                  40                  45

Thr Ile Ser Cys Lys Ala Ser Gln Ser Val Asp Tyr Asp Gly Asp Ser
    50                  55                  60

Tyr Leu Asn Trp Tyr Gln Gln Ile Pro Gly Gln Pro Pro Lys Leu Leu
65                  70                  75                  80

Ile Tyr Asp Ala Ser Asn Leu Val Ser Gly Ile Pro Pro Arg Phe Ser
                85                  90                  95

Gly Ser Gly Ser Gly Thr Asp Phe Thr Leu Asn Ile His Pro Val Glu
            100                 105                 110

Lys Val Asp Ala Ala Thr Tyr His Cys Gln Gln Ser Thr Glu Asp Pro
        115                 120                 125

Trp Thr Phe Gly Gly Gly Thr Lys Leu Glu Ile Lys Gly Gly Gly Gly
    130                 135                 140

Ser Gly Gly Gly Gly Ser Gly Gly Gly Gly Ser Gln Val Gln Leu Gln
145                 150                 155                 160

Gln Ser Gly Ala Glu Leu Val Arg Pro Gly Ser Ser Val Lys Ile Ser
                165                 170                 175

Cys Lys Ala Ser Gly Tyr Ala Phe Ser Ser Tyr Trp Met Asn Trp Val
            180                 185                 190

Lys Gln Arg Pro Gly Gln Gly Leu Glu Trp Ile Gly Gln Ile Trp Pro
        195                 200                 205

Gly Asp Gly Asp Thr Asn Tyr Asn Gly Lys Phe Lys Gly Lys Ala Thr
    210                 215                 220

Leu Thr Ala Asp Glu Ser Ser Ser Thr Ala Tyr Met Gln Leu Ser Ser
225                 230                 235                 240

Leu Ala Ser Glu Asp Ser Ala Val Tyr Phe Cys Ala Arg Arg Glu Thr
                245                 250                 255

Thr Thr Val Gly Arg Tyr Tyr Tyr Ala Met Asp Tyr Trp Gly Gln Gly
            260                 265                 270
```

```
Thr Thr Val Thr Val Ser Ser Gly Gly Ser Asp Ala His Lys Ser Glu
        275                 280                 285

Val Ala His Arg Phe Lys Asp Leu Gly Glu Glu Asn Phe Lys Ala Leu
    290                 295                 300

Val Leu Ile Ala Phe Ala Gln Tyr Leu Gln Gln Cys Pro Phe Glu Asp
305                 310                 315                 320

His Val Lys Leu Val Asn Glu Val Thr Glu Phe Ala Lys Thr Cys Val
                325                 330                 335

Ala Asp Glu Ser Ala Glu Asn Cys Asp Lys Ser Leu His Thr Leu Phe
            340                 345                 350

Gly Asp Lys Leu Cys Thr Val Ala Thr Leu Arg Glu Thr Tyr Gly Glu
        355                 360                 365

Met Ala Asp Cys Cys Ala Lys Gln Glu Pro Glu Arg Asn Glu Cys Phe
    370                 375                 380

Leu Gln His Lys Asp Asp Asn Pro Asn Leu Pro Arg Leu Val Arg Pro
385                 390                 395                 400

Glu Val Asp Val Met Cys Thr Ala Phe His Asp Asn Glu Glu Thr Phe
                405                 410                 415

Leu Lys Lys Tyr Leu Tyr Glu Ile Ala Arg Arg His Pro Tyr Phe Tyr
            420                 425                 430

Ala Pro Glu Leu Leu Phe Phe Ala Lys Arg Tyr Lys Ala Ala Phe Thr
        435                 440                 445

Glu Cys Cys Gln Ala Ala Asp Lys Ala Ala Cys Leu Leu Pro Lys Leu
    450                 455                 460

Asp Glu Leu Arg Asp Glu Gly Lys Ala Ser Ser Ala Lys Gln Arg Leu
465                 470                 475                 480

Lys Cys Ala Ser Leu Gln Lys Phe Gly Glu Arg Ala Phe Lys Ala Trp
                485                 490                 495

Ala Val Ala Arg Leu Ser Gln Arg Phe Pro Lys Ala Glu Phe Ala Glu
            500                 505                 510

Val Ser Lys Leu Val Thr Asp Leu Thr Lys Val His Thr Glu Cys Cys
        515                 520                 525

His Gly Asp Leu Leu Glu Cys Ala Asp Asp Arg Ala Asp Leu Ala Lys
    530                 535                 540

Tyr Ile Cys Glu Asn Gln Asp Ser Ile Ser Ser Lys Leu Lys Glu Cys
545                 550                 555                 560

Cys Glu Lys Pro Leu Leu Glu Lys Ser His Cys Ile Ala Glu Val Glu
                565                 570                 575

Asn Asp Glu Met Pro Ala Asp Leu Pro Ser Leu Ala Ala Asp Phe Val
            580                 585                 590

Glu Ser Lys Asp Val Cys Lys Asn Tyr Ala Glu Ala Lys Asp Val Phe
        595                 600                 605

Leu Gly Met Phe Leu Tyr Glu Tyr Ala Arg Ala
    610                 615
```

<210> SEQ ID NO 145
<211> LENGTH: 1563
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

```
gaattcgcca ccatggccgt gatggcacct agaacactgg tcctgctgct gagcggagcc     60
```

-continued

```
ctggcactga cacagacttg ggccggacag gtccagctgg tgcagagcgg ggcagaggtc    120
aagaaacccg gagaaagtct gaagatctca tgcaaaggga gtggatactc attcaccagc    180
tattggattg cctgggtgag gcagatgcct ggcaaggggc tggaatacat gggcctgatc    240
tatccagggg acagcgatac aaaatactcc ccctctttcc agggccaggt cacaatttcc    300
gtggacaaga gtgtctcaac tgcctatctg cagtggagct ccctgaaacc tagcgattcc    360
gcagtgtact tttgtgccag gcacgacgtc gggtattgca cagatcgcac ttgtgctaag    420
tggccagagt ggctgggagt gtggggacag ggaaccctgg tcacagtgtc tagtggagga    480
ggaggctcaa gcggaggagg ctctggagga ggagggtctc agagtgtgct gactcagcca    540
ccttcagtca gcgcagctcc tggacagaag gtgaccatct cctgctctgg cagctctagt    600
aacattggca acaattacgt gagctggtat cagcagctgc ctggcaccgc ccccaaagctg    660
ctgatctacg accacacaaa tcggcccgct ggggtgcctg atagattcag tgggtcaaaa    720
agcggaacct ccgcttctct ggcaattagc ggctttcgct ccgaggacga agctgattac    780
tattgtgcat cttgggacta cacactgagt ggctgggtgt tcggaggcgg gactaagctg    840
accgtgctgg gggcagccga accaaagtca agcgataaaa ctcatacctg cccaccatgt    900
cctgcaccag agctgctggg aggaccttcc gtgttcctgt ttcctccaaa gccaaaagac    960
accctgatga tcagccgaac accagaagtg acttgcgtgg tcgtggacgt ctcccacgag   1020
gaccccgaag tgaagtttaa ctggtacgtg gatggcgtcg aggtgcataa tgccaagacc   1080
aaaccccgag aggaacagta caactcaact tatcgggtcg tgagcgtcct gaccgtgctg   1140
caccaggact ggctgaacgg gaaagagtat aagtgcaaag tgtctaataa ggccctgccc   1200
gctcctatcg agaaaacaat tagcaaggca aaaggccagc caagagaacc ccaggtgtac   1260
acttatcccc cttctaggga cgagctgacc aagaaccagg tgagcctgac atgtctggtc   1320
aaaggatttt accccagtga tattgctgtg gagtgggaat ccaatggcca gcctgaaaac   1380
aattataaga ccacaccacc cgtgctggac tccgatggat ctttcgctct ggtgtccaag   1440
ctgactgtcg ataaatctcg gtggcagcag ggcaacgtgt ttagttgttc agtcatgcat   1500
gaggcactgc acaatcatta cacacagaag agcctgtccc tgtctcccgg caaatgagga   1560
tcc                                                                 1563
```

```
<210> SEQ ID NO 146
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Gln Val Gln
            20                  25                  30

Leu Val Gln Ser Gly Ala Glu Val Lys Lys Pro Gly Glu Ser Leu Lys
        35                  40                  45

Ile Ser Cys Lys Gly Ser Gly Tyr Ser Phe Thr Ser Tyr Trp Ile Ala
    50                  55                  60

Trp Val Arg Gln Met Pro Gly Lys Gly Leu Glu Tyr Met Gly Leu Ile
65                  70                  75                  80
```

-continued

```
Tyr Pro Gly Asp Ser Asp Thr Lys Tyr Ser Pro Ser Phe Gln Gly Gln
                85                  90                  95

Val Thr Ile Ser Val Asp Lys Ser Val Ser Thr Ala Tyr Leu Gln Trp
            100                 105                 110

Ser Ser Leu Lys Pro Ser Asp Ser Ala Val Tyr Phe Cys Ala Arg His
        115                 120                 125

Asp Val Gly Tyr Cys Thr Asp Arg Thr Cys Ala Lys Trp Pro Glu Trp
    130                 135                 140

Leu Gly Val Trp Gly Gln Gly Thr Leu Val Thr Val Ser Ser Gly Gly
145                 150                 155                 160

Gly Gly Ser Ser Gly Gly Gly Ser Gly Gly Gly Gly Ser Gln Ser Val
                165                 170                 175

Leu Thr Gln Pro Pro Ser Val Ser Ala Ala Pro Gly Gln Lys Val Thr
            180                 185                 190

Ile Ser Cys Ser Gly Ser Ser Ser Asn Ile Gly Asn Asn Tyr Val Ser
        195                 200                 205

Trp Tyr Gln Gln Leu Pro Gly Thr Ala Pro Lys Leu Leu Ile Tyr Asp
    210                 215                 220

His Thr Asn Arg Pro Ala Gly Val Pro Asp Arg Phe Ser Gly Ser Lys
225                 230                 235                 240

Ser Gly Thr Ser Ala Ser Leu Ala Ile Ser Gly Phe Arg Ser Glu Asp
                245                 250                 255

Glu Ala Asp Tyr Tyr Cys Ala Ser Trp Asp Tyr Thr Leu Ser Gly Trp
            260                 265                 270

Val Phe Gly Gly Gly Thr Lys Leu Thr Val Leu Gly Ala Ala Glu Pro
        275                 280                 285

Lys Ser Ser Asp Lys Thr His Thr Cys Pro Pro Cys Pro Ala Pro Glu
    290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
        355                 360                 365

Ser Thr Tyr Arg Val Val Ser Val Leu Thr Val Leu His Gln Asp Trp
    370                 375                 380

Leu Asn Gly Lys Glu Tyr Lys Cys Lys Val Ser Asn Lys Ala Leu Pro
385                 390                 395                 400

Ala Pro Ile Glu Lys Thr Ile Ser Lys Ala Lys Gly Gln Pro Arg Glu
                405                 410                 415

Pro Gln Val Tyr Thr Tyr Pro Pro Ser Arg Asp Glu Leu Thr Lys Asn
            420                 425                 430

Gln Val Ser Leu Thr Cys Leu Val Lys Gly Phe Tyr Pro Ser Asp Ile
        435                 440                 445

Ala Val Glu Trp Glu Ser Asn Gly Gln Pro Glu Asn Asn Tyr Lys Thr
    450                 455                 460

Thr Pro Pro Val Leu Asp Ser Asp Gly Ser Phe Ala Leu Val Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
```

500 505 510

Ser Leu Ser Pro Gly Lys
515

<210> SEQ ID NO 147
<211> LENGTH: 792
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147
gaattcgcta caatggccgt gatggcaccc cgaacactgg tcctgctgct gagcggcgca 60
ctggcactga cacagacttg ggctggagaa cctaagagct ccgacaaaac ccacacatgc 120 ccccccttgtc cagctccaga actgctggga ggaccatccg tgttcctgtt tccacccaag 180
cccaaagata cactgatgat ctctcgaact cccgaggtca cctgcgtggt cgtggacgtc 240
agtcacgagg accccgaagt caagttcaac tggtacgtgg acggcgtcga agtgcataat 300
gcaaagacta aaccacggga ggaacagtac aactcaacat atagagtcgt gagcgtcctg 360
actgtgctgc atcaggattg gctgaacggc aaggagtata agtgcaaagt gagcaataag 420
gccctgcctg ctccaatcga gaaaaccatt agcaaggcaa aagggcagcc cagggaacct 480
caggtgtaca ccctgcctcc aagccgcgac gagctgacaa agaaccaggt ctccctgctg 540
tgtctggtga aaggattcta tcctagtgat attgccgtgg agtgggaatc aaatggccag 600
ccagagaaca attacatgac ttggcccccct gtgctggact ctgatgggag tttctttctg 660
tattccaagc tgaccgtgga caaatctaga tggcagcagg gaaacgtctt ttcttgtagt 720
gtgatgcacg aagccctgca caatcattac acacagaagt cactgagcct gtcccctggc 780
aaatgaggat cc 792

<210> SEQ ID NO 148
<211> LENGTH: 261
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Glu Pro Lys
20 25 30

Ser Ser Asp Lys Thr His Thr Cys Pro Pro Cys Pro Ala Pro Glu Leu
35 40 45

Leu Gly Gly Pro Ser Val Phe Leu Phe Pro Pro Lys Pro Lys Asp Thr
50 55 60

Leu Met Ile Ser Arg Thr Pro Glu Val Thr Cys Val Val Val Asp Val
65 70 75 80

Ser His Glu Asp Pro Glu Val Lys Phe Asn Trp Tyr Val Asp Gly Val
85 90 95

Glu Val His Asn Ala Lys Thr Lys Pro Arg Glu Glu Gln Tyr Asn Ser
100 105 110

Thr Tyr Arg Val Val Ser Val Leu Thr Val Leu His Gln Asp Trp Leu
115 120 125

-continued

```
Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Leu Cys Leu Val Lys Gly Phe Tyr Pro Ser Asp Ile Ala
            180                 185                 190

Val Glu Trp Glu Ser Asn Gly Gln Pro Glu Asn Asn Tyr Met Thr Trp
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260
```

<210> SEQ ID NO 149
<211> LENGTH: 1539
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 149

```
gaattcgcca ccatggccgt gatggctcct agaaccctgg tgctgctgct gtctggagct     60

ctggctctga ctcagacctg ggctggagac atccagatga cccagtctcc atcctccctg    120

tctgcatctg taggagacag agtcaccatc acttgccggg caagtcagga cgttaacacc    180

gctgtagctt ggtatcagca gaaaccaggg aaagccccta agctcctgat ctattctgca    240

tcctttttgt acagtggggt cccatcaagg ttcagtggca gtcgatctgg gacagatttc    300

actctcacca tcagcagtct gcaacctgaa gattttgcaa cttactactg tcaacagcat    360

tacactaccc cacccacttt cggccaaggg accaaagtgg agatcaaagg tggttctggt    420

ggtggttctg gtggtggttc tggtggtggt tctggtggtg gttctggtga agtgcagctg    480

gtggagtctg gggggaggctt ggtacagcct ggcgggtccc tgagactctc ctgtgcagcc    540

tctggattca acattaaaga tacttatatc cactgggtcc ggcaagctcc agggaagggc    600

ctggagtggg tcgcacgtat ttatcccaca aatggttaca cacggtatgc ggactctgtg    660

aagggccgat tcaccatctc cgcagacact tccaagaaca ccgcgtatct gcaaatgaac    720

agtctgagag ctgaggacac ggccgtttat tactgttcaa gatggggcgg agacggtttc    780

tacgctatgg actactgggg ccaagggacc ctggtcaccg tctcctcagc cgccgagccc    840

aagagcagcg ataagaccca cacctgccct ccctgtccag ctccagaact gctgggagga    900

cctagcgtgt tcctgtttcc ccctaagcca aaagacactc tgatgatttc caggactccc    960

gaggtgacct gcgtggtggt ggacgtgtct cacgaggacc ccgaagtgaa gttcaactgg   1020

tacgtggatg gcgtggaagt gcataatgct aagacaaaac caagagagga acagtacaac   1080

tccacttatc gcgtcgtgag cgtgctgacc gtgctgcacc aggactggct gaacgggaag   1140

gagtataagt gcaaagtcag taataaggcc ctgcctgctc caatcgaaaa aaccatctct   1200

aaggccaaag gccagccaag ggagccccag gtgtacacat acccacccag cagagacgaa   1260
```

```
ctgaccaaga accaggtgtc cctgacatgt ctggtgaaag gcttctatcc tagtgatatt   1320

gctgtggagt gggaatcaaa tggacagcca gagaacaatt acaagaccac acctccagtg   1380

ctggacgagg atggcagctt cgccctggtg tccaagctga cagtggataa atctcgatgg   1440

cagcagggga acgtgtttag ttgttcagtg atgcatgaag ccctgcacaa tcattacact   1500

cagaagagcc tgtccctgtc tcccggcaaa tgaggatcc                         1539
```

<210> SEQ ID NO 150
<211> LENGTH: 510
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

```
Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Asp Ile Gln
            20                  25                  30

Met Thr Gln Ser Pro Ser Ser Leu Ser Ala Ser Val Gly Asp Arg Val
        35                  40                  45

Thr Ile Thr Cys Arg Ala Ser Gln Asp Val Asn Thr Ala Val Ala Trp
    50                  55                  60

Tyr Gln Gln Lys Pro Gly Lys Ala Pro Lys Leu Leu Ile Tyr Ser Ala
65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
            100                 105                 110

Ala Thr Tyr Tyr Cys Gln Gln His Tyr Thr Thr Pro Pro Thr Phe Gly
        115                 120                 125

Gln Gly Thr Lys Val Glu Ile Lys Gly Gly Ser Gly Gly Gly Ser Gly
    130                 135                 140

Gly Gly Ser Gly Gly Gly Ser Gly Gly Gly Ser Gly Glu Val Gln Leu
145                 150                 155                 160

Val Glu Ser Gly Gly Gly Leu Val Gln Pro Gly Gly Ser Leu Arg Leu
                165                 170                 175

Ser Cys Ala Ala Ser Gly Phe Asn Ile Lys Asp Thr Tyr Ile His Trp
            180                 185                 190

Val Arg Gln Ala Pro Gly Lys Gly Leu Glu Trp Val Ala Arg Ile Tyr
        195                 200                 205

Pro Thr Asn Gly Tyr Thr Arg Tyr Ala Asp Ser Val Lys Gly Arg Phe
    210                 215                 220

Thr Ile Ser Ala Asp Thr Ser Lys Asn Thr Ala Tyr Leu Gln Met Asn
225                 230                 235                 240

Ser Leu Arg Ala Glu Asp Thr Ala Val Tyr Tyr Cys Ser Arg Trp Gly
                245                 250                 255

Gly Asp Gly Phe Tyr Ala Met Asp Tyr Trp Gly Gln Gly Thr Leu Val
            260                 265                 270

Thr Val Ser Ser Ala Ala Glu Pro Lys Ser Ser Asp Lys Thr His Thr
        275                 280                 285

Cys Pro Pro Cys Pro Ala Pro Glu Leu Leu Gly Gly Pro Ser Val Phe
    290                 295                 300
```

-continued

```
Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Tyr Pro Pro
                405                 410                 415

Ser Arg Asp Glu Leu Thr Lys Asn Gln Val Ser Leu Thr Cys Leu Val
            420                 425                 430

Lys Gly Phe Tyr Pro Ser Asp Ile Ala Val Glu Trp Glu Ser Asn Gly
        435                 440                 445

Gln Pro Glu Asn Asn Tyr Lys Thr Thr Pro Pro Val Leu Asp Glu Asp
    450                 455                 460

Gly Ser Phe Ala Leu Val Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510


<210> SEQ ID NO 151
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

gaattcgcca ccatggccgt gatggctcct agaaccctgg tgctgctgct gtctggagct     60

ctggctctga ctcagacctg ggctggagac atccagatga cccagtctcc atcctccctg    120

tctgcatctg taggagacag agtcaccatc acttgccggg caagtcagga cgttaacacc    180

gctgtagctt ggtatcagca gaaaccaggg aaagccccta agctcctgat ctattctgca    240

tcctttttgt acagtggggt cccatcaagg ttcagtggca gtcgatctgg gacagatttc    300

actctcacca tcagcagtct gcaacctgaa gattttgcaa cttactactg tcaacagcat    360

tacactaccc cacccacttt cggccaaggg accaaagtgg agatcaaagg tggttctggt    420

ggtggttctg gtggtggttc tggtggtggt tctggtggtg gttctggtga agtgcagctg    480

gtggagtctg gggaggctt ggtacagcct ggcgggtccc tgagactctc ctgtgcagcc    540

tctggattca acattaaaga tacttatatc cactgggtcc ggcaagctcc agggaagggc    600

ctggagtggg tcgcacgtat ttatcccaca aatggttaca cacggtatgc ggactctgtg    660

aagggccgat tcaccatctc cgcagacact tccaagaaca ccgcgtatct gcaaatgaac    720

agtctgagag ctgaggacac ggccgtttat tactgttcaa gatggggcgg agacggtttc    780

tacgctatgg actactgggg ccaagggacc ctggtcaccg tctcctcagc cgccgagccc    840

aagagcagcg ataagaccca cacctgccct ccctgtccag ctccagaact gctgggagga    900
```

```
cctagcgtgt tcctgtttcc ccctaagcca aaagacactc tgatgatttc caggactccc    960

gaggtgacct gcgtggtggt ggacgtgtct cacgaggacc ccgaagtgaa gttcaactgg   1020

tacgtggatg gcgtggaagt gcataatgct aagacaaaac caagagagga acagtacaac   1080

tccacttatc gcgtcgtgag cgtgctgacc gtgctgcacc aggactggct gaacgggaag   1140

gagtataagt gcaaagtcag taataaggcc ctgcctgctc caatcgaaaa aaccatctct   1200

aaggccaaag gccagccaag ggagccccag gtgtacacac tgccacccag cagagacgaa   1260

ctgaccaaga accaggtgtc cctgatctgt ctggtgaaag gcttctatcc tagtgatatt   1320

gctgtggagt gggaatcaaa tggacagcca gagaacagat acatgacctg gcctccagtg   1380

ctggacagcg atggcagctt cttcctgtat tccaagctga cagtggataa atctcgatgg   1440

cagcagggga acgtgtttag ttgttcagtg atgcatgaag ccctgcacaa tcattacact   1500

cagaagagcc tgtccctgtc tcccggcaaa tgaggatcc                          1539
```

```
<210> SEQ ID NO 152
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Asp Ile Gln
            20                  25                  30

Met Thr Gln Ser Pro Ser Ser Leu Ser Ala Ser Val Gly Asp Arg Val
        35                  40                  45

Thr Ile Thr Cys Arg Ala Ser Gln Asp Val Asn Thr Ala Val Ala Trp
    50                  55                  60

Tyr Gln Gln Lys Pro Gly Lys Ala Pro Lys Leu Leu Ile Tyr Ser Ala
65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
            100                 105                 110

Ala Thr Tyr Tyr Cys Gln Gln His Tyr Thr Thr Pro Pro Thr Phe Gly
        115                 120                 125

Gln Gly Thr Lys Val Glu Ile Lys Gly Gly Ser Gly Gly Gly Ser Gly
    130                 135                 140

Gly Gly Ser Gly Gly Gly Ser Gly Gly Gly Ser Gly Glu Val Gln Leu
145                 150                 155                 160

Val Glu Ser Gly Gly Gly Leu Val Gln Pro Gly Gly Ser Leu Arg Leu
                165                 170                 175

Ser Cys Ala Ala Ser Gly Phe Asn Ile Lys Asp Thr Tyr Ile His Trp
            180                 185                 190

Val Arg Gln Ala Pro Gly Lys Gly Leu Glu Trp Val Ala Arg Ile Tyr
        195                 200                 205

Pro Thr Asn Gly Tyr Thr Arg Tyr Ala Asp Ser Val Lys Gly Arg Phe
    210                 215                 220

Thr Ile Ser Ala Asp Thr Ser Lys Asn Thr Ala Tyr Leu Gln Met Asn
225                 230                 235                 240
```

```
Ser Leu Arg Ala Glu Asp Thr Ala Val Tyr Tyr Cys Ser Arg Trp Gly
                245                 250                 255

Gly Asp Gly Phe Tyr Ala Met Asp Tyr Trp Gly Gln Gly Thr Leu Val
            260                 265                 270

Thr Val Ser Ser Ala Ala Glu Pro Lys Ser Ser Asp Lys Thr His Thr
        275                 280                 285

Cys Pro Pro Cys Pro Ala Pro Glu Leu Leu Gly Gly Pro Ser Val Phe
    290                 295                 300

Leu Phe Pro Pro Lys Pro Lys Asp Thr Leu Met Ile Ser Arg Thr Pro
305                 310                 315                 320

Glu Val Thr Cys Val Val Val Asp Val Ser His Glu Asp Pro Glu Val
                325                 330                 335

Lys Phe Asn Trp Tyr Val Asp Gly Val Glu Val His Asn Ala Lys Thr
            340                 345                 350

Lys Pro Arg Glu Glu Gln Tyr Asn Ser Thr Tyr Arg Val Val Ser Val
        355                 360                 365

Leu Thr Val Leu His Gln Asp Trp Leu Asn Gly Lys Glu Tyr Lys Cys
    370                 375                 380

Lys Val Ser Asn Lys Ala Leu Pro Ala Pro Ile Glu Lys Thr Ile Ser
385                 390                 395                 400

Lys Ala Lys Gly Gln Pro Arg Glu Pro Gln Val Tyr Thr Leu Pro Pro
                405                 410                 415

Ser Arg Asp Glu Leu Thr Lys Asn Gln Val Ser Leu Ile Cys Leu Val
            420                 425                 430

Lys Gly Phe Tyr Pro Ser Asp Ile Ala Val Glu Trp Glu Ser Asn Gly
        435                 440                 445

Gln Pro Glu Asn Arg Tyr Met Thr Trp Pro Pro Val Leu Asp Ser Asp
    450                 455                 460

Gly Ser Phe Phe Leu Tyr Ser Lys Leu Thr Val Asp Lys Ser Arg Trp
465                 470                 475                 480

Gln Gln Gly Asn Val Phe Ser Cys Ser Val Met His Glu Ala Leu His
                485                 490                 495

Asn His Tyr Thr Gln Lys Ser Leu Ser Leu Ser Pro Gly Lys
            500                 505                 510
```

<210> SEQ ID NO 153
<211> LENGTH: 792
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153

```
gaattcgcca ccatggccgt gatggctcct agaaccctgg tgctgctgct gtctggagct     60

ctggctctga ctcagacctg ggctggagag cccaagagca gcgataagac ccacacctgc    120

cctccctgtc cagctccaga actgctggga ggacctagcg tgttcctgtt tccccctaag    180

ccaaaagaca ctctgatgat ttccaggact cccgaggtga cctgcgtggt ggtggacgtg    240

tctcacgagg accccgaagt gaagttcaac tggtacgtgg atggcgtgga agtgcataat    300

gctaagacaa aaccaagaga ggaacagtac aactccactt atcgcgtcgt gagcgtgctg    360

accgtgctgc accaggactg gctgaacggg aaggagtata agtgcaaagt cagtaataag    420

gccctgcctg ctccaatcga aaaaaccatc tctaaggcca aaggccagcc aagggagccc    480

caggtgtaca cactgccacc cagcagagac gaactgacca agaaccaggt gtccctgatc    540
```

tgtctggtga aaggcttcta tcctagtgat attgctgtgg agtgggaatc aaatggacag 600
ccagagaaca gatacatgac ctggcctcca gtgctggaca gcgatggcag cttcttcctg 660
tattccaagc tgacagtgga taaatctcga tggcagcagg ggaacgtgtt tagttgttca 720
gtgatgcatg aagccctgca caatcattac actcagaaga gcctgtccct gtctcccggc 780
aaatgaggat cc 792

<210> SEQ ID NO 154
<211> LENGTH: 261
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Glu Pro Lys
20 25 30

Ser Ser Asp Lys Thr His Thr Cys Pro Pro Cys Pro Ala Pro Glu Leu
35 40 45

Leu Gly Gly Pro Ser Val Phe Leu Phe Pro Pro Lys Pro Lys Asp Thr
50 55 60

Leu Met Ile Ser Arg Thr Pro Glu Val Thr Cys Val Val Val Asp Val
65 70 75 80

Ser His Glu Asp Pro Glu Val Lys Phe Asn Trp Tyr Val Asp Gly Val
85 90 95

Glu Val His Asn Ala Lys Thr Lys Pro Arg Glu Glu Gln Tyr Asn Ser
100 105 110

Thr Tyr Arg Val Val Ser Val Leu Thr Val Leu His Gln Asp Trp Leu
115 120 125

Asn Gly Lys Glu Tyr Lys Cys Lys Val Ser Asn Lys Ala Leu Pro Ala
130 135 140

Pro Ile Glu Lys Thr Ile Ser Lys Ala Lys Gly Gln Pro Arg Glu Pro
145 150 155 160

Gln Val Tyr Thr Leu Pro Pro Ser Arg Asp Glu Leu Thr Lys Asn Gln
165 170 175

Val Ser Leu Ile Cys Leu Val Lys Gly Phe Tyr Pro Ser Asp Ile Ala
180 185 190

Val Glu Trp Glu Ser Asn Gly Gln Pro Glu Asn Arg Tyr Met Thr Trp
195 200 205

Pro Pro Val Leu Asp Ser Asp Gly Ser Phe Phe Leu Tyr Ser Lys Leu
210 215 220

Thr Val Asp Lys Ser Arg Trp Gln Gln Gly Asn Val Phe Ser Cys Ser
225 230 235 240

Val Met His Glu Ala Leu His Asn His Tyr Thr Gln Lys Ser Leu Ser
245 250 255

Leu Ser Pro Gly Lys
260

<210> SEQ ID NO 155
<211> LENGTH: 3381
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 155
gaattcgcga ccatggccgt gatggctcct cggacactgg tgctgctgct gagtggggct 60
ctggctctga cacagacttg ggctggacag gtgcagctgc aggagtccgg aggaggactg 120
gtgaagccag gagggtccct gagactgtct tgcgccgcta gtggcttcac ctttagctcc 180
tactggatgt cttgggtgag gcaggcacct ggcaagggac tggagtgggt ggcaaacatc 240
aatcgcgacg gatcagccag ctactatgtg gatagcgtca agggcaggtt tacaattagt 300
cgcgacgatg ctaaaaactc actgtacctg cagatgaata gcctgcgggc agaggatact 360
gccgtgtact attgcgccag agacagggga gtcggctatt tcgatctgtg ggggagagga 420
actctggtga ccgtctctag tgctagcacc ggaggcgggg gatctggcgg aggaggcagt 480
ggaggaggag ggtcccagtc tgctctgaca cagccagcaa gtgtgtcagg cagccccggg 540
cagtcaatca ctattagctg tactggcacc tcaagcgacg tgggaggcta caactttgtc 600
agctggtatc agcagcaccc tggaaaagcc ccaaagctga tgatctacga cgtgagcgat 660
cgaccttccg gcgtctctga tcggttctcc gggtctaaga gtggaaatac tgcctccctg 720
atcatttctg ggctgcaggc tgacgatgag gcagactact attgctcctc ttatggaagt 780
tcaagcaccc atgtgatctt cgggggaggc acaaaagtga ctgtcctggg cgcagcctca 840
gatgctcaca aaagcgaggt ggcacatcgg ttcaaggacc tgggggagga aaactttaaa 900
gccctggtgc tgattgcatt cgcccagtac ctgcagcaga gcccatttga ggaccacgtg 960
aagctggtca acgaggtgac cgagttcgcc aaaacatgcg tggccgacga gtccgctgaa 1020
aattgtgata agtctctgca tactctgttt ggagataaac tgtgcaccgt ggccacactg 1080
cgagagacct acggcgaaat ggcagactgc tgtgccaagc aggagccaga aagaaacgag 1140
tgcttcctgc agcacaaaga cgataaccca aatctgccac gactggtgcg accagaagtg 1200
gacgtcatgt gtactgcttt ccacgataat gaggaaacct ttctgaagaa atacctgtat 1260
gagatcgccc ggagacatcc ctacttttat gcacctgaac tgctgttctt tgccaaaaga 1320
tacaaggctg cattcaccga gtgctgtcag gccgctgata aagcagcctg cctgctgcca 1380
aagctggacg agctgcgaga tgaaggcaag gcctcctctg ctaaacagag actgaagtgt 1440
gccagcctgc agaaattcgg cgagagggct tttaaggctt gggcagtggc acgactgtcc 1500
cagagattcc ctaaggcaga gtttgccgaa gtctctaaac tggtgactga cctgaccaag 1560
gtgcacaccg agtgctgtca tggcgacctg ctggaatgcg ccgacgatcg cgctgatctg 1620
gcaaagtaca tctgtgagaa ccaggacagc attagttcaa agctgaaaga gtgctgtgaa 1680
aaacccctgc tggagaagag ccactgcatc gcagaggtgg aaaacgacga aatgcccgcc 1740
gatctgccta gtctggctgc agacttcgtg gagtcaaaag atgtctgtaa gaattacgct 1800
gaagcaaagg atgtgttcct gggcatgttt ctgtacgagt atgctaggcg ccacccagac 1860
tactccgtgg tcctgctgct gaggctggcc aagacctatg agaccacact ggaaaaatgc 1920
tgtgccgctg cagatcccca tgagtgctat gccaaagtgt tcgacgagtt caagccactg 1980
gtcgaggaac cccagaacct gattaagcag aattgtgagc tgtttgaaca gctgggcgag 2040
tacaaattcc agaacgccct gctggtgcgc tatacaaaga aagtccctca ggtgagcaca 2100
ccaactctgg tggaagtctc caggaatctg ggaaaggtcg gctctaaatg ctgtaagcac 2160
cccgaggcca aacgcatgcc ttgcgctgaa gattacctgt ccgtggtcct gaaccagctg 2220

-continued

```
tgtgtgctgc atgagaagac cccagtctct gaccgggtga caaaatgctg tactgaaagt   2280

ctggtgaatc gacggccctg ctttagcgcc ctggaggtgg atgaaacata tgtccctaag   2340

gagttccagg ctgaaacctt cacatttcac gcagacatct gtactctgtc cgagaaagaa   2400

agacagatta agaaacagac cgccctggtc gagctggtga agcataaacc caaggccaca   2460

aaagaacagc tgaaggctgt gatggacgat ttcgccgctt ttgtcgagaa atgctgtaag   2520

gctgacgata aggaaacttg ctttgcagag gaagggaaga aactggtggc agcatcccag   2580

gctgcactgg gactggcagc tgcactgcag gtccagctgg tgcagtctgg cgccgaggtg   2640

aagaaacctg ggaaagtct gaaaatctcc tgtaagggca gtgggtactc attcaccagc   2700

tattggattg cctgggtgag gcagatgcca ggaaagggcc tggagtacat gggactgatc   2760

tatcctggcg acagcgatac aaaatactca ccaagctttc agggccaggt cacaattagc   2820

gtggataagt ccgtctctac tgcctatctg cagtggagct ccctgaaacc tagtgactca   2880

gccgtgtact tctgcgctcg ccacgacgtc ggctattgca cagatcgaac ttgtgccaag   2940

tggccagagt ggctgggagt gtggggacag ggaaccctgg tgacagtctc tagtggggga   3000

ggcgggtcaa gcggaggagg gtccggagga ggaggaagcc agtccgtgct gacccagccc   3060

ccttctgtca gtgccgctcc tggccagaag gtgacaatct catgcagcgg gtcctctagt   3120

aacattggaa acaattacgt gagctggtat cagcagctgc cagggaccgc tcccaagctg   3180

ctgatctacg atcatacaaa tagacctgca ggagtgccag acaggttttc cggctctaaa   3240

agtgggacct cagccagcct ggctattagc ggcttccggt ccgaggacga agcagattac   3300

tattgtgcct cctgggacta tacactgtct ggctgggtgt tcggcggggg aactaagctg   3360

accgtcctgg ggtgaggatc c                                             3381
```

<210> SEQ ID NO 156
<211> LENGTH: 1124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 156

```
Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Gln Val Gln
            20                  25                  30

Leu Gln Glu Ser Gly Gly Gly Leu Val Lys Pro Gly Gly Ser Leu Arg
        35                  40                  45

Leu Ser Cys Ala Ala Ser Gly Phe Thr Phe Ser Ser Tyr Trp Met Ser
    50                  55                  60

Trp Val Arg Gln Ala Pro Gly Lys Gly Leu Glu Trp Val Ala Asn Ile
65                  70                  75                  80

Asn Arg Asp Gly Ser Ala Ser Tyr Tyr Val Asp Ser Val Lys Gly Arg
                85                  90                  95

Phe Thr Ile Ser Arg Asp Asp Ala Lys Asn Ser Leu Tyr Leu Gln Met
            100                 105                 110

Asn Ser Leu Arg Ala Glu Asp Thr Ala Val Tyr Tyr Cys Ala Arg Asp
        115                 120                 125

Arg Gly Val Gly Tyr Phe Asp Leu Trp Gly Arg Gly Thr Leu Val Thr
    130                 135                 140

Val Ser Ser Ala Ser Thr Gly Gly Gly Gly Ser Gly Gly Gly Gly Ser
```

-continued

```
145                 150                 155                 160

Gly Gly Gly Gly Ser Gln Ser Ala Leu Thr Gln Pro Ala Ser Val Ser
                165                 170                 175

Gly Ser Pro Gly Gln Ser Ile Thr Ile Ser Cys Thr Gly Thr Ser Ser
            180                 185                 190

Asp Val Gly Gly Tyr Asn Phe Val Ser Trp Tyr Gln Gln His Pro Gly
        195                 200                 205

Lys Ala Pro Lys Leu Met Ile Tyr Asp Val Ser Asp Arg Pro Ser Gly
    210                 215                 220

Val Ser Asp Arg Phe Ser Gly Ser Lys Ser Gly Asn Thr Ala Ser Leu
225                 230                 235                 240

Ile Ile Ser Gly Leu Gln Ala Asp Asp Glu Ala Asp Tyr Tyr Cys Ser
                245                 250                 255

Ser Tyr Gly Ser Ser Ser Thr His Val Ile Phe Gly Gly Gly Thr Lys
            260                 265                 270

Val Thr Val Leu Gly Ala Ala Ser Asp Ala His Lys Ser Glu Val Ala
        275                 280                 285

His Arg Phe Lys Asp Leu Gly Glu Glu Asn Phe Lys Ala Leu Val Leu
    290                 295                 300

Ile Ala Phe Ala Gln Tyr Leu Gln Gln Ser Pro Phe Glu Asp His Val
305                 310                 315                 320

Lys Leu Val Asn Glu Val Thr Glu Phe Ala Lys Thr Cys Val Ala Asp
                325                 330                 335

Glu Ser Ala Glu Asn Cys Asp Lys Ser Leu His Thr Leu Phe Gly Asp
            340                 345                 350

Lys Leu Cys Thr Val Ala Thr Leu Arg Glu Thr Tyr Gly Glu Met Ala
        355                 360                 365

Asp Cys Cys Ala Lys Gln Glu Pro Glu Arg Asn Glu Cys Phe Leu Gln
    370                 375                 380

His Lys Asp Asp Asn Pro Asn Leu Pro Arg Leu Val Arg Pro Glu Val
385                 390                 395                 400

Asp Val Met Cys Thr Ala Phe His Asp Asn Glu Glu Thr Phe Leu Lys
                405                 410                 415

Lys Tyr Leu Tyr Glu Ile Ala Arg Arg His Pro Tyr Phe Tyr Ala Pro
            420                 425                 430

Glu Leu Leu Phe Phe Ala Lys Arg Tyr Lys Ala Ala Phe Thr Glu Cys
        435                 440                 445

Cys Gln Ala Ala Asp Lys Ala Ala Cys Leu Leu Pro Lys Leu Asp Glu
    450                 455                 460

Leu Arg Asp Glu Gly Lys Ala Ser Ser Ala Lys Gln Arg Leu Lys Cys
465                 470                 475                 480

Ala Ser Leu Gln Lys Phe Gly Glu Arg Ala Phe Lys Ala Trp Ala Val
                485                 490                 495

Ala Arg Leu Ser Gln Arg Phe Pro Lys Ala Glu Phe Ala Glu Val Ser
            500                 505                 510

Lys Leu Val Thr Asp Leu Thr Lys Val His Thr Glu Cys Cys His Gly
        515                 520                 525

Asp Leu Leu Glu Cys Ala Asp Asp Arg Ala Asp Leu Ala Lys Tyr Ile
    530                 535                 540

Cys Glu Asn Gln Asp Ser Ile Ser Ser Lys Leu Lys Glu Cys Cys Glu
545                 550                 555                 560

Lys Pro Leu Leu Glu Lys Ser His Cys Ile Ala Glu Val Glu Asn Asp
                565                 570                 575
```

```
Glu Met Pro Ala Asp Leu Pro Ser Leu Ala Ala Asp Phe Val Glu Ser
            580                 585                 590

Lys Asp Val Cys Lys Asn Tyr Ala Glu Ala Lys Asp Val Phe Leu Gly
        595                 600                 605

Met Phe Leu Tyr Glu Tyr Ala Arg Arg His Pro Asp Tyr Ser Val Val
    610                 615                 620

Leu Leu Leu Arg Leu Ala Lys Thr Tyr Glu Thr Thr Leu Glu Lys Cys
625                 630                 635                 640

Cys Ala Ala Ala Asp Pro His Glu Cys Tyr Ala Lys Val Phe Asp Glu
                645                 650                 655

Phe Lys Pro Leu Val Glu Glu Pro Gln Asn Leu Ile Lys Gln Asn Cys
            660                 665                 670

Glu Leu Phe Glu Gln Leu Gly Glu Tyr Lys Phe Gln Asn Ala Leu Leu
        675                 680                 685

Val Arg Tyr Thr Lys Lys Val Pro Gln Val Ser Thr Pro Thr Leu Val
    690                 695                 700

Glu Val Ser Arg Asn Leu Gly Lys Val Gly Ser Lys Cys Cys Lys His
705                 710                 715                 720

Pro Glu Ala Lys Arg Met Pro Cys Ala Glu Asp Tyr Leu Ser Val Val
                725                 730                 735

Leu Asn Gln Leu Cys Val Leu His Glu Lys Thr Pro Val Ser Asp Arg
            740                 745                 750

Val Thr Lys Cys Cys Thr Glu Ser Leu Val Asn Arg Arg Pro Cys Phe
        755                 760                 765

Ser Ala Leu Glu Val Asp Glu Thr Tyr Val Pro Lys Glu Phe Gln Ala
    770                 775                 780

Glu Thr Phe Thr Phe His Ala Asp Ile Cys Thr Leu Ser Glu Lys Glu
785                 790                 795                 800

Arg Gln Ile Lys Lys Gln Thr Ala Leu Val Glu Leu Val Lys His Lys
                805                 810                 815

Pro Lys Ala Thr Lys Glu Gln Leu Lys Ala Val Met Asp Asp Phe Ala
            820                 825                 830

Ala Phe Val Glu Lys Cys Cys Lys Ala Asp Asp Lys Glu Thr Cys Phe
        835                 840                 845

Ala Glu Glu Gly Lys Lys Leu Val Ala Ala Ser Gln Ala Ala Leu Gly
    850                 855                 860

Leu Ala Ala Ala Leu Gln Val Gln Leu Val Gln Ser Gly Ala Glu Val
865                 870                 875                 880

Lys Lys Pro Gly Glu Ser Leu Lys Ile Ser Cys Lys Gly Ser Gly Tyr
                885                 890                 895

Ser Phe Thr Ser Tyr Trp Ile Ala Trp Val Arg Gln Met Pro Gly Lys
            900                 905                 910

Gly Leu Glu Tyr Met Gly Leu Ile Tyr Pro Gly Asp Ser Asp Thr Lys
        915                 920                 925

Tyr Ser Pro Ser Phe Gln Gly Gln Val Thr Ile Ser Val Asp Lys Ser
    930                 935                 940

Val Ser Thr Ala Tyr Leu Gln Trp Ser Ser Leu Lys Pro Ser Asp Ser
945                 950                 955                 960

Ala Val Tyr Phe Cys Ala Arg His Asp Val Gly Tyr Cys Thr Asp Arg
                965                 970                 975

Thr Cys Ala Lys Trp Pro Glu Trp Leu Gly Val Trp Gly Gln Gly Thr
            980                 985                 990
```

```
Leu Val Thr Val Ser Ser Gly Gly  Gly Gly Ser Ser Gly  Gly Gly Ser
        995                 1000                 1005

Gly Gly  Gly Gly Ser Gln Ser  Val Leu Thr Gln Pro  Pro Ser Val
    1010                 1015                 1020

Ser Ala  Ala Pro Gly Gln Lys  Val Thr Ile Ser Cys  Ser Gly Ser
    1025                 1030                 1035

Ser Ser  Asn Ile Gly Asn Asn  Tyr Val Ser Trp Tyr  Gln Gln Leu
    1040                 1045                 1050

Pro Gly  Thr Ala Pro Lys Leu  Leu Ile Tyr Asp His  Thr Asn Arg
    1055                 1060                 1065

Pro Ala  Gly Val Pro Asp Arg  Phe Ser Gly Ser Lys  Ser Gly Thr
    1070                 1075                 1080

Ser Ala  Ser Leu Ala Ile Ser  Gly Phe Arg Ser Glu  Asp Glu Ala
    1085                 1090                 1095

Asp Tyr  Tyr Cys Ala Ser Trp  Asp Tyr Thr Leu Ser  Gly Trp Val
    1100                 1105                 1110

Phe Gly  Gly Gly Thr Lys Leu  Thr Val Leu Gly
    1115                 1120
```

<210> SEQ ID NO 157
<211> LENGTH: 2604
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157

```
gaattcgcga ccatggctgt gatggctcct agaacactgg tgctgctgct gtccggggct     60

ctggctctga ctcagacttg ggctgggcag gtgcagctgc aggagtctgg aggaggactg    120

gtgaagccag gagggtctct gcgactgagt tgcgccgctt caggcttcac ctttagctcc    180

tactggatga gctgggtccg ccaggcacca gggaagggac tggagtgggt ggccaacatc    240

aatcgagacg ggagcgcttc ctactatgtg gatagcgtca agggaaggtt tacaattagt    300

cgcgacgatg ccaaaaactc actgtacctg cagatgaata gcctgcgagc tgaggatact    360

gcagtctact attgcgctag agacaggggc gtggggtatt tcgatctgtg ggaagaggc     420

actctggtga ccgtctctag tgcaagcacc ggaggaggag gatcaggcgg aggaggcagc    480

ggaggaggcg ggtctcagag tgccctgacc cagccagctt cagtgagcgg gtccccagga    540

cagagcatca caatttcctg tactggcacc tcaagcgacg tcggaggcta caactttgtg    600

agctggtatc agcagcaccc aggcaaagcc cccaagctga tgatctacga cgtctccgat    660

cgacctagcg gggtgtccga tcggttctct ggaagtaaat caggcaatac cgcctctctg    720

atcattagtg ggctgcaggc cgacgatgag gctgactact attgctcctc ttatggaagt    780

tcaagcacac atgtgatctt cgggggaggc acaaaagtga ctgtcctggg agcagcctcc    840

gatgcacaca aatctgaggt ggcccatcgg ttcaaggacc tgggcgagga aaactttaaa    900

gccctggtgc tgattgcctt cgctcagtac ctgcagcaga gcccctttga ggaccacgtg    960

aagctggtca acgaggtgac cgagttcgcc aaaacatgcg tggcagacga gtccgccgaa   1020

aattgtgata agtctctgca tactctgttt ggagataaac tgtgtaccgt ggccacactg   1080

cgggagacct atggcgaaat ggctgactgc tgtgcaaagc aggagcccga aagaaacgag   1140

tgcttcctgc agcacaaaga cgataacccc aatctgcctc gcctggtgcg acctgaagtg   1200

gacgtcatgt gtactgcctt ccacgataat gaggaaacct ttctgaagaa atacctgtat   1260
```

```
gagatcgctc ggagacatcc ctacttttat gcccctgaac tgctgttctt tgctaaaaga   1320

tacaaggctg cattcaccga gtgctgtcag gccgctgata aagcagcctg cctgctgccc   1380

aagctggacg agctgagaga tgaagggaag gcttcctctg caaaacagag gctgaagtgt   1440

gctagcctgc agaaattcgg cgagagggcc ttcaaggcat gggcagtggc tcgactgagc   1500

cagagattcc ctaaggccga gtttgctgaa gtctccaaac tggtgactga cctgaccaag   1560

gtgcacacag agtgctgtca tggcgacctg ctggaatgcg ccgacgatcg cgcagatctg   1620

gccaagtaca tctgtgagaa tcaggactct attagttcaa agctgaaaga gtgctgtgaa   1680

aaacccctgc tggagaagag ccactgcatc gccgaggtgg aaaacgacga aatgcctgct   1740

gatctgccaa gtctggctgc agactttgtc gagtcaaaag atgtgtgtaa gaattacgca   1800

gaagccaagg atgtgttcct gggcatgttt ctgtacgagt atgcaaggcg ccaccctgac   1860

tactccgtgg tcctgctgct gaggctggct aagacctatg agaccacact ggaaaaatgc   1920

tgtgccgctg cagatccaca tgagtgctat gccaaagtct tcgacgagtt caagccactg   1980

gtggaggaac cccagaacct gattaagcag aattgtgagc tgtttgaaca gctgggcgag   2040

tacaaattcc agaacgccct gctggtgcgc tatacaaaga aagtccctca ggtgagcaca   2100

ccaactctgg tggaagtctc caggaatctg ggcaaggtcg ggtctaaatg ctgtaagcac   2160

cccgaggcta aacgcatgcc ttgcgcagaa gattacctgt ctgtggtcct gaaccagctg   2220

tgtgtgctgc atgagaagac accagtcagt gaccgggtga caaaatgctg tactgaaagt   2280

ctggtgaatc gacggccttg cttttcagcc ctggaggtcg atgaaactta tgtgccaaag   2340

gagttccagg cagaaacctt cacatttcac gccgacatct gtacactgtc cgagaaagaa   2400

agacagatta agaaacagac tgccctggtc gagctggtga agcataaacc caaggctact   2460

aaagaacagc tgaaggcagt catggacgat ttcgccgctt ttgtggagaa atgctgtaag   2520

gcagacgata aggaaacctg cttcgccgag gaaggcaaga aactggtggc agcctctcag   2580

gctgcactgg ggctgtgagg atcc                                          2604
```

```
<210> SEQ ID NO 158
<211> LENGTH: 865
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Gln Val Gln
            20                  25                  30

Leu Gln Glu Ser Gly Gly Gly Leu Val Lys Pro Gly Gly Ser Leu Arg
        35                  40                  45

Leu Ser Cys Ala Ala Ser Gly Phe Thr Phe Ser Ser Tyr Trp Met Ser
    50                  55                  60

Trp Val Arg Gln Ala Pro Gly Lys Gly Leu Glu Trp Val Ala Asn Ile
65                  70                  75                  80

Asn Arg Asp Gly Ser Ala Ser Tyr Tyr Val Asp Ser Val Lys Gly Arg
                85                  90                  95

Phe Thr Ile Ser Arg Asp Asp Ala Lys Asn Ser Leu Tyr Leu Gln Met
            100                 105                 110
```

-continued

```
Asn Ser Leu Arg Ala Glu Asp Thr Ala Val Tyr Tyr Cys Ala Arg Asp
        115                 120                 125

Arg Gly Val Gly Tyr Phe Asp Leu Trp Gly Arg Gly Thr Leu Val Thr
    130                 135                 140

Val Ser Ser Ala Ser Thr Gly Gly Gly Gly Ser Gly Gly Gly Gly Ser
145                 150                 155                 160

Gly Gly Gly Gly Ser Gln Ser Ala Leu Thr Gln Pro Ala Ser Val Ser
                165                 170                 175

Gly Ser Pro Gly Gln Ser Ile Thr Ile Ser Cys Thr Gly Thr Ser Ser
            180                 185                 190

Asp Val Gly Gly Tyr Asn Phe Val Ser Trp Tyr Gln Gln His Pro Gly
        195                 200                 205

Lys Ala Pro Lys Leu Met Ile Tyr Asp Val Ser Asp Arg Pro Ser Gly
    210                 215                 220

Val Ser Asp Arg Phe Ser Gly Ser Lys Ser Gly Asn Thr Ala Ser Leu
225                 230                 235                 240

Ile Ile Ser Gly Leu Gln Ala Asp Asp Glu Ala Asp Tyr Tyr Cys Ser
                245                 250                 255

Ser Tyr Gly Ser Ser Ser Thr His Val Ile Phe Gly Gly Gly Thr Lys
            260                 265                 270

Val Thr Val Leu Gly Ala Ala Ser Asp Ala His Lys Ser Glu Val Ala
        275                 280                 285

His Arg Phe Lys Asp Leu Gly Glu Glu Asn Phe Lys Ala Leu Val Leu
    290                 295                 300

Ile Ala Phe Ala Gln Tyr Leu Gln Gln Ser Pro Phe Glu Asp His Val
305                 310                 315                 320

Lys Leu Val Asn Glu Val Thr Glu Phe Ala Lys Thr Cys Val Ala Asp
                325                 330                 335

Glu Ser Ala Glu Asn Cys Asp Lys Ser Leu His Thr Leu Phe Gly Asp
            340                 345                 350

Lys Leu Cys Thr Val Ala Thr Leu Arg Glu Thr Tyr Gly Glu Met Ala
        355                 360                 365

Asp Cys Cys Ala Lys Gln Glu Pro Glu Arg Asn Glu Cys Phe Leu Gln
    370                 375                 380

His Lys Asp Asp Asn Pro Asn Leu Pro Arg Leu Val Arg Pro Glu Val
385                 390                 395                 400

Asp Val Met Cys Thr Ala Phe His Asp Asn Glu Glu Thr Phe Leu Lys
                405                 410                 415

Lys Tyr Leu Tyr Glu Ile Ala Arg Arg His Pro Tyr Phe Tyr Ala Pro
            420                 425                 430

Glu Leu Leu Phe Phe Ala Lys Arg Tyr Lys Ala Ala Phe Thr Glu Cys
        435                 440                 445

Cys Gln Ala Ala Asp Lys Ala Ala Cys Leu Leu Pro Lys Leu Asp Glu
    450                 455                 460

Leu Arg Asp Glu Gly Lys Ala Ser Ser Ala Lys Gln Arg Leu Lys Cys
465                 470                 475                 480

Ala Ser Leu Gln Lys Phe Gly Glu Arg Ala Phe Lys Ala Trp Ala Val
                485                 490                 495

Ala Arg Leu Ser Gln Arg Phe Pro Lys Ala Glu Phe Ala Glu Val Ser
            500                 505                 510

Lys Leu Val Thr Asp Leu Thr Lys Val His Thr Glu Cys Cys His Gly
        515                 520                 525

Asp Leu Leu Glu Cys Ala Asp Asp Arg Ala Asp Leu Ala Lys Tyr Ile
```

```
    530                 535                 540

Cys Glu Asn Gln Asp Ser Ile Ser Ser Lys Leu Lys Glu Cys Cys Glu
545                 550                 555                 560

Lys Pro Leu Leu Glu Lys Ser His Cys Ile Ala Glu Val Glu Asn Asp
                565                 570                 575

Glu Met Pro Ala Asp Leu Pro Ser Leu Ala Ala Asp Phe Val Glu Ser
            580                 585                 590

Lys Asp Val Cys Lys Asn Tyr Ala Glu Ala Lys Asp Val Phe Leu Gly
        595                 600                 605

Met Phe Leu Tyr Glu Tyr Ala Arg Arg His Pro Asp Tyr Ser Val Val
    610                 615                 620

Leu Leu Leu Arg Leu Ala Lys Thr Tyr Glu Thr Thr Leu Glu Lys Cys
625                 630                 635                 640

Cys Ala Ala Ala Asp Pro His Glu Cys Tyr Ala Lys Val Phe Asp Glu
                645                 650                 655

Phe Lys Pro Leu Val Glu Glu Pro Gln Asn Leu Ile Lys Gln Asn Cys
            660                 665                 670

Glu Leu Phe Glu Gln Leu Gly Glu Tyr Lys Phe Gln Asn Ala Leu Leu
        675                 680                 685

Val Arg Tyr Thr Lys Lys Val Pro Gln Val Ser Thr Pro Thr Leu Val
    690                 695                 700

Glu Val Ser Arg Asn Leu Gly Lys Val Gly Ser Lys Cys Cys Lys His
705                 710                 715                 720

Pro Glu Ala Lys Arg Met Pro Cys Ala Glu Asp Tyr Leu Ser Val Val
                725                 730                 735

Leu Asn Gln Leu Cys Val Leu His Glu Lys Thr Pro Val Ser Asp Arg
            740                 745                 750

Val Thr Lys Cys Cys Thr Glu Ser Leu Val Asn Arg Arg Pro Cys Phe
        755                 760                 765

Ser Ala Leu Glu Val Asp Glu Thr Tyr Val Pro Lys Glu Phe Gln Ala
    770                 775                 780

Glu Thr Phe Thr Phe His Ala Asp Ile Cys Thr Leu Ser Glu Lys Glu
785                 790                 795                 800

Arg Gln Ile Lys Lys Gln Thr Ala Leu Val Glu Leu Val Lys His Lys
                805                 810                 815

Pro Lys Ala Thr Lys Glu Gln Leu Lys Ala Val Met Asp Asp Phe Ala
            820                 825                 830

Ala Phe Val Glu Lys Cys Cys Lys Ala Asp Asp Lys Glu Thr Cys Phe
        835                 840                 845

Ala Glu Glu Gly Lys Lys Leu Val Ala Ala Ser Gln Ala Ala Leu Gly
    850                 855                 860

Leu
865
```

<210> SEQ ID NO 159
<211> LENGTH: 2628
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 159

```
gaattcgcga ccatggctgt gatggctcca cgaaccctgg tcctgctgct gtccggcgca      60

ctggcactga ctcagacttg ggctggggat gctcataagt ctgaggtggc acacaggttc     120
```

```
aaagatctgg gcgaggaaaa ctttaaggcc ctggtcctga tcgctttcgc acagtacctg    180
cagcagagcc cttttgagga ccacgtgaaa ctggtcaacg aggtgaccga gttcgccaag    240
acatgcgtgg ctgacgagtc agcagaaaat tgtgataaaa gcctgcatac cctgtttggg    300
gataagctgt gcaccgtggc cacactgaga gagacatacg gagaaatggc cgactgctgt    360
gctaaacagg agcctgaaag gaacgagtgc ttcctgcagc ataaggacga taacccaaat    420
ctgcccagac tggtgaggcc agaagtggac gtcatgtgta ctgctttcca cgataatgag    480
gaaacctttc tgaagaaata cctgtatgag atcgcccgga gacatcctta cttttatgca    540
ccagaactgc tgttctttgc caaacgctac aaggccgctt tcaccgagtg ctgtcaggca    600
gccgataaag ctgcatgcct gctgcccaag ctggacgagc tgcgagatga agggaaggca    660
agctccgcca aacagcggct gaagtgtgct agcctgcaga aattcggaga gcgagccttc    720
aaggcatggg ctgtggcacg actgagtcag cgattcccta aggctgagtt tgcagaagtc    780
tcaaaactgg tgactgacct gaccaaggtg cacaccgagt gctgtcatgg cgacctgctg    840
gaatgcgccg acgatagagc cgatctggct aagtacatct gtgagaatca ggactctatt    900
tctagtaagc tgaaagagtg ctgtgaaaaa cccctgctgg agaagagcca ctgcatcgcc    960
gaggtggaaa acgacgaaat gcctgctgat ctgccatccc tggccgctga cttcgtggag   1020
tctaaagatg tctgtaagaa ttacgccgaa gctaaggatg tgttcctggg catgtttctg   1080
tacgagtatg ctaggcgcca cccagactac agcgtggtcc tgctgctgcg gctggccaaa   1140
acctatgaga ccacactgga aaagtgctgt gcagccgctg atccccatga gtgctatgcc   1200
aaagtgttcg acgagttcaa gcccctggtc gaggaacctc agaacctgat caagcagaat   1260
tgtgagctgt ttgaacagct gggcgagtac aagttccaga acgccctgct ggtgagatat   1320
accaagaaag tcccacaggt gagtactccc accctggtgg aggtctcacg caatctggga   1380
aaagtgggca gcaaatgctg taagcaccct gaggccaagc gaatgccatg cgctgaagat   1440
tacctgtctg tggtcctgaa ccagctgtgt gtgctgcatg agaaaactcc agtcagtgac   1500
agggtgacaa agtgctgtac tgaatccctg gtgaatcgac ggccatgctt ttctgccctg   1560
gaggtggatg aaacatatgt ccccaaagag ttccaggctg aaacattcac ttttcacgca   1620
gacatctgta ctctgtccga gaaggaacgc cagattaaga aacagaccgc cctggtcgag   1680
ctggtgaagc ataaacccaa ggccacaaaa gaacagctga aggctgtgat ggacgatttc   1740
gcagcctttg tcgagaaatg ctgtaaggca gacgataagg aaacttgctt tgccgaggaa   1800
ggcaagaaac tggtggctgc aagccaggca gctctgggac tggcagcagc tctgcaggtc   1860
cagctggtgc agtccggagc agaggtgaag aaacctggag aaagtctgaa aatctcctgt   1920
aagggaagcg gctactcctt cacctcttat tggattgcct gggtgcggca gatgccaggg   1980
aaaggactgg agtacatggg cctgatctat cccggggaca gcgatacaaa gtacagtcct   2040
tcatttcagg gccaggtcac aatttccgtg gataaaagcg tctccactgc ctatctgcag   2100
tggtcaagcc tgaagccctc tgacagtgca gtgtacttct gcgccaggca cgacgtcggc   2160
tattgcacag atcgcacttg tgccaagtgg cctgagtggc tgggagtgtg gggacaggga   2220
accctggtca cagtctcctc tggcggagga ggcagttcag gaggaggcag cggaggagga   2280
gggtcacaga gcgtgctgac acagccacct tccgtctctg cagcaccagg acagaaagtg   2340
actatcagtt gctcaggaag ctcctctaac attggcaaca attacgtgtc ctggtatcag   2400
cagctgcccg gaaccgctcc taagctgctg atctacgatc acacaaatcg accagcagga   2460
```

gtgccagacc ggttcagcgg gtccaagtct ggaactagtg catcactggc cattagcggg 2520
ttcaggtccg aggacgaagc tgattactat tgcgcatctt gggactatac cctgagtgga 2580
tgggtgttcg gaggcgggac taagctgacc gtcctgggct gaggatcc 2628

<210> SEQ ID NO 160
<211> LENGTH: 873
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Asp Ala His
20 25 30

Lys Ser Glu Val Ala His Arg Phe Lys Asp Leu Gly Glu Glu Asn Phe
35 40 45

Lys Ala Leu Val Leu Ile Ala Phe Ala Gln Tyr Leu Gln Gln Ser Pro
50 55 60

Phe Glu Asp His Val Lys Leu Val Asn Glu Val Thr Glu Phe Ala Lys
65 70 75 80

Thr Cys Val Ala Asp Glu Ser Ala Glu Asn Cys Asp Lys Ser Leu His
85 90 95

Thr Leu Phe Gly Asp Lys Leu Cys Thr Val Ala Thr Leu Arg Glu Thr
100 105 110

Tyr Gly Glu Met Ala Asp Cys Cys Ala Lys Gln Glu Pro Glu Arg Asn
115 120 125

Glu Cys Phe Leu Gln His Lys Asp Asp Asn Pro Asn Leu Pro Arg Leu
130 135 140

Val Arg Pro Glu Val Asp Val Met Cys Thr Ala Phe His Asp Asn Glu
145 150 155 160

Glu Thr Phe Leu Lys Lys Tyr Leu Tyr Glu Ile Ala Arg Arg His Pro
165 170 175

Tyr Phe Tyr Ala Pro Glu Leu Leu Phe Phe Ala Lys Arg Tyr Lys Ala
180 185 190

Ala Phe Thr Glu Cys Cys Gln Ala Ala Asp Lys Ala Ala Cys Leu Leu
195 200 205

Pro Lys Leu Asp Glu Leu Arg Asp Glu Gly Lys Ala Ser Ser Ala Lys
210 215 220

Gln Arg Leu Lys Cys Ala Ser Leu Gln Lys Phe Gly Glu Arg Ala Phe
225 230 235 240

Lys Ala Trp Ala Val Ala Arg Leu Ser Gln Arg Phe Pro Lys Ala Glu
245 250 255

Phe Ala Glu Val Ser Lys Leu Val Thr Asp Leu Thr Lys Val His Thr
260 265 270

Glu Cys Cys His Gly Asp Leu Leu Glu Cys Ala Asp Asp Arg Ala Asp
275 280 285

Leu Ala Lys Tyr Ile Cys Glu Asn Gln Asp Ser Ile Ser Ser Lys Leu
290 295 300

Lys Glu Cys Cys Glu Lys Pro Leu Leu Glu Lys Ser His Cys Ile Ala
305 310 315 320

Glu Val Glu Asn Asp Glu Met Pro Ala Asp Leu Pro Ser Leu Ala Ala
325 330 335

Asp Phe Val Glu Ser Lys Asp Val Cys Lys Asn Tyr Ala Glu Ala Lys
340 345 350

Asp Val Phe Leu Gly Met Phe Leu Tyr Glu Tyr Ala Arg Arg His Pro
355 360 365

Asp Tyr Ser Val Val Leu Leu Leu Arg Leu Ala Lys Thr Tyr Glu Thr
370 375 380

Thr Leu Glu Lys Cys Cys Ala Ala Ala Asp Pro His Glu Cys Tyr Ala
385 390 395 400

Lys Val Phe Asp Glu Phe Lys Pro Leu Val Glu Glu Pro Gln Asn Leu
405 410 415

Ile Lys Gln Asn Cys Glu Leu Phe Glu Gln Leu Gly Glu Tyr Lys Phe
420 425 430

Gln Asn Ala Leu Leu Val Arg Tyr Thr Lys Lys Val Pro Gln Val Ser
435 440 445

Thr Pro Thr Leu Val Glu Val Ser Arg Asn Leu Gly Lys Val Gly Ser
450 455 460

Lys Cys Cys Lys His Pro Glu Ala Lys Arg Met Pro Cys Ala Glu Asp
465 470 475 480

Tyr Leu Ser Val Val Leu Asn Gln Leu Cys Val Leu His Glu Lys Thr
485 490 495

Pro Val Ser Asp Arg Val Thr Lys Cys Cys Thr Glu Ser Leu Val Asn
500 505 510

Arg Arg Pro Cys Phe Ser Ala Leu Glu Val Asp Glu Thr Tyr Val Pro
515 520 525

Lys Glu Phe Gln Ala Glu Thr Phe Thr Phe His Ala Asp Ile Cys Thr
530 535 540

Leu Ser Glu Lys Glu Arg Gln Ile Lys Lys Gln Thr Ala Leu Val Glu
545 550 555 560

Leu Val Lys His Lys Pro Lys Ala Thr Lys Glu Gln Leu Lys Ala Val
565 570 575

Met Asp Asp Phe Ala Ala Phe Val Glu Lys Cys Cys Lys Ala Asp Asp
580 585 590

Lys Glu Thr Cys Phe Ala Glu Glu Gly Lys Lys Leu Val Ala Ala Ser
595 600 605

Gln Ala Ala Leu Gly Leu Ala Ala Ala Leu Gln Val Gln Leu Val Gln
610 615 620

Ser Gly Ala Glu Val Lys Lys Pro Gly Glu Ser Leu Lys Ile Ser Cys
625 630 635 640

Lys Gly Ser Gly Tyr Ser Phe Thr Ser Tyr Trp Ile Ala Trp Val Arg
645 650 655

Gln Met Pro Gly Lys Gly Leu Glu Tyr Met Gly Leu Ile Tyr Pro Gly
660 665 670

Asp Ser Asp Thr Lys Tyr Ser Pro Ser Phe Gln Gly Gln Val Thr Ile
675 680 685

Ser Val Asp Lys Ser Val Ser Thr Ala Tyr Leu Gln Trp Ser Ser Leu
690 695 700

Lys Pro Ser Asp Ser Ala Val Tyr Phe Cys Ala Arg His Asp Val Gly
705 710 715 720

Tyr Cys Thr Asp Arg Thr Cys Ala Lys Trp Pro Glu Trp Leu Gly Val
725 730 735

Trp Gly Gln Gly Thr Leu Val Thr Val Ser Ser Gly Gly Gly Gly Ser
740 745 750

-continued

Ser Gly Gly Gly Ser Gly Gly Gly Gly Ser Gln Ser Val Leu Thr Gln
755 760 765

Pro Pro Ser Val Ser Ala Ala Pro Gly Gln Lys Val Thr Ile Ser Cys
770 775 780

Ser Gly Ser Ser Ser Asn Ile Gly Asn Asn Tyr Val Ser Trp Tyr Gln
785 790 795 800

Gln Leu Pro Gly Thr Ala Pro Lys Leu Leu Ile Tyr Asp His Thr Asn
805 810 815

Arg Pro Ala Gly Val Pro Asp Arg Phe Ser Gly Ser Lys Ser Gly Thr
820 825 830

Ser Ala Ser Leu Ala Ile Ser Gly Phe Arg Ser Glu Asp Glu Ala Asp
835 840 845

Tyr Tyr Cys Ala Ser Trp Asp Tyr Thr Leu Ser Gly Trp Val Phe Gly
850 855 860

Gly Gly Thr Lys Leu Thr Val Leu Gly
865 870

<210> SEQ ID NO 161
<211> LENGTH: 1860
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 161
gaattcgcga ccatggccgt gatggctcct agaacactgg tgctgctgct gtccggggct 60
ctggctctga ctcagacttg ggctgggcag gtgcagctgc aggagagcgg aggaggactg 120
gtgaaaccag gagggtctct gcgactgagt tgcgcagctt caggcttcac ctttagctcc 180
tactggatgt cctgggtccg acaggcacct gggaagggac tggaatgggt ggccaacatc 240
aatcgggacg gaagcgcttc ctactatgtg gatagcgtca aaggccgctt taccattagt 300
cgagacgatg ctaagaactc actgtacctg cagatgaata gcctgcgcgc tgaggataca 360
gcagtctact attgcgcaag ggaccgagga gtgggatatt tcgatctgtg gggacgaggc 420
actctggtga ccgtctctag tgccagcaca ggcggaggag gatcaggagg aggaggcagc 480
ggaggaggcg ggtctcagag tgccctgact cagccagctt cagtgagcgg gtccccccgga 540 cagagcatca ccatttcctg taccggcaca tcaagcgacg tcggaggcta caactttgtg 600
tcctggtatc agcagcaccc aggaaaggcc cccaaactga tgatctacga cgtctctgat 660
cggcctagcg gcgtgtccga tagattctct ggcagtaagt cagggaatac tgcctctctg 720
atcattagtg gcctgcaggc cgacgatgag gctgactact attgctcctc ttatgggagt 780
tcaagcaccc atgtgatctt tgggggaggc acaaaagtga ctgtcctggg gggaggctcc 840
gatgcacaca agtctgaggt cgcccatagg ttcaaagacc tgggcgagga aaactttaag 900
gccctggtgc tgattgcttt cgcacagtac ctgcagcagt gcccatttga agatcacgtg 960
aaactggtca acgaggtgac agagttcgcc aagacttgcg tggcagacga gtccgccgaa 1020
aattgtgata aatctctgca tacactgttt ggggataagc tgtgtaccgt ggccacactg 1080
agagagactt atggagaaat ggctgactgc tgtgcaaaac aggagcctga aaggaacgag 1140
tgcttcctgc agcacaagga cgataacccc aatctgcctc gactggtgcg gccagaagtg 1200
gacgtcatgt gtaccgcttt ccacgataat gaggaaacat ttctgaagaa atacctgtat 1260
gagatcgccc ggagacatcc ctacttttat gctcctgaac tgctgttctt tgcaaagcgc 1320

-continued

```
tacaaagcag ccttcacaga gtgctgtcag gctgcagata aggccgcttg cctgctgcca   1380

aaactggacg agctgaggga tgaagggaaa gcttcctctg caaagcagcg cctgaaatgt   1440

gcatccctgc agaagttcgg cgagcgggcc tttaaagcct gggctgtggc aagactgtcc   1500

cagaggttcc ccaaggccga gtttgctgaa gtctctaagc tggtgactga cctgaccaaa   1560

gtgcacactg agtgctgtca tggcgacctg ctggaatgcg ccgacgatag agcagatctg   1620

gccaagtaca tctgtgagaa tcaggacagc attagttcaa agctgaaaga gtgctgtgaa   1680

aagcccctgc tggagaaaag ccactgcatt gctgaggtgg aaaacgacga aatgcctgca   1740

gatctgccaa gtctggcagc cgacttcgtc gagagcaagg atgtgtgtaa aaattatgcc   1800

gaagctaagg acgtgttcct gggcatgttt ctgtacgagt atgcaagagc ctgaggatcc   1860


<210> SEQ ID NO 162
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Gln Val Gln
            20                  25                  30

Leu Gln Glu Ser Gly Gly Gly Leu Val Lys Pro Gly Gly Ser Leu Arg
        35                  40                  45

Leu Ser Cys Ala Ala Ser Gly Phe Thr Phe Ser Ser Tyr Trp Met Ser
    50                  55                  60

Trp Val Arg Gln Ala Pro Gly Lys Gly Leu Glu Trp Val Ala Asn Ile
65                  70                  75                  80

Asn Arg Asp Gly Ser Ala Ser Tyr Tyr Val Asp Ser Val Lys Gly Arg
                85                  90                  95

Phe Thr Ile Ser Arg Asp Asp Ala Lys Asn Ser Leu Tyr Leu Gln Met
            100                 105                 110

Asn Ser Leu Arg Ala Glu Asp Thr Ala Val Tyr Tyr Cys Ala Arg Asp
        115                 120                 125

Arg Gly Val Gly Tyr Phe Asp Leu Trp Gly Arg Gly Thr Leu Val Thr
    130                 135                 140

Val Ser Ser Ala Ser Thr Gly Gly Gly Gly Ser Gly Gly Gly Gly Ser
145                 150                 155                 160

Gly Gly Gly Gly Ser Gln Ser Ala Leu Thr Gln Pro Ala Ser Val Ser
                165                 170                 175

Gly Ser Pro Gly Gln Ser Ile Thr Ile Ser Cys Thr Gly Thr Ser Ser
            180                 185                 190

Asp Val Gly Gly Tyr Asn Phe Val Ser Trp Tyr Gln Gln His Pro Gly
        195                 200                 205

Lys Ala Pro Lys Leu Met Ile Tyr Asp Val Ser Asp Arg Pro Ser Gly
    210                 215                 220

Val Ser Asp Arg Phe Ser Gly Ser Lys Ser Gly Asn Thr Ala Ser Leu
225                 230                 235                 240

Ile Ile Ser Gly Leu Gln Ala Asp Asp Glu Ala Asp Tyr Tyr Cys Ser
                245                 250                 255

Ser Tyr Gly Ser Ser Ser Thr His Val Ile Phe Gly Gly Gly Thr Lys
            260                 265                 270
```

```
Val Thr Val Leu Gly Gly Gly Ser Asp Ala His Lys Ser Glu Val Ala
        275                 280                 285

His Arg Phe Lys Asp Leu Gly Glu Glu Asn Phe Lys Ala Leu Val Leu
    290                 295                 300

Ile Ala Phe Ala Gln Tyr Leu Gln Gln Cys Pro Phe Glu Asp His Val
305                 310                 315                 320

Lys Leu Val Asn Glu Val Thr Glu Phe Ala Lys Thr Cys Val Ala Asp
                325                 330                 335

Glu Ser Ala Glu Asn Cys Asp Lys Ser Leu His Thr Leu Phe Gly Asp
            340                 345                 350

Lys Leu Cys Thr Val Ala Thr Leu Arg Glu Thr Tyr Gly Glu Met Ala
        355                 360                 365

Asp Cys Cys Ala Lys Gln Glu Pro Glu Arg Asn Glu Cys Phe Leu Gln
    370                 375                 380

His Lys Asp Asp Asn Pro Asn Leu Pro Arg Leu Val Arg Pro Glu Val
385                 390                 395                 400

Asp Val Met Cys Thr Ala Phe His Asp Asn Glu Glu Thr Phe Leu Lys
                405                 410                 415

Lys Tyr Leu Tyr Glu Ile Ala Arg Arg His Pro Tyr Phe Tyr Ala Pro
            420                 425                 430

Glu Leu Leu Phe Phe Ala Lys Arg Tyr Lys Ala Ala Phe Thr Glu Cys
        435                 440                 445

Cys Gln Ala Ala Asp Lys Ala Ala Cys Leu Leu Pro Lys Leu Asp Glu
    450                 455                 460

Leu Arg Asp Glu Gly Lys Ala Ser Ser Ala Lys Gln Arg Leu Lys Cys
465                 470                 475                 480

Ala Ser Leu Gln Lys Phe Gly Glu Arg Ala Phe Lys Ala Trp Ala Val
                485                 490                 495

Ala Arg Leu Ser Gln Arg Phe Pro Lys Ala Glu Phe Ala Glu Val Ser
            500                 505                 510

Lys Leu Val Thr Asp Leu Thr Lys Val His Thr Glu Cys Cys His Gly
        515                 520                 525

Asp Leu Leu Glu Cys Ala Asp Asp Arg Ala Asp Leu Ala Lys Tyr Ile
    530                 535                 540

Cys Glu Asn Gln Asp Ser Ile Ser Ser Lys Leu Lys Glu Cys Cys Glu
545                 550                 555                 560

Lys Pro Leu Leu Glu Lys Ser His Cys Ile Ala Glu Val Glu Asn Asp
                565                 570                 575

Glu Met Pro Ala Asp Leu Pro Ser Leu Ala Ala Asp Phe Val Glu Ser
            580                 585                 590

Lys Asp Val Cys Lys Asn Tyr Ala Glu Ala Lys Asp Val Phe Leu Gly
        595                 600                 605

Met Phe Leu Tyr Glu Tyr Ala Arg Ala
    610                 615
```

<210> SEQ ID NO 163
<211> LENGTH: 1611
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 163
gaattcgcca ctatggccgt catggcacct agaacactgg tcctgctgct gagcggggca     60
ctggcactga cacagacttg ggctgggtcc gtcgtcctgc tgctgagact ggctaagacc 120
tacgagacca cactggaaaa atgctgtgcc gctgcagacc cccacgagtg ctatgccaag 180
gtgttcgatg agttcaagcc tctggtcgag gaaccacaga acctgatcaa gcagaattgt 240
gagctgttcg aacagctggg cgagtacaaa tttcagaacg ccctgctggt gaggtataca 300
aagaaagtgc cccaggtctc tacacctact ctggtggagg tcagtaggaa tctgggcaag 360
gtcgggtcaa aatgctgtaa gcacccagag gccaaacgca tgccctgcgc tgaagactac 420
ctgtctgtgg tcctgaacca gctgtgtgtg ctgcatgaga agacccctgt gagcgatcga 480
gtcaccaaat gctgtacaga aagcctggtg aatcggagac cctgcttttc cgctctggag 540
gtggacgaaa catatgtccc taaggagttc aatgcagaaa ccttcacatt tcacgccgat 600
atctgtactc tgtccgagaa ggaacgccag attaagaaac agaccgccct ggtggagctg 660
gtcaagcata aaccaaaggc tactaaggaa cagctgaaag cagtgatgga cgatttcgcc 720
gcttttgtcg agaaatgctg taaggcagac gataaggaaa cctgctttgc cgaggaaggc 780
aagaaactgg tggcagccag ccaggctgca ctgggactgg gagggtccgg aggctctgga 840
ggaagtggag ggtcaggagg cgacatccag atgacacaga gcccaagctc cctgtcagca 900
agcgtgggcg accgagtcac tattacctgt cgggcctccc aggatgtgaa tactgcagtc 960
gcctggtacc agcagaaacc aggaaaggct cccaaactgc tgatctactc cgcatctttc 1020
ctgtatagcg gcgtgccatc caggtttagt ggatcacgca gcggcacaga cttcacactg 1080
actatttcta gtctgcagcc cgaggatttt gccacttact attgccagca gcactatact 1140
acccccccta ccttcggaca gggcacaaag gtggagatca agggaggatc tggaggagga 1200
agtggaggag gatcaggagg aggaagcgga ggaggcagcg gagaggtgca gctggtcgaa 1260
tctggaggag gactggtgca gcctggaggg tctctgcgac tgagttgtgc cgcttcaggc 1320
tttaacatca aggacaccta cattcattgg gtgcggcagg cacctgggaa gggactggag 1380
tgggtcgcta gaatctatcc aactaatggg tacaccagat atgccgacag cgtgaaggga 1440
aggttcacca ttagcgccga tacatccaaa aacactgctt acctgcagat gaacagcctg 1500
cgcgctgagg atacagcagt gtactattgc agtcgatggg gcggcgatgg gttctacgca 1560
atggactact ggggacaggg gactctggtc accgtcagca gctgaggatc c 1611

<210> SEQ ID NO 164
<211> LENGTH: 534
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Ser Val Val
            20                  25                  30

Leu Leu Leu Arg Leu Ala Lys Thr Tyr Glu Thr Thr Leu Glu Lys Cys
        35                  40                  45

Cys Ala Ala Ala Asp Pro His Glu Cys Tyr Ala Lys Val Phe Asp Glu
    50                  55                  60

Phe Lys Pro Leu Val Glu Glu Pro Gln Asn Leu Ile Lys Gln Asn Cys
65                  70                  75                  80

-continued

```
Glu Leu Phe Glu Gln Leu Gly Glu Tyr Lys Phe Gln Asn Ala Leu Leu
                85                  90                  95

Val Arg Tyr Thr Lys Lys Val Pro Gln Val Ser Thr Pro Thr Leu Val
            100                 105                 110

Glu Val Ser Arg Asn Leu Gly Lys Val Gly Ser Lys Cys Cys Lys His
        115                 120                 125

Pro Glu Ala Lys Arg Met Pro Cys Ala Glu Asp Tyr Leu Ser Val Val
    130                 135                 140

Leu Asn Gln Leu Cys Val Leu His Glu Lys Thr Pro Val Ser Asp Arg
145                 150                 155                 160

Val Thr Lys Cys Cys Thr Glu Ser Leu Val Asn Arg Arg Pro Cys Phe
                165                 170                 175

Ser Ala Leu Glu Val Asp Glu Thr Tyr Val Pro Lys Glu Phe Asn Ala
            180                 185                 190

Glu Thr Phe Thr Phe His Ala Asp Ile Cys Thr Leu Ser Glu Lys Glu
        195                 200                 205

Arg Gln Ile Lys Lys Gln Thr Ala Leu Val Glu Leu Val Lys His Lys
    210                 215                 220

Pro Lys Ala Thr Lys Glu Gln Leu Lys Ala Val Met Asp Asp Phe Ala
225                 230                 235                 240

Ala Phe Val Glu Lys Cys Cys Lys Ala Asp Asp Lys Glu Thr Cys Phe
                245                 250                 255

Ala Glu Glu Gly Lys Lys Leu Val Ala Ala Ser Gln Ala Ala Leu Gly
            260                 265                 270

Leu Gly Gly Ser Gly Gly Ser Gly Gly Ser Gly Gly Ser Gly Gly Asp
        275                 280                 285

Ile Gln Met Thr Gln Ser Pro Ser Ser Leu Ser Ala Ser Val Gly Asp
    290                 295                 300

Arg Val Thr Ile Thr Cys Arg Ala Ser Gln Asp Val Asn Thr Ala Val
305                 310                 315                 320

Ala Trp Tyr Gln Gln Lys Pro Gly Lys Ala Pro Lys Leu Leu Ile Tyr
                325                 330                 335

Ser Ala Ser Phe Leu Tyr Ser Gly Val Pro Ser Arg Phe Ser Gly Ser
            340                 345                 350

Arg Ser Gly Thr Asp Phe Thr Leu Thr Ile Ser Ser Leu Gln Pro Glu
        355                 360                 365

Asp Phe Ala Thr Tyr Tyr Cys Gln Gln His Tyr Thr Thr Pro Pro Thr
    370                 375                 380

Phe Gly Gln Gly Thr Lys Val Glu Ile Lys Gly Gly Ser Gly Gly Gly
385                 390                 395                 400

Ser Gly Gly Gly Ser Gly Gly Gly Ser Gly Gly Gly Ser Gly Glu Val
                405                 410                 415

Gln Leu Val Glu Ser Gly Gly Gly Leu Val Gln Pro Gly Gly Ser Leu
            420                 425                 430

Arg Leu Ser Cys Ala Ala Ser Gly Phe Asn Ile Lys Asp Thr Tyr Ile
        435                 440                 445

His Trp Val Arg Gln Ala Pro Gly Lys Gly Leu Glu Trp Val Ala Arg
    450                 455                 460

Ile Tyr Pro Thr Asn Gly Tyr Thr Arg Tyr Ala Asp Ser Val Lys Gly
465                 470                 475                 480

Arg Phe Thr Ile Ser Ala Asp Thr Ser Lys Asn Thr Ala Tyr Leu Gln
                485                 490                 495

Met Asn Ser Leu Arg Ala Glu Asp Thr Ala Val Tyr Tyr Cys Ser Arg
```

500 505 510

Trp Gly Gly Asp Gly Phe Tyr Ala Met Asp Tyr Trp Gly Gln Gly Thr
515 520 525

Leu Val Thr Val Ser Ser
530

<210> SEQ ID NO 165
<211> LENGTH: 1860
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165

```
gaattcgcga ccatggccgt gatggctcct agaacactgg tgctgctgct gtccggggct     60
ctggctctga ctcagacttg ggctgggcag gtgcagctgc aggagagcgg aggaggactg    120
gtgaaaccag gagggtctct gcgactgagt tgcgcagctt caggcttcac ctttagctcc    180
tactggatgt cctgggtccg acaggcacct gggaagggac tggaatgggt ggccaacatc    240
aatcgggacg gaagcgcttc ctactatgtg gatagcgtca aaggccgctt taccattagt    300
cgagacgatg ctaagaactc actgtacctg cagatgaata gcctgcgcgc tgaggataca    360
gcagtctact attgcgcaag ggaccgagga gtgggatatt tcgatctgtg gggacgaggc    420
actctggtga ccgtctctag tgccagcaca ggcggaggag gatcaggagg aggaggcagc    480
ggaggaggcg ggtctcagag tgccctgact cagccagctt cagtgagcgg gtcccccgga    540
cagagcatca ccatttcctg taccggcaca tcaagcgacg tcggaggcta caactttgtg    600
tcctggtatc agcagcaccc aggaaaggcc cccaaactga tgatctacga cgtctctgat    660
cggcctagcg gcgtgtccga tagattctct ggcagtaagt cagggaatac tgcctctctg    720
atcattagtg gcctgcaggc cgacgatgag gctgactact attgctcctc ttatgggagt    780
tcaagcaccc atgtgatctt tgggggaggc acaaaagtga ctgtcctggg gggaggctcc    840
gatgcacaca agtctgaggt cgcccatagg ttcaaagacc tgggcgagga aaactttaag    900
gccctggtgc tgattgcttt cgcacagtac ctgcagcagt gcccatttga agatcacgtg    960
aaactggtca acgaggtgac agagttcgcc aagacttgcg tggcagacga gtccgccgaa   1020
aattgtgata aatctctgca tacactgttt ggggataagc tgtgtaccgt ggccacactg   1080
agagagactt atggagaaat ggctgactgc tgtgcaaaac aggagcctga aaggaacgag   1140
tgcttcctgc agcacaagga cgataacccc aatctgcctc gactggtgcg gccagaagtg   1200
gacgtcatgt gtaccgcttt ccacgataat gaggaaacat ttctgaagaa atacctgtat   1260
gagatcgccc ggagacatcc ctacttttat gctcctgaac tgctgttctt tgcaaagcgc   1320
tacaaagcag ccttcacaga gtgctgtcag gctgcagata aggccgcttg cctgctgcca   1380
aaactggacg agctgaggga tgaagggaaa gcttcctctg caaagcagcg cctgaaatgt   1440
gcatccctgc agaagttcgg cgagcgggcc tttaaagcct gggctgtggc aagactgtcc   1500
cagaggttcc ccaaggccga gtttgctgaa gtctctaagc tggtgactga cctgaccaaa   1560
gtgcacactg agtgctgtca tggcgacctg ctggaatgcg ccgacgatag agcagatctg   1620
gccaagtaca tctgtgagaa tcaggacagc attagttcaa agctgaaaga gtgctgtgaa   1680
aagcccctgc tggagaaaag ccactgcatt gctgaggtgg aaaacgacga aatgcctgca   1740
gatctgccaa gtctggcagc cgacttcgtc gagagcaagg atgtgtgtaa aaattatgcc   1800
```

gaagctaagg acgtgttcct gggcatgttt ctgtacgagt atgcaagagc ctgaggatcc 1860

<210> SEQ ID NO 166
<211> LENGTH: 617
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 166

Glu Phe Ala Thr Met Ala Val Met Ala Pro Arg Thr Leu Val Leu Leu
1 5 10 15

Leu Ser Gly Ala Leu Ala Leu Thr Gln Thr Trp Ala Gly Gln Val Gln
20 25 30

Leu Gln Glu Ser Gly Gly Gly Leu Val Lys Pro Gly Gly Ser Leu Arg
35 40 45

Leu Ser Cys Ala Ala Ser Gly Phe Thr Phe Ser Ser Tyr Trp Met Ser
50 55 60

Trp Val Arg Gln Ala Pro Gly Lys Gly Leu Glu Trp Val Ala Asn Ile
65 70 75 80

Asn Arg Asp Gly Ser Ala Ser Tyr Tyr Val Asp Ser Val Lys Gly Arg
85 90 95

Phe Thr Ile Ser Arg Asp Asp Ala Lys Asn Ser Leu Tyr Leu Gln Met
100 105 110

Asn Ser Leu Arg Ala Glu Asp Thr Ala Val Tyr Tyr Cys Ala Arg Asp
115 120 125

Arg Gly Val Gly Tyr Phe Asp Leu Trp Gly Arg Gly Thr Leu Val Thr
130 135 140

Val Ser Ser Ala Ser Thr Gly Gly Gly Gly Ser Gly Gly Gly Gly Ser
145 150 155 160

Gly Gly Gly Gly Ser Gln Ser Ala Leu Thr Gln Pro Ala Ser Val Ser
165 170 175

Gly Ser Pro Gly Gln Ser Ile Thr Ile Ser Cys Thr Gly Thr Ser Ser
180 185 190

Asp Val Gly Gly Tyr Asn Phe Val Ser Trp Tyr Gln Gln His Pro Gly
195 200 205

Lys Ala Pro Lys Leu Met Ile Tyr Asp Val Ser Asp Arg Pro Ser Gly
210 215 220

Val Ser Asp Arg Phe Ser Gly Ser Lys Ser Gly Asn Thr Ala Ser Leu
225 230 235 240

Ile Ile Ser Gly Leu Gln Ala Asp Asp Glu Ala Asp Tyr Tyr Cys Ser
245 250 255

Ser Tyr Gly Ser Ser Ser Thr His Val Ile Phe Gly Gly Gly Thr Lys
260 265 270

Val Thr Val Leu Gly Gly Gly Ser Asp Ala His Lys Ser Glu Val Ala
275 280 285

His Arg Phe Lys Asp Leu Gly Glu Glu Asn Phe Lys Ala Leu Val Leu
290 295 300

Ile Ala Phe Ala Gln Tyr Leu Gln Gln Cys Pro Phe Glu Asp His Val
305 310 315 320

Lys Leu Val Asn Glu Val Thr Glu Phe Ala Lys Thr Cys Val Ala Asp
325 330 335

Glu Ser Ala Glu Asn Cys Asp Lys Ser Leu His Thr Leu Phe Gly Asp
340 345 350

```
Lys Leu Cys Thr Val Ala Thr Leu Arg Glu Thr Tyr Gly Glu Met Ala
        355                 360                 365

Asp Cys Cys Ala Lys Gln Glu Pro Glu Arg Asn Glu Cys Phe Leu Gln
    370                 375                 380

His Lys Asp Asp Asn Pro Asn Leu Pro Arg Leu Val Arg Pro Glu Val
385                 390                 395                 400

Asp Val Met Cys Thr Ala Phe His Asp Asn Glu Glu Thr Phe Leu Lys
                405                 410                 415

Lys Tyr Leu Tyr Glu Ile Ala Arg Arg His Pro Tyr Phe Tyr Ala Pro
            420                 425                 430

Glu Leu Leu Phe Phe Ala Lys Arg Tyr Lys Ala Ala Phe Thr Glu Cys
        435                 440                 445

Cys Gln Ala Ala Asp Lys Ala Ala Cys Leu Leu Pro Lys Leu Asp Glu
    450                 455                 460

Leu Arg Asp Glu Gly Lys Ala Ser Ser Ala Lys Gln Arg Leu Lys Cys
465                 470                 475                 480

Ala Ser Leu Gln Lys Phe Gly Glu Arg Ala Phe Lys Ala Trp Ala Val
                485                 490                 495

Ala Arg Leu Ser Gln Arg Phe Pro Lys Ala Glu Phe Ala Glu Val Ser
            500                 505                 510

Lys Leu Val Thr Asp Leu Thr Lys Val His Thr Glu Cys Cys His Gly
        515                 520                 525

Asp Leu Leu Glu Cys Ala Asp Asp Arg Ala Asp Leu Ala Lys Tyr Ile
    530                 535                 540

Cys Glu Asn Gln Asp Ser Ile Ser Ser Lys Leu Lys Glu Cys Cys Glu
545                 550                 555                 560

Lys Pro Leu Leu Glu Lys Ser His Cys Ile Ala Glu Val Glu Asn Asp
                565                 570                 575

Glu Met Pro Ala Asp Leu Pro Ser Leu Ala Ala Asp Phe Val Glu Ser
            580                 585                 590

Lys Asp Val Cys Lys Asn Tyr Ala Glu Ala Lys Asp Val Phe Leu Gly
        595                 600                 605

Met Phe Leu Tyr Glu Tyr Ala Arg Ala
    610                 615
```

<210> SEQ ID NO 167
<211> LENGTH: 1611
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 167

```
gaattcgcca ctatggccgt gatggcacct agaacactgg tcctgctgct gagcggggca     60

ctggcactga cacagacttg ggctggagac attcagatga cacagagccc aagctccctg    120

tccgcatctg tgggcgaccg agtcacaatc acttgccggg cctcccagga tgtgaacact    180

gctgtcgcat ggtaccagca gaaaccaggg aaggctccca aactgctgat ctacagtgca    240

tcattcctgt atagtggcgt gccatcaagg tttagcggct cccgatctgg aaccgacttc    300

accctgacaa tctctagtct gcagcccgag gattttgcca catactattg ccagcagcac    360

tataccacac cccctacttt cgggcaggga accaaggtgg agatcaaggg agggagcgga    420

ggagggtccg gaggagggtc tggaggcggg agtggaggag ggtcaggaga ggtgcagctg    480

gtcgaaagcg gaggaggact ggtgcagcct ggaggcagcc tgcgactgtc ctgtgccgct    540
```

```
tctggcttta acatcaagga cacctacatt cattgggtgc ggcaggcacc tggcaaagga    600

ctggagtggg tggctagaat ctatccaact aatggataca ccagatatgc tgacagcgtg    660

aagggcaggt ttactatcag tgctgataca tcaaagaaca ctgcatacct gcagatgaat    720

agcctgcgcg ccgaggatac cgctgtgtac tattgtagcc gatggggggg agacggcttc    780

tacgccatgg attattgggg acagggcacc ctggtgacag tctcaagcgg agggagtgga    840

ggctcaggag gaagcggagg gtccggaggc tctgtggtcc tgctgctgag actggctaag    900

acctacgaga ctaccctgga aaaatgctgt gcagccgctg acccccacga gtgctatgca    960

aaggtgttcg atgagttcaa gcctctggtc gaggaaccac agaacctgat caagcagaat   1020

tgtgagctgt tcgaacagct gggcgagtac aagtttcaga acgccctgct ggtgaggtat   1080

acaaagaaag tgccccaggt cagcactcct accctggtgg aggtctccag gaatctgggg   1140

aaggtcggat ctaagtgctg taaacaccca gaggcaaaac gcatgccctg cgccgaagac   1200

tacctgtccg tggtcctgaa tcagctgtgt gtgctgcatg agaagacccc tgtgtctgat   1260

cgagtcacca aatgctgtac agaaagtctg gtgaaccgga gaccctgctt ttctgccctg   1320

gaggtggacg aaacatatgt ccctaaggag ttcaatgccg aaacattcac ttttcacgct   1380

gatatctgta cactgtccga gaaggaacgc cagattaaga aacagactgc tctggtggag   1440

ctggtcaagc ataaaccaaa ggcaaccaag gaacagctga aagccgtgat ggacgatttc   1500

gcagcctttg tcgagaagtg ctgtaaagcc gacgataagg aaacttgttt cgccgaggaa   1560

ggcaaaaaac tggtcgcagc atcacaggca gcactgggac tgtgaggatc c             1611
```

```
<210> SEQ ID NO 168
<211> LENGTH: 534
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Asp Ile Gln
            20                  25                  30

Met Thr Gln Ser Pro Ser Ser Leu Ser Ala Ser Val Gly Asp Arg Val
        35                  40                  45

Thr Ile Thr Cys Arg Ala Ser Gln Asp Val Asn Thr Ala Val Ala Trp
    50                  55                  60

Tyr Gln Gln Lys Pro Gly Lys Ala Pro Lys Leu Leu Ile Tyr Ser Ala
65                  70                  75                  80

Ser Phe Leu Tyr Ser Gly Val Pro Ser Arg Phe Ser Gly Ser Arg Ser
                85                  90                  95

Gly Thr Asp Phe Thr Leu Thr Ile Ser Ser Leu Gln Pro Glu Asp Phe
            100                 105                 110

Ala Thr Tyr Tyr Cys Gln Gln His Tyr Thr Thr Pro Pro Thr Phe Gly
        115                 120                 125

Gln Gly Thr Lys Val Glu Ile Lys Gly Gly Ser Gly Gly Gly Ser Gly
    130                 135                 140

Gly Gly Ser Gly Gly Gly Ser Gly Gly Gly Ser Gly Glu Val Gln Leu
145                 150                 155                 160

Val Glu Ser Gly Gly Gly Leu Val Gln Pro Gly Gly Ser Leu Arg Leu
```

```
                165                 170                 175

Ser Cys Ala Ala Ser Gly Phe Asn Ile Lys Asp Thr Tyr Ile His Trp
            180                 185                 190

Val Arg Gln Ala Pro Gly Lys Gly Leu Glu Trp Val Ala Arg Ile Tyr
        195                 200                 205

Pro Thr Asn Gly Tyr Thr Arg Tyr Ala Asp Ser Val Lys Gly Arg Phe
    210                 215                 220

Thr Ile Ser Ala Asp Thr Ser Lys Asn Thr Ala Tyr Leu Gln Met Asn
225                 230                 235                 240

Ser Leu Arg Ala Glu Asp Thr Ala Val Tyr Tyr Cys Ser Arg Trp Gly
                245                 250                 255

Gly Asp Gly Phe Tyr Ala Met Asp Tyr Trp Gly Gln Gly Thr Leu Val
            260                 265                 270

Thr Val Ser Ser Gly Gly Ser Gly Gly Ser Gly Gly Ser Gly Gly Ser
        275                 280                 285

Gly Gly Ser Val Val Leu Leu Leu Arg Leu Ala Lys Thr Tyr Glu Thr
    290                 295                 300

Thr Leu Glu Lys Cys Cys Ala Ala Ala Asp Pro His Glu Cys Tyr Ala
305                 310                 315                 320

Lys Val Phe Asp Glu Phe Lys Pro Leu Val Glu Glu Pro Gln Asn Leu
                325                 330                 335

Ile Lys Gln Asn Cys Glu Leu Phe Glu Gln Leu Gly Glu Tyr Lys Phe
            340                 345                 350

Gln Asn Ala Leu Leu Val Arg Tyr Thr Lys Lys Val Pro Gln Val Ser
        355                 360                 365

Thr Pro Thr Leu Val Glu Val Ser Arg Asn Leu Gly Lys Val Gly Ser
    370                 375                 380

Lys Cys Cys Lys His Pro Glu Ala Lys Arg Met Pro Cys Ala Glu Asp
385                 390                 395                 400

Tyr Leu Ser Val Val Leu Asn Gln Leu Cys Val Leu His Glu Lys Thr
                405                 410                 415

Pro Val Ser Asp Arg Val Thr Lys Cys Cys Thr Glu Ser Leu Val Asn
            420                 425                 430

Arg Arg Pro Cys Phe Ser Ala Leu Glu Val Asp Glu Thr Tyr Val Pro
        435                 440                 445

Lys Glu Phe Asn Ala Glu Thr Phe Thr Phe His Ala Asp Ile Cys Thr
    450                 455                 460

Leu Ser Glu Lys Glu Arg Gln Ile Lys Lys Gln Thr Ala Leu Val Glu
465                 470                 475                 480

Leu Val Lys His Lys Pro Lys Ala Thr Lys Glu Gln Leu Lys Ala Val
                485                 490                 495

Met Asp Asp Phe Ala Ala Phe Val Glu Lys Cys Cys Lys Ala Asp Asp
            500                 505                 510

Lys Glu Thr Cys Phe Ala Glu Glu Gly Lys Lys Leu Val Ala Ala Ser
        515                 520                 525

Gln Ala Ala Leu Gly Leu
    530
```

<210> SEQ ID NO 169
<211> LENGTH: 1860
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 169
gaattcgcga ccatggccgt gatggctcct agaacactgg tgctgctgct gtccggggct 60
ctggctctga ctcagacttg ggctgggcag gtgcagctgc aggagagcgg aggaggactg 120
gtgaaaccag gagggtctct gcgactgagt tgcgcagctt caggcttcac ctttagctcc 180
tactggatgt cctgggtccg acaggcacct gggaagggac tggaatgggt ggccaacatc 240
aatcgggacg gaagcgcttc ctactatgtg gatagcgtca aaggccgctt taccattagt 300
cgagacgatg ctaagaactc actgtacctg cagatgaata gcctgcgcgc tgaggataca 360
gcagtctact attgcgcaag ggaccgagga gtgggatatt tcgatctgtg ggacgaggc 420 actctggtga ccgtctctag tgccagcaca ggcggaggag gatcaggagg aggaggcagc 480
ggaggaggcg ggtctcagag tgccctgact cagccagctt cagtgagcgg gtcccccgga 540
cagagcatca ccatttcctg taccggcaca tcaagcgacg tcggaggcta caactttgtg 600
tcctggtatc agcagcaccc aggaaaggcc cccaaactga tgatctacga cgtctctgat 660
cggcctagcg gcgtgtccga tagattctct ggcagtaagt cagggaatac tgcctctctg 720
atcattagtg gcctgcaggc cgacgatgag gctgactact attgctcctc ttatgggagt 780
tcaagcaccc atgtgatctt tgggggaggc acaaaagtga ctgtcctggg gggaggctcc 840
gatgcacaca agtctgaggt cgcccatagg ttcaaagacc tgggcgagga aaactttaag 900
gccctggtgc tgattgcttt cgcacagtac ctgcagcagt gcccatttga agatcacgtg 960
aaactggtca acgaggtgac agagttcgcc aagacttgcg tggcagacga gtccgccgaa 1020
aattgtgata aatctctgca tacactgttt ggggataagc tgtgtaccgt ggccacactg 1080
agagagactt atggagaaat ggctgactgc tgtgcaaaac aggagcctga aaggaacgag 1140
tgcttcctgc agcacaagga cgataacccc aatctgcctc gactggtgcg gccagaagtg 1200
gacgtcatgt gtaccgcttt ccacgataat gaggaaacat ttctgaagaa atacctgtat 1260
gagatcgccc ggagacatcc ctacttttat gctcctgaac tgctgttctt tgcaaagcgc 1320
tacaaagcag ccttcacaga gtgctgtcag gctgcagata aggccgcttg cctgctgcca 1380
aaactggacg agctgaggga tgaagggaaa gcttcctctg caaagcagcg cctgaaatgt 1440
gcatccctgc agaagttcgg cgagcgggcc tttaaagcct gggctgtggc aagactgtcc 1500
cagaggttcc ccaaggccga gtttgctgaa gtctctaagc tggtgactga cctgaccaaa 1560
gtgcacactg agtgctgtca tggcgacctg ctggaatgcg ccgacgatag agcagatctg 1620
gccaagtaca tctgtgagaa tcaggacagc attagttcaa agctgaaaga gtgctgtgaa 1680
aagcccctgc tggagaaaag ccactgcatt gctgaggtgg aaaacgacga aatgcctgca 1740
gatctgccaa gtctggcagc cgacttcgtc gagagcaagg atgtgtgtaa aaattatgcc 1800
gaagctaagg acgtgttcct gggcatgttt ctgtacgagt atgcaagagc ctgaggatcc 1860

<210> SEQ ID NO 170
<211> LENGTH: 617
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

Glu Phe Ala Thr Met Ala Val Met Ala Pro Arg Thr Leu Val Leu Leu
1 5 10 15

-continued

```
Leu Ser Gly Ala Leu Ala Leu Thr Gln Thr Trp Ala Gly Gln Val Gln
            20                  25                  30

Leu Gln Glu Ser Gly Gly Gly Leu Val Lys Pro Gly Gly Ser Leu Arg
        35                  40                  45

Leu Ser Cys Ala Ala Ser Gly Phe Thr Phe Ser Ser Tyr Trp Met Ser
    50                  55                  60

Trp Val Arg Gln Ala Pro Gly Lys Gly Leu Glu Trp Val Ala Asn Ile
65                  70                  75                  80

Asn Arg Asp Gly Ser Ala Ser Tyr Tyr Val Asp Ser Val Lys Gly Arg
                85                  90                  95

Phe Thr Ile Ser Arg Asp Asp Ala Lys Asn Ser Leu Tyr Leu Gln Met
            100                 105                 110

Asn Ser Leu Arg Ala Glu Asp Thr Ala Val Tyr Tyr Cys Ala Arg Asp
        115                 120                 125

Arg Gly Val Gly Tyr Phe Asp Leu Trp Gly Arg Gly Thr Leu Val Thr
    130                 135                 140

Val Ser Ser Ala Ser Thr Gly Gly Gly Gly Ser Gly Gly Gly Gly Ser
145                 150                 155                 160

Gly Gly Gly Gly Ser Gln Ser Ala Leu Thr Gln Pro Ala Ser Val Ser
                165                 170                 175

Gly Ser Pro Gly Gln Ser Ile Thr Ile Ser Cys Thr Gly Thr Ser Ser
            180                 185                 190

Asp Val Gly Gly Tyr Asn Phe Val Ser Trp Tyr Gln Gln His Pro Gly
        195                 200                 205

Lys Ala Pro Lys Leu Met Ile Tyr Asp Val Ser Asp Arg Pro Ser Gly
    210                 215                 220

Val Ser Asp Arg Phe Ser Gly Ser Lys Ser Gly Asn Thr Ala Ser Leu
225                 230                 235                 240

Ile Ile Ser Gly Leu Gln Ala Asp Asp Glu Ala Asp Tyr Tyr Cys Ser
                245                 250                 255

Ser Tyr Gly Ser Ser Ser Thr His Val Ile Phe Gly Gly Gly Thr Lys
            260                 265                 270

Val Thr Val Leu Gly Gly Gly Ser Asp Ala His Lys Ser Glu Val Ala
        275                 280                 285

His Arg Phe Lys Asp Leu Gly Glu Glu Asn Phe Lys Ala Leu Val Leu
    290                 295                 300

Ile Ala Phe Ala Gln Tyr Leu Gln Gln Cys Pro Phe Glu Asp His Val
305                 310                 315                 320

Lys Leu Val Asn Glu Val Thr Glu Phe Ala Lys Thr Cys Val Ala Asp
                325                 330                 335

Glu Ser Ala Glu Asn Cys Asp Lys Ser Leu His Thr Leu Phe Gly Asp
            340                 345                 350

Lys Leu Cys Thr Val Ala Thr Leu Arg Glu Thr Tyr Gly Glu Met Ala
        355                 360                 365

Asp Cys Cys Ala Lys Gln Glu Pro Glu Arg Asn Glu Cys Phe Leu Gln
    370                 375                 380

His Lys Asp Asp Asn Pro Asn Leu Pro Arg Leu Val Arg Pro Glu Val
385                 390                 395                 400

Asp Val Met Cys Thr Ala Phe His Asp Asn Glu Glu Thr Phe Leu Lys
                405                 410                 415

Lys Tyr Leu Tyr Glu Ile Ala Arg Arg His Pro Tyr Phe Tyr Ala Pro
            420                 425                 430

Glu Leu Leu Phe Phe Ala Lys Arg Tyr Lys Ala Ala Phe Thr Glu Cys
```

-continued

```
        435                 440                 445

Cys Gln Ala Ala Asp Lys Ala Ala Cys Leu Leu Pro Lys Leu Asp Glu
    450                 455                 460

Leu Arg Asp Glu Gly Lys Ala Ser Ser Ala Lys Gln Arg Leu Lys Cys
465                 470                 475                 480

Ala Ser Leu Gln Lys Phe Gly Glu Arg Ala Phe Lys Ala Trp Ala Val
                485                 490                 495

Ala Arg Leu Ser Gln Arg Phe Pro Lys Ala Glu Phe Ala Glu Val Ser
            500                 505                 510

Lys Leu Val Thr Asp Leu Thr Lys Val His Thr Glu Cys Cys His Gly
        515                 520                 525

Asp Leu Leu Glu Cys Ala Asp Asp Arg Ala Asp Leu Ala Lys Tyr Ile
    530                 535                 540

Cys Glu Asn Gln Asp Ser Ile Ser Ser Lys Leu Lys Glu Cys Cys Glu
545                 550                 555                 560

Lys Pro Leu Leu Glu Lys Ser His Cys Ile Ala Glu Val Glu Asn Asp
                565                 570                 575

Glu Met Pro Ala Asp Leu Pro Ser Leu Ala Ala Asp Phe Val Glu Ser
            580                 585                 590

Lys Asp Val Cys Lys Asn Tyr Ala Glu Ala Lys Asp Val Phe Leu Gly
        595                 600                 605

Met Phe Leu Tyr Glu Tyr Ala Arg Ala
    610                 615


<210> SEQ ID NO 171
<211> LENGTH: 1605
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171

gaattcgcga ccatggctgt gatggctcct cgaaccctgg tgctgctgct gtccggcgct     60

ctggctctga ctcagacttg ggctggctcc gtggtgctgc tgctgaggct ggccaaaacc    120

tacgagacca cactggaaaa gtgctgtgcc gctgcagacc ctcacgagtg ctatgctaaa    180

gtcttcgatg agttcaagcc cctggtggag gaacctcaga acctgatcaa acagaattgt    240

gagctgttcg aacagctggg cgagtacaag tttcagaacg ccctgctggt gcgctatacc    300

aagaaagtgc cacaggtcag cactcccacc ctggtggagg tctccagaaa tctggggaaa    360

gtgggatcta aatgctgtaa gcaccctgag gcaaagagga tgccatgcgc cgaagactac    420

ctgagcgtgg tcctgaacca gctgtgtgtg ctgcatgaga aaaccccagt gtccgatcgc    480

gtcaccaagt gctgtacaga aagcctggtg aaccggagac catgcttctc cgccctggag    540

gtcgacgaaa catacgtgcc caaggagttt aatgctgaaa cattcacttt ccacgcagat    600

atctgtaccc tgagcgagaa ggaacgacag attaagaaac agacagccct ggtggagctg    660

gtcaagcata aacccaaggc caccaaagaa cagctgaagg ctgtcatgga cgatttcgcc    720

gcttttgtgg agaaatgctg taaggcagac gataaggaaa catgcttcgc cgaggaaggc    780

aagaaactgg tggcagcatc ccaggctgca ctgggactgg gagggagtgg acaggtgcag    840

ctggtccaga gcggagcaga ggtgaagaaa cccggcgaat cactgaaaat cagctgtaag    900

gggtccggat actcttttac tagttattgg attgcctggg tgcggcagat gcctggcaaa    960

gggctggagt acatggggct gatctatccc ggagactctg atacaaagta ctcacctagc   1020
```

```
ttccagggcc aagtgactat tagcgtcgac aaatccgtgt ctaccgctta tctgcagtgg   1080

agctccctga agcctagtga ttcagctgtc tacttttgcg cacgacacga cgtgggctat   1140

tgcaccgatc ggacatgtgc caagtggcca gagtggctgg gagtgtgggg acagggaact   1200

ctggtgaccg tctctagtgg aggcggggga tcaagcggag gaggatctgg aggaggaggc   1260

agccagtccg tcctgactca gccaccttct gtgagtgcag ctccaggaca gaaggtgacc   1320

atctcatgca gcggctcctc tagtaacatt gggaacaatt acgtgagctg gtatcagcag   1380

ctgccaggaa cagctcccaa actgctgatc tacgaccata ctaataggcc tgcaggcgtg   1440

ccagatcgct tctccggctc taagagtggg acatcagcaa gcctggccat ttccggcttt   1500

agatctgagg acgaagccga ttactattgt gctagttggg actatactct gtcagggtgg   1560

gtcttcgggg gaggcacaaa gctgactgtg ctgggatgag gatcc                   1605
```

<210> SEQ ID NO 172
<211> LENGTH: 532
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

```
Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Ser Val Val
            20                  25                  30

Leu Leu Leu Arg Leu Ala Lys Thr Tyr Glu Thr Thr Leu Glu Lys Cys
        35                  40                  45

Cys Ala Ala Ala Asp Pro His Glu Cys Tyr Ala Lys Val Phe Asp Glu
    50                  55                  60

Phe Lys Pro Leu Val Glu Glu Pro Gln Asn Leu Ile Lys Gln Asn Cys
65                  70                  75                  80

Glu Leu Phe Glu Gln Leu Gly Glu Tyr Lys Phe Gln Asn Ala Leu Leu
                85                  90                  95

Val Arg Tyr Thr Lys Lys Val Pro Gln Val Ser Thr Pro Thr Leu Val
            100                 105                 110

Glu Val Ser Arg Asn Leu Gly Lys Val Gly Ser Lys Cys Cys Lys His
        115                 120                 125

Pro Glu Ala Lys Arg Met Pro Cys Ala Glu Asp Tyr Leu Ser Val Val
    130                 135                 140

Leu Asn Gln Leu Cys Val Leu His Glu Lys Thr Pro Val Ser Asp Arg
145                 150                 155                 160

Val Thr Lys Cys Cys Thr Glu Ser Leu Val Asn Arg Arg Pro Cys Phe
                165                 170                 175

Ser Ala Leu Glu Val Asp Glu Thr Tyr Val Pro Lys Glu Phe Asn Ala
            180                 185                 190

Glu Thr Phe Thr Phe His Ala Asp Ile Cys Thr Leu Ser Glu Lys Glu
        195                 200                 205

Arg Gln Ile Lys Lys Gln Thr Ala Leu Val Glu Leu Val Lys His Lys
    210                 215                 220

Pro Lys Ala Thr Lys Glu Gln Leu Lys Ala Val Met Asp Asp Phe Ala
225                 230                 235                 240

Ala Phe Val Glu Lys Cys Cys Lys Ala Asp Asp Lys Glu Thr Cys Phe
                245                 250                 255
```

```
Ala Glu Glu Gly Lys Lys Leu Val Ala Ala Ser Gln Ala Ala Leu Gly
            260                 265                 270

Leu Gly Gly Ser Gly Gln Val Gln Leu Val Gln Ser Gly Ala Glu Val
        275                 280                 285

Lys Lys Pro Gly Glu Ser Leu Lys Ile Ser Cys Lys Gly Ser Gly Tyr
    290                 295                 300

Ser Phe Thr Ser Tyr Trp Ile Ala Trp Val Arg Gln Met Pro Gly Lys
305                 310                 315                 320

Gly Leu Glu Tyr Met Gly Leu Ile Tyr Pro Gly Asp Ser Asp Thr Lys
                325                 330                 335

Tyr Ser Pro Ser Phe Gln Gly Gln Val Thr Ile Ser Val Asp Lys Ser
            340                 345                 350

Val Ser Thr Ala Tyr Leu Gln Trp Ser Ser Leu Lys Pro Ser Asp Ser
        355                 360                 365

Ala Val Tyr Phe Cys Ala Arg His Asp Val Gly Tyr Cys Thr Asp Arg
    370                 375                 380

Thr Cys Ala Lys Trp Pro Glu Trp Leu Gly Val Trp Gly Gln Gly Thr
385                 390                 395                 400

Leu Val Thr Val Ser Ser Gly Gly Gly Gly Ser Ser Gly Gly Gly Ser
                405                 410                 415

Gly Gly Gly Gly Ser Gln Ser Val Leu Thr Gln Pro Pro Ser Val Ser
            420                 425                 430

Ala Ala Pro Gly Gln Lys Val Thr Ile Ser Cys Ser Gly Ser Ser Ser
        435                 440                 445

Asn Ile Gly Asn Asn Tyr Val Ser Trp Tyr Gln Gln Leu Pro Gly Thr
    450                 455                 460

Ala Pro Lys Leu Leu Ile Tyr Asp His Thr Asn Arg Pro Ala Gly Val
465                 470                 475                 480

Pro Asp Arg Phe Ser Gly Ser Lys Ser Gly Thr Ser Ala Ser Leu Ala
                485                 490                 495

Ile Ser Gly Phe Arg Ser Glu Asp Glu Ala Asp Tyr Tyr Cys Ala Ser
            500                 505                 510

Trp Asp Tyr Thr Leu Ser Gly Trp Val Phe Gly Gly Gly Thr Lys Leu
        515                 520                 525

Thr Val Leu Gly
    530
```

<210> SEQ ID NO 173
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

```
Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Ala Trp Val Arg Gln Met Pro Gly Lys Gly Leu Glu Tyr Met
        35                  40                  45

Gly Leu Ile Tyr Pro Gly Asp Ser Asp Thr Lys Tyr Ser Pro Ser Phe
    50                  55                  60

Gln Gly Gln Val Thr Ile Ser Val Asp Lys Ser Val Ser Thr Ala Tyr
```

65 70 75 80

Leu Gln Trp Ser Ser Leu Lys Pro Ser Asp Ser Ala Val Tyr Phe Cys
85 90 95

Ala Arg His Asp Val Gly Tyr Cys Thr Asp Arg Thr Cys Ala Lys Trp
100 105 110

Pro Glu Trp Leu Gly Val Trp Gly Gln Gly Thr Leu Val Thr Val Ser
115 120 125

Ser Gly Gly Gly Gly Ser Ser Gly Gly Gly Ser Gly Gly Gly Gly Ser
130 135 140

Gln Ser Val Leu Thr Gln Pro Pro Ser Val Ser Ala Ala Pro Gly Gln
145 150 155 160

Lys Val Thr Ile Ser Cys Ser Gly Ser Ser Ser Asn Ile Gly Asn Asn
165 170 175

Tyr Val Ser Trp Tyr Gln Gln Leu Pro Gly Thr Ala Pro Lys Leu Leu
180 185 190

Ile Tyr Asp His Thr Asn Arg Pro Ala Gly Val Pro Asp Arg Phe Ser
195 200 205

Gly Ser Lys Ser Gly Thr Ser Ala Ser Leu Ala Ile Ser Gly Phe Arg
210 215 220

Ser Glu Asp Glu Ala Asp Tyr Tyr Cys Ala Ser Trp Asp Tyr Thr Leu
225 230 235 240

Ser Gly Trp Val Phe Gly Gly Gly Thr Lys Leu Thr Val Leu Gly
245 250 255

<210> SEQ ID NO 174
<211> LENGTH: 248
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

Gln Val Gln Leu Gln Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Asn Arg Asp Gly Ser Ala Ser Tyr Tyr Val Asp Ser Val
50 55 60

Lys Gly Arg Phe Thr Ile Ser Arg Asp Asp Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Arg Gly Val Gly Tyr Phe Asp Leu Trp Gly Arg Gly Thr
100 105 110

Leu Val Thr Val Ser Ser Ala Ser Thr Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Thr Ile Ser Cys Thr Gly
145 150 155 160

Thr Ser Ser Asp Val Gly Gly Tyr Asn Phe Val Ser Trp Tyr Gln Gln
165 170 175

```
His Pro Gly Lys Ala Pro Lys Leu Met Ile Tyr Asp Val Ser Asp Arg
            180                 185                 190

Pro Ser Gly Val Ser Asp Arg Phe Ser Gly Ser Lys Ser Gly Asn Thr
        195                 200                 205

Ala Ser Leu Ile Ile Ser Gly Leu Gln Ala Asp Asp Glu Ala Asp Tyr
    210                 215                 220

Tyr Cys Ser Ser Tyr Gly Ser Ser Ser Thr His Val Ile Phe Gly Gly
225                 230                 235                 240

Gly Thr Lys Val Thr Val Leu Gly
                245


<210> SEQ ID NO 175
<211> LENGTH: 24
<212> TYPE: PRT
<213> ORGANISM: Homo sapiens

<400> SEQUENCE: 175

Met Lys Trp Val Thr Phe Ile Ser Leu Leu Phe Leu Phe Ser Ser Ala
1               5                   10                  15

Tyr Ser Arg Gly Val Phe Arg Arg
            20


<210> SEQ ID NO 176
<211> LENGTH: 29
<212> TYPE: PRT
<213> ORGANISM: Homo sapiens

<400> SEQUENCE: 176

Thr Cys Cys Cys Lys Ser Ser Cys Leu Arg Leu Ile Thr Ser His Leu
1               5                   10                  15

Lys Ala Ser Gln Pro Thr Met Arg Ile Arg Glu Arg Lys
            20                  25


<210> SEQ ID NO 177
<211> LENGTH: 17
<212> TYPE: PRT
<213> ORGANISM: Unknown
<220> FEATURE:
<223> OTHER INFORMATION: Description of Unknown: Stanniocalcin signal
      sequence

<400> SEQUENCE: 177

Met Leu Gln Asn Ser Ala Val Leu Leu Leu Leu Val Ile Ser Ala Ser
1               5                   10                  15

Ala


<210> SEQ ID NO 178
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus signal sequence

<400> SEQUENCE: 178

Met Pro Thr Trp Ala Trp Trp Leu Phe Leu Val Leu Leu Leu Ala Leu
1               5                   10                  15

Trp Ala Pro Ala Arg Gly
            20


<210> SEQ ID NO 179
<211> LENGTH: 5
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Gly Gly Gly Gly Ser
1 5

<210> SEQ ID NO 180
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Gly Gly Ser Gly
1

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Gly Gly Ser Gly Gly Ser Gly Gly Ser Gly Gly Ser Gly Gly
1 5 10

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Asp Arg Ser Glu Asp Phe
1 5

<210> SEQ ID NO 183
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Gly Gly Gly Ser
1

<210> SEQ ID NO 184
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Gly Gly Ser Gly Gly Gly Ser Gly Gly Gly Ser Gly Gly Gly Ser Gly 1 5 10 15

Gly Gly

<210> SEQ ID NO 185
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 185

Ala Ala Ala Leu
1

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Gly Gly Ser Gly Gly Ser Gly
1 5

<210> SEQ ID NO 187
<211> LENGTH: 609
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Met Lys Trp Val Thr Phe Ile Ser Leu Leu Phe Leu Phe Ser Ser Ala
1 5 10 15

Tyr Ser Arg Gly Val Phe Arg Arg Asp Ala His Lys Ser Glu Val Ala
20 25 30

His Arg Phe Lys Asp Leu Gly Glu Glu Asn Phe Lys Ala Leu Val Leu
35 40 45

Ile Ala Phe Ala Gln Tyr Leu Gln Gln Cys Pro Phe Glu Asp His Val
50 55 60

Lys Leu Val Asn Glu Val Thr Glu Phe Ala Lys Thr Cys Val Ala Asp
65 70 75 80

Glu Ser Ala Glu Asn Cys Asp Lys Ser Leu His Thr Leu Phe Gly Asp
85 90 95

Lys Leu Cys Thr Val Ala Thr Leu Arg Glu Thr Tyr Gly Glu Met Ala
100 105 110

Asp Cys Cys Ala Lys Gln Glu Pro Glu Arg Asn Glu Cys Phe Leu Gln
115 120 125

His Lys Asp Asp Asn Pro Asn Leu Pro Arg Leu Val Arg Pro Glu Val
130 135 140

Asp Val Met Cys Thr Ala Phe His Asp Asn Glu Glu Thr Phe Leu Lys
145 150 155 160

Lys Tyr Leu Tyr Glu Ile Ala Arg Arg His Pro Tyr Phe Tyr Ala Pro
165 170 175

Glu Leu Leu Phe Phe Ala Lys Arg Tyr Lys Ala Ala Phe Thr Glu Cys
180 185 190

```
Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```

<210> SEQ ID NO 188
<211> LENGTH: 698
<212> TYPE: PRT
<213> ORGANISM: Homo sapiens

<400> SEQUENCE: 188

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365

His Glu Arg Leu Lys Cys Asp Glu Trp Ser Val Asn Ser Val Gly Lys
```

-continued 370 375 380

Ile Glu Cys Val Ser Ala Glu Thr Thr Glu Asp Cys Ile Ala Lys Ile
385 390 395 400

Met Asn Gly Glu Ala Asp Ala Met Ser Leu Asp Gly Gly Phe Val Tyr
405 410 415

Ile Ala Gly Lys Cys Gly Leu Val Pro Val Leu Ala Glu Asn Tyr Asn
420 425 430

Lys Ser Asp Asn Cys Glu Asp Thr Pro Glu Ala Gly Tyr Phe Ala Val
435 440 445

Ala Val Val Lys Lys Ser Ala Ser Asp Leu Thr Trp Asp Asn Leu Lys
450 455 460

Gly Lys Lys Ser Cys His Thr Ala Val Gly Arg Thr Ala Gly Trp Asn
465 470 475 480

Ile Pro Met Gly Leu Leu Tyr Asn Lys Ile Asn His Cys Arg Phe Asp
485 490 495

Glu Phe Phe Ser Glu Gly Cys Ala Pro Gly Ser Lys Lys Asp Ser Ser
500 505 510

Leu Cys Lys Leu Cys Met Gly Ser Gly Leu Asn Leu Cys Glu Pro Asn
515 520 525

Asn Lys Glu Gly Tyr Tyr Gly Tyr Thr Gly Ala Phe Arg Cys Leu Val
530 535 540

Glu Lys Gly Asp Val Ala Phe Val Lys His Gln Thr Val Pro Gln Asn
545 550 555 560

Thr Gly Gly Lys Asn Pro Asp Pro Trp Ala Lys Asn Leu Asn Glu Lys
565 570 575

Asp Tyr Glu Leu Leu Cys Leu Asp Gly Thr Arg Lys Pro Val Glu Glu
580 585 590

Tyr Ala Asn Cys His Leu Ala Arg Ala Pro Asn His Ala Val Val Thr
595 600 605

Arg Lys Asp Lys Glu Ala Cys Val His Lys Ile Leu Arg Gln Gln Gln
610 615 620

His Leu Phe Gly Ser Asn Val Thr Asp Cys Ser Gly Asn Phe Cys Leu
625 630 635 640

Phe Arg Ser Glu Thr Lys Asp Leu Leu Phe Arg Asp Asp Thr Val Cys
645 650 655

Leu Ala Lys Leu His Asp Arg Asn Thr Tyr Glu Lys Tyr Leu Gly Glu
660 665 670

Glu Tyr Val Lys Ala Val Gly Asn Leu Arg Lys Cys Ser Thr Ser Ser
675 680 685

Leu Leu Glu Ala Cys Thr Phe Arg Arg Pro
690 695

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 189

His His His His His His
1 5

MULTIVALENT HETEROMULTIMER SCAFFOLD DESIGN AND CONSTRUCTS

CROSS-REFERENCE TO RELATED APPLICATIONS

This application is a continuation of U.S. application Ser. No. 15/001,078, filed Jan. 19, 2016, which claims the benefit of U.S. application Ser. No. 13/941,450, filed Jul. 13, 2013, which claims the benefit of U.S. Application Ser. No. 61/671,640, filed Jul. 13, 2012; U.S. Application Ser. No. 61/697,245, filed Sep. 5, 2012; U.S. Application Ser. No. 61/758,701, filed Jan. 30, 2013; and U.S. Application Ser. No. 61/845,945, filed Jul. 12, 2013; which are hereby incorporated by reference in their entirety.

SEQUENCE LISTING

The instant application contains a Sequence Listing which has been submitted electronically in ASCII format and is hereby incorporated by reference in its entirety. Said ASCII copy, created Jan. 12, 2016, is named 0969895_SL.txt and is 558,695 bytes in size.

FIELD OF INVENTION

The field of the invention is the rational design of a scaffold for custom development of biotherapeutics.

DESCRIPTION OF RELATED ART

In the realm of therapeutic proteins, antibodies with their multivalent target binding features are excellent scaffolds for the design of drug candidates. Advancing these features further, designed bispecific antibodies and other fused multispecific therapeutics exhibit dual or multiple target specificities and an opportunity to create drugs with novel modes of action. The development of such multivalent and multispecific therapeutic proteins with favorable pharmacokinetics and functional activity has been a challenge.

Human serum albumin (HSA, or HA), a protein of 585 amino acids in its mature form is responsible for a significant proportion of the osmotic pressure of serum and also functions as a carrier of endogenous and exogenous ligands. The role of albumin as a carrier molecule and its stable nature are desirable properties for use as a carrier and transporter of polypeptides in vivo.

Human serum albumin possesses many desirable characteristics. HSA is found throughout the body, but more specifically in the interstitial space and in blood at serum concentrations of 40 g/L which is equivalent to 0.7 mM (Yeh et al., Proc. Natl. Acad. Sci. USA, 89:1904-1908 (1992)). HSA is considered to be the most abundant protein of the serum and is responsible for maintaining osmolarity. HSA has favorable pharmacokinetic properties and is cleared very slowly by the liver and kidney displaying in vivo half-lives up to several weeks (Yeh et al., Proc. Natl. Acad. Sci. USA, 89:1904-1908 (1992); Waldmann, T. A., Albumin Structure, Function and Uses, pp. 255-273 (1977); Sarav et al., J Am Soc Nephrol 20:1941-1952(2009)). HSA lacks enzymatic activity and antigenicity thereby eliminating potentially undesirable side effects. HSA acts as a carrier for endogenous as well as exogenous ligands. HSA is also known to penetrate and be retained in the interstitium of tumors (see Elsadek and Kratz, J. Control. Release (2012) 157:4-28). Combined, these features can be extended, at least partially, onto albumin based fusion protein. The poor pharmacokinetic properties displayed by therapeutic proteins can then be circumvented.

SUMMARY OF THE INVENTION

An object of the present invention is to provide multivalent heteromultimer scaffolds and methods of designing same. In one aspect of the invention there is provided a heteromultimer comprising: a first polypeptide construct that comprises (i) a first transporter polypeptide; and a second polypeptide construct that comprises (ii) a second transporter polypeptide; wherein each of said first and second transporter polypeptide comprises an amino acid sequence with at least 90% identity to a segment of an albumin polypeptide; and wherein said first and second transporter polypeptides are obtained by segmentation of said albumin polypeptide at a segmentation site, such that the segmentation results in a deletion of zero to 3 amino acid residues at the segmentation site, wherein said transporter polypeptides self-assemble to form a quasi-native structure of the monomeric form of said albumin polypeptide.

In another aspect of the invention there is provided a heteromultimer comprising: a first polypeptide construct that comprises (i) a first transporter polypeptide; and a second polypeptide construct that comprises (ii) a second transporter polypeptide; wherein each of said first and second transporter polypeptide comprises an amino acid sequence with at least 90% identity to a segment of an albumin polypeptide; and wherein said first and second transporter polypeptides are obtained by segmentation of said albumin polypeptide at a segmentation site, and wherein at least one of said first and second transporter polypeptides comprises at least one mutation of an amino acid residue to cysteine or an analog thereof such that said cysteine forms a disulfide bond with the other transporter polypeptide, such that said transporter polypeptides self-assemble to form a quasi-native structure of the monomeric form of said albumin polypeptide.

In another aspect of the invention there is provided a heteromultimer comprising: a first polypeptide construct that comprises (i) a first transporter polypeptide; and (ii) at least one first cargo polypeptide that is an antigen-binding polypeptide construct that binds to CD3, CD19, CD20, HER2 or HER3, and a second polypeptide construct that comprises (iii) a second transporter polypeptide; and (iv) at least one second cargo polypeptide wherein each of said first and second transporter polypeptide comprises an amino acid sequence with at least 90% identity to a segment of an albumin polypeptide; and wherein said first and second transporter polypeptides are obtained by segmentation of said albumin polypeptide at a segmentation site, wherein said transporter polypeptides self-assemble to form a quasi-native structure of the monomeric form of said albumin polypeptide.

In another aspect of the invention there is provided a host cell comprising nucleic acid encoding a heteromultimer of the invention.

In another aspect of the invention there is provided a pharmaceutical composition comprising a heteromultimer of the invention and an adjuvant.

In another aspect of the invention there is provided a method of treating cancer comprising providing to a patient in need thereof an effective amount of the pharmaceutical composition of the invention.

In another aspect of the invention there is provided a method of inhibiting growth of a tumor, comprising contacting the tumor with an effective amount of a heteromultimer the invention.

In another aspect of the invention there is provided a method of shrinking a tumor, comprising contacting the tumor with an effective amount of a heteromultimer of the invention.

In another aspect of the invention there is provided a method of designing self-associating polypeptides from a protein of interest comprising: segmenting said protein at at-least one segmentation site to obtain at least two polypeptide segments such that said polypeptide segments self-assemble to form a heteromultimer, wherein said heteromultimer forms a quasi-native monomeric structure of said protein, the method comprising the steps of selecting at least one loop of the protein of interest that has a high solvent accessible surface area and limited contact with the rest of the structure of said protein, and introducing one segmentation site per selected loop, resulting in a complementary interface between the at least two polypeptide segments, wherein the interface is apolar, extensive and interdigitate.

In another aspect of the invention there is provided a heteromultimer designed by a method of the invention.

In another aspect of the invention there is provided a therapeutic scaffold comprising a heteromultimer designed by a method of the invention.

Provided herein are multifunctional heteromultimers and methods to design them. In certain embodiments are heteromultimers, each heteromultimer comprising: at least a first polypeptide construct that comprises at least one cargo molecule, and a first transporter polypeptide; and at least a second polypeptide construct that comprises at least one cargo molecule and a second transporter polypeptide; wherein the transporter polypeptides are derived by segmentation of a protein such that said transporter polypeptides self-assemble to form a quasi-native structure of said protein or analog thereof. In certain embodiments, at least one cargo molecule is a drug, or a therapeutic agent. In certain embodiment more the one cargo molecule of the same nature is present on the transporter polypeptide. In certain embodiments, at least one cargo molecule is a biomolecule. In an embodiment, the at least one biomolecule is a DNA, RNA, PNA or polypeptide. In an embodiment, at least one cargo molecule is a polypeptide. In certain embodiments, each transporter polypeptide is unstable and preferentially forms a heteromultimer with at least one other transporter polypeptide. In certain embodiments, each transporter polypeptide is stable and preferentially forms a heteromultimer with at least one other transporter polypeptide. In certain embodiments, the heteromultimerization interface comprises at least one disulfide bond. In certain embodiments, the heteromultimerization interface does not comprise a disulfide bond.

In certain embodiments is a heteromultimer that comprises: at least two polypeptide constructs, each polypeptide construct comprising at least one cargo polypeptide attached to a transporter polypeptide, wherein said transporter polypeptides are derived from a protein by segmentation of said protein, each transporter polypeptide comprising an amino acid sequence with at least 90% identity to a segment of said protein, and wherein said transporter polypeptides self-assemble to form a quasi-native monomeric structure of said protein or analog thereof. In certain embodiments, the heteromultimer is a heterodimer. In an embodiment, the heteromultimer is bispecific. In an embodiment, the heteromultimer is multispecific. In certain embodiments, the heteromultimer is bivalent. In an embodiment the heteromultimer is multivalent. In an embodiment, the heteromultimer is multifunctional. In certain embodiments, at least one transporter polypeptide is not derived from an antibody. In certain embodiments, the transporter polypeptides are not derived from an antibody. In certain embodiments, the transporter polypeptides are derivatives of albumin. In certain embodiments of the hetermultimer described herein, the transporter polypeptides are derived from human serum albumin (HSA or HA) of SEQ ID No. 1. In certain embodiments of the hetermultimer described herein, the transporter polypeptides are derived from alloalbumins (HAA). In certain embodiments of the hetermultimer described herein, the transporter polypeptides are derived from sequence homologous to the human serum albumin (HSA or HA) of SEQ ID No. 1. In certain embodiments, the transporter polypeptides are derived from a fragment of human serum albumin (HSA or HA), wherein said HSA comprises a sequence as shown in SEQ ID No. 1.

In some embodiments of the heteromultimer described herein, the transporter polypeptides are derivatives of an annexin protein. In an embodiment, the transporter polypeptides are derived from different annexin proteins. In certain embodiments, the transporter polypeptides are derived from the same annexin protein. In an embodiment, at least one transporter polypeptide is derived from Annexin A1 or lipocortin I. In certain embodiments of the heteromultimer, all transporter polypeptides are derived from Annexin A1 of SEQ ID NO: 14. In certain embodiments of the heteromultimer, at least one transporter polypeptides is derived from a sequence homologous to SEQ ID NO: 14. In an embodiment, at least one transporter polypeptide is derived from Annexin A2 or annexin II. In certain embodiments of the heteromultimer, all transporter polypeptides are derived from Annexin A2 or lipocortin II. In an embodiment, at least one transporter polypeptide is derived from Annexin like protein. In certain embodiments of the heteromultimer, all transporter polypeptides are derived from Annexin like protein. In an embodiment, at least one transporter polypeptide is derived from the group comprising Annexin A1-Annexin A7. In an embodiment of the heteromultimer described herein, all transporter polypeptides are derived from the group comprising Annexin A1-Annexin A7. SEQ ID No.-14. In certain embodiments, the first annexin based transporter polypeptide has a sequence comprising SEQ ID NO:15, and the second annexin based transporter polypeptide has a sequence comprising SEQ ID NO: 16.

In some embodiments of the heteromultimer described herein, the transporter polypeptides are derivatives of transferrin. In an embodiment, at least one transporter polypeptide is derived from transferrin. In certain embodiments of the heteromultimer, at least one transporter polypeptides are derived from transferrin of SEQ ID NO: 19 or analog thereof. In certain embodiments of the heteromultimer, at least one transporter polypeptide is derived from a polypeptide sequence homologous to the transferrin. In certain embodiments of the heteromultimer described herein, at least one transporter polypeptide is derived from apo-transferrin. In certain embodiments, the first transferrin based transporter polypeptide has a sequence comprising SEQ ID NO:15 and the second transferrin based transporter polypeptide has a sequence comprising SEQ ID NO: 16.

In certain embodiments of the heteromultimer, at least one cargo molecule is a cargo polypeptide. In an embodiment of the heteromultimer described herein, all cargo molecules are cargo polypeptides. In certain embodiments, the cargo polypeptides are therapeutic proteins or fragments or variants thereof. In certain embodiments, the cargo polypeptides are antigens or fragments or variants thereof. In certain embodiments, the cargo polypeptides are antigen receptors or fragments or variants thereof. In some embodiments, the cargo polypeptide is an antibody, an antibody domain, a ligand or a receptor that binds a target polypeptide. In some embodiments, at least one cargo polypeptide is fused to the transporter polypeptide. In certain embodiments, at least one cargo polypeptide is attached to the N-terminus of the transporter polypeptide. In some embodiments, at least one cargo polypeptide is attached to the C-terminus of the transporter polypeptide. In some embodiments, at least one cargo polypeptide is chemically linked to the transporter polypeptide. In some embodiments of the heteromultimers described herein, at least one cargo polypeptide comprises GLP-1 or fragment or variant thereof. In some embodiments, at least one cargo polypeptide comprises glucagon or fragment or variant thereof. In an embodiment, at least one cargo polypeptide comprises an EGF-A like domain.

Provided herein are heteromultimers, each heteromultimer comprising: at least a first polypeptide construct that comprises at least one cargo polypeptide and a first transporter polypeptide; and at least a second polypeptide construct that comprises at least one cargo polypeptide and a second transporter polypeptide. In certain embodiments, the heteromultimer is a heterodimer. In an embodiment, the heteromultimer is multispecific. In an embodiment, the heteromultimer is bispecific. In certain embodiments of the heteromultimer, the transporter polypeptides are derivatives of the same protein. In certain embodiments, the transporter polypeptides are derivatives of albumin. In certain embodiments of the hetermultimer described herein, the transporter polypeptides are derived from human serum albumin of SEQ ID No. 1. In certain embodiments, the transporter polypeptides are derivatives of an annexin. In an embodiment, the transporter polypeptides are derivatives of Annexin A2. In some embodiments, the transporter polypeptides are derivatives of transferrin.

In certain embodiments, are heteromultimers, each heteromultimer comprising: at least a first polypeptide construct that comprises at least one cargo polypeptide and a first transporter polypeptide comprising a first segment of human serum albumin; and at least a second polypeptide construct that comprises at least one cargo polypeptide and a second transporter polypeptide comprising a second segment of human serum albumin; wherein said transporter polypeptides self-assemble to form a quasi-native structure of albumin or analog thereof. In certain embodiments, the first and second segments of human serum albumin are from non-overlapping regions of the protein. In certain embodiments, there is an overlap between the sequences of the first and second segments of human serum albumin. In some embodiments, the overlap is a 5% overlap. In an embodiment, the overlap is a 10% overlap. In certain embodiments, the first segment of human serum albumin comprises a sequence of SEQ ID NO:2, and the second segment of human serum albumin comprises a sequence of SEQ ID NO: 3. In certain embodiments, the first segment of human serum albumin comprises a sequence of SEQ ID NO:8, and the second segment of human serum albumin comprises a sequence of SEQ ID NO: 10.

In certain embodiments, are heteromultimers, each heteromultimer comprising: at least a first polypeptide construct that comprises at least one cargo polypeptide and a first transporter polypeptide comprising a sequence of SEQ ID NO:2; and at least a second polypeptide construct that comprises at least one cargo polypeptide, and a second transporter polypeptide comprising a sequence of SEQ ID NO: 3. In certain embodiments, are heteromultimers, each heteromultimer comprising: at least a first polypeptide construct that comprises at least one cargo polypeptide and a first transporter polypeptide comprising a sequence of SEQ ID NO:8; and at least a second polypeptide construct that comprises at least one cargo polypeptide and a second transporter polypeptide comprising a sequence of SEQ ID NO: 10. In certain embodiments of the hetermultimer described herein, at least one transporter polypeptide is derived from alloalbumins. In certain embodiments, both transporter polypeptides are derived from alloalbumins. In certain embodiments, all transporter polypeptides are derivatives of the same alloalbumin. In some other embodiments, the transporter polypeptides are derivatives of different alloalbumins. In some embodiments, each transporter polypeptide is an alloalbumin derivative based on an alloalbumin selected from Table 1. In certain embodiments, the first polypeptide construct comprises two cargo polypeptides. In some embodiments, the second polypeptide construct comprises two cargo polypeptides. In some embodiment, at least one of the polypeptide constructs is engineered by introducing mutations. In certain embodiments, the introduced mutations improve the functionality of the polypeptide construct as compared to the non-mutated form of the construct. In certain embodiments the introduced mutations improve one or more of the stability, half-life and heteromultimer formation of the transporter polypeptide.

Provided herein is a heteromultimer comprising: at least a first polypeptide construct that comprises (i) a first transporter polypeptide; and (ii) at least one cargo polypeptide and at least a second polypeptide construct that comprises (iii) a second transporter polypeptide and (iv) at least one cargo polypeptide; wherein said transporter polypeptides are derived from a protein by segmentation of said protein, each transporter polypeptide comprising an amino acid sequence with at least 90% identity to a segment of said protein, and wherein said transporter polypeptides self-assemble to form a quasi-native structure of said protein.

In certain embodiments is a heteromultimer described herein, wherein the transporter polypeptides are derived from a protein by segmentation of said protein, each transporter polypeptide comprising an amino acid sequence with at least 95% identity to a segment of said protein.

In certain embodiments is a heteromultimer described herein, wherein the transporter polypeptides are derived from a protein by segmentation of said protein, each transporter polypeptide comprising an amino acid sequence with at least 99% identity to a segment of said protein.

In certain embodiments, the heteromultimer is a heterodimer. In some embodiments, at least one transporter polypeptide is not derived from an antibody. In exemplary embodiments, each transporter polypeptide is an albumin derivative. In some embodiments, at least one of said first and second transporter polypeptides comprise at least one mutation of an amino acid residue to cystine such that said cysteine forms a disulfide bond with a cysteine residue on another transporter polypeptide. In certain embodiments, said first and second transporter polypeptide comprise at least one mutation of an amino acid residue to cystine such that said cysteine forms a disulfide bond with a cysteine residue on another transporter polypeptide. In some embodiments are provided heteromutlimers wherein each transporter polypeptide is an albumin derivative, the first transporter polypeptide comprising at least one mutation selected from A194C, L198C, W214C, A217C, L331C and A335C. In some embodiments, the second transporter polypeptide is an elbumin derivative comprising at least one mutation selected from L331C, A335C, V343C, L346C, A350C, V455C, and N458C.

In some embodiments provided are heteromultimers described herein, wherein said first transporter polypeptide has a sequence comprising SEQ ID NO:35 or analog or variant thereof, and wherein said second transporter polypeptide has a sequence comprising SEQ ID NO:36 or analog or variant thereof. In some embodiments, said first transporter polypeptide has a sequence comprising SEQ ID NO:37 or analog or variant thereof, and wherein said second transporter polypeptide has a sequence comprising SEQ ID NO:38 or analog or variant thereof. In certain embodiments, said first transporter polypeptide has a sequence comprising SEQ ID NO:39 or analog or variant thereof, and wherein said second transporter polypeptide has a sequence comprising SEQ ID NO:40 or analog or variant thereof. In exemplary embodiments, said first transporter polypeptide has a sequence comprising SEQ ID NO:41 or analog or variant thereof, and wherein said second transporter polypeptide has a sequence comprising SEQ ID NO:42 or analog or variant thereof. In certain embodiments, said first transporter polypeptide has a sequence comprising SEQ ID NO:43 or analog or variant thereof, and wherein said second transporter polypeptide has a sequence comprising SEQ ID NO:44 or analog or variant thereof. In an embodiment, said first transporter polypeptide has a sequence comprising SEQ ID NO:45 or analog or variant thereof, and wherein said second transporter polypeptide has a sequence comprising SEQ ID NO:46 or analog or variant thereof. In one embodiment, said first transporter polypeptide has a sequence comprising SEQ ID NO:47 or analog or variant thereof, and wherein said second transporter polypeptide has a sequence comprising SEQ ID NO:48 or analog or variant thereof. In certain embodiments, said first transporter polypeptide has a sequence comprising SEQ ID NO:49 or analog or variant thereof, and wherein said second transporter polypeptide has a sequence comprising SEQ ID NO:50 or analog or variant thereof.

In certain embodiments of the heteromultimer described herein, at least one cargo polypeptide binds a target antigen, and wherein said target antigen is at least one of a-chain (CD25) of IL-2R, Amyloid beta, anti-EpCAM, anti-CD3, CD16, CD20, CD22, CD23, CD3, CD4, CD52, CD80, CTLA-4, EGFR, EpCAM, F protein of RSV, G250, glycoprotein IIB/IIIa R, HER2, HER2/neu R, HSP90, IgE antibody, IL-12, IL-23, IL-1b, IL-5, IL-6, RANKL, TNF alpha, TNFR, VEGF-A, glucagon receptor, GLP receptor, and LDL receptor.

Provided herein are heteromultimers, each heteromultimer comprising: at least a first polypeptide construct that comprises at least one cargo polypeptide and a first transporter polypeptide; and at least a second polypeptide construct that comprises at least one cargo polypeptide and a second transporter polypeptide. In certain embodiments, at least one cargo polypeptide is selected from the proteins listed in Table 2 or fragments, variants or derivatives thereof. In certain embodiments, at least one cargo polypeptide is selected from ligand, receptor, or antibody to one or more proteins listed in Table 2, or fragment, variant or derivative of said ligand, receptor or antibody. In certain embodiments, at least one cargo polypeptide targets a cell surface antigen from the group consisting of CD19, CD20, CD22, CD25, CD30, CD33, CD40, CD56, CD64, CD70, CD74, CD79, CD105, Cd138, CD174, CD205, CD227, CD326, CD340, MUC16, GPNMB, PSMA, Cripto, ED-B, TMEFF2, EphB2, EphA2, FAP, integrin, Mesothelin, EGFR, TAG-72, GD2, CAIX, 5T4. In certain embodiments, are heteromultimers, each heteromultimer comprising: at least a first polypeptide construct that comprises at least one cargo polypeptide and a first transporter polypeptide; and at least a second polypeptide construct that comprises at least one cargo polypeptide and a second transporter polypeptide, wherein at least one at least one cargo polypeptide is an antibody, or fragment or variant thereof. In certain embodiments, all cargo polypeptides are antibodies or fragments or variants thereof. In some embodiments, the cargo polypeptide is an antibody that binds to a protein listed in Table 2. In some embodiments, the antibody fragment comprises antibody Fc or Fab or Fv region. In some embodiment the cargo polypeptide is a non-antibody protein like nanobodies, affibody, maxibody, adnectins, domain antibody, evibody, ankyrin repeat proteins, anticalins, camlids or ligand protein or polypeptide binding to a therapeutically relavant target. In some embodiments, the antibody or its fragment is derived from an immunoglobulin selected from the group consisting of IgG, IgA, IgD, IgE, and IgM. In certain embodiments, the IgG is of subtype selected from IgG1, IgG2a, IgG2b, IgG3 and IgG4. In certain embodiments, the antibody is multispecific.

Provided herein are heteromultimers, each heteromultimer comprising: at least a first polypeptide construct that comprises at least one cargo polypeptide and a first transporter polypeptide; and at least a second polypeptide construct that comprises at least one cargo polypeptide and a second transporter polypeptide, wherein at least one cargo polypeptide is a therapeutic antibody. In some embodiments of the heteromultimers described herein, at least one cargo polypeptide is a therapeutic antibody or fragment or variant thereof, wherein the antibody is selected from antibody is selected from abagovomab, adalimumab, alemtuzumab, aurograb, bapineuzumab, basiliximab, belimumab, bevacizumab, briakinumab, canakinumab, catumaxomab, certolizumab pegol, certuximab, daclizumab, denosumab, efalizumab, galiximab, gemtuzumab ozagamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranizumab, reslizumab, rituximab, teplizumab, toclizumab, tositumomab, trastuzumab, Proxinium, Rencarex, ustekinumab, and zalutumumab. In certain embodiments, the therapeutic antibody binds a disease related target antigen such as cancer antigen, inflammatory disease antigen or a metabolic disease antigen. In certain embodiments, the target antigen could be a protein on a cell surface and the cell could belong to the group of B-cell, T-cell, stromal cell, endothelial cell, vascular cell, myeloid cell, hematopoietic cell or carcinoma cell.

Provided herein are heteromultimers, each heteromultimer comprising: at least a first polypeptide construct that comprises at least one cargo molecule, fragment; and at least a second polypeptide construct that comprises at least one cargo molecule and a second transporter polypeptide, wherein at least one cargo polypeptide is an enzyme, enzyme inhibitor, hormone, therapeutic polypeptide, antigen, radiotoxin and chemotoxin inclusive of but not restricted to neurotoxins, interferons, cytokine fusion toxins and chemokine fusion toxins, cytokine, antibody fusion protein or variant or fragment thereof. In some embodiments of the heteromultimers described herein, at least one cargo polypeptide comprises GLP-1 or fragment or variant thereof. In some embodiments, at least one cargo polypeptide comprises glucagon or fragment or variant thereof. In an embodiment, at least one cargo polypeptide comprises an EGF-A like domain. In certain embodiments, the toxin is an immunotoxin such as Denileukin diftitox and Anti-CD22 immunotoxin such as CAT-3888 and CAT-8015. In certain embodiments, the toxin is saporin. In some embodiments, the toxin is a mitotoxin. In some embodiments, the toxin is a diphtheria toxin. In some embodiments, the toxin is botulinux toxin type A. In some embodiments, the toxin is ricin or a fragment there of. In some embodiments, the toxin is a toxin from RTX family of toxins.

Provided herein are heteromultimers, each heteromultimer comprising: at least a first polypeptide construct that comprises at least one cargo polypeptide and a first transporter polypeptide; and at least a second polypeptide construct that comprises at least one cargo polypeptide and a second transporter polypeptide, wherein the cargo polypeptide is attached to the transporter polypeptide by chemical conjugation, native ligation, chemical ligation, a disulfide bond or direct fusion or fusion via a linker. In certain embodiments, linkers for attaching cargo molecules such as cargo polypeptides to transporter polypeptides are selected from the linkers described in U.S. Pat. Nos. 5,482,858, 5,258,498 and 5,856,456, US2009060721, U.S. Pat. Nos. 6,492,123, 4,946,778, 5,869,620, 7,385,032, 5,073,627, 5,108,910, 7,977,457, 5,856,456, 7,138,497, 5,837,846, 5,990,275, EP1088888 incorporated by reference herein.

Provided herein are host cells comprising nucleic acid encoding a heteromultimer described herein. In certain embodiments, the nucleic acid encoding the first polypeptide construct and the nucleic acid encoding the second polypeptide construct are present in a single vector. In certain embodiments, the nucleic acid encoding the first polypeptide construct and the nucleic acid encoding the second polypeptide construct are present in separate vectors.

Provided herein is a method of making a heteromultimer, wherein said method comprises: culturing a host cell described herein such that the nucleic acid encoding a heteromultimer described herein is expressed; and recovering the heteromultimer from the cell culture. In some embodiments, the host cell is a prokaryotic cell or a eukaryotic cell. In some embodiments, the host cell is *E. coli*. In certain embodiments, the host cell is yeast cell. In some embodiments, the yeast is *S. cerevisiae*. In some embodiments, the yeast is *Pichia*. In a certain embodiment, the yeast is *Pichia pastoris*. In some embodiments, the yeast is glycosylation deficient, and/or protease deficient. In some embodiments, the host cell is a bacterial cell. In some embodiments, the host cell expressing a heteromultimer descried herein is a mammalian cell. In certain embodiments, the mammalian cell is a CHO cell, a BHK cell, NSO cell, COS cell or a human cell.

Provided is a pharmaceutical composition that comprises a heteromultimer described herein and a pharmaceutically acceptable adjuvant. Also provided are methods of treating an individual suffering from a disease or disorder, said method comprising administering to the individual an effective amount of a formulation or pharmaceutical composition described herein. In certain embodiments is a method of treating cancer in a patient, said method comprising administering to the patient a therapeutically effective amount of a heteromultimer described herein. In some embodiments is a method of treating an immune disorder in a patient, said method comprising administering to the patient a therapeutically effective amount of a heteromultimer described herein. Also provided is a method of treating an infectious disease in a patient, said method comprising administering to the patient a therapeutically effective amount of a heteromultimer described herein. In certain embodiments is a method of treating a cardiovascular disorder in a patient, said method comprising administering to the patient a therapeutically effective amount of a heteromultimer described herein. In certain embodiments is a method of treating a respiratory disorder in a patient, said method comprising administering to the patient a therapeutically effective amount of a heteromultimer described herein. In certain embodiments is a method of treating a metabolic disorder in a patient, said method comprising administering to the patient a therapeutically effective amount of a heteromultimer described herein. In certain embodiments is a method of treating one or more of Congenital adrenal hyperplasia, Gaucher's disease, Hunter syndrome, Krabbe disease, Metachromatic leukodystrophy, Niemann-Pick disease, Phenylketonuria (PKU), *Porphyria*, Tay-Sachs disease, and Wilson's disease in a patient, said method comprising administering to the patient a therapeutically effective amount of a heteromultimer described herein. Provided are methods of treating cancer comprising providing to a patient in need thereof an effective amount of the pharmaceutical composition described herein. In certain embodiments is a method of inhibiting growth of a tumor, comprising contacting the tumor with an effective amount of the heteromultimer described herein. In some embodiments is a method of shrinking a tumor, comprising contacting the tumor with an effective amount of the heteromultimer provided herein.

Provided is a kit for detecting the presence of a biomarker of interest in an individual, said kit comprising (a) an amount of a heteromultimer described herein, wherein said heteromultimer comprises at least one cargo polypeptide such that said cargo polypeptide is capable of binding to the biomarker of interest; and (b) instructions for use.

Provided herein are heteromultimer proteins that comprise at least two polypeptide constructs, wherein each polypeptide construct comprises at least one cargo polypeptide, and an albumin based polypeptide, such that said polypeptide constructs self-assemble to form the heteromultimer.

In certain embodiments, the cargo polypeptide is fused to the albumin or alloalbumin based transporter polypeptide. In some embodiments, the cargo polypeptide is fused to the transferrin based transporter polypeptide. In certain embodiments, the cargo polypeptide is fused to the annexin based transporter polypeptide. In some embodiments, the fusion is at the N terminus of the transporter polypeptide. In certain embodiments, the fusion is at the C terminus of the transporter polypeptide. In some embodiments, the fusion involves a bridging linker or spacer molecule. In some embodiments, the cargo polypeptide is chemically conjugated to the transporter polypeptide. In certain embodiments, the cargo polypeptide is attached to the transporter polypeptide by means of chemical ligation or a disulfide bond.

Provided herein are heteromultimer proteins that comprise at least two polypeptide constructs, wherein each polypeptide construct comprises at least one cargo polypeptide, and a transporter polypeptide, such that said transporter polypeptides self-assemble to form the heteromultimer. In some embodiments, each transporter polypeptide is an alloalbumin based polypeptide, such that said alloalbumin based polypeptides self-assemble to form the heteromultimer. In some embodiments, each transporter polypeptide is a transferrin based polypeptide. In some embodiments, each transporter polypeptide is an annexin based polypeptide. In certain embodiments, each monomeric transporter polypeptide is unstable and preferentially forms a heteromultimer with at least one other transporter polypeptide.

In some embodiments, a heteromultimer described herein is a heterodimer. In some embodiments cargo polypeptide is an antibody, enzyme, hormone, therapeutic polypeptide, antigen, chemotoxin, radiotoxin, cytokine or variant or fragment thereof. In some embodiments, the cargo polypeptide of one polypeptide construct functions in synergy with the cargo polypeptide of another polypeptide construct.

Provided herein are heteromultimer proteins that comprise at least two polypeptide constructs, wherein each polypeptide construct comprises at least one cargo polypeptide, and an annexin based polypeptide, such that said annexin based polypeptides self-assemble to form the heteromultimer with a quasi-native structure of monomeric annexin or analog thereof. In some embodiments, the annexin is Annexin A1. In some embodiments, a heteromultimer described herein is a heterodimer. In some embodiments cargo polypeptide is an antibody, enzyme, hormone, therapeutic polypeptide, antigen, chemotoxin, radiotoxin, cytokine, ligand to a receptor, receptor or variant or fragment thereof. In some embodiments, the cargo polypeptide of one polypeptide construct functions in synergy with the cargo polypeptide of another polypeptide construct. In some embodiments the cargo polypeptide can be an agonist or antagonist to the cargo polypeptide of another polypeptide construct.

Provided herein are heterodimer proteins that comprise at least two monomeric fusion proteins, wherein each monomeric fusion proteins comprises at least one cargo polypeptide fused to an albumin derived polypeptide, such that said albumin derived polypeptides self-assemble to form the multifunctional heterodimer. In certain embodiments are heterodimeric proteins comprising a first monomer which comprises at least one cargo polypeptide fused to an albumin derived polypeptide; and a second monomer that comprises at least one cargo polypeptide fused to an albumin derived polypeptide. In certain embodiments, the at least one cargo polypeptide of the first monomer is different from the at least one cargo polypeptide of the second monomer. In certain embodiments, the at least one cargo polypeptide of the first monomer is the same as the at least one cargo polypeptide of the second monomer.

In certain embodiments are heteromultimer proteins that comprise at least two monomeric fusion proteins, wherein each monomeric fusion proteins comprises at least one cargo polypeptide fused to an alloalbumin derived polypeptide, such that said alloalbumin derived polypeptides self-assemble to form the multifunctional heteromultimer. In certain embodiments are heteromultimer proteins that comprise at least two monomeric fusion proteins, wherein each monomeric fusion proteins comprises at least one cargo polypeptide fused to a transferrin derived polypeptide, such that said transferrin derived polypeptides self-assemble to form the heteromultimer. In certain embodiments are heteromultimer proteins that comprise at least two monomeric fusion proteins, wherein each monomeric fusion proteins comprises at least one cargo polypeptide fused to an annexin derived polypeptide, such that said annexin derived polypeptides self-assemble to form the heteromultimer. In certain embodiments, the annexin is Annexin A2.

In certain embodiments are heteromultimer proteins comprising a first polypeptide construct which comprises at least one cargo polypeptide fused to an alloalbumin derived polypeptide; and a second polypeptide construct that comprises at least one cargo polypeptide fused to an alloalbumin derived polypeptide. In certain embodiments, the at least one cargo polypeptide of the first polypeptide construct is different from the at least one cargo polypeptide of the second polypeptide construct. In certain embodiments, the at least one cargo polypeptide of the first polypeptide construct is the same as the at least one cargo polypeptide of the second polypeptide construct.

Provided herein is a heteromultimer that comprises: at least two monomers, each comprising a transporter polypeptide and optionally at least one cargo molecule attached to said transporter polypeptide, wherein each transporter polypeptide is obtained by segmentation of a whole protein such that said transporter polypeptides self-assemble to form quasi-native whole protein. In certain embodiments, the heteromultimer is multispecific. In certain embodiments, the transporter polypeptides are not derived from an antibody. In some embodiments, each monomer preferentially forms the heteromultimer as compared to a monomer or a homomultimer. In an embodiment of the heteromultimer, at least one cargo molecule is a therapeutic agent, or a biomolecule. In some embodiments, at least one cargo molecule is a biomolecule which is selected from a polypeptide, DNA, PNA, or RNA. In some embodiments, each transporter polypeptide is a derivate of albumin or alloalbumin. In an embodiment, each transporter polypeptide is a derivate of annexin. In certain embodiments, each transporter polypeptide is a derivate of transferrin.

In certain embodiments are pharmaceutical formulations that comprise an albumin-based and/or alloalbumin-based heteromultimeric protein described herein and a pharmaceutically acceptable diluent or carrier. In certain embodiments are pharmaceutical formulations that comprise a transferrin-based heteromultimeric protein described herein and a pharmaceutically acceptable diluent or carrier. In certain embodiments are pharmaceutical formulations that comprise an annexin-based heteromultimeric protein described herein and a pharmaceutically acceptable diluent or carrier. In certain embodiments are pharmaceutical formulations that comprise an Annexin-A2 based heteromultimeric protein described herein and a pharmaceutically acceptable diluent or carrier. In certain embodiments, a formulation described herein is provided as part of a kit or container. In certain embodiments, the kit or container is packaged with instructions pertaining to extended shelf life of the therapeutic protein. In some embodiments, a heteromultimer described herein is used in a method of treating (e.g., ameliorating) preventing, or diagnosing a disease or disease symptom in an individual, comprising the step of administering said formulation to the individual.

Provided herein is a method of obtaining fusion protein scaffolds with a known number of conjugation sites based on any transport protein of interest.

Also provided are transgenic organisms modified to contain nucleic acid molecules described herein to encode and express monomeric fusion proteins described herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 8B shows Albumin and FIG. 8A shows heteromultimer scaffold ABH1

FIG. 9 discloses SEQ ID NO: 180, 181, 181, and 181, respectively, in order of appearance.

DETAILED DESCRIPTION

Figure 1:
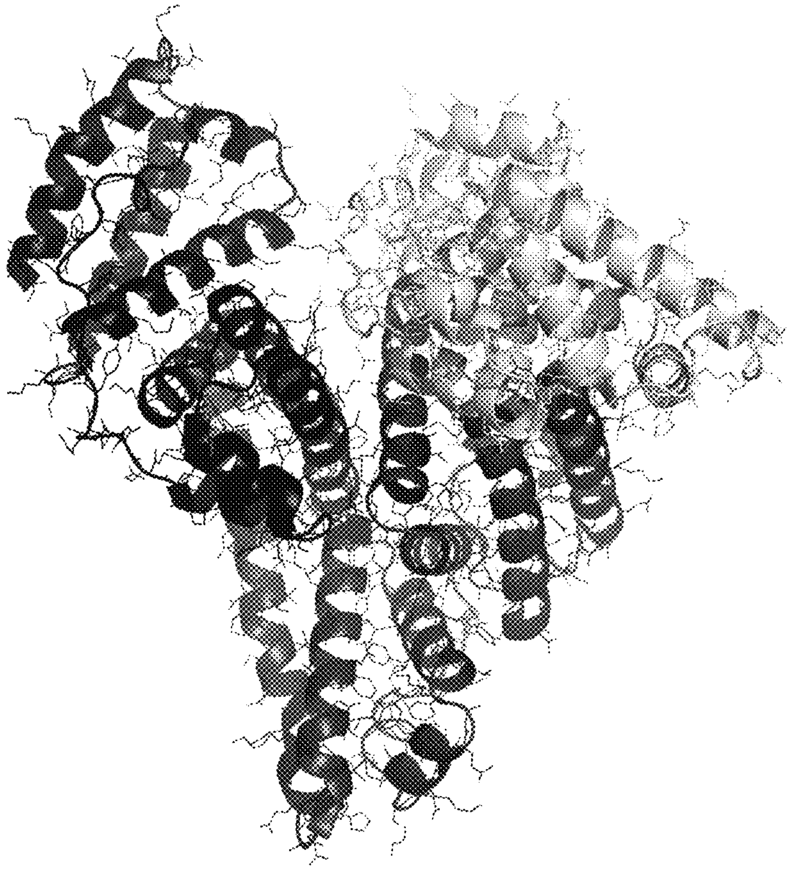
FIG. 1 depicts the structure of the Human Serum Albumin (HSA) molecule. The alpha helical sections of the secondary structure are shown schematically along with the bonds represented as sticks.

In the realm of therapeutic proteins, bispecific molecules exhibit dual target specificities or are able to simultaneously perform multiple functional roles by providing the necessary spatiotemporal organization necessary for drug action. In one aspect, bispecific molecules are particularly interesting when the mode of therapeutic action involves retargeting of effector cells or molecules to a target such as a tumor cell [Muller D. and Kontermann R. E. (2010) *Biodrugs* 24, 89-98]. The development of bispecific therapeutic proteins with favorable pharmacokinetics and functional activity in stable and homogeneous condition has been a challenge. Attempts have been made to assemble bispecific units from multiple antigen binding domains using a number of approaches. These techniques have involved using heterodimeric antibody IgG molecule, using leucine zipper proteins such as the Fos/Jun pair or other scaffolds assembled from the alternate organizations of the light and heavy chains of the variable domains in an antibody. Kipriyanov and Le Gall have reviewed the design of a variety of bispecific constructs [Kipriyanov S. M. & Le Gall F. (2004) *Curr Opin Drug Discov Dev* 7, 233-242]. The use of a heterodimeric antibody IgG molecule wherein mutations are introduced in the CH3 domain of the antibody to achieve the heterodimer and hence introduce the two unique antigen binding sites into one molecule is very attractive because of the natural immunoglobulin like structure of this construct. Further, the Fc portion of the antibody is involved in interactions with the neonatal Fc receptor (FcRn) which mediates an endocytic salvage pathway and this is attributed to improved serum half-life of the antibody molecule [Roopenian D. & Akilesh S. (2007) *Nature Rev Immunol* 7, 715-725]. On the other hand, antibody based bispecific molecules have been problematic in clinical trials because of the strong cytokine responses as a result of the concurrent effector activity induced via the Fc portion of the bispecific antibody [Weiner L. M.; Alpaugh R. K. et al. (1996) *Cancer Immunol Immunother* 42, 141-150]. This highlights the needs for novel scaffolds that can aid in the design of bispecific and immunoconjugate molecules.

The human serum album (HSA) protein is the most abundant component of blood, accounting for close to 60% of the total protein in blood serum at a concentration of about 40 mg/ml. Albumin is also one of the longest-lived proteins in the circulatory system with a half-life of about 19 days. Interestingly, the same endocytic salvage pathway dependent on FcRn molecules that prevents antibody degradation is known to interact with the HSA molecule as well [Chaudhary C.; Mehnaz S. et al. (2003) *J Exp Med* 197, 315-322].

HSA (shown in FIG. 1) is a non-glycosylated 585-residue single polypeptide protein and the 3-dimensional structure of the protein was first observed using X-ray crystallography by Carter and coworkers [reviewed in Carter, D.C. & Ho, J. X. (1994) *Adv Prot Chem* 45, 153-203]. The HSA protein consists of three homologous domains: DI, DII, DIII, attributed to gene duplication, a feature common to the serum albumin in other species as well [Gray J. E. & Doolittle R. F. (1992) *Protein Sci* 1, 289-302]. Each of the three domains have been expressed and characterized separately and shown to be independently stable [Dockal M., Carter D.C. & Ruker F. (1999) *J Biol Chem* 274, 29303-29310]. Each domain is made up of 10 helical segments and based on the inter-helical organization each domain can be further classified into 2 sub-domains comprised of helix 1-6 and 7-10 respectively. HSA has 17 disulphide bonds in total and all these cysteine pairs forming the linkages are within the individual domains. In general, HSA is a very stable due to the large number of disulphide bonds as well as the predominantly helical fold. The sequence identities of albumin molecules across a number of species is quite large, greater than 70% among albumin cDNA derived from humans, horse, bovine, rat, etc. [Carter, D. C. & Ho, J. X. (1994) *Adv Prot Chem* 45, 153-203].

Split protein pairs have been used as sensors to understand protein-protein interactions in the area of functional proteomics. The approach involves identifying suitable segments from a protein that can reconstitute to form an active native-like protein. Generating new split proteins is technically demanding. For a protein to be split in a functionally useful manner, the segmentation site has to yield two segments that efficiently reconstitute into the quasi-native protein when associated to each other. Further, the component protein segments should be soluble enough to stay in solution and selectively associate with the partner segments such that manufacture yields and purification will be economical. Deriving split protein segments that would recombine to form the quasi-native structure resembling the monomeric native protein is quite challenging [Tafelmeyer P., Johnsson N. & Johnsson K. *Chem & Biol* 11, 681-689]. Such split proteins have not been used in the design of protein therapeutics, or as cargo delivery vehicles in the past.

The present invention provides heteromultimers comprisng a first monomer that comprises (i) a first transporter polypeptide; and a second monomer that comprises (ii) a second transporter polypeptide; wherein each of said first and second transporter polypeptide comprises an amino acid sequence with at least 90% identity to a segment of an albumin polypeptide; and wherein said first and second transporter polypeptides are obtained by segmentation of said albumin polypeptide at a segmentation site, wherein said transporter polypeptides self-assemble to form a quasi-native structure of the monomeric form of said albumin polypeptide. In one embodiment, the segmentation site is selected such that it resides on a loop of the albumin polypeptide that has a high solvent accessible surface area (SASA) and limited contact with the rest of the albumin structure, b) results in a complementary interface between the transporter polypeptides, wherein the interface is apolar, extensive and interdigitate. Such heteromultimers exhibit stability comparable to that of wild-type albumin. The first and second monomers may further comprise at least one cargo polypeptide. Heteromultimers comprising said at least one cargo polypeptide may be used as therapeutics for the treatment of disease.

Definitions

It is to be understood that this invention is not limited to the particular protocols; cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "HSA", "HA", "albumin", "human serum albumin" and various capitalized, hyphenated and unhyphenated forms is a reference to one or more such proteins and includes variants, derivatives, fragments, equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

A "heteromultimer" or "heteromultimeric polypeptide" is a molecule comprising at least a first monomer comprising a first transporter polypeptide and a second monomer comprising a second transporter polypeptide, wherein the second polypeptide differs in amino acid sequence from the first polypeptide by at least one amino acid residue. The heteromultimer can comprise a "heterodimer" formed by the first and second transporter polypeptides. In certain embodiments, the heteromultimer can form higher order tertiary structures such as, but not restricted to trimers and tetramers. In some embodiments, transporter polypeptides in addition to the first and second transporter polypeptides are present. In certain embodiments, the assembly of transporter polypeptides to form the heteromultimer is driven by surface area burial. In some embodiments, the transporter polypeptides interact with each other by means of electrostatic interactions and/or salt-bridge interactions that drive heteromultimer formation by favoring heteromultimer formation and/or disfavoring homomultimer formation. In some embodiments, the transporter polypeptides interact with each other by means of hydrophobic interactions that drive heteromultimer formation by favoring heteromultimer formation and/or disfavoring homomultimer formation. In certain embodiments, the transporter polypeptides interact with each other by means of covalent bond formation. In certain embodiments, the covalent bonds are formed between naturally present or introduced cysteines that drive heteromultimer formation. In certain embodiments of the heteromultimers described herein, no covalent bonds are formed between the monomers. In some embodiments, the transporter polypeptides interact with each other by means of packing/size-complementarity/knobs-into-holes/protruberance-cavity type interactions that drive heteromultimer formation by favoring heteromultimer formation and/or disfavoring homomultimer formation. In some embodiments, the transporter polypeptides interact with each other by means of cation-pi interactions that drive heteromultimer formation by favoring heteromultimer formation and/or disfavoring homomultimer formation. In certain embodiments the individual transporter polypeptides cannot exist as isolated monomers in solution. In certain embodiments, the heteromultimer is the preferred state of the individual transporter polypeptides as compared to the monomer.

The term "bispecific" is intended to include any agent, e.g., heteromultimer, monomer, protein, peptide, or protein or peptide complex, which has two different binding specificities. For example, in some embodiments, the molecule may bind to, or interact with, (a) a cell surface target molecule and (b) an Fc receptor on the surface of an effector cell. In certain embodiments of a heteromultimer described herein, at least one monomer is bispecific formed by attaching to the same transporter polypeptide, two cargo molecules with different binding specificities. In certain embodiments of a heteromultimer described herein, the heteromultimer is itself bispecific formed by attaching to the transporter polypeptides, at least two cargo molecules with different specificities. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface target molecule such as but not limited to cell surface antigens, (b) an Fc receptor on the surface of an effector cell, and (c) at least one other component. Accordingly, embodiments of the heteromultimers described herein, are inclusive of, but not limited to, bispecific, trispecific, tetraspecific, and other multispecific molecules. In certain embodiments, these molecules are directed to cell surface antigens, such as CD30, and to other targets, such as Fc receptors on effector cells.

Unless indicated otherwise, the expression "multivalent" is used throughout this specification to denote a heteromultimer comprising at least two sites of attachment for target molecules. The multivalent heteromultimer is designed to have multiple binding sites for desired targets. In certain embodiments, the binding sites are on at least one cargo molecules attached to a transporter polypeptide. In certain embodiments, at least one binding site is on a transporter polypeptide. The expression "bivalent" is used throughout this specification to denote a heteromultimer comprising two target binding sites. In certain embodiments of a bivalent heteromultimer, both binding sites are on the same monomer. The expression "trivalent" is used throughout this specification to denote a heteromultimer comprising three target binding sites. The expression "tetravalent" is used throughout this specification to denote a heteromultimer comprising four target binding sites.

"Fusion proteins" and polypeptides are created by joining two or more genes that originally code for separate polypeptides. Translation of this fusion gene results in a single polypeptide with functional properties derived from each of the original polypeptides. In embodiments of the heteromultimers described herein, at least one monomer may comprise a fusion protein formed by the fusion of at least one cargo polypeptide to the N- or C-terminus of a transporter polypeptide.

The term "substantially purified" refers to a heteromultimer described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the protein has been secreted, including medium either before or after a proliferation step. The term also may encompass buffers or reagents that contain host cell lysates, such as in the case where a heteromultimer described herein is produced intracellularly and the host cells are lysed or disrupted to release the heteromultimer.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two monomeric polypeptides which interact with each other and result in the transformation of unfolded or improperly folded polypeptides to native, properly folded polypeptides.

As used herein, the term "modulated serum half-life" means the positive or negative change in circulating half-life of a cargo polypeptide that is comprised by a heteromultimer described herein relative to its native form. Serum half-life is measured by taking blood samples at various time points after administration of heteromultimer, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of a cargo polypeptide comprised by a heteromultimer described herein, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M) (see, e.g., Creighton, Proteins: Structures and Molecular Properties (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of heteromultimer being administered, which will relieve to some extent one or more of the symptoms of the disease, condition or disorder being treated. Compositions containing the heteromultimer described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

The term "segmentation" refers to a precise internal splice of the original protein sequence which results in "segments" of the protein sequence that preferentially associate as heteromultimers to form a quasi-native protein structure. Alternatively, segmentation can include deletion of more than one amino acid residue. In one embodiment, the deletion is one amino acid residue. In another embodiment, the deletion is two amino acid residues. In another embodiment, the deletion is three amino acid residues.

Quasi-Native Monomer Structure:

With reference to a monomeric native protein or its structure, quasi-native proteins and/or 'quasi-native structures' or quasi-native monomeric structures are heteromultimer assemblies of polypeptides derived from segments of the monomeric native protein such that said heteromultimer assemblies present functional and structural characteristics comparable to the monomeric native protein. In some embodiments, the segments are components of a polypeptide construct that also comprise other molecular entities. Proteins are naturally dynamic molecules and display an ensemble of structural configurations although we ascribe a native structure to it, such as the one obtained by X-ray crystallography. The quasi-native structures can be considered to resemble one of the alternate structural configurations in the ensemble. On a different front, homologous proteins sequences or proteins belonging to common structural families tend to fold into similar structural geometries. The member proteins belonging to this family can be deemed to achieve a quasi-native structure relative to each other. Some of the unique sequences in the protein family could also exhibit similar functional attributes and hence can be referred to as quasi-native proteins relative to each other. In the case of heteromultimers described here comprising of two or more polypeptide constructs each of which have a transporter polypeptide component, the transporter polypeptides assemble to form a quasi-native structure similar to the native monomeric form of the protein that the transporter polypeptides are derived from. The reference native protein in this case is the monomer protein from which each transporter polypeptide is derived and the reference native structure is the structure of the protein from which the transporter polypeptide is derived. We describe a case where two or more different polypeptides self-assemble to form a heteromultimer with structural and functional characteristics comparable to the native protein which itself is a monomeric entity. In some embodiments, the assembled heteromultimer has at least 50% of the activity of the monomeric native protein. In some embodiments, the assembled heteromultimer has at least 60% of the activity of the monomeric native protein. In specific embodiments, the assembled heteromultimer has at least 75% of the activity of the monomeric native protein. In some embodiments, the assembled heteromultimer has at least 80% of the activity of the monomeric native protein. In particular embodiments, the assembled heteromultimer has at least 90% of the activity of the monomeric native protein. In some embodiments, the assembled heteromultimer has at least 95% of the activity of the monomeric native protein. In some embodiments, the assembled heteromultimer has at least 99% of the activity of the monomeric native protein. In certain embodiments provided are, heteromultimers comprising transporter polypeptides derived from albumin or allo-albumin such that the transporter polypeptides self-assemble to form a heteromultimer that exhibits native albumin like structural and/or functional characteristics such as FcRn, SPARC and/or gp60 binding. In certain embodiments are heteromultimers comprising transporter polypeptides, each transporter polypeptide comprising an amino acid sequence that has at least 75% sequence identity with an amino acid segment obtained from the native monomeric protein. In some embodiments are heteromultimers comprising transporter polypeptides, each transporter polypeptide comprising an amino acid sequence that has at least 80% sequence identity with an amino acid segment obtained from the native monomeric protein. In exemplary embodiments are heteromultimers comprising transporter polypeptides, each transporter polypeptide comprising an amino acid sequence that has at least 85% sequence identity with an amino acid segment obtained from the native monomeric protein. In specific embodiments are heteromultimers comprising transporter polypeptides, each transporter polypeptide comprising an amino acid sequence that has at least 90% sequence identity with an amino acid segment obtained from the native monomeric protein. In certain embodiments are heteromultimers comprising transporter polypeptides, each transporter polypeptide comprising an amino acid sequence that has at least 95% sequence identity with an amino acid segment obtained from the native monomeric protein. In some embodiments are heteromultimers comprising transporter polypeptides, each transporter polypeptide comprising an amino acid sequence that has at least 99% sequence identity with an amino acid segment obtained from the native monomeric protein. In some embodiments, the native monomeric protein is a mammalian albumin or derivative or analog thereof. In certain embodiments, the native monomeric protein is human serum albumin. In certain embodiments, we present polypeptide segments derived from transferrin that self-assemble to form a heteromultimer that exhibits native transferrin like structural and functional characteristics. In certain embodiments, we present polypeptide segments derived from annexin that self-assemble to form a heteromultimer that exhibits native annexin like structural and functional characteristics. These heteromultimers are referred to as being quasi-native.

Transporter Polypeptide

As used herein, the term "transporter polypeptide" or "transporter polypeptide" or "transporter peptide" or "transporter" refers to a polypeptide, such that said transporter polypeptide is capable of forming heteromultimeric proteins with other such transporter polypeptides in solution, and wherein said heteromultimeric proteins have a quasi-native structure of a monomeric protein from which at least one transporter polypeptide is derived. In certain embodiments of the heteromultimers described herein, all transporter polypeptides are derived from the same albumin or alloalbumin protein. In certain other embodiments, the heteromultimers are formed by transporter polypeptides derived from various albumin and alloalbumin proteins. In certain embodiments of the heteromultimers described herein, the transporter polypeptides are derived from transferrin. In certain embodiments of the heteromultimers described herein, all transporter polypeptides are derived from annexin proteins. In certain embodiments, the heteromultimers are formed by transporter polypeptides derived from the same annexin protein. In some embodiments, the heteromultimers are formed by transporter polypeptides derived from different annexin proteins. In an embodiment, the heteromultimers are formed by transporter polypeptides derived from annexin A2.

In certain embodiments, transporter polypeptides are segments of a monomeric whole protein, wherein said segments are capable of assembling to form a heteromultimer such that said heteromultimer forms a quasi-native structure similar to the native monomeric whole protein. In an embodiment, the transporter polypeptides are segments from a beta-barrel protein. In certain embodiments provided are, heteromultimers comprising transporter polypeptides that assemble to form a quasi-native structure similar to a native monomeric protein, each transporter polypeptide comprising an amino acid sequence with at least 50% identity to a segment of the native monomeric protein. In certain embodiments provided are, heteromultimers comprising transporter polypeptides that assemble to form a quasi-native structure similar to a native monomeric protein, each transporter polypeptide comprising an amino acid sequence with at least 60% identity to a segment of the native monomeric protein. In certain embodiments provided are, heteromultimers comprising transporter polypeptides that assemble to form a quasi-native structure similar to a native monomeric protein, each transporter polypeptide comprising an amino acid sequence with at least 75% identity to a segment of the native monomeric protein. In certain embodiments provided are, heteromultimers comprising transporter polypeptides that assemble to form a quasi-native structure similar to a native monomeric protein, each transporter polypeptide comprising an amino acid sequence with at least 80% identity to a segment of the native monomeric protein. In certain embodiments provided are, heteromultimers comprising transporter polypeptides that assemble to form a quasi-native structure similar to a native monomeric protein, each transporter polypeptide comprising an amino acid sequence with at least 90% identity to a segment of the native monomeric protein. In certain embodiments provided are, heteromultimers comprising transporter polypeptides that assemble to form a quasi-native structure similar to a native monomeric protein, each transporter polypeptide comprising an amino acid sequence with at least 95% identity to a segment of the native monomeric protein. In certain embodiments provided are, heteromultimers comprising transporter polypeptides that assemble to form a quasi-native structure similar to a native monomeric protein, each transporter polypeptide comprising an amino acid sequence with at least 99% identity to a segment of the native monomeric protein. In an embodiment, the native monomeric protein is a beta-propeller protein. In some embodiments, the native monomeric protein is a helical bundle protein. In embodiments, the transporter polypeptides are generated from for instance, but not restricted to proteins comprising a zinc finger motif, a helix-turn-helix motif or a beta-hairpin motif. In some embodiments, the transporter polypeptides comprise segments obtained from non-immunogenic proteins that are structurally stable, and have favorable biological properties.

Transporter polypeptides are derived from a protein by segmentation of the protein at a segmentation site. The segmentation site is designed on the basis of the following two decision criteria.

First, the segmentation site is selected such that it resides on a loop within the protein that has a high relative SASA and limited contact with the rest of the protein structure. In one embodiment, the segmentation site resides in a loop that is flexible and accessible. In another embodiment, the segmentation site resides in a loop that is less likely to contribute to the protein core stability and thus impact stability of the assembled quasi-native protein structure relative to the intact protein structure.

Second, the segmentation site is selected such that it results in a complementary interface between the transporter polypeptides, wherein the interface is apolar, extensive and interdigitated. The apolarity of the interface relates to the number of apolar amino acids in the interface. As is known in the art, amino acids can be broadly classified as polar and apolar residues. While polar residues interact favourably with water in the solvent environment, apolar residues do not make energetically favourable contact with water. For this reason, the apolar residues in a protein tend to cluster with other apolar residues and exclude water molecules from their local environment and this is energetically favourable. Such interactions involving apolar residues is also referred to as hydrophobic contact.

The buried surface area at the interface is derived from the loss in the molecular or solvent accessible surface between the unassociated and associated states of the two interacting polypeptides. In one embodiment, the interface buried area is between about 6000 $Å^2$ and about 2000 $Å^2$. In another embodiment, the interface buried area is between about 4000 $Å^2$ and 2000 $Å^2$. In another embodiment, the interface buried area is between about 3000 $Å^2$ and 2000 $Å^2$. In one embodiment, the apolar contribution to the interface buried area is greater than 50% of the net buried surface area at the interface.

With respect to the interface and its interdigitation, an important factor driving any protein-protein interaction and complex formation is the contact of surface residues at the interface formed between the two contacting proteins. Physico-chemical and structural complementarity of the two contacting protein surfaces in the associated form is a hallmark of favourable and stable complex formation. The physico-chemical complementarity is defined by the preferable interactions and could comprise hydrogen bonds, charge based salt-bridges, various types of electrostatic interactions, hydrophobic and van der Waals contacts across interacting protein surface. The protein surface at the 3-dimensional level is defined by protuberances and cavities formed due to the differences in size and orientation of various amino acids that constitute the surface region. In an favourable protein-protein interface, the protuberance and cavities from the two interacting protein surfaces interdigitate to result in structural complementarity. The larger and more extensive the interface between the interacting proteins, the protein-protein contact is potentially more stable.

In one embodiment, the interface between the two transported polypeptides is rich in hotspot residues, i.e. individual residues or group of residues involved in a well-connected network of interactions. The interactions could be based on typical interactions observed in proteins such as hydrogen bonds, charged residue interactions such as salt-bridges, van der Waals contacts which show strong structural complementarity and hydrophobic residue clusters. This maximizes the interface stability and prevents the complex from dissociating.

In one embodiment, the segmentation site is selected to retain a natural disulfide bond present in the protein from which the transporter polypeptides are derived, across the segmented sections so as to covalently connect the two segments. That was meant to further increase the stability of the heterodimerizing quasi-native protein-like structure that self assembles from the two derived segments following segmentation. In this embodiment, loop regions in the protein sequence are chosen that satisfy the disulfide criteria described here i.e. have a disulfide very close to the segmentation site in the loop region. Besides the function of covalently crosslinking the two chains, this disulfide could also serve as a surrogate for the loop being open.

In another embodiment, a disulphide link across the two segments is engineered by introducing individual amino acid to cysteine mutations at selected positions on each of the two derived segments.

In another embodiment, we engineer amino acids at the interface of the two segments to further increase or improve the hotspots at the interface or enhance the structural and physico-chemical complementarity between the two segments in the assembled quasi-native albumin structure.

Albumin

As used herein, "albumin" refers collectively to albumin protein or amino acid sequence, or an albumin segment or variant, having one or more functional activities (e.g., biological activities) of albumin. In particular "albumin" refers to human albumin or segments thereof (see for example, EP 201 239, EP 322 094 WO 97/24445, WO95/23857) especially the mature form of human albumin as shown in FIG. 1, or albumin from other vertebrates, or segments thereof, or analogs or variants of these molecules or fragments thereof. In certain embodiments, albumin refers to a truncated version of albumin.

The term "quasi-native albumin" refers to a heteromultimer molecule that has structure and/or function similar to the whole albumin, and wherein said heteromultimer molecule is formed by the assembly of two or more monomeric polypeptides designed based on the sequence of the whole albumin. In certain embodiments, the polypeptides of interest here comprise "segments" that preferentially associate as heteromultimeric pairs to form a quasi-native protein. In some embodiment this quasi-native protein is quasi-native albumin. In some embodiments, the quasi-native albumin has 90% of the activity of the whole albumin. In some embodiments, the quasi-native albumin has 75% of the activity of whole-albumin. In an embodiment, the quasi-native albumin has 50% of the activity of whole albumin. In some embodiments, the quasi-native albumin has 50-75% of the activity of whole albumin. In an embodiment, quasi-native albumin has 80% of the activity of whole albumin. In some embodiments, the quasi-native albumin retains about 90% of the structural characteristics of the whole albumin as determined by structural modeling. In some embodiments, the quasi-native albumin retains about 80% of the structural characteristics of the whole albumin as determined by structural modeling. In some embodiments, the quasi-native albumin retains about 70% of the structural characteristics of the whole albumin as determined by structural modeling. In some embodiments, the quasi-native albumin retains about 50% of the structural characteristics of the whole albumin as determined by structural modeling. In some embodiments, the quasi-native albumin retains about 50-75% of the structural characteristics of the whole albumin as determined by structural modeling.

The terms, human serum albumin (HSA) and human albumin (HA) are used interchangeably herein. The terms, "albumin and serum albumin" are broader, and encompass human serum albumin (and fragments and variants thereof) as well as albumin from other species (and fragments and variants thereof).

In certain embodiments, each albumin-based monomer of the heteromultimeric proteins described herein is based on a variant of normal HA. Each cargo polypeptide portion of the heteromultimeric proteins of the invention may also be variants of the Therapeutic proteins as described herein. The term "variants" includes insertions, deletions and substitutions, either conservative or non conservative, where such changes do not substantially alter one or more of the oncotic, useful ligand-binding and non-immunogenic properties of albumin, or the active site, or active domain which confers the therapeutic activities of the Therapeutic proteins. In certain embodiments variants also could mean alternate heteromultimer species derived by segmenting the albumin at alternate locations in its primary sequence.

In certain embodiments, the heteromultimeric proteins described herein include naturally occurring polymorphic variants of human albumin and fragments of human albumin, for example those fragments disclosed in EP 322 094 (namely HA (Pn), where n is 369 to 419).

In certain embodiments, the albumin is derived from any vertebrate, especially any mammal that includes but is not limited to human, cow, sheep, rat, mouse, rabbit, horse, dog or pig. In certain embodiments, the albumin is derived from non-mammalian albumins including, but are not limited to hen and salmon.

The sequence of human albumin is as shown, in the preprotein form with the N-terminal signaling residues MKWVTFISLLFLFSSAYSRGVFRR (SEQ ID NO: 175):

SEQ ID NO: 187

```
MKWVTFISLLFLFSSAYSRGVFRRDAHKSEVAHRFKDLGEENFKALVLIA

FAQYLQQCPFEDHVKLVNEVTEFAKTCVADESAENCDKSLHTLFGDKLCT

VATLRETYGEMADCCAKQEPERNECFLQHKDDNPNLPRLVRPEVDVMCTA

FHDNEETFLKKYLYEIARRHPYFYAPELLFFAKRYKAAFTECCQAADKAA

CLLPKLDELRDEGKASSAKQRLKCASLQKFGERAFKAWAVARLSQRFPKA

EFAEVSKLVTDLTKVHTECCHGDLLECADDRADLAKYICENQDSISSKLK

ECCEKPLLEKSHCIAEVENDEMPADLPSLAADFVESKDVCKNYAEAKDVF

LGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKC

CTESLVNRRPCFSALEVDETYVPKEFNAETFTFHADICTLSEKERQIKKQ

TALVELVKHKPKATKEQLKAVMDDFAAFVEKCCKADDKETCFAEEGKKLV

AASQAALGL
```

Alloalbumin

An alloalbumin is a genetic variant of albumin. In certain embodiments the alloalbumin is human alloalbumin (HAA). Alloalbumins that differ in electrophoretic mobility from albumin have been identified through population genetics surveys in the course of clinical electrophoresis, or in blood donor surveys. As markers of mutation and migration, alloalbumins are of interest to geneticists, biochemists, and anthropologists, but most of these alloalbumin are not associated with disease (Minchioti et al. Human Mutations 29(8), 1007-1016(2008)).

TABLE 1

List of substitutions comprised by various allo-albumins as compared to HA of SEQ ID NO: 1. Thermostability, half-life information and other HAAs are provided in Krogh-hansen et al. Biochim Biophys Acta 1747, 81-88(2005); and WO2011051489 incorporated by reference herein.

| Mutation | Thermostability (C) (positive = stabilizing, negative = destabilizing) | Effect on half-life (% change) |
|---|---|---|
| H3Y | N/A | N/A |
| H3Q | N/A | N/A |
| Q32Stop | N/A | N/A |
| E60K | N/A | N/A |
| D63N | 6.07 | N/A |
| L66P | N/A | N/A |
| E82K | 2.03 | N/A |
| R114G | N/A | N/A |
| R114Stop | N/A | N/A |
| E119K | N/A | N/A |
| V122E | 0.57 | N/A |
| H128R | N/A | N/A |
| Y140C | N/A | N/A |
| A175Stop | N/A | N/A |
| C177F | -1.59 | N/A |
| R218H | N/A | N/A |
| R218P | N/A | N/A |
| K225Q* | -4.86 | N/A |
| K240E | N/A | N/A |
| E244Stop | N/A | N/A |
| Q268R | N/A | N/A |
| D269G | 3.67 | N/A |
| K276N | 4.87 | N/A |
| K313N | -7.16 | N/A |
| D314G | -0.38 | N/A |
| D314V | N/A | N/A |
| N318K | N/A | N/A |
| A320T, & -1R | N/A | 6.16 |
| E321K | 1.42 | N/A |
| E333K | -2.56 | N/A |
| E354K | N/A | N/A |
| E358K | N/A | N/A |
| K359K | -6.56 | N/A |
| D365H | 0.89 | N/A |

TABLE 1-continued

List of substitutions comprised by various allo-albumins as compared to HA of SEQ ID NO: 1. Thermostability, half-life information and other HAAs are provided in Krogh-hansen et al. Biochim Biophys Acta 1747, 81-88(2005); and WO2011051489 incorporated by reference herein.

| Mutation | Thermostability (C) (positive = stabilizing, negative = destabilizing) | Effect on half-life (% change) |
|---|---|---|
| D365V | N/A | N/A |
| E368G | N/A | N/A |
| K372E | N/A | N/A |
| D375N | N/A | N/A |
| D375H | -0.09 | N/A |
| E376K | N/A | N/A |
| E376Q | N/A | N/A |
| E382K | N/A | N/A |
| Q385Stop | N/A | N/A |
| Y401Stop | N/A | N/A |
| R410C | N/A | N/A |
| E479K | N/A | N/A |
| D494N | N/A | 0.84 |
| E501K | 0.13 | N/A |
| E505K | 1.87 | N/A |
| I513N | N/A | N/A |
| V533M | N/A | N/A |
| K536E | N/A | N/A |
| K541E | 6.12 | N/A |
| D550G | N/A | N/A |
| D550A | N/A | N/A |
| K560E | 0.70 | N/A |
| D563N | 4.17 | N/A |
| E565K | N/A | N/A |
| E570K | -6.53 | N/A |
| K573E | 2.08 | 2.7 |
| K574N | N/A | N/A |
| L575insertion (TCCCKSSCLRLITSH LKASQPTMRIRERK) (SEQ ID NO: 176) | -5.30 | N/A |
| Frameshift after 567; Stop at 582 | N/A | -5.7% |
| Frameshift after 572; Stop at 578 | N/A | -8.9% |

Annexin:

As used herein, “annexin” refers to a group of cellular proteins found in eukaryotic organisms. Annexin is also known as lipocortin. As used herein “annexin” may refer to any annexin protein, or to specific annexin proteins such as “annexin A1,” “annexin A2,” and “annexin A5.” Annexins are characterized by their calcium dependent ability to bind negatively charged phospholipids (i.e. membrane walls). Annexins are characterized by a repeat protein scaffold limited to 30-50 kDa in size with fairly ubiquitous tissue distribution. The basic structure of an annexin is composed of two domains: a structurally conserved C terminal “core” region and a divergent N terminal domain. The core region binds the phospholipid cellular membrane in a Ca' dependent manner. The N terminal region binds cytoplasmic proteins. Annexins are important in various cellular and physiological processes and provide a membrane scaffold. The C terminal core is composed of four annexin repeats. Annexin is characterized by its flexible repeat-like nature that influences its intrinsic membrane-sensing abilities. For instance, the affinity towards specific biomembranes can be controlled by the number of repeats. With the characteristic phospholipid sensing, annexin can be useful to sense/target intestinal junctions for drug delivery. Another potential application for an annexin is targeting intestinal tight junctions and the Zonula Occludens region (ZO-1), which is known to be particularly difficult to traverse for larger protein therapeutics, significantly impairing drug absorption.

The term “quasi-native annexin” refers to a heteromultimer molecule that has structure and/or function similar to the whole annexin, and wherein said heteromultimer molecule is formed by the assembly of two or more monomeric polypeptides designed based on the sequence of the whole annexin. In certain embodiments, the monomeric polypeptides are “segments” that preferentially associate as heteromultimeric pairs to form a quasi-native protein. In some embodiments, the quasi-annexin has 90% of the activity of the whole annexin. In some embodiments, the quasi-annexin has 75% of the activity of whole-annexin. In an embodiment, the quasi-annexin has 50% of the activity of whole annexin. In some embodiments, the quasi-annexin has 50-75% of the activity of whole annexin. In an embodiment, quasi-annexin has 80% of the activity of whole annexin. In some embodiments, the quasi-annexin has 90% of the structure of whole annexin as determined by molecular modeling. In some embodiments, the quasi-annexin has 80% of the structure of whole annexin as determined by molecular modeling. In some embodiments, the quasi-annexin has 70% of the structure of whole annexin as determined by molecular modeling. In some embodiments, the quasi-annexin has 50% of the structure of whole annexin as determined by molecular modeling. In some embodiments, the quasi-annexin has 50%-75% of the structure of whole annexin as determined by molecular modeling.

The sequence of Human wild-type Annexin A2 is as shown:

SEQ ID NO: 14

GSAVSPYPTFNPSSDVAALHKAIMVKGVDEATII-DILTKRNNAQRQQIKAAYLQETG KPLDETLKKA-LTGHLEEVVLALLKTPAQFDADELRAAMKGLGTD-EDTLIEILASRTN KEIRDINRVYREELKRDLAKDITSDTSGDFR-NALLSLAKGDRSEDFGVNEDLADSDA RALYEA-GERRKGTDVNVENTILTTRSYPQLRRVFQKYT-KYSKHDMNKVLDLELKGD

IEKCLTAIVKCATSKPAFFAEKLHQAMKGVGTRHKALIRIMVSRSEIDMNDIKAFYQ KMYGISLCQAILDETKGDYEKILVALCGGN

Transferrin:

Transferrins are monomeric proteins of about 76 kDa molecular weight present in all vertebrates and function as a iron-binding and transporting protein. Recombinant human transferrin and its fusions is being considered for the management of various diseases including thalassemia, atransferrinemia, age related macular degeneration, type 2 diabetes, during stem cell transplantation and in the treatment of acute infectious disease caused by the anthrax bacteria. Transferrin is stable in the gastrointestinal environment and a number of studies have shown that intact protein-transferrin conjugates can be orally delivered and remain bioactive.

The term "quasi-transferrin" refers to a heteromultimer molecule that has structure and/or function similar to the whole transferrin, and wherein said heteromultimer molecule is formed by the assembly of two or more monomeric polypeptides designed based on the sequence of the whole transferrin. In certain embodiments, the monomeric polypeptides are "segments" that preferentially associate as heteromultimeric pairs to form a quasi-native protein. In some embodiments, the quasi-transferrin has 90% of the activity of the whole transferrin. In some embodiments, the quasi-transferrin has 75% of the activity of whole-transferrin. In an embodiment, the quasi-transferrin has 50% of the activity of whole transferrin. In some embodiments, the quasi-transferrin has 50-75% of the activity of whole transferrin. In an embodiment, quasi-transferrin has 80% of the activity of whole transferrin. In some embodiments, the quasi-transferrin has 90% of the structure of whole transferrin as determined by molecular modeling. In some embodiments, the quasi-transferrin has 80% of the structure of whole transferrin as determined by molecular modeling. In some embodiments, the quasi-transferrin has 70% of the structure of whole transferrin as determined by molecular modeling. In some embodiments, the quasi-transferrin has 50% of the structure of whole transferrin as determined by molecular modeling. In some embodiments, the quasi-transferrin has 50%-75% of the structure of whole transferrin as determined by molecular modeling.

The sequence of wildtype Human Transferrin is as shown:

```
                                              SEQ ID NO: 188
MRLAVGALLV CAVLGLCLAV PDKTVRWCAV SEHEATKCQS

FRDHMKSVIP SDGPSVACVK KASYLDCIRA IAANEADAVT

LDAGLVYDAY LAPNNLKPVV AEFYGSKEDP QTFYYAVAVV

KKDSGFQMNQ LRGKKSCHTG LGRSAGWNIP IGLLYCDLPE

PRKPLEKAVA NFFSGSCAPC ADGTDFPQLC QLCPGCGCST

LNQYFGYSGA FKCLKDGAGD VAFVKHSTIF ENLANKADRD

QYELLCLDNT RKPVDEYKDC HLAQVPSHTV VARSMGGKED

LIWELLNQAQ EHFGKDKSKE FQLFSSPHGK DLLFKDSAHG

FLKVPPRMDA KMYLGYEYVTA IRNLREGTC PEAPTDECKP

VKWCALSHHE RLKCDEWSVNS VGKIECVSA ETTEDCIAKI

MNGEADAMSL DGGFVYIAGKC GLVPVLAEN YNKSDNCEDT

PEAGYFAVAV VKKSASDLTWD NLKGKKSCH TAVGRTAGWN
```

-continued

```
IPMGLLYNKI NHCRFDEFFSE GCAPGSKKD SSLCKLCMGS

GLNLCEPNNK EGYYGYTGAFR CLVEKGDVA FVKHQTVPQN

TGGKNPDPWA KNLNEKDYELL CLDGTRKPV EEYANCHLAR

APNHAVVTRK DKEACVHKILR QQQHLFGSN VTDCSGNFCL

FRSETKDLLF RDDTVCLAKLH DRNTYEKYL GEEYVKAVGN

LRKCSTSSLL EACTFRRP
```

Cargo Molecule:

A heteromultimer described herein comprises polypeptides that comprise at least one cargo molecule, and at least one transporter polypeptide, said cargo molecule and transporter polypeptide associated with one another, by means inclusive of, but not restricted to genetic fusion or chemical conjugation. In some embodiments, the cargo polypeptide is fused to either the N or C terminus of the transporter polypeptide. In some embodiments, the cargo polypeptides are fused to both the N and C terminus of the transporter polypeptide. In some embodiment the cargo polypeptide is conjugated to Cysteine 34 position of the transporter polypeptide derived by segmenting human albumin. In certain embodiments, at least one cargo molecule is a therapeutic agent. In certain agents, the cargo molecule is a toxin. In certain embodiments, the cargo molecule is an antigen, or analogs thereof. In an embodiment, the cargo molecule is a natural product, analog, or prodrug thereof. In certain embodiments, the cargo molecule is a therapeutic agent such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6mercaptopurine, 6thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In certain embodiment, the cargo molecule is a biomolecule. In an embodiment, the cargo molecule is a natural or synthetic nucleic acid. In some embodiments, at least one cargo molecule is one or more of a DNA, PNA, and/or RNA oligomer. In certain embodiments, a heteromultimer described herein comprises monomeric proteins that comprise at least one cargo polypeptide, or fragments or variants thereof, and at least one transporter polypeptide, said cargo polypeptide and transporter polypeptide associated with one another, by means inclusive of, but not restricted to genetic fusion or chemical conjugation As used herein, "Cargo polypeptide" refers to proteins, polypeptides, antibodies, peptides or fragments or variants thereof, having one or more therapeutic and/or biological activities. Cargo polypeptides encompassed by the invention include but are not limited to, proteins, polypeptides, peptides, antibodies, substrates or ligands to therapeutically relevant target proteins and biologics. (The terms peptides, proteins, and polypeptides are used interchangeably herein.) Specifically the term "Cargo polypeptide" encompasses antibodies and fragments and variants thereof. Thus a heteromultimer described herein may contain at least a fragment or variant of a cargo polypeptide, and/or at least a fragment or variant of an antibody. Additionally, in certain embodiments, the term "Cargo polypeptide" refers to the endogenous or naturally occurring correlate of a cargo polypeptide.

As a non-limiting example, a "Cargo biomolecule" is a biomolecule such as but not restricted to a protein, DNA, or RNA that is useful to treat, prevent or ameliorate a disease, condition or disorder. As a non-limiting example, a "Cargo polypeptide" may be one that binds specifically to a particular cell type (normal (e.g., lymphocytes) or abnormal e.g., (cancer cells)) and therefore may be used to target a compound (drug, or cytotoxic agent) to that cell type specifically.

In another non-limiting example, a "Cargo molecule" is a molecule that has a biological, activity, and in particular, a biological activity that is useful for treating preventing or ameliorating a disease. A non-inclusive list of biological activities that may be possessed by a Cargo molecule, for instance a Cargo polypeptide includes, enhancing the immune response, promoting angiogenesis, inhibiting angiogenesis, regulating hematopoietic functions, stimulating nerve growth, enhancing an immune response, inhibiting an immune response, or any one or more of the biological activities described herein.

Cargo polypeptides corresponding to a cargo polypeptide portion of a heteromultimer protein described herein, such as cell surface and secretory proteins, are often modified, by the attachment of one or more oligosaccharide groups. The modification, referred to as glycosylation, can dramatically affect the physical properties of proteins and can be important in protein stability, secretion, and localization. Glycosylation occurs at specific locations along the polypeptide backbone. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be any amino acid except proline. N-acetylneuramic acid (also known as sialic acid) is usually the terminal residue of both N-linked and Blinked oligosaccharides. Variables such as protein structure and cell type influence the number and nature of the carbohydrate units within the chains at different glycosylation sites. Glycosylation isomers are also common at the same site within a given cell type.

Table 2 provides a non-exhaustive list of Cargo polypeptides that correspond to a Cargo polypeptide portion of a heteromultimer described herein. The "Cargo Polypeptide" column discloses Cargo polypeptide molecules followed by parentheses containing scientific and brand names that comprise, or alternatively consist of, that Cargo polypeptide molecule or a fragment or variant thereof. In an embodiment the cargo molecule is a molecule that binds to a protein disclosed in the "Cargo polypeptide" column, or in Zhu et al. (Nucleic Acids Res. 38(1), D787-D791 (2009)); Wishart et al. (Nucleic Acids Res 36, D901-D906 (2008)); Ahmed et al. (Nucleic Acids Res 39, D960-D967 (2011)) incorporated by reference herein, or a protein that belongs in the class of therapeutic target molecules.

"Cargo polypeptide" as used herein may refer either to an individual Cargo polypeptide molecule (as defined by the amino acid sequence obtainable from the CAS and Genbank accession numbers), or to the entire group of Cargo polypeptide associated with a given Cargo polypeptide molecule disclosed in this column, or a Cargo polypeptide that binds to a polypeptide molecule disclosed in this column.

TABLE 2

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| EPO (Erythropoietin; Epoetin alfa; Epoetin beta; Gene-activated erythropoietin; Darbepoetin-alpha; NESP; Epogen; Procrit; Eprex; Erypo; Espo; Epoimmun; EPOGIN; NEORECORMON; HEMOLINK; Dynepo; ARANESP) | Stimulates cellular differentiation of bone-marrow stem cells at an early stage of erythropoiesis; accelerates the proliferation and maturation of terminally differentiating cells into erythrocytes; and modulates the level of circulating erythrocytes. | Cell proliferation assay using a erythroleukemic cell line TF-1. (Kitamura et al. 1989 J. Cell. Physiol. 140: 323) | Anemia; Anemia in Renal Disease; Anemia in Oncology Patients; Bleeding Disorders; Chronic Renal Failure; Chronic Renal Failure in Pre-Dialysis Patients; Renal Disease; End-Stage Renal Disease; End-Stage Renal Disease in Dialysis Patients; Chemotherapy; Chemotherapy in Cancer Patients; Anemia in zidovudine-treated HIV patients; Anemia in zidovudine-treated patients; Anemia in HIV patients; Anemia in premature infants; Surgical patients (pre and/or post surgery); Surgical patients (pre and/or post surgery) who are anemic; Surgical patients (pre and/or post surgery) who are undergoing elective surgery; Surgical patients (pre and/or post surgery) who are undergoing elective, non-cardiac surgery; Surgical patients (pre and/or post surgery) who are undergoing elective, non-cardiac, non-vascular surgery; Surgical patients (pre and/or post surgery) who are undergoing elective, |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | | | non-vascular surgery; Surgical patients (pre and/or post surgery) who are undergoing cardiac and/or vascular surgery; Aplastic anemia; Refractory anemia; Anemia in Inflammatory Bowel Disease; Refractory anemia in Inflammatory Bowel Disease; Transfusion avoidance; Transfusion avoidance for surgical patients; Transfusion avoidance for elective surgical patients; Transfusion avoidance for elective orthopedic surgical patients; Patients who want to Increase Red Blood Cells. |
| G-CSF (Granulocyte colony-stimulating factor; Granulokine; KRN 8601; Filgrastim; Lenograstim; Meograstim; Nartograstim; Neupogen; NOPIA; Gran; GRANOCYTE; Granulokine; Neutrogin; Neu-up; Neutromax) | Stimulates the proliferation and differentiation of the progenitor cells for granulocytes and monocytes-macrophages. | Proliferation of murine NFS-60 cells (Weinstein et al, Proc Natl Acad Sci USA 1986; 83, pp5010-4) | Chemoprotection; Adjunct to Chemotherapy; Inflammatory disorders; Cancer; Leukemia; Myelocytic leukemia; Neutropenia, Primary neutropenias (e.g.; Kostmann syndrome); Secondary neutropenia; Prevention of neutropenia; Prevention and treatment of neutropenia in HIV-infected patients; Prevention and treatment of neutropenia associated with chemotherapy; Infections associated with neutropenias; Myelopysplasia; Autoimmune disorders; Psoriasis; Mobilization of hematopoietic progenitor cells; Wound Healing; Autoimmune Disease; Transplants; Bone marrow transplants; Acute myelogeneous leukemia; Lymphoma, Non-Hodgkin's lymphoma; Acute lymphoblastic leukemia; Hodgkin's disease; Accelerated myeloid recovery; Glycogen storage disease. |
| GM-CSF (Granulocyte-macrophage colony-stimulating factor; rhuGM-CSF; BI 61012; Prokine; Molgramostim; Sargramostim; GM-CSF/IL 3 fusion; Milodistim; Leucotropin; PROKINE; LEUKOMAX; Interberin; Leukine; Leukine Liquid; Pixykine) | Regulates hematopoietic cell differentiation, gene expression, growth, and function. | Colony Stimulating Assay: Testa, N. G., et al., "Assays for hematopoietic growth factors." Balkwill FR (edt) Cytokines, A practical Approach, pp 229-44; IRL Press Oxford 1991. | Bone Marrow Disorders; Bone marrow transplant; Chemoprotection; Hepatitis C; HIV Infections; Cancer; Lung Cancer; Melanoma; Malignant melanoma; Mycobacterium avium complex; Mycoses; Leukemia; Myeloid Leukemia; Infections; Neonatal infections; Neutropenia; Mucositis; Oral Mucositis; Prostate Cancer; Stem Cell Mobilization; Vaccine Adjuvant; Ulcers (such as Diabetic, Venous Stasis, or Pressure Ulcers); Prevention of neutropenia; Acute myelogenous leukemia; Hematopoietic progenitor cell mobilization; Lymphoma; Non-Hodgkin's lymphoma; Acute Lymphoblastic Leukemia; Hodgkin's disease; Accelerated myeloid recovery; Transplant Rejection; Xenotransplant Rejection. |
| Human growth hormone (Pegvisamont; Somatrem; Somatropin; TROVERT; PROTROPIN; BIO-TROPIN; HUMATROPE; NUTROPIN; NUTROPIN AQ; NUTROPHIN; NORDITROPIN; GENOTROPIN; SAIZEN; SEROSTIM) | Binds to two GHR molecules and Induces signal transduction through receptor dimerization | Ba/F3-hGHR proliferation assay, a novel specific bioassay for serum human growth hormone. J Clin Endocrinol Metab 2000 Nov; 85(11): 4274-9 Plasma growth hormone (GH) immunoassay and tibial bioassay, Appl Physiol 2000 Dec; 89(6): 2174-8 Growth hormone (hGH) receptor mediated cell mediated | Acromegaly; Growth failure; Growth hormone replacement; Growth hormone deficiency; Pediatric Growth Hormone Deficiency; Adult Growth Hormone Deficiency; Idiopathic Growth Hormone Deficiency; Growth retardation; Prader-Willi Syndrome; Prader-Willi Syndrome in children 2 years or older; Growth deficiencies; Growth failure associated with chronic renal insufficiency; Osteoporosis; Postmenopausal osteoporosis; Osteopenia, Osteoclastogenesis; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | proliferation, Growth Horm IGF Res 2000 Oct; 10(5): 248-55 International standard for growth hormone, Horm Res 1999; 51 Suppl 1: 7-12 | burns; Cachexia; Cancer Cachexia; Dwarfism; Metabolic Disorders; Obesity; Renal failure; Turner's Syndrome; Fibromyalgia; Fracture treatment; Frailty, AIDS wasting; Muscle Wasting; Short Stature; Diagnostic Agents; Female Infertility; lipodystrophy. |
| Insulin (Human insulin; Insulin aspart; Insulin Glargine; Insulin lispro; Lys-B28 Pro-B29; lyspro; LY 275585; diarginylinsulin; Des-B26-B30-insulin-B25-amide; Insulin detemir; LABI; NOVOLIN; NOVORAPID; HUMULIN; NOVOMIX 30; VELOSULIN; NOVOLOG; LANTUS; ILETIN; HUMALOG; MACRULIN; EXUBRA; INSUMAN; ORALIN; ORALGEN; HUMAHALE; HUMAHALIN) | Stimulates glucose uptake and promotes glycogenesis and lipogenesis. | Insulin activity may be assayed in vitro using a [3-H]-glucose uptake assay. (J Biol Chem 1999 Oct. 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Interferon alfa (Interferon alfa-2b; recombinant; Interferon alfa-n1; Interferon alfa-n3; Peginterferon alpha-2b; Ribavirin and interferon alfa-2b; Interferon alfacon-1; interferon consensus; YM 643; CIFN; interferon-alpha consensus; recombinant methionyl consensus interferon; recombinant consensus interferon; CGP 35269; RO 253036; RO 258310; INTRON A; PEG-INTRON; OIF; OMNIFERON; PEG-OMNIFERON; VELDONA; PEG-REBETRON; ROFERON A; WELLFERON; ALFERON N/LDO; REBETRON; ALTEMOL; VIRAFERON PEG; PEGASYS; VIRAFERON; VIRAFON; AMPLIGEN; INFERGEN; INFAREX; ORAGEN) | Confers a range of cellular responses including antiviral, antiproliferative, antitumor and immunomodulatory activities; stimulate production of two enzymes: a protein kinase and an oligoadenylate synthetase. | Anti-viral assay: Rubinstein S, Familletti PC, Pestka S. (1981) Convenient assay for interferons. J. Virol. 37(2): 755-8; Anti-proliferation assay: Gao Y, et al (1999) Sensitivity of an epstein-barr virus-positive tumor line, Daudi, to alpha interferon correlates with expression of a GC-rich viral transcript. Mol Cell Biol. 19(11): 7305-13. | Viral infections; HIV Infections; Hepatitis; Chronic Hepatitis; Hepatitis B; Chronic Hepatitis B; Hepatitis C; Chronic Hepatitis C; Hepatitis D; Chronic Hepatitis D; Human Papillomavirus; Herpes Simplex Virus Infection; External Condylomata Acuminata; HIV; HIV Infection; Oncology; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Bacterial Infections; Chemoprotection; Thrombocytopenia; Multiple Sclerosis; Pulmonary Fibrosis; Age-Related Macular Degeneration; Macular Degeneration; Crohn's Disease; Neurological Disorders; Arthritis; Rheumatoid Arthritis; Ulcerative Colitis; Osteoporosis, Osteopenia, Osteoclastogenesis; Fibromyalgia; Sjogren's Syndrome; Chronic Fatigue Syndrome; Fever; Hemmorhagic Fever; Viral Hemmorhagic Fevers; Hyperglycemia; Diabetes; Diabetes Insipidus; Diabetes mellitus; Type 1 diabetes; Type 2 diabetes; Insulin |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | | | resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Calcitonin (Salmon Calcitonin (Salcatonin); Calcitonin human-salmon hybrid; Forcaltonin; Fortical; Calcitonin; Calcitonina Almirall; Calcitonina Hubber; Calcimar; Calsynar; Calogen; Miacalcic; Miacalcin; SB205614; Macritonin; Cibacalcin; Cibacalcina; Cibacalcine; Salmocalcin; PowderJect Calcitonin) (CAS-21215-62-3) | Regulates levels of calcium and phosphate in serum; causes a reduction in serum calcium--an effect opposite to that of human parathyroid hormone. | Hypocalcemic Rat Bioassay, bone resorbing assay and the pit assay, CT receptor binding assay, CAMP stimulation assay: J Bone Miner Res 1999 Aug; 14(8): 1425-31 | Bone Disorders; Fracture prevention; Hypercalcemia; Malignant hypercalcemia; Osteoporosis; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Interferon beta (Interferon beta-1a; Interferon beta 1b; Interferon-beta-serine; SH 579; ZK 157046; BCDF; beta-2 IF; Interferon-beta-2; rhIL-6; SJ0031; DL 8234; FERON; IFNbeta; BETASERON; AVONEX; REBIF; BETAFERON; SIGOSIX) | Modulates MHC antigen expression, NK cell activity and IFNg production and IL12 production in monocytes. | Anti-viral assay: Rubinstein S, Familletti PC, Pestka S. (1981) Convenient assay for interferons. J. Virol. 37(2): 755-8; Anti-proliferation assay: Gao Y, et al (1999) Sensitivity of an epstein-barr virus-positive tumor line, Daudi, to alpha interferon correlates with expression of a GC-rich viral transcript. Mol Cell Biol. 19(11): 7305-13. | Multiple Sclerosis; Oncology; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Bacterial Infections; Chemoprotection; Thrombocytopenia; Viral infections; HIV Infections; Hepatitis; Chronic Hepatitis; Hepatitis B; Chronic Hepatitis B; Hepatitis C; Chronic Hepatitis C; Hepatitis D; Chronic Hepatitis D; Human Papillomavirus; Herpes Simplex Virus Infection; External Condylomata Acuminata; HIV; HIV Infection; Pulmonary Fibrosis; Age-Related Macular Degeneration; Macular Degeneration; Crohn's Disease; Neurological Disorders; Arthritis; Rheumatoid Arthritis; Ulcerative Colitis; Osteoporosis, Osteopenia, Osteoclastogenesis; Fibromyalgia; Sjogren's Syndrome; Chronic Fatigue Syndrome; Fever; Hemmorhagic Fever; Viral Hemmorhagic Fevers; Hyperglycemia; Diabetes; Diabetes |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | | | Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Growth hormone releasing factor; Growth hormone releasing hormone (Sermorelin acetate; Pralmorelin; Somatorelin; Somatoliberin; Geref; Gerel; Groliberin) | Acts on the anterior pituitary to stimulate the production and secretion of growth hormone and exert a trophic effect on the gland. | Growth hormone-releasing peptides (GHRPs) are known to release growth hormone (GH) in vivo and in vitro by a direct action on receptors in anterior pituitary cells. Biological activity can be measured in cell lines expressing growth hormone releasing factor receptor (Mol Endocrinol 1992 Oct; 6(10): 1734-44, Molecular Endocrinology, Vol 7, 77-84). | Acromegaly; Growth failure; Growth hormone replacement; Growth hormone deficiency; Pediatric Growth Hormone Deficiency; Adult Growth Hormone Deficiency; Idiopathic Growth Hormone Deficiency; Growth retardation; Prader-Willi Syndrome; Prader-Willi Syndrome in children 2 years or older; Growth deficiencies; Growth failure associated with chronic renal insufficiency; Osteoporosis; Osteopenia, Osteoclastogenesis; Postmenopausal osteoporosis; burns; Cachexia; Cancer Cachexia; Dwarfism; Metabolic Disorders; Obesity; Renal failure; Turner's Syndrome; Fibromyalgia; Fracture treatment; Frailty, AIDS wasting; Muscle Wasting; Short Stature; Diagnostic Agents; Female Infertility; lipodystrophy. |
| IL-2 (Aldesleukin; interleukin-2 fusion toxin; T cell growth factor; PROLEUKIN; IMMUNACE; CELEUK; ONCOLIPIN 2; MACROLIN) | Promotes the growth of B and T cells and augments NK cell and CTL cell killing activity. | T cell proliferation assay "Biological activity of recombinant human interleukin-2 produced in Escherichia coli." Science 223: 1412-1415, 1984. natural killer (NK) cell and CTL cytotoxicity assay "Control of homeostasis of CD8+ memory T cells by opposing cytokines. Science 288: 675-678, 2000; CTLL-2 Proliferation: Gillis et al (1978) J. Immunol. 120, 2027 | Cancer; Solid Tumors; Metastatic Renal Cell Carcinoma; Metastatic Melanoma; Malignant Melanoma; Melanoma; Renal Cell Carcinoma; Renal Cancer; Lung Cancer (e.g,. Non-Small Cell Lung Cancer or Small Cell Lung Cancer); Colon Cancer; Breast Cancer; Liver Cancer; Leukemia; Preleukemia; Hematological Malignancies; Hematological Disorders; Acute Myeloid Leukemia; Melanoma; Malignant Melanoma; Non-Hodgkin's Lymphoma; Ovarian Cancer; Prostate Cancer; Brain Cancer; Glioma; Glioblastoma Multiforme; Hepatitis; Hepatitis C; Lymphoma; HIV Infection (AIDS); Inflammatory Bowel Disorders; Kaposi's Sarcoma; Multiple Sclerosis; Arthritis; Rheumatoid Arthritis; Transplant Rejection; Diabetes; Type 1 Diabetes Mellitus; Type 2 Diabetes. |
| Parathyroid hormone; parathyrin (PTH; Ostabolin; ALX1-11; hPTH 1-34; LY 333334; MN 10T; parathyroid hormone (1-31); FORTEO; PARATHAR) | Acts in conjuction with calcitonin to control calcium and phosphate metabolism; elevates blood calcium level; stimulates the activity of osteocytes; enhances absorption of Ca+/Pi from small intestine | Adenylyl cyclase stimulation in rat osteosarcoma cells, ovariectomized rat model of osteoporosis: IUBMB Life 2000 Feb; 49(2): 131-5 | Bone Disorders; Fracture prevention; Hypercalcemia; Malignant hypercalcemia; Osteoporosis; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | into blood; promotes reabsorption of Ca+ and inhibits Pi by kidney tubules. | | disease; osteoclast differentiation inhibition; bone disorders; bone healing and regeneration. |
| Resistin | Mediates insulin resistance in Type II diabetes; inhibits insulin-stimulated glucose uptake | Ability of resistin to influence type II diabetes can be determined using assays known in the art: Pontoglio et al., J Clin Invest 1998 May 15; 101(10): 2215-22. | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| TR6 (DcR3; Decoy Receptor 3; FASTR) | Inhibits Fas Ligand and AIM-2 (TL5, LIGHT) mediated apoptosis. | Cellular apoptosis can be measured by annexin staining, TUNEL staining, measurement of caspase levels. Inhibition of cell growth can also be directly measured, for example by ALOMAR Blue staining. Assay refs: cytotoxicity assay on human fibrosarcoma (Epsevik and Nissen-Meyer, 1986, J. Immunol. methods). | Fas Ligand or LIGHT induced apoptotic disorders: hepatitis; liver failure (including fulminant liver failure); graft versus host disease; graft rejection; myelodysplastic syndrome; renal failure; insulin dependent diabetes mellitus; rheumatoid arthritis; inflammatory bowel disease; autoimmune disease; toxic epidermal necrolysis; multiple sclerosis. |
| DeCAF (D-SLAM; BCM-like membrane protein; BLAME (B lymphocyte activator macrophage expressed))x | Inhibits proliferation and differentiation of B cells; Antagonize BLyS activity | DeCAF activity can be determined using assays known in the art, such as for example, those described in Examples 32-33 of International Publication No. WO0111046. | B cell and/or T cell mediated immune disorders; Immunodeficiency (e.g., Common Variable Immunodeficiency, Selective IgA Deficiency) |
| BLyS (B Lymphocyte Stimulator; Neutrokine alpha; TL7; BAFF; TALL-1; THANK; radiolabeled BLyS) | Promotes proliferation, differentiation and survival of B cells; Promotes immunoglobulin production by B cells. | BLyS activity can be determined using assays known in the art, such as, for example, the costimulatory proliferation assay and other assays disclosed by Moore et al., 1999, Science, 285(5425): 260-3. | B cell and/or T cell mediated immune disorders, particularly immune system disorders associated with low B cell numbers or low serum immunoglobulin; Immunodeficiency (e.g., Common Variable Immunodeficiency, Selective IgA Deficiency). Radiolabeled forms: lymphoma, non-Hodgkins lymphoma, chronic lymphocytic leukemia, multiple myeloma. |
| Anti-BLyS single chain antibody (scFvI116A01, scFvI050B11, scFvI006D08) and others. | Agonize or antagonize BlyS activity. | BLyS agonist or antagonist activity can be determined using assays known in the art, such as, for example, a modified version the costimulatory proliferation assay disclosed by Moore et al., 1999, Science, 285(5425): 260-3, in which BlyS is mixed or preincubated with the anti-BlyS antibody prior to being applied to the responder B lymphocytes. | B cell and/or T cell mediated immune disorders; Autoimmune disorders, particularly autoimmune diseases associated with the production of autoantibodies; Rheumatoid Arthritis, Systemic Lupus Erythmatosus; Sjogren's Syndrome, cancers expressing Blys as an autocrine growth factor, e.g. certain chronic lymphocytic leukemias. |
| MPIF-1 (Myeloid Progenitor Inhibitory Factor; CK beta-8; | Inhibits myeloid progenitor cells; and activates monocytes | MPIF-1 activity can be measured using the myeloprotection assay | Chemoprotection; Adjunct to Chemotherapy; Inflammatory disorders; Cancer; Leukemia; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Mirostipen) | | and chemotaxis assay described in U.S. Pat. No. 6,001,606. | Myelocytic leukemia; Neutropenia, Primary neutropenias (e.g.; Kostmann syndrome); Secondary neutropenia; Prevention of neutropenia; Prevention and treatment of neutropenia in HIV-infected patients; Prevention and treatment of neutropenia associated with chemotherapy; Infections associated with neutropenias; Myelopysplasia; Autoimmune disorders; Psoriasis; Mobilization of hematopoietic progenitor cells; Wound Healing; Autoimmune Disease; Transplants; Bone marrow transplants; Acute myelogeneous leukemia; Lymphoma, Non-Hodgkin's lymphoma; Acute lymphoblastic leukemia; Hodgkin's disease; Accelerated myeloid recovery; Glycogen storage disease. |
| KDI (Keratinocyte Derived Interferon; Interferon Kappa Precursor) | Inhibits bone marrow proliferation; and shows antiviral activity. | KDI activity can be measured using the antiviral and cell proliferation assays described in Examples 57-63 of International Publication No. WO0107608. | Multiple sclerosis; Hepatitis; Cancer; Viral infections, HIV infections, Leukemia. |
| TNFR2 (p75) (ENBREL) | Binds both TNFα and TNFβ; mediates T-cell proliferation by TNF; reduces signs and structural damage in patients with moderately to severely active rheumatoid arthritis (RA). | T-cell proliferation can be measured using assays known in the art. For example, "Lymphocytes: a practical approach" edited by: SL Rowland, AJ McMichael - chapter 6, pages 138-160 Oxford University Press (2000); and "Current Protocols on CD-ROM" section 3.12 Proliferation Assays for T-cell Function John Wiley & Soncs, Inc. (1999). | Autoimmune disease; Rheumatoid Arthritis; Psoriatic arthritis; Still's Disease; Ankylosing Spondylitis; Cardiovascular Diseases; Vasulitis; Wegener's granulomatosis; Amyloidosis; Systemic Lupus Erythematosus, Insulin-Dependent Diabetes Mellitus; Immunodeficiency Disorders; Infection; Inflammation; Inflammatory Bowel Disease; Chrohn's Disease; Psoriasis; AIDS; Graft Rejection; Graft Versus Host Disease. |
| Keratinocyte growth factor 2 (Repifermin; KGF-2; Fibroblast Growth Factor-10; FGF-10) | Stimulates epithelial cell growth. | KGF-2 activity can be measured using the wound healing assays and epithelial cell proliferation assays described in U.S. Pat. No. 6,077,692. | Stimulate Epithelial Cell Proliferation; Stimulate Basal Keratinocytes; Wound Healing; Stimulate Hair Follicle Production; Healing Of Dermal Wounds. Wound Healing; Eye Tissue Wounds, Dental Tissue Wounds, Oral Cavity Wounds, Diabetic Ulcers, Dermal Ulcers, Cubitus Ulcers, Arterial Ulcers, Venous Stasis Ulcers, Burns Resulting From Heat Exposure Or Chemicals, or Other Abnormal Wound Healing Conditions such as Uremia, Malnutrition, Vitamin Deficiencies or Complications Associated With Systemic Treatment With Steroids, Radiation Therapy or Antineoplastic Drugs or Antimetabolites; Promote Dermal Reestablishment Subsequent To Dermal Loss; Increase the Adherence Of Skin Grafts To A Wound Bed; Stimulate Re-Epithelialization from The Wound Bed; To Promote Skin Strength; Improve The Appearance Of Aged Skin; Proliferate Hepatocytes, Lung, Breast, Pancreas, Stomach, Bladder, Small Intestine, Large Intestine; Sebocytes, Hair Follicles, Type II Pneumocytes, |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Mucin-Producing Goblet Cells, or Other Epithelial Cells, Endothelial Cells, Keratinocytes, or Basal Keratinocytes (and Their Progenitors) Contained Within The Skin, Lung, Liver, Bladder, Eye, Salivary Glands, or Gastrointestinal Tract; Reduce The Side Effects Of Gut Toxicity That Result From Radiation, Chemotherapy Treatments Or Viral Infections; Cytoprotector, especially of the Small Intestine Mucosa or Bladder; Mucositis (Mouth Ulcers); Regeneration Of Skin; Full and/or Partial Thickness Skin Defects, including Burns, (e.g., Repopulation Of Hair Follicles, Sweat Glands, And Sebaceous Glands); Psoriasis; Epidermolysis Bullosa; Blisters; Gastric and/or Doudenal Ulcers; Reduce Scarring; Inflamamatory Bowel Diseases; Crohn's Disease; Ulcerative Colitis; Gut Toxicity; Lung Damage; Repair Of Alveoli And/or Brochiolar Epithelium; Acute Or Chronic Lung Damage; Emphysema, ARDS; Inhalation Injuries; Hyaline Membrane Diseases; Infant Respiratory Distress Syndrome; Bronchopulmonary Displasia In Premature Infants; Fulminant Liver Failure; Cirrhosis, Liver Damage caused by Viral Hepatitis and/or Toxic Substances; Diabetes Mellitus; Inflammation. |
| TR2 (and TR2sv1, TR2SV2; TNFRSF14; HVEM; Herpes Virus Entry Mediator; ATAR) | Inhibits B cell proliferation, and mediates and inhibits Herpes Simplex Virus (HSV) infection. | Co-stimulation B-cell proliferation assay and Ig production assay (Moore et al., 1999, Science, 285(5425): 260-3.). HSV-1 and HSV-2 Infectivity Assay: International Publication No. WO 97/ 04658 | Herpes; immune disorders; autoimmune disease; graft versus host disease; graft rejection; variable immunodeficiency; immunodeficiency syndromes; cancer. |
| Macrophage derived chemokine, MDC (Ckbeta-13) | Chemotactic for monocyte-derived dendritic cells and IL-2-activated natural killer cells. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Inflammatory diseases; wound healing; angiogenesis; AIDS infection. |
| HAGDG59 (Retinal short-chain dehydrogenase) | Activates MIP1a release in Dendritic Cells. | Dendritic cell assays are well known in the art. For example, J. Immunol. 158: 2919-2925 (1997); J. Leukoc. Biol. 65: 822-828 (1999). | Immune disorders; cancer; viral infection; inflammation; sepsis; arthritis; asthma. |
| GnRH (Gonadotropin Releasing Hormone) | Promotes release of follicle-stimulating hormone and luteinizing hormone from anterior pituitary. | GnRH is known to cause the release of follicle stimulating hormone (FSH) and/or luteinizing hormone (LH) in vivo by a direct action on receptors in anterior pituitary gonadotropes. GnRH activity can be determined by measuring FSH levels in the medium of cultured | Infertility; Kallmann's syndrome or other forms of hypergonadotropic hypergonadism (failure to go through puberty naturally). |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | gonadotropes before and after GnRH supplementation. For example, Baker et al. Biol Reprod 2000 Sep; 63(3): 865-71. | |
| Teprotide | Inhibits angiotensin converting enzyme (ACE). | Inhibition of ACE can be determined using assays known in the art. For example, Anzenbacherova et al., J. Pharma Biomed Anal 2001 Mar; 24(5-6): 1151-6. | Hypertension; congestive heart failure. |
| Human chemokine HCC-1 (ckBeta-1; HWFBD) | Involved in inflammation, allergy, tissue rejection, viral infection, and tumor biology; enhances proliferation of CD34+ myeloid progenitor cells. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Autoimmune disorders; Immunity; Vascular and Inflammatory disorders; HIV; AIDS; infectious diseases. |
| ACE2 inhibitor (DX512) | Inhibits production of angiotensin II which induces aldosterone production, arteriolar smooth muscle vasoconstriction, and proliferation of cardiac fibroblasts, Induces angiogenesis; an enzyme that converts angiotensin I to angiotensin1-9; also cleaves des-Arg, bradykinin and neurotensin. | Inhibition of angiotensin can be determined using assays known in the art. For example, in vitro using a proliferation assay with rat cardiac fibroblasts as described in Naunyn Schmiedebergs Arch Pharmacol 1999 May; 359(5): 394-9. | Treatment for elevated angiotensin II and/or aldosterone levels, which can lead to vasoconstriction, impaired cardiac output and/or hypertension; Cardiovascular Disease; Cardiac Failure; Diabetes; Type II Diabetes; Proteinuria; Renal disorders, congestive heart failure. |
| TR1 (OCIF; Osteoclastogenesis inhibitory factor; osteoprotegerin, OPG; tumor necrosis factor receptor superfamily member 11B precursor;) | Inhibits osteoclastogenesis and bone resorption, and induces fibroblast proliferation. | Coculture Assay for Osteoclastogenesis, Bone resorption assay using fetal long-bone organ culture system, dentine resorption assay, and fibroblast proliferation assays are each described in Kwon et al., FASEB J. 12: 845-854 (1998). | Osteoporosis; Paget's disease; osteopenia; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration; organ calcification; vascular calcification. |
| Human chemokine Ckbeta-7 | Chemotactic for both activated (CD3+) T cells and nonactivated (CD14−) lymphocytes and (CD4+) and (CD8+) T lymphocytes and (CD45RA+) T cells | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer; Wound healing; Inflammatory disorders; Immmunoregulatory disorders; Atherosclerosis; Parasitic Infection; Rheumatoid Arthritis; Asthma; Autoimmune disorders. |
| CKbeta4 (HGBAN46; HE9DR66) | Attracts and activates microbicidal leukocytes; Attracts CCR6-expressing immature dendritic cells and memory/effector T cells; B-cell chemotaxis; inhibits proliferation of myeloid progenitors; chemotaxis of PBMC's. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer; Solid Tumors; Chronic Infection; Autoimmune Disorders; Psoriasis; Asthma; Allergy; Hematopoiesis; Wound Healing; Bone Marrow Failure; Silicosis; Sarcoidosis; Hyper-Eosinophilic Syndrome; Lung Inflammation; Fibrotic Disorders; Atherosclerosis; Periodontal diseases; Viral diseases; Hepatitis. |
| Leptin | Controls obesity through regulation of appetite, reduction of | in vivo modulation of food intake, reduction in body weight, and | Hyperglycemia; Diabetes; Diabetes Insipidus; Diabetes mellitus; Type 1 diabetes; Type 2 diabetes; Insulin |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | body weight, and lowering of insulin and glucose level. | lowering of insulin and glucose levels in ob/ob mice, radioimmunoassay (RIA) and activation of the leptin receptor in a cell-based assay. Protein Expr Purif 1998 Dec; 14(3): 335-42 | resistance; Insulin deficiency; Hyperlipidemia; Hyperketonemia; Non-insulin dependent Diabetes Mellitus (NIDDM); Insulin-dependent Diabetes Mellitus (IDDM); a Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Immunological Disorders; Immunosuppression. |
| IL-1 receptor antagonist (Anakinra; soluble interleukin-1 receptor; IRAP; KINERET; ANTRIL) | Binds IL1 receptor without activating the target cells; inhibits the binding of IL1-alpha and IL1-beta; and neutralizes the biologic activity of IL1-alpha and IL1-beta. | 1) Competition for IL-1 binding to IL-1 receptors in YT-NCI or C3H/HeJ cells (Carter et al., Nature 344: 633-638, 1990); 2) Inhibition of IL-1-induced endothelial cell-leukocyte adhesion (Carter et al., Nature 344: 633-638, 1990); 3) Proliferation assays on A375-C6 cells, a human melanoma cell line highly susceptible to the antiproliferative action of IL-1 (Murai T et al., J. Biol. Chem. 276: 6797-6806, 2001). | Autoimmune Disease; Arthritis; Rheumatoid Arthritis; Asthma; Diabetes; Diabetes Mellitus; GVHD; Inflammatory Bowel Disorders; Chron's Disease; Ocular Inflammation; Psoriasis; Septic Shock; Transplant Rejection; Inflammatory Disorders; Rheumatic Disorders; Osteoporosis; Postmenopausal Osteoporosis; Stroke. |
| TREM-1 (Triggering Receptor Expressed on Monocytes 1) | Mediates activation of neutrophil and monocytes; Stimulates neutrophil and monocyte-mediated inflammatory response; Promotes secretion of TNF, IL-8, and MCP-1; Induces neutrophil degranulation, Ca2+ mobilization and tyrosine phosphorylation of extracellular signal-related kinase 1 (ERK1), ERK2 and phospholipase C-gamma. | Secretion of cytokines, chemokines, degranulation, and cell surface activation markers can be determined using assays described in Bouchon et al, J Immunol 2000 May 15; 164(10): 4991-5. | Inflammation; Sepsis; bacterial infection; autoimmune diseases; GVHD. |
| HCNCA73 | Induces T-cell activation-expression of CD152 marker; Stimulates release of TNF-a and MIP-1a from immature, monocyte-derived dendritic cells; Promotes maturation of dendritic cells. | FMAT can be used to measure T-cell surface markers (CD69, CD152, CD71, HLA-DR) and T-cell cytokine production (e.g., IFNg production). J. of Biomol. Screen. 4: 193-204 (1999). Other T-cell proliferation assays: "Lymphocytes: a practical approach" edited by: SL Rowland, AJ McMichael - Chapter 6, pages 138-160 Oxford University Press (2000); WO 01/21658 Examples 11-14, 16-17 and 33. | Autoimmune disorders; Inflammation of the gastrointestinal tract; Cancer; Colon Cancer; Allergy; Crohn's disease. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
| --- | --- | --- | --- |
| VEGF-2 (Vascular Endothelial Growth Factor-2; VEGF-C) | Promotes endothelial cell proliferation. | VEGF activity can be determined using assays known in the art, such as those disclosed in International Publication No. WO0045835, for example. | Coronary artery disease; Critical limb ischemia; Vascular disease; proliferation of endothelial cells, both vascular and lymphatic. Antagonists may be useful as anti-angiogenic agents; Cancer. |
| HCHNF25 (jumping translocation breakpoint) | Activates MIP1a Release in Dendritic Cells. | Dendritic cell assays are well known in the art. For example, J. Immunol. 158: 2919-2925 (1997); J. Leukoc. Biol. 65: 822-828 (1999). | Immune disorders; cancer. |
| HLDOU18 (Bone Morphogenic Protein 9 (BMP9); Growth differentiation factor-2 precursor (GDF-2 precursor)) | Activates L6/GSK3 kinase assay. | Assays for activation of GSK3 kinase activity are well known in the art. For example, Biol. Chem. 379(8-9): (1998) 1101-1110.; Biochem J. 1993 Nov 15; 296 (Pt 1): 15-9. | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Glucagon-Like-Peptide 1 (GLP1; Insulinotropin) | Stimulates the synthesis and release of insulin; enhances the sensitivity of adipose, muscle, and liver tissues towards insulin; stimulates glucose uptake; slows the digestive process; suppresses appetite; blocks the secretion of glucagon. | GLP1 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Exendin-4 (AC-2993) | Stimulates the synthesis and release of insulin; enhances the sensitivity of adipose, muscle, and liver tissues towards insulin; stimulates glucose uptake; slows the digestive process; suppresses appetite; blocks the secretion of glucagon. | Exendin-4 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| T20 (T20 HIV inhibitory peptide, DP178; DP178 HIV inhibitory peptide) | a peptide from residues 643-678 of the HIV gp41 transmembrane protein ectodomain which binds to gp41 in its resting state and prevents transformation to the fusogenic state | Virus inhibition assays as described in Zhang et al., Sep. 26 2002, Sciencexpress (www.sciencexpress.org). | HIV; AIDS; SIV (simian immunodeficiency virus) infection. |
| T1249 (T1249 HIV inhibitory peptide; T1249 anti-HIV peptide) | a second generation HIV fusion inbitor | Virus inhibition assays as described in Zhang et al., Sep. 26 2002, Sciencexpress (www.sciencexpress.org). | HIV; AIDS; SIV (simian immunodeficiency virus) infection |
| Interferon Hybrids, specifically preferred: IFNalpha A/D hybrid (BglII version) IFNalpha A/D hybrid (PvuII version) IFNalpha A/F hybrid IFNalpha A/B hybrid IFNbeta 1/alpha D hybrid (IFNbeta-1/alpha-1 hybrid) IFNalpha/beta hybrid | Confers a range of cellular responses including antiviral, antiproliferative, antitumor and immunomodulatory activities; stimulate production of two enzymes: a protein kinase and an oligoadenylate synthetase. Also, modulates MHC antigen expression, NK cell activity and IFNg production and IL12 production in monocytes. | Anti-viral assay: Rubinstein S, Familletti PC, Pestka S. (1981) Convenient assay for interferons. J. Virol. 37(2): 755-8; Anti-proliferation assay: Gao Y, et al (1999) Sensitivity of an epstein-barr virus-positive tumor line, Daudi, to alpha interferon correlates with expression of a GC-rich viral transcript. Mol Cell Biol. 19(11): 7305-13. | Viral infections; HIV Infections; Hepatitis; Chronic Hepatitis; Hepatitis B; Chronic Hepatitis B; Hepatitis C; Chronic Hepatitis C; Hepatitis D; Chronic Hepatitis D; Human Papillomavirus; Herpes Simplex Virus Infection; External Condylomata Acuminata; HIV; HIV Infection; Oncology; Cancer; Solid Tumors; Melanoma; Malignant Melanoma; Renal Cancer (e.g., Renal Cell Carcinoma); Lung Cancer (e.g., Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Bacterial Infections; Chemoprotection; Thrombocytopenia; Multiple Sclerosis; Pulmonary Fibrosis; Age-Related Macular Degeneration; Macular Degeneration; Crohn's Disease; Neurological Disorders; Arthritis; Rheumatoid Arthritis; Ulcerative Colitis; Osteoporosis, Osteopenia, Osteoclastogenesis; Fibromyalgia; Sjogren's Syndrome; Chronic Fatigue Syndrome; Fever; Hemmorhagic Fever; Viral Hemmorhagic Fevers; Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| B-type natriuretic peptide (BNP, brain natriuretic peptide) | stimulates smooth muscle relaxation and vasodilation, natriuresis, and suppression of renin-angiotensin and endothelin. | Inhibition of angiotensin can be determined using assays known in the art, for example using an in vitro proliferation assay with rat cardiac fibroblasts as described in Naunyn Schmiedebergs Arch Pharmacol 1999 May; 359(5): 394-9. Vasodilation can be measured in animals by measuring the myogenic responses of small renal arteries in an isobaric arteriograph system (see Am J Physiol Regul Integr Comp Physiol 2002 Aug; 283(2): R349-R355). Natriuesis is determined by measuring the amount of sodium in the urine. | Congestive heart failure; cardiac volume overload; cardiac decompensation; Cardiac Failure; Left Ventricular Dysfunction; Dyspnea |
| α-defensin, including alpha 1 defensin, alpha 2 defensin, alpha 3 defensin (myeloid-related defensin; DEFA1; neutrophil-specific defensin; CAF) | Suppression of HIV replication; active against bacteria, fungi, and enveloped viruses. | Virus inhibition assays as described in Zhang et al., Sep. 26 2002, Sciencexpress (www.sciencexpress.org). | HIV, AIDS; ARC. |
| Phosphatonin (matrix extracellular phosphoglycoprotein; MEPE) | Regulation of phosphate metabolism. | Blood phosphate levels can be measured using methods known in the art such as the Hypophosphatemic Rat Bioassay. Zoolog Sci 1995 Oct; 12(5): 607-10. | Hyperphosphatemia; Hyperphosphatemia in chronic renal failure; hypophosphatemia; Osteomalacia; Rickets; X-linked dominant hypophosphatemic rickets/osteomalacia (XLH); autosomal dominant hypophosphatemic rickets/osteomalacia (ADHR); tumor-induced rickets/osteomalacia (TIO). |
| P1pal-12 (pepducin, PAR1-based pepducin) | Regulation of protease-activated receptor (PAR) signal transduction and thrombin-mediated aggregation of human platelets. | Platelet aggregation can be measured using methods known in the art such as described in Nature Medicine 2002 Oct; 8(10): 1161-1165. | Protection against systemic platelet activation, thrombus, heart attack, stroke, and/or coagulation disorders. |
| P4pal-10 (pepducin, PAR4-based pepducin) | Regulation of protease-activated receptor (PAR) signal transduction and thrombin-mediated aggregation of human platelets. | Platelet aggregation can be measured using methods known in the art such as described in Nature Medicine 2002 Oct; 8(10): 1161-1165. | Protection against systemic platelet activation, thrombus, heart attack, stroke, and/or coagulation disorders. |
| HRDFD27 | Involved in the proliferation of T cells; Production of TNFgamma. | T-cell proliferation can be measured using assays known in the art. For example, “Lymphocytes: a practical approach” edited by: SL Rowland, AJ McMichael - chapter 6, pages 138-160 Oxford University Press (2000); and “Current Protocols on CD-ROM” section 3.12 Proliferation Assays for T-cell Function John Wiley & Soncs, Inc. (1999). | Chemoprotection; Adjunct to Chemotherapy; Inflammatory disorders; Cancer; Leukemia; Myelocytic leukemia; Neutropenia, Primary neutropenias (e.g.; Kostmann syndrome); Secondary neutropenia; Prevention of neutropenia; Prevention and treatment of neutropenia in HIV-infected patients; Prevention and treatment of neutropenia associated with chemotherapy; Infections associated with neutropenias; Myelopysplasia; Autoimmune disorders; Psoriasis; Mobilization of hematopoietic progenitor cells; Wound Healing; Autoimmune Disease; Transplants; Bone marrow transplants; Acute myelogeneous leukemia; Lymphoma, Non- |

TABLE 2-continued

| Cargo Polypeptide | Biological Activity | Exemplary Activity Assay | Indication |
|---|---|---|---|
| Non-exhaustive list of Cargo polypeptides that correspond to a Cargo polypeptide portion of a heteromultimer | | | |
| | | | Hodgkin's lymphoma; Acute lymphoblastic leukemia; Hodgkin's disease; Accelerated myeloid recovery; Glycogen storage disease |
| HWHGZ51 (CD59; Metastasis-associated GPI-adhered protein homolog) | Stimulates an immune response and induces inflammation by inducing mononuclear cell, eosinophil and PMN infiltration; Inhibits growth of breast cancer, ovarian cancer, leukemia, and melanoma; Overexpressed in colon, lung, breast and rectal tumors; Regulates glucose and/or FFA update by adipocytes and skeletal muscle; Induces redifferentiation of chondrocytes | The ability to affect chondrocyte differentiation can be measured using methods known in the art, such as described in Bone (1995) Sep; 17(3): 279-86. | Skeletal diseases and disorders; Musculoskeletal diseases and disorders; Bone fractures and/or breaks; Osteoporosis (postmenopausal, senile, or idiopathic juvenile); Gout and/or pseudogout; Paget's disease; Osteoarthritis; Tumors and/or cancers of the bone (osteochondromas, benign chondromas, chondroblastomas, chondromyxoid fibromas, osteoid osteomas, giant cell tumors, multiple myelomas, osteosarcomas, fibrosarcomas, malignant fibrous histiocytomas, chondrosarcomas, Ewing's tumors, and/or malignant lymphomas); Bone and joint infections (osteomyelitits and/or infectious arthritis); Charcot's joints; Heel spurs; Sever's disease; Sport's injuries; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Kidney diseases and disorders; Shonlein-Henoch purpura, Berger disease, celiac disease, dermatitis herpetiformis, Chron disease; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Kidney disorders; Hyperinsulinemia; Hypoinsulinemia; Immunological disorders (e.g. arthritis, asthma, immunodeficiency diseases, AIDS, rheumatoid arthritis, granulomatous disease, inflammatory bowl disease, sepsis, acne, neutropenia, neutrophilia, psoriasis, hypersensitivities, T-cell mediated |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | | | cytotoxicity, host-versus-graft disease, autoimmunity disorders, demyelination, systemic lupus erythematosis, drug induced hemolytic anemia, rheumatoid arthritis, Sjorgren's disease, scleroderma) |
| C17 (cytokine-like protein C17) | Inhibits glucose and/or FFA uptake by adipocytes; Induces proliferation of kidney mesangial cells; Regulation of cytokine production and antigen presentation | Proliferation of kidney mesangial cells can be assayed using techniques described in J. Investig. Med. (1998) Aug; 46(6): 297-302. | Kidney diseases and disorders; Shonlein-Henoch purpura, Berger disease, celiac disease, dermatitis herpetiformis, Chron disease; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Kidney disorders; Hyperinsulinemia; Hypoinsulinemia; Hematopoietic disorders; Immunological diseases and disorders; Developmental diseases and disorders; Hepatic diseases and disorders; Cancer (particularly leukemia); Immunological disorders (e.g. arthritis, asthma, immunodeficiency diseases, AIDS, rheumatoid arthritis, granulomatous disease, inflammatory bowl disease, sepsis, acne, neutropenia, neutrophilia, psoriasis, hypersensitivities, T-cell mediated cytotoxicity, host-versus-graft disease, autoimmunity disorders, demyelination, systemic lupus erythematosis, drug induced hemolytic anemia, rheumatoid arthritis, Sjorgren's disease, scleroderma) |
| HDPBQ71 | Regulates production and secretion of IFNgamma; Activation of myeloid cells and/or hematopoietic cells | Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., ""Lymphocytes: a practical approach"" Chapter 6: 138-160 (2000); Gonzalez et al., J Clin Lab Anal 8(5): 225-233 (1995); Billiau et al., Ann NY Acad Sci 856: | Blood disorders and infection (e.g., viral infections, tuberculosis, infections associated with chronic granulomatosus disease and malignant osteoporosis); Autoimmune disease (e.g., rheumatoid arthritis, systemic lupus erythematosis, multiple sclerosis); Immunodeficiency, boosting a T cell-mediated immune response, and suppressing a T cell-mediated immune response; Inflammation and inflammatory disorders; Idiopathic pulmonary fibrosis; Neoplastic diseases (e.g., leukemia, lymphoma, melanoma); Neoplasms and cancers, such as, for example, leukemia, lymphoma, melanoma, and prostate, breast, lung, colon, pancreatic, esophageal, stomach, brain, liver and urinary cancer;. Benign |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | | 22-32 (1998); Boehm et al., Annu Rev Immunol 15: 749-795 (1997), and Rheumatology (Oxford) 38(3): 214-20 (1999) | dysproliferative disorders and pre-neoplastic conditions, such as, for example, hyperplasia, metaplasia, and/or dysplasia; Anemia; Pancytopenia; Leukopenia; Thrombocytopenia; Hodgkin's disease; Acute lymphocytic anemia (ALL); Plasmacytomas; Multiple myeloma; Burkitt's lymphoma; Arthritis; AIDS; Granulomatous disease; Inflammatory bowel disease; Sepsis; Neutropenia; Neutrophilia; Psoriasis; Suppression of immune reactions to transplanted organs and tissues; Hemophilia; Hypercoagulation; Diabetes mellitus; Endocarditis; Meningitis; Lyme Disease; Asthma; Allergy |
| Oscar (osteoclast-associated receptor isoform-3) | Regulator of osteoclast differentiation; regulator of innate and adaptive immune responses | Assay to detect osteoclast differentiation is described in J. Exp. Med. (2002) Jan 21; 195(2): 201-9. | Skeletal diseases and disorders; Musculoskeletal diseases and disorders; Bone fractures and/or breaks; Osteoporosis (postmenopausal, senile, or idiopathic juvenile); Gout and/or pseudogout; Paget's disease; Osteoarthritis; Tumors and/or cancers of the bone (osteochondromas, benign chondromas, chondroblastomas, chondromyxoid fibromas, osteoid osteomas, giant cell tumors, multiple myelomas, osteosarcomas, fibrosarcomas, malignant fibrous histiocytomas, chondrosarcomas, Ewing's tumors, and/or malignant lymphomas); Bone and joint infections (osteomyelitits and/or infectious arthritis); Charcot's joints; Heel spurs; Sever's disease; Sport's injuries |
| Tumstatin (T5, T7 or T8 peptide; α3(IV)NC1) | Inhibits angiogenesis; Inhibits tumor growth; Inhibits protein synthesis | A tumor cell proliferation assay is described in J. Biol. Chem. (1997) 272: 20395-20401. Protein synthesis can be measured as described in Science (2002) Jan 4; 295(5552): 140-3. | Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Angiogenesis |
| CNTF (Ciliary neurotrophic factor) | Enhances myelin formation; Reduces photoreceptor degradation; Regulates calcium currents | Regulation of myelin formation can be assayed as described in J. Neurosci. (2002) Nov. 1; 22(21): 9221-7. | Neurological and neural diseases and disorders, particularly diseases and disorders associated with myelin and demyelination, such as, for example, ALS, multiple sclerosis, Huntington's disease; Neuronal and spinal cord injuries; Disorders of the eye, such as, for example, retinitis pigmentosa, blindness, color-blindness, macular degeneration. |
| Somatostatin (Octreotide; octreotide acetate; Sandostating LAR ®) | Inhibits growth hormone, glucagons and insulin; Suppresses LF response to GnRH; | Inhibition of growth hormone release in humans by somatostatin can be measured as | Cancer; Metastatic carcinoid tumors; Vasoactive Intestinal Peptide secreting adenomas; Diarrhea and Flushing; Prostatic disorders and |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | Decreases splanchnic blood flow; Inhibits release of serotonin, gastrin, vasoactive intestinal peptide, secretin, motilin, and pancreatic polypeptide. | described in J. Clin. Endocrinol. Metab. (1973) Oct; 37(4): 632-4. Inhibition of insulin secretion by somatostatin can be measured as described in the Lancet (1973) Dec. 8; 2(7841): 1299-1301. | cancers; Breast cancer; Gastrointestinal disorders and cancers; Cancers of the endocrine system; Head and neck paragangliomas; Liver disorders and cancers; Nasopharyngeal cancers; Thyroid disorders and cancers; Acromegaly; Carcinoid Syndrome; Gallbladder disorders, such as gallbladder contractility diseases and abnormal bile secretion; Psoriasis; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Kidney disorders; Neurological disorders and diseases, including Alzheimers Disease, Parkinson's disease and dementia; Neuropsychotic disorders, including Bipolar affective disorder; Rheumatoid arthritis; Hypertension; Intracranial hypertension; Esophageal varices; Graves' disease; Seizures; Epilepsy; Gastritis; Angiogenesis; |
| IL-22 (IL22, interleukin-22; IL17D, IL27) | Stimulates glucose uptake in skeletal muscle cells; increases skeletal muscle insulin sensitivity. | IL-22 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| HCE1P80 | Stimulates glucose uptake in; increases insulin sensitivity, | HCE1P80 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| HDRMI82 | Stimulates glucose uptake; increases insulin sensitivity. | HDRMI82 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| HDALV07 (adiponectin; gelatin-binding 28k protein precursor; adipose most abundant gene transcript; APM-1; GBP28; ACRP30; ADIPOQ) | Modulates insulin action | Insulin activity may be assayed in vitro using a [3-H]-glucose uptake assay. (J Biol Chem 1999 Oct 22; 274(43): 30864-30873). | Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Hyperglycemia; Familial combined hyperlipidemia; Metabolic syndrome; Inflammatory disorders; Atherogenic disorders |
| C Peptide | An insulin precursor involved in insulin regulation | C-peptide concentrations can be measured using assays well known in the art, such as the one described in PNAS (1970) Sep; 67(1): 148-55 | Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Hyperglycemia; Familial combined hyperlipidemia; Metabolic syndrome |
| HCBOG68 (enteric adipokine; Fat SID; proline rich acidic protein) | Controls proliferation/ differentiation or metabolism/ physiology/pathology/ of adipocytes and adipose tissue in response to dietary conditions. | Activation of cAMP-mediated transcription in adipocytes can be assayed using methods known in the art (Berger et al., Gene 66: 1-10 (1998); Cullen and Malm, Methods in Enzymol 216: 362-368 (1992); Henthorn et al., Proc Natl Acad Sci USA 85: 6342-6346 (1988); | Treatment of Obesity; treatment of Diabetes; suppression of body weight gain; suppression of appetite. Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | Reusch et al., Mol Cell Biol 20(3): 1008-1020 (2000); and Klemm et al., J Biol Chem 273: 917-923 (1998)). | With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. Other indications for antibodies and/or antagonists, include treatment of weight loss; treatment of AIDS wasting; appetite stimulant; treatment of cachexia. |
| PYY (Peptide YY), including $PYY_{3-36}$ (amino acid residues 31-64 of full length PYY, amino acid residues 3-36 of mature PYY) | Decreases appetite; increases satiety; decreases food intake. | Appetite and food intake can be can be measured by methods known in the art (Batterham et al. Nature 2002; 418: 650654) | Most preferred: Treatment of Obesity; treatment of Diabetes; suppression of body weight gain; suppression of appetite. Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. Other indications for antibodies, antagonists: treatment of weight loss; treatment of AIDS wasting; appetite stimulant; treatment of cachexia. |
| WNT10b | Inhibits adipogenesis. | WNT10b activity can be measured using adipogenesis inhibition assays (Ross et al., Science 2000; 289(5481): 950-953 | Most preferred: Treatment of Obesity; suppression of body weight gain; suppression of appetite. Other indications: Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM). |
| WNT11 | Promotes cardiogenesis. | WNT11 activity can be measured using assays known in the art, including cardiogenesis assays (Eisenberg et al., Dev Dyn 1999 Sep; 216(1): 45-58). | Treatment of Cardiovascular disorders; Congestive Heart Failure; Myocardial Infarction. |
| Herstatin | Inhibits cancer proliferation. | Herstatin activity can be measured using cell proliferation assays known in the art (Doherty et al., PNAS 1999; 96(19): 10869-10874. | Oncology; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer); Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Hairy Cell Leukemia; Chronic |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Myelogeonus Leukemia; Hematological Malignancies; Hematological Disorders; Multiple Myeloma. |
| Adrenomedullin | stimulates vasodilation; promotes bone growth. | Vasodilation can be measured using assays known in the art (Ashton et al. Pharmacology 2000; 61(2): 101-105. The promotion of bone growth can be measured using assays known in the art, such as the osteoblast proliferation assay (Cornish et al. Am J Physiol 1997 Dec; 273(6 Pt 1): E1113-20). | Treatment of Congestive Heart Failure; Hypertension; Myocardial Infarction; Septic Shock; Osteoporosis; Postmenopausal osteoporosis; Osteopenia. |
| Nogo Receptor | Receptor for the axon growth inhibitor, Nogo. | The promotion of axon regeneration and growth can be measured using assays known in the art (Fournier et al. Nature 2001; 409(6818): 341-346). | Treatment of Central Nervous System Damage; Spinal Cord Injury; Peripheral Nerve Damage; Neurodegenerative Diseases; Parkinson's Disease; Alzheimer's Disease; Huntington's Disease; Amyotrophic Lateral Sclerosis; Progressive Supranuclear Palsy; Creutzfeld-Jacob Disease; Motor Neuron Disease. |
| CART (Cocaine- and Amphetamine-Regulated Transcript) | Inhibits food intact and fat storage; promotes lipid oxidation. | Appetite and food intake can be can be measured by methods known in the art (Batterham et al. Nature 2002; 418: 650654) | Most preferred: Treatment of Obesity; suppression of body weight gain; suppression of appetite. Other indications: Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM). |
| RegIV (Colon Specific Gene; Colon Specific Protein) | Stimulates glucose uptake; increases insulin sensitivity. | RegIV activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Cosyntropin (Cortrosyn) (CAS-16960-16-0) | Synthetic corticotropin; stimulates the release of cortisol. | The activity of cosyntropin can be assessed in vivo by measuring serum cortisol levels. (Frank et al. J. Am. Vet. Med. Assoc. 1998 212(10): 1569-71). | Endocrine; Addison's disease; Cushing's syndrome; pituitary dysfunction; acute adrenal crisis |
| Pexiganan Acetate (CAS-172820-23-4) | Disrupts bacterial membranes. | Pexiganan acetate activity can be assessed using in vitro antibacterial assays known in the art. (Zasloff et al., Antimicrobial Agents and Chemotherapy 1999, 43: 782-788). | Treatment of Infectious Diseases; Treatment of Bacterial Infections. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Pramlintide (Amylin) (CAS-151126-32-8) | Slows gastric emptying; decreases food intake. | Appetite and food intake can be can be measured by methods known in the art (Batterham et al. Nature 2002; 418: 650654) | Treatment of Obesity; treatment of Diabetes; suppression of body weight gain; suppression of appetite; treatment of endocrine disorders; Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. Other indications for antibodies, antagonists: treatment of weight loss; treatment of AIDS wasting; appetite stimulant; treatment of cachexia. |
| Teriparatide (CAS-52232-67-4) | Acts in conjuction with calcitonin to control calcium and phosphate metabolism; elevates blood calcium level; stimulates the activity of osteocytes; enhances absorption of Ca+/Pi from small intestine into blood; promotes reabsorption of Ca+ and inhibits Pi by kidney tubules. | Adenylyl cyclase stimulation in rat osteosarcoma cells, ovariectomized rat model of osteoporosis: IUBMB Life 2000 Feb; 49(2): 131-5 | Bone Disorders; Fracture prevention; Hypercalcemia; Malignant hypercalcemia; Osteoporosis; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Terlipressin (triglycyl lycine vasopressin) (CAS-14636-12-5) | Analog of vasopressin; induces vasoconstriction. | Terlipressin activity can be measured using assays of vasoconstriction, such as the isolated arterial ring preparation. (Landstrom et al., Hum Reprod 1999 Jan; 14(1): 151-5). | Variceal hemorrhage; cirrhosis; portal hypertension; hepatorenal syndrome; Blood-related disorders |
| Ularitide (CAS-118812-69-4) | Stimulates natriuresis, diuresis, and vasodilation. | Ularitide activity can be assessed by measuring cGMP accumulation in rat renal cells. (Valentin et al., Hypertension 1993 Apr; 21(4): 432-8). | Excretory disorders; Acute renal failure; asthma; congestive heart failure; hypertension; pulmonary hypertension; cardiovascular disorders |
| Aprotinin (Trasylol) (CAS-9087-70-1; CAS-11061-94-2; CAS-12407-79-3) | Serine protease inhibitor; attenuates Systemic Inflammatory Response, fibrinolysis and thrombin-induced platelet aggregation. | Inhibition of thrombin-induced platelet aggregation can be measured using methods known in the art. (Poullis et al., J Thorac Cardiovasc Surg 2000 Aug; 120(2): 370-8). | Inhibition of fibrinolysis; reduction of blood loss during surgery; Treatment of Inflammation and Immune Disorders. |
| Aspartocin (CAS-4117-65-1; CAS-1402-89-7) | Antibacteria | Aspartocin activity can be assessed using in vitro antibacterial assays known in the art. (Zasloff et al., Antimicrobial Agents and Chemotherapy 1999, 43: 782-788). | Treatment of Infectious Diseases; treatment of bacterial infections. |
| Calcitonin (Calcimar) (CAS-21215-62-3) | Regulates levels of calcium and phosphate in serum; causes a reduction in serum calcium--an effect | Hypocalcemic Rat Bioassay, bone resorbing assay and the pit assay, CT receptor binding assay, CAMP stimulation | Musculoskeletal; Osteroporosis; Paget's disease; hypercalcemia; Bone Disorders; Fracture prevention; Malignant hypercalcemia; Osteopenia, Osteoclastogenesis; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | opposite to that of human parathyroid hormone. | assay: J Bone Miner Res 1999 Aug; 14(8): 1425-31 | osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Carperitide (HANP; recombinant human atrial natriuretic peptide) (CAS-89213-87-6) | Stimulates natriuresis, diuresis, and vasodilation. | Carperitide activity can be assessed in vitro by measuring cGMP accumulation in a number of cell lines, including PC12 cells and cultured human glomerular cells. (Medvede et al., Life Sci 2001 Aug 31; 69(15): 1783-90; Green et al., J Am Soc Nephrol 1994 Oct; 5(4): 1091-8). | Treatment of Heart Failure; Cardiovascular disorders; Respiratory disorders; Acute respiratory distress syndrome. |
| Desirudin (recombinant hirudin; Revasc) (CAS-120993-53-5) | Inhibits thrombin; inhibits blood clotting. | Desirudin activity can be assessed using blood clotting assays known in the art, such as in vitro platelet aggragation assays. (Glusa, Haemostasis 1991; 21 Suppl 1: 116-20). | Blood-related disorder; Thrombosis; thrombocytopenia; hemorrhages. |
| Emoctakin (interleukin 8) (CAS-142298-00-8) | proinflammatory cytokine | | Treatment of Inflammation, Immune disorders, RSV infection. |
| Felypressin (CAS-56-59-7) | Derivative of Vasopressin; Stimulates vasoconstriction; Induces local anesthesia. | Felypressin vasoconstriction activity can be measured using assays of vasoconstriction, such as the isolated arterial ring preparation. (Landstrom et al., Hum Reprod 1999 Jan; 14(1): 151-5). | Treatment of pain; to induce local anesthesia. |
| Glucagon (CAS-16941-32-5) | Induces hyperglycemia. | Glucagon activity may be assayed in vitro using a [3-H]-glucose uptake assay. (J Biol Chem 1999 Oct 22; 274(43): 30864-30873). | Hypoglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Endocrine disorders. |
| Nagrestipen (CAS-166089-33-4) | | | Inflammation; Immune |
| Pentigetide (Pentyde) (CAS-62087-72-3) | | | Respiratory; Allergy; Immune |
| Proinsulin (CAS-67422-14-4) | Stimulates glucose uptake and promotes glycogenesis and lipogenesis. | Insulin activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; |

TABLE 2-continued

| Non-exhaustive list of Cargo polypeptides that correspond to a Cargo polypeptide portion of a heteromultimer | | | |
|---|---|---|---|
| Cargo Polypeptide | Biological Activity | Exemplary Activity Assay | Indication |
| | | | Metabolic Disorders; Immune Disorders; Obesity; Vascular Disorders; Suppression of Body Weight; Suppression of Appetite; Syndrome X. |
| Becaplermin (Regranex; recombinant PDGF-BB) (CAS-165101-51-9) | Promotes wound healing. | Becaplermin activity can be assessed using animal wound healing models known in the art. (Saba et al., Ann Plast Surg 2002 Jul; 49(1): 62-6). | Stimulate Epithelial Cell Proliferation; Stimulate Basal Keratinocytes; Promote Wound Healing; Stimulate Hair Follicle Production; Healing Of Dermal Wounds. Wound Healing; Eye Tissue Wounds, Dental Tissue Wounds, Oral Cavity Wounds, Diabetic Ulcers, Dermal Ulcers, Cubitus Ulcers, Arterial Ulcers, Venous Stasis Ulcers, Burns Resulting From Heat Exposure Or Chemicals, or Other Abnormal Wound Healing Conditions such as Uremia, Malnutrition, Vitamin Deficiencies or Complications Associated With Systemic Treatment With Steroids, Radiation Therapy or Antineoplastic Drugs or Antimetabolites; Promote Dermal Reestablishment Subsequent To Dermal Loss; Increase the Adherence Of Skin Grafts To A Wound Bed; Stimulate Re-Epithelialization from The Wound Bed; To Promote Skin Strength; Improve The Appearance Of Aged Skin; Proliferate Hepatocytes, Lung, Breast, Pancreas, Stomach, Bladder, Small Intestine, Large Intestine; Sebocytes, Hair Follicles, Type II Pneumocytes, Mucin-Producing Goblet Cells, or Other Epithelial Cells, Endothelial Cells, Keratinocytes, or Basal Keratinocytes (and Their Progenitors) Contained Within The Skin, Lung, Liver, Bladder, Eye, Salivary Glands, or Gastrointestinal Tract; Reduce The Side Effects Of Gut Toxicity That Result From Radiation, Chemotherapy Treatments Or Viral Infections; Cytoprotector, especially of the Small Intestine Mucosa or Bladder; Mucositis (Mouth Ulcers); Regeneration Of Skin; Full and/or Partial Thickness Skin Defects, including Burns, (e.g., Repopulation Of Hair Follicles, Sweat Glands, And Sebaceous Glands); Psoriasis; Epidermolysis Bullosa; Blisters; Gastric and/or Doudenal Ulcers; Reduce Scarring; Inflamamatory Bowel Diseases; Crohn's Disease; Ulcerative Colitis; Gut Toxicity; Lung Damage; Repair Of Alveoli And/or Brochiolar Epithelium; Acute Or Chronic Lung Damage; Emphysema, ARDS; Inhalation Injuries; Hyaline Membrane Diseases; Infant Respiratory Distress Syndrome; Bronchopulmonary Displasia In Premature Infants; Fulminant Liver Failure; Cirrhosis, Liver Damage caused by Viral Hepatitis and/or Toxic Substances; Diabetes Mellitus; Inflammation; Cancer; Digestive disorders. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Ghrelin (Genbank Accession No. AB029434) | Stimulates release of growth hormone from anterior pituitary. Stimulates appetite and reduces fat burning. | Appetite and food intake can be can be measured by methods known in the art (Batterham et al. Nature 2002; 418: 650654) | Endocrine; loss of body weight; loss of body weight associated with cancer or anorexia nervosa; loss of appetite; excessive appetite; body weight gain; Obesity; Diabetes; Acromegaly; Growth failure; Growth hormone deficiency; Growth failure and growth retardation Prader-Willi syndrome in children 2 years or older; Growth deficiencies; Growth failure associated with chronic renal insufficiency; Postmenopausal osteoporosis; burns; cachexia; cancer cachexia; dwarfism; metabolic disorders; obesity; renal failure; Turner's Syndrome, pediatric and adult; fibromyalgia; fracture treatment; frailty, AIDS wasting |
| Ghrelin - binding antibody including antibody fragment, or dominant-negative form of Ghrelin | Inhibits growth hormone release in response to Ghrelin; inhibits increase in appetite. | Appetite and food intake can be can be measured by methods known in the art (Batterham et al. Nature 2002; 418: 650654) | Endocrine; Obesity; Diabetes; body weight gain; excessive appetite; loss of appetite; loss of body weight. |
| receptor NOGO-66 peptide fragment (Genbank Accession No. NP_008939 (amino acids 62-101)) | | | Neurodegenerative disorders; spinal cord injury; neuronal injury; brain trauma; stroke; multiple sclerosis; demyelinating disorders; neural activity and neurological diseases; neural cell (e.g., neuron, glial cell, and schwann cell) regeneration and/or growth |
| Gastric inhibitory polypeptide (GIP), including GIP fragments (Genbank Accession No. NM_004123) | Increases nutrient uptake and tryglyceride accumulation in adipocytes, which leads to obesity and insulin resistance. | Nutrient uptake and tryglyceride accumulation can be measured by methods described in Miyawaki et al., Nat. Medicine, 2002, Vol 8(7): 738-742. | Most preferred: loss of body weight, AIDS wasting, cachexia, and loss of appetite. Other: Obesity; Diabetes; insulin resistance; body weight gain; excessive appetite. |
| Gastric inhibitory polypeptide antibody, or antibody fragments | Increased use of fat as predominant energy source; decreased accumulation of fat in adipocytes. | Fat utilization as an energy source can be measured as described in Miyawaki et al., Nat. Medicine, 2002, Vol 8(7): 738-742. | Obesity; Diabetes; Insulin resistance; body weight gain. |
| Gastric inhibitory peptide receptor or receptor fragments or variants including soluble fragments or variants (Genbank Accession Number NM_000164) | Increased use of fat as predominant energy source; decreased accumulation of fat in adipocytes. | Fat utilization as an energy source can be measured as described in Miyawaki et al., Nat. Medicine, 2002, Vol 8(7): 738-742. | Most preferred: Obesity; Diabetes; body weight gain; excessive appetite; insulin resistance. Other: loss of body weight, AIDS wasting, loss of appetite. |
| POMC (proopiomelanocortin), including fragments or variants (such as, for example, alpha-melanocyte stimulating hormone, αMSH, | Activity of POMC-derived fragments are diverse, and well-known in the art. See, for example, Hadley et al., Ann N Y Acad Sci 1999 Oct. 20; 885: 1-21; | | Preferred: resistance to stress; anti-inflammatory activity; analgesic activity; increased skin pigmentation; increased protein catabolism; increased gluconeogenesis; obesity; diabetes. Other: decreased protein catabolism, decreased skin |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| gamma melanocyte stimulating hormone, γMSH, beta-melanocyte stimulating hormone, βMSH, adrenocorticotropin, ACTH, beta-endorphin, met-enkephalin) (Genbank Accession No. NM_000930) | Dores, Prog Clin Biol Res 1990; 342: 22-7; Blalock, Ann N Y Acad Sci. 1999 Oct. 20; 885: 161-72). | | pigmentation, Addison's disease, Cushing's syndrome |
| HP 467, HP228 (U.S. Pat. No. 6,350,430) | See U.S. Pat. No. 6,350,430 | See U.S. Pat. No. 6,350,430 | Resistance to stress; anti-inflammatory activity; analgesic activity; increased skin pigmentation; increased protein catabolism; increased gluconeogenesis. |
| NDP (U.S. Pat. No. 6,350,430) | See U.S. Pat. No. 6,350,430 | See U.S. Pat. No. 6,350,430 | Resistance to stress; anti-inflammatory activity; analgesic activity; increased skin pigmentation; increased protein catabolism; increased gluconeogenesis. |
| Interleukin-21 (IL-21) | Immunomodulator; inhibits interferon gamma production by Th1 cells, | IL-21 activity can be assessed by measuring interferon gamma production in Th1 cells. (Wurster et al.,: J Exp Med 2002 Oct. 7; 196(7): 969-77) | Autoimmune disorders; Inflammatory disorders; Treatment of Psoriasis; Rheumatoid Arthritis; Inflammatory bowel disease. |
| Interleukin-4 (IL-4) | Immunomodulator; promotes the differentiation of T cells into Th2 phenotype. | IL-4 activity can be assessed by measuring Th1/Th2 cytokine responses of isolated spleen cells in vitro. (Waltz et al., Horm Metab Res 2002 Oct; 34(10): 561-9). | Treatment of Psoriasis; Autoimmune disorders; Rheumatoid Arthritis; Inflammatory bowel disease; Inflammatory disorders. |
| Osteoclast Inhibitory Lectin (OCIL) | Inhibits osteoclast formation. | Osteoclast Inhibitory Lectin activity can be assessed using osteoclast formation assays known in the art. (Zhou et al., J Biol Chem 2002 Dec. 13; 277(50): 48808-15) | Treatment of Bone Disorders; Osteoporosis; Fracture prevention; Hypercalcemia; Malignant hypercalcemia; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone healing and regeneration. |
| PCSK9 Inhibitor | Inhibits the interaction of PCSK9 with LDL Receptor. | Further LDL lowering through targeting PCSK9 for coronary artery disease. (Cao et al. Endocrine, Metabolic & Immune Disorders-Drug Targets 2008, 8, 238-243) | Treatment of coronary heart disease. |

In one embodiment, the cargo polypeptide is an antigen binding polypeptide construct. In another embodiment, the cargo polypeptide is an antigen-binding polypeptide construct that is an antibody, or fragment or variant thereof. In one embodiment, the antigen-binding polypeptide construct is a Fab fragment of an antibody, or an scFv, or a single domain antibody or fragment thereof.

In one embodiment the cargo polypeptide is selected from an antigen-binding polypeptide construct that binds to CD3, CD19, CD20, HER2, or HER3. Suitable examples of antigen binding polypeptide constructs are known in the art and include those derived from anti-CD3, anti-CD19, anti-HER2, and anti-HER3 antibodies.

Functional Activity:

"A polypeptide having functional activity" refers to a polypeptide capable of displaying one or more known functional activities associated with the full-length, pro-protein, and/or mature form of a cargo polypeptide. Such functional activities include, but are not limited to, biological activity, antigenicity [ability to bind (or compete with a polypeptide for binding) to an anti-polypeptide antibody], immunogenicity (ability to generate antibody which binds to a specific polypeptide described herein), ability to form multimers with polypeptides described herein, and ability to bind to a receptor or ligand for a polypeptide. In certain embodiments, the functional activity includes the ability to improve the expression and stability of a partner protein.

"A polypeptide having biological activity" refers to a polypeptide exhibiting activity similar to, but not necessarily identical to, an activity of a therapeutic protein described herein, including mature forms, as measured in a particular biological assay, with or without dose dependency. In the case where dose dependency does exist, it need not be identical to that of the polypeptide, but rather substantially similar to the dose-dependence in a given activity as compared to the polypeptide described herein (i.e., the candidate polypeptide will exhibit greater activity or not more than about 25-fold less, or not more than about tenfold less activity, or not more than about three-fold less activity relative to a polypeptide described herein, or presented in Table 2).

In certain embodiments, a heteromultimer described herein has at least one biological and/or therapeutic activity associated with the cargo molecule when said cargo molecule is not linked to the transporter polypeptide. In certain embodiments, a heteromultimer described herein has at least one biological and/or therapeutic activity associated with the cargo polypeptide when said cargo polypeptide is not linked to the transporter polypeptide. In certain embodiments, a heteromultimeric protein described herein has at least one biological and/or therapeutic activity associated with the cargo polypeptide portion (or fragment or variant thereof) when said cargo polypeptide is not linked to the albumin or alloalbumin based polypeptide.

The heteromultimeric proteins described herein can be assayed for functional activity (e.g., biological activity) using or routinely modifying assays known in the art, as well as assays described herein. Additionally, one of skill in the art may routinely assay fragments of a protein corresponding to a cargo protein portion of an albumin or alloalbumin based monomeric polypeptide, for activity using assays referenced in its corresponding row of Table 2 (e.g., in column 3 of Table 2). In certain embodiments, are assay of fragments of an albumin protein corresponding to an albumin protein portion of a heteromultimer, for activity using assays known in the art and/or as described in the Examples section below.

For example, in one embodiment where one is assaying for the ability of a heteromultimeric protein described herein to bind or compete with a Cargo polypeptide for binding to an anti-Cargo polypeptide antibody and/or anti-albumin antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In certain embodiments, where a binding partner (e.g., a receptor or a ligand) is identified for a cargo molecule comprised by a heteromultimer described herein, binding to that binding partner by a heteromultimer described herein is assayed, e.g., by means well-known in the art, such as, for example, reducing and non-reducing gel chromatography, protein affinity chromatography, and affinity blotting. See generally, Phizicky et al., Microbiol. Rev. 59:94-123 (1995). In another embodiment, the ability of physiological correlates of a heteromultimeric protein to bind to a substrate(s) of polypeptides corresponding to the cargo protein portion of the heteromultimer can be routinely assayed using techniques known in the art.

Biological Activities

In certain embodiments, heteromultimers described herein, are used in assays to test for one or more biological activities. If a heteromultimer exhibits an activity in a particular assay, it is likely that at least one cargo protein comprised by one or more monomers of the heteromultimer is implicated in the diseases associated with the biological activity. Thus, the heteromultimer is of use in a treatment of the associated disease.

In certain embodiments, provided is a method of treating a disease or disorder comprising administering to a patient in which such treatment, prevention or amelioration is desired, a heteromultimer described herein, in an amount effective to treat, prevent or ameliorate the disease or disorder.

Provided herein are monomeric albumin or alloalbumin based fusion proteins produced by a cell, wherein said proteins are encoded by polynucleotides, wherein said monomeric proteins comprise at least one cargo protein, and an albumin or alloalbumin derived polypeptide, such that said monomers form heteromultimers in solution. In certain embodiments, when the polynucleotides are used to express the encoded protein from a cell, the cell's natural secretion and processing steps produces a protein that lacks at least one signal sequence. The specific amino acid sequence of the signal sequence is well known in the art.

In certain embodiments, heteromultimers described herein are used in the diagnosis, prognosis, prevention and/or treatment of diseases and/or disorders of the endocrine system. In some embodiments, heteromultimers described herein are used in the diagnosis, prognosis, prevention and/or treatment of diseases and/or disorders of the nervous system.

In certain embodiments, heteromultimers described herein are used in the diagnosis, prognosis, prevention and/or treatment of diseases and/or disorders of the immune system. In certain embodiments, heteromultimers described herein are used in the diagnosis, prognosis, prevention and/or treatment of diseases and/or disorders of the respiratory system.

In certain embodiments, heteromultimers described herein are used in the diagnosis, prognosis, prevention and/or treatment of diseases and/or disorders of the cardiovascular system. In some embodiments, heteromultimers described herein are used in the diagnosis, prognosis, prevention and/or treatment of diseases and/or disorders of the reproductive system.

In certain embodiments, heteromultimers described herein are used in the diagnosis, prognosis, prevention and/or treatment of diseases and/or disorders of the digestive system. In certain embodiments, heteromultimer proteins described herein are used in the diagnosis, prognosis, prevention and/or treatment of diseases or disorders relating to the blood.

In certain embodiments, heteromultimers described herein are used in the diagnosis and/or prognosis of diseases and/or disorders associated with at least one tissue(s) in which at least one gene of interest is expressed, wherein a heteromultimer described herein comprises a cargo molecule that binds said at least one gene of interest.

In some embodiments, heteromultimers described herein and/or polynucleotides encoding the albumin/alloalbumin based monomers that associate to form heteromultimers described herein, are used in the diagnosis, detection and/or treatment of diseases and/or disorders associated with activities that include, but are not limited to, prohormone activation, neurotransmitter activity, cellular signaling, cellular proliferation, cellular differentiation, and cell migration.

Therapeutic Uses:

In an aspect, heteromultimers described herein are directed to antibody-based therapies which involve administering heteromultimers described comprising cargo polypeptide(s) which is an antibody, a fragment or variant of an antibody, to a patient for treating one or more of the disclosed diseases, disorders, or conditions. Therapeutic compounds described herein include, but are not limited to, heteromultimers described herein, nucleic acids encoding heteromultimers described herein.

In a specific embodiment, are antibody-based therapies which involve administering heteromultimers described herein comprising at least a fragment or variant of an antibody to a patient for treating one or more diseases, disorders, or conditions, including but not limited to: neural disorders, immune system disorders, muscular disorders, reproductive disorders, gastrointestinal disorders, pulmonary disorders, cardiovascular disorders, renal disorders, proliferative disorders, and/or cancerous diseases and conditions, and/or as described elsewhere herein.

A summary of the ways in which the heteromultimer proteins of the invention comprising at least a fragment or variant of an antibody are used therapeutically includes binding locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the heteromultimers described herein for diagnostic, monitoring or therapeutic purposes without undue experimentation.

The heteromultimers described herein, comprising at least a fragment or variant of an antibody may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in an embodiment, human antibodies, fragments derivatives, analogs, or nucleic acids, are administered to a human patient for therapy or prophylaxis.

Gene Therapy:

In a specific embodiment, nucleic acids comprising sequences encoding heteromultimer proteins described herein are administered to treat, inhibit or prevent a disease or disorder associated with aberrant expression and/or activity of a protein, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available in the art can be used.

Demonstration of Therapeutic or Prophylactic Activity:

The heteromultimers or pharmaceutical compositions described herein are tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a heteromultimer, and the effect of such heteromultimer upon the tissue sample is observed.

Therapeutic/Prophylactic Administration and Composition

Provided are methods of treatment, inhibition and prophylaxis by administration to a subject of an effective amount of a heteromultimer or pharmaceutical composition described herein. In an embodiment, the heteromultimer is substantially purified (e.g., substantially free from substances that limit its effect or produce undesired side-effects). In certain embodiments, the subject is an animal, including but not limited to animals such as cows, pigs, horses, chickens, cats, dogs, etc., and in certain embodiments, a mammal, and most preferably human.

Various delivery systems are known and can be used to administer a heteromultimer formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the heteromultimer compositions described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it is desirable to administer the heteromultimers, or compositions described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the heteromultimers or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the heteromultimers or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment comprising a nucleic acid encoding a heteromultimer described herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

Also provided herein are pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the heteromultimer is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Methods of Recombinant and Synthetic Production of Heteromultimer Proteins:

In certain embodiments are heteromultimers produced as recombinant molecules by secretion from yeast, a microorganism such as a bacterium, or a human or animal cell line. In embodiments, the polypeptides are secreted from the host cells.

Embodiments include a cell, such as a yeast cell transformed to express a heteromultimer protein described herein. In addition to the transformed host cells themselves, are provided culture of those cells, preferably a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away. Many expression systems are known and may be used, including bacteria (for example *E. coli* and *Bacillus subtilis*), yeasts (for example *Saccharomyces cerevisiae, Kluyveromyces lactis* and *Pichia pastoris*, filamentous fungi (for example *Aspergillus*), plant cells, animal cells and insect cells.

A heteromultimer described herein is produced in conventional ways, for example from a coding sequence inserted in the host chromosome or on a free plasmid. The yeasts are transformed with a coding sequence for the desired protein in any of the usual ways, for example electroporation. Methods for transformation of yeast by electroporation are disclosed in Becker & Guarente (1990) Methods Enzymol. 194, 182.

Successfully transformed cells, i.e., cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) J. Mol. Biol. 98, 503 or Berent et al. (1985) Biotech. 3, 208. Alternatively, the presence of the protein in the supernatant can be detected using antibodies.

Useful yeast plasmid vectors include pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, 7RP1, LEU2 and URA3. Plasmids pRS413-416 are Yeast Centromere plasmids (Ycps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary honmopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase 1, enzymes that remove protruding, single-stranded termini with their 3'5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

Exemplary genera of yeast contemplated to be useful in the practice of the present invention as hosts for expressing the albumin, fusion proteins are Pichua (formerly classified as *Hansenula*), *Saccharomyces, Kluyveromyces, Aspergillus, Candida, Torulopsis, Torulaspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis*, and the like. Preferred genera are those selected from the group consisting of *Saccharomyces, Schizosaccharomyces, Kluyveromyces, Pichia* and *Torulaspora*. Examples of *Saccharomyces* spp. are *S. cerevisiae, S. italicus* and *S. rouxii.*

Examples of *Kluyveromyces* spp. are *K. fragilis, K. lactis* and *K. marxianus*. A suitable *Torulaspora* species is *T. delbrueckii*. Examples of *Pichia* (*Hansenula*) spp. are *P. angusta* (formerly *H. polymorpha*), *P. anomala* (formerly *H. anomala*) and *P. pastoris*. Methods for the transformation of *S. cerevisiae* are taught generally in EP 251 744, EP 258 067 and WO 90/01063, all of which are incorporated herein by reference.

Preferred exemplary species of *Saccharomyces* include *S. cerevisiae, S. italicus, S. diastaticus*, and *Zygosaccharomyces rouxii*. Preferred exemplary species of *Kluyveromyces* include *K. fragilis* and *K. lactis*. Preferred exemplary species of *Hansenula* include *H. polymorpha* (now *Pichia angusta*), *H. anomala* (now *Pichia anomala*), and *Pichia capsulata*. Additional preferred exemplary species of *Pichia* include *P. pastoris*. Preferred exemplary species of *Aspergillus* include *A. niger* and *A. nidulans*. Preferred exemplary species of *Yarrowia* include *Y. lipolytica*. Many preferred yeast species are available from the ATCC. For example, the following preferred yeast species are available from the ATCC and are useful in the expression of albumin fusion proteins: *Saccharomyces cerevisiae*, Hansen, teleomorph strain BY4743 yap3 mutant (ATCC Accession No. 4022731); *Saccharomyces cerevisiae* Hansen, teleomorph strain BY4743 hsp150 mutant (ATCC Accession No. 4021266); *Saccharomyces cerevisiae* Hansen, teleomorph strain BY4743 pmt1 mutant (ATCC Accession No. 4023792); *Saccharomyces cerevisiae* Hansen, teleomorph (ATCC Accession Nos. 20626; 44773; 44774; and 62995); *Saccharomyces diastaticus* Andrews et Gilliland ex van der Walt, teleomorph (ATCC Accession No. 62987); *Kluyveromyces lactis* (Dombrowski) van der Walt, teleomorph (ATCC Accession No. 76492); *Pichia angusta* (Teunisson et al.) Kurtzman, teleomorph deposited as *Hansenula polymorpha* de Morais et Maia, teleomorph (ATCC Accession No. 26012); *Aspergillus niger* van Tieghem, anamorph (ATCC Accession No. 9029); *Aspergillus niger* van Tieghem, anamorph (ATCC Accession No. 16404); *Aspergillus nidulans* (Eidam) Winter, anamorph (ATCC Accession No. 48756); and *Yarrowia lipolytica* (Wickerham et al.) van der Walt et von Arx, teleomorph (ATCC Accession No. 201847).

Suitable promoters for *S. cerevisiae* include those associated with the PGKI gene, GAL1 or GAL10 genes, CYCI, PH05, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, alpha-mating factor pheromone, [a mating factor pheromone], the PRBI promoter, the GUT2 promoter, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (1990) J. Biol. Chem. 265, 10857-10864 and the glucose repressible jbpl gene promoter as described by Hoffman & Winston (1990) Genetics 124, 807-816.

Methods of transforming *Pichia* for expression of foreign genes are taught in, for example, Cregg et al. (1993), and various Phillips patents (e.g. U.S. Pat. No. 4,857,467, incorporated herein by reference), and *Pichia* expression kits are commercially available from Invitrogen BV, Leek, Netherlands, and Invitrogen Corp., San Diego, Calif. Suitable promoters include AOX1 and AOX2. Gleeson et al. (1986) J. Gen. Microbiol. 132, 3459-3465 include information on *Hansenula* vectors and transformation, suitable promoters being MOX1 and FMD1; whilst EP 361 991, Fleer et al. (1991) and other publications from Rhone-Poulenc Rorer teach how to express foreign proteins in *Kluyveromyces* spp., a suitable promoter being PGKI.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter. Alternatively, they may be different in which case the termination signal of the *S. cerevisiae* ADHI gene is preferred.

In certain embodiments, the desired heteromultimer protein is initially expressed with a secretion leader sequence, which may be any leader effective in the yeast chosen. Leaders useful in *S. cerevisiae* include that from the mating factor alpha polypeptide (MFα-1) and the hybrid leaders of EP-A-387 319. Such leaders (or signals) are cleaved by the yeast before the mature albumin is released into the surrounding medium. Further such leaders include those of *S. cerevisiae* invertase (SUC2) disclosed in JP 62-096086 (granted as 911036516), acid phosphatase (PHOS), the pre-sequence of MFa-1, 0 glucanase (BGL2) and killer toxin; *S. diastaticus* glucoarnylase Il; *S. carlsbergensis* α-galactosidase (MEL1); *K. lactis* killer toxin; and *Candida glucoarnylase.*

Provided are vectors containing a polynucleotide encoding a heteromultimer protein described herein, host cells, and the production of the heteromultimer proteins by synthetic and recombinant techniques. The vector may be, for example, a phage, plasmid, viral, or retroviral vector. Retroviral vectors may be replication competent or replication defective. In the latter case, viral propagation generally will occur only in complementing host cells.

In certain embodiments, the polynucleotides encoding heteromultimer proteins described herein are joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In certain embodiments, the polynucleotide insert is operatively linked to an appropriate promoter, such as the phage lambda PL promoter, the *E. coli* lac, trp, phoA and rac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, NSO, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A; pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

In one embodiment, polynucleotides encoding a heteromultimer protein described herein are fused to signal sequences that will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the heteromultimeric proteins are fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-.rho. series) available from New England Biolabs. In a specific embodiment, polynucleotides albumin fusion proteins of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that are fused to a heteromultimeric protein in order to direct its secretion in mammalian cells include, but are not limited to, the MPIF-1 signal sequence (e.g., amino acids 1-21 of GenBank Accession number AAB51134), the stanniocalcin signal sequence (MLQNSAVLLLLVISASA) (SEQ ID NO: 177), and a consensus signal sequence (MPTWAWWLFLVLLLALWAPARG) (SEQ ID NO: 178). A suitable signal sequence that may be used in conjunction with baculoviral expression systems is the gp67 signal sequence (e.g., amino acids 1-19 of GenBank Accession Number AAA72759).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/10036; WO89/10404; and WO91/06657, which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., Bio/technology 10:169(1992) and in Biblia and Robinson Biotechnol. Prog. 11:1(1995) which are herein incorporated by reference.

Also provided are host cells containing vector constructs described herein, and additionally host cells containing nucleotide sequences that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the coding sequence corresponding to a Cargo polypeptide is replaced with a heteromultimer protein corresponding to the Cargo polypeptide), and/or to include genetic material. The genetic material operably associated with the endogenous polynucleotide may activate, alter, and/or amplify endogenous polynucleotides.

In addition, techniques known in the art may be used to operably associate heterologous polynucleotides (e.g., polynucleotides encoding an albumin protein, or a fragment or variant thereof) and/or heterologous control regions (e.g., promoter and/or enhancer) with endogenous polynucleotide sequences encoding a Therapeutic protein via homologous recombination (see, e.g., U.S. Pat. No. 5,641,670, issued Jun. 24, 1997; International Publication Number WO 96/29411; International Publication Number WO 94/12650; Koller et al., Proc. Natl. Acad. Sci. USA 86:8932-8935 (1989); and Zijlstra et al., Nature 342:435-438 (1989), the disclosures of each of which are incorporated by reference in their entireties).

Heteromultimer proteins described herein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. Most preferably, high performance liquid chromatography ("HPLC") is employed for purification.

In certain embodiments the heteromultimer proteins of the invention are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, heteromultimer proteins described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

Provided are heteromultimers which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed herein include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The heteromultimer proteins are modified with a detectable label, such as an enzymatic, fluorescent, isotopic or affinity label to allow for detection and isolation of the protein.

Examples of suitable enzymes include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, heteromultimer proteins or fragments or variants thereof are attached to macrocyclic chelators that associate with radiometal ions.

As mentioned, the heteromultimer described herein is modified by either natural processes, such as post-translational processing, or by chemical modification techniques which are well known in the art. It will be appreciated that the same type of modification may be present in the same or varying degrees at several sites in a given polypeptide. Polypeptides of the invention may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, heteromultimeric proteins may also be attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

In embodiments where the heteromultimeric protein comprises only the VH domain of an antibody, it may be necessary and/or desirable to coexpress the protein with the VL domain of the same antibody, such that the VH-albumin fusion protein and VL protein will associate (either covalently or non-covalently) post-translationally.

In embodiments where the heteromultimeric protein comprises only the VL domain of an antibody, it may be necessary and/or desirable to coexpress the fusion protein with the VH domain of the same antibody, such that the VL-albumin fusion protein and VH protein will associate (either covalently or non-covalently) post-translationally.

Also provided herein are chemically modified derivatives of the heteromultimeric proteins which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The proteins may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a Therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 105,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

The presence and quantity of heteromultimer proteins described herein may be determined using ELISA, a well known immunoassay known in the art. In one ELISA protocol that would be useful for detecting/quantifying heteromultimers described herein, comprises the steps of coating an ELISA plate with an anti-human serum albumin antibody, blocking the plate to prevent non-specific binding, washing the ELISA plate, adding a solution containing the protein described herein (at one or more different concentrations), adding a secondary anti-cargo polypeptide specific antibody coupled to a detectable label (as described herein or otherwise known in the art), and detecting the presence of the secondary antibody. In an alternate version of this protocol, the ELISA plate might be coated with the anti-cargo polypeptide specific antibody and the labeled secondary reagent might be the anti-human albumin specific antibody.

Various publications are cited herein, the disclosures of which are incorporated by reference in their entireties.

EXAMPLES

The examples below are given so as to illustrate the practice of this invention. They are not intended to limit or define the entire scope of this invention.

Example 1: The Protein Splitting Method

Specific protein-protein association is driven by strong surface complementarity between interacting partners and the accompanying structural and thermodynamic changes. The surface complementarity provides an opportunity to form contacts that support the creation of favorable electrostatic and hydrophobic interactions. Electrostatic interactions involve the formation of salt bridges, hydrogen bonds and the pervasive dispersion interactions. Solvent exclusion and reorganization around non-polar atomic groups at the interface and its associated entropic effects play a role in the hydrophobic component of the binding thermodynamics. Residues with geometries that are optimized for hydrophobic interaction with one another will form contacts (i.e. stacking, pi-pi, cation-pi contacts favorable for stabilizing a protein-protein interface). Similar thermodynamic effects control multi-step protein folding processes that involve the pre-organization of secondary structural units and tertiary domains, which is followed by their association to form the folded quaternary state of the protein. An alternate mechanism to protein folding and binding involves a coupled protein folding and binding process that ultimately results in the quaternary state of the protein. It is reasonable to assume that there would be aspects of both the processes in action during the quaternary structure formation of a complex protein. In the context of some protein-protein association, the individual protein components need to be co-expressed or be present in the same medium and each of the components or monomers will stably fold into its final structural state only on association with its obligate partner. (FIG. 6)

As described here, generation of a split protein involves recognizing a segmentation site in the native protein, using information from sequence, secondary structure and fold that will yield at least two transporter polypeptides that efficiently form the quasi-native protein structure by self-assembling to form a heteromultimer together. For example, these split protein transporter polypeptides selectively self-assemble and form the quasi-native state when co-expressed. While generating a split protein complementary pair of transporter polypeptides, in a way, the attempt is to emulate a number of naturally occurring obligate protein-protein complexes that exhibit their functionality as a complex while being non-functional in their uncomplexed state. A successful implementation of the strategy results in polypeptides that selectively self-assemble to form heteromultimers with each other, are soluble as individual entities and for functional relevance, do not impair the folding, binding and activity of other components in the environment. The intrinsic nature of the polypeptides to reconstitute with each other has applications in area of creating heteromultimeric fusion entities out of cargo molecules that are not efficient at forming multimers by themselves. In some embodiment, the functional role of the split protein segments is to act as transporter polypeptides that drive heteromultimerization and spatial localization of the multiple cargo molecules fused to the transporter polypeptides.

The segmentation sites within the human serum albumin invented here were designed on the basis of following decision criteria. (1) The segmentation site should reside on a loop with high relative SASA and limited residue contact count to rest of the protein. This was aimed to maximize the chances of finding flexible and accessible loops that are less likely to contribute to the protein core stability and thus impact stability of the assembled quasi-native albumin structure relative to the human serum albumin. (2) The interface should be rich in hotspot residues. By hotspot we mean individual or group of residues involved in a well-connected networks of interactions. The interactions could be based on typical interactions observed in proteins such as hydrogen bonds, charged residue interactions such as salt-bridges, van der Waals contacts which show strong structural complementarity and hydrophobic residue clusters. That is to maximize the interface stability and prevent the complex from dissociating. (3) The interface should be as apolar, extensive and interdigitate as possible. Again, that was to maximize the chances that the two chains exist as a permanent complex and do not dissociate into its individual components. (4) In one embodiment we aimed to retain a natural disulfide bond present in the human serum albumin across the segmented sections so as to covalently connect the two chains. That was meant to further increase the stability of the heterodimerizing quasi-native albumin like structure that self assembles from the two derived segments following segmentation. We locate loop regions in the human serum albumin structure/sequence that satisfy the disulfide criteria described here i.e. have a disulfide very close to the segmentation site in the loop region. Besides the obvious advantage of covalently crosslinking the two chains, this disulfide could also serve as a surrogate for the loop being open on segmentation. (5) In one embodiment, we engineer a disulphide link across the two segments by introducing individual amino acid to cysteine mutations at selected positions on each of the two derived segments. (6) In one embodiment, we engineer amino acids at the interface of the two segments to further increase or improve the hotspots at the interface or enhance the structural and physico-chemical complementarity between the two segments in the assembled quasi-native albumin structure.

Table 3 below shows the interface parameters and association free energies for AlbuCORE scaffolds. The buried interface area between the quasi-native structure derived from assembly of the first and second segment derived from HSA can be computed using a structure based computation using algorithms known in the art (e.g. H. Edelsbrunner and P. Koehl. The weighted volume derivative of a space filling diagram. Proc. Natl. Acad. Sci. (USA) 100, 2203-2208 (2003)). The computed area can be further classified into polar and apolar surface area. The apolar area is an indicator of buried hydrophobic amino acid side chains at the interface. The AAGassoc refers to the computed free energy difference between the associated state and the unassociated state of the two segment structures. The theoretically computed free energy accounts for hydrogen bonds and other electrostatic interactions, van der waals contact, desolvation effects and surface complementarity between the two contacting segment surfaces. Methods to compute free energy of association are known in the art (e.g. Simonson T, Archontis G, Karplus M. Free energy simulations come of age: protein-ligand recognition. Acc Chem Res. (2002) 35, 430-7)

TABLE 3

Interface parameters and association free energies for AlbuCORE scaffolds

| Scaffold | Interface Buried Area (Å$^2$) | Carbon (apolar) Area (Å$^2$) | Carbon (apolar) contribution (%) | $\Delta\Delta G_{assoc}$ (kcal/mol) |
|---|---|---|---|---|
| AlbuCORE_1A | 2892.0 | 1963.2 | 67.88 | −39.13 |
| AlbuCORE_2A | 2282.4 | 1508.2 | 66.08 | −41.11 |
| AlbuCORE_3 | 3395.6 | 2298.3 | 67.68 | −52.69 |
| AlbuCORE_4 | 5550.6 | 3690.8 | 66.49 | −180.99 |
| AlbuCORE_6 | 3278.3 | 2149.2 | 65.56 | −55.57 |

TABLE 3-continued

Interface parameters and association free energies for AlbuCORE scaffolds

| Scaffold | Interface Buried Area ($Å^2$) | Carbon (apolar) Area ($Å^2$) | Carbon (apolar) contribution (%) | $\Delta\Delta G_{assoc}$ (kcal/mol) |
|---|---|---|---|---|
| AlbuCORE_7 | 3925.9 | 2541.2 | 64.73 | −75.20 |
| AlbuCORE_9 | 4227.0 | 2709.1 | 64.09 | −122.49 |
| AlbuCORE_13 | 2982.1 | 1978.7 | 66.35 | −71.80 |

Figure 32:
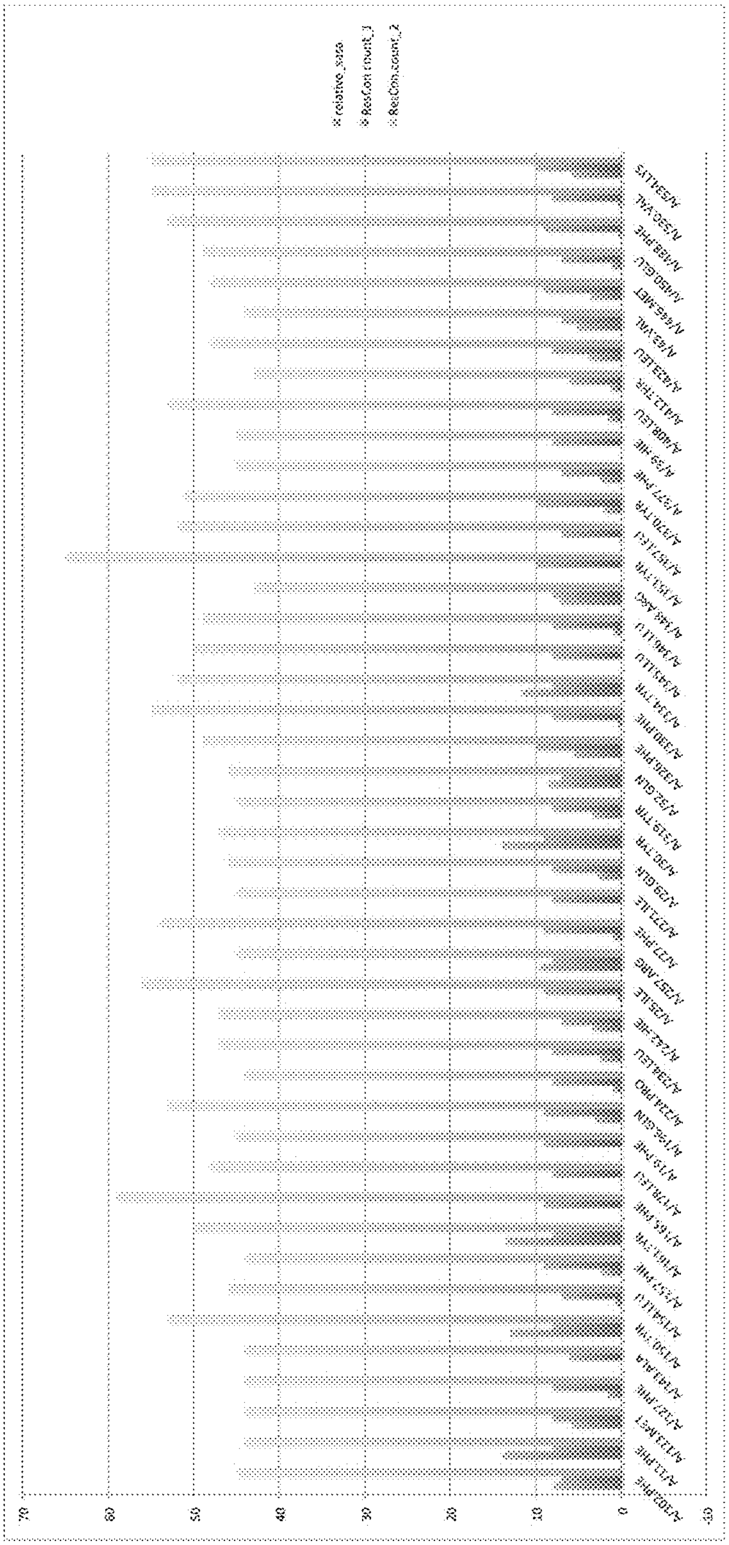
FIG. 32 Plot of residue contacts made by a subset of residues in the human serum albumin derived from its 3-dimensional structure.

FIG. 32 shows a plot of residue contacts made by a subset of residues in the human serum albumin derived from its 3-dimensional structure. Residue contacts can be defined by the inter-residue or certain intra-residue atom-atom interaction that fall within a specified distance range and are of certain physico-chemical nature. Residues or groups of residues with strong residue contacts can be recognized as hotspots. Such residue contact analysis can also be employed to determine loop (or unstructured secondary structural regions in the 3D protein structure) residues, such as those making limited residue contact. The plot also shows residue-wise solvent accessible surface area (SASA) which can be computed using algorithms known in the art (e.g. H. Edelsbrunner and P. Koehl. The weighted volume derivative of a space filling diagram. Proc. Natl. Acad. Sci. (USA) 100, 2203-2208 (2003)).

Figure 3:
FIG. 3 depicts two albumin-based polypeptides expressed separately. The two polypeptides are shown in light and dark grey respectively. Each polypeptide comprises two fusion sites for functional cargo proteins and these sites are represented as spheres. The disulphide residues in structure are shown as sticks.
Figure 33:
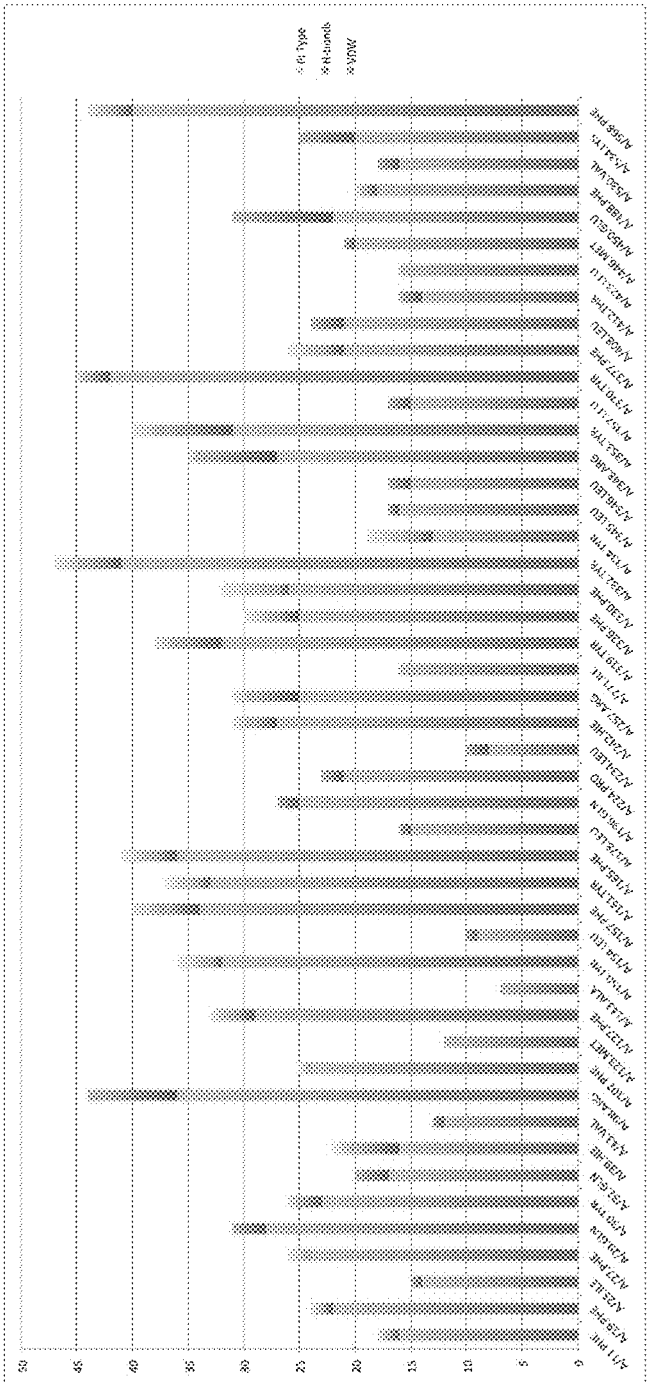
FIG. 33 Plot of nature of contacts and interactions achieved by select hotspot residues in human serum albumin.
Figure 34:
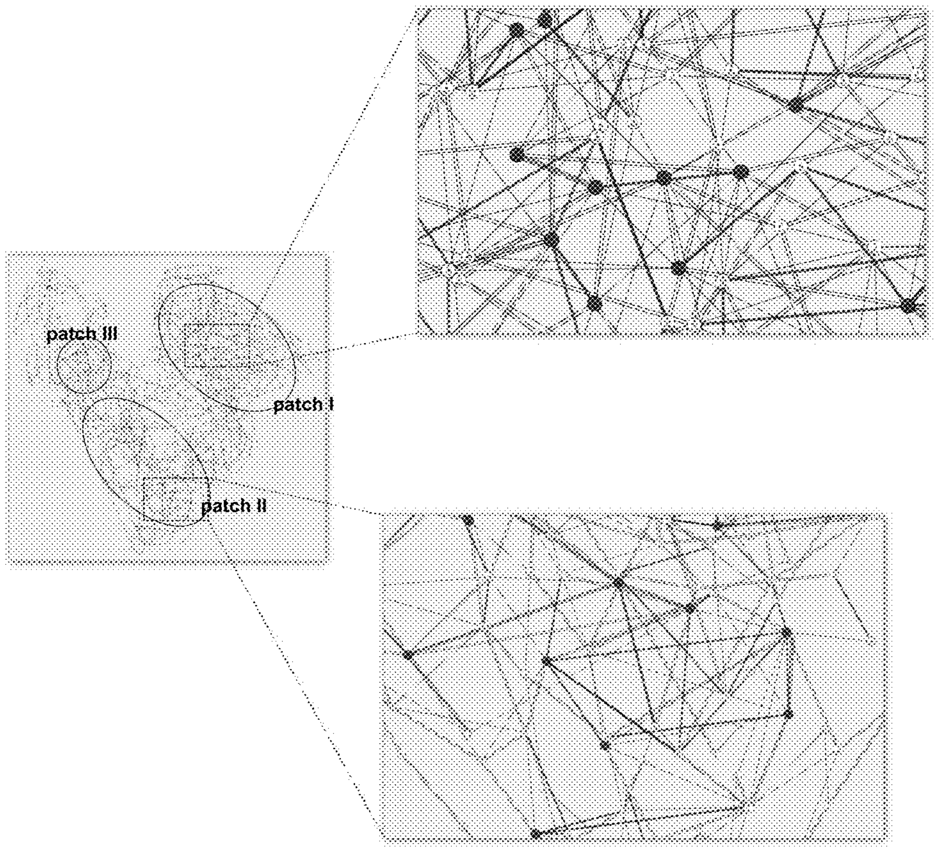
FIG. 34 A graphical representation of hot spot residues or clusters (patches) of hotspot residues in human serum albumin.

FIG. 33 shows a plot of nature of contacts and interactions achieved by select hotspot residues in human serum albumin. FIG. 34 is a graphical representation of hot spot residues or clusters (patches) of hotspot residues in human serum albumin.

ideally fold into the quasi-native structure of HSA, when the segmentation point is moved along the protein sequence. The analysis indicates that a large surface area, of the order of about 2000 $Å^2$ or greater is buried when the split segmentation is introduced anywhere between residues 30 and 520 with a few exceptions, retaining hydrophobic interfaces. In some embodiment the computed molecular surface area is employed instead of the solvent accessible surface area. In some embodiment the buried surface area is in the range of 2000 $Å^2$ to 6000 $Å^2$. A larger buried interface was observed for the non-covalent ABH1. Additionally, the analysis also revealed that some loop regions are relatively surface exposed. Albumin has an exceptionally large number of disulfide bridges that contribute to the stability of the native protein structure. Section of the protein near residues 110, 190, 300, 390 and 500 provide sites for segmentation that do not split the residues involved in a disulphide link across the two transporter polypeptides. Segmentation in other regions would result in heterodimers with a cross linking disulphide bond between the two transporter polypeptide pairs. FIG. 3 presents a model representation of one such quasi-native albumin structure derived by removal of a loop from residues 294 to 303 in the HSA sequence. The total buried surface area for the two albumin based polypeptides of SEQ ID No. 2, and SEQ ID No: 3 shown herein is approximately 2500 $Å^2$. This is within the average range of 1910-3880 $Å^2$ observed in a number of protein-protein heterodimeric and homodimeric co-complex structures [Bahadhur R. P. & Zacharias M. (2008) *Cell Mol Life Sci* 65, 1059-1072]. This suggests that there is a strong likelihood for the two polypeptides to selectively associate with each other if the folding pathway of the two polypeptides is fairly independent of each other.

TABLE 4

New segmentation sites in HSA (AlbuCORE) and nature of loop where the segmentation was introduced. The column "loop length" refer to the length (in amino acid residues) of the loop connecting the two nearest secondary structure elements, and the column "sec str distance" shows the distance between the Cα carbons of the N- and C-termini of those same secondary structure elements (all α-helices in this case). Interface S-S indicates the disulfide bond at the interface of the derived segments (transporter polypeptides).

| Scaffold | Segmentation/Deletion | Interface S-S | loop length | sec str distance |
|---|---|---|---|---|
| AlbuCORE_1A | segment@(339-340) | 316.CYS-361.CYS | 5 res | 12.3 Å |
| AlbuCORE_2A | segment@(300-301) | none | 13 res | 28.4 Å |
| AlbuCORE_3 | segment@(364-365) | 360.CYS-369.CYS | 3 res | 7.2 Å |
| AlbuCORE_4 | segment@(441-442) | 437.CYS-448.CYS | 7 res | 6.0 Å |
| AlbuCORE_6 | delete(84) | 75.CYS-91.CYS | 12 res | 12.2 Å |
| AlbuCORE_7 | segment@(171-172) | 168.CYS-177.CYS | 4 res | 5.7 Å |
| AlbuCORE_9 | segment@(281-282) | 278.CYS-289.CYS | 2 res | 9.1 Å |
| AlbuCORE_13 | segment@(114-115) | none | 14 res | 36.4 Å |

Example 2:Preparation of HA/Alloalbumin Based Heteromultimer Proteins

Shown is a method to determine the segmentation site along the HSA sequence and structure that will yield monomeric polypeptide chains that stably fold and self-assemble to form a quasi-native quaternary structure of the original protein. One of the critical requirements for such stable association is the formation of a large buried area of surface complementarity at the interface between the polypeptide chains. The native fold of the original protein provides indication of the natural complementarity of regions within the protein.

Figure 2:
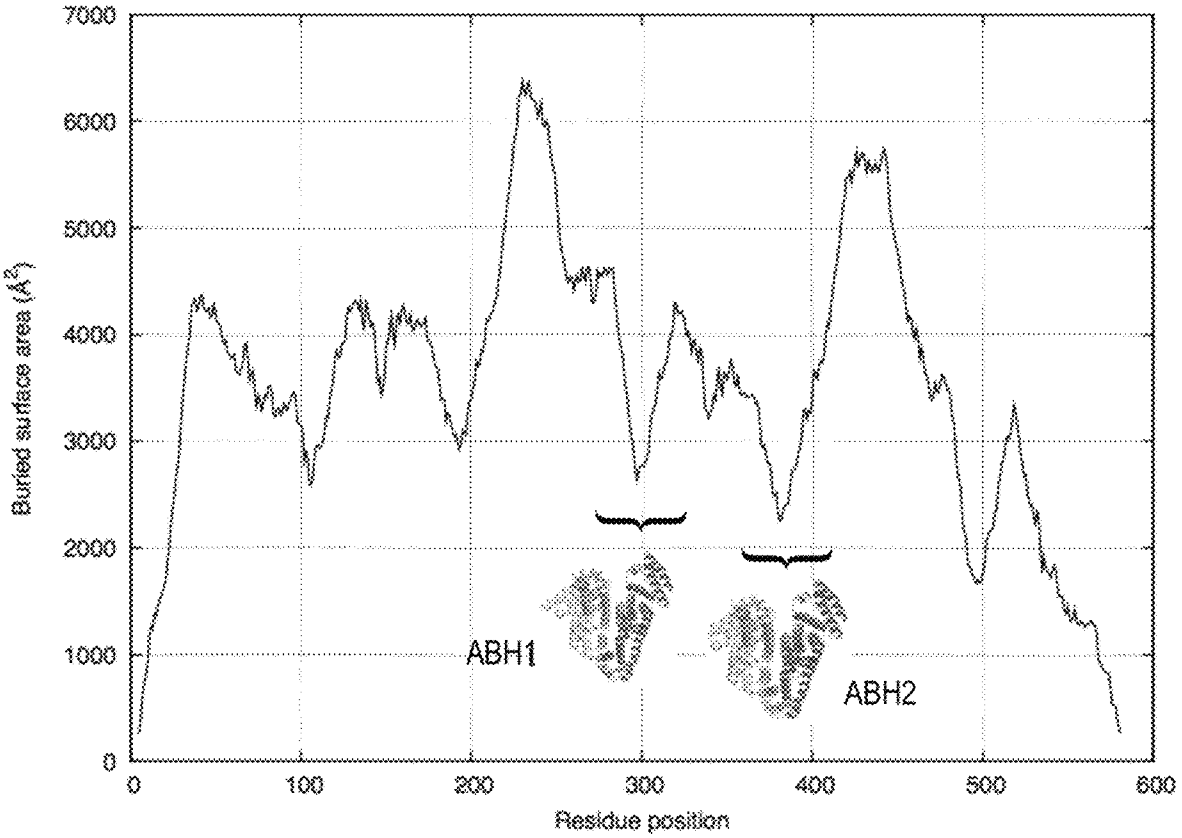
FIG. 2 is a plot of buried solvent accessible surface area at the interface of two albumin-based polypeptides. ABH1 is represented by the structure to the left, while ABH2 is represented by the right structure.
Figure 4:
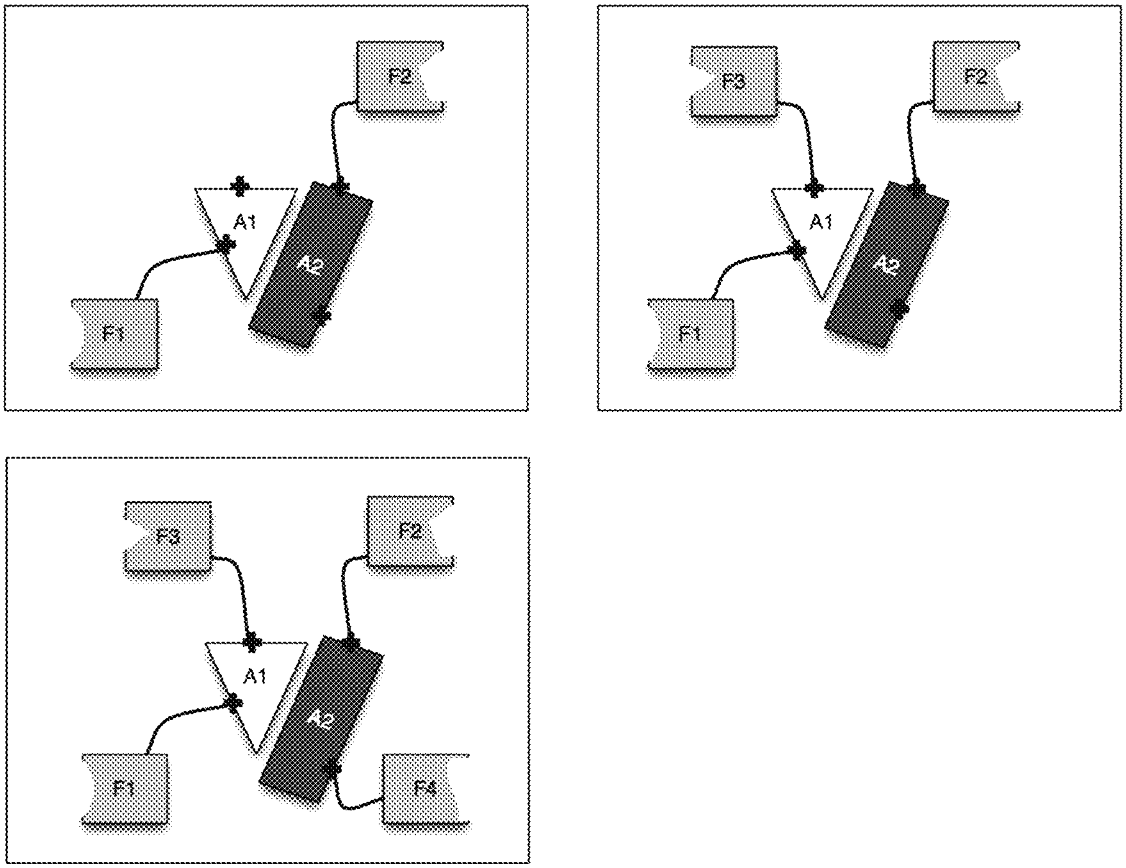
FIG. 4 is a schematic representation of bispecific and other multifunctional therapeutics based on the multispecific heteromultimer described herein. The albumin-based, or alloalbumin-based polypeptides are denoted A1 and A2. Multifunctional heteromultimers are obtained by conjugating antigen binding motifs, cytokines and other forms of signaling molecules, chemotoxin, radiotoxins or other functionally relevant immunoconjugates to N and/or C terminal sites on A1 and A2 and this is represented by the □ symbol.

FIG. 2 shows the solvent accessible surface area buried at the interface of two albumin-based polypeptides that would In an aspect of this invention, selective formation of a stable quasi-native structure with the two polypeptides (the pair formed by SEQ ID No. 2 and SEQ ID No. 3 or the transporter pair formed by SEQ ID No. 8 and SEQ ID No. 10) gives us the opportunity to employ these polypeptides to drive the formation of bispecific or other multifunctional molecules after fusing the appropriate cargo proteins of interest to the N or C terminus of the albumin based polypeptides employed as transporter polypeptides. A number of other alternate segmentation patterns resulting in transporter polypeptide pair heterodimer can be designed. The fused cargo proteins can be antigen binding domains or other payloads such as chemotoxins, radiotoxins or cytokines (as represented in FIG. 4). The resulting heterodimers have many of the favorable properties intrinsic to HSA including properties like half-life and stability in serum, tissue penetrability transport characteristics and low immunogenicity. Traditional linkers such as $(Gly_4Ser)_x$ (SEQ ID NO: 179) can be used for the fusion of the cargo protein with the transporter polypeptide.

Figure 5:
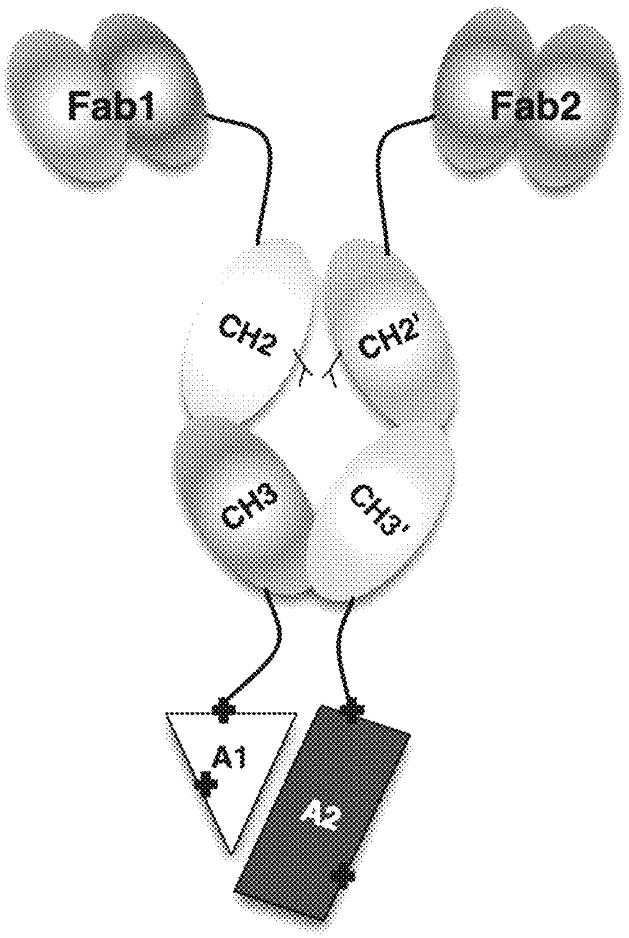
FIG. 5 is a schematic of a bispecific antibody derived from a heterodimeric Fc domain. Albumin or alloalbumin based polypeptides are connected to the C-terminal of the Fc to selectively drive the formation of heterodimers.

In another aspect of this invention, each of the HSA based transporter polypeptides is fused independently to the C-terminus of two heavy chains in a bispecific Fc molecule (as represented in FIG. 5). The strong and selective pairing of the two transporter polypeptides (such as SEQ ID No. 2, and SEQ ID No. 3) drives the selectively heterodimerization of the Fc and also contribute to its stability and other valuable pharmacokinetic properties.

Serum albumin preprotein NP_000468.1 GI 4502027 mRNA sequence from NM_000477.5, Consensus CDS (CCDS) ID 3555.1

SEQ ID No. 4: Residue 1-29 (EFATMAVMAPRTLVLLLSGALALTQTWAG) is the N-terminal export signal sequence region that gets cleaved. This sequence fulfills the same role as the natural signal sequence but it's optimized for mammalian and CHO cell lines.

```
SEQ ID No. 1: gi|4502027|ref|NP_000468.11 serum albumin
preproprotein [Homo sapiens] In parentheses is the N-
terminal export sequence that is cleaved resulting in
serum albumin.
(EFATMAVMAPRTLVLLLSGALALTQTWAG)DAHKSEVAHRFKDLGEENFKAL

VLIAFAQYLQQCPFEDHVKLVNEVTEFAKTCVADESAENCDKSLHTLFGDKLC

TVATLRETYGEMADCCAKQEPERNECFLQHKDDNPNLPRLVRPEVDVMCTAFH

DNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKL

VTDLTKVHTECCHGDLLECADDRADLAKYICENQDSISSKLKECCEKPLLEKS

HCIAEVENDEMPADLPSLAADFVESKDVCKNYAEAKDVFLGMFLYEYARRHPD

YSVVLLLRLAKTYETTLEKCCAAADPHECYAKVFDEFKPLVEEPQNLIKQNCE

LFEQLGEYKFQNALLVRYTKKVPQVSTPTLVEVSRNLGKVGSKCCKHPEAKRM

PCAEDYLSVVLNQLCVLHEKTPVSDRVTKCCTESLVNRRPCFSALEVDETYVP

KEFNAETFTFHADICTLSEKERQIKKQTALVELVKHKPKATKEQLKAVMDDFA

AFVEKCCKADDKETCFAEEGKKLVAASQAALGL

SEQ ID No. 5: Human serum albumin nucleotide CCDS Sequence
(1852 nt)
GAATTCGCCACTATGGCTGTGATGGCCCCTAGGACCCTGGTGCTGCTGCTGTCCGGA

GCTCTGGCTCTGACTCAGACCTGGGCTGGAGATGCACACAAGAGTGAGGTTGCTCAT

CGGTTTAAAGATTTGGGAGAAGAAAATTTCAAAGCCTTGGTGTTGATTGCCTTTGCT

CAGTATCTTCAGCAGTGTCCATTTGAAGATCATGTAAAATTAGTGAATGAAGTAACT

GAATTTGCAAAAACATGTGTTGCTGATGAGTCAGCTGAAAATTGTGACAAATCACTT

CATACCCTTTTTGGAGACAAATTATGCACAGTTGCAACTCTTCGTGAAACCTATGGT

GAAATGGCTGACTGCTGTGCAAAACAAGAACCTGAGAGAAATGAATGCTTCTTGCAA

CACAAAGATGACAACCCAAACCTCCCCCGATTGGTGAGACCAGAGGTTGATGTGATG

TGCACTGCTTTTCATGACAATGAAGAGACATTTTTGAAAAAATACTTATATGAAATT

GCCAGAAGACATCCTTACTTTTATGCCCCGGAACTCCTTTTCTTTGCTAAAAGGTAT

AAAGCTGCTTTTACAGAATGTTGCCAAGCTGCTGATAAAGCTGCCTGCCTGTTGCCA

AAGCTCGATGAACTTCGGGATGAAGGGAAGGCTTCGTCTGCCAAACAGAGACTCAAG

TGTGCCAGTCTCCAAAAATTTGGAGAAAGAGCTTTCAAAGCATGGGCAGTAGCTCGC

CTGAGCCAGAGATTTCCCAAAGCTGAGTTTGCAGAAGTTTCCAAGTTAGTGACAGAT

CTTACCAAAGTCCACACGGAATGCTGCCATGGAGATCTGCTTGAATGTGCTGATGAC

AGGGCGGACCTTGCCAAGTATATCTGTGAAAATCAAGATTCGATCTCCAGTAAACTG

AAGGAATGCTGTGAAAAACCTCTGTTGGAAAAATCCCACTGCATTGCCGAAGTGGAA

AATGATGAGATGCCTGCTGACTTGCCTTCATTAGCTGCTGATTTTGTTGAAAGTAAG

GATGTTTGCAAAAACTATGCTGAGGCAAAGGATGTCTTCCTGGGCATGTTTTTGTAT
```

-continued

GAATATGCAAGAAGGCATCCTGATTACTCTGTCGTGCTGCTGCTGAGACTTGCCAAG

ACATATGAAACCACTCTAGAGAAGTGCTGTGCCGCTGCAGATCCTCATGAATGCTAT

GCCAAAGTGTTCGATGAATTTAAACCTCTTGTGGAAGAGCCTCAGAATTTAATCAAA

CAAAATTGTGAGCTTTTTGAGCAGCTTGGAGAGTACAAATTCCAGAATGCGCTATTA

GTTCGTTACACCAAGAAAGTACCCCAAGTGTCAACTCCAACTCTTGTAGAGGTCTCA

AGAAACCTAGGAAAAGTGGGCAGCAAATGTTGTAAACATCCTGAAGCAAAAAGAATG

CCCTGTGCAGAAGACTATCTATCCGTGGTCCTGAACCAGTTATGTGTGTTGCATGAG

AAAACGCCAGTAAGTGACAGAGTCACCAAATGCTGCACAGAATCCTTGGTGAACAGG

CGACCATGCTTTTCAGCTCTGGAAGTCGATGAAACATACGTTCCCAAAGAGTTTAAT

GCTGAAACATTCACCTTCCATGCAGATATATGCACACTTTCTGAGAAGGAGAGACAA

ATCAAGAAACAAACTGCACTTGTTGAGCTCGTGAAACACAAGCCCAAGGCAACAAAA

GAGCAACTGAAAGCTGTTATGGATGATTTCGCAGCTTTTGTAGAGAAGTGCTGCAAG

GCTGACGATAAGGAGACCTGCTTTGCCGAGGAGGGTAAAAAACTTGTTGCTGCAAGT

CAAGCTGCCTTAGGCTTATGA

The protein and nucleotide sequence of albumin based polypeptides useful as transporter polypeptides are as follows:

Albumin based heteromultimer 1:
Albumin based Transporter polypeptide 1-Ver 1: SEQ ID No. 2:
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPR

LVRPEVDVMCTAFHDNEETFLKKYLYEIARRHPYFYAPELLFFAKRYKAAFTECCQA

ADKAACLLPKLDELRDEGKASSAKQRLKCASLQKFGERAFKAWAVARLSQRFPKAEF

AEVSKLVTDLTKVHTECCHGDLLECADDRADLAKYICENQDSISSKLKECCEKPLLE

KSHCIAEV

Nucleotide sequence encoding Albumin based Transporter polypeptide 1-Ver 1: SEQ ID No. 6:
GATGCACACAAGAGTGAGGTTGCTCATCGGTTTAAAGATTTGGGAGAAGAAAATTTC

AAAGCCTTGGTGTTGATTGCCTTTGCTCAGTATCTTCAGCAGTGTCCATTTGAAGAT

CATGTAAAATTAGTGAATGAAGTAACTGAATTTGCAAAAACATGTGTTGCTGATGAG

TCAGCTGAAAATTGTGACAAATCACTTCATACCCTTTTTGGAGACAAATTATGCACA

GTTGCAACTCTTCGTGAAACCTATGGTGAAATGGCTGACTGCTGTGCAAAACAAGAA

CCTGAGAGAAATGAATGCTTCTTGCAACACAAAGATGACAACCCAAACCTCCCCCGA

TTGGTGAGACCAGAGGTTGATGTGATGTGCACTGCTTTTCATGACAATGAAGAGACA

TTTTTGAAAAAATACTTATATGAAATTGCCAGAAGACATCCTTACTTTTATGCCCCG

GAACTCCTTTTCTTTGCTAAAAGGTATAAAGCTGCTTTTACAGAATGTTGCCAAGCT

GCTGATAAAGCTGCCTGCCTGTTGCCAAAGCTCGATGAACTTCGGGATGAAGGGAAG

GCTTCGTCTGCCAAACAGAGACTCAAGTGTGCCAGTCTCCAAAAATTTGGAGAAAGA

GCTTTCAAAGCATGGGCAGTAGCTCGCCTGAGCCAGAGATTTCCCAAAGCTGAGTTT

GCAGAAGTTTCCAAGTTAGTGACAGATCTTACCAAAGTCCACACGGAATGCTGCCAT

GGAGATCTGCTTGAATGTGCTGATGACAGGGCGGACCTTGCCAAGTATATCTGTGAA

-continued

AATCAAGATTCGATCTCCAGTAAACTGAAGGAATGCTGTGAAAAACCTCTGTTGGAA

AAATCCCACTGCATTGCCGAAGTGTGA

Albumin based Transporter polypeptide 2-Ver1: SEQ ID No. 3:
SLAADFVESKDVCKNYAEAKDVFLGMFLYEYARRHPDYSVVLLLRLAKTYETTLEKC

CAAADPHECYAKVFDEFKPLVEEPQNLIKQNCELFEQLGEYKFQNALLVRYTKKVPQ

VSTPTLVEVSRNLGKVGSKCCKHPEAKRMPCAEDYLSVVLNQLCVLHEKTPVSDRVT

KCCTESLVNRRPCFSALEVDETYVPKEFNAETFTFHADICTLSEKERQIKKQTALVE

LVKHKPKATKEQLKAVMDDFAAFVEKCCKADDKETCFAEEGKKLVAASQAALGL

Nucleotide sequence encoding Albumin based Transporter polypeptide
2-Ver1: SEQ ID No. 7:
TCATTAGCTGCTGATTTTGTTGAAAGTAAGGATGTTTGCAAAAACTATGCTGAGGCA

AAGGATGTCTTCCTGGGCATGTTTTTGTATGAATATGCAAGAAGGCATCCTGATTAC

TCTGTCGTGCTGCTGCTGAGACTTGCCAAGACATATGAAACCACTCTAGAGAAGTGC

TGTGCCGCTGCAGATCCTCATGAATGCTATGCCAAAGTGTTCGATGAATTTAAACCT

CTTGTGGAAGAGCCTCAGAATTTAATCAAACAAAATTGTGAGCTTTTTGAGCAGCTT

GGAGAGTACAAATTCCAGAATGCGCTATTAGTTCGTTACACCAAGAAAGTACCCCAA

GTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTG

GTCCTGAACCAGTTATGTGTGTTGCATGAGAAAACGCCAGTAAGTGACAGAGTCACC

AAATGCTGCACAGAATCCTTGGTGAACAGGCGACCATGCTTTTCAGCTCTGGAAGTC

GATGAAACATACGTTCCCAAAGAGTTTAATGCTGAAACATTCACCTTCCATGCAGAT

ATATGCACACTTTCTGAGAAGGAGAGACAAATCAAGAAACAAACTGCACTTGTTGAG

CTCGTGAAACACAAGCCCAAGGCAACAAAAGAGCAACTGAAAGCTGTTATGGATGAT

TTCGCAGCTTTTGTAGAGAAGTGCTGCAAGGCTGACGATAAGGAGACCTGCTTTGCC

GAGGAGGGTAAAAAACTTGTTGCTGCAAGTCAAGCTGCCTTAGGCTTATGA

Albumin based heteromultimer 2:
Albumin based Transporter polypeptide 1-Ver 2: SEQ ID No. 8:
DAHKSEVAHRFKDLGEENFKALVLIAFAQYLQQCPFEDHVKLVNEVTEFAKTCVADE

SAENCDKSLHTLFGDKLCTVATLRETYGEMADCCAKQEPERNECFLQHKDDNPNLPR

LVRPEVDVMCTAFHDNEETFLKKYLYEIARRHPYFYAPELLFFAKRYKAAFTECCQA

ADKAACLLPKLDELRDEGKASSAKQRLKCASLQKFGERAFKAWAVARLSQRFPKAEF

AEVSKLVTDLTKVHTECCHGDLLECADDRADLAKYICENQDSISSKLKECCEKPLLE

KSHCIAEVENDEMPADLPSLAADFVESKDVCKNYAEAKDVFLGMFLYEYARA

Nucleotide sequence encoding Albumin based Transporter polypeptide
1-Ver 2: SEQ ID No. 9:
GATGCACACAAGAGTGAGGTTGCTCATCGGTTTAAAGATTTGGGAGAAGAAAATTTC

AAAGCCTTGGTGTTGATTGCCTTTGCTCAGTATCTTCAGCAGTGTCCATTTGAAGAT

CATGTAAAATTAGTGAATGAAGTAACTGAATTTGCAAAAACATGTGTTGCTGATGAG

TCAGCTGAAAATTGTGACAAATCACTTCATACCCTTTTTGGAGACAAATTATGCACA

GTTGCAACTCTTCGTGAAACCTATGGTGAAATGGCTGACTGCTGTGCAAAACAAGAA

CCTGAGAGAAATGAATGCTTCTTGCAACACAAAGATGACAACCCAAACCTCCCCCGA

TTGGTGAGACCAGAGGTTGATGTGATGTGCACTGCTTTTCATGACAATGAAGAGACA

TTTTTGAAAAAATACTTATATGAAATTGCCAGAAGACATCCTTACTTTTATGCCCCG

GAACTCCTTTTCTTTGCTAAAAGGTATAAAGCTGCTTTTACAGAATGTTGCCAAGCT

-continued

GCTGATAAAGCTGCCTGCCTGTTGCCAAAGCTCGATGAACTTCGGGATGAAGGGAAG

GCTTCGTCTGCCAAACAGAGACTCAAGTGTGCCAGTCTCCAAAAATTTGGAGAAAGA

GCTTTCAAAGCATGGGCAGTAGCTCGCCTGAGCCAGAGATTTCCCAAAGCTGAGTTT

GCAGAAGTTTCCAAGTTAGTGACAGATCTTACCAAAGTCCACACGGAATGCTGCCAT

GGAGATCTGCTTGAATGTGCTGATGACAGGGCGGACCTTGCCAAGTATATCTGTGAA

AATCAAGATTCGATCTCCAGTAAACTGAAGGAATGCTGTGAAAAACCTCTGTTGGAA

AAATCCCACTGCATTGCCGAAGTGGAAAATGATGAGATGCCTGCTGACTTGCCTTCA

TTAGCTGCTGATTTTGTTGAAAGTAAGGATGTTTGCAAAAACTATGCTGAGGCAAAG

GATGTCTTCCTGGGCATGTTTTTGTATGAATATGCAAGAGCATGA

Albumin based Transporter polypeptide 2-Ver 2: SEQ ID No. 10:
SVVLLLRLAKTYETTLEKCCAAADPHECYAKVFDEFKPLVEEPQNLIKQNCELFEQL

GEYKFQNALLVRYTKKVPQVSTPTLVEVSRNLGKVGSKCCKHPEAKRMPCAEDYLSV

VLNQLCVLHEKTPVSDRVTKCCTESLVNRRPCFSALEVDETYVPKEFNAETFTFHAD

ICTLSEKERQIKKQTALVELVKHKPKATKEQLKAVMDDFAAFVEKCCKADDKETCFA

EEGKKLVAASQAALGL

Nucleotide sequence encoding Albumin based Transporter polypeptide 2-Ver 2: SEQ ID No. 11:
TCTGTCGTGCTGCTGCTGAGACTTGCCAAGACATATGAAACCACTCTAGAGAAGTGC

TGTGCCGCTGCAGATCCTCATGAATGCTATGCCAAAGTGTTCGATGAATTTAAACCT

CTTGTGGAAGAGCCTCAGAATTTAATCAAACAAAATTGTGAGCTTTTTGAGCAGCTT

GGAGAGTACAAATTCCAGAATGCGCTATTAGTTCGTTACACCAAGAAAGTACCCCAA

GTGTCAACTCCAACTCTTGTAGAGGTCTCAAGAAACCTAGGAAAAGTGGGCAGCAAA

TGTTGTAAACATCCTGAAGCAAAAAGAATGCCCTGTGCAGAAGACTATCTATCCGTG

GTCCTGAACCAGTTATGTGTGTTGCATGAGAAAACGCCAGTAAGTGACAGAGTCACC

AAATGCTGCACAGAATCCTTGGTGAACAGGCGACCATGCTTTTCAGCTCTGGAAGTC

GATGAAACATACGTTCCCAAAGAGTTTAATGCTGAAACATTCACCTTCCATGCAGAT

ATATGCACACTTTCTGAGAAGGAGAGACAAATCAAGAAACAAACTGCACTTGTTGAG

CTCGTGAAACACAAGCCCAAGGCAACAAAAGAGCAACTGAAAGCTGTTATGGATGAT

TTCGCAGCTTTTGTAGAGAAGTGCTGCAAGGCTGACGATAAGGAGACCTGCTTTGCC

GAGGAGGGTAAAAAACTTGTTGCTGCAAGTCAAGCTGCCTTAGGCTTATGA

Generation and Expression of HA or HAA Based Heteromultimers

Figure 6A:
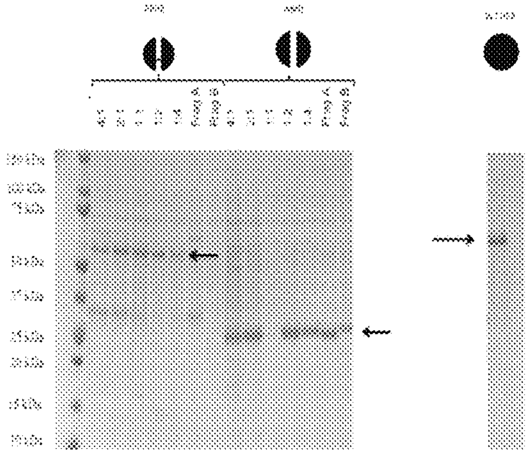
FIG. 6A shows a non-reducing SDS-PAGE gel profile of ABH2, ABH1 and WT HSA. The two fragment polypeptides of ABH1 and ABH2 were co-expressed in different DNA ratios, as indicated by the ratios at the top of the figure. As controls and to observe homodimerization, fragments A and B were expressed independently.
Figure 6B:
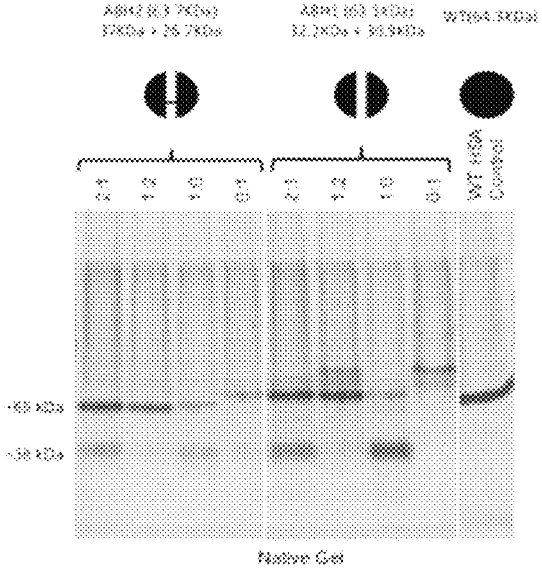
FIG. 6B shows native gel electrophoresis profiles of full-length HSA and heterodimer scaffolds Albumin-based heteromultimer-1 (ABH1) and Albumin-based heteromultimer-2 (ABH2) formed by coexpression of HSA based transporter polypeptides.
Figure 16A:
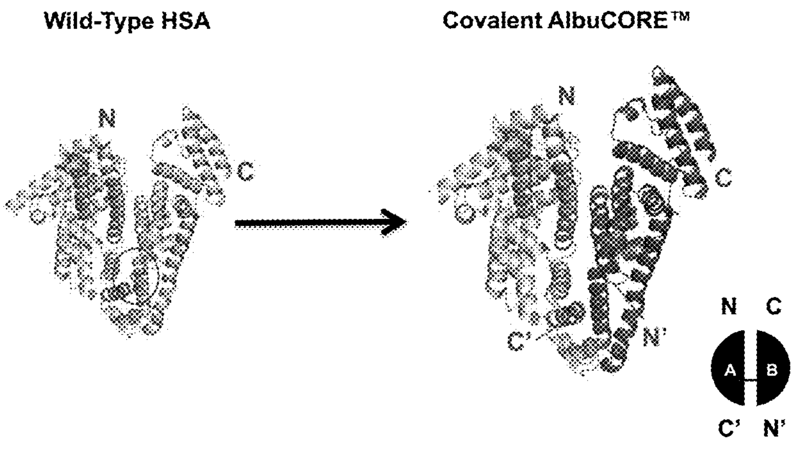
Figure 16B:
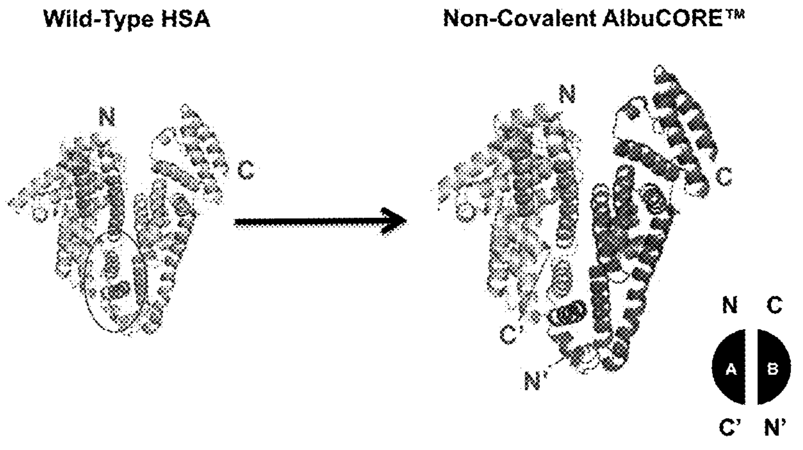

The genes encoding the full length WT HA and the HA based transporter polypeptide monomers were constructed via gene synthesis using codons optimized for human/mammalian expression. The constructs were designed from known full-length Human Serum Albumin Preprotein (GENEBANK: NP_000468.1), after exclusion of the signal sequence EFATMAVMAPRTLVLLLSGALALTQTWAG (SEQ ID NO: 4). The final gene products were subcloned into the mammalian expression vector pTT5 (NRC-BRI, Canada) (Durocher et al). High level and high-throughput recombinant protein production by transient transfection of suspension-growing human CHO-3E7 was performed. See Table 3 for construct boundaries of the two scaffolds described here: Albumin based heteromultimer 1 (ABH1) and Albumin based heteromultimer 2 (ABH2). Albumin based heteromultimer 2 comprises one disulfide bond between the two transporter polypeptides, while Albumin based heteromultimer 1 is formed entirely by non-covalent interactions. FIGS. 16A and 16B depict the protein structure and symbolic rendering of ABH1 and ABH2 respectively. As the two figures demonstrate, both ABH constructs are composed of two transporter polypeptides A and B, sequences described in Table 3. FIG. 6A provides SDS-PAGE (non-reducing) gel analysis of the two heteromultimer constructs (ABH1 and ABH2), after co-expression (different DNA transfection ratios are shown). WT full-length HSA is shown as control. As expected, ABH2 retains the disulfide linkage in non-reducing SDS-PAGE, with a MW roughly double the non-disulfide linked ABH1. FIG. 6A also demonstrates that formation of heterodimers in ABH2 is dependent on DNA transfection ratio, with the 1:1 producing the most heterodimeric product. Finally, 6A demonstrates that fragment A of ABH2, when expressed as stand-alone molecule, is more susceptible to forming homodimers and staying monomeric, a result also observed in FIG. 6B. FIG. 6B provides Native gel analysis of the two Albumin based heteromultimer constructs (ABH1 and ABH2), after co-expression (1:1 DNA level). WT full-length HSA is shown as control. ABH1 and ABH2 both form a complex of expected mass, comparable to the full-length WT HSA. Furthermore, upon expression, neither the transporter polypeptides forming ABH1 nor the ones forming ABH2 homodimerize; rather they preferably form a stable hetercomplex. See Table 5 below for details.

TABLE 5

Albumin based heteromultimer constructs

| Construct | Segment Boundaries* | MW (KDa) |
|---|---|---|
| Wild Type HA | 1:585 (SEQ ID NO: 1) | 64.3 |
| ABH1 | 1:293 (SEQ ID NO: 2) | 32.2 |
| (AlbuCORE 2) | 304:585 (SEQ ID NO: 3) | 30.9 |
| ABH2 | 1:337 (SEQ ID NO: 8) | 37 |
| (AlbuCORE 1) | 342:585 (SEQ ID NO: 10) | 26.7 |

WT-HSA and the two Albumin based heteromultimers (ABH1 and ABH2) were expressed in CHO-3E7 cell line grown in suspension in FreeStyle F17 medium (Invitrogen) supplemented with 0.1% w/v pluronic and 4 mM glutamine. The day of transfection cell density should be around 1.5-2 million cells/ml and viability must be greater than 97%. Transfection was carried out as described in patent application WO 2009/137911 using a mixture of plasmid DNA made of 5% pTTo-GFP plasmid (green fluorescent protein to determine transfection efficiency, Table 4), 15% pTT22-AKT plasmid, 21% HSA plasmids (10.63% of each), 68.37% of Salmon Sperm DNA. Following transfection, the shake flask containing cells was then placed on an orbital shaker set to 120 rpm in a humidified incubator with 5% CO2 at 37° C. Twenty-four hours post-transfection, 1% w/v TN1 and 0.5 mM VPA (Valproic acid) were added to the cultures. The cultures were then transferred on an orbital shaker (120 rpm) placed in a humidified incubator with 5% CO2 set at 32° C. At 24-48 hours, GFP positive cells should be between 30-60% as determined by flow cytometry. Cells were harvested 7 days post-transfection and spun at 4,000 rpm for 20 minutes. The supernatant was filter-sterilized (clarified) using a 0.45 μm filter (Millipore). The supernatant was stored at 4° C. for short-term storage and at −80° C. for long-term storage. Prior to purification, the frozen supernatant was thawed at 37° C., re-filtered and degassed through a 0.45 μm membrane filter under vacuum for 5-10 minutes.

TABLE 6

Cell viability at different stages of expression for WT and ABH1 construct.

| HSA scaffold | % GFP 48 hrs post-transfection | % viability 48 hrs post-transfection | % viability 48 hrs post-transfection |
|---|---|---|---|
| Wild Type HSA | 67 | 94.6 | 72.3 |
| ABH2 | 66.3 | 93.6 | 77.1 |

Purification of ABH2, HSA and Heteromultimers

As observed from FIG. 6A, the 1:1 DNA transfection ratio of the two transporter polypeptides produced the highest level of heterodimeric ABH2 product. CHO cells transiently co-expressing this ratio of the two polypeptides were cultured as described above. Subsequent heterodimer purification was carried out as follows. The wild-type human Albumin was transfected into CHO cells and purified similarly to the ABH2.

Figure 6C:
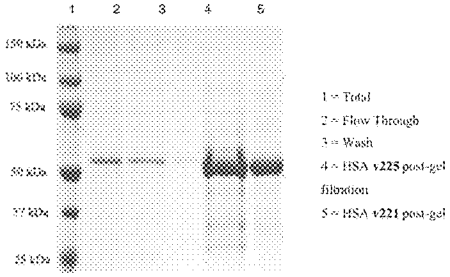
FIG. 6C is a native gel of initial, flowthrough, wash and final elute after the Blue Sepharose purification of WT-HSA (v225) and ABH2 (v221).

Purification was performed by gravity flow using a bench-top QIAGEN-tip 500 column packed with a Blue Sepharose matrix (GE Healthcare). The Blue Sepharose matrix was equilibrated with 20 ml of PBS pH 7.2. The sample was loaded at a flow rate of 5 ml/min and subsequently washed with with 20 ml of PBS. The protein was eluted with 0.1 M Na2HPO4 pH 7.2 supplemented with 1 M NaCl and collected in 1 ml fractions (20 ml total). Fractions containing HSA (as per Bradford protein assay) were pooled, and applied on a HiLoad 16/60 Superdex 200 prep grade gel filtration column coupled to an AKTA Express system (GE Healthcare) using a flow rate of 1 ml/ml. Protein with a purity of >85% was collected; fractions containing pure sample were pooled and concentrated by centrifugation using an Amicon Ultra membrane with a cutoff weight of 10 000 MWCO. FIG. 6C shows SDS-PAGE (non-reducing) analysis of the ABH2 heteromultimer and WT HSA, both after the final stage of purification. Both constructs show the expected MW.

Purification yields were comparable to wild-type full length HSA, at about 10 mg/L. This result was also comparable to the 9 mg/L generated by V1087 control performed in HEK cells. Yields were determined by nanodrop A280 measured after Blue Sepharose and size exclusion chromatography.

Stability Determination of Albumin Based Heteromultimers Using Differential Scanning Calorimetry (DSC)

Figure 7:
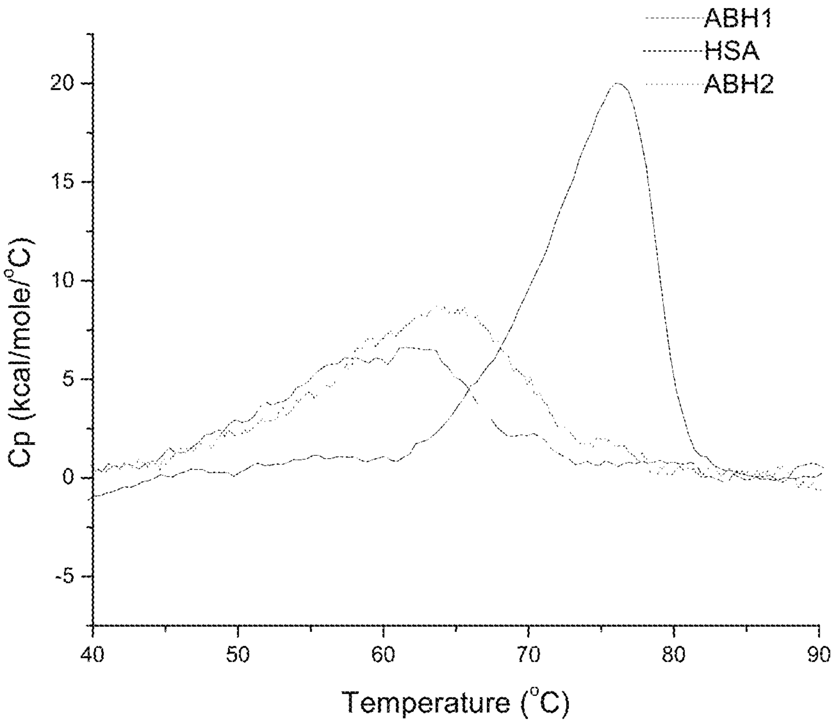
FIG. 7 shows stability of wild type HSA and heterodimer scaffolds ABH1 and ABH2 studied using Differential Scanning calorimetry

All DSC experiments were carried out using a GE or MicroCal VP-Capillary instrument. The proteins were buffer-exchanged into PBS (pH 7.4) and diluted to 0.3 to 0.7 mg/mL with 0.137 mL loaded into the sample cell and measured with a scan rate of 1° C./min from 20 to 100° C. Data was analyzed using the Origin software (GE Healthcare) with the PBS buffer background subtracted. See Table 7 and FIG. 7 for resulting melting temperature determined.

TABLE 7

Melting temperature for Albumin based heteromultimers

| Molecule | Measured Mass (Da) | Theoretical MW (Da) | Tm° C. |
|---|---|---|---|
| HSA Wild Type | 66620 | 66470 | 75 |
| ABH2 | 66100 | 65880 | 63 |
| ABH1 | Not determined | Not determined | 60 |

Evaluation of FcRn Binding of HSA and ABH2 Using Surface Plasmon Resonance

Figure 8A:
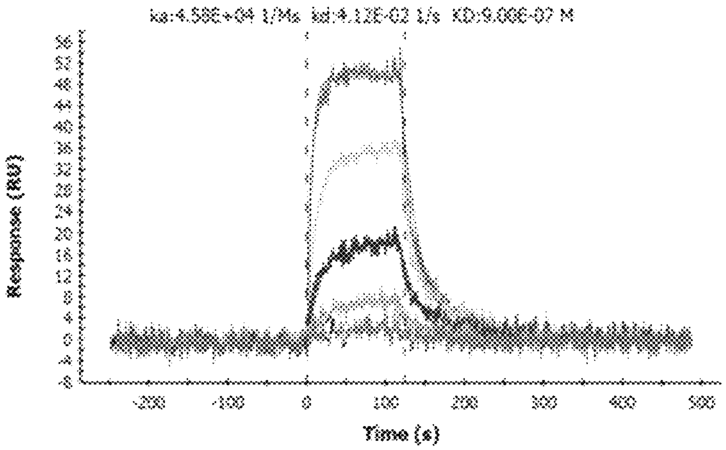
FIGS. 8A-8B show equilibrium binding isotherms 3000 nM FcRN 3× dilution series over 3000 RUs.
Figure 8B:
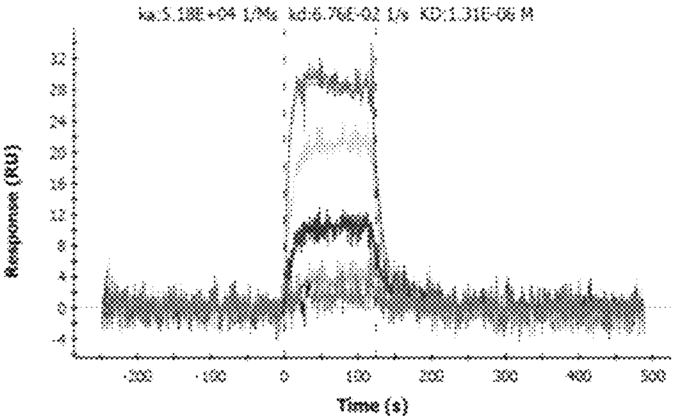

As seen in FIGS. 8A-B, when HSA and a HSA-based heteromultimer are immobilized on the SPR surface, affinity towards FcRn appears to be comparable between the full length WT HSA and ABH2, indicating FcRn binding functionality of albumin is retained by the heteromultimer formed by the self-assembly of albumin based transporter polypeptides. The following Table 8 illustrates FcRn binding data. Values in parenthesis refer to standard deviation.

TABLE 8

Kinetic and Equilibrium fit of FcRn Binding of HSA and ABH2 using Surface Plasmon Resonance

| | Ka (1/Ms) Grouped Fitted | Kd (1/s) Grouped Fitted | KD (M) Grouped Fitted | |
|---|---|---|---|---|
| HSA | 5.3E+04 (7E+03) | 7.0E−02 (2.0E−02) | 1.4E−06 (6.0E−07) | Kinetic fit |
| ABH2 | 5.0E+04 (4E+03) | 4.2E−02 (8.0E−03) | 8.0E−07 (2.0E−07) | Kinetic fit |
| HSA | | | 9.0E−07 (1.0E−07) | Equilibrium Fit |
| ABH2 | | | 9.0E−07 (1.0E−07) | Equilibrium Fit |

Example 3: Generation and Expression of Albumin Based Heteromultimers with Mono- and Tetravalency Comprising Anti-Her2/Neu and Anti-CD16 scFv Bioactive Fusions Multivalent heteromultimer ABH2 was generated by expressing its single monomeric transporter polypeptides, SEQ ID NO: 8 and SEQ ID NO: 10, fused at one or both termini to cargo polypeptides that are either antiHer2scFv (4D5) and/or anti-CD16 scFv (NM3E). The term 4D5 as used herein throughout refers to the humanized sequences of the 4D5 antibody and corresponds to the amino acid sequence of the variable domains in the trastuzumab antibody along with the linker region between the Vl and Vh domains in the scFv molecular format. These form a set of 8 base construct monomers based on transporter polypeptide 1 and 8 base construct monomers based on transporter polypeptide 2. Different combinations of these base constructs were combined upon co-expression to form heteromultimers displaying all combination of the two cargo polypeptides at any of the four terminal positions of the two transporter polypeptides, ranging from monovalent to tetravalent.

Figure 9:
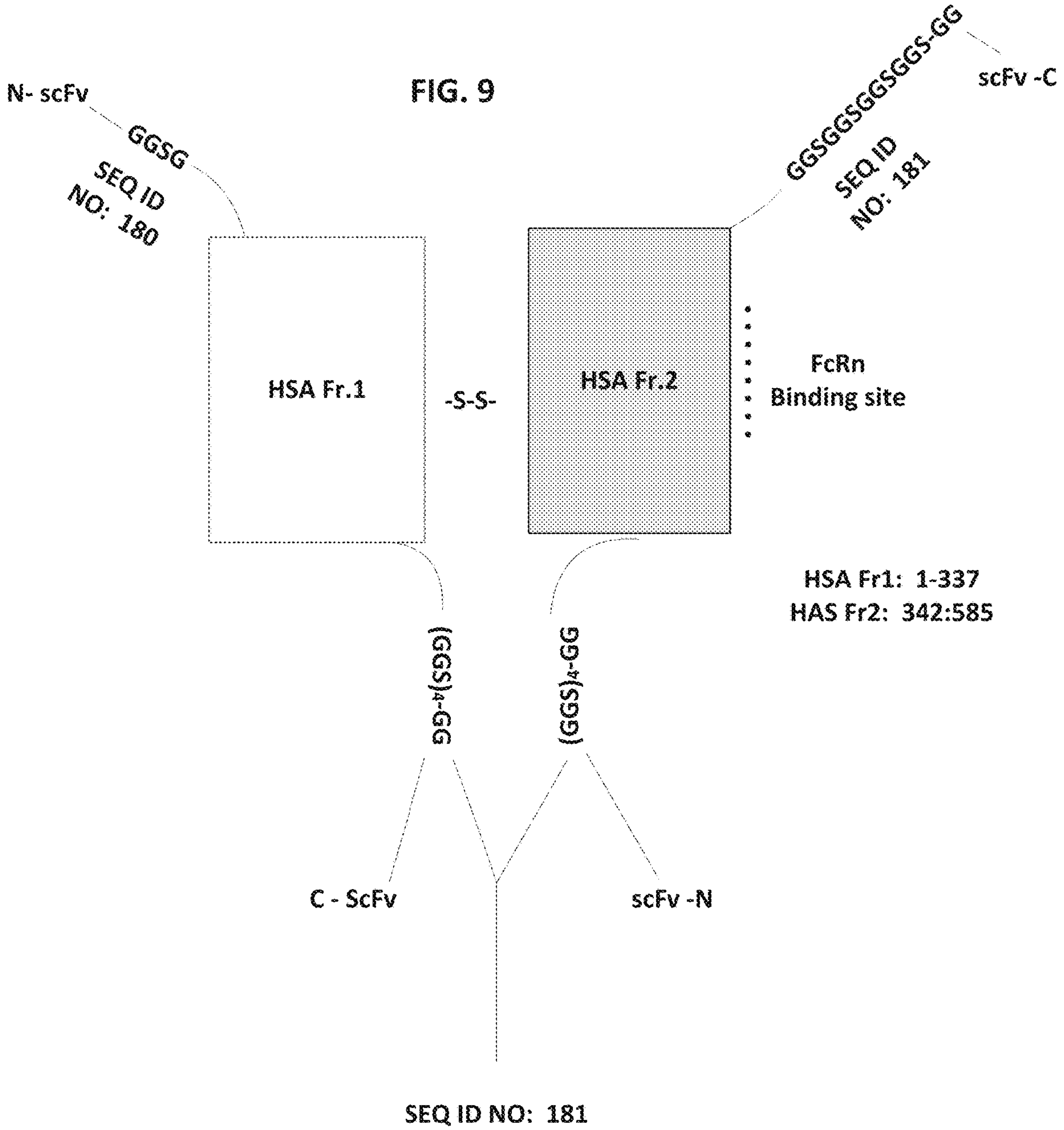
FIG. 9 shows scheme for multivalent Albumin based heteromultimers comprising anti-Her2/neu and anti-CD16 scFv bioactive fusions.

As shown in FIG. 9, the bioactive cargo polypeptides were fused to the heteromultimer transporter polypeptides via a GGSG linker (SEQ ID NO: 180), for the N terminus of one monomer and a longer (GGS)4GG (SEQ ID NO: 181) linker for all other termini in the other monomer. Table 9 illustrates the 16 base constructs (Base construct #1-Base construct #16) that were generated by fusing the 4D5 and NM3E cargo polypeptides to either N or C terminus of transporter polypeptide 1 (F1) or transporter polypeptide 2 (F2). F1: corresponds to SEQ ID 8 and F2 corresponds to SEQ ID 10.

TABLE 9

| # | Fusion 1 | Fusion 2 | Fusion 3 | SEQ ID NOs (nucleotide/amino acid): |
|---|---|---|---|---|
| | Single Fusions | | | |
| 1 | NM3E2 | F1 | | 95/96 |
| 2 | F1 | NM3E2 | | 97/98 |
| 3 | NM3E2 | F2 | | 99/100 |
| 4 | F2 | NM3E2 | | 101/102 |
| 5 | 4D5 | F1 | | 103/104 |
| 6 | F1 | 4D5 | | 105/106 |
| 7 | 4D5 | F2 | | 107/108 |
| 8 | F2 | 4D5 | | 109/110 |
| | Double Fusions | | | |
| 9 | NM3E2 | F1 | NM3E2 | 111/112 |
| 10 | NM3E2 | F2 | NM3E2 | 113/114 |
| 11 | 4D5 | F1 | 4D5 | 115/116 |
| 12 | 4D5 | F2 | 4D5 | 117/118 |
| 13 | NM3E2 | F1 | 4D5 | 119/120 |
| 14 | 4D5 | F1 | NM3E2 | 121/122 |
| 15 | NM3E2 | F2 | 4D5 | 123/124 |
| 16 | 4D5 | F2 | NM3E2 | 125/126 |

Figure 10A:
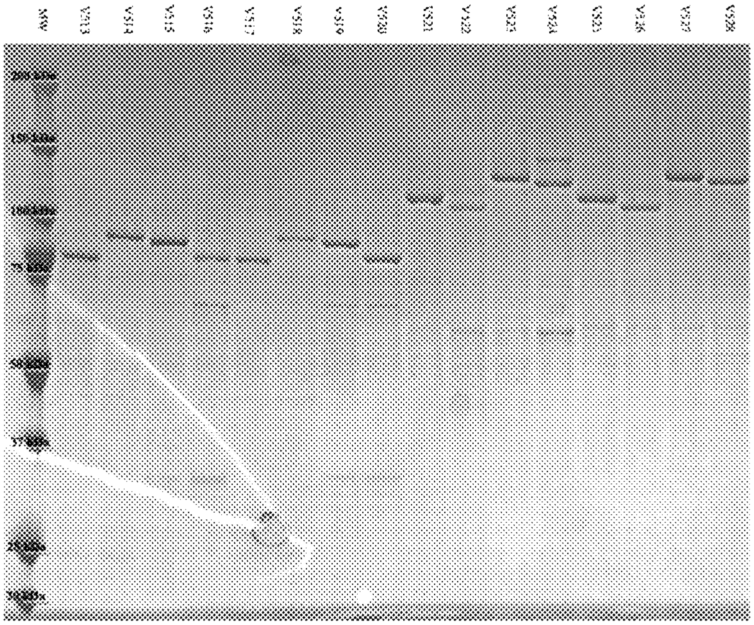
FIGS. 10A-10B contain a non-reducing SDS PAGE analysis of the heteromultimer ABH2 fusions described in Table 8. The gel indicates all constructs form the correct complex with expected MW.
Figure 10B:
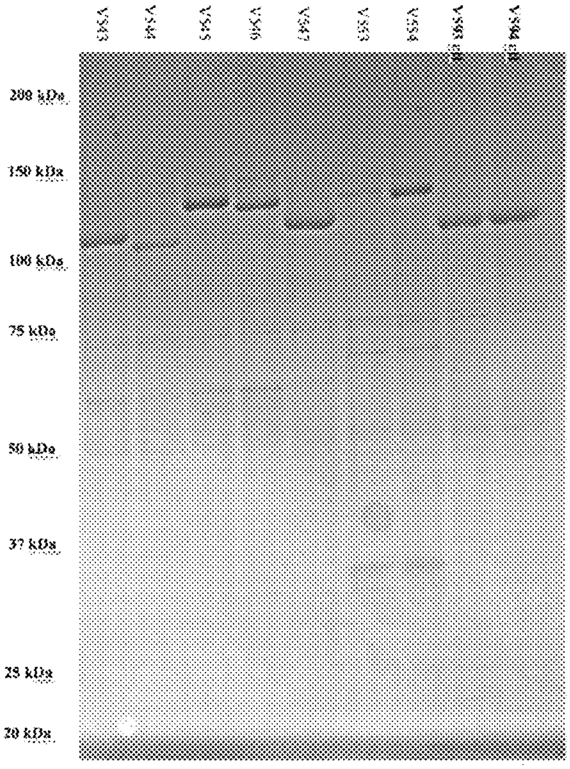

Multivalent constructs were generated as outlined in Example 2 using heteromultimer ABH2. The final gene products were subcloned into the mammalian expression vector pTT5 (NRC-BRI, Canada) (Durocher et al). High level and high-throughput recombinant protein production by transient transfection of suspension-growing human CHO-3E7 was performed. Additional detail regarding the preparation and expression of these constructs are found in Example 11. Purification was performed by application of the cellular supernatant with expressed protein to a QIAGEN-tip 500 column packed with Blue Sepharose matrix (GE Healthcare) coupled to an AKTA Express system (GE Healthcare) using a flow rate of 1 ml/ml. The column was equilibrated with equilibrated with sample buffer composed of 20 ml of PBS pH 7.2, 300 mM NaCl. The sample was loaded at a flow rate of 5 ml/min and subsequently washed with sample buffer. The protein was eluted by application of NaCl gradient ranging from 300 mM to 2000 mM. Fractions eluting in higher salt concentration were the purest and were pooled, concentrated and subsequently applied to a HiLoad 16/60 Superdex 200 prep grade gel filtration column coupled to an AKTA Express system (GE Healthcare) using a flow rate of 1 ml/ml. Protein with a purity of >85% was collected; fractions containing pure sample were pooled and concentrated by centrifugation using an Amicon Ultra membrane with a cutoff weight of 10 000 MWCO. FIGS. 10A-10B shows SDS-PAGE (non-reducing) analysis of the ABH2 heteromultimer fused to different cargo polypeptides. The position of those polypeptides in the heteromultimer relative to the transporter polypeptides is outlined in table 10 below. All constructs showed the expected molecular weight.

TABLE 10

Monovalent, multivalent, and multispecific constructs that were generated by fusing the 4D5 and NM3 cargo polypeptides to either N or C terminus of transporter polypeptide 1 or transporter polypeptide 2 of ABH2.

| Variant | N terminus-transporter polypeptide 1 (SEQ ID No: 8) | C terminus-transporter polypeptide 1 (SEQ ID No: 8) | N terminus-transporter polypeptide 2 (SEQ ID No: 10) | C terminus-transporter polypeptide 2 (SEQ ID No: 10) | Valency | Sequences (polypeptide) |
|---|---|---|---|---|---|---|
| 513 | NM3E | | | | monovalent | SEQ ID NO: 96<br>SEQ ID NO: 10 |
| 514 | | NM3E | | | monovalent | SEQ ID No: 98<br>SEQ ID NO: 10 |

TABLE 10-continued

Monovalent, multivalent, and multispecific constructs that were generated by fusing the 4D5 and NM3 cargo polypeptides to either N or C terminus of transporter polypeptide 1 or transporter polypeptide 2 of ABH2.

| Variant | N terminus-transporter polypeptide 1 (SEQ ID No: 8) | C terminus-transporter polypeptide 1 (SEQ ID No: 8) | N terminus-transporter polypeptide 2 (SEQ ID No: 10) | C terminus-transporter polypeptide 2 (SEQ ID No: 10) | Valency | Sequences (polypeptide) |
|---|---|---|---|---|---|---|
| 515 | | | NM3E | | monovalent | SEQ ID NO: 8<br>SEQ ID No: 100 |
| 516 | | | | NM3E | monovalent | SEQ ID NO: 8<br>SEQ ID No: 102 |
| 517 | 4D5 | | | | monovalent | SEQ ID No: 104<br>SEQ ID NO: 10 |
| 518 | | 4D5 | | | monovalent | SEQ ID No: 106<br>SEQ ID NO: 10 |
| 519 | | | 4D5 | | monovalent | SEQ ID NO: 8<br>SEQ ID No: 108 |
| 520 | | | | 4D5 | monovalent | SEQ ID NO: 8<br>SEQ ID No: 110 |
| 521 | NM3E | | NM3E | | bivalent | SEQ ID No: 96<br>SEQ ID No: 100 |
| 522 | NM3E | | | NM3E | bivalent | SEQ ID No: 96<br>SEQ ID No: 102 |
| 523 | | NM3E | NM3E | | bivalent | SEQ ID No: 98<br>SEQ ID No: 100 |
| 524 | | NM3E | | NM3E | bivalent | SEQ ID No: 98<br>SEQ ID No: 102 |
| 525 | 4D5 | | 4D5 | | bivalent | SEQ ID No: 104<br>SEQ ID No: 108 |
| 526 | 4D5 | | | 4D5 | bivalent | SEQ ID No: 104<br>SEQ ID No: 110 |
| 527 | | 4D5 | 4D5 | | bivalent | SEQ ID No: 106<br>SEQ ID No: 108 |
| 528 | | 4D5 | | 4D5 | bivalent | SEQ ID No:<br>106 + 108/110 |
| 529 | NM3E | NM3E | | | bivalent | SEQ ID No:112<br>SEQ ID NO: 10 |
| 530 | | | NM3E | NM3E | bivalent | SEQ ID NO: 8<br>SEQ ID No: 114 |
| 531 | 4D5 | 4D5 | | | bivalent | SEQ ID No: 116<br>SEQ ID NO: 10 |
| 532 | | | 4D5 | 4D5 | bivalent | SEQ ID NO: 8<br>SEQ ID No: 118 |
| 540 | 4D5 | 4D5 | | 4D5 | trivalent | SEQ ID No: 116<br>SEQ ID No: 110 |
| 542 | 4D5 | 4D5 | 4D5 | 4D5 | tetravalent | SEQ ID No: 116<br>SEQ ID No: 118 |
| 543 | NM3E | | 4D5 | | bispecific | SEQ ID No: 96<br>SEQ ID No: 108 |
| 544 | NM3E | | | 4D5 | bispecific | SEQ ID No: 96<br>SEQ ID No: 110 |
| 545 | | NM3E | 4D5 | | bispecific | SEQ ID No: 98<br>SEQ ID No: 108 |
| 546 | | NM3E | | 4D5 | bispecific | SEQ ID No: 98<br>SEQ ID No: 110 |
| 547 | 4D5 | | NM3E | | bispecific | SEQ ID No: 104<br>SEQ ID No: 100 |
| 548 | | 4D5 | NM3E | | bispecific | SEQ ID No: 106<br>SEQ ID No: 100 |
| 549 | 4D5 | | | NM3E | bispecific | SEQ ID No: 104<br>SEQ ID No: 102 |
| 550 | | 4D5 | | NM3E | bispecific | SEQ ID No: 106<br>SEQ ID No: 102 |
| 551 | NM3E | 4D5 | | | bispecific | SEQ ID No: 120<br>SEQ ID NO: 10 |
| 552 | 4D5 | NM3E | | | bispecific | SEQ ID No: 122<br>SEQ ID NO: 10 |
| 553 | | | NM3E | 4D5 | bispecific | SEQ ID NO: 8<br>SEQ ID No: 124 |
| 554 | | | 4D5 | NM3E | bispecific | SEQ ID NO: 8<br>SEQ ID No: 126 |
| 593 | 4D5 | | | NM3E | bispecific | SEQ ID No: 128 |
| 594 | NM3E | | | 4D5 | bispecific | SEQ ID No: 130 |

SPR Binding of Monovalent ABH2 Fused to a Single antiCD16scFv

Purified heteromultimer ABH2 fused to a single antiCD16scFv to the N terminus of transporter polypeptide SEQ ID 10 (construct v515) was used in a binding experiment using Surface Plasmon Resonance (SPR). Soluble CD16 was covalently immobilized onto a CM5 surface and ABH2 fused to antiCD16scFv was captured and binding kinetics were determined.

SPR supplies.

GLM sensorchips, the Biorad ProteOn amine coupling kit (EDC, sNHS and ethanolamine), and 10 mM sodium acetate buffers were purchased from Bio-Rad Laboratories (Canada) Ltd. (Mississauga, ON). Recombinant Her-2 protein was purchased from eBioscience (San Diego, Calif.). HEPES buffer, EDTA, and NaCl were purchased from Sigma-Aldrich (Oakville, ON). 10% Tween 20 solution was purchased from Teknova (Hollister, Calif.). SPR biosensor assays. All surface plasmon resonance assays were carried out using a BioRad ProteOn XPR36 instrument (Bio-Rad Laboratories (Canada) Ltd. (Mississauga, ON)) with HBST running buffer (10 mM HEPES, 150 mM NaCl, 3.4 mM EDTA, and 0.05% Tween 20 pH 7.4) at a temperature of 25° C. The CD16 capture surface was generated using a GLM sensorchip activated by a 1:5 dilution of the standard Bio-Rad sNHS/EDC solutions injected for 300 s at 30 μL/min in the analyte (horizontal) direction. Immediately after the activation, a 4.0 μg/mL solution of CD16 in 10 mM NaOAc pH 4.5 was injected in the ligand (vertical) direction at a flow rate of 25 μL/min until approximately 3000 resonance units (RUs) were immobilized. Remaining active groups were quenched by a 300 s injection of 1M ethanolamine at 30 μL/min in the analyte direction, and this also ensures mock-activated interspots are created for blank referencing.

A 500 nM 3-fold dilution series of V515 was injected over 3000 RUs CD16aWT (L6) compared to blank (L5). Flow rate 50 uL/min for 120s, with a 240s disassociation phase. Injections were repeated in standard running buffer (DPBS/3.4 mM EDTA/0.05% Tween20) and running buffer with an additional 350 mM NaCl. Sensorgrams were aligned and double-referenced using the buffer blank injection and interspots, and the resulting sensorgrams were analyzed using ProteOn Manager software v3.0. Typically, $K_D$ values were determined from binding isotherms using the Equilibrium Fit model. For high affinity interactions with slow off-rates, kinetic and affinity values were additionally determined by fitting the referenced sensorgrams to the 1:1 Langmuir binding model using local Rmax, and affinity constants ($K_D$ M) were derived from the resulting rate constants ($k_d$ $s^{-1}$/$k_a$ $M^{-1}$ $s^{-1}$). All $K_D$ values are reported as the mean and standard deviation from three independent runs.

As shown in Table 11, ABH2 heteromultimer fused to a single antiCD16scFv has full activity and binds its target with good reproducibility and KD similar to the free anti CD16 scFv (NM3E).

TABLE 11

SPR data for monovalent ABH2 fused to a single antiCD16scFv.

| | Injection #1 | | | Injection #2 | | | | |
|---|---|---|---|---|---|---|---|---|
| | ka 1/Ms | kd 1/s | KD M | ka 1/Ms | kd 1/s | KD M | KD (M) Ave | KD SD |
| NM3E | 5.37E+04 | 5.76E−03 | 1.07E−07 | 5.89E+04 | 6.03E−03 | 1.02E−07 | 1.05E−07 | 4.E−09 |
| V515 Dec | 6.11E+04 | 6.71E−03 | 1.10E−07 | | | | | |
| V515 Jan | 5.58E+04 | 7.30E−03 | 1.31E−07 | | | | | |

Example 4 Preparation of HA or HAA Based Heteromultimer Proteins Wherein Cargo Protein(s) Comprise One or More EGF-A Like Domain The peptide sequence of the EGF-A domain in PCSK9 protein or another polypeptide sequence homologous to the EGF-A domain, capable of specifically binding the low density lipoprotein receptor (LDL-R) is derived by sequencing or from a database such as GenBank. The cDNA for the cargo polypeptide comprising EGF-A like domain is isolated by a variety of means including but not exclusively, from cDNA libraries, by RT-PCR and by PCR using a series of overlapping synthetic oligonucleotide primers, all using standard methods. In certain examples, the cargo protein is engineered to improve stability, target binding features or other biophysical or therapeutically relevant properties. The polypeptide is employed as the cargo protein in the creation of a heteromultimer with application in the treatment of hypercholesterolemia. The first and second monomeric fusion polypeptide sequence is derived by fusing the cargo protein sequence directly or with an intermediate linker peptide to the N-terminus and/or C-terminus of HA or HAA based transporter polypeptide such as SEQ ID No: 2, SEQ ID NO: 3, SEQ ID NO: 8 or SEQ ID NO: 10. This monomeric fusion protein sequence is reverse translated to its corresponding DNA sequence to be introduced in an expression vector, sequence optimized for expression in a particular cell line of interest. The first and second monomeric fusion proteins are transfected and coexpressed in the cell line of interest. In certain cases, the transfection is in 1:1 ratio for the two vectors. In some examples, the ratio is selected from 1.5:1, 2:1, 1:1.5, 1:2 etc.

Example 5 Preparation of HA or HAA Based Heteromultimeric Proteins Wherein Cargo Protein(s) are the GLP-1 and/or Glucagon The peptide sequence of GLP-1 or another polypeptide sequence homologous to this peptide, capable of specifically binding the GLP-1 receptor or acting as a GLP-1 agonist is derived by sequencing or from a database such as GenBank. Alternately, the peptide sequence of Glucagon or another polypeptide sequence homologous to this peptide, capable of specifically binding the Glucagon receptor or acting as a Glucagon receptor agonist is derived by sequencing or from a database such as GenBank. The cDNA for each cargo polypeptide comprising GLP-1 or Glucagon is isolated by a variety of means including but not exclusively, from cDNA libraries, by RT-PCR and by PCR using a series of overlapping synthetic oligonucleotide primers, all using standard methods. In certain examples, these GLP-1 or Glucagon based cargo polypeptides are engineered to improve stability, target binding features or other biophysical or therapeutically relevant properties. These GLP-1 and Glucagon based polypeptides are employed as one or more cargo molecules in the creation of a heteromultimer with application in the treatment of type-2 diabetes or another disease related to glucose metabolism. The first and second monomeric fusion polypeptide sequence is derived by fusing the cargo protein sequence directly or with an intermediate linker peptide to the N-terminus and/or C-terminus of HA or HAA based transporter polypeptide such as SEQ ID No: 2, SEQ ID NO: 3, SEQ ID NO: 8 or SEQ ID NO: 10. The fusion proteins can be monospecific with either GLP-1 or Glucagon like polypeptides or be bispecific (coagonist) with both the GLP-1 and Glucagon like polypeptides. Each monomeric fusion protein sequence is reverse translated to its corresponding DNA sequence to be introduced in an expression vector, sequence optimized for expression in a particular cell line of interest. The first and second monomeric fusion proteins are transfected and coexpressed in the cell line of interest. In certain cases, the transfection is in 1:1 ratio for the two vectors. In some examples, the ratio is selected from 1.5:1, 2:1, 1:1.5, 1:2 etc.

```
Sequence of Cargo molecule GLP-1
SEQ ID No: 12: HAEGTFTSDVSSYLEGQAAKEFIAWLVKGRG

Sequence of Cargo molecule Glucagon
SEQ ID NO: 13: HSQGTFTSDYSKYLDSRRAQDFVQWLMNT
```

Example 6: Annexin Protein Repeat as Membrane-Sensing Multivalent Scaffold

Figure 11:
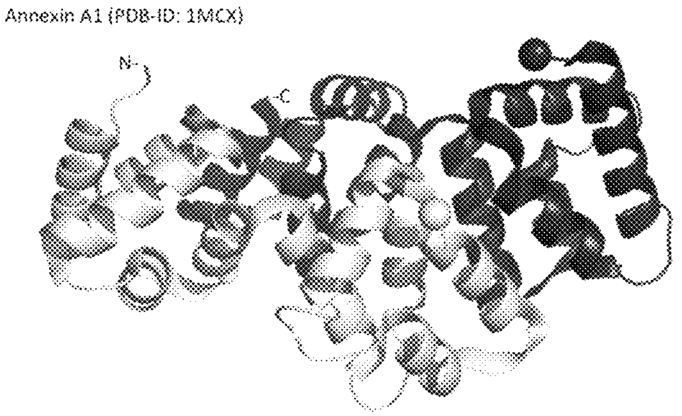
FIG. 11 shows structure of Annexin molecule based on the PDB structure 1MCX. The two monomers that will be derived by splitting the Annexin molecule are color coded as light and dark grey units. The sites of fusion for the cargo protein are represented as spheres.

Annexin is split with an extensive interface to generate a multivalent heteromultimer scaffold comprising two transporter polypeptides. Annexin is a 346 residue protein (PDB ID 1MCX). Heteromultimer comprising two transporter polypeptides based on annexin split in the region between residue 186 and 194 is shown in FIG. 11. When coexpressed in solution, the large interfacial area between the two transporter polypeptides leads to self-assembly of the heterodimer. The self-assembly of the two units allows for the design of multivalent construct with transporter polypeptides based on the annexin core. Two structures are available, Pig and Human. The two structures are superimposable with an rmsd of 0.6 A. The following stretch of sequence can be removed from the human Annexin sequence DRSEDF (SEQ ID NO: 182) (residues 160 through 165). The truncation does not break any secondary structure element and does not involve introducing or removing any Proline residue.

```
Human annexin WT Sequence SEQ ID NO: 14:
GSAVSPYPTFNPSSDVAALHKAIMVKGVDEATIIDILTKRNNAQRQQIKA

AYLQETGKPLDETLKKALTGHLEEVVLALLKTPAQFDADELRAAMKGLGT

DEDTLIEILASRTNKEIRDINRVYREELKRDLAKDITSDTSGDFRNALLS

LAKGDRSEDFGVNEDLADSDARALYEAGERRKGTDVNVFNTILTTRSYPQ

LRRVFQKYTKYSKHDMNKVLDLELKGDIEKCLTAIVKCATSKPAFFAEKL
```

-continued

```
HQAMKGVGTRHKALIRIMVSRSEIDMNDIKAFYQKMYGISLCQAILDETK

GDYEKILVALCGGN

Sequence of Annexin based transporter polypeptide-
1: SEQ ID NO: 15:
SAVSPYPTFNPSSDVAALHKAIMVKGVDEATIIDILTKRNNAQRQQIKAA

YLQETGKPLDETLKKALTGHLEEVVLALLKTPAQFDADELRAAMKGLGTD

EDTLIEILASRTNKEIRDINRVYREELKRDLAKDITSDTSGDFRNALLSL

AKG

Sequence of Annexin based transporter polypeptide-
2: SEQ ID NO: 16:
GVNEDLADSDARALYEAGERRKGTDVNVFNTILTTRSYPQLRRVFQKYTK

YSKHDMNKVLDLELKGDIEKCLTAIVKCATSKPAFFAEKLHQAMKGVGTR

HKALIRIMVSRSEIDMNDIKAFYQKMYGISLCQAILDETKGDYEKILVAL

CGGN
```

Figure 12:
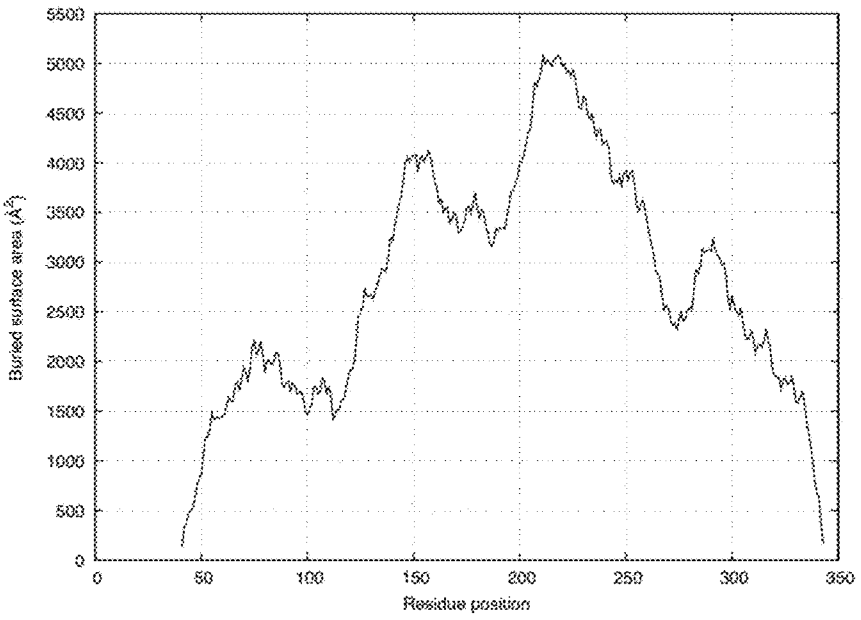
FIG. 12 shows a plot of the buried solvent accessible surface area at the interface of Annexin based transporter polypeptide-1, and Annexin based transporter polypeptide-2.

FIG. 12 shows a plot of the buried solvent accessible surface area at the interface of Annexin based transporter polypeptide-1 (ABT-1), and Annexin based transporter polypeptide-2 (ABT-2). A split annexin near residue position 186 forms a heterodimer with about 3200 $Å^2$ of buried surface area. The transporter polypeptides such as ABT-1 and ABT-2 based on Annexin can be used to attach cargo biomolecules using the same methods as described above for albumin based transporter polypeptides.

Example 7: Transferrin as a Multivalent Scaffold

Figure 13:
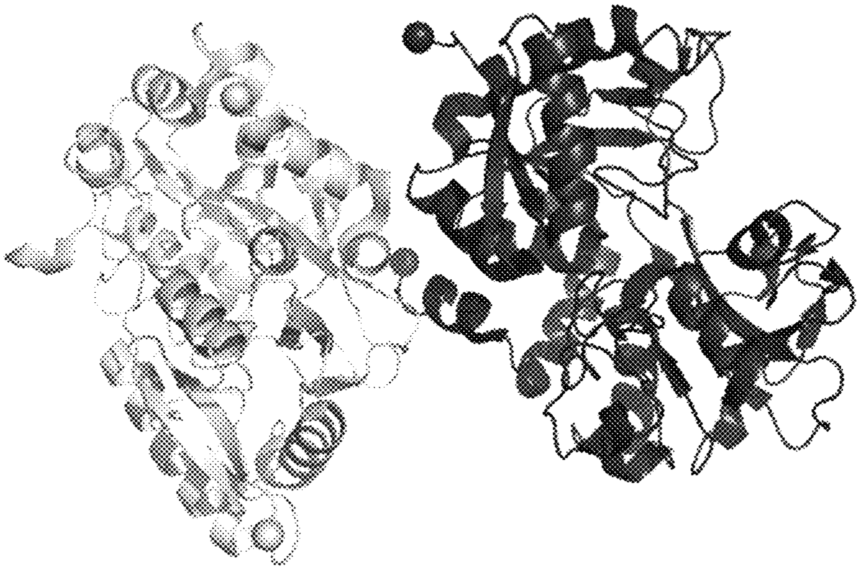
FIG. 13 shows structure of transferrin molecule based on the PDB structure 1H76. The two monomers derived by splitting the transferrin molecule are color coded as light and dark grey units. The sites of fusion for the cargo protein are represented as spheres.

Based on the large number of therapeutically relevant properties of transferrin, this protein presents itself as an interesting scaffold molecule for the design of multivalent protein fusion drugs following the creation of a self-assembling protein and its split component parts. The structure of transferrin is shown in FIG. 13 based on the crystal structure (1H76) available in the protein data bank [Hall D R et al. Acta Crystallogr D 2002, 58, 70-80]. The transferrin molecule is composed of two structurally similar lobes, the N and C terminal lobes, connected by a short peptide linker between residues 333 and 342.

A heterodimer is designed based on transferrin protein, said heterodimer comprising a first transporter polypeptide involving residues 1-333 of transferrin and a second transporter polypeptide composed of residues from 342 to the C-terminus of the original transferrin sequence. When coexpressed, the two transporter polypeptides fold independently and pair to form a quasi-transferrin scaffold capable of maintaining its therapeutically relevant properties. Furthermore, such a Transferrin scaffold allows for the production of multivalent fusion molecules, e.g. a multivalent GLP-1 fusion with trasnsporter polypeptides based on transferring. These fusions can be similar to the GLP-1-fusion polypeptides with Albumin based transporter polypeptides.

Figure 14:
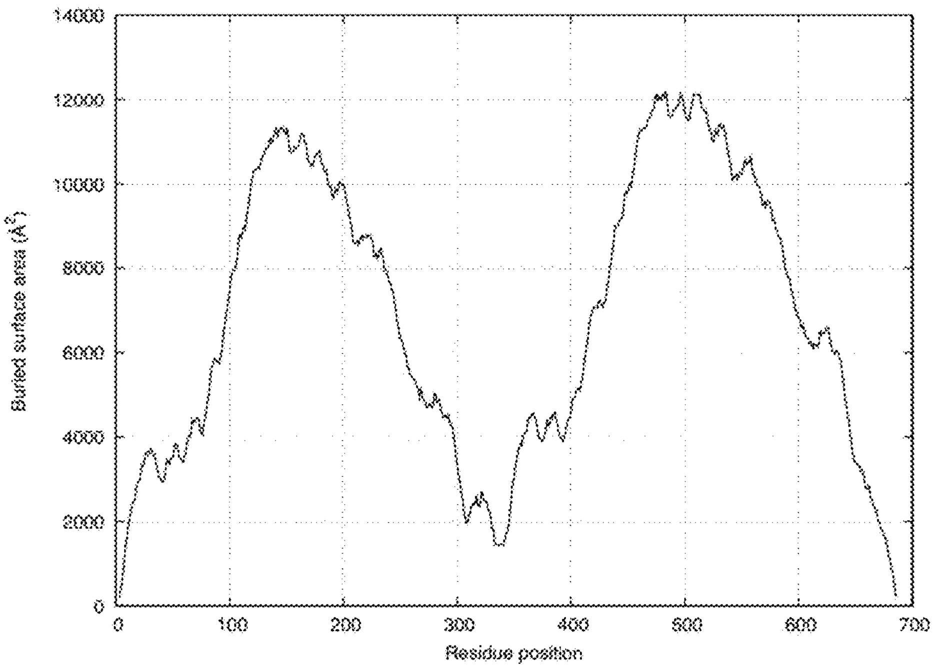
FIG. 14 shows a plot of the buried solvent accessible surface area at the interface of two transferrin based transporter polypeptides described herein. A split transferrin near residue position 330 as designed herein, forms a heterodimer with about 1800 Å$^2$ of buried surface area.

FIG. 13 provides structure of transferrin molecule based on the PDB structure 1H76. The two monomering transporter polypeptides derived by splitting the transferrin molecule are color coded as light and dark grey units. The sites of fusion for the cargo molecules are represented as spheres. FIG. 14 shows a plot of the buried solvent accessible surface area at the interface of two transferrin based polypeptides. A split transferrin near residue position 330 such as the two transporter polypeptides shown below, forms a heterodimer with about 1800 Å2 of buried surface area.

Sequence of Transferrin based transporter polypeptide-1:

```
SEQ ID NO: 17:
MRLAVGALLVCAVLGLCLAVPDKTVRWCAVSEHEATKCQS

FRDHMKSVIPSDGPSVACVKKASYLDCIRAIAANEADAVT

LDAGLVYDAYLAPNNLKPVVAEFYGSKEDPQTFYYAVAVV

KKDSGFQMNQLRGKKSCHTGLGRSAGWNIPIGLLYCDLPE

PRKPLEKAVANFFSGSCAPCADGTDFPQLCQLCPGCGCST

LNQYFGYSGAFKCLKDGAGDVAFVKHSTIFENLANKADRD

QYELLCLDNTRKPVDEYKDCHLAQVPSHTVVARSMGGKED

LIWELLNQAQEHFGKDKSKEFQLFSSPHGKDLLFKDSAHG

FLKVPPRMDAKMYLGYEYVTAIRNLREG.
```

Sequence of Transferrin based transporter polypeptide-2:

```
SEQ ID NO: 18:
ECKPVKWCALSHHE RLKCDEWSVN SVGKIECVSA ETTEDCIAKI

MNGEADAMSL DGGFVYIAGK CGLVPVLAEN YNKSDNCEDT

PEAGYFAVAV VKKSASDLTW DNLKGKKSCH TAVGRTAGWN

IPMGLLYNKI NHCRFDEFFS EGCAPGSKKD SSLCKLCMGS

GLNLCEPNNK EGYYGYTGAF RCLVEKGDVA FVKHQTVPQN

TGGKNPDPWA KNLNEKDYEL LCLDGTRKPV EEYANCHLAR

APNHAVVTRK DKEACVHKIL RQQQHLFGSN VTDCSGNFCL

FRSETKDLLF RDDTVCLAKL HDRNTYEKYL GEEYVKAVGN

LRKCSTSSLL EACTFRRP
```

Example 8: Design of Disulfide Stabilized HA or HAA Based Heteromultimer Proteins Albumin based transporter polypeptides were designed wherein as compared to albumin, specific positions were mutated to cysteine in each of the transporter polypeptides to enable the selective formation of a disulfide link between two transporter polypeptide, resulting in a stable heterodimer with a quasi-native albumin monomer structure.

The residues for the introduction of cysteines were selected taking into consideration the following factors:

a. Form a covalent bond between the two transporter polypeptides, thereby increasing the stability of the heteromultimer and the resultant quasi-native monomeric form.

b. must be within specific CA-CA and CB-CB limits to form a disulphide bond c. compatible local environment (generally preferring shorter hydrophobic side chains in partially solvent exposed regions) is not likely to interfere with existing polar contacts.

Mutagenesis was performed by QuickChange, and expression and purification were performed as presented in Examples 1 and 2 above.

Table 12 below identifies a number of albumin-based heteromultimers comprising introduced cysteines that were designed. ABH3-8 were designed based on the ABH2 design, while ABH9-12 were based on the ABH1 design.

TABLE 12

Albumin based heteromultimers comprising introduced cysteines

| Hetero-multimer | Variant ID | Transporter polypeptide 1 (first-last amino acid of the N-terminal albumin segment are denoted) | Transporter polypeptide 2 (first-last amino acid of the C-terminal albumin segment are denoted) | New Cys in transporter polypeptide 1 | New CYS in transporter polypeptide 2 |
|---|---|---|---|---|---|
| ABH3 | 881 | 1-337 (SEQ ID NO 19) | 342-585 (SEQ ID NO 20) | A217C | V343C |
| ABH4 | 882 | 1-337 (SEQ ID NO 21) | 342-585 (SEQ ID NO 22) | L331C | A350C |
| ABH5 | 883 | 1-337 (SEQ ID NO 23) | 342-585 (SEQ ID NO 24) | A217C | L346C |
| ABH6 | 884 | 1-337 (SEQ ID NO 25) | 342-585 (SEQ ID NO 26) | W214C | V343C |
| ABH7 | 885 | 1-337 (SEQ ID NO 27) | 342-585 (SEQ ID NO 28) | A335C | L346C |
| ABH8 | 886 | 1-337 (SEQ ID NO 29) | 342-585 (SEQ ID NO 30) | L198C | V455C |
| ABH9 | 887 | 1-293 (SEQ ID NO 31) | 304-585 (SEQ ID NO 32) | A217C | A335C |
| ABH10 | 888 | 1-293 (SEQ ID NO 33) | 304-585 (SEQ ID NO 34) | A217C | L331C |
| ABH11 | 889 | 1-293 (SEQ ID NO 35) | 304-585 (SEQ ID NO 36) | L198C | N458C |
| ABH12 | 890 | 1-293 (SEQ ID NO 37) | 304-585 (SEQ ID NO 38) | A194C | V455C |

Figure 35:
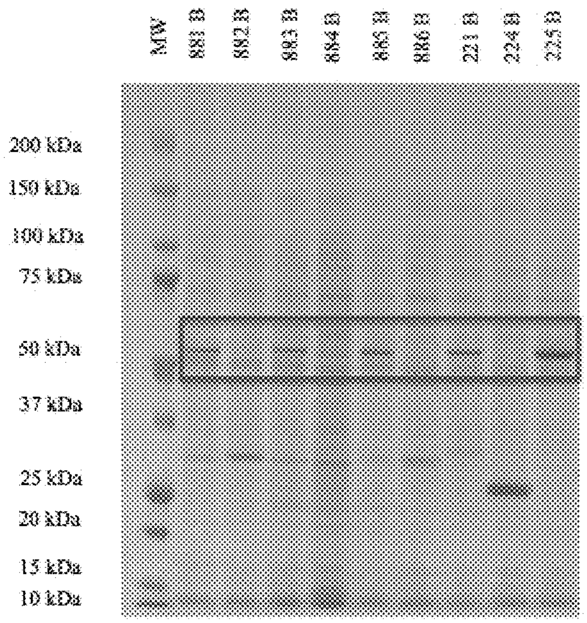
FIG. 35 shows a gel demonstrating the expression of several albumin-based heteromultimers comprising introduced cysteine residues.
Figure 36A:
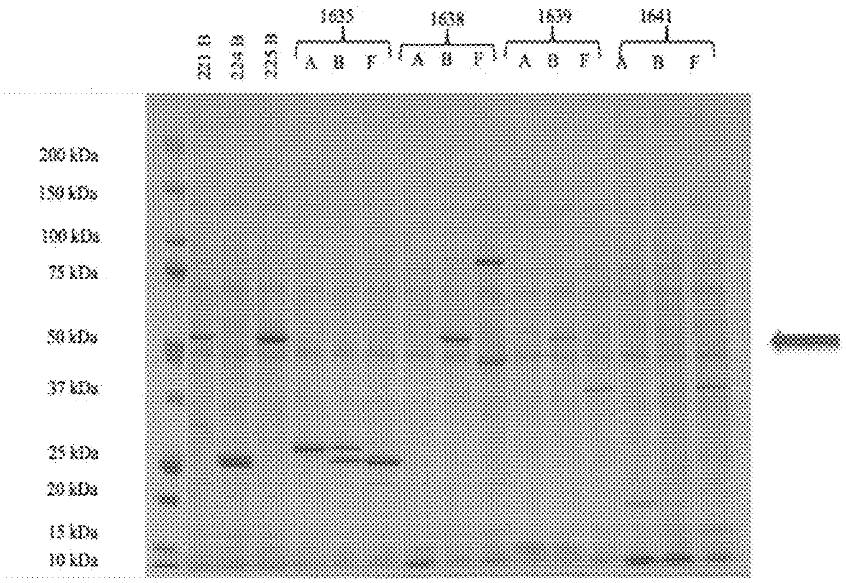
FIG. 36A provides a non-reducing gel showing the expression of heteromultimer variants 1635, 1638, 1639, and 1641.
Figure 36B:
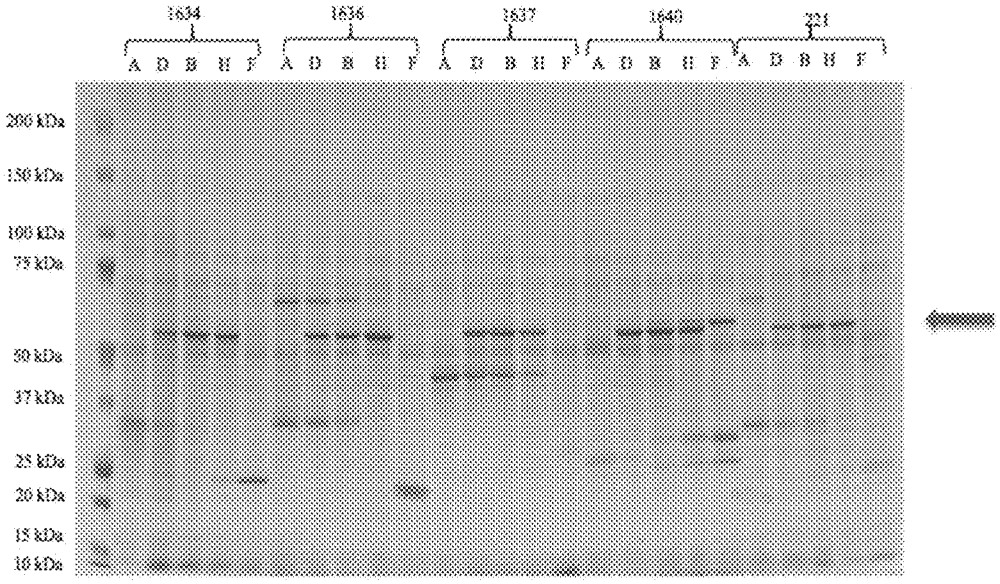
FIG. 36B provides a non-reducing gel showing the expression of heteromultimer variants 1634, 1636, 1637, 1640, and 221. CHO cells were transfected with the following DNA ratios: Ratio A=plasmid A:plasmid B 100%:0%; Ratio D=plasmid A:plasmid B 66%:34%; Ratio B=plasmid A:plasmid B 50%:50%; Ratio H=plasmid A: plasmid B 34%:66%; and Ratio F=plasmid A:plasmid B 0%/100%.

Variants ABH3, ABH4, ABH5, ABH6, ABH7 and ABH8 were expressed with DNA ratio 1:1 (Fragment 1:Fragment 2) in small scale 2 mL CHO cultures. A gel of expression is shown in FIG. 35. WT-Albumin (v225) along with previous variants AlbuCORE 1 and AlbuCORE 2 were also expressed as controls. Variant ABH3, ABH5 and ABH7 expressed similarly to ABH2, while the remaining variants displayed lower expression and possible disulfide scrambling, noticeable by multiple bands in non-reducing SDS PAGE, potentially because of the presence of the natural disulfide positions as well as the introduced cysteine mutations. Recovery of expression may be achieved by changing the cut site (see Example 9) or transfecting with different DNA ratios. No Linkers were present at the termini of these constructs. Introduction of the disulfide bonding cysteine mutations in variants such as ABH9, ABH10, ABH11 and ABH12 are expected to address this issue since they lack a natural disulfide bonding positions in the original interface.

Figure 15A:
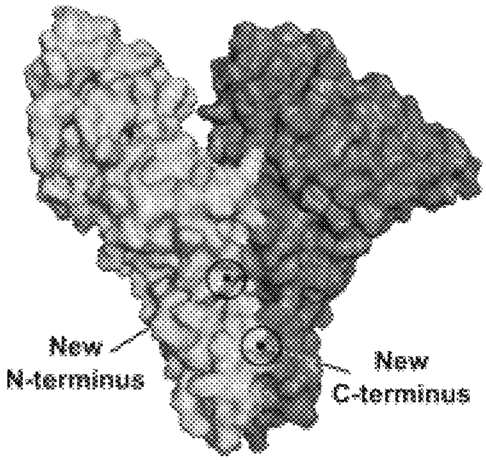
FIGS. 15A-15P depict heteromultimers comprising albumin based transporter polypeptides that self-associate to form quasi-native monomeric albumin. Each pair of transporter polypeptides is obtained by segmentation of albumin at a unique site, different from the other FIGS. 16A and 16B provides the structures of ABH2 and ABH1 respectively. Both diagrams include a) the location of the cut site in WT-HSA to create the albumin-based protein, b) location of the new C' and N' cut sites and c) a simplified circular rendering of both ABH1 and ABH2, utilized in numerous later examples.
Figure 15C:
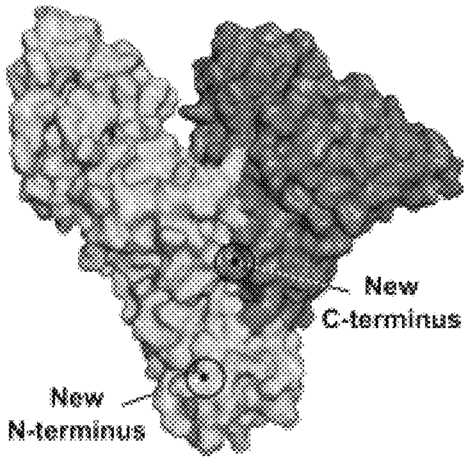
Figure 15B:
Figure 15D:
Figure 15E:
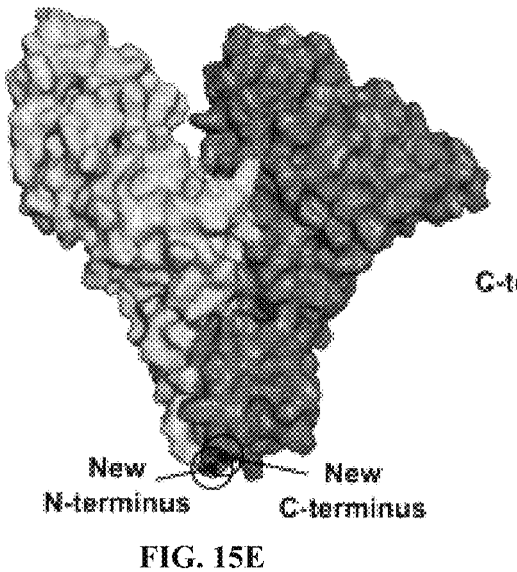
Figure 15G:
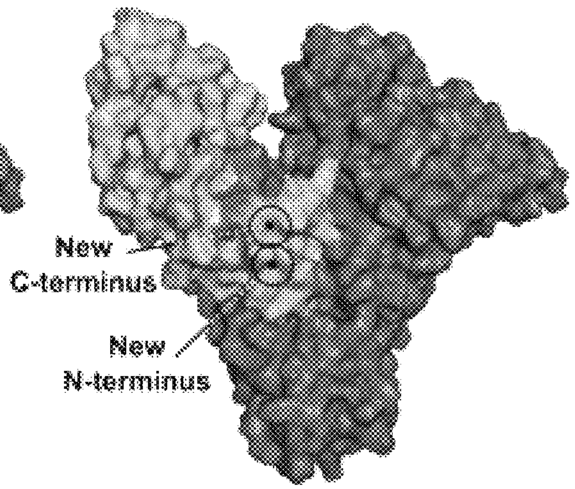
Figure 15F:
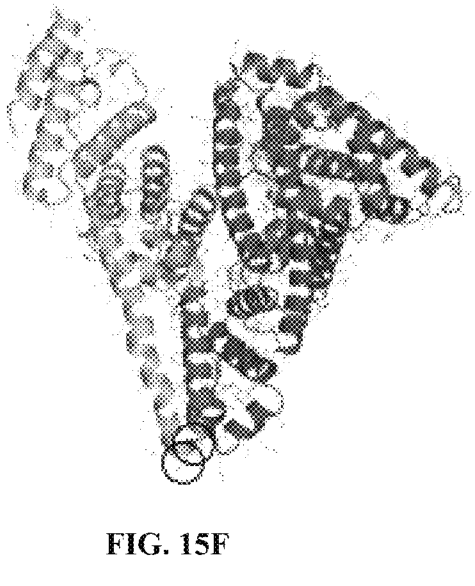
Figure 15H:
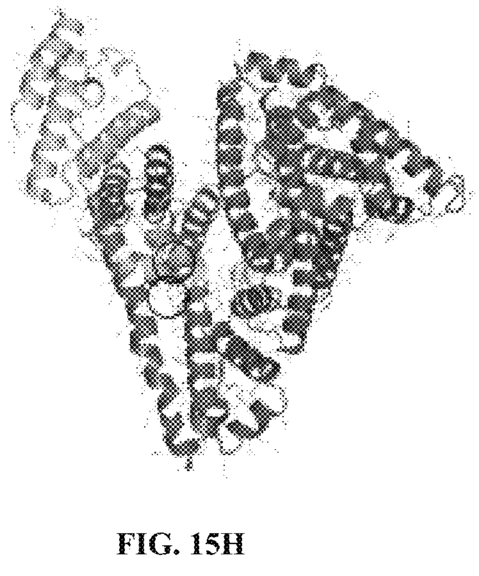
Figure 15I:
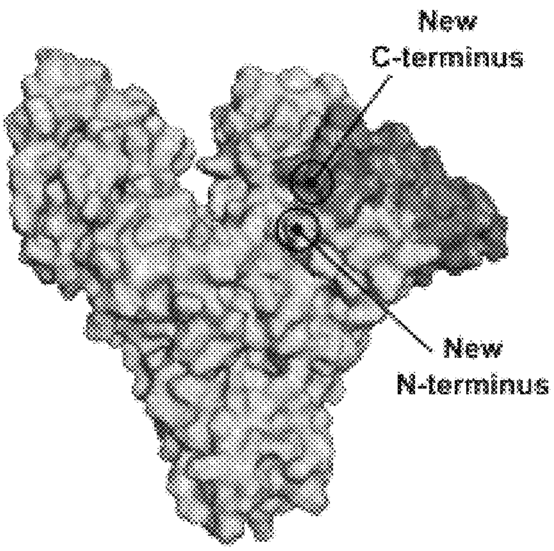
Figure 15J:
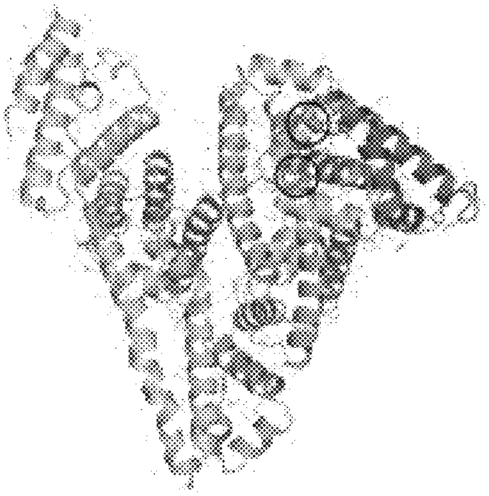
Figure 15K:
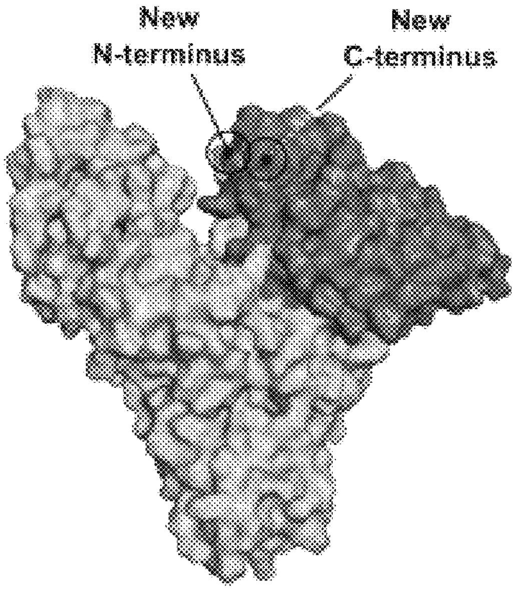
Figure 15L:
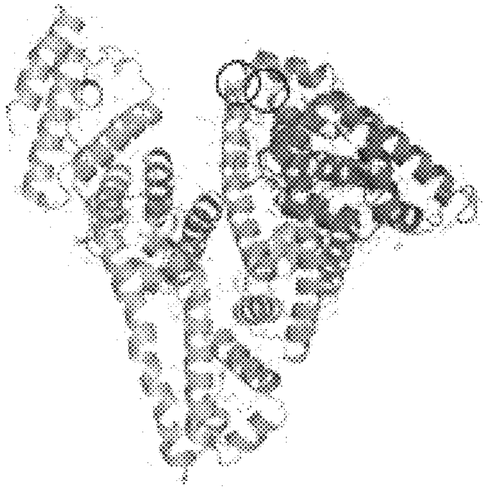
Figure 15M:
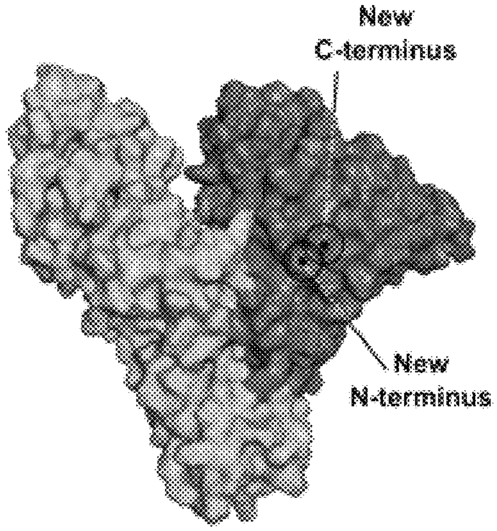
Figure 15O:
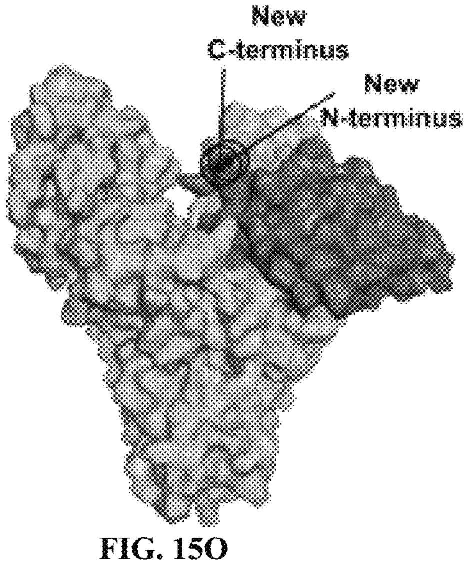
Figure 15N:
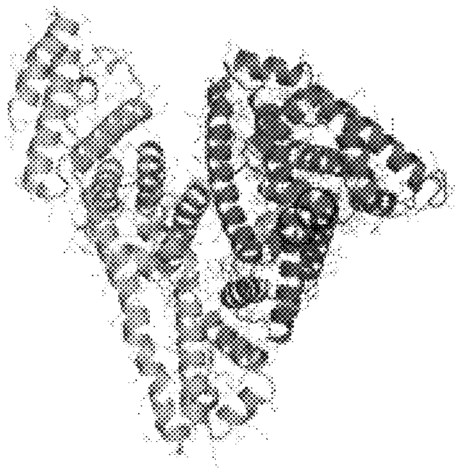
Figure 15P:
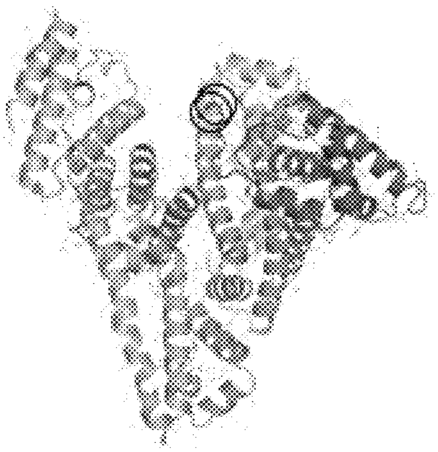

Example 9: Design of HA or HAA Based Heteromultimer Proteins Based on Different Segmentation Sites Table 13 below provides heteromultimer constructs as described herein comprising transporter polypeptides designed by segmenting albumin at various sites as shown in FIGS. 15A-15P and listed in Table 1. Differently from previous constructs described in Example 8 and proceeding ones, all AlbuCORE constructs in Example 9 were created with a GGGGS linker (SEQ ID NO: 179) fused to the C terminus of Fragment 1 and the N terminus of fragment 2. This was done for multiple reasons: 1) The presence of a short linker re-creates a typical fusion molecule and allows us to understand the compatibility of the cut site(s) with the presence of a linker. 2) The presence of a linker may also help stabilize the local environment surrounding the cut site, including shielding some exposed hydrophobic patches. 3) Presence of a linker reduces the number of variables in subsequent phases, when a warhead is fused to the molecule. See Table 13 for expression results. Expression was initially tested in small scale CHO cultures with the two fragment in each AlbuCORE variant performed in different combinations of ratios. The gel in the FIGS. 35A and B illustrates the expression results.

TABLE 13

Albumin based heteromultimers constructs based on different albumin segments.

| Heteromultimer | ID | Transporter polypeptide 1 (first-last amino acid of the N-terminal albumin segment are denoted) | Transporter polypeptide 2 (first-last amino acid of the C-terminal albumin segment are denoted) |
|---|---|---|---|
| ABH13 | AlbuCORE_1A | 1-339 (SEQ ID NO 39) | 340-585 (SEQ ID NO 40) |
| ABH14 | AlbuCORE_2A | 1-300 (SEQ ID NO 41) | 301-585 (SEQ ID NO 42) |
| ABH15 | AlbuCORE_3 | 1-364 (SEQ ID NO 43) | 365-585 (SEQ ID NO 44) |
| ABH16 | AlbuCORE_4 | 1-441 (SEQ ID NO 45) | 442-585 (SEQ ID NO 46) |
| ABH17 | AlbuCORE_6 | 1-83 (SEQ ID NO 47) | 85-585 (SEQ ID NO 48) |
| ABH18 | AlbuCORE_7 | 1-171 (SEQ ID NO 49) | 172-585 (SEQ ID NO 50) |
| ABH19 | AlbuCORE_9 | 1-281 (SEQ ID NO 51) | 282-585 (SEQ ID NO 52) |
| ABH20 | AlbuCORE_13 | 1-114 (SEQ ID NO 53) | 115-585 (SEQ ID NO 54) |

Expression of selected variants was performed as described in Example 2, while purification was carried out as described in Example 17. The characteristics of these molecules with respect to the linkers used, disulphide cross-links, and a summary of the expression results are shown in Table 14.

TABLE 14

Results of expression of variants listed in Table 13 (table discloses "GGGGS" as SEQ ID NO: 179):

| SEQ ID (polypeptide) | Variant | Scaffold | Split/ Deletion | frag1: frag2 | frag1 MW | frag2 MW | Interface S-S [disulfide link between the two fragments forming AlbuCORE] | Optimal DNA ratio (Fragment 1: Fragment 2) | Expression (compared to AlbuCORE_1 and cloned WT HSA). Rough estimate based on band intensity (assessed by software). | Linkers |
|---|---|---|---|---|---|---|---|---|---|---|
| 39 + 40 | 1634 | AlbuCORE_1A | nick(339-340) | 1-339:340-585 | 39.03 kDa | 28.10 kDa | 316.CYS-361.CYS | 1:1 | ~30% better than closely related AlbuCORE_1. Single fragments still visible in 1:0 and 0:1 DNA ratios. When in excess, no clear signs of multimerization | Fragment 1: GGGGS (new C terminus) Fragment 2: GGGGS (new N terminus) |

TABLE 14-continued

Results of expression of variants listed in Table 13 (table discloses "GGGGS" as SEQ ID NO: 179):

| SEQ ID (polypeptide) | Variant | Scaffold | Split/ Deletion | frag1: frag2 | frag1 MW | frag2 MW | Interface S-S [disulfide link between the two fragments forming AlbuCORE] | Optimal DNA ratio (Fragment 1: Fragment 2) | Expression (compared to AlbuCORE_1 and cloned WT HSA). Rough estimate based on band intensity (assessed by software). | Linkers |
|---|---|---|---|---|---|---|---|---|---|---|
| 41 + 42 | 1635 | AlbuCORE_2A | nick(300-301) | 1-300:301-585 | 34.53 kDa | 32.59 kDa | N/A | Only 1:1, 1:0 and 0:1 was tested | Expression is ~30% better than AlbuCORE_1 but needs native gel for assessment of complex. | Fragment 1: GGGGS (new C terminus) Fragment 2: GGGGS (new N terminus) |
| 43 + 44 | 1636 | AlbuCORE_3 | nick(364-365) | 1-364:365-585 | 41.78 kDa | 25.35 kDa | 360.CYS-369.CYS | 1:2 | ~30-50% better. Fragment 1 tends to multimerize when in access (DNA ratio not optimized) | Fragment 1: GGGGS (new C terminus) Fragment 2: GGGGS GS (new N terminus) |
| 45 + 46 | 1637 | AlbuCORE_4 | nick(441-442) | 1-441:442-585 | 50.65 kDa | 16.48 kDa | 437.CYS-448.CYS | 1:2 | ~30-50% better. Fragment 1 in excess when DNA ratio not optimized No signs of multimerization. | Fragment 1: GGGGS (new C terminus) Fragment 2: GGGGS (new N terminus) |
| 47 + 48 | 1638 | AlbuCORE_6 | Δ(84) | 1-83:85-585 | 9.68 kDa | 57.29 kDa | 75.CYS-91.CYS | Only 1:1, 1:0 and 0:1 was tested | Faint dimer band present, 1:1 appears fine. Fragment 2 tends to multimerize when expressed in 0:1 DNA ratio. In 1:1 no clear signs of scrambling nor multimerization. | Fragment 1: GGGGS (new C terminus) Fragment 2: GGGGS (new N terminus) |
| 49 + 50 | 1639 | AlbuCORE_7 | nick(171-172) | 1-171:172-585 | 20.18 kDa | 46.95 kDa | 168.CYS-177.CYS | Weak expression | 50% or more lower. | Fragment 1: GGGGS (new C terminus) Fragment |

TABLE 14-continued

Results of expression of variants listed in Table 13 (table discloses "GGGGS" as SEQ ID NO: 179):

| SEQ ID (polypeptide) | Variant | Scaffold | Split/ Deletion | frag1: frag2 | frag1 MW | frag2 MW | Interface S-S [disulfide link between the two fragments forming AlbuCORE] | Optimal DNA ratio (Fragment 1: Fragment 2) | Expression (compared to AlbuCORE_1 and cloned WT HSA). Rough estimate based on band intensity (assessed by software). | Linkers |
|---|---|---|---|---|---|---|---|---|---|---|
| | | | | | | | | | | 2: GGGGS (new N terminus) |
| 51 + 52 | 1640 | AlbuCORE_9 | nick(281-282) | 1-281:282-585 | 32.43 kDa | 34.70 kDa | 278.CYS-289.CYS | 2:1 | ~30-50% better. Fragment 1 tends to multimerize when in access (DNA ratio not optimized). Results unclear for 0:1 lane. | Fragment 1: GGGGS (new C terminus) Fragment 2: GGGGS (new N terminus) |
| 53 + 54 | 1641 | AlbuCORE_13 | nick(114-115) | 1-114:115-585 | 13.31 kDa | 53.82 kDa | N/A | Weak expression | 50% or more lower. | Fragment 1: GGGGS (new C terminus) Fragment 2: GGGGS (new N terminus) |
| This is ABH2 | 221 | AlbuCORE_1 (CONTROL) | nick(338-341) | 1-337:342-585 | 38.48 kDa | 27.51 kDa | 316.CYS-361.CYS | | Weak expression of Fragment 1 and Fragment 2 still visible in 1:0 and 0:1. The single fragments show sign of aggregation, likely due to disulfide scrambling. Awaiting reducing SDS-PAGE to confirm. | Fragment 1: GGGGS (new C terminus) Fragment 2: GGGGS (new N terminus) |

Example 10: Multiple Cargo Proteins

The heteromultimer proteins described herein (e.g, containing a cargo polypeptide (or fragment or variant thereof) fused to transporter albumin segment or variant thereof) may additionally be fused to other proteins to generate "multifusion proteins". These multifusion proteins can be used for a variety of applications. For example, fusion of the proteins described herein to His-tag IgG domains, and maltose binding protein facilitates purification. (See e.g EP A 394,827; Traunecker et al., Nature 331:84-86 (1988)). Nuclear localization signals fused to the polypeptides can target the protein to a specific subcellular localization. Furthermore, the fusion of additional protein sequences to proteins described herein may further increase the solubility and/or stability of the heteromultimer. The heteromultimer proteins described above can be made using or routinely modifying techniques known in the art and/or by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian or yeast expression vector.

For example, if pC4 (ATCC Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide encoding a heteromultimeric protein described herein (generated and isolated using techniques known in the art), is ligated into this BamHI site. Note that the polynucleotide encoding the fusion protein of the invention is cloned without a stop codon; otherwise an Fc containing fusion protein will not be produced.

If the naturally occurring signal sequence is used to produce the heteromultimeric protein described herein, pC4 does not need a second signal peptide. Alternatively, if the naturally occurring signal sequence is not used, the vector can be modified to include a heterologous signal sequence. (See, e.g., International Publication No. WO 96/34891.)

Example 11. Preparation of Anti-Her2, Monospecific, Mono- to Tetra-Valent Cargo-Loaded Albumin-Based Polypeptides; Anti-Her2×Her3 Bi-Specific, Bivalent Cargo Loaded Albumin-Based Polypeptides; and Various Controls A number of different cargo-loaded albumin based transporter polypeptides were prepared as described in this example. The anti-HER2 scFvs described in Table 8 of Example 3 were prepared as follows. Briefly, ABH2 was loaded with anti-Her2 scFvs in various cis and trans configurations according to the methods described here. The final mono-specific polypeptide ranged from mono to tetravalent. Details of the amino acid and nucleic acid sequences of the component polypeptides are also shown in Table 8. In a similar fashion, ABH2 was also loaded with anti-Her2 and anti-Her3 scFvs in both cis and trans configurations, producing bi-specific, bivalent molecules. As controls utilized in various Examples, V1087, single scFvs, one-arm Fcs and bivalent Fcs were also produced.

ABH2 Loaded with Anti-Her2 4D5 scFv.

Figure 17:
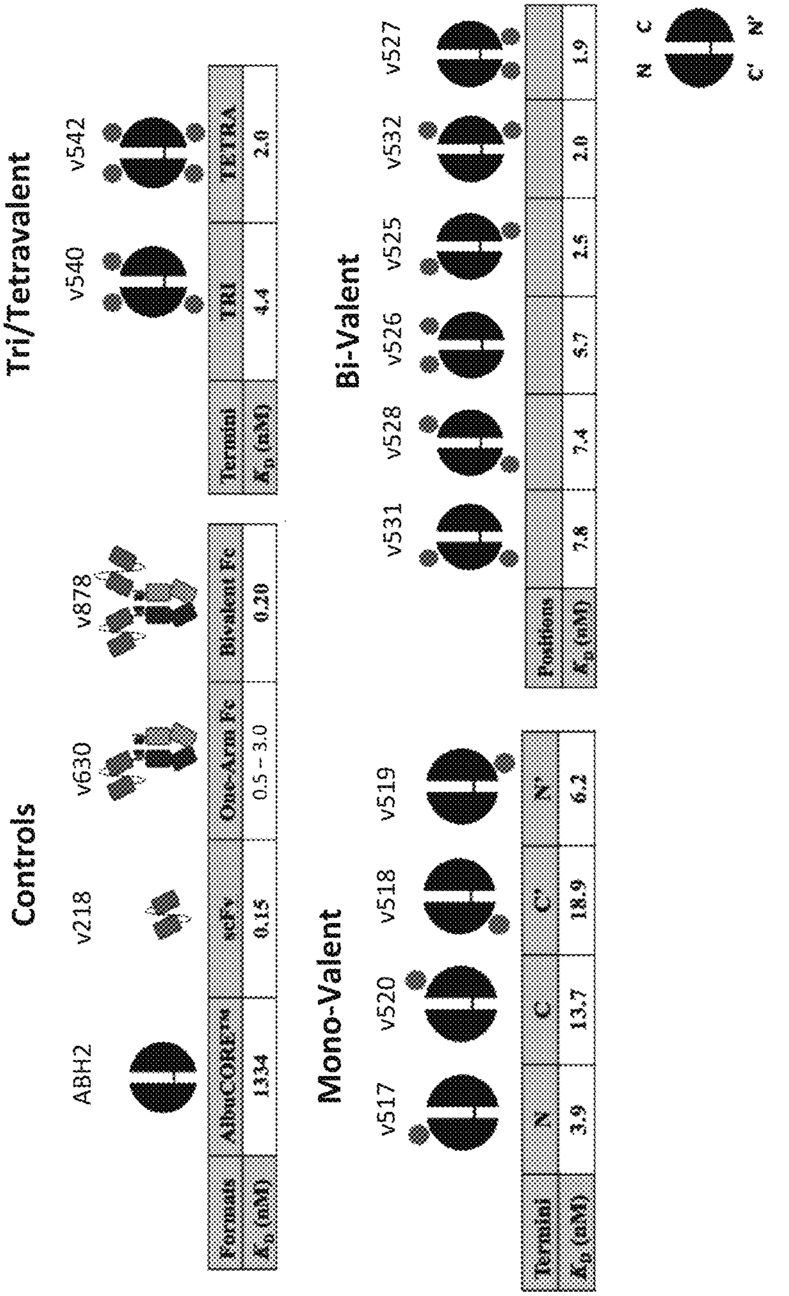
FIG. 17 depicts various mono, bi, tri and tetra-valent configurations of anti-Her2 scFv that can be attached to ABH2. Controls included the ABH2 scaffold, the anti-HER2 scFV, the one-armed Fc and the bivalent Fc. Additionally, the ability of the various ABH2 constructs to bind to SKOV cells expressing Her2 is indicated with the $K_D$ values within the tables.

The different possible configurations of ABH2 loaded anti-Her2 are schematically rendered in FIG. 17. As this figure shows, numerous cis and trans variations were prepared depending on whether the scFv is attached to the N or C termini of either fragment A or B of ABH2. A short GGSG linker (SEQ ID NO: 180) was designed at the natural N terminus of ABH2 Fragment 1 and a longer $(GGS)_4GG$ linker (SEQ ID NO: 181) was designed at the C terminus of ABH2 Fragment 1 and N and C termini of ABH2 Fragment 2. The final gene products were subcloned into the mammalian expression vector pTT5 (NRC-BRI, Canada) (Durocher et al). High level and high-throughput recombinant protein production by transient transfection of suspension-growing human CHO-3E7 was performed. Purification was performed by application of the cellular supernatant with expressed protein to a QIAGEN-tip 500 column packed with Blue Sepharose matrix (GE Healthcare) coupled to an AKTA Express system (GE Healthcare) using a flow rate of 1 ml/ml. The column was equilibrated with equilibrated with sample buffer composed of 20 ml of PBS pH 7.2, 300 mM NaCl. The sample was loaded at a flow rate of 5 ml/min and subsequently washed with sample buffer. The protein was eluted by application of NaCl gradient ranging from 300 mM to 2000 mM. Fractions eluting in higher salt concentration were the purest and were pooled, concentrated and subsequently applied to a HiLoad 16/60 Superdex 200 prep grade gel filtration column coupled to an AKTA Express system (GE Healthcare) using a flow rate of 1 ml/ml. Protein with a purity of >85% was collected; fractions containing pure sample were pooled and concentrated by centrifugation using an Amicon Ultra membrane with a cutoff weight of 10 000 MWCO. FIGS. 10A-10B shows SDS-PAGE (non-reducing) analysis of the ABH2 heteromultimer fused to different cargo polypeptides. The position of those polypeptides in the heteromultimer relative to the transporter polypeptides is outlined in Table 8, and in FIG. 17. All constructs showed the expected molecular weight.

Monovalent ABH2 fused to one anti-Her2 4D5 scFv fusion are exemplified by variants 517, 518, 519, 520 as described in Table 8. Bivalent and trivalent ABH2 fused to two or three anti-Her2 4D5 scFv fusions are exemplified by variants 525, 526, 527, 528, 531, 532, 540 as described in Table 8. All of these variants were produced by co-expression of the two Albumin fragments as described in the following paragraph. Finally, attaching anti-Her2 scFvs to all four possible termini formed the tetravalent fusion protein, referred to as variant 542.

ABH2 Loaded with Anti-Her2×Anti-Her3 scFvs (Variants 1377, 1378, and 1090).

Different versions of albumin-based heteromultimers fused to anti-HER2 and anti-HER3 were prepared. The anti-HER2 and anti-HER3 warheads that were used target the same receptors as MM-111, with the main difference being the anti-HER2 warhead, which was either the non-neutralizing B1D2 warhead used in MM-111 or the neutralizing 4D5 warhead. AlbuCORE_1 (ABH2) fragment 1 was fused to anti-HER3 at the N terminus through a GGGS linker (SEQ ID NO: 183) and complexed with fragment 2 fused to antiHER2 (4D5) through a (GGSG)4GG linker (SEQ ID NO: 184) positioned at the N terminus of fragment 2 (yielding variant 1378, with warheads in trans) or the C terminus of fragment 2 (yielding v1377, with warheads in cis). A third type of AlbuCORE_1 (ABH2) molecule was formed by combining fragment 1 fused to antiHER3 at its N terminus through a GGGS linker (SEQ ID NO: 183) and fragment 2 fused to antiHER2 (B1D2) at its C terminus through a GGGS linker (SEQ ID NO: 183) (variant number 1090). This molecule has warheads in cis and is almost identical to MM-111. The main differences between the MM-111 polypeptide and the ABH2-based polypeptide are that 1) the linkers used in the MM-111 polypeptide were more hydrophobic, while the linkers used on the ABH2-based polypeptides were polyGLY)(S) and 2) The ABH2-based polypeptides lack the C34S/N504Q mutation originally introduced by Merrimack.

MM_111 and Derivatives (variant 1087, 1088, and 1089)

The MM-111 molecule is a single polypeptide fusion protein of two scFvs, anti-Her2 (B1D2) and anti-Her3 (H3), linked to the C and N termini, respectively, of a modified human serum albumin protein, and is produced by Merrimack. The resulting molecule is bispecific and bivalent. As a control, a variant of the MM-111 molecule was constructed in which the anti-Her3 (H3) warhead was fused to the N terminus of albumin by a short AAS linker, while anti-Her2 (B1D2) was fused to the C terminus through an AAAL linker (SEQ ID NO: 185) to create the benchmark control variant 1087. This control variant lacks the C34S/N504Q mutation originally introduced by Merrimack in their MM-111 molecule. Additional MM-111-related molecules were constructed: 1) albumin fused to only the anti-Her3 (H3) warhead at the N terminus (v1088) and 2) the anti-Her2 (B1D2) fused to the C terminus (v1089). In both these cases the linkers used were identical to MM-111. All molecules were expressed in a 1:1 ratio in CHO cells and purified as described for the multimeric 4D5 fusions.

Single Anti-Her2 scFvs

Free Anti-Her2 human scFv (v218) was expressed in 1 L CHO3E7 cells (v218). A (His)6 tag (SEQ ID NO: 189) was fused to the C terminus through a cleavable linker containing a TEV protease site. The protein was purified by metal (Co2+) affinity (column volume=1 mL) coupled to a fractogel system followed by Superdex 200 size exclusion chromatography. Post purification yields were 3.6 mg of 4D5 scFv after Co2+ affinity and 1.38 mg after size exclusion.

Figure 31A:
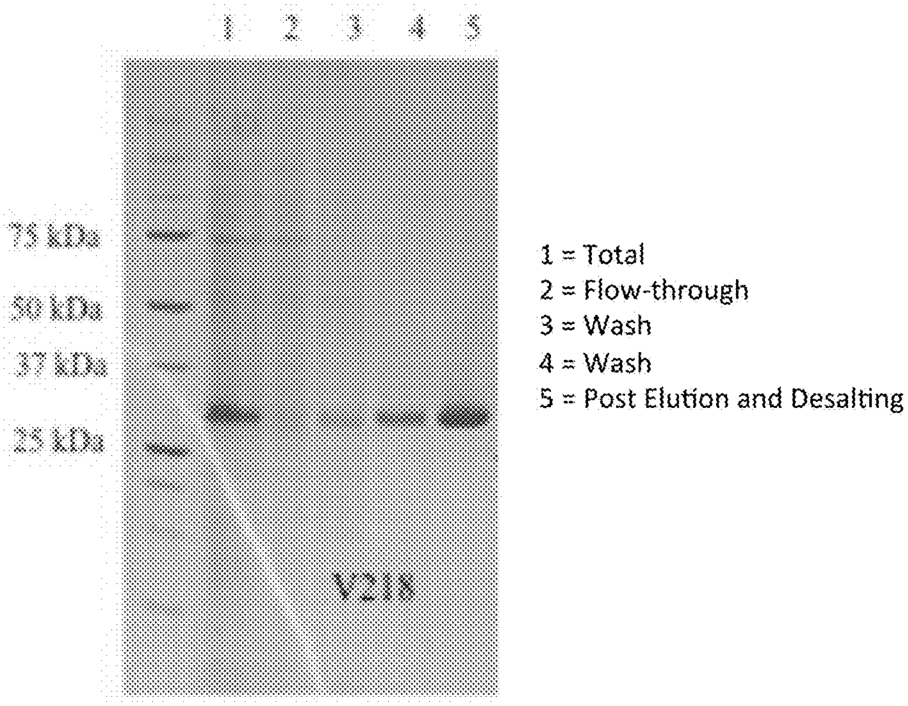
FIG. 31A shows a SDS-PAGE of the v218 expression product before, during and after purification using Co2+ affinity.
Figure 31B:
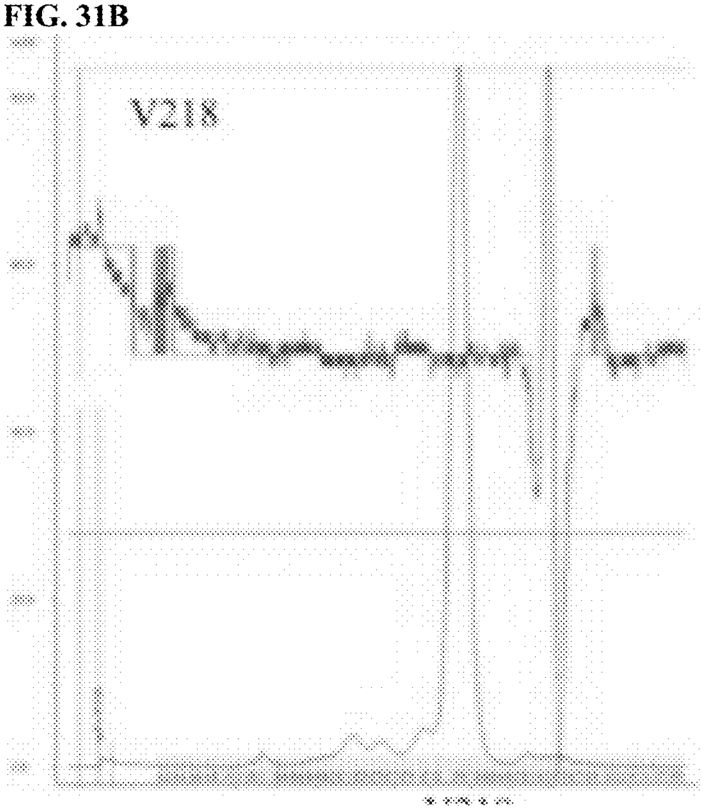
FIG. 31B is a chromatogram of the same construct after additional purification via gel filtration.

FIG. 31A is a SDS-PAGE depicting the purification of v218 after Co2+ affinity. The expression product post-washes, column elution and desalting are provided. FIG. 31B is the chromatography profile of the variant following the second purification through the size exclusion column.

Control Fc Molecules (878, 628 and 630):

A single anti-Her2 (4D5) human scFv was fused to an Fc fragment to produce a monovalent, mono-specific antibody product. In order to ensure formation of the heterodimeric Fc, heterodriver mutations were included in the Fc chain.

V878: OA4-scFv-B1D2, a monovalent anti-Her2 antibody, where the Her2 binding domain is a scFv on chain A, and the Fc region is a heterodimer having the mutations L351Y_F405A_Y407V in Chain A, and T366L_K392M_T394W in Chain B.

V628: a bivalent anti-Her2 antibody, where both Her2 binding domains are in the scFv format, and the Fc region is a heterodimer having the mutations L351Y_S400E_F405A_Y407V in Chain A, and T366I_N390R_K392M_T394W in Chain B.

V630: a monovalent anti-Her2 antibody, where the Her2 binding domain is an scFv, and the Fc region is a heterodimer having the mutations L351Y_S400E_F405A_Y407Vin Chain A, and T366I_N390R_K392M_T394W in Chain B.

Table 15 provides a listing of the polypeptide sequences for the variants described in this section.

TABLE 15

| Variant | Polypeptide A SEQ ID No: (nt/aa) | Polypeptide B SEQ ID No: (nt/aa) |
|---|---|---|
| 1377 | 161/162 | 163/164 |
| 1378 | 165/166 | 167/168 |
| 1090 | 169/170 | 171/172 |
| 1087 | 155/156 | |
| 1088 | 157/158 | |
| 1089 | 159/160 | |
| 218 | 93/94 | |
| 878 | 145/146 | |
| 628 | 151/152 | 149/150 |
| 630 | 153/154 | 149/150 |
| 1092 | 137/138 | 139/140 |
| 1093 | 141/142 | 143/144 |
| 1094 | 133/134 | |
| 1095 | 135/136 | |

Example 12. Target Binding to SKOV Cells by ABH2 Fused to Anti-Her2 4D5 scFvs in Multivalent Configurations The affinity of ABH2 anti-Her2 fusion proteins to $Her2^+$ cells was examined in this Example. The various scFv attachment configurations are provided in FIG. 17. The ABH2 (AlbuCORE™) alone, the anti-Her2 scFv alone, a monovalent one-armed Fc molecule and a bivalent two-armed Fc molecule were utilized as controls. These are summarized in the "Controls" panel of FIG. 17. The ABH2 protein was constructed as per Example 2 and the fusion proteins were created as per Example 11.

FACS Binding Assessment

The binding affinity of the various anti-Her2 ABH2 constructs and controls to SKOV cells expressing Her2 was assessed via FACS. Detection was performed using an anti-HSA polyclonal (FITC labeled). All $K_D$ determined are apparent.

Whole Cell Binding by FACS Protocol:

Once cells have reached sufficient viability, (ie $2\times10^6$cells/ml cells (>80% viability)) the media was aspirated from the T75 culture flask and washed with cold PBS, which was subsequently aspirated. 3 mL dissociation buffer per flask was added and cells counted. The suspension was then centrifuged at 1050 rpm for 5 minutes and cells resuspended in RPMI media containing 5% FBS @ 1×10e5 cells/100 μl. 100 ul of cell suspension was added to eppendorf tubes with the subsequent addition of 10 μl/tube of the primary antibody (goat anti human HSA). The cells were then incubated for 2 hours at 4° C. on a rotating support. Tubes were then centrifuged for two minutes at 2000 rpm at room temperature. The media was aspirated, and the pellet washed with 500 ul RPMI media containing 5% FBS and re-centrifuged. The secondary antibody (Alexa Fluor 488-conjugated anti goat IgG) was added to final concentration of 2 ug/sample. The pellet was resuspended in 100 ul solution, incubated for 1 hour at 4 C on rotating support and centrifuged 2 minutes at 2000 rpm. The cells were then washed with 500 ul RPMI media containing 5% FBS re-centrifuged and re-suspended in 500 ul per pellet for flow cytometric analysis.

The $K_D$ values for each construct are provided below the representative rendering in FIG. 17. All $K_D$ determined are apparent and values represent an average of six concentrations tested per molecule, up to 3 μM. As the figure demonstrates, increasing the valency tends to increase binding affinity, indicated by the decrease in apparent $K_D$ value. Generally, anti-Her2 scFv attached to the N termini of either fragment polypeptide exhibits greater affinity for Her2 than one attached to the C terminus. In some embodiments, this property of the multispecific multivalent species to reduce effective affinity on fusion at specific positions can be employed to attenuate the affinity and activity of some fusion partner species.

Example 13. Bi-Specific Binding of ABH2 Fused to Anti-Her2 and Anti-Her 3 scFvs

The binding affinity of an ABH2 loaded in a cis configuration with anti-Her2 and anti-Her3 scFvs to MALME-3M cells were assessed and compared to the v1087 control. Both the fusion protein and control were constructed as per Example 11.

FACS Analysis of Bi-Specific Binding

Figure 18A:
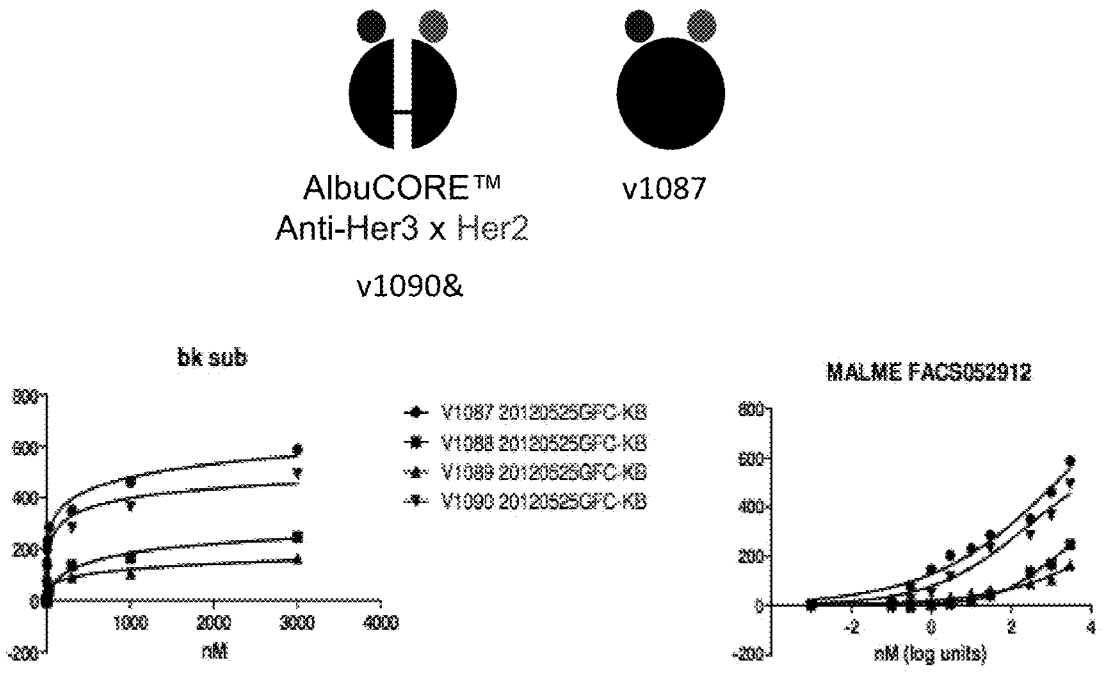
FIG. 18A shows the binding curves of four anti-Her3×Her2 loaded constructs (v1087, v1088, v1089 and v1090 to MALME-3M cells. Affinity for the cells was evaluated using FACS with FITC-labeled anti-HSA antibodies. The lower left graph displays the concentration on a linear scale while the lower right is on a logarithmic scale.
Figure 18B:
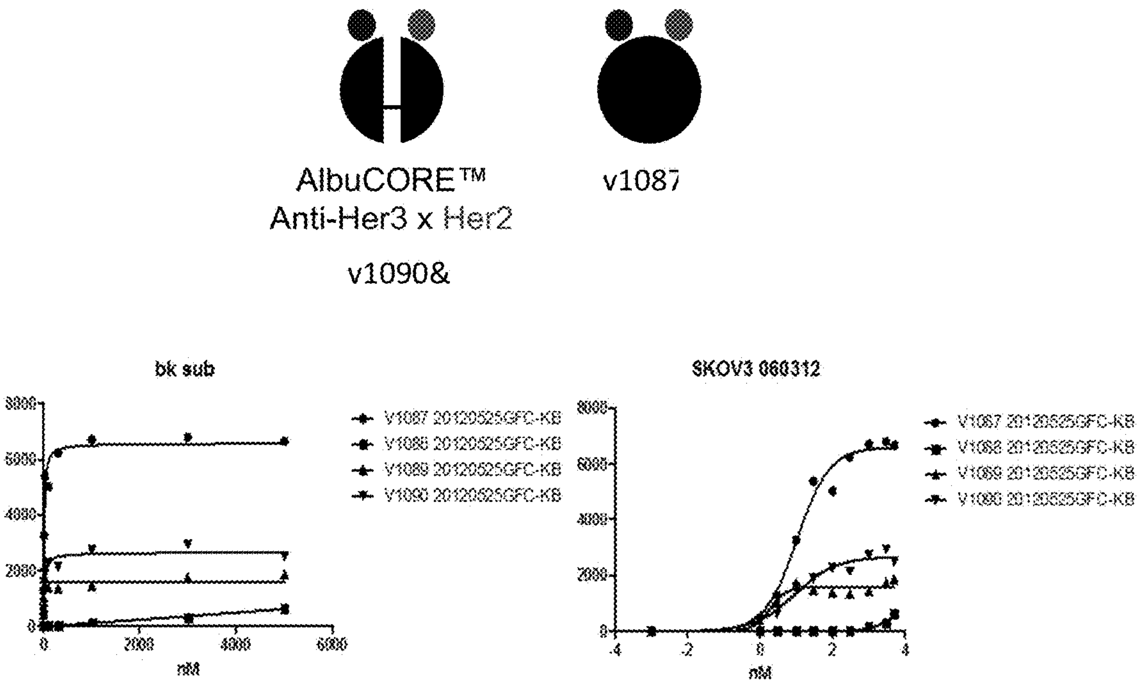
FIG. 18B shows the binding curves of the aforementioned four constructs to SKOV-3 cells. The lower left graph displays a linear scale while the lower right displays a logarithmic one.
Figure 19A:
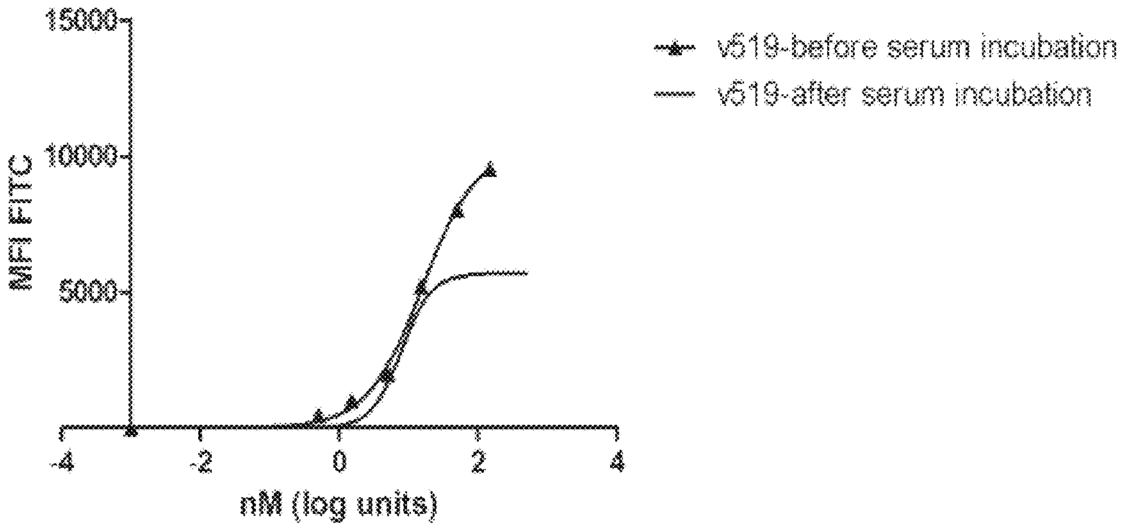
FIGS. 19A-19D demonstrate the stability of four anti-Her2 (v519, v520, v518 and v517) loaded ABH2 in human sera. Binding affinity to SKOV-3 cells was assessed using FACS with FITC-labeled anti-HSA antibody.
Figure 19B:
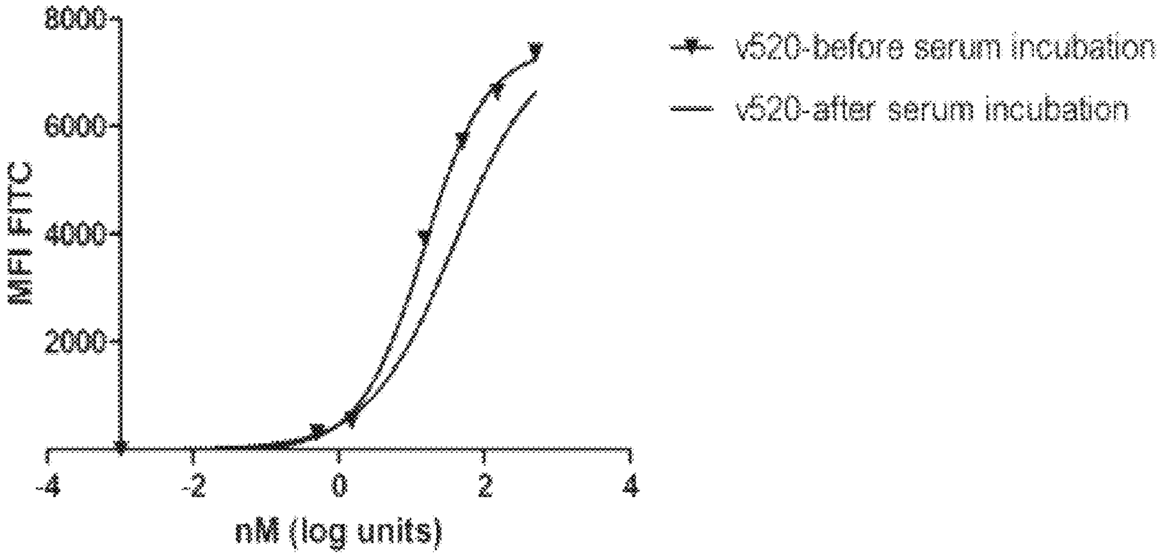
Figure 19C:
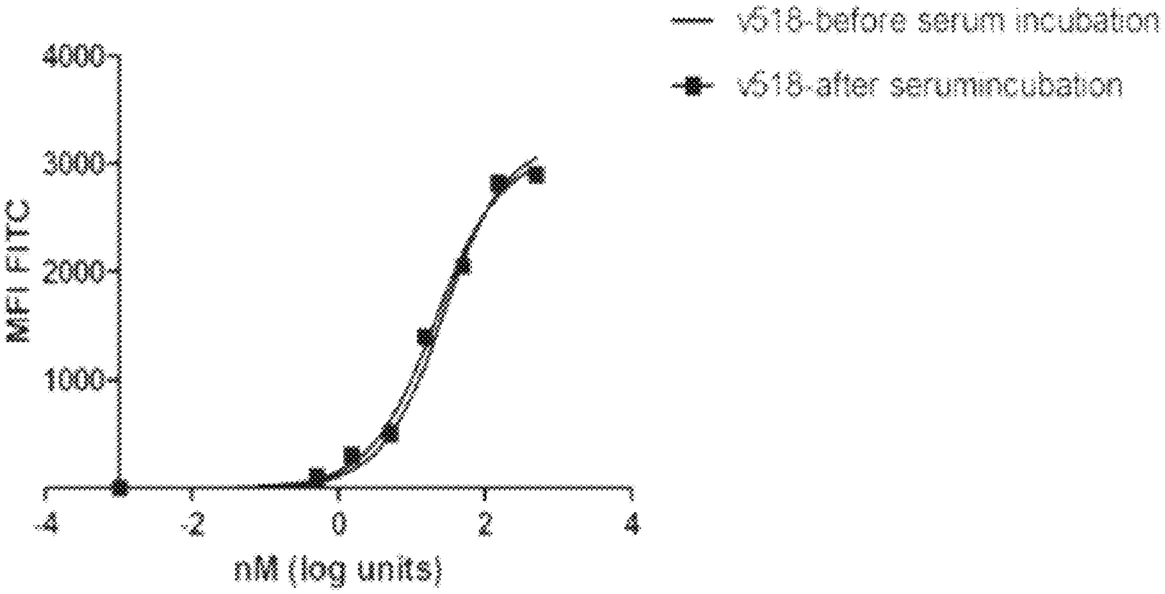
Figure 19D:
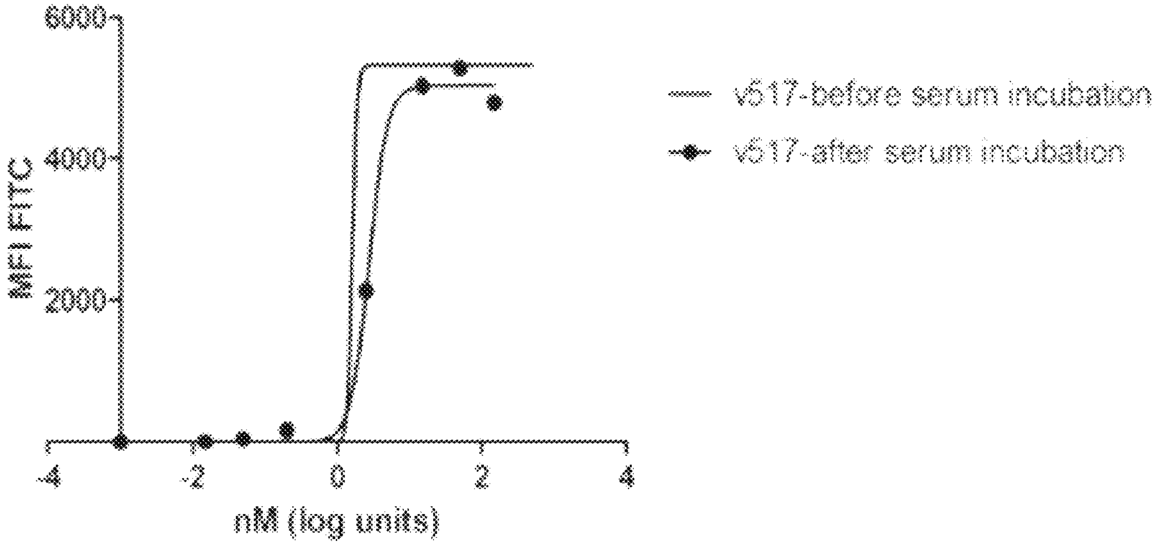

The binding affinity of an exemplary albumin-based heteromultimer variant 1090 (anti-Her2×anti-Her3 ABH2) to MALME-3M and SKOV cells was evaluated using FACS with FITC-labeled anti-HSA antibodies, as described in Example 12. As described in Example 11, v1090 comprises B1D2/H3 fusions, Merrimack's linker length, and the less hydrophobic linker polyGLY)(S). FIG. 18A depicts the binding of variants 1088, 1089 and 1090 compared to the control 1087 in SKOV cells. FIG. 18B depicts the binding of variants 1088, 1089 and 1090 compared to the control 1087 in MALME-3M cells. Table 16 below provides data regarding characterization of the binding of these variants in both cell types. All units in Table 16 are nM unless otherwise indicated. Binding to MALME-3M cells for 1087 and 1090 was 5-55 nM and 200-10,000 nM, respectively. Binding to SKOV cells for 1087 and 1090 was 10 nM and 9.4 nM, respectively.

TABLE 16

Binding data for variants in SKOV and MALME-3M cells.

| Variant | warhead at natural N terminus (pos. 1) | warhead at natural C terminus (pos. 2) | Kd (MALME 20120529) | Bmax (MALME 2012529) | Kd (SKOV 20120803 | HillSlope (MALME 20120529) | Bmax (MALME 20120603) |
|---|---|---|---|---|---|---|---|
| 1087 (MM-111) | HER3 | HER2 | 12 uM | 1469 | 10.69 | 0.97 | 6583 |
| 1088 (Unsplit HSA) | HER3 | — | 0.8 uM | 74 | 5 uM | 1.0 | |
| 1089 (Unsplit HSA) | — | HER2 | 60 uM | 1149 | 1.8 | 1.8 | 1572 |
| 1090 (AlbuCORE) | HER3 | HER2 | 0.2 uM | 323 | 9.4 | 0.7 | 2658 |

Example 14. Serum Stability of ABH2 Fused to Anti-Her2

The stability of ABH2 loaded with an anti-Her2 in human sera was performed to assess potential proteolytic cleavage of the linker. Five variants were tested: v517, v518, v519, and v520

Human Sera Incubation and Subsequent FACS Analysis.

The anti-Her2 ABH2 fusion proteins described above was tested for binding to SKOV cells and then incubated in previously frozen human sera at 100 μg/ml (Sigma #H4522) for 24 hours at room temperature, before being re-tested for binding to the same stock of SKOV cells. Detection was performed using goat FITC labeled polyclonal anti-HSA antibody. The fusion protein's binding affinity to SKOV-3 cells was assessed using FACS, with pre-incubation proteins used as a control. FIGS. 19A to D depicts the binding curve of both the pre-incubation and post-incubation samples of the variants tested.

As shown in FIGS. 19A to D, all fusions appeared stable and capable of binding to the target antigen after serum incubation.

Example 15. FcRn Binding of ABH2 Fused to Anti-Her2 and Anti-Her3 scFvs

Figure 20A:
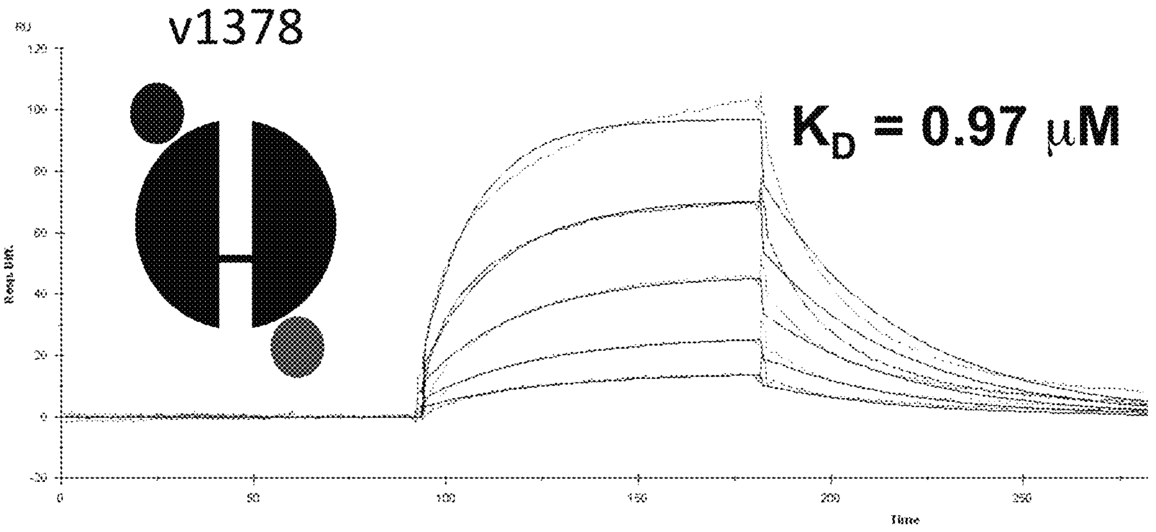
FIGS. 20A and 20B show the binding affinity of bispecific anti-Her2×Her3 ABH2 (v1378) to FcRn as compared to the v1087 (MM-111) control. The graphs represent the surface plasmon resonance (SPR) curves of the two compounds represented as Resp. Diff. over Time.

The affinity of ABH2 loaded in a trans configuration with anti-Her2 and anti-Her3 scFvs was assessed for binding to FcRn and compared to both wild-type HSA and the 1087 control. For this experiment the benchmark control v1087 and one of the AlbuCORE HER2/HER3 fusions (v1378) was used. FIG. 20A illustrates the trans configuration of the v1378 fusion.

FcRn Binding.

Human FcRn (hFcRn) was immobilized on the SPR surface and purified anti-Her3×Her2 ABH2 (v1378) and v1087 were flowed over at pH 6.0. Methods are identical to Example 2, except the directionality of the assay was reversed.

Figure 20B:
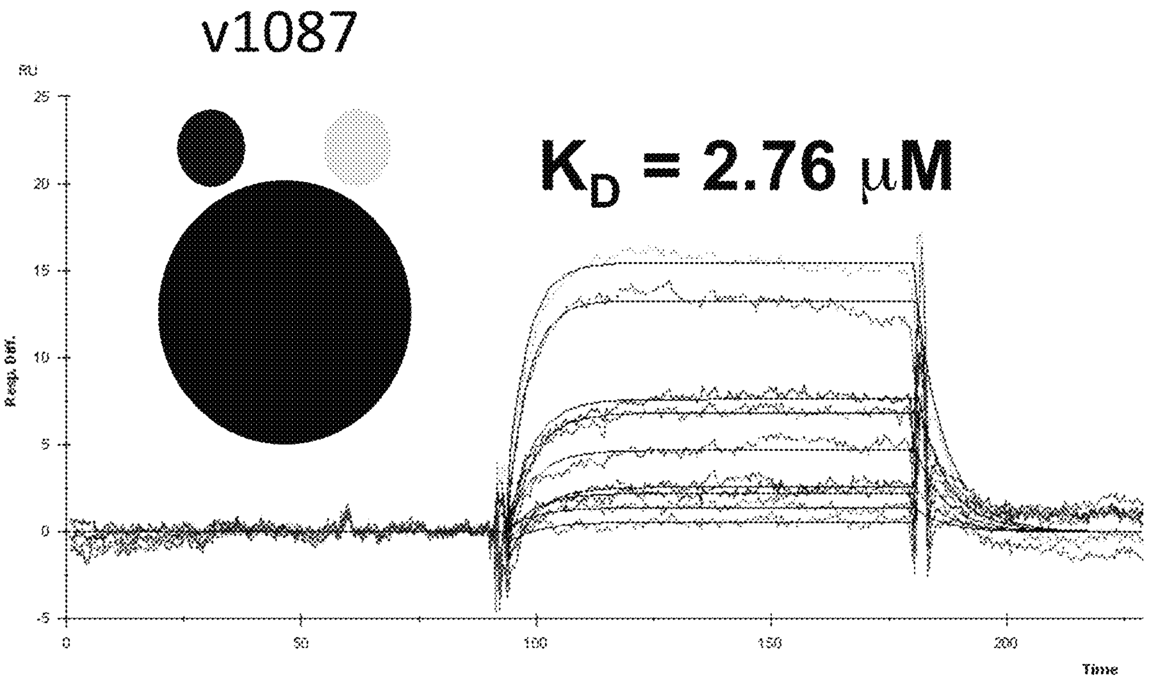

FIGS. 20A and 20B show the different binding curves of Anti-Her2×Her3 ABH2 and V1087 respectively. The Anti-Her2×Her3 ABH2 bound hFcRn with a KD of 0.97 μM, while the V1087 molecule bound hFcRn with a KD of 2.76 μM. From the figures, it can be seen that both the fusion ABH2 and v1087 are comparable in FcRn binding affinity to wild-type-HSA (Kd=1.4 μM at pH 5.5, as described in Chaudhury, C et al. *Biochemistry* 2006, 45, 4983-4990).

Example 16. Bench-Top Stability of ABH2 and Monovalent Anti-Her2 ABH2

The bench-top stability of both the ABH2 scaffold and a monovalent ABH2 anti-Her2 fusion protein (v517) was assessed over a five-day period at three different temperatures.

Benchtop Stability

Figure 21:
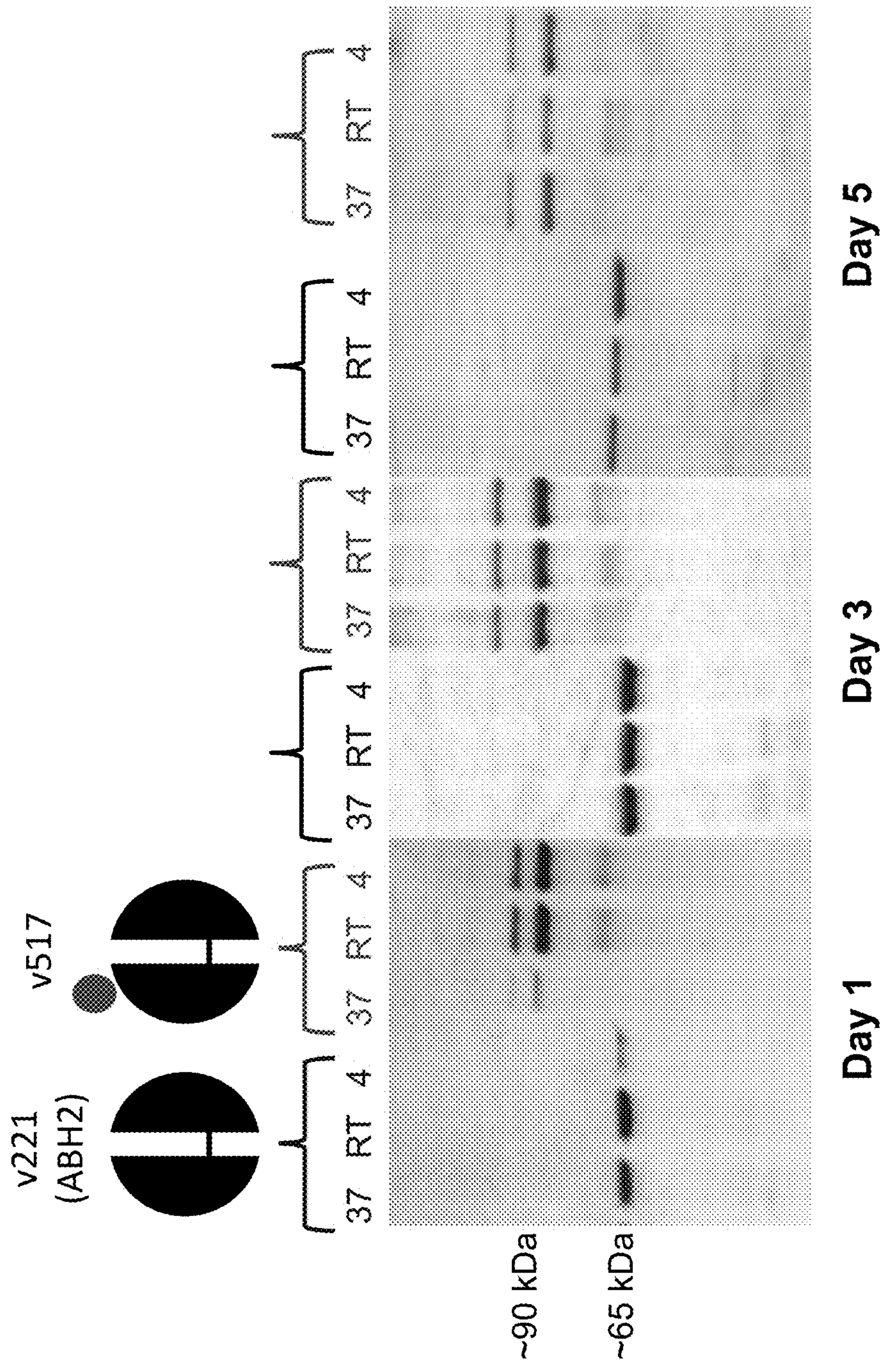
FIG. 21 depicts the native gel profiles of both the ABH2 scaffold (v221) and a monovalent anti-Her2 ABH2 (v517) incubated for five days at three temperatures (37° C., room temperature and 4° C.).

Samples from each molecule were divided into nine tubes, with each tube containing ~10 μg of protein. An initial amount of material corresponding to 10 μg of protein was placed in PBS at 1 mg/mL and incubated at 37° C. (bath), room temperature (RT) or 4° C. (fridge); protein stability was assessed over the course of five days. At each time point an aliquot was extracted and mixed 1:1 with Commassie Blue loading buffer with subsequent freezing. After the last time step all aliquots were thawed and loaded on a native gel, along with reducing and non-reducing SDS-PAGE. FIG. 21 is a native gel of the ABH2 scaffold and anti-Her2 ABH2 fusion on days 1, 3 and 5. As the figure demonstrates, both the ABH2 scaffold and the anti-Her2 ABH2 remained stable over the 5 day period. The doublet band visible for the fusion protein likely represents two different reduction states of the disulfide. In presence of reducing agent the two bands in fact collapse into one.

Example 17. Purification Optimization Using the AlbuPure® Process

As an alternate to the Blue Sepharose purification described in Example 2, which leads to some amount of residual contaminants in the elution and the need for high salt elution, a AlbuPure® based affinity purification method was employed. Optimization procedures consisted in testing binding to the Blue Sepharose matrix in both batch and direct mode, different elution protocols were tried, along with different pH and temperatures. Finally a specific resin (i.e. AlbuPure®) tailored towards the purification of albumin and albumin fusions was tested. Different binding and elution conditions were tested using AlbuPure®, involving binding in presence of different salts and elution using a pH gradient or competing detergents.

Purification of Wild-Type HSA: Comparison of Blue Sepharose to AlbuPure®

Figure 22A:
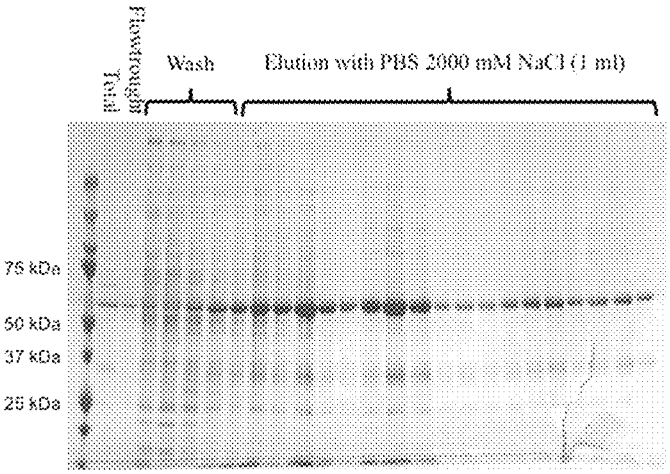
FIG. 22A depicts the native gel profile of the total, flowthrough, wash and elution fractions of WT HSA after Blue Sepharose purification.
Figure 22B:
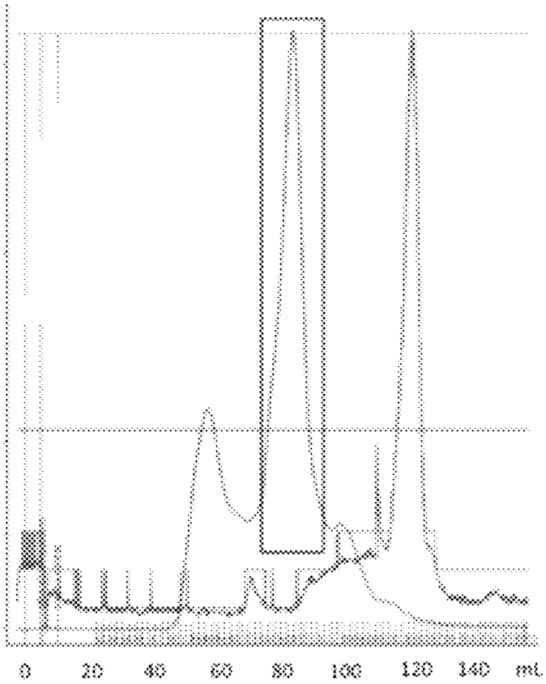
FIG. 22B is a chromatogram of WT-HSA after Blue Sepharose purification applied to a gel filtration column. Different peaks represent different protein products.

Blue Sepharose purification was performed on wild-type HSA as per methods described in Example 2. FIG. 22A is a non-reducing SDS-PAGE gel profile of the total, flow-through, wash and elution fractions obtained during the Blue Sepharose purification. FIG. 22B represents the LC analysis of the Blue Sepharose elution fraction after gel filtration (SEC). As can be seen from the numerous peaks in the chromatogram, there was significant protein and ion contamination even after the purification. AlbuPure® purification was performed on wild-type HSA as follows. The cellular supernatant containing wild-type HSA was solubilized in PBS. Prepacked AlbuPure® columns (column volume: 1 mL) were equilibrated in 50 mM sodium acetate at pH 5.3. After loading the supernatant the column was washed three times with solutions containing 50 mM sodium acetate but increasing pH (i.e. $1^{st}$ was pH 6; $2^{nd}$ wash pH 7). The final wash was performed in ammonium acetate, pH 8.0. The protein of interest was then eluted using a solution containing 50 mM ammonium acetate, pH 7.0 supplemented with 10 mM sodium octanoate. The AlbuPure® process only required one step to obtain a comparable amount of protein to that of Blue Sepharose. Protein yields from 500 mL initial CHO culture are shown in Table 17 below.

TABLE 17

Protein yields after purification

| Variant ID | Blue Sepharose purification (pre SEC) | Blue Sepharose purification (post SEC) | AlbuCORE (octanoate elution) | Initial cell culture | Comments |
|---|---|---|---|---|---|
| V221 (naked HSA) | 8.6 mg | 2.79 mg | 10.34 mg | 500 mL | |
| V519 | 3.3 mg | 1.8 mg | 8.16 mg | 500 mL | HER2 fusion. Warhead appears to be proteolytically cleaved |
| V520 | 4 mg | 0.93 mg | 4.3 mg | 500 mL | HER2 fusion. Warhead appears to be proteolytically cleaved |

Figure 22C:
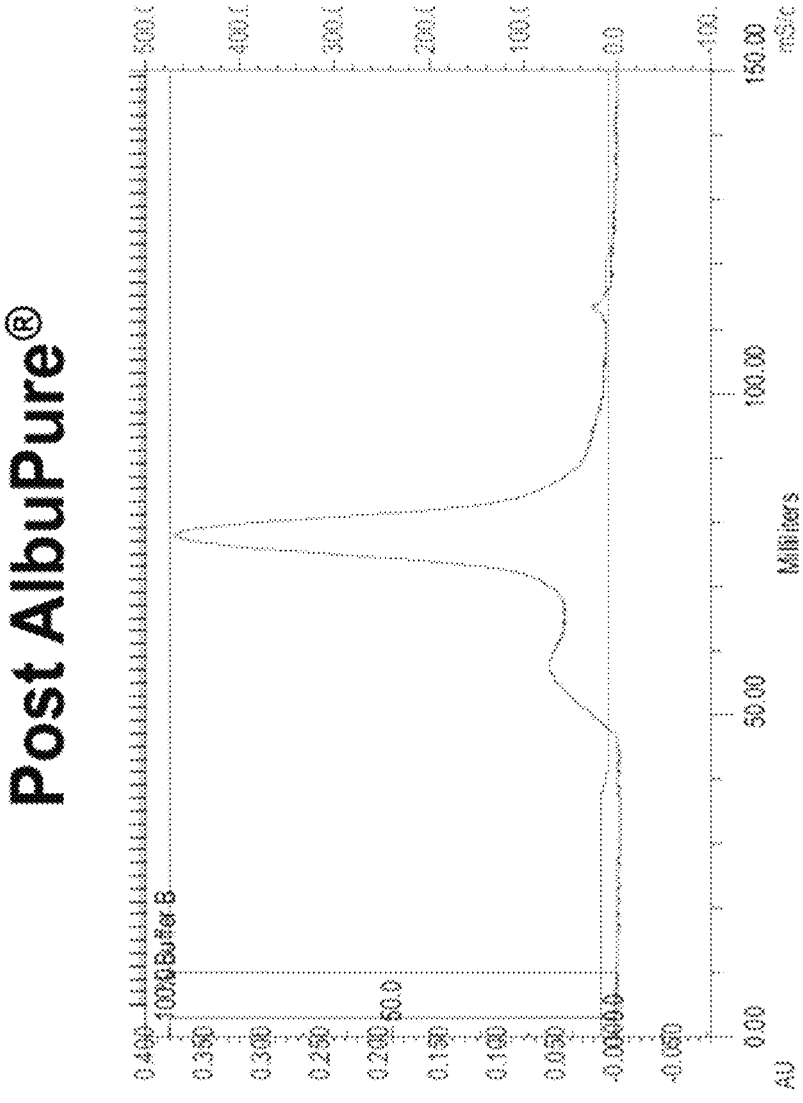
FIG. 22C is a chromatogram of WT-HSA after AlbuPure purification, fractionated via application to gel filtration column.

FIG. 22C represents a LC analysis of the AlbuPure affinity column elution fraction after gel filtration (SEC) A comparison of FIGS. 22B and 22C demonstrate that the AlbuPure process results in a final solution with a much higher level of purity than that from Blue Sepharose along with lower amount of higher MW aggregating protein.

Purification of Engineered AlbuCOREs: Comparison of Wild-Type HSA and Engineered AlbuCOREs Using AlbuPure®

The two fragment peptides of AlbuCORE-1A, 3, 6 and 9 described in Table 11 were transiently co-expressed in CHO cells using separate vectors. The optimal DNA ratio for expression of the two fragments constituting the different AlbuCORE molecules were (fragment1:fragment 2) AlbuCORE-1=1:1; AlbuCORE-3=1:2; AlbuCORE-6=1:1; AlbuCORE-9=2:1. All expressions were transient and performed in identical fashion to the previous AlbuCORE molecules. Wild-type HSA was also transiently expressed in CHO cells. Expression yields of the fusion proteins were within 75% of the WT-HSA (approx. 50-70 mg/L). Amount of material was determined by A280 after albupure purification.

Figure 23A:
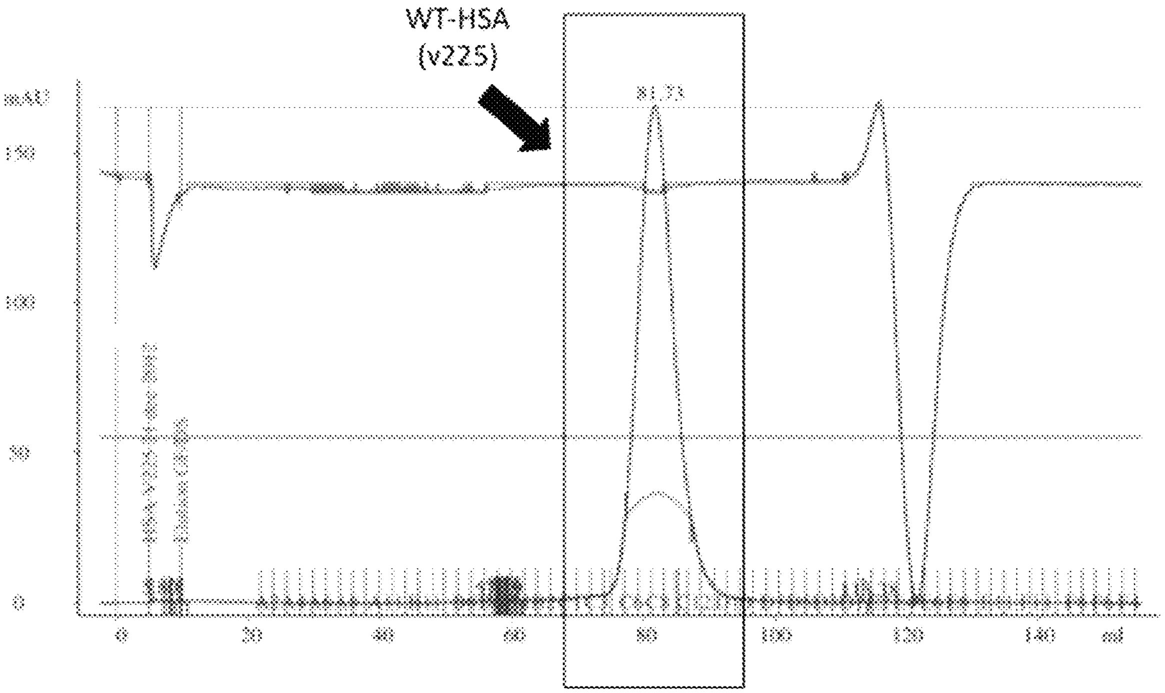
FIG. 23A is a chromatogram of the liquid chromatography analysis of WT-HSA (v225) after AlbuPure purification and gel filtration.
Figure 23B:
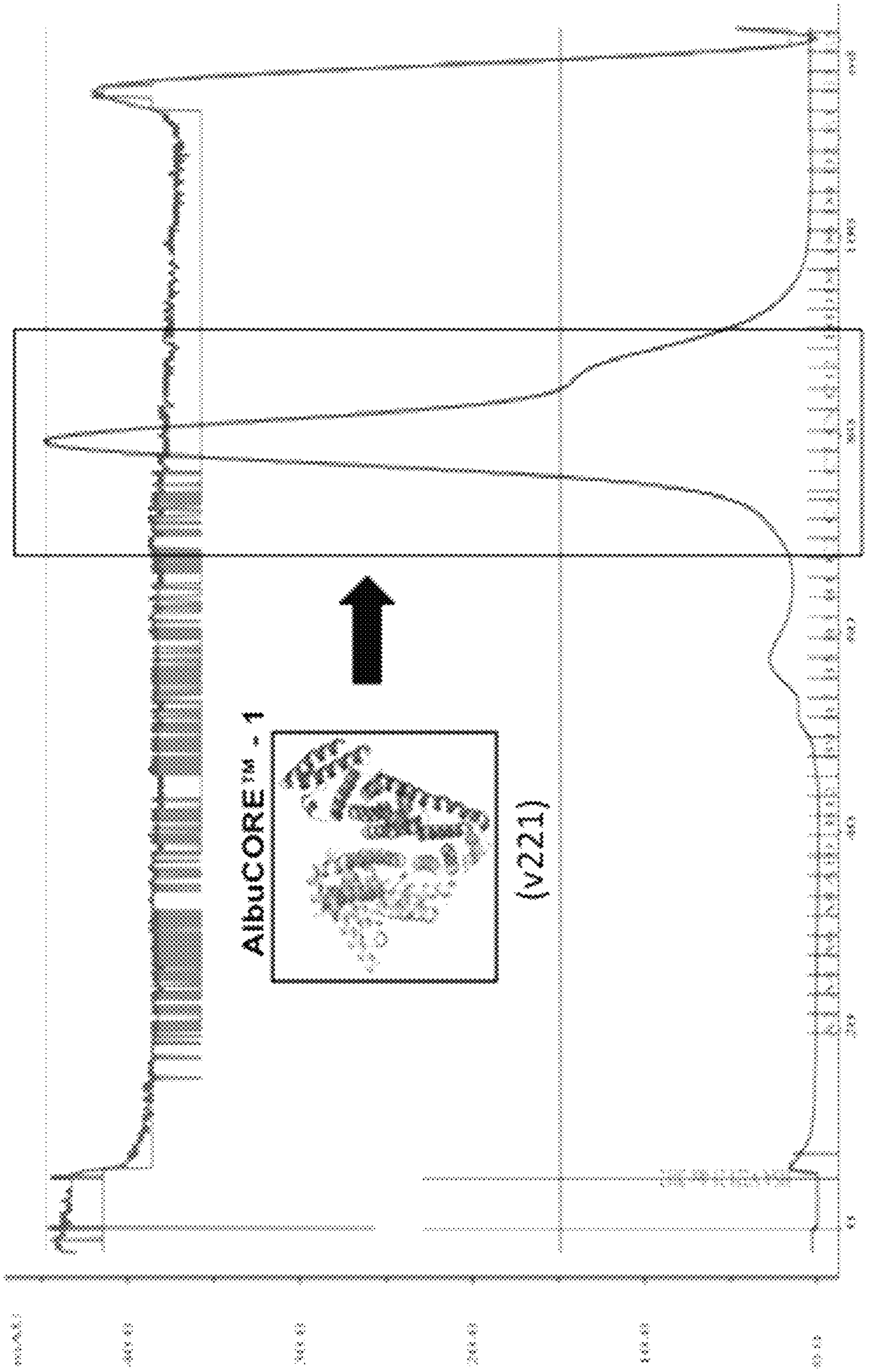
FIGS. 23B-23E are chromatograms of AlbuCORE scaffolds 1 (v225), 3 (v1636), 6 (v1638) and 9 (v1640) respectively after AlbuPure purification, separated into fractions and analyzed via gel filtration LC.
Figure 23C:
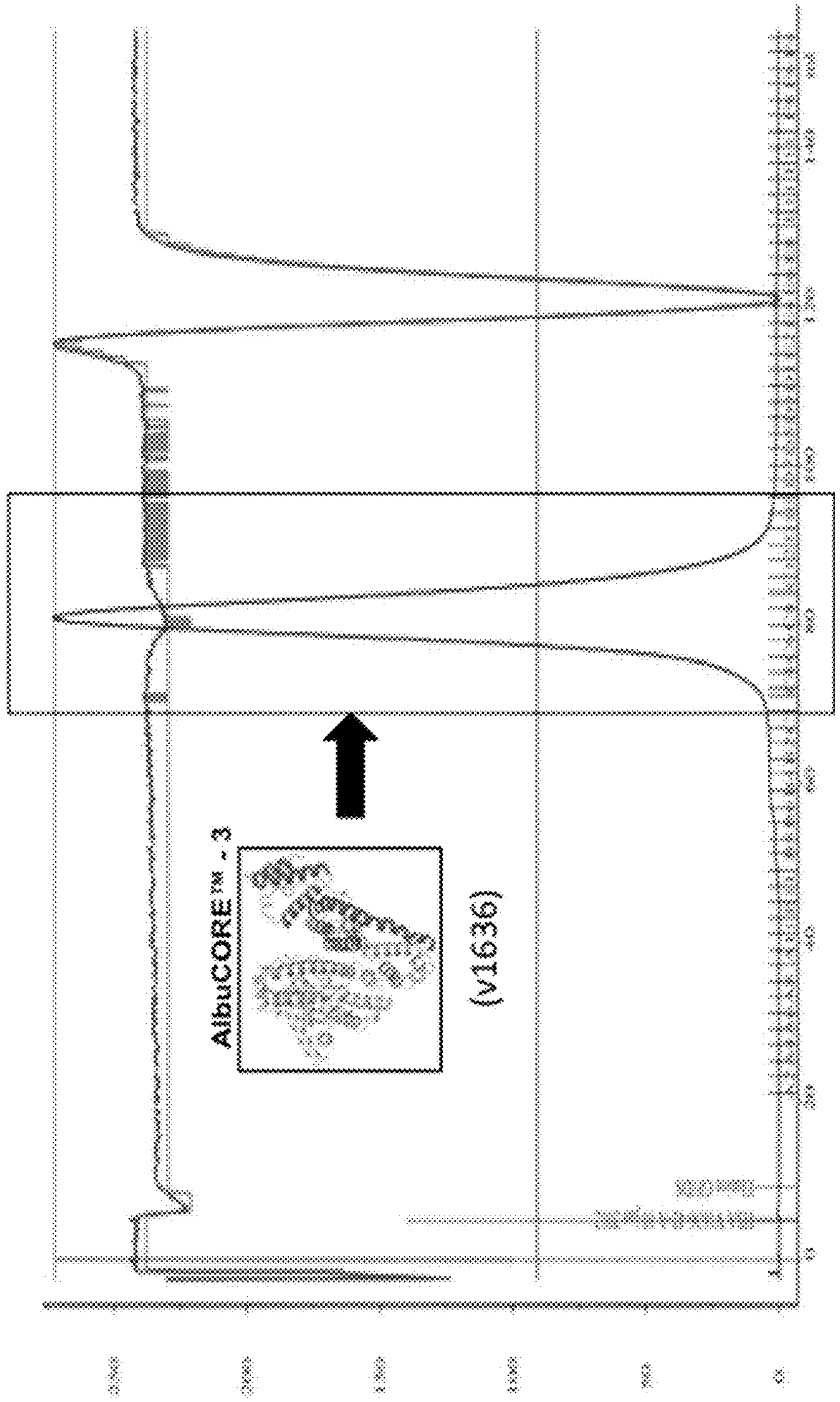
Figure 23D:
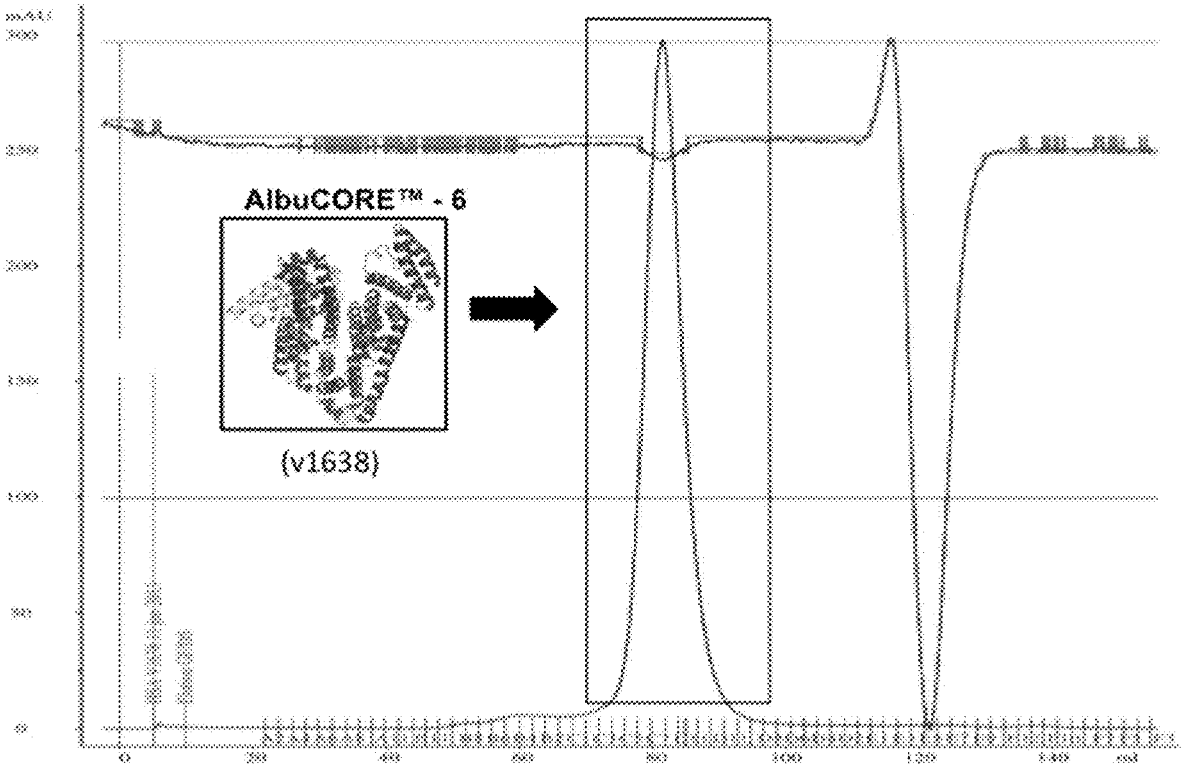
Figure 23E:
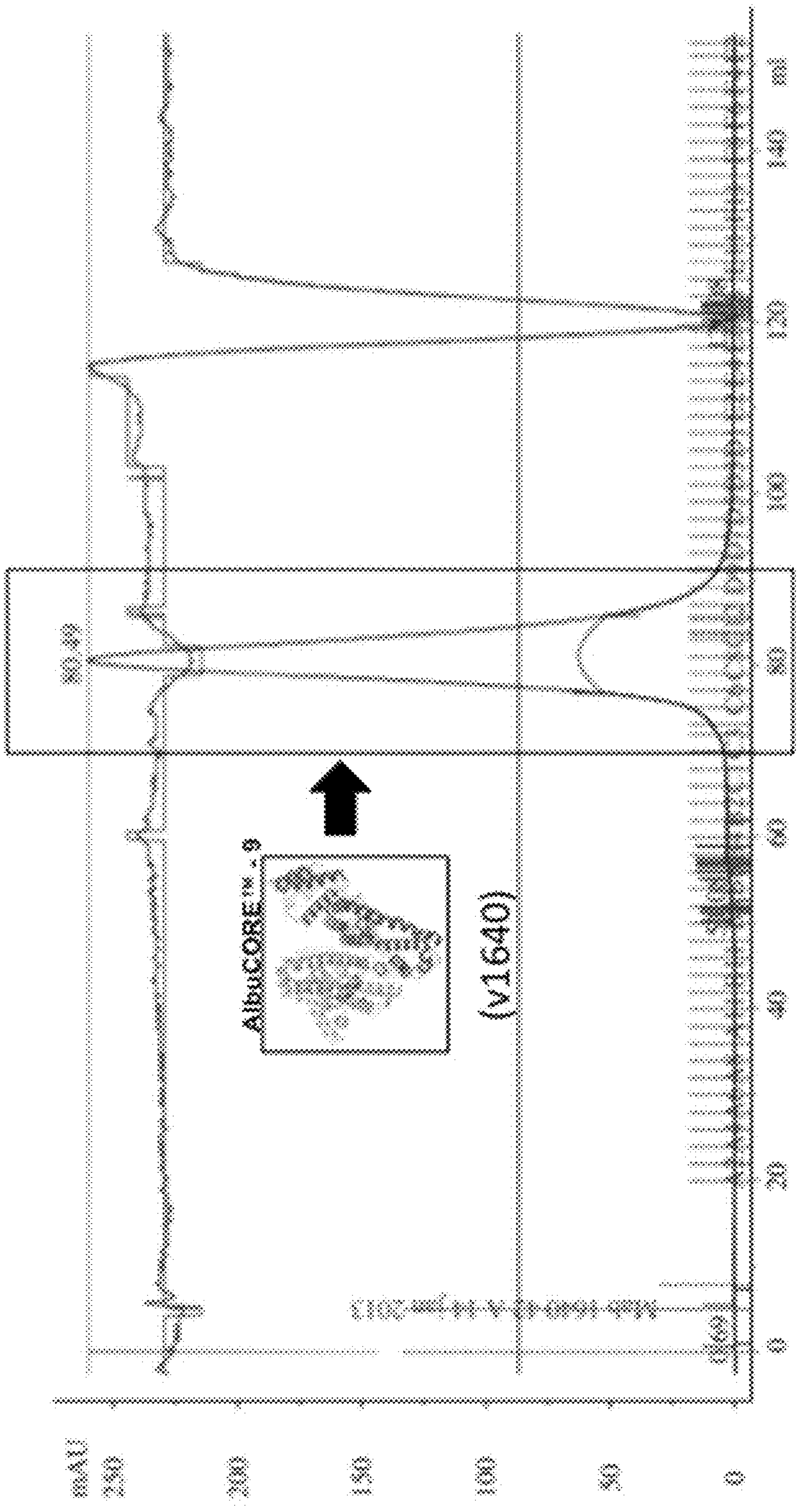

After co-expression, the AlbuCORE scaffolds were purified using the AlbuPure® protocol described above. To assess purity, the elute from the AlbuPure® affinity column was run through a gel filtration system (SEC) and the flowthrough analyzed using LC. The same was performed for wild-type HSA. FIG. 23A represents the chromatogram of the wild-type HSA, while FIGS. 23B, 23C, 23D, and 23E are chromatograms of AlbuCORE 1, 3, 6 and 9 respectively. As these Figs. demonstrate, AlbuPure® purification yields are comparable results between wild-type and engineered AlbuCORE. The yields in terms of mg of purified protein from 500 mL initial CHO culture after AlbuPure® purification were determined to be: AlbuCORE-1=16 mg; AlbuCORE-3=25 mg; AlbuCORE-6=27; AlbuCORE-9=25 mg.

Scale-Up Expression and Purification of AlbuCORE-1

AlbuCORE-1 was transiently co-expressed in CHO using the pTT5 vector at a ratio of 1:1 fragment A:B, see example 2. Purified yields of AlbuCORE-1 in CHO cells were approx. 10 mg/L, which is comparable to the 9 mg/L yield of v1087 in CHO cells, calculated from the same amount of starting material.

Figure 24A:
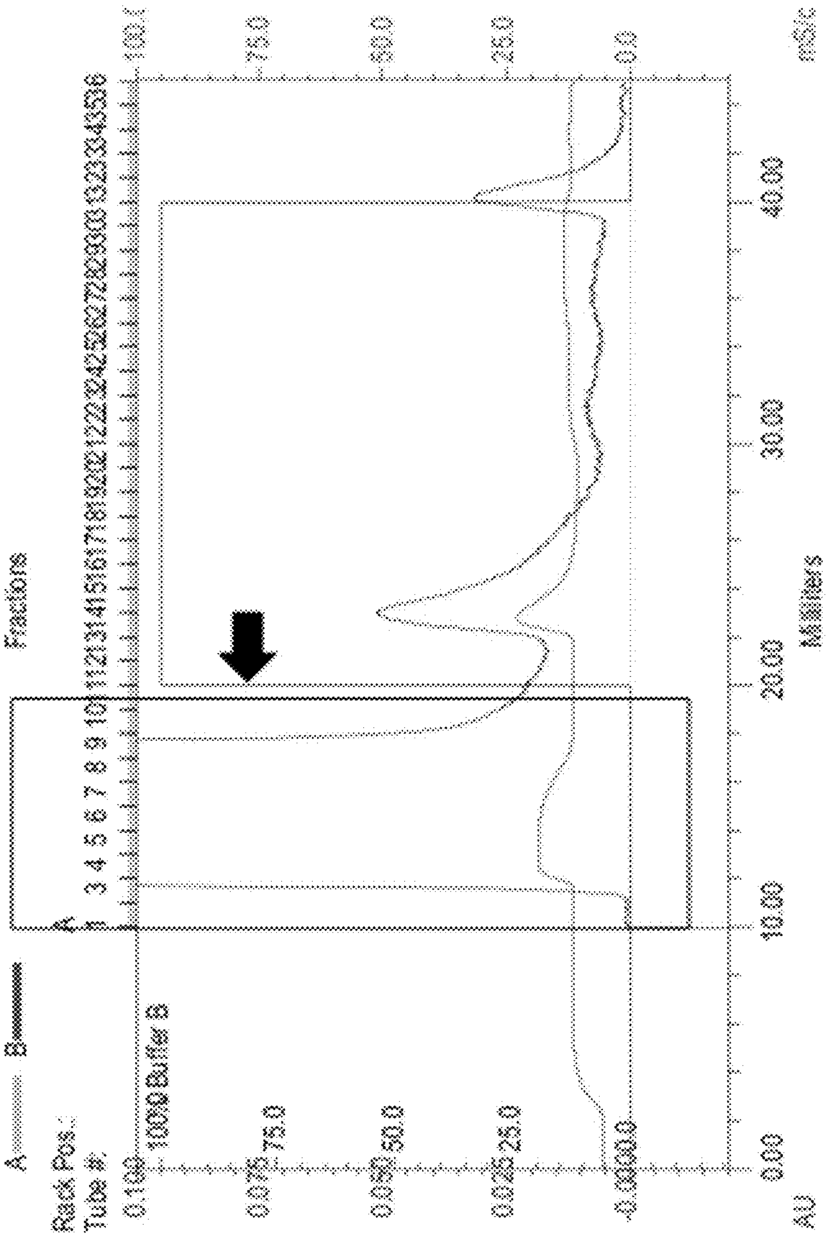
FIG. 24A represents the gel filtration LC analysis of an albumin scaffold (v221) after AlbuPure purification. The express product was scaled-up via via transient co-expression in CHO cells.

AlbuCORE-1 was purified using the AlbuPURE protocol described above. The affinity column elute was applied to a gel filtration-LC analysis system. FIG. 24A represents the chromatogram of the AlbuPure purification. The main peak represents the protein of interest.

Figure 24B:
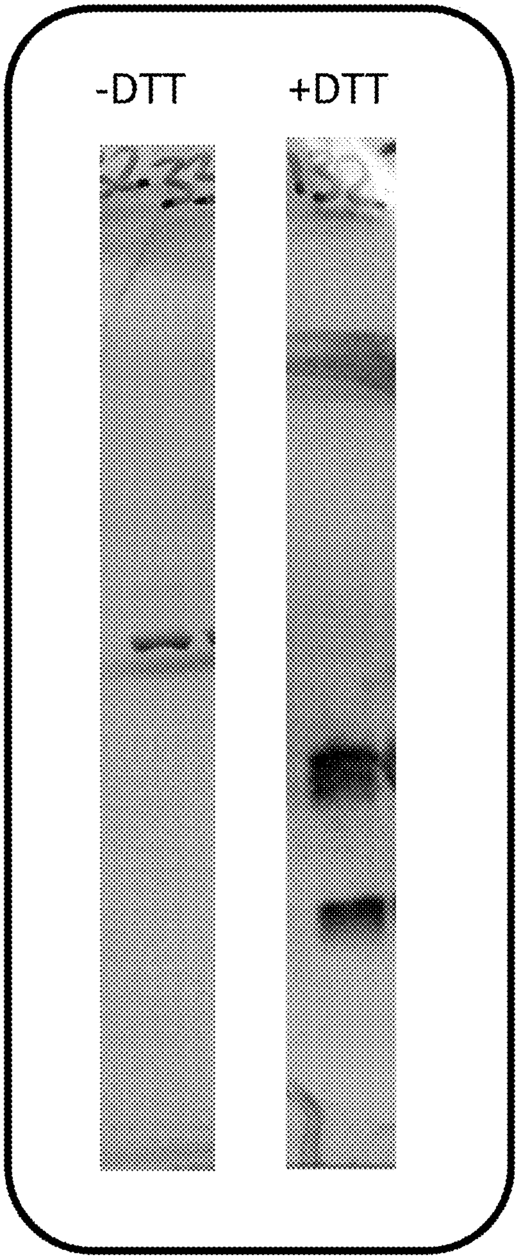
FIG. 24B shows non-reducing (indicated by the −DTT) and reducing (indicated by the +DTT) SDS-PAGE gel profiles of the same variant.

The purified samples were also analyzed via reducing and non-reducing SDS-PAGE gels, depicted in FIG. 24B. As the Fig. demonstrates, in non-reducing conditions, the key elution product is the whole AlbuCORE-1 protein; in reducing conditions, the AlbuCORE-1 protein separates into the two fragments previous described. Significantly, there is little contamination, especially when compared with FIG. 22A.

SDS-PAGE and LC/MS Analysis of AlbuCORE-1 and WT HSA

Figure 25A:
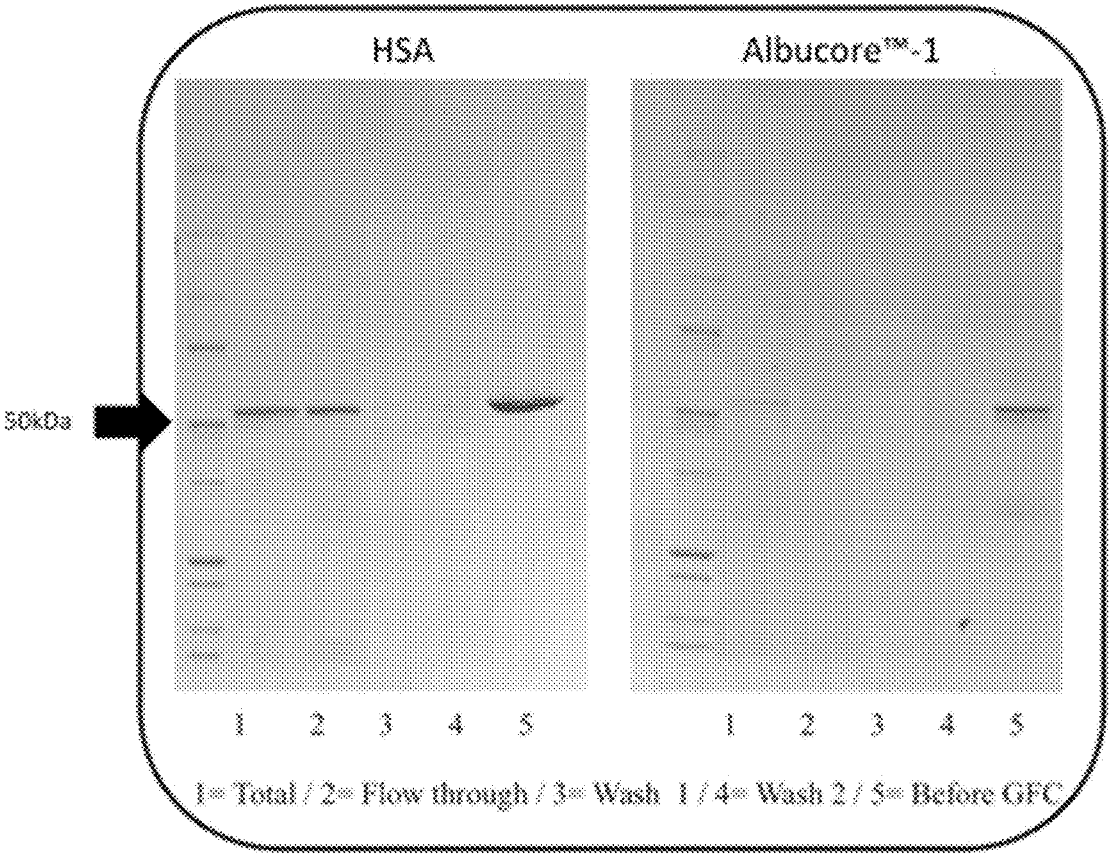
FIG. 25A represents the native gel profiles of the total, flowthrough, wash and final elute of WT-HSA and Albu-CORE-A proteins after the Albupure purification.

The total, flowthrough, wash and elute of the wild-type HSA and AlbuCORE-1 purifications were collected and analyzed via non-reducing SDS-PAGE. As shown in FIG. 25A, representing the aforementioned gel profiles, demonstrate, there is little contamination after the AlbuPure process (compare FIG. 25A and FIG. 22A) and there is also no homodimer formation.

Figure 25B:
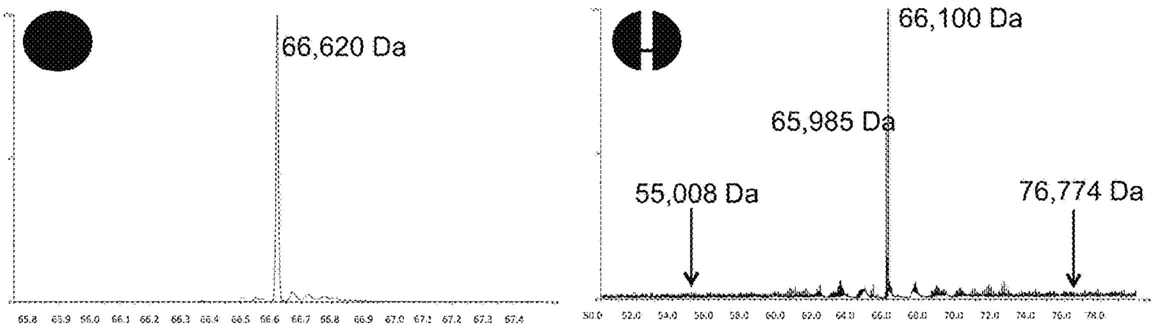
FIG. 25B represents an LC/MS analysis of the same two proteins.

The purified protein was then analyzed using LC/MS. The protein samples were analyzed by LC-MS using an Agilent 1100 HPLC system coupled to an LTQ-Orbitrap XL hybrid mass spectrometer (ThermoFisher Scientific) via a high-flow electrospray interface. The samples (2.5m) were injected onto a 2.1×10 mm Poros R2 column (Applied Biosystems) and eluted using a 2 mL/min gradient of 20-90% ACN, 0.1% FA over 3 minutes. The flow was split post-column to direct 100 μL/min into the electrospray interface. The column and solvent were heated to 80° C. to improve protein peak shape. The LTQ-Orbitrap XL was calibrated using ThermoFisher Scientific's LTQ Positive Ion ESI calibration solution (caffeine, MRFA and Ultramark 1621), and tuned using a 25 ug/uL solution of BSA. The cone voltage (source fragmentation setting) was 40 V, the FT resolution was 7,500 and the scan range was m/z 400-4,000. The protein spectra were deconvoluted using ThermoFisher's Promass software (input range: m/z 2500-3050; output mass range: 100,000-160,000 Da; Peak width: 1.5; Merge width: 0.5; Baseline removal: 0.5 (low)). The abundances of the hetero- and homodimer antibody species were determined directly from the resulting molecular weight profiles. The linearity of response was confirmed using defined mixtures of antibodies. Limits of detection were approximately 2%. FIG. 25B provides the spectrograms of purified AlbuCORE-1 and WT-HSA. As the spectrogram for AlbuCORE-1 demonstrates, there is no homodimer formation (such as A:A or B:B). Variation from the theoretical molecular weight may be due to ion binding, miscellaneous ligands, or glycation.

Example 18. Spatial Organization of Termini of Albumin-Based Polypeptides

Figure 26A:
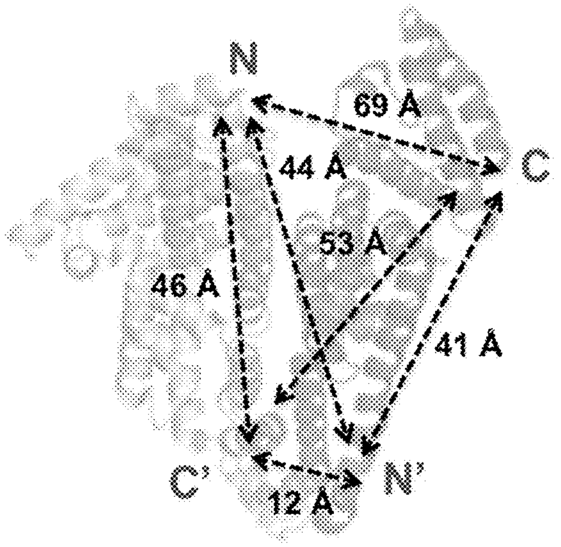
FIG. 26A is a diagram indicating the degree of spatial separation between the four termini in ABH2.
Figure 26B:
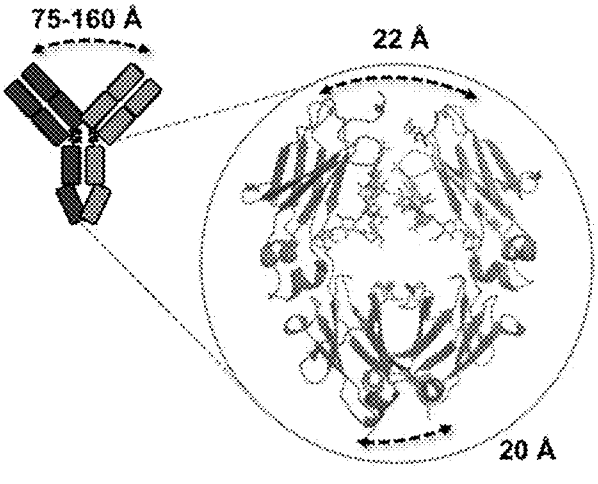
FIG. 26B is a comparative diagram demonstrating the degree of spatial separation between the variable regions of a normal antibody molecule.
Figure 26C:
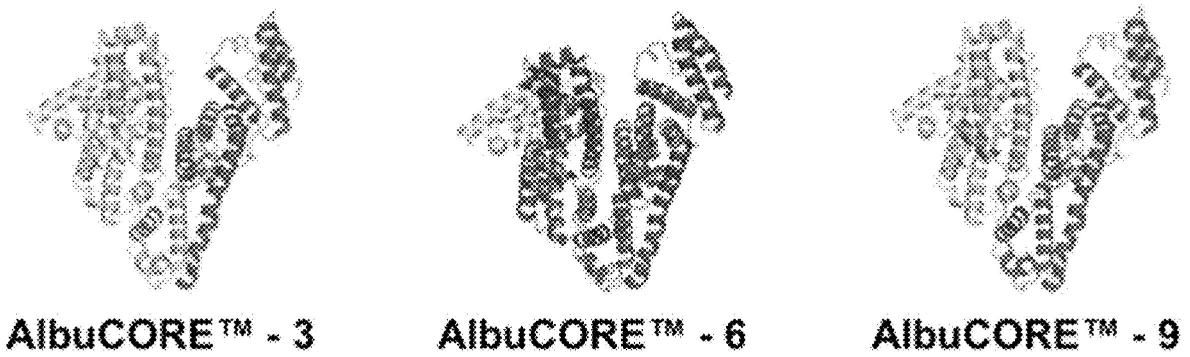
FIG. 26C shows four Albucore scaffolds which have different and variable inter-termini distances for alternative antigen binding.

Albumin-based polypeptides provide an alternative scaffold to antibodies for delivery of cargo molecules. As the difference between FIGS. 26A and 26B demonstrate, engineered albumin-based polypeptides have a greater degree of positional freedom compared to regular antibodies, as the spatial separation between the four termini varies significantly more. Distances were determined after modeling the AlbuCORE molecule onto one of the available crystal structures: PDBID=4EMX. Furthermore, the four termini are also oriented at different planar angles. Finally, the distances and angles between the termini can be subject to further modulation by choosing different segmentations sites, binding domains and/or linkers. FIG. 26C demonstrates alternative AlbuCORE scaffolds available to vary the inter-termini distances for antigen binding optimization in multivalent binding modes.

Figure 27:
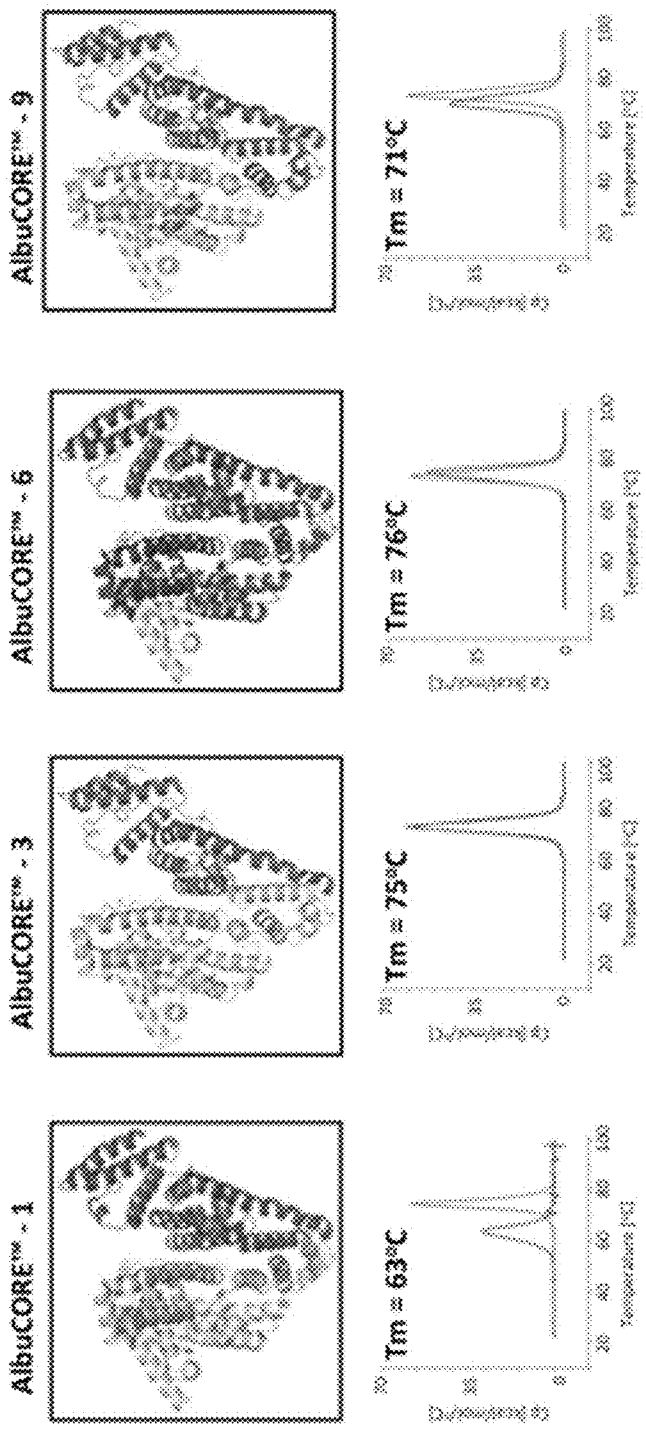
FIG. 27 shows the DSC melting curves of AlbuCORE scaffolds 1, 3, 6 and 9. In each graph, the curve and melting point of each albumin-based scaffold is compared to the curve and 75° C. melting point of the WT HSA.

Example 19. Stability of Additional Albumin-Based Polypeptides as Measured Via DSC To determine the stability and melting points of additional AlbuCORE polypeptides, DSC experiments were performed on AlbuCORE-3, 6 and 9 as well as controls WT-Albumin and AlbuCORE-1. DSC experiments were performed as set out in Example 2. FIG. 27 shows the melting curve of four scaffolds, as compared to that of the WT-HSA. As the Fig. shows, scaffolds 3, 6 and 9 possess melting points very similar to the 75° C. demonstrated by the wild-type. Furthermore, AlbuCORE-6 was found to be more thermally stable than wild-type HSA, at 76° C. Additional DSC experiments were performed on AlbuCORE 1A and 4. The Tm of AlbuCORE 1A was 66° C. and the Tm of AlbuCORE-4 was 70° C. AlbuCORE-1A narrows the gap between the two fragments in AlbuCORE 1 (ABH1) to one residue only and adds a GGGGS linker (SEQ ID NO: 179) to both the N and C non natural termini. The same applies to AlbuCORE 2 (ABH2) and AlbuCORE-2A.

Example 20: Preparation of Anti-CD3×CD19 Heteromultimer Constructs

Anti-CD3 and anti-CD19 scFvs were attached to several different antibody platforms as follows. The albumin-based polypeptide platform was AlbuCORE-1; controls included WT-HSA, the Azymetric scaffold (v873) and the anti-CD3×CD19 BiTE control v891.

Figure 29:
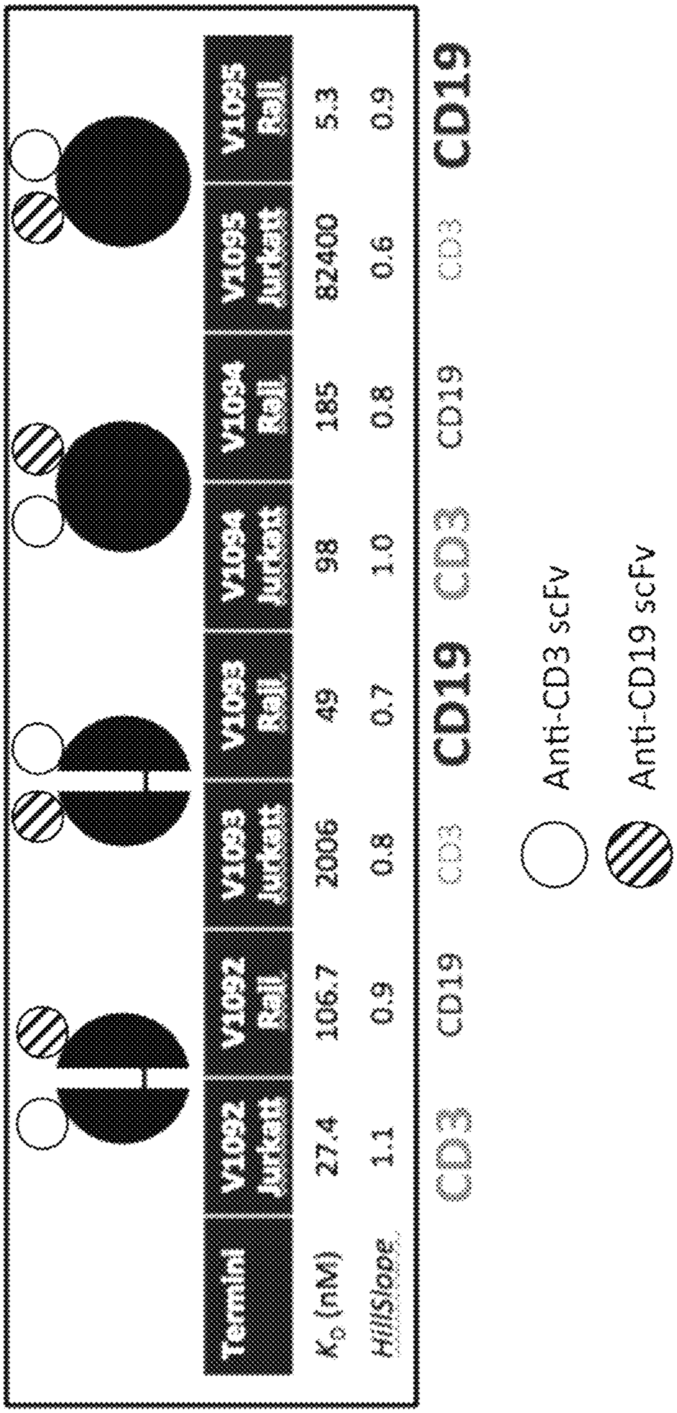
FIG. 29 provides the Ka and Hill Slope measurements of four anti-CD3×CD19 bispecific bivalent heteromultimers on either a WT-HSA or spliced albumin scaffold. The binding tests assessed the variant's ability to bind Jurkat or Raji cells as analyzed using FACS.

ABH2 loaded with anti-CD19×anti-CD3 scFvs (1092, 1093, 1094, and 1095): The sequences for the anti-CD19 and anti-CD3 scFvs were chosen from two molecules that are currently in clinical trials and are well documented and tested for stability and production. The anti-CD19 and anti-CD3 scFv were directly adopted from the BiTE molecule blinatumomab. The antiCD3 scFv was chosen in the VH-VL orientation, consistent with what used in BiTE. The benchmark molecule was BiTE. AlbuCORE_1 (ABH2) CD3/CD19 fusions were created by attaching the antiCD3 warhead to the natural N terminus of fragment 1 and the antiCD19 to the C terminus of fragment 2 (v1092). A second molecule was created where the warheads were reversed (i.e. anti-CD19 warhead at the natural N terminus of fragment 1 and the anti-CD3 at the C terminus of fragment 2, v1093). The linkers used were identical to the ones used for the multivalent HER2 AlbuCORE experiments: GGGS (SEQ ID NO: 183) at the N terminus of fragment 1 and $(GGSG)_4GG$ (SEQ ID NO: 184) at the C terminus of fragment 2. Expression and purification were performed as previously described for the multivalent HER2. Molecules 1093 and 1094 were designed to accommodate two different fusions at their natural termini. The scFv fusions were linked to the albumin molecule through a GGS linker at the N terminus and a GGSG linker (SEQ ID NO: 180) at the C terminus. The length of the linkers reflect the ones used in the MM-111 molecule, despite having a different sequence type. Schematic representations of these molecules are shown in FIG. 29.

Figure 28A:
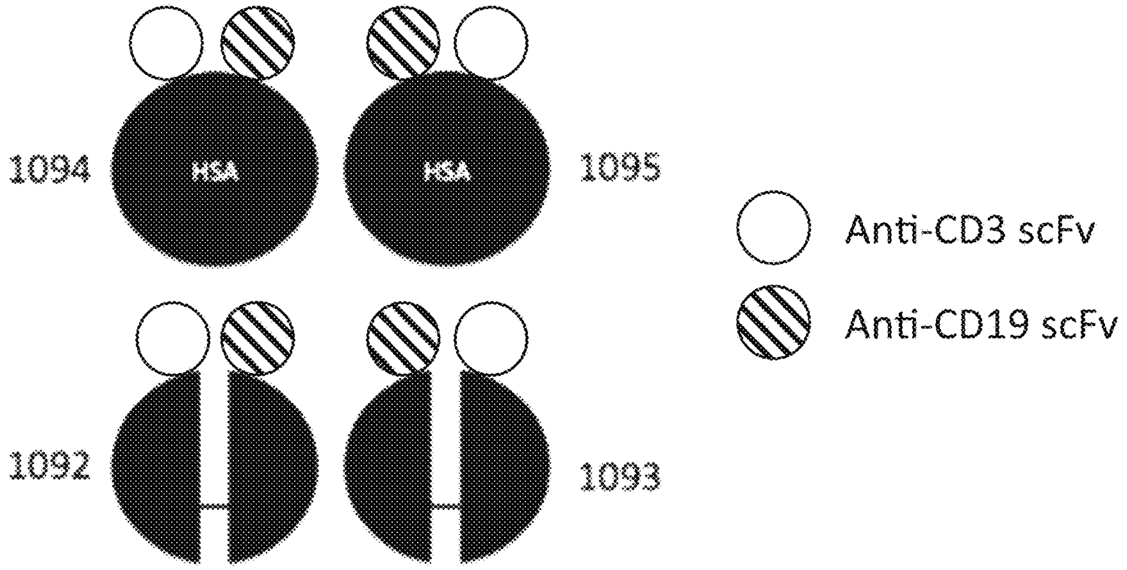
FIG. 28A is the schematic rendering of anti-CD3×CD19 bispecific bivalent heteromultimers on either a WT-HSA or a spliced albumin scaffold.
Figure 28B:
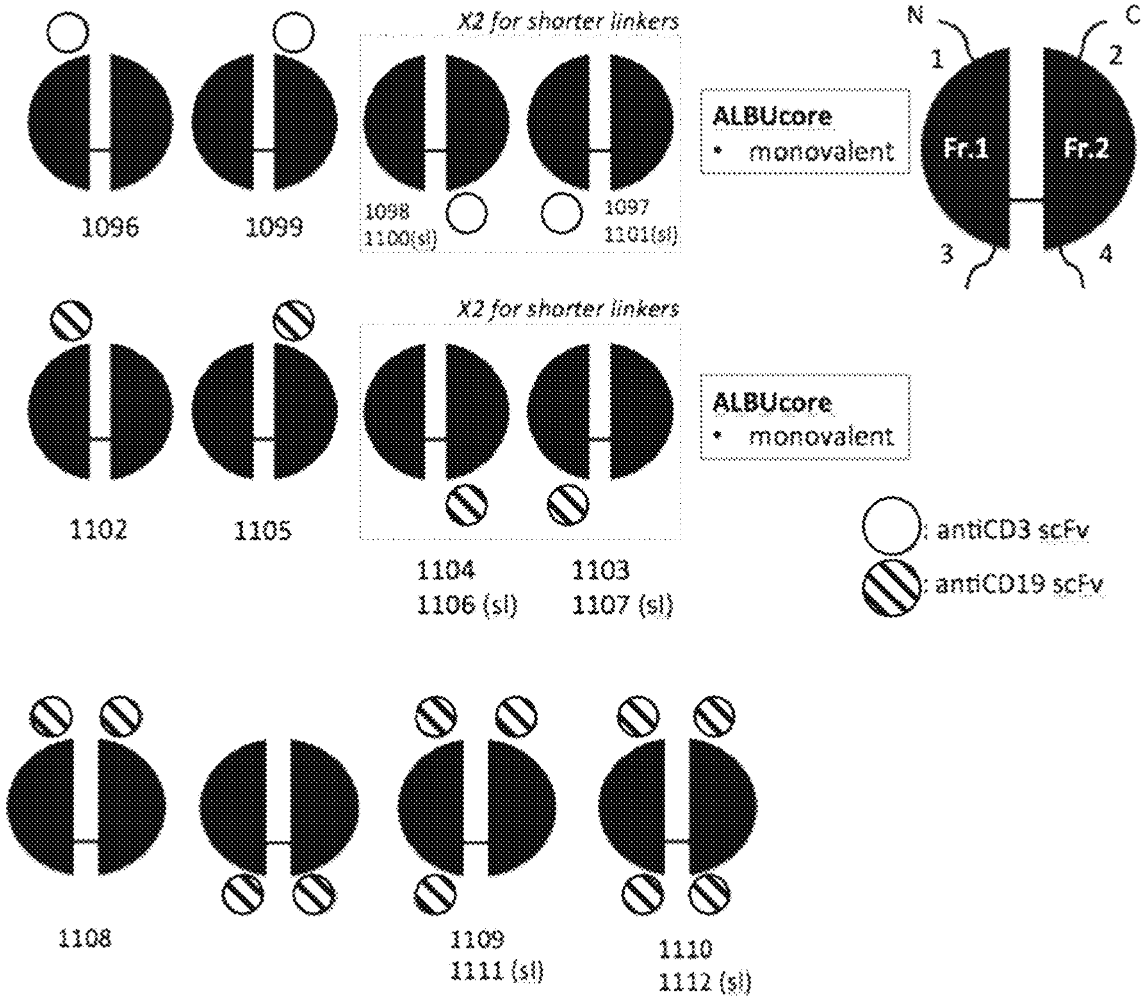
FIG. 28B represents the schematic renderings of additional mononvalent anti-CD3 heteromultimer constructs as well as both monovalent and multivalent anti-CD19 heteromultimer constructs.

Additional monovalent and multivalent CD19 heteromultimers and monovalent CD3 heteromultimers based on ABH2 in which the relative positions of the cargo polypeptides were changed were designed with schematic representations of some of these heteromultimers shown in FIG. 28B. These heteromultimers were generated by expressing its single monomeric transporter polypeptides, SEQ ID NO: 8 and SEQ ID NO: 10, fused at one or both termini to cargo polypeptides that are either antiCD19scFv (CD19) and/or anti-CD3 scFv (CD3). Different combinations of these base constructs were combined upon co-expression to form heteromultimers displaying all combination of the two cargo polypeptides at any of the four terminal positions of the two transporter polypeptides, ranging from monovalent to tetravalent. Table 18 illustrates the base constructs (that were generated by fusing the CD3 and/or CD19 cargo polypeptides to either N or C terminus of transporter polypeptide 1 (F1) or transporter polypeptide 2 (F2). Fl: corresponds to SEQ ID 8 and F2 corresponds to SEQ ID 10.

TABLE 18

Base constructs for CD3 and CD19 monovalent and multivalent constructs

| # | Fusion 1 | Fusion 2 | Fusion 3 | Polypeptide SEQ ID NOs: |
|---|---|---|---|---|
| | Single Fusions | | | |
| 1 | CD3 | F1 | | 137/138 |
| 2 | F1 | CD3 | | 119/120 |
| 3 | F1 | CD3 (short linker) | | 181/182 |
| 4 | CD3 | F2 | | 179/180 |
| 5 | CD3 (short linker) | F2 | | 177/178 |
| 6 | F2 | CD3 | | 141/142 |
| 7 | CD19 | F1 | | 143/144 |
| 8 | F1 | CD19 | | 183/184 |
| 9 | F1 | CD19 (short linker) | | 189/190 |
| 10 | CD19 | F2 | | 187/188 |
| 11 | CD19 (short linker) | F2 | | 185/186 |
| 12 | F2 | CD19 | | 139/140 |
| | Double Fusions | | | |
| 13 | CD19 | F1 | CD19 | 191/192 |
| 14 | CD19 | F1 | CD19 (shorter linker) | 193/194 |
| 15 | CD19 | F2 | CD19 | 195/196 |
| 16 | CD19 (shorter linker) | F2 | CD19 | 197/198 |
| 17 | CD3 | HSA | CD19 | 133/134 |
| 18 | CD19 | HSA | CD3 | 135/136 |

As shown in FIG. 28B, the bioactive cargo polypeptides were fused to the heteromultimer transporter polypeptides via a GGSG linker (SEQ ID NO: 180), for the N terminus of one monomer and a longer $(GGS)_4GG$ linker (SEQ ID NO: 181) for all other termini in the other monomer. In addition a version of each fusion protein was created with a shorter linker at their non-natural terminus (ie C' of Fragment 1 and N' of Fragment 2) formed by the sequence GGSGGSG (SEQ ID NO: 186), replacing $(GGS)_4GG$ (SEQ ID NO: 181).

A summary of the heteromultimers that were prepared are shown in Table 19.

TABLE 19

Monovalent, multivalent, and multispecific constructs that were generated by fusing the CD3 and CD19 cargo polypeptides to either N or C terminus of transporter polypeptide 1 or transporter polypeptide 2 of ABH2.

| Variant | N terminus-transporter polypeptide 1 (SEQ ID No: 8) | C terminus-transporter polypeptide 1 (SEQ ID No: 8) | N terminus-transporter polypeptide 2 (SEQ ID No: 10) | C terminus-transporter polypeptide 2 (SEQ ID No: 10) | Valency | Sequences (Polypeptide) |
|---|---|---|---|---|---|---|
| 1096 | CD3 | | | | monovalent | SEQ ID No: 138<br>SEQ ID NO: 10 |
| 1097 | | CD3 | | | monovalent | SEQ ID No: 120<br>SEQ ID NO: 10 |
| 1101 (shorter linker) | | CD3 | | | monovalent | SEQ ID No: 182<br>SEQ ID NO: 10 |
| 1098 | | | CD3 | | monovalent | SEQ ID NO: 8<br>SEQ ID No: 180 |
| 1100 (shorter linker) | | | CD3 | | monovalent | SEQ ID NO: 8<br>SEQ ID No: 178 |
| 1099 | | | | CD3 | monovalent | SEQ ID NO: 8<br>SEQ ID No: 142 |
| 1102 | CD19 | | | | monovalent | SEQ ID No: 144<br>SEQ ID NO: 10 |
| 1103 | | CD19 | | | monovalent | SEQ ID No: 184<br>SEQ ID NO: 10 |
| 1107 | | CD19 | | | monovalent | SEQ ID No: 190<br>SEQ ID NO: 10 |
| 1104 | | | CD19 | | monovalent | SEQ ID NO: 8<br>SEQ ID No: 188 |

TABLE 19-continued

Monovalent, multivalent, and multispecific constructs that were generated by fusing the CD3 and CD19 cargo polypeptides to either N or C terminus of transporter polypeptide 1 or transporter polypeptide 2 of ABH2.

| Variant | N terminus-transporter polypeptide 1 (SEQ ID No: 8) | C terminus-transporter polypeptide 1 (SEQ ID No: 8) | N terminus-transporter polypeptide 2 (SEQ ID No: 10) | C terminus-transporter polypeptide 2 (SEQ ID No: 10) | Valency | Sequences (Polypeptide) |
|---|---|---|---|---|---|---|
| 1106 | | | CD19 | | monovalent | SEQ ID NO: 8 SEQ ID No: 186 |
| 1105 | | | | CD19 | monovalent | SEQ ID NO: 8 SEQ ID No: 140 |
| 1108 | CD19 | | | CD19 | bivalent | SEQ ID No: 144 SEQ ID No: 140 |
| 1109 | CD19 | CD19 | | CD19 | trivalent | SEQ ID No: 192 SEQ ID No: 140 |
| 1110 | CD19 | CD19 | CD19 | CD19 | tetravalent | SEQ ID No: 192 SEQ ID No: 196 |
| 1111 (shorter linker at non-natural terminus) | CD19 | CD19 | | CD19 | trivalent | SEQ ID No: 194 SEQ ID No: 140 |
| 1112 (shorter linker at non-natural termini) | CD19 | CD19 | CD19 | CD19 | tetravalent | SEQ ID No: 194 SEQ ID No: 198 |
| 1092 | CD3 | | | CD19 | bispecific | SEQ ID No: 138 SEQ ID No: 140 |
| 1093 | CD19 | | | CD3 | bispecific | SEQ ID No: 144 SEQ ID No: 142 |

Multivalent constructs were generated as outlined in Example 2 using heteromultimer ABH2. The final gene products were subcloned into the mammalian expression vector pTT5 (NRC-BRI, Canada) (Durocher et al). High level and high-throughput recombinant protein production by transient transfection of suspension-growing human CHO-3E7 was performed as described in Example 2.

Figure 28C:
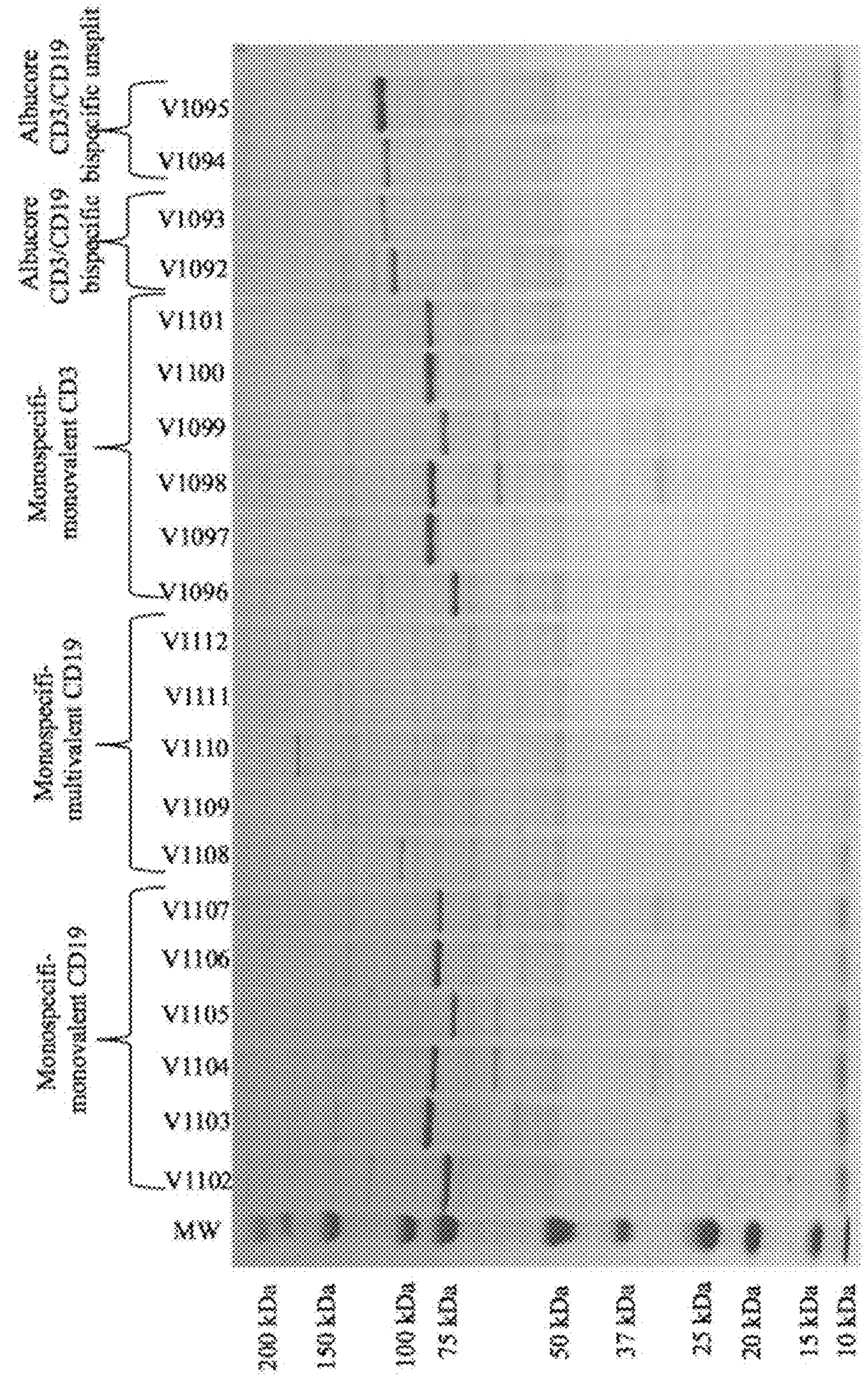
FIG. 28C represents a non-reducing PAGE gel of the previous described constructs after each was expressed in a suspension growing human CHO system.

The expression results are shown in FIG. 28C. The monovalent CD3 and CD19 fusions express at similar levels. The expression of monovalent CD3 and CD19 have the same pattern (in terms of MW) as the one observed with HER2 fusions, indicating that variations in migration on non-reducing gel are independent of the warhead type.

Example 21: Ability of Anti-CD3×CD19 Loaded Albumin-Based Polypeptide to Bind to B-Cells and T-Cells The ability of Anti-CD3×CD19 loaded AlbuCORE-1 (v1092 and 1093) to $CD3^+$ and $CD19^+$ cells was assessed using FACS and compared to WT-HSA loaded with the same anti-CD scFvs (1094 and 1095). The AlbuCORE-1 constructs were additionally tested against the Azymetric™ and the BiTE MT-103 for B-cell and T-cell binding as follows. The method was carried out as described in Example 13, but in MALME-3M cells and SKOV cells.

The results are shown in FIG. 29 which shows the $K_D$ and Hill Slope data for the tested variants in Jurkat and Raji cells.

Example 22: Ability of Anti-CD13×CD19 Loaded Albumin-Based Polypeptide to Bind to B-Cells and T-Cells The ability of variants 1092, and 1093 to bridge B- and T-cells was determined as follows. Whole Cell Bridging by FACS $1\times10^6$ cells/ml suspended in RPMI were labeled with 0.3 μM of the appropriate CellTrace label and mixed and incubated at 37° C. in a water bath for 25 minutes. Pellets were resuspended in 2 ml of L10+GS1+$NaN_3$ to a final concentration $5\times10^6$ cells/ml. Cell suspensions were analyzed (1/5 dilution) by flow cytometry to verify the appropriate cell labeling and laser settings. Flow-check and flow-set Fluorospheres were used to verify instrument standardization, optical alignment and fluidics.

After flow cytometry verification, and prior to bridging, each cell line was mixed together at the desired ratio, at a final concentration of $1\times10^6$ cells/ml.

T:T bridging was assessed with Jurkat-violet+Jurkat-FarRed, B:B was assessed with RAJI-violet+RAJI-FarRed and T:B bridging was assessed with Jurkat-violet+RAJI-FarRed.

Antibody variants were diluted to 2× in L10+GS1+NaN3 at room temperature then added to cells followed by gentle mixing and a 30 min incubation.

Following the 30 min incubation 2 μl of propidium iodide was added and slowly mixed and immediately analyzed by flow cytometry.

Bridging % was calculated as the percentage of events that are simultaneously labeled violet and Far-red.

Figure 30A:
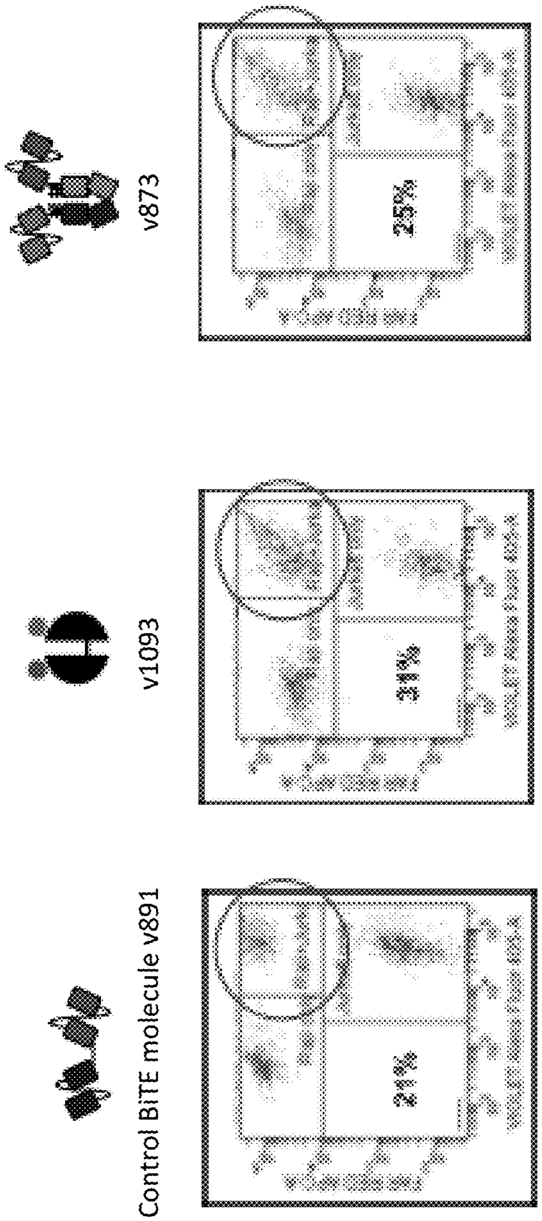
FIG. 30A displays FACS cell population graphs of the BiTE-like control (v891), an anti-CD3×CD19 albumin-based heteromultimer (v1092) and an anti-CD3×CD19 Het-Fc-based heteromultimer (v873). Binding to Raji and Jurkat cells was assessed.

FIG. 30A compares the ability of v1092, a bi-specific CD3/CD19 antibody (v873) and the BiTE-like control v891 to bridge Jurkat CD3 T cells (bottom right quadrant) with Raji CD19 B cells (top left quadrant) by FACS. Bridged T-B cells appear in top right quadrant. This result demonstrates that at concentrations of as low as 0.3 nM v1092 is able to specifically bridge Jurkat T cells and Raji B cells to a similar extent (31% of total cells) as BiTE (21% of total cells) and a bi-specific CD3/CD19 antibody with an heterodimeric Fc (25%).

Figure 30B:
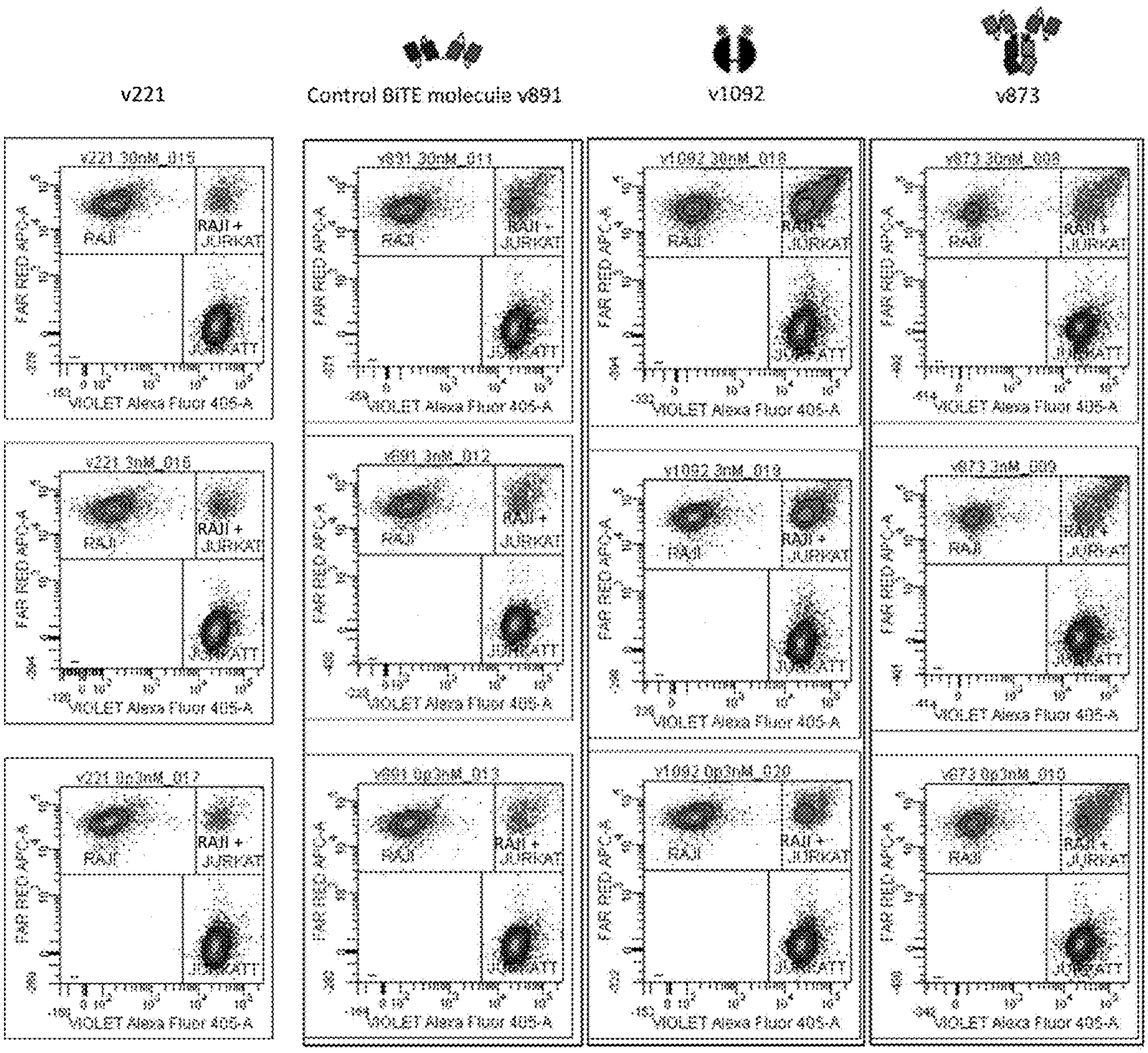
FIG. 30B shows additional FACS graphs of the three aforementioned constructs and as compared against an albumin control (v221).

FIG. 30B compares the ability of v1092, to the controls v891, v873, and v221. This figure shows that v1092 is able to bridge Jurkat T cells and Raji B cells to a similar extent to v891 (BITE).

All publications, patents and patent applications mentioned in this specification are herein incorporated by reference into the specification to the same extent as if each individual publication, patent or patent application was specifically and individually indicated to be incorporated herein by reference.

What is claimed:

1. A heteromultimer comprising:

a first polypeptide construct comprising (i) a first transporter polypeptide comprising a first segment of albumin, and (ii) at least one first cargo molecule; and a second polypeptide construct comprising (iii) a second transporter polypeptide comprising a second segment of albumin, wherein a) said first segment of albumin and said second segment of albumin are obtained by segmentation of an albumin polypeptide at a segmentation site to delete zero to 3 amino acid residues at the segmentation site, b) said first transporter polypeptide and said second transporter polypeptide are different from each other, and c) said first transporter polypeptide and said second transporter polypeptide self-assemble to form a quasi-native structure of albumin.

2. The heteromultimer of claim 1, wherein a) the segmentation site resides on a loop of the albumin polypeptide that has a high solvent accessible surface area (SASA) and limited contact with the rest of the albumin polypeptide, orb) the segmentation results in a complementary interface between the first segment of albumin and the second segment of albumin wherein the complementary interface is apolar, extensive and interdigitate.

3. The heteromultimer of claim 2, wherein the segmentation deletes zero to 2 amino acid residues at the segmentation site, or deletes zero or 1 amino acid residues at the segmentation site.

4. The heteromultimer of claim 2, wherein at least one naturally occurring disulphide bond is formed between the first segment of albumin and the second segment of albumin.

5. The heteromultimer of claim 2, wherein at least one of said first and second transporter polypeptides comprises at least one mutation of an amino acid residue to cysteine such that said cysteine forms a disulfide bond with a cysteine residue on the other transporter polypeptide.

6. The heteromultimer of claim 2, wherein the thermal stability of the quasi-native structure is within approximately 20° C. of the thermal stability of albumin, or wherein the quasi-native structure of albumin has a melting temperature greater than 65° C., 70° C., or 75° C., wherein the thermal stability is measured by differential scanning calorimetry.

7. The heteromultimer of claim 6 wherein the C-terminus and N-terminus introduced at the segmentation site are each fused to a linker.

8. The heteromultimer of claim 7, wherein the linker is a GGGGS (SEQ ID NO:179) peptide sequence.

9. The heteromultimer of claim 2, wherein a) at least one of said first segment of albumin and the second segment of albumin is a segment of an alloalbumin polypeptide;

b) the first segment of albumin and the second segment of albumin are segments of an alloalbumin polypeptide;

c) the first segment of albumin and the second segment of albumin are segments of the same type of albumin polypeptide; or d) the first segment of albumin and the second segment of albumin are segments of different types of albumin polypeptides.

10. The heteromultimer of claim 2, wherein said first segment of albumin and said second segment of albumin are from a mammalian albumin.

11. The heteromultimer of claim 2, wherein said first segment of albumin and/or said second segment of albumin each comprise an amino acid sequence with at least 95% sequence identity to human albumin.

12. The heteromultimer of claim 2, wherein said albumin polypeptide is human serum albumin having a sequence of SEQ ID NO: 1 without the signal peptide sequence.

13. The heteromultimer of claim 12, wherein the location of the segmentation site is between residues 339 and 340, between residues 300 and 301, between residues 364 and 365, between residues 441 and 442, between residues 171 and 172, between residues 281 and 282, or between residues 114 and 115 of the albumin polypeptide sequence of SEQ ID NO:1, wherein the numbering of residues begins with the first residue after the signal sequence.

14. The heteromultimer of claim 12, wherein the segmentation site deletes a residue at a location corresponding to residue 84 of the albumin polypeptide sequence of SEQ ID NO:1, wherein the numbering of residues begins with the first residue after the signal sequence.

15. The heteromultimer of claim 1, wherein a) said first transporter polypeptide comprises the sequence set forth in SEQ ID NO:39 without the signal peptide sequence, and wherein said second transporter polypeptide comprises the sequence set forth in SEQ ID NO:40 without the signal peptide sequence;

b) said first transporter polypeptide comprises the sequence set forth in SEQ ID NO:41 without the signal peptide sequence, and wherein said second transporter polypeptide comprises the sequence set forth in SEQ ID NO:42 without the signal peptide sequence;

c) said first transporter polypeptide comprises the sequence set forth in SEQ ID NO:43 without the signal peptide sequence, and wherein said second transporter polypeptide comprises the sequence set forth in SEQ ID NO:44 without the signal peptide sequence;

d) said first transporter polypeptide comprises the sequence set forth in SEQ ID NO:45 without the signal peptide sequence, and wherein said second transporter polypeptide comprises the sequence set forth in SEQ ID NO:46 without the signal peptide sequence;

e) said first transporter polypeptide comprises the sequence set forth in SEQ ID NO:47 without the signal peptide sequence, and wherein said second transporter polypeptide comprises the sequence set forth in SEQ ID NO:48 without the signal peptide sequence;

f) said first transporter polypeptide comprises the sequence set forth in SEQ ID NO:49 without the signal peptide sequence, and wherein said second transporter polypeptide comprises the sequence set forth in SEQ ID NO:50 without the signal peptide sequence;

g) said first transporter polypeptide comprises the sequence set forth in SEQ ID NO:51 without the signal peptide sequence, and wherein said second transporter polypeptide comprises the sequence set forth in SEQ ID NO:52 without the signal peptide sequence; or h) said first transporter polypeptide comprises the sequence set forth in SEQ ID NO:53 without the signal peptide sequence, and wherein said second transporter polypeptide comprises the sequence set forth in SEQ ID NO:54 without the signal peptide sequence.

16. The heteromultimer of claim 2, wherein said second polypeptide construct further comprises at least one second cargo molecule.

17. The heteromultimer of claim 2, wherein the activity of the cargo molecule is altered on fusion to the transporter polypeptide relative to its unfused format, or wherein the activity of the cargo molecule is attenuated on fusion to the transporter polypeptide relative to its unfused format.

18. The heteromultimer of claim 16, wherein the at least one first cargo molecule or the at least one second cargo molecule is a therapeutic agent, a toxin, a natural product or prodrug, a cargo polypeptide, or a nucleic acid.

19. The heteromultimer of claim 18, wherein the first polypeptide construct comprises one first cargo polypeptide or two first cargo polypeptides, and/or the second polypeptide construct comprises one second cargo polypeptide or two second cargo polypeptides.

20. The heteromultimer of claim 19, wherein at least one of the first cargo polypeptides or at least one of the second cargo polypeptides is an antigen-binding polypeptide construct.

21. The heteromultimer of claim 20, wherein the antigen binding polypeptide construct binds CD3, CD19, CD20, HER2, or HER3.

22. The heteromultimer of claim 16, wherein the first cargo molecule is a cargo polypeptide, and the second cargo molecule is a toxin, and/or the first cargo molecule is a toxin, and the second cargo molecule is a cargo polypeptide.

23. The heteromultimer of claim 16, wherein the first cargo molecule and/or the second cargo molecule bind a target antigen selected from at least one of alpha-chain (CD25) of IL-2R, Amyloid beta, anti-EpCAM, anti-CD3, CD16, CD20, CD22, CD23, CD3, CD4, CD52, CD80, CTLA-4, EGFR, EpCAM, F protein of RSV, G250, glycoprotein TUB/ilia R, HER2, HER3, IGF1R, EGFR, HSP90, IgE antibody, IL-12, IL-23, IL-1 beta, IL-5, IL-6, RANKL, TNF alpha, TNFR, TRAIL, VEGF-A, glucagon receptor, GLP receptor, and LDL receptor.

24. A composition comprising the heteromultimer of claim 1 and a pharmaceutically acceptable carrier.

25. One or more nucleic acids encoding the heteromultimer according to claim 1.

26. One or more vectors comprising the one or more nucleic acids according to claim 25.

27. A host cell comprising the one or more vectors according to claim 26.

28. A method of preparing the heteromultimer according to claim 1, comprising expressing one or more nucleic acids encoding the heteromultimer in a host cell.

29. A method of preparing self-assembling polypeptides from an albumin comprising: segmenting said albumin at one or more segmentation sites to obtain at least two albumin segments that self-assemble to form a quasi-native albumin structure, the method comprising the steps of a) selecting at least one loop of an albumin that has a high solvent accessible surface area and limited contact with the rest of the structure of said albumin, and b) introducing one segmentation site deleting zero to three amino acid residues at the segmentation site per selected loop to obtain at least two albumin segments having a complementary interface between the at least two albumin segments, wherein the interface is apolar, extensive and interdigitate.

30. A heteromultimer comprising:

a first polypeptide construct comprising (i) a first transporter polypeptide comprising a first segment of albumin, and a second polypeptide construct comprising (iii) a second transporter polypeptide comprising a second segment of albumin, wherein a) said first segment of albumin and said second segment of albumin are obtained by segmentation of an albumin polypeptide at a segmentation site to delete zero to 3 amino acid residues at the segmentation site, b) said first transporter polypeptide and said second transporter polypeptide are different from each other, and c) said first transporter polypeptide and said second transporter polypeptide self-assemble to form a quasi-native structure of albumin.

31. A composition comprising the heteromultimer of claim 30 and a pharmaceutically acceptable carrier.

32. One or more nucleic acids encoding the heteromultimer according to claim 30.

33. One or more vectors comprising the one or more nucleic acids according to claim 32.

34. A host cell comprising the one or more vectors according to claim 33.

35. A method of preparing the heteromultimer according to claim 30, comprising expressing one or more nucleic acids encoding the heteromultimer in a host cell.

36. The heteromultimer of claim 1, wherein a) said first transporter polypeptide comprises a sequence having at least 95% sequence identity to the sequence set forth in SEQ ID NO:39 without the signal peptide sequence, and wherein said second transporter polypeptide comprises a sequence having at least 95% sequence identity to the sequence set forth in SEQ ID NO:40 without the signal peptide sequence;

b) said first transporter polypeptide comprises a sequence having at least 95% sequence identity to the sequence set forth in SEQ ID NO:41 without the signal peptide sequence, and wherein said second transporter polypeptide comprises a sequence having at least 95% sequence identity to the sequence set forth in SEQ ID NO:42 without the signal peptide sequence;

c) said first transporter polypeptide comprises a sequence having at least 95% sequence identity to the sequence set forth in SEQ ID NO:43 without the signal peptide sequence, and wherein said second transporter polypeptide comprises a sequence having at least 95% sequence identity to the sequence set forth in SEQ ID NO:44 without the signal peptide sequence;

d) said first transporter polypeptide comprises a sequence having at least 95% sequence identity to the sequence set forth in SEQ ID NO:45 without the signal peptide sequence, and wherein said second transporter polypeptide comprises a sequence having at least 95% sequence identity to the sequence set forth in SEQ ID NO:46 without the signal peptide sequence;

e) said first transporter polypeptide comprises a sequence having at least 95% sequence identity to the sequence set forth in SEQ ID NO:47 without the signal peptide sequence, and wherein said second transporter polypeptide comprises a sequence having at least 95% sequence identity to the sequence set forth in SEQ ID NO:48 without the signal peptide sequence;

f) said first transporter polypeptide comprises a sequence having at least 95% sequence identity to the sequence set forth in SEQ ID NO:49 without the signal peptide sequence, and wherein said second transporter polypeptide comprises a sequence having at least 95% sequence identity to the sequence set forth in SEQ ID NO:50 without the signal peptide sequence;

g) said first transporter polypeptide comprises a sequence having at least 95% sequence identity to the sequence set forth in SEQ ID NO:51 without the signal peptide sequence, and wherein said second transporter polypeptide comprises a sequence having at least 95% sequence identity to the sequence set forth in SEQ ID NO:52 without the signal peptide sequence; or h) said first transporter polypeptide comprises a sequence having at least 95% sequence identity to the sequence set forth in SEQ ID NO:53 without the signal peptide sequence, and wherein said second transporter polypeptide comprises a sequence having at least 95% sequence identity to the sequence set forth in SEQ ID NO:54 without the signal peptide sequence.

* * * * *

UNITED STATES PATENT AND TRADEMARK OFFICE
CERTIFICATE OF CORRECTION

| | |
|---|---|
| PATENT NO. | : 11,248,037 B2 |
| APPLICATION NO. | : 16/417969 |
| DATED | : February 15, 2022 |
| INVENTOR(S) | : Surjit Bhimarao Dixit et al. |

It is certified that error appears in the above-identified patent and that said Letters Patent is hereby corrected as shown below:

On the Title Page

At the (73) Assignee, please delete "ZYMEWORKS INC," and insert --ZYMEWORKS BC INC.--

Signed and Sealed this
Thirtieth Day of May, 2023

Katherine Kelly Vidal
*Director of the United States Patent and Trademark Office*